US008933197B2

(12) United States Patent
Stemmer et al.

(10) Patent No.: US 8,933,197 B2
(45) Date of Patent: *Jan. 13, 2015

(54) COMPOSITIONS COMPRISING MODIFIED BIOLOGICALLY ACTIVE POLYPEPTIDES

(75) Inventors: Willem P. Stemmer, Los Gatos, CA (US); Volker Schellenberger, Palo Alto, CA (US)

(73) Assignee: Amunix Operating Inc., Mountain View, CA (US)

( * ) Notice: Subject to any disclaimer, the term of this patent is extended or adjusted under 35 U.S.C. 154(b) by 1022 days.

This patent is subject to a terminal disclaimer.

(21) Appl. No.: 12/228,859

(22) Filed: Aug. 15, 2008

(65) Prior Publication Data

US 2009/0092582 A1    Apr. 9, 2009

Related U.S. Application Data

(60) Provisional application No. 60/956,109, filed on Aug. 15, 2007, provisional application No. 60/981,073, filed on Oct. 18, 2007, provisional application No. 60/986,569, filed on Nov. 8, 2007.

(51) Int. Cl.
| C07K 14/00 | (2006.01) |
| C07K 14/52 | (2006.01) |
| C07K 14/75 | (2006.01) |
| A61K 38/00 | (2006.01) |
| A61K 38/22 | (2006.01) |
| A61K 38/19 | (2006.01) |

(52) U.S. Cl.
USPC ........... 530/350; 530/351; 530/324; 530/399; 514/1.1

(58) Field of Classification Search
None
See application file for complete search history.

(56) References Cited

U.S. PATENT DOCUMENTS

| 3,992,518 A | 11/1976 | Chien et al. |
| 4,088,864 A | 5/1978 | Theeuwes et al. |
| 4,200,984 A | 5/1980 | Fink |
| 4,284,444 A | 8/1981 | Bernstein et al. |
| 4,398,908 A | 8/1983 | Siposs |
| 4,435,173 A | 3/1984 | Siposs et al. |
| 4,542,025 A | 9/1985 | Tice et al. |
| 4,684,479 A | 8/1987 | D'arrigo |
| 4,861,800 A | 8/1989 | Buyske |
| 4,897,268 A | 1/1990 | Tice et al. |
| 4,933,185 A | 6/1990 | Wheatley et al. |
| 4,976,696 A | 12/1990 | Sanderson et al. |
| 4,988,337 A | 1/1991 | Ito |
| 5,017,378 A | 5/1991 | Turner et al. |
| 5,089,474 A | 2/1992 | Castro et al. |
| 5,176,502 A | 1/1993 | Sanderson et al. |
| 5,186,938 A | 2/1993 | Sablotsky et al. |
| 5,215,680 A | 6/1993 | D'arrigo |
| 5,223,409 A | 6/1993 | Ladner et al. |
| 5,270,176 A | 12/1993 | Dorschug et al. |
| 5,298,022 A | 3/1994 | Bernardi |
| 5,318,540 A | 6/1994 | Athayde et al. |
| 5,407,609 A | 4/1995 | Tice et al. |
| 5,492,534 A | 2/1996 | Athayde et al. |
| 5,554,730 A | 9/1996 | Woiszwillo et al. |
| 5,573,776 A | 11/1996 | Harrison et al. |
| 5,578,709 A | 11/1996 | Woiszwillo |
| 5,599,907 A | 2/1997 | Anderson et al. |
| 5,660,848 A | 8/1997 | Moo-Young |
| 5,739,276 A | 4/1998 | Shon et al. |
| 5,756,115 A | 5/1998 | Moo-Young et al. |
| 5,874,104 A | 2/1999 | Adler-Moore et al. |
| 5,916,588 A | 6/1999 | Popescu et al. |
| 5,942,252 A | 8/1999 | Tice et al. |
| 5,965,156 A | 10/1999 | Proffitt et al. |
| 5,981,719 A | 11/1999 | Woiszwillo et al. |
| 6,024,983 A | 2/2000 | Tice et al. |
| 6,043,094 A | 3/2000 | Martin et al. |
| 6,056,973 A | 5/2000 | Allen et al. |
| 6,090,925 A | 7/2000 | Woiszwillo et al. |
| 6,110,498 A | 8/2000 | Rudnic et al. |
| 6,126,966 A | 10/2000 | Abra et al. |
| 6,183,770 B1 | 2/2001 | Muchin et al. |
| 6,254,573 B1 | 7/2001 | Haim et al. |
| 6,268,053 B1 | 7/2001 | Woiszwillo et al. |
| 6,284,276 B1 | 9/2001 | Rudnic et al. |
| 6,294,170 B1 | 9/2001 | Boone et al. |
| 6,294,191 B1 | 9/2001 | Meers et al. |
| 6,294,201 B1 | 9/2001 | Kettelhoit et al. |

(Continued)

FOREIGN PATENT DOCUMENTS

| WO | WO 89/09051 A1 | 10/1989 |
| WO | WO 97/33552 A1 | 9/1997 |

(Continued)

OTHER PUBLICATIONS

Prinz, et al. The role of the thioredoxin and glutaredoxin pathways in reducing protein disulfide bonds in the *Escherichia coli* cytoplasm. J. Biol. Chem., 1997, vol. 272(25): 15661-15667.*

European search report and search opinion dated Jan. 27, 2011 for Application No. 08795371.7.

International search report and written opinion dated Dec. 20, 2010 for PCT Application No. US10/02147.

Ackerman et al. Ion Channels—Basic Science and Clinical Disease. New Engl. J. Med.1997; 336:1575-1595.

(Continued)

*Primary Examiner* — Robert Landsman
*Assistant Examiner* — Bruce D Hissong
(74) *Attorney, Agent, or Firm* — Wilson Sonsini Goodrich & Rosati

(57) ABSTRACT

The present invention relates to biologically active polypeptides linked to one or more accessory polypeptides. The present invention also provides recombinant polypeptides including vectors encoding the subject proteinaceous entities, as well as host cells comprising the vectors. The subject compositions have a variety of utilities including a range of pharmaceutical applications.

12 Claims, 98 Drawing Sheets

(56) References Cited

U.S. PATENT DOCUMENTS

| | | | |
|---|---|---|---|
| 6,303,148 B1 | 10/2001 | Hennink et al. | |
| 6,309,370 B1 | 10/2001 | Haim et al. | |
| 6,316,024 B1 | 11/2001 | Allen et al. | |
| 6,329,186 B1 | 12/2001 | Nielsen et al. | |
| 6,352,716 B1 | 3/2002 | Janoff et al. | |
| 6,352,721 B1 | 3/2002 | Faour | |
| 6,361,796 B1 | 3/2002 | Rudnic et al. | |
| 6,395,302 B1 | 5/2002 | Hennink et al. | |
| 6,406,713 B1 | 6/2002 | Janoff et al. | |
| 6,458,387 B1 | 10/2002 | Scott et al. | |
| 6,500,448 B1 * | 12/2002 | Johnson et al. | 424/423 |
| 6,514,532 B2 | 2/2003 | Rudnic et al. | |
| 6,517,859 B1 | 2/2003 | Tice et al. | |
| 6,534,090 B2 | 3/2003 | Puthli et al. | |
| 6,572,585 B2 | 6/2003 | Choi | |
| 6,669,961 B2 | 12/2003 | Kim et al. | |
| 6,713,086 B2 | 3/2004 | Qiu et al. | |
| 6,715,485 B1 | 4/2004 | Djupesland | |
| 6,733,753 B2 | 5/2004 | Boone et al. | |
| 6,743,211 B1 | 6/2004 | Prausnitz et al. | |
| 6,759,057 B1 | 7/2004 | Weiner et al. | |
| 6,814,979 B2 | 11/2004 | Rudnic et al. | |
| 6,838,093 B2 | 1/2005 | Flanner et al. | |
| 6,890,918 B2 | 5/2005 | Burnside et al. | |
| 6,905,688 B2 | 6/2005 | Rosen et al. | |
| 6,945,952 B2 | 9/2005 | Kwon | |
| 7,045,318 B2 | 5/2006 | Ballance | |
| 7,235,626 B1 | 6/2007 | Cochran | |
| 7,276,475 B2 | 10/2007 | Defrees et al. | |
| 7,413,537 B2 | 8/2008 | Ladner et al. | |
| 7,442,778 B2 | 10/2008 | Gegg et al. | |
| 7,452,967 B2 | 11/2008 | Bertin | |
| 7,514,257 B2 | 4/2009 | Lee et al. | |
| 7,528,242 B2 | 5/2009 | Anderson et al. | |
| 7,846,455 B2 | 12/2010 | Collins et al. | |
| 2002/0042079 A1 | 4/2002 | Simon et al. | |
| 2003/0049689 A1 | 3/2003 | Edwards et al. | |
| 2003/0171267 A1 * | 9/2003 | Rosen et al. | 514/12 |
| 2003/0181381 A1 | 9/2003 | Himmelspach et al. | |
| 2003/0190740 A1 * | 10/2003 | Altman | 435/226 |
| 2004/0043446 A1 | 3/2004 | DeFrees et al. | |
| 2004/0106118 A1 | 6/2004 | Kolmar et al. | |
| 2004/0259780 A1 | 12/2004 | Glasebrook et al. | |
| 2005/0042721 A1 | 2/2005 | Fang et al. | |
| 2005/0048512 A1 | 3/2005 | Kolkman et al. | |
| 2005/0118136 A1 | 6/2005 | Leung et al. | |
| 2005/0123997 A1 | 6/2005 | Lollar | |
| 2005/0260605 A1 | 11/2005 | Punnonen et al. | |
| 2005/0287153 A1 | 12/2005 | Dennis | |
| 2006/0026719 A1 | 2/2006 | Kieliszewski et al. | |
| 2006/0084113 A1 | 4/2006 | Ladner et al. | |
| 2006/0287220 A1 | 12/2006 | Li et al. | |
| 2006/0293232 A1 | 12/2006 | Levy et al. | |
| 2007/0048282 A1 | 3/2007 | Rosen et al. | |
| 2007/0161087 A1 | 7/2007 | Glaesner et al. | |
| 2007/0191272 A1 | 8/2007 | Stemmer et al. | |
| 2007/0203058 A1 | 8/2007 | Lau et al. | |
| 2007/0212703 A1 | 9/2007 | Stemmer et al. | |
| 2007/0244301 A1 | 10/2007 | Siekmann et al. | |
| 2008/0039341 A1 | 2/2008 | Schellenberger et al. | |
| 2008/0167238 A1 | 7/2008 | Rosen et al. | |
| 2008/0176288 A1 | 7/2008 | Leung et al. | |
| 2008/0193441 A1 | 8/2008 | Trown et al. | |
| 2008/0286808 A1 | 11/2008 | Schellenberger et al. | |
| 2008/0312157 A1 | 12/2008 | Levy et al. | |
| 2009/0060862 A1 | 3/2009 | Chang et al. | |
| 2009/0099031 A1 | 4/2009 | Stemmer et al. | |
| 2009/0117104 A1 | 5/2009 | Baker et al. | |
| 2010/0189682 A1 | 7/2010 | Schellenberger et al. | |
| 2010/0239554 A1 | 9/2010 | Schellenberger et al. | |
| 2010/0260706 A1 | 10/2010 | Bogin et al. | |
| 2011/0151433 A1 | 6/2011 | Schellenberger et al. | |

FOREIGN PATENT DOCUMENTS

| | | |
|---|---|---|
| WO | WO 99/41383 A1 | 8/1999 |
| WO | WO 99/49901 A1 | 10/1999 |
| WO | WO 02/077036 A2 | 10/2002 |
| WO | WO 2005/025499 A2 | 3/2005 |
| WO | WO 2005/025499 A3 | 5/2005 |
| WO | WO 2006/081249 A2 | 8/2006 |
| WO | WO 2006/081249 A3 | 2/2007 |
| WO | WO 2007/103455 A2 | 9/2007 |
| WO | WO 2007/103515 A2 | 9/2007 |
| WO | WO 2007/103455 A3 | 11/2007 |
| WO | WO 2007/103515 A3 | 4/2008 |
| WO | WO 2008/049931 A1 | 5/2008 |
| WO | WO 2008/155134 A1 | 12/2008 |
| WO | WO 2010/091122 A1 | 8/2010 |

OTHER PUBLICATIONS

Adam, et al. High affinity restricts the localization and tumor penetration of single-chain fv antibody molecules. Cancer Res. 2001; 61(12):4750-5.

Adam, et al. Increased affinity leads to improved selective tumor delivery of single-chain Fv antibodies. Cancer Res. 1998; 58(3):485-90.

Alam, et al. Expression and purification of a mutant human growth hormone that is resistant to proteolytic cleavage by thrombin, plasmin and human plasma in vitro. J Biotechnol. 1998; 65(2-3):183-90.

Altschul et al. Basic Local Alignment Search Tool. J. Mol. Biol. 1990; 215:403-410.

Alvarez, et al. Improving Protein Pharmacokinetics by Genetic Fusion to Simple Amino Acid Sequences. J Biol Chem. 2004; 279: 3375-81.

Amin, et al. Construction of stabilized proteins by combinatorial consensus mutagenesis. Protein Eng Des Sel. 2004; 17: 787-93.

Antcheva, et al. Proteins of circularly permuted sequence present within the same organism: the major serine proteinase inhibitor from *Capsicum annuum* seeds. Protein Sci. 2001; 10: 2280-90.

Araki, et al. Four disulfide bonds' allocation of Na+, K(+)-ATPase inhibitor (SPAI). Biochemical and biophysical research communications. 1990. 172(1): 42-46. (Abstract Only).

Arap, et al. Steps toward mapping the human vasculature by phage display. Nat Med. 2002; 8: 121-7.

Arnau, et al. Current strategies for the use of affinity tags and tag removal for the purification of recombinant proteins. Protein Expr Purif. 2006; 48(1):1-13.

Arndt, et al. Factors influencing the dimer to monomer transition of an antibody single-chain Fv fragment. Biochemistry. 1998; 37(37):12918-26.

Assadi-Porter, et al. Sweetness determinant sites of brazzein, a small, heat-stable, sweet-tasting protein. Arch Biochem Biophys. 2000; 376:259-265.

Aster, et al. The Folding and Structural Integrity of the first LIN-12 Module of Human Notch1 are Calcium-Dependent. Biochemistry 1999; 38:4736-4742.

Baneyx, et al. Recombinant protein folding and misfolding in *Escherichia coli*. Nat Biotechnol. 2004; 22(11):1399-408.

Baron, et al. From cloning to a commercial realization: human alpha interferon. Crit Rev Biotechnol. 1990; 10(3):179-90.

Barta, et al. Repeats with variations: accelerated evolution of the Pin2 family of proteinase inhibitors. Trends Genet. 2002; 18: 600-3.

Bateman, et al. Granulins: the structure and function of an emerging family of growth factors. J Endocrinol. 1998; 158: 145-151.

Beissinger, et al. How chaperones fold proteins. Biol Chem. 1998; 379(3):245-59.

Belew, et al. Purification of recombinant human granulocyte-macrophage colony-stimulating factor from the inclusion bodies produced by transformed *Escherichia coli* cells. J Chromatogr A. 1994; 679(1):67-83.

Bensch et al. hBD-1: a novel beta-defensin from human plasma. FEBS Lett 1995; 368:331-335.

Berger, et al. Phoenix mutagenesis: one-step reassembly of multiply cleaved plasmids with mixtures of mutant and wild-type fragments. Anal Biochem. 1993; 214: 571-9.

(56) References Cited

OTHER PUBLICATIONS

Beste, et al. Small antibody-like proteins with prescribed ligand specificities derived from the lipocalin fold. Proc Natl Acad Sci USA. 1999; 96: 1898-1903.

Binz, et al. Engineering novel binding proteins from nonimmunoglobulin domains. Nature Biotechnology 2005; 23:1257.

Bird, et al. Single-chain antigen-binding proteins. Science. 1988; 242(4877):423-6.

Bittner, et al. Recombinant human erythropoietin (rhEPO) loaded poly(lactide-co-glycolide) microspheres: influence of the encapsulation technique and polymer purity on microsphere characteristics. Eur J Pharm Biopharm. 1998; 45(3):295-305.

Blanchette, et al. Principles of transmucosal delivery of therapeutic agents, Biomedicine & Pharmacotherapy. 2004; 58:142-152.

Bloch, Jr., et al. H NMR structure of an antifungal gamma-thionin protein SI alpha 1: Similarity to scorpion toxins. Proteins. 1998; 32: 334-49.

Bodenmuller, et al. The Neuropeptide Head Activator Loses Its Biological Acitivity by Dimerization. EMBO J. Aug. 1986; 5(8): 1825-1829.

Boder, et al. Directed evolution of antibody fragments with monovalent femtomolar antigen-binding affinity. Proc Natl Acad Sci U S A. 2000; 97(20):10701-5.

Brooks, et al. Evolution of amino acid frequencies in proteins over deep time: inferred order of introduction of amino acids into the genetic code. Mol Biol Evol. 2002; 19, 1645-1655.

Buchner. Supervising the fold: functional principles of molecular chaperones. FASEB J. 1996; 10(1):10-19.

Calabrese, et al. Crystal Structure of Phenylalanine Ammonia Lyase: Multiple Helix Dipoles Implicated in Catalysis. Biochemistry. 2004; 43: 11403-16.

Calvete, et al. Snake venom disintegrins: Evolution of structure and function. Toxicon. 2005; 45:1063-1074.

Calvete, et al. Snake venom disintegrins: Novel dimeric disintegrins and structural diversification by disulfphide bond engineering. Biochem J. 2003; 372:725-734.

Calvete, et al. Disulphide-bond pattern and molecular modelling of the dimeric disintegrin EMF-10, a potent and selective integrin alpha5beta1 antagonist from Eristocophis macmahoni venom. Biochem J. 2000; 345 Pt 3:573-81.

Cao, et al. Development of a compact anti-BAFF antibody in *Escherichia coli*. Appl Microbiol Biotechnol. 2006; 73(1):151-7.

Carr, et al. Solution structure of a trefoil-motif-containing cell growth factor, porcine spasmolytic protein. PNAS 1994; 91:2206-2210.

Castor, et al. Septic cutaneous lesions caused by*Mycobacterium malmoense* in a patient with hairy cell leukemia. Eur. J. Clin. Microbiol. Infect. Dis. 1994; 13(2):145-148.

Chen, et al. Expression, purification, and in vitro refolding of a humanized single-chain Fv antibody against human CTLA4 (CD152). Protein Expr Purif. 2006; 46(2):495-502.

Chen, et al. Crystal structure of a bovine neurophysin II dipeptide complex at 2.8 A determined from the single-wavelength anomalous scattering signal of an incorporated iodine atom. Proc Natl Acad Sci U S A. 1991; 88: 4240-4.

Chirino, et al. Minimizing the immunogenicity of protein therapeutics. Drug Discovery Today. 2004; 9:82-90.

Chong, et al. Determination of Disulfide Bond Assignments and N-Glycosylation Sites of the Human Gastrointestinal Carcinoma Antigen GA733-2 (CO17-1A, EGP, KS1-4, KSA, and Ep-CAM. J. Biol. Chem. 2001; 276:5804-5813.

Chong, et al. Disulfide Bond Assignments of Secreted Frizzled-related Protein-1 Provide Insights about Frizzled Homology and Netrin Modules. J. Biol. Chem. 2002; 277:5134-5144.

Chou, et al. Prediction of Protein Conformation. Biochemistry. 1974; 13: 222-245.

Chowdhury, et al. Improving antibody affinity by mimicking somatic hypermutation in vitro. Nat Biotechnol. 1999; 17(6):568-72.

Christmann, et al. The cystine knot of a squash-type protease inhibitor as a structural scaffold for *Escherichia coli* cell surface display of conformationally constrained peptides. Protein Eng. 1999; 12:797-806.

Clark, et al. Long-acting growth hormones produced by conjugation with polyethylene glycol. J Biol Chem. 1996; 271(36):21969-77.

Clark, et al. Recombinant human growth hormone (GH)-binding protein enhances the growth-promoting activity of human GH in the rat. Endocrinology. 1996; 137(10):4308-15.

Cleland, et al. Emerging protein delivery methods. Current Opinion in Biotechnology. 2001; 12:212-219.

Coia, et al. Use of mutator cells as a means for increasing production levels of a recombinant antibody directed against Hepatitis B. Gene. 1997; 201: 203-9.

Collen, et al. Polyethylene Glycol—Derivatized Cysteine-Substitution Variants of Recombinant Staphylokinase for Single-Bolus Treatment of Acute Myocardial Infarction. Circulation. 2000; 102: 1766-72.

Conticello, et al. Mechanisms for evolving hypervariability: the case of conopeptides. Mol. Biol. Evol. 2001; 18:120-131.

Corisdeo, et al. Functional expression and display of an antibody Fab fragment in *Escherichia coli*: study of vector designs and culture conditions. Protein Expr Purif. 2004; 34(2):270-9.

Craik, et al. Plant cyclotides: A unique family of cyclic and knotted proteins that defines the cyclic cystine knot structural motif. J Mol Biol. 1999; 294: 1327-1336.

Crameri, et al. Improved Green Fluorescent Protein by Molecular Evolution Using DNA Shuffling. Nature Biotechnology. 1996; 14: 315-319.

Cull, et al. Screening for receptor ligands using large libraries of peptides linked to the C terminus of the lac repressor. Proc. Natl. Acad. Sci. USA. 1992; 89: 1865-1869.

Daley, et al. Structure and dynamics of a beta-helical antifreeze protein. Biochemistry. 2002; 41: 5515-25.

Daniel et al. Screening for potassium channel modulators by a high through-put 86-rubidium efflux assay in a 96-well microtiter plate. J. Pharmacol. Meth. 1991; 25:185-193.

Danner, et al. T7 phage display: a novel genetic selection system for cloning RNA-binding proteins from cDNA libraries. Proc Natl Acad Sci U S A. 2001; 98: 12954-9.

D'Aquino, et al. The magnitude of the backbone conformational entropy change in protein folding. Proteins. 1996; 25: 143-56.

Dattani, et al. An investigation into the lability of the bioactivity of human growth hormone using the ESTA bioassay. Horm Res. 1996; 46(2):64-73.

Dauplais, et al. On the convergent evolution of animal toxins. Conservation of a diad of functional residues in potassium channel-blocking toxins with unrelated structures. J Biol Chem. 1997; 272: 4302-9.

De Kruif, et al. Selection and application of human single chain Fv antibody fragments from a semi-synthetic phage antibody display library with designed CDR3 regions. J Mol Biol. 1995; 248: 97-105.

De, et al. Crystal Structure of a disulfide-linked "trefoil" motif found in a large family of putative growth factors. PNAS 1994; 91:1084-1088.

Deckert, et al. Pharmacokinetics and microdistribution of polyethylene glycol-modified humanized A33 antibody targeting colon cancer xenografts. Int J Cancer. 2000; 87: 382-90.

Der Maur, et al. Direct in vivo screening of intrabody libraries constructed on a highly stable single-chain framework. J Biol Chem. 2002; 277(47):45075-85.

Desplancq, et al. Multimerization behaviour of single chain Fv variants for the tumour-binding antibody B72.3. Protein Eng. 1994; 7(8):1027-33.

Dhalluin, et al. Structural and biophysical characterization of the 40 kDa PEG-interferon-alpha2a and its individual positional isomers. Bioconjug Chem. 2005; 16: 504-17.

Di Lullo, et al. Mapping the ligand-binding sites and disease-associated mutations on the most abundant protein in the human, type I collagen. J Biol Chem. 2002; 277(6):4223-31.

Dietrich, et al.; ABC of oral bioavailability: transporters as gatekeepers in the gut. Gut. 2005; 52:1788-1795.

(56) References Cited

OTHER PUBLICATIONS

Dolezal, et al. ScFv multimers of the anti-neuraminidase antibody NC10: shortening of the linker in single-chain Fv fragment assembled in V(L) to V(H) orientation drives the formation of dimers, trimers, tetramers and higher molecular mass multimers. Protein Eng. 2000; 13(8):565-74.
Dooley, et al. Stabilization of antibody fragments in adverse environments. Biotechnol Appl Biochem. 1998; 28 ( Pt 1):77-83.
Doyle, et al. Crystal structures of a complexed and peptide-free membrane protein-binding domain: molecular basis of peptide recognition by PDZ. Cell. Jun. 28, 1996;85(7):1067-76.
Dufton. Classification of elapid snake neurotoxins and cytotoxins according to chain length: evolutionary implications. J. Mol. Evol. 1984; 20:128-134.
Dumoulin, et al. Single-domain antibody fragments with high conformational stability. Protein Sci. 2002; 11(3):500-15.
Dutton, et al. A New Level of Conotoxin Diversity, a Non-native Disulfide Bond Connectivity in -Conotoxin AuIB Reduces Structural Definition but Increases Biological Activity. J. Biol Chem. 2002; 277: 48849-48857.
Dyson, et al. Production of soluble mammalian proteins in *Escherichia coli*: identification of protein features that correlate with successful expression. BMC Biotechnol. 2004; 4:32.
Fajloun, et al. Maurotoxin Versus Pil/HsTx1 Scorpion Toxins. Toward New Insights in the Understanding of Their Distinct Disulfide Bridge Patterns. J. Biol. Chem. 2000; 275:39394-402.
Felici, et al. Selection of antibody ligands from a large library of oligopeptides expressed on a multivalent exposition vector. J Mol Biol. 1991; 222: 301-310.
Fisher, et al. Genetic selection for protein solubility enabled by the folding quatliy control feature of the twin-arginin translocation pathway. Protein Science. 1996; (online).
Fitzgerald, et al. Interchangeability of *Caenorhabditis elegans* DSL proteins and intrinsic signalling activity of their extracellular domains in vivo Development. 1995; 121:4275-82.
Franz, et al. Percutaneous absorption on the relevance of in vitro data. J Invest Dermatol. 1975; 64(3):190-5.
Frenal, et al. Exploring structural features of the interaction between the scorpion toxinCnErg1 and ERG K+ channels. Proteins. 2004; 56: 367-375.
Gamez, et al. Development of pegylated forms of recombinant *Rhodosporidium toruloides* phenylalanine ammonia-lyase for the treatment of classical phenylketonuria. Mol Ther. 2005; 11: 986-9.
Gilkes, et al. Domains in microbial beta-1, 4-glycanases: sequence conservation, function, and enzyme families. Microbiol Rev. 1991; 55: 303-15.
Graff, et al. Theoretical analysis of antibody targeting of tumor spheroids: importance of dosage for penetration, and affinity for retention. Cancer Res. 2003; 63(6):1288-96.
Gray, et al. Peptide Toxins From Venomous Conus Snails. Annu Rev Biochem 1988; 57:665-700.
Greenwald, et al. Effective drug delivery by PEGylated drug conjugates. Adv Drug Deliv Rev. 2003; 55: 217-50.
Guncar, et al. Crystal structure of MHC class II-associated p41 Ii fragment bound to cathepsin L reveals the structural basis for differentiation between cathepsins L and S EMBO J 1999; 18:793-803.
Guo, et al. Crystal Structure of the Cysteine-rich Secretory Protein Stecrisp Reveals That the Cysteine-rich Domain Has a K+ Channel Inhibitor-like Fold. J Biol Chem. 2005; 280: 12405-12.
Gupta, et al. A classification of disulfide patterns and its relationship to protein structure and function. Protein Sci. 2004; 13: 2045-2058.
Gustafsson, et al. Codon bias and heterologous protein expression. Trends Biotechnol. 2004; 22: 346-53.
Hamers-Casterman, et al. Naturally occurring antibodies devoid of light chains. Nature. 1993; 363(6428):446-8.
Hammer. New methods to predict MHC-binding sequences within protein antigens. Curr Opin Immunol 1995; 7: 263-9.
Harris, et al. Effect of pegylation on pharmaceuticals. Nat Rev Drug Discov. 2003; 2: 214-21.

Henninghausen, et al. Mouse whey acidic protein is a novel member of the family of 'four-disulfide core' proteins. Nucleic Acids Res. 1982; 10:2677-2684.
Hermeling, et al. Structure-immunogenicty relationships of therapeutic proteins. Pharm. Res. 2004; 21: 897-903.
Higgins, et al. Polyclonal and clonal analysis of human CD4+ T-lymphocyte responses to nut extracts. J. Immunol. 1995; 155:5777-85.
Hill, et al. Conotoxin TVIIA, a novel peptide from the venom of *Conus tulipa* 1. Isolation, characterization and chemical synthesis. Eur J Biochem. 2000; 267: 4642-8.
Hinds, et al. PEGylated insulin in PLGA microparticles. In vivo and in vitro analysis. J Control Release. Jun. 2, 2005;104(3):447-60.
Hirel, et al. Extent of N-terminal methionine excision from *Escherichia coli* proteins is governed by the side-chain length of the penultimate amino acid. Proc Natl Acad Sci U S A. 1989; 86(21):8247-51.
Hogg. Dislfide Bonds as Switches for Protein Function. Trends Biochem Sci, 2003; 28: 210-4.
Holevinsky, et al. ATP-sensitive K+ channel opener acts as a potent Cl- channel inhibitor in vascular smooth muscle cells. J. Membrane Biology. 1994; 137:59-70.
Hopp, et al. Prediction of protein antigenic determinants from amino acid sequences. Proc Natl Acad Sci U S A 1981; 78:3824-3828.
Hsu, et al. Vaccination against gonadotropin-releasing hormone (GnRH) using toxin receptor-binding domain-conjugated GnRH repeats. Cancer Res. 2000; 60(14):3701-5.
Hudson, et al. High avidity scFv multimers; diabodies and triabodies. J Immunol Methods. 1999; 231(1-2):177-89.
Hugli. Structure and function of C3a anaphylatoxin. Curr Topics Microbiol Immunol. 1990; 153:181-208.
Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.
Iwasaki, et al. Solution structure of midkine, a new heparin-binding growth factor. Embo J. 1997; 16: 6936-6946.
Jackson, et al. al. The characterization of paclitaxel-loaded microspheres manufactured from blends of poly(lactic-co-glycolic acid) (PLGA) and low molecular weight diblock copolymers. Int J Pharm. Sep. 5, 2007;342(1-2):6-17.
Johansson, et al. Modifications increasing the efficacy of recombinant vaccines; marked increase in antibody titers with moderately repetitive variants of a therapeutic allergy vaccine. Vaccine. 2007; 25(9):1676-82.
Jonassen, et al. Finding flexible patterns in unaligned protein sequences. Protein Sci 1995; 4:1587-1595.
Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.
Jones, et al. Replacing the complementarity-determining regions in a human antibody with those from a mouse. Nature. 1986; 321(6069):522-5.
Jonsson, et al. Quantitative sequence-activity models (QSAM)—tools for sequence design. Nucleic Acids Res. 1993; 21: 733-9.
Jung, et al. Improving in vivo folding and stability of a single-chain Fv antibody fragment by loop grafting. Protein Eng. 1997; 10(8):959-66.
Kamikubo, et al. Disulfide bonding arrangements in active forms of the somatomedin B domain of human vitronectin. Biochemistry. 2004; 43: 6519-6534.
Kaufman. Current Protocols in Molecular Biology 16.12. Frederick M. Ausubel, et al., eds. Wiley. 1991.
Kay, et al. An M13 phage library displaying random 38-amino-acid peptides as a source of novel sequences with affinity to selected targets. Gene. 1993; 128: 59-65.
Kelly, et al. Isolation of a Colon Tumor Specific Binding Peptide Using Phage Display Selection Neoplasia, 2003; 5: 437-44.
Khan, et al. Solubilization of recombinant ovine growth hormone with retention of native-like secondary structure and its refolding from the inclusion bodies of *Escherichia coli*. Biotechnol Prog. 1998; 14(5):722-8.

(56) References Cited

OTHER PUBLICATIONS

Kim, et al. Three-dimensional Solution Structure of the Calcium Channel Antagonist ω-Agatoxin IVA: Consensus Molecular Folding of Calcium Channel Blockers. J. Mol. Biol.1995; 250:659-671.

Kimble, et al. The LIN12/Notch signaling pathway and its regulation. Annu Rev Cell Dev Biol 1997; 13:333-361.

Kissel, et al. ABA-triblock copolymers from biodegradable polyester A-blocks and hydrophilic poly(ethylene oxide) B-blocks as a candidate for in situ forming hydrogel delivery systems for proteins. Adv Drug Deliv Rev. 2002; 54(1):99-134.

Kochendoerfer. Chemical and biological properties of polymer-modified proteins. Expert Opin Biol Ther. 2003; 3: 1253-61.

Koide, et al. The fibronectin type III domain as a scaffold for novel binding proteins. J Mol Biol. 1998; 284: 1141-51.

Kornblatt, et al. Cross-linking of cytochrome oxidase subunits with difluorodinitrobenzene. Can J. Biochem. 1980; 58: 219-224.

Kortt, et al. Single-chain Fv fragments of anti-neuraminidase antibody NC10 containing five- and ten-residue linkers form dimers and with zero-residue linker a trimer. Protein Eng. 1997; 10(4):423-33.

Kou, et al. Preparation and characterization of recombinant protein ScFv(CD11c)-TRP2 for tumor therapy from inclusion bodies in *Escherichia coli*. Protein Expr Purif. 2007; 52(1):131-8.

Kristensen, et al. Proteolytic selection for protein folding using filamentous bacteriophages. Fold Des. 1998; 3: 321-8.

Kubetzko, et al. Protein PEGylation decreases observed target association rates via a dual blocking mechanism. Mol Pharmacol. 2005; 68: 1439-54.

Kwon, et al. Biodegradable triblock copolymer microspheres based on thermosensitive sol-gel transition. Pharm Res. 2004; 21(2):339-43.

Lane, et al. Influence of post-emulsification drying processes on the microencapsulation of human serum albumin. Int J Pharm. 2006; 307(1):16-22.

Lapatto, et al. X-ray structure of antistasin at 1.9 Å resolution and its modelled complex with blood coagulation factor Xa. Embo J. 1997; 16: 5151-61.

Lauber, et al. Homologous Proteins with Different Folds: The Three-dimensional Structures of Domains 1 and 6 of the Multiple Kazal-type Inhibitor LEKTI. J. Mol. Biol. 2003; 328:205-219.

Le Gall, et al. Di-, tri- and tetrameric single chain Fv antibody fragments against human CD19: effect of valency on cell binding. FEBS Lett. 1999; 453(1-2):164-8.

Lee, et al. A recombinant human G-CSF/GM-CSF fusion protein from *E. coli* showing colony stimulating activity on human bone marrow cells. Biotechnol Lett. 2003; 25(3):205-11.

Lee. Mucosal drug delivery. J Natl Cancer Inst Monogr. 2001; 29:41-44.

Leong, et al. Adapting pharmacokinetic properties of a humanized anti-interleukin-8 antibody for therapeutic applications using site-specific pegylation. Cytokine. 2001; 16(3):106-19.

Leong, et al. Optimized expression and specific activity of IL-12 by directed molecular evolution. Proc. Natl. Acad. Sci. USA 2003; 100:1163-1168.

Leung, et al. A method for random mutagenesis of a defined DNA segment using a modified polymerase chain reaction. Technique. 1989; 1: 11-15.

Leung-Hagesteijn, et al. UNC-5, a transmembrane protein with immunoglobulin and thrombospondin type 1 domains, guides cell and pioneer axon migrations in C. elegans. Cell 1992; 71:289-99.

Levitt. A simplified representation of protein conformations for rapid simulation of protein folding. J Mol Biol 1976; 104, 59-107.

Levy, et al. Isolation of trans-acting genes that enhance soluble expression of scFv antibodies in the *E. coli* cytoplasm by lambda phage display. J Immunol Methods. 2007; 321(1-2):164-73.

Lin, et al. Metal-chelating affinity hydrogels for sustained protein release. J Biomed Mater Res A. 2007; 83(4):954-64.

Lirazan, et al. The Spasmodic Peptide Defines a New Conotoxin Superfamily. Biochemistry. 2000; 39: 1583-8.

Liu et al. The Human beta-Defensin-1 and alpha-Defensins Are Encoded by Adjacent Genes: Two Peptide Families with Differing Disulfide Topology Share a Common Ancestry. Genomics. 1997; 43:316-320.

Lowman, et al. Selecting high-affinity binding proteins by monovalent phage display. Biochemistry. 1991; 30: 10832-10838.

MacPherson, et al. Antibodies: a Laboratory Manual, and Animal Cell Culture Cold Spring Harbor Laboratory, Cold Spring Harbor, NY. 1988.

Maggio. Intravail™: highly effective intranasal delivery of peptide and protein drugs Expert Opinion in Drug Delivery 2006; 3: 529-539.

Maggio. A Renaissance in Peptide Therapeutics in Underway. Drug Delivery Reports. 2006; 23-26.

Maillere et al. Role of thiols in the presentation of a snake toxin to murine T cells. J. Immunol. 1993; 150, 5270-5280.

Maillere, et al. Immunogenicity of a disulphide-containing neurotoxin: presentation to T-cells requires a reduction step. Toxicon, 1995; 33(4): 475-482.

Marshall, et al. Enhancing the activity of a beta-helical antifreeze protein by the engineered addition of coils. Biochemistry, 2004; 43: 11637-11646.

Martin, et al. Rational design of a CD4 mimic that inhibits HIV-1 entry and exposes cryptic neutralization epitopes. Nat. Biotechnol. 2003; 21: 71-76.

Martineau, et al. Expression of an antibody fragment at high levels in the bacterial cytoplasm. J Mol Biol. 1998; 280(1):117-27.

McDonald, et al. Significance of blood vessel leakiness in cancer. Cancer Res. 2002; 62: 5381-5.

McNulty, et al. High-resolution NMR structure of the chemically-synthesized melanocortin receptor binding domain AGRP(87-132) of the Agouti-Related Protein. Biochemistry. 2001; 40: 15520-7.

McPherson, et al. eds. The Series Methods in Enzymology (Academic Press, Inc.): PCR 2: a practical approach. 1987.

Meier, et al. Determination of a high-precision NMR structure of the minicollagen cysteine rich domain from Hydra and characterization of its disulfide bond formation. FEBS Lett. 2004; 569: 112-6.

Menez, A. Immunology of snake toxins. In: Snake Toxins. A. L. Harvey (Ed). Pergamon Press, Inc. New York. 1991. (Table of contents only).

Miljanich. Ziconotide: neuronal calcium channel blocker for treating severe chronic pain. Curr. Med. Chem. 2004; 23: 3029.

Misenheimer, et al. Biophysical Characterization of the Signature Domains of Thrombospondin-4 and Thrombospondin-2. J. Biol. Chem. 2005; 280:41229-41235.

Misenheimer, et al. Disulfide Connectivity of Recombinant C-terminal Region of Human Thrombospondin 2 J. Biol. Chem. 2001; 276:45882-7.

Mitraki, et al. Protein Folding Intermediates and Inclusion Body Formation. Bio/Technology. 1989; 7:690-697.

Mogk, et al. Mechanisms of protein folding: molecular chaperones and their application in biotechnology. Chembiochem. Sep. 2, 2002;3(9):807-14.

Mrsny, et al. Bacterial toxins as tools for mucosal vaccination. Drug Discovery Today. 2002; 4:247-258.

Narmoneve, et al. Self-assembling short oligopeptides and the promotion of angiogenesis. Biomaterials. 2005; 26:4837-4846.

Nielsen, et al. Di-/Tri-peptide transporters as drug delivery targets: Regulation of transport under physiological and patho-physiological conditions. Current Drug Targets. 2003; 4:373-388.

Nielsen, et al. Solution Structure of μ-Conotoxin PIIIA, a Preferential Inhibitor of Persistent Tetrodotoxin-sensitive Sodium Channels. J. Biol. Chem 2002; 277: 27247-27255.

Nord, et al. Binding proteins selected from combinatorial libraries of an α-helical bacterial receptor domain. Nat Biotechnol, 1997; 15: 772-777.

O'Connell, et al. Phage versus phagemid libraries for generation of human monoclonal antibodies. J Mol Biol. 2002; 321: 49-56.

Ofir, et al. Versatile protein microarray based on carbohydrate-binding modules. Proteomics. 2005; 5(7):1806-14.

Okten, et al. Myosin VI walks hand-over-hand along actin. Nat Struct Mol Biol. 2004; 11(9):884-7.

(56) References Cited

OTHER PUBLICATIONS

O'Leary, et al. Solution Structure and Dynamics of a Prototypical Chordin-like Cysteine-rich Repeat (von Willebrand Factor Type C Module) from Collagen IIA, J Biol Chem. 2004; 279: 53857-66.

Oslo, ed. Remington's Pharmaceutical Sciences. 16th edition. 1980.

Padiolleau-Lefavre, et al. Expression and detection strategies for an scFv fragment retaining the same high affinity than Fab and whole antibody: Implications for therapeutic use in prion diseases. Mol Immunol. 2007; 44(8):1888-96.

Pallaghy, et al. A common structural motif incorporating a cystine knot and a triple-stranded beta-sheet in toxic and inhibitory polypeptides. Protein Sci 1994; 3:1833-1839.

Pallaghy, et al. Three-dimensional Structure in Solution of the Calcium Channel Blocker ω-Conotoxin. J Mol Biol 1993; 234:405-420.

Pan, et al. Structure and expression of fibulin-2, a novel extracellular matrix protein with multiple EGF-like repeats and consensus motifs for calcium binding . . . J. Cell. Biol. 1993; 123: 1269-127.

Panda. Bioprocessing of therapeutic proteins from the inclusion bodies of *Escherichia coli*. Adv Biochem Eng Biotechnol. 2003; 85:43-93.

Patra, et al. Optimization of inclusion body solubilization and renaturation of recombinant human growth hormone from *Escherichia coli*. Protein Expr Purif. 2000; 18(2):182-92.

Pelegrini, et al. Plant gamma-thionins: novel insights on the mechanism of action of a multi-functional class of defense proteins. Int J Biochem Cell Biol. 2005; 37: 2239-53.

Pepinsky, et al. Improved pharmacokinetic properties of a polyethylene glycol-modified form of interferon-beta-la with preserved in vitro bioactivity. J Pharmacol Exp Ther. 2001; 297: 1059-66.

Petersen, et al. The dual nature of human extracellular superoxide dismutase: one sequence and two structures. Proc. Natl. Acad. Sci. USA 2003; 100:13875-80.

Pimanda, et al. The von Willebrand factor-reducing activity of thrombospondin-1 is located in the calcium-binding/C-terminal sequence and requires a free thiol at position 974. Blood. 2002; 100: 2832-2838.

Pokidysheva, et al. The Structure of the Cys-rich Terminal Domain of Hydra Minicollagen, Which Is Involved in Disulfide Networks of the Nematocyst Wall. J Biol Chem. 2004; 279: 30395-401.

Popkov, et al. Isolation of human prostate cancer cell reactive antibodies using phage display technology. J. Immunol. Methods. 2004; 291:137-151.

Qi, et al. Structural Features and Molecular Evolution of Bowman-Birk Protease Inhibitors and Their Potential Application (283-292). Act Biochim Biophys Sin (Shanghai) 2005; 37: 283-292.

Rao, et al. Molecular and Biotechnological Aspects of Microbial Proteases. Microbiol Mol Biol Rev. 1998; 62(3): 597-635.

Rasmussen, et al. Tumor cell-targeting by phage-displayed peptides. Cancer Gene Ther. 2002; 9: 606-12.

Rawlings, et al. Evolutionary families of peptidase inhibitors. Biochem J. 2004; 378: 705-16.

Rebay, et al. Specific EGF repeats of Notch mediate interactions with Delta and serrate: Implications for notch as a multifunctional receptor. Cell 1991; 67:687-699.

Roberge, et al. Construction and optimization of a CC49-based scFv-beta-lactamase fusion protein for ADEPT. Protein Eng Des Sel. 2006; 19(4):141-5.

Rosa, et al. Influence of the co-encapsulation of different non-ionic surfactants on the properties of PLGA insulin-loaded microspheres. J Control Release. 2000; 69(2):283-95.

Rosenfeld, et al. Biochemical, Biophysical, and Pharmacological Characterization of Bacterially Expressed Human Agouti-Related Protein. Biochemistry. 1998; 37: 16041-52.

Roussel, et al. Complexation of Two Proteic Insect Inhibitors to the Active Site of Chymotrypsin Suggests Decoupled Roles for Binding and Selectivity. J Biol Chem. 2001; 276: 38893-8.

Sahadev, et al. Production of active eukaryotic proteins through bacterial expression systems: a review of the existing biotechnology strategies. Mol Cell Biochem. 2008; 307(1-2):249-64.

Sambrook, et al. Molecular Cloning: A Laboratory Manual, 2nd Edition; Current Protocols in Molecular Biology. 1989.

Scholle, et al. Efficient construction of a large collection of phage-displayed combinatorial peptide libraries. Comb. Chem. & HTP Screening. 2005; 8:545-551.

Schultz-Cherry, et al. The type 1 repeats of thrombospondin 1 activate latent transforming growth factor-beta. J. Biol. Chem. 1994; 269:26783-8.

Schultz-Cherry, et al. Regulation of Transforming Growth Factor-beta Activation by Discrete Sequences of Thrombospondin. J. Biol. Chem. 1995; 270:7304-7310.

Schulz, et al. Potential of NIR-FT-Raman spectroscopy in natural carotenoid analysis. Biopolymers 2005; 80:34-49.

Scopes. Protein Purification: Principles and Practice. Castor, ed. Springer-Verlag. 1994.

Shen, et al. A Type I Peritrophic Matrix Protein from the Malaria Vector Anopheles gambiae Binds to Chitin. Cloning, Expression, and Characterization. J Biol Chem. 1998; 273: 17665-70.

Sidhu, et al. Phage display for selection of novel binding peptides. Methods Enzymol. 2000; 328: 333-63.

Silverman, et al. Multivalent avimer proteins evolved by exon shuffling of a family of human receptor domains. Nat Biotechnol 2005; 23:1556-1561.

Simonet, et al. Structural and functional properties of a novel serine protease inhibiting peptide family in arthropods. Comp Biochem Physiol B Biochem Mol Biol. 2002; 132: 247-55.

Singh, et al. ProPred: Prediction of HLA-DR binding sites. Bioinformatics. 2001; 17: 1236-1237.

Skinner, et al. Purification and characterization of two classes of neurotoxins from the funnel web spider, *Agelenopsis aperta*. J. Biol. Chem. 1989; 264:2150-2155.

Smith, et al. Single-step purification of polypeptides expressed in *Escherichia coli* as fusions with glutathione S-transferase. Gene. 1988; 67(1):31-40.

Smith, et al. Phage Display. Chem Rev. 1997; 97: 391-410.

So, et al. Contribution of conformational stability of hen lysozyme to induction of type 2 T-helper immune responses. Immunology. 2001; 104: 259-268.

Srivastava, et al. Application of self-assembled ultra-thin film coatings to stabilize macromolecule encapsulation in alginate microspheres. J Microencapsul. 2005; 22(4):397-411.

Stamos, et al. Crystal structure of the HGF beta-chain in complex with the Sema domain of the Met receptor. Embo J. 2004; 23: 2325-35.

Steipe, et al. Sequence statistics reliably predict stabilizing mutations in a protein domain. J Mol Biol. 1994; 240(3):188-92.

Stemmer, et al. Single-step assembly of a gene and entire plasmid from large numbers of oligodeoxyribonucleotides. Gene 1995; 164(1):49-53.

Stemmer. Rapid evolution of a protein in vitro by DNA shuffling Nature. 1994; 370: 389-391.

Stickler, et al. Human population-based identification of CD4(+) T-cell peptide epitope determinants. J Immunol Methods. 2003; 281: 95-108.

Stites, et al. Empirical evaluation of the influence of side chains on the conformational entropy of the polypeptide backbone. Proteins. 1995; 22: 132-140.

Stoll, et al. A mechanistic analysis of carrier-mediated oral delivery of protein therapeutics. J Control Release. 2000; 64: 217-28.

Sturniolo, et al. Generation of tissue-specific and promiscuous HLA ligand databases using DNA microarrays and virtual HLA class II matrices. Natural Biotechnol. 1999; 17: 555-561.

Suetake, et al. Production and characterization of recombinant tachycitin, the Cys-rich chitin-binding protein. Protein Eng. 2002; 15: 763-9.

Suetake, et al. Chitin-binding Proteins in Invertebrates and Plants Comprise a Common Chitin-binding Structural Motif. J Biol Chem. 2000; 275: 17929-32.

Summers, et al. Baculovirus structural polypeptides. Virology. 1978; 84(2):390-402.

Takahashi, et al. Solution structure of hanatoxinl, a gating modifier of voltage-dependent K+ channels: common surface features of gating modifier toxins. J Mol Biol, 2000; 297: 771-80.

(56) References Cited

OTHER PUBLICATIONS

Takenobu, et al. Development of p53 protein transduction therapy using membrane-permeable peptides and the application to oral cancer cells. Mol Cancer Ther. 2002; 1: 1043-9.

Tam, et al. A biomimetic strategy in the synthesis and fragmentation of cyclic protein. Protein Sci. 1998; 7:1583.

Tavladoraki, et al. A single-chain antibody fragment is functionally expressed in the cytoplasm of both *Escherichia coli* and transgenic plants. Eur J Biochem. 1999; 262(2):617-24.

Tax, et al. Sequence of C. elegans lag-2 reveals a cell-signalling domain shared with Delta and Serrate of *Drosophila*. Nature 1994; 368: 150-154.

Thai, et al. Antigen stability controls antigen presentation. J. Biol. Chem. 2004; 279: 50257-50266.

Tolkatchev, et al. Design and Solution Structure of a Well-Folded Stack of Two beta-Hairpins Based on the Amino-Terminal Fragment of Human Granulin A. Biochemistry, 2000; 39: 2878-86.

Torres, et al. Solution structure of a defensin-like peptide from platypus venom. Biochem J. 1999; 341 ( Pt 3): 785-794.

Tur, et al. A novel approach for immunization, screening and characterization of selected scFv libraries using membrane fractions of tumor cells. Int J Mol Med. 2003; 11: 523-7.

Valente, et al. Optimization of the primary recovery of human interferon alpha2b from *Escherichia coli* inclusion bodies. Protein Expr Purif. 2006; 45(1):226-34.

Van Den Hooven, et al. Disulfide Bond Structure of the AVR9 Elicitor of the Fungal Tomato Pathogen *Cladosporium fulvum*: Evidence for a Cystine Knot. Biochemistry 2001; 40:3458-3466.

Van Vlijmen, et al. A novel database of disulfide patterns and its application to the discovery of distantly related homologs. J Mol. Biol. 2004; 335:1083-1092.

Vanhercke, et al. Reducing mutational bias in random protein libraries. Anal Biochem. 2005; 339: 9-14.

Vardar, et al. Nuclear Magnetic Resonance Structure of a Prototype Lin12-Notch Repeat Module from Human Notch1 . Biochemistry 2003; 42:7061-7067.

Venkatachalam, et al. Conformation of polypeptide chains. Annu Rev Biochem. 1969; 38: 45-82.

Ventura. Sequence determinants of protein aggregation: tools to increase protein solubility. Microb Cell Fact. 2005; 4(1):11.

Vestergaard-Bogind, et al. Single-file diffusion through the $Ca^{2+}$-activated $K^+$ channel of human red cells. J. Membrane Biol. 1985; 88:67-75.

Voisey, et al. Agouti: from Mouse to Man, from Skin to Fat Pigment Cell Res. 2002; 15: 10-18.

Vranken, et al. A 30 residue fragment of the carp granulin 1 protein folds into a stack of two β hairpins similar to that found in the native protein J Pept Res. 1999; 53: 590-7.

Wang, et al. Structure-function studies of omega-atracotoxin, a potent antagonist of insect voltage-gated calcium channels. Eur J Biochem. 1999; 264: 488-494.

Ward, et al. Binding activities of a repertoire of single immunoglobulin variable domains secreted from *Escherichia coli*. Nature. 1989; 341(6242):544-6.

Watters, et al. An optimized method for cell-based phage display panning. Immunotechnology. 1997; 3: 21-29.

Weiss, et al. A cooperative model for receptor recognition and cell adhesion: evidence from the molecular packing in the 1.6-A crystal structure of the pheromone Er-1 from the ciliated protozoan Euplotes raikovi. Proc Natl Acad Sci U SA 1995; , 92: 10172-6.

Werle, et al. The potential of cystine-knot microproteins as novel pharmacophoric scaffolds in oral peptide drug delivery. J. Drug Targeting 2006; 14:137-146.

Werther, et al. Humanization of an anti-lymphocyte function-associated antigen (LFA)-1 monoclonal antibody and reengineering of the humanized antibody for binding to rhesus LFA-1. J Immunol. 1996; 157(11):4986-95.

Whitlow, et al. Multivalent Fvs: characterization of single-chain Fv oligomers and preparation of a bispecific Fv. Protein Eng. 1994;-7(8):1017-26.

Winter, et al. Humanized antibodies. Trends Pharmacol Sci. May 1993;14(5):139-43.

Wittrup. Protein engineering by cell-surface display. Curr Opin Biotechnol. 2001; 12: 395-9.

Worn, et al. Correlation between in vitro stability and in vivo performance of anti-GCN4 intrabodies as cytoplasmic inhibitors. J Biol Chem. 2000; 275(4):2795-803.

Worn, et al. Stability engineering of antibody single-chain Fv fragments. J Mol Biol. 2001; 305(5):989-1010.

Wrammert, et al. Rapid cloning of high-affinity human monoclonal antibodies against influenza virus. Nature. 2008; 453(7195):667-71.

Xiong, et al. A Novel Adaptation of the Integrin PSI Domain Revealed from Its Crystal Structure. J Biol Chem. 2004; 279: 40252-4.

Xu, et al. Solution Structure of BmP02, a New Potassium Channel Blocker from the Venom of the Chinese Scorpion Buthus martensi Karsch. Biochemistry 2000; 39:13669-13675.

Yamazaki, et al. A possible physiological function and the tertiary structure of a 4-kDa peptide in legumes. Eur J Biochem. 2003; 270: 1269-1276.

Yang, et al. Intestinal Peptide transport systems and oral drug availability. Pharmaceutical Research. 1999; 16: 1331-1343.

Yang, et al. CDR walking mutagenesis for the affinity maturation of a potent human anti-HIV-1 antibody into the picomolar range. J Mol Biol. 1995; 254:392-403.

Yang, et al. Tailoring structure-function and pharmacokinetic properties of single-chain Fv proteins by site-specific PEGylation. Protein Eng. 2003; 16: 761-70.

Yankai, et al. Ten tandem repeats of beta-hCG 109-118 enhance immunogenicity and anti-tumor effects of beta-hCG C-terminal peptide carried by mycobacterial heat-shock protein HSP65. Biochem Biophys Res Commun. 2006; 345(4):1365-71.

Yuan, et al. Solution structure of the transforming growth factor beta-binding protein-like module, a domain associated with matrix fibrils. Embo J. 1997; 16: 6659-66.

Zaveckas, et al. Effect of surface histidine mutations and their number on the partitioning and refolding of recombinant human granulocyte-colony stimulating factor (Cys17Ser) in aqueous two-phase systems containing chelated metal ions. J Chromatogr B Analyt Technol Biomed Life Sci. 2007; 852(1-2):409-19.

Zhu, et al. Molecular cloning and sequencing of two 'short chain' and two 'long chain' K(+) channel-blocking peptides from the Chinese scorpion *Buthus martensii* Karsch. FEBS Lett 1999; 457:509-514.

Ausubel, et al. eds. Current Protocols in Molecular Biology. Wiley. 1987.

Bulaj, et al. Efficient oxidative folding of conotoxins and the radiation of venomous cone snails. Proc Natl Acad Sci U S A. 2003; 100 Suppl 2:14562-8.

Chen, et al. Site-directed mutations in a highly conserved region of *Bacillus thuringiensis* delta-endotoxin affect inhibition of short circuit current across *Bombyx mori* midguts. Proc Natl Acad Sci U S A. 1993; 90(19):9041-5.

Freshney, R.I. Culture of Animal Cells. Second Edition. Alan R. Liss, Inc. 1987.

Gomez-Duarte, et al. Expression of fragment C of tetanus toxin fused to a carboxyl-terminal fragment of diphtheria toxin in *Salmonella typhi* CVD 908 vaccine strain. Vaccine. 1995; 13(16):1596-602.

Harlow, et al. Antibodies: a Laboratory Manual. Cold Spring Harbor Laboratory, Cold Spring Harbor, NY. 1988.
McPherson, et al. eds. PCR 2: a practical approach. Oxford University Press. 1995.
Pi, et al. Analysis of expressed sequence tags from the venom ducts of *Conus striatus*: focusing on the expression profile of conotoxins. Biochimie 2006; 88(2):131-40.
Terpe, K. Overview of tag protein fusions: from molecular and biochemical fundamentals to commercial systems. Appl Microbiol Biotechnol. Jan. 2003;60(5):523-33.
Schulz, et al. Engineering disulfide bonds of the novel human beta-defensins hBD-27 and hBD-28: differences in disulfide formation and biological activity among human beta-defensins. Biopolymers. 2005;80(1):34-49.
International search report dated Oct. 29, 2010 for PCT Application No. US10/37855.

(56) References Cited

OTHER PUBLICATIONS

Ellis, et al. Valid and invalid implementations of GOR secondary structure predictions. Comput Appl Biosci. Jun. 1994;10(3):341-8. (Abstract only).
European search report dated Feb. 4, 2010 for Application No. 6804210.
European search report dated Mar. 26, 2009 for Application No. 7752636.6.
European search report dated Mar. 5, 2009 for Application No. 7752549.1.
International search report dated Jan. 17, 2008 for PCT Application No. US2006/37713.
International search report dated Dec. 26, 2007 for PCT Application No. US2007/05952.
International search report dated Mar. 16, 2009 for PCT Application No. US2008/09787.
International search report dated Apr. 20, 2010 for PCT Application No. US10/23106.
International search report dated Sep. 26, 2007 for PCT Application No. US2007/05857.
Kohn, et al. Random-coil behavior and the dimensions of chemically unfolded proteins. Proc Natl Acad Sci U S A. Aug. 24, 2004;101(34):12491-6.
Kratzner, et al. Structure of *Ecballium elaterium* trypsin inhibitor II (EETI-II): a rigid molecular scaffold. Acta Crystallogr D Biol Crystallogr. Sep. 2005;61(Pt 9):1255-62.
Murtuza, et al. Transplantation of skeletal myoblasts secreting an IL-1 inhibitor modulates adverse remodeling in infarcted murine myocardium. Proc Natl Acad Sci U S A. Mar. 23, 2004;101(12):4216-21.
Salloum, et al. Anakinra in experimental acute myocardial infarction—does dosage or duration of treatment matter? Cardiovasc Drugs Ther. Apr. 2009;23(2):129-35.
Wentzel, et al. Sequence requirements of the GPNG beta-turn of the *Ecballium elaterium* trypsin inhibitor II explored by combinatorial library screening. J Biol Chem. Jul. 23, 1999;274(30):21037-43.
Weimer, et al. Prolonged in-vivo half-life of factor VIIa by fusion to albumin. Thromb Haemost. Apr. 2008;99(4):659-67. (Abstract only).
Buscaglia, et al. Tandem amino acid repeats from *Trypanosoma cruzi* shed antigens increase the half-life of proteins in blood. Blood. Mar. 15, 1999;93(6):2025-32.
International search report dated Jul. 12, 2011 for PCT Application No. US20/61590.
Uversky, et al. Why are "natively unfolded" proteins unstructured under physiologic conditions? Proteins. Nov. 15, 2000;41(3):415-27.
Walker, et al. Using protein-based motifs to stabilize peptides. J Pept Res. Nov. 2003;62(5):214-26.
Wright, et al. Intrinsically unstructured proteins: re-assessing the protein structure-function paradigm. J Mol Biol. Oct. 22, 1999;293(2):321-31.
Cell Therapeutics Press Reease. Cell Therapeutics Inc.'s Polyglutamate (PG) Technology Highlighted at International Polymer Therapeutics Meeting; Novel Recombinant Technology Extends PG Platform to G-CSF. Jan. 4, 2002. PR Newswire.
Chou, Fasman Analyses of prior art sequences. 1974.
Conference abstracts: Antibodies and Beyond Antibodies. Loews Coronado Bay Resort, Coronado, CA. Jun. 1-2, 2006.
Exhibit 1: Percentage Secondary Structure of Random Sequence URP by Chou-Fasman Analysis. Date unknown.
Extract from USPTO with regard to assignment of U.S. Appl. No. 60/743,410. Assignment Data not available.
Extract from USPTO with regard to assignment of U.S. Appl. No. 60/743,622. Assignment Data not available.
Internet printout for Chou Fasman algorithm, 1974. Available at www.biogem.org/tool/chou-fasman.
Mehvar, et al. Modulation of the pharmacokinetics and pharmacodynamics of proteins by polyethylene glycol conjugation. J Pharm Pharm Sci. Jan.-Apr. 2000;3(1):125-36.
Opposition dated Feb. 13, 2014 by Novo Nordisk against EP Application No. 07752636.6.
Opposition dated Feb. 17, 2014 by XL-Protein GmBH against EP Application No. 07752636.6.
Schellenberger, V. Engineering of Microproteins for Pharmaceutical Applications. PowerPoint Presentation. Date unknown.
Schlapschy, et al. Fusion of a recombinant antibody fragment with a homo-amino-acid polymer; effects on biophysical properties and prolonged plasma half-life. Protein Eng Des Sel. Jun. 2007;20(6):273-84. Epub Jun. 26, 2007.
Tepitope analyses of prior art sequences. Date unknown.
Thomson Pharma. Literature & News Report. Antibodies and Beyond Antibodies. Coronado, CA. Jun. 1-2, 2006.

\* cited by examiner

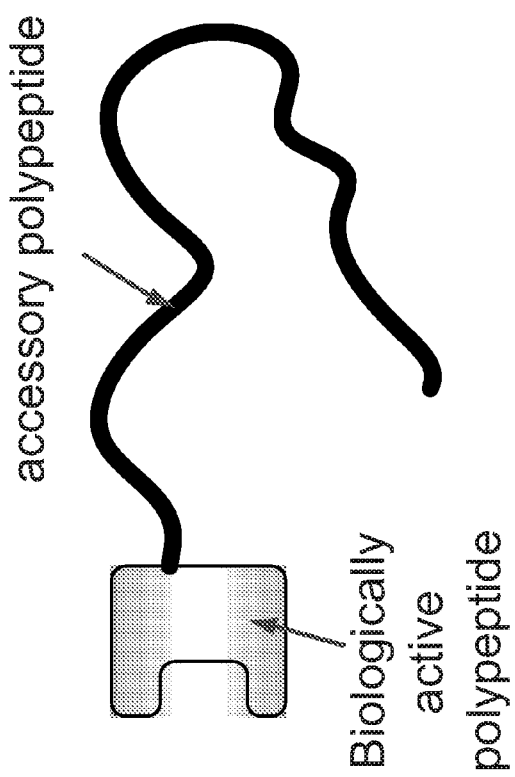
Fig. 1: Modification of polypeptides

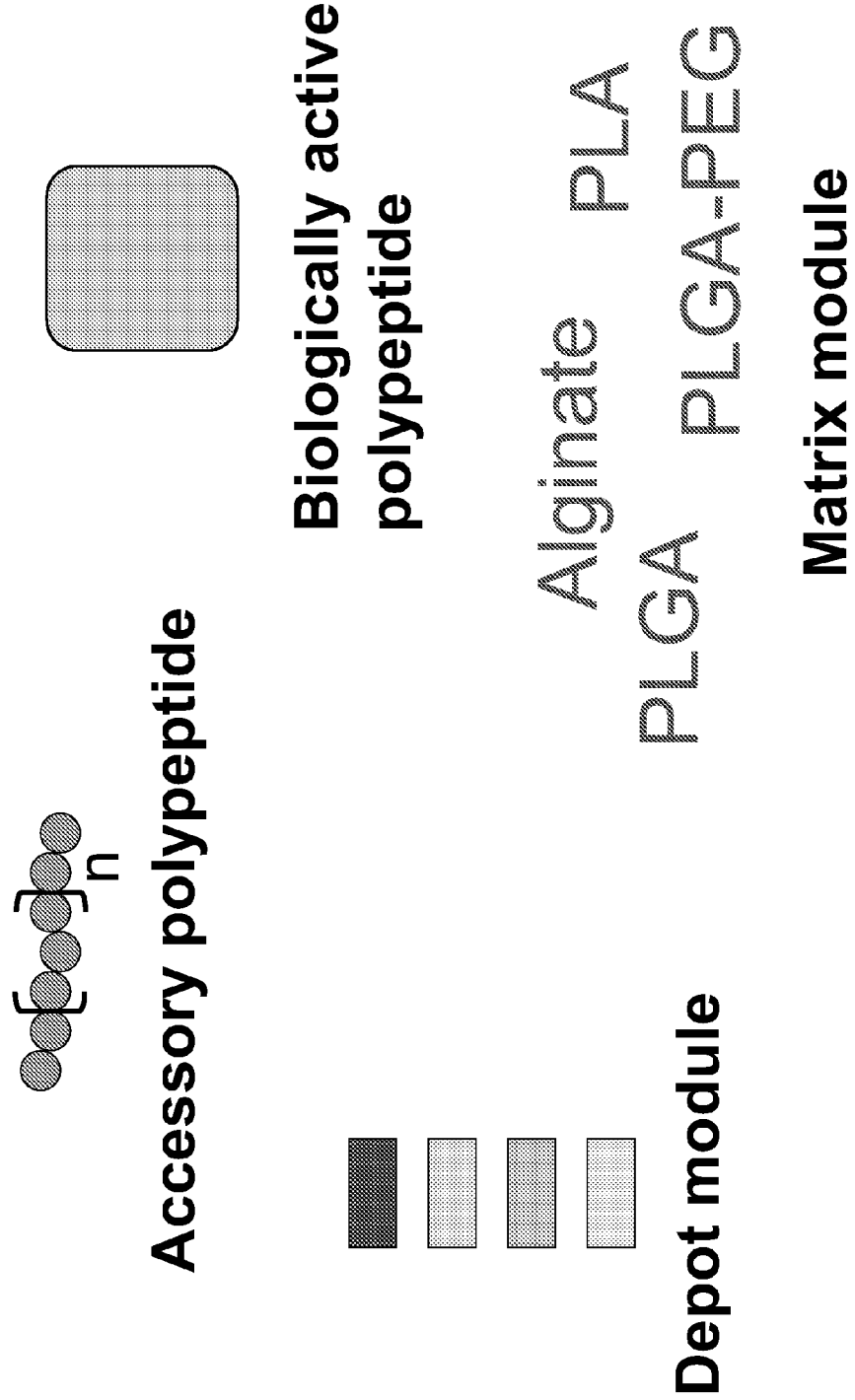

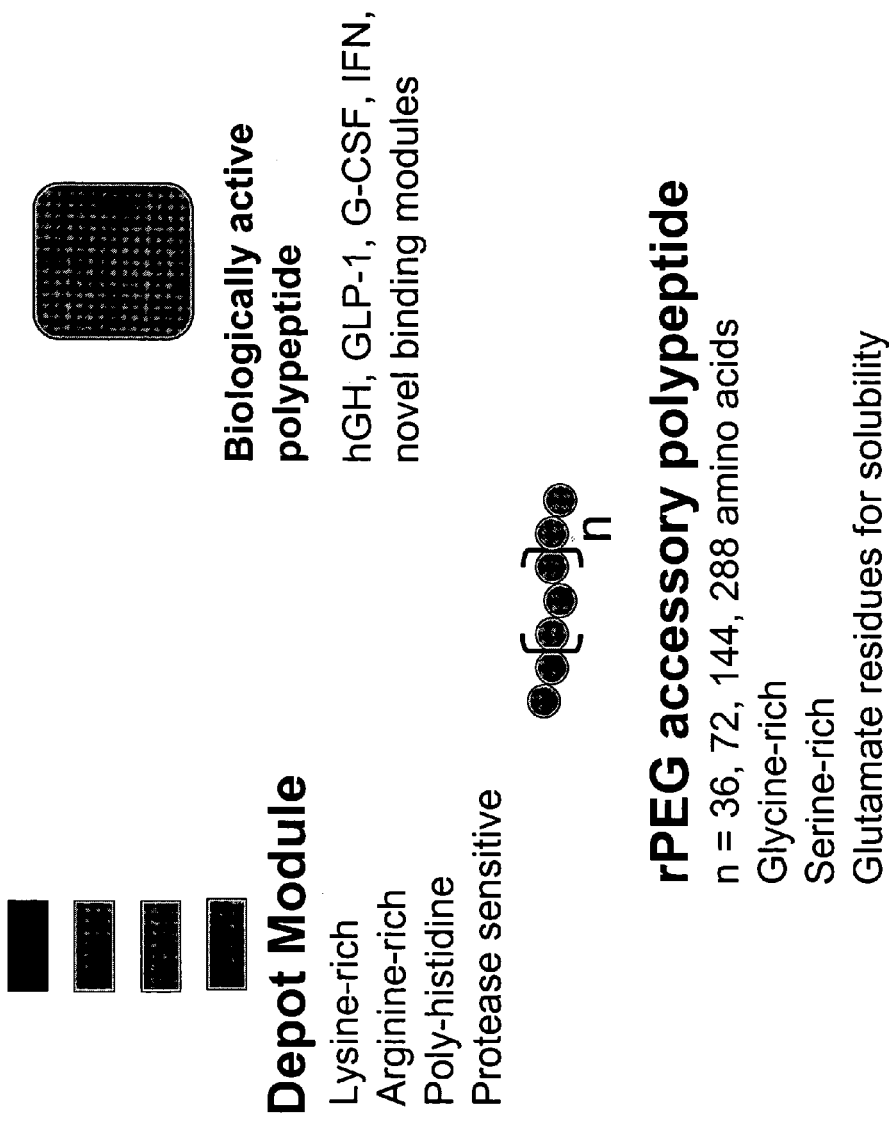

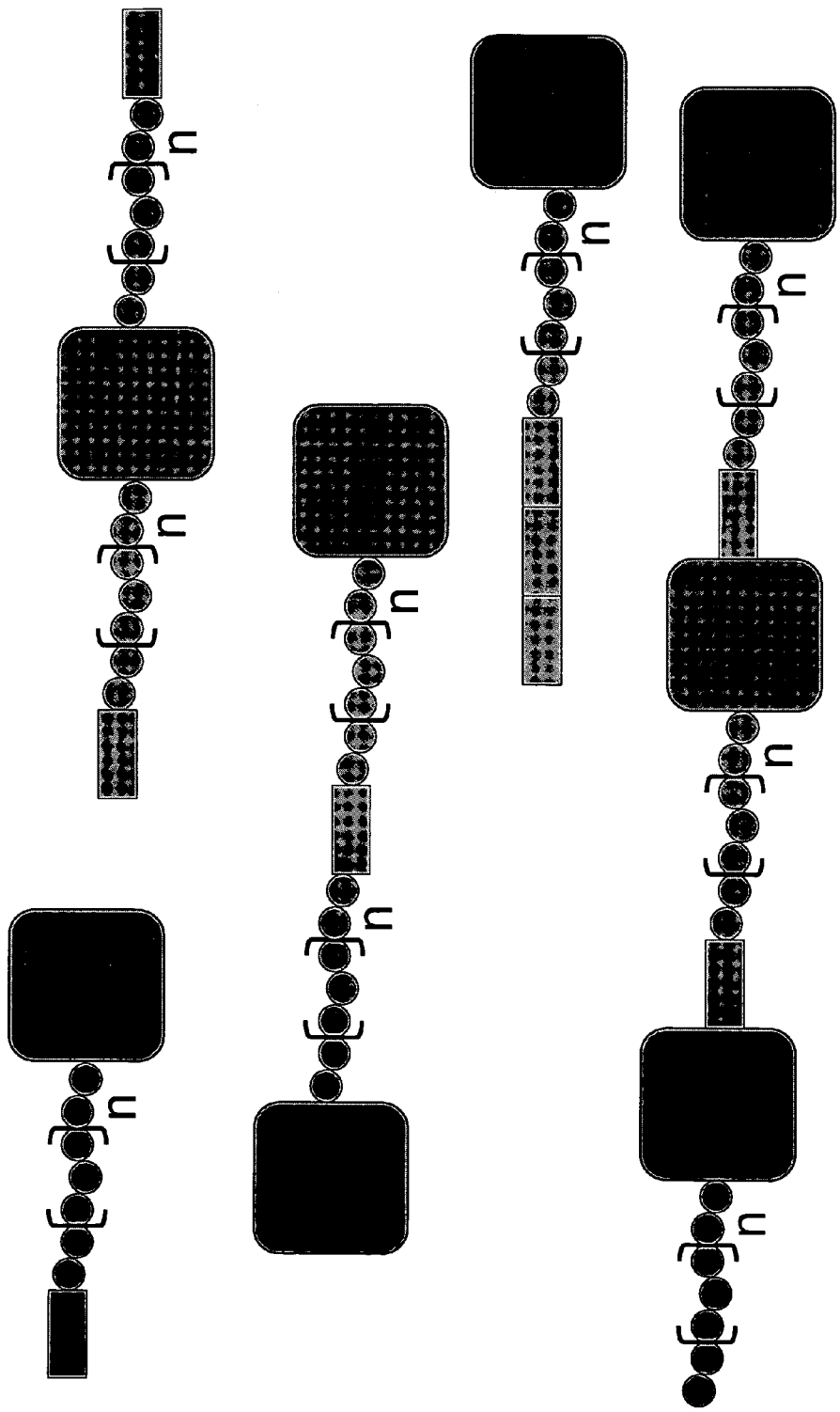
Fig. 4: Examples of modified polypeptides

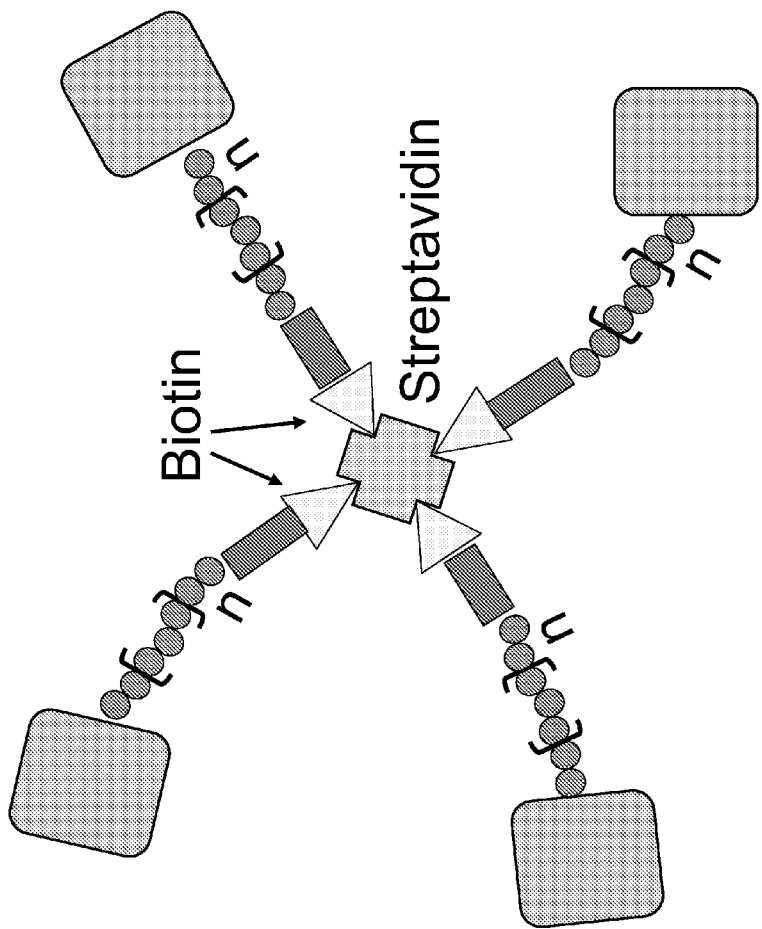
Fig. 5: A modified polypeptide forming tetramers

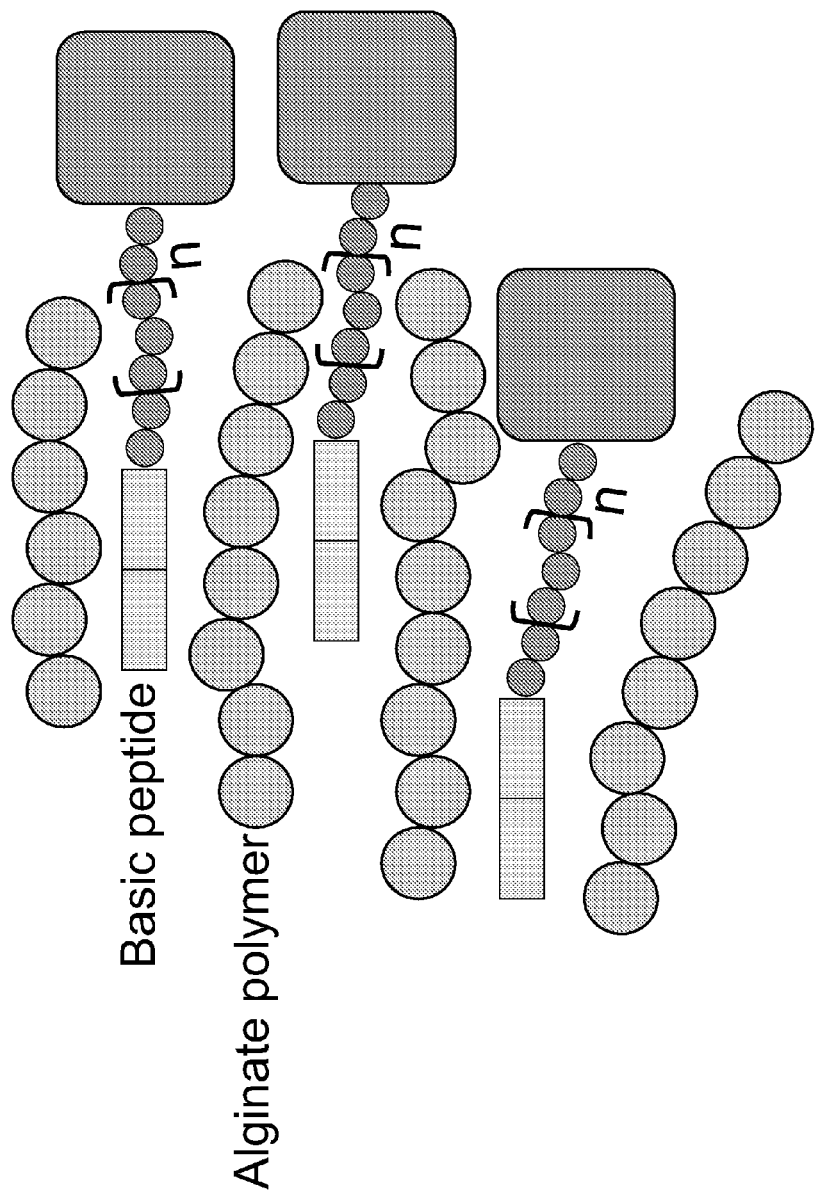
Fig. 6: Incorporation of a modified polypeptide into alginate microspheres

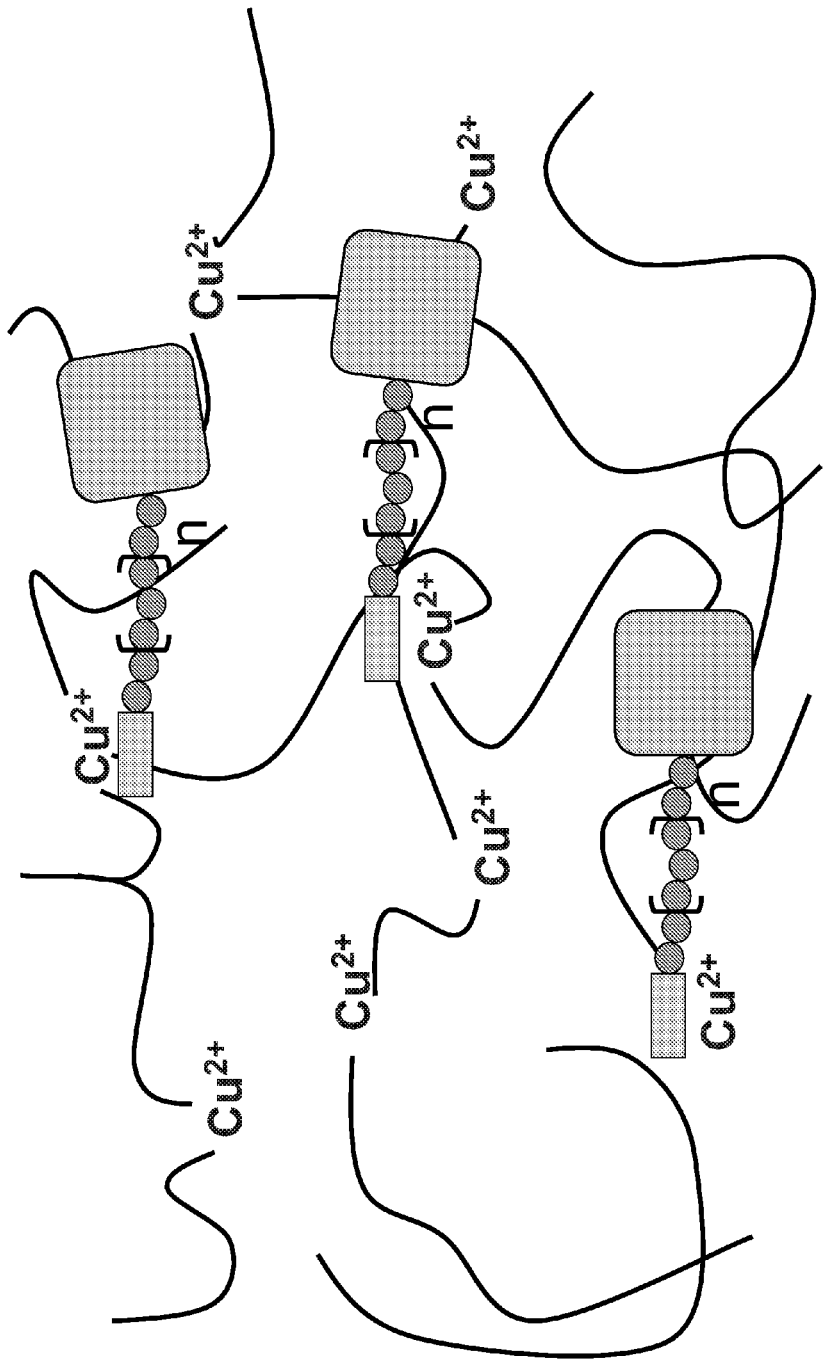
Fig. 7: Poly(His)-rPEG modified polypeptide in a chelating hydrogel

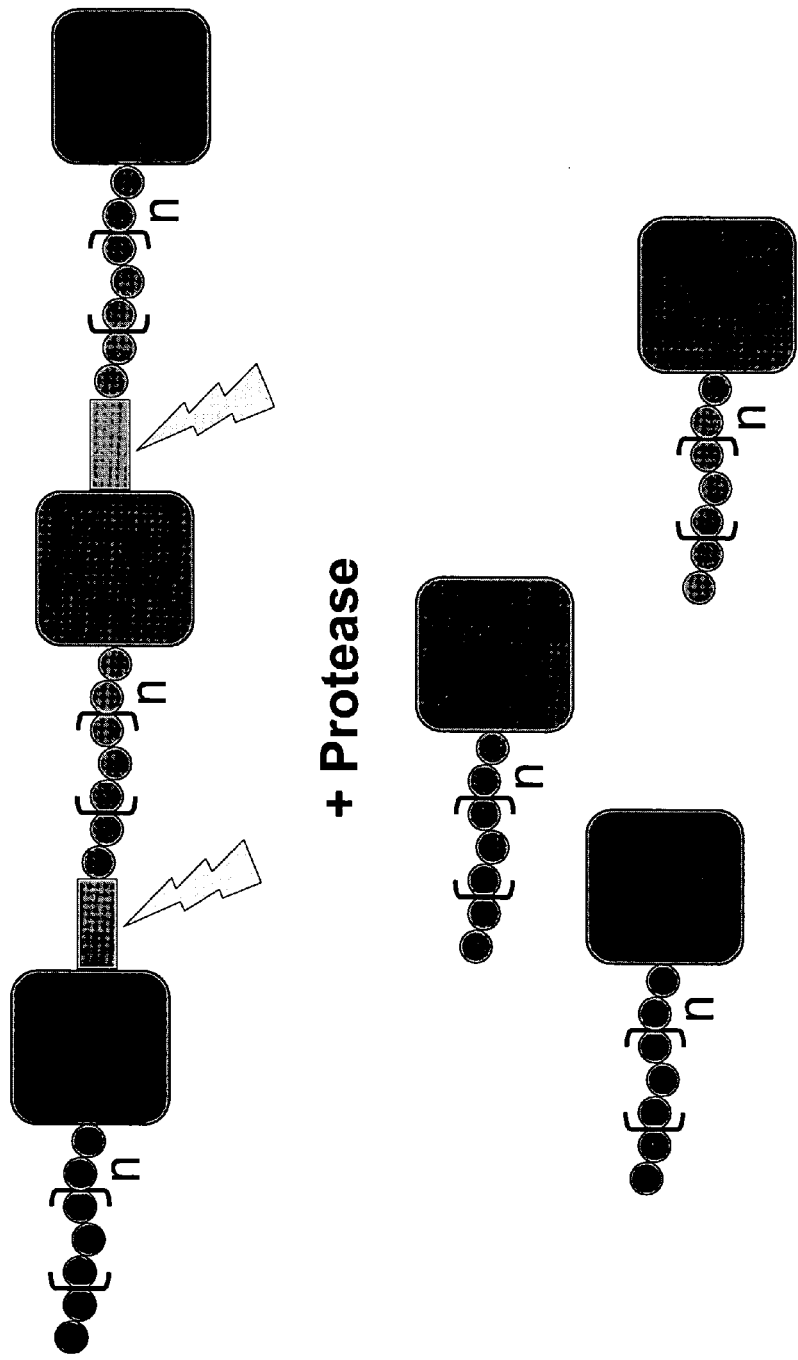
Fig. 8: Protease sensitive multimeric modified polypeptides

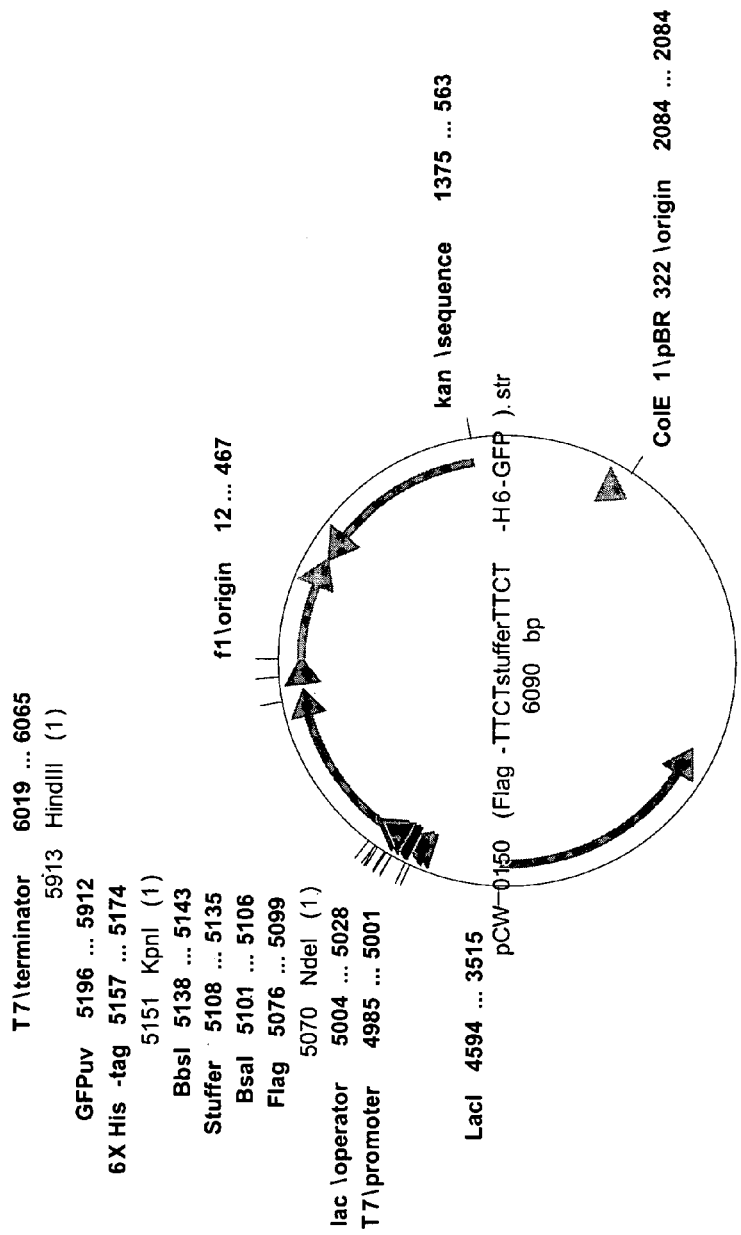
Fig. 9: Schematic of plasmid pCW0150

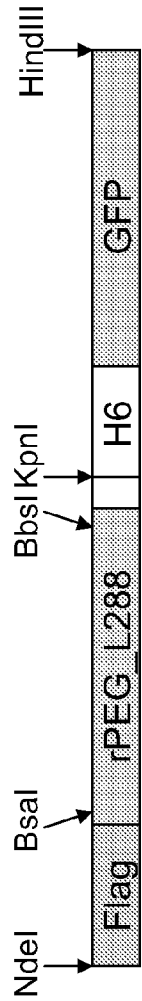
Fig.10: rPEG(L288)-GFP expression construct
Flag-rPEG_L288-H6-GFP
(LCW0169.004)

Fig.11: DNA and amino acid sequence of rPEG(L288)

Fig. 12: hGH-rPEG and GLP-1-rPEG
CBD-GLP1-rPEG_L288
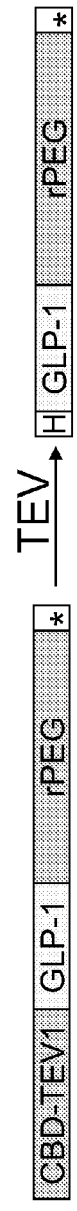
CBD-hGH-rPEG_L288
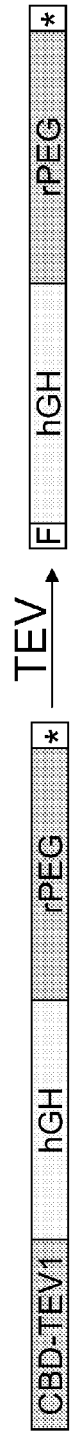

Fig. 13: Examples of sequences of rPEG-modified polypeptides (hGH)-GEGEGEGEGEGEGEGE...

...GEGGGEGEGGEGEGEGGGE-(hIFNa)

(hIFNa)-GGSGGEGGSGEGGSGGEGGS...

(hGCSF)-SESSSESSSESSESSESESE-(hGCSF)

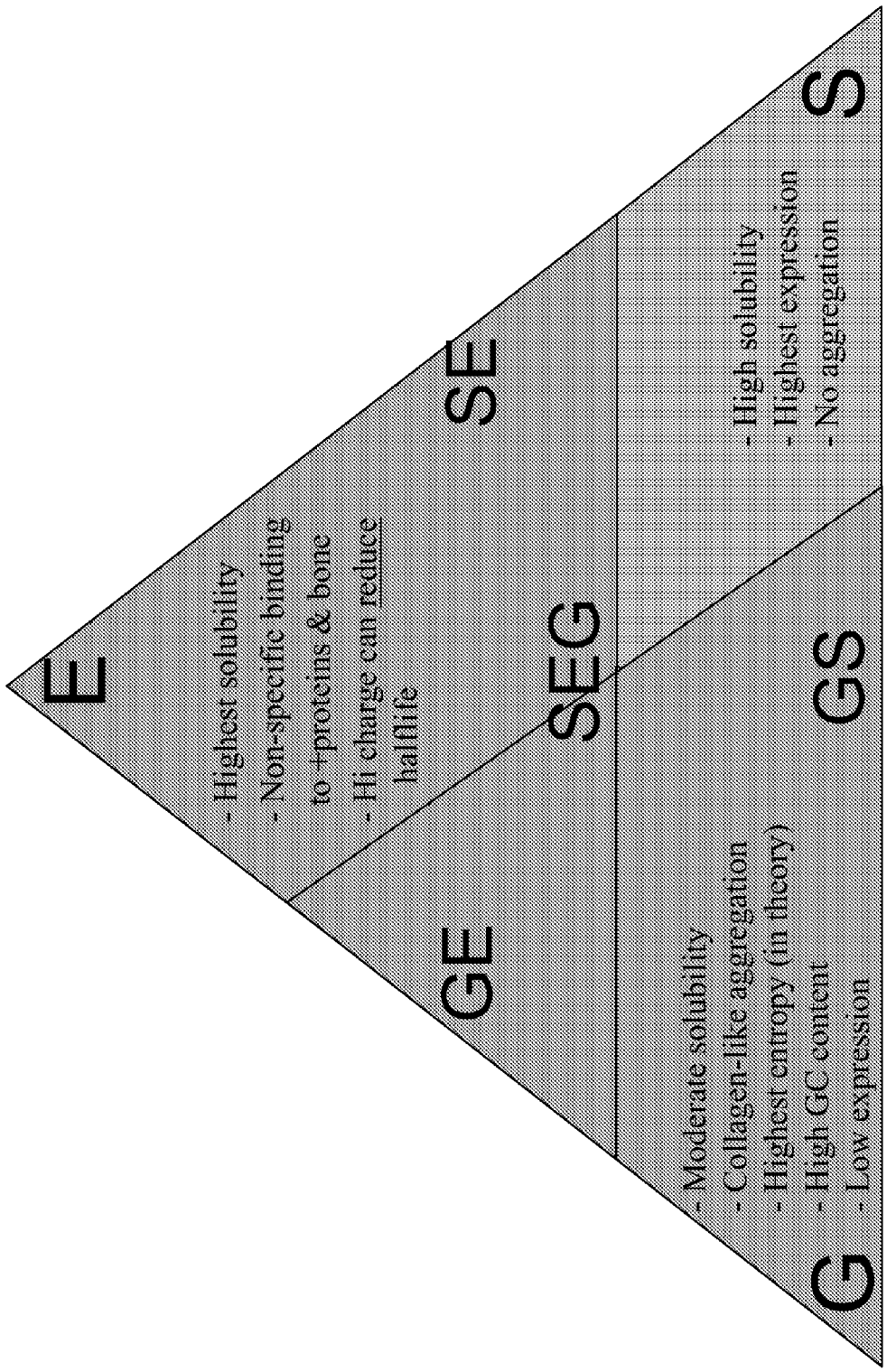
Fig. 14: Sequence Optimization Trends

Fig.15: Sequence Optimization Trends

- Gly-based

- Poly-G   G/G/G/G/G/G/G/G/G/                   0% charged      low solubility
  - rPEG H   GGSGGSGGGSGGE/GGSGGSGGSGGE/          8% charged      moderate solubility
  - rPEG J   GGSGGE/GGSGGE/GGSGGE/GGSGGE          16% charged     high solubility pH>7
  - rPEG K   GEGGGEGGE/GEGGGEGGE/GEGGGE           33% charged     high solubility
  - rPEG M   GE/GE/GE/GE/GE/GE/GE/GE/GE           50% charged     non-specific binding
  - Poly-E   E/E/E/E/E/E/E/E/E/E/E/E/             100% charged    non-specific binding

- Ser-based

- rPEG O   SSSSSE/SSSSSE/SSSSSE/SSSS            16% charged     soluble, hi-expressed
  - rPEG L   SSSESSESSSSE/SSSESSESSSSE/           25% charged     soluble, hi-expressed
  - rPEG N   SSSSSESSSSESSSSSSE/                  33% charged     soluble, hi-expressed

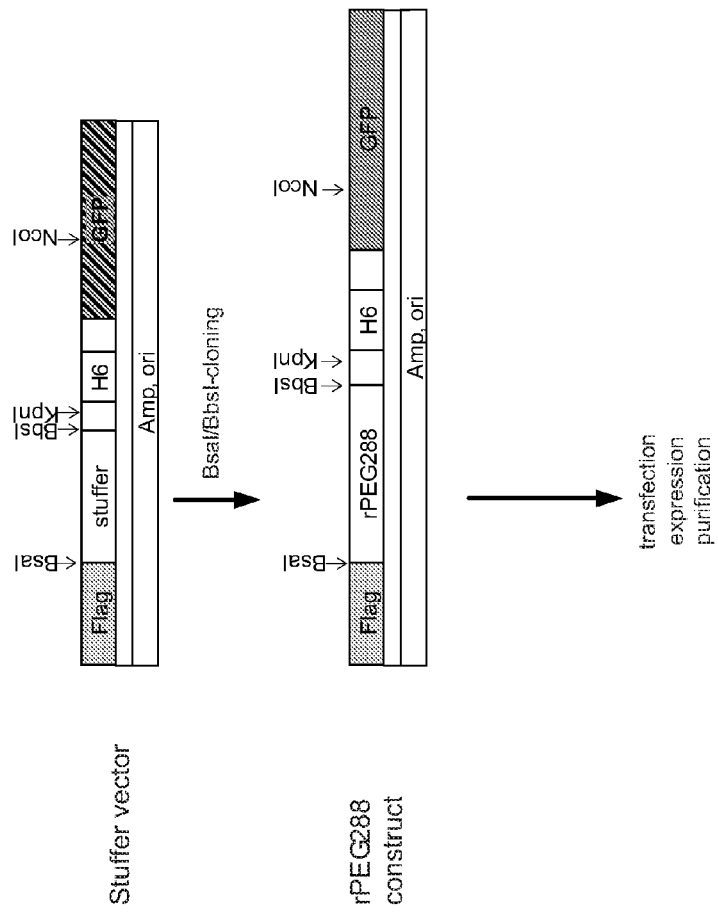
Fig. 16: Construction of rPEG_J288 construct

Fig. 17: Sequence of rPEG_J288 accessory polypeptide

```
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
G   G   S   G   G   E   G   G   S   G   G   E   G   G   S   G   G   E
GGTGGTTCTGGTGGTGAAGGTGGTTCTGGTGGTGAAGGTGGTTCTGGTGGTGAA
```

Fig.18: Design of the pCW0051 stuffer vector

```
         Flag                    BsaI                                                            BbsI
M  D  Y  K  D  D  D  D  K  G  S  P  G  *  *  P  R  *  *  G  G  S  S  L  E
ATGGATTATAAAGACGATGACGATAAAGGGTCTCCAGGTTAGTAACCTAGTTGATAGGAGTTCGTCTTCACTCGAG KpnI       6x His-tag
G  T  H  H  H  H  H  H  E  L  V  P  V  E  K  M
GGTACCCATCACCATCACCATCACGAGCTCGTACCGGTAGAAAAATG
```

Recognition sequences of the restriction sites are underlined. The overhangs that will be generated by BsaI and BbsI digest are shown in italics. The figure illustrates that BsaI and BbsI digest of pCW0051 generates compatible overhangs.

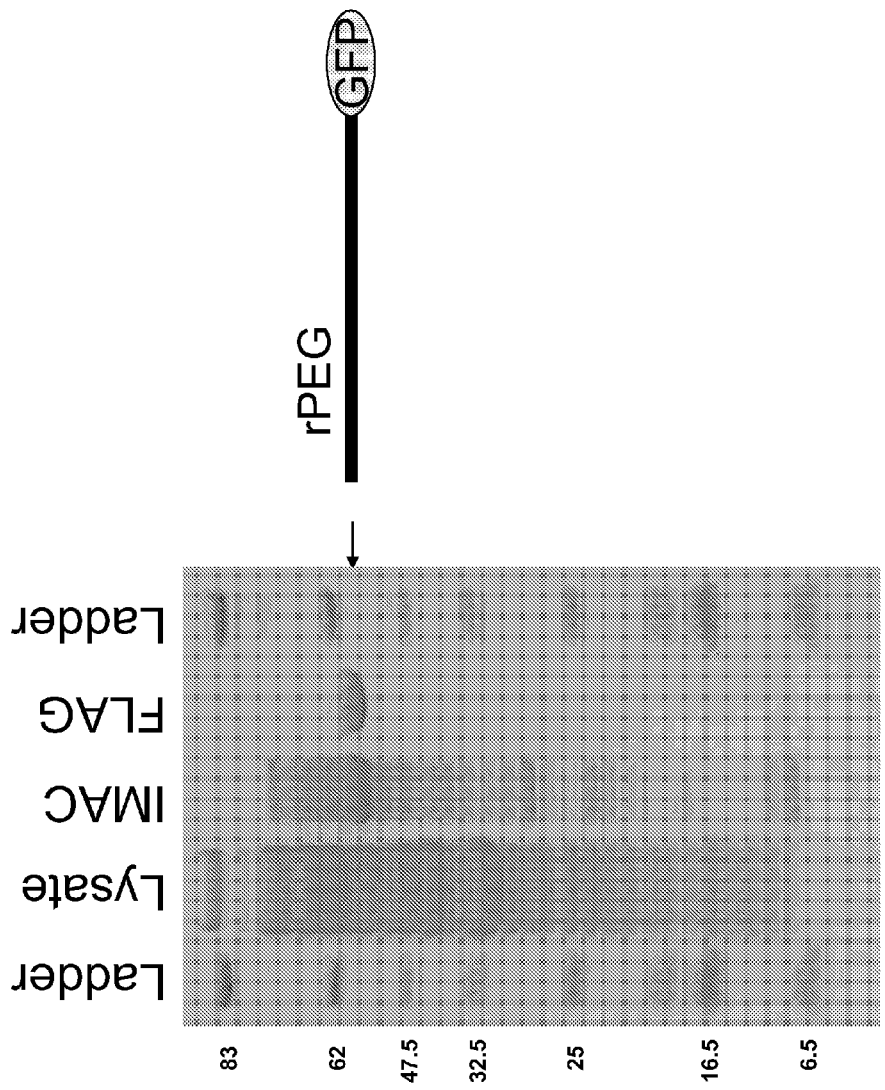
Fig. 19: Purification of Flag-rPEG_J288-H6-GFP

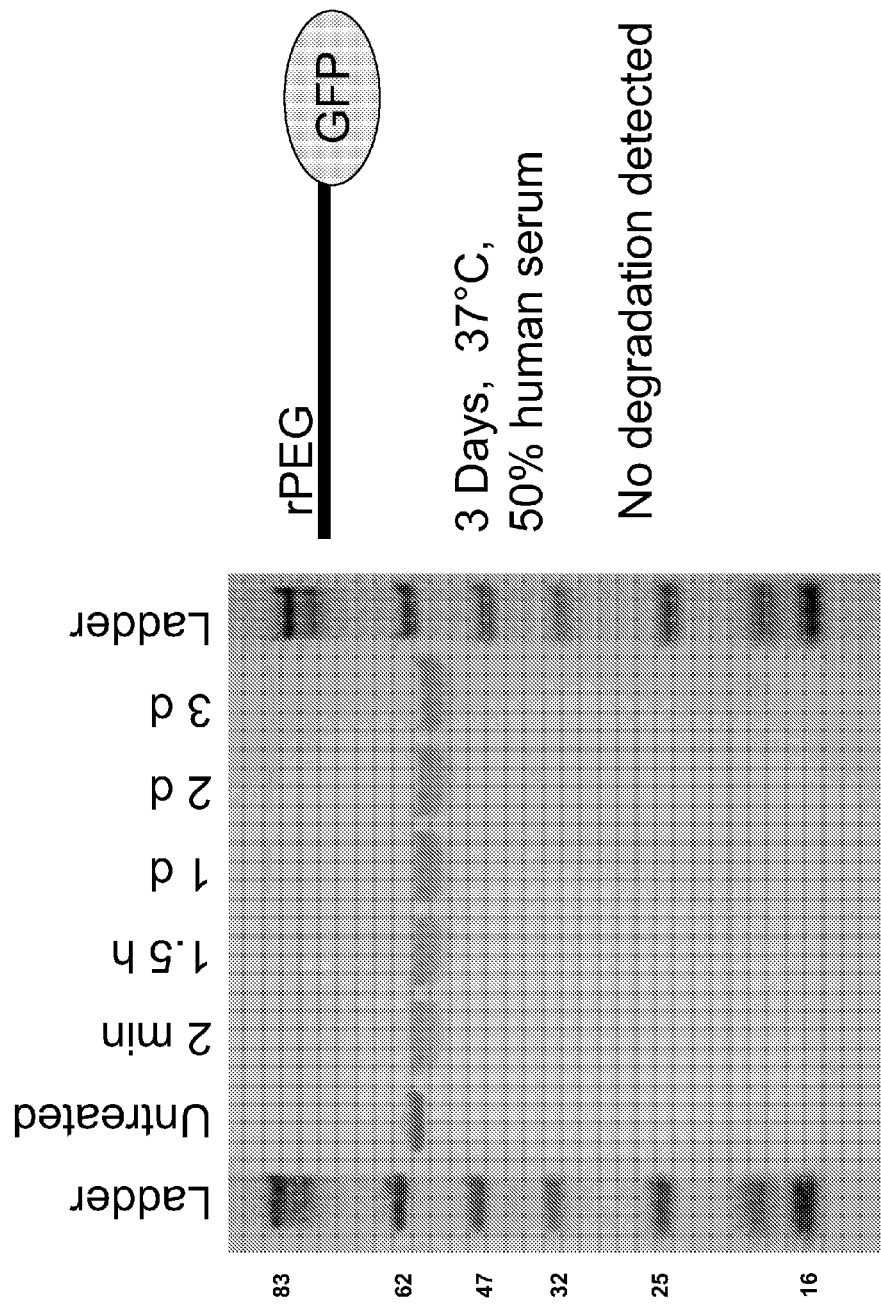
Fig. 20: Serum stability of rPEG_J288-modified GFP

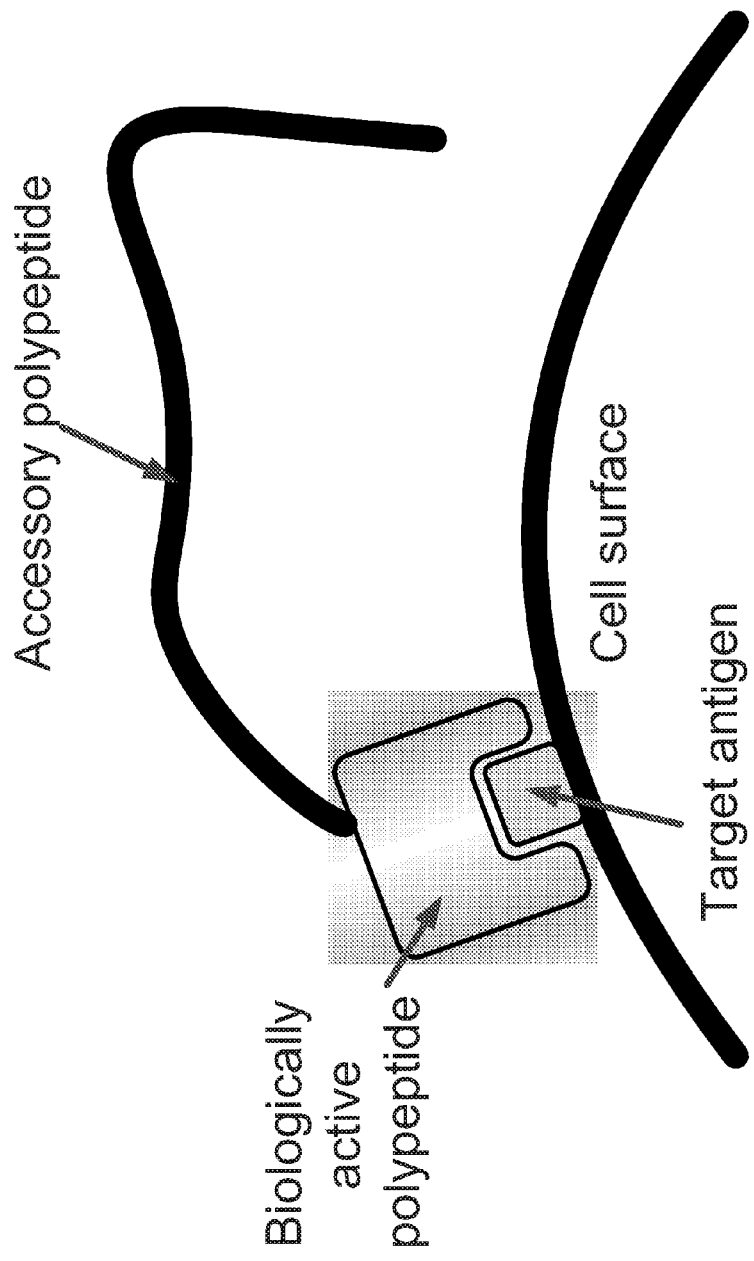
Fig. 21: Interaction of an accessory-modified polypeptide with a cellular target

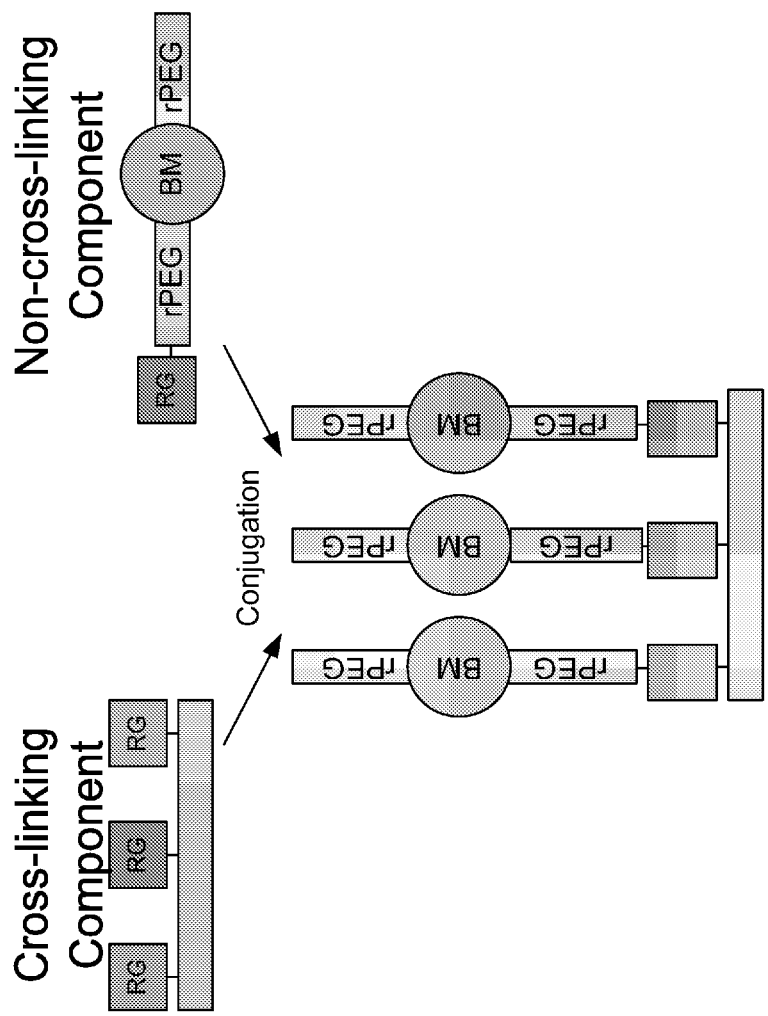
Fig. 22: Crosslinked accessory polypeptides

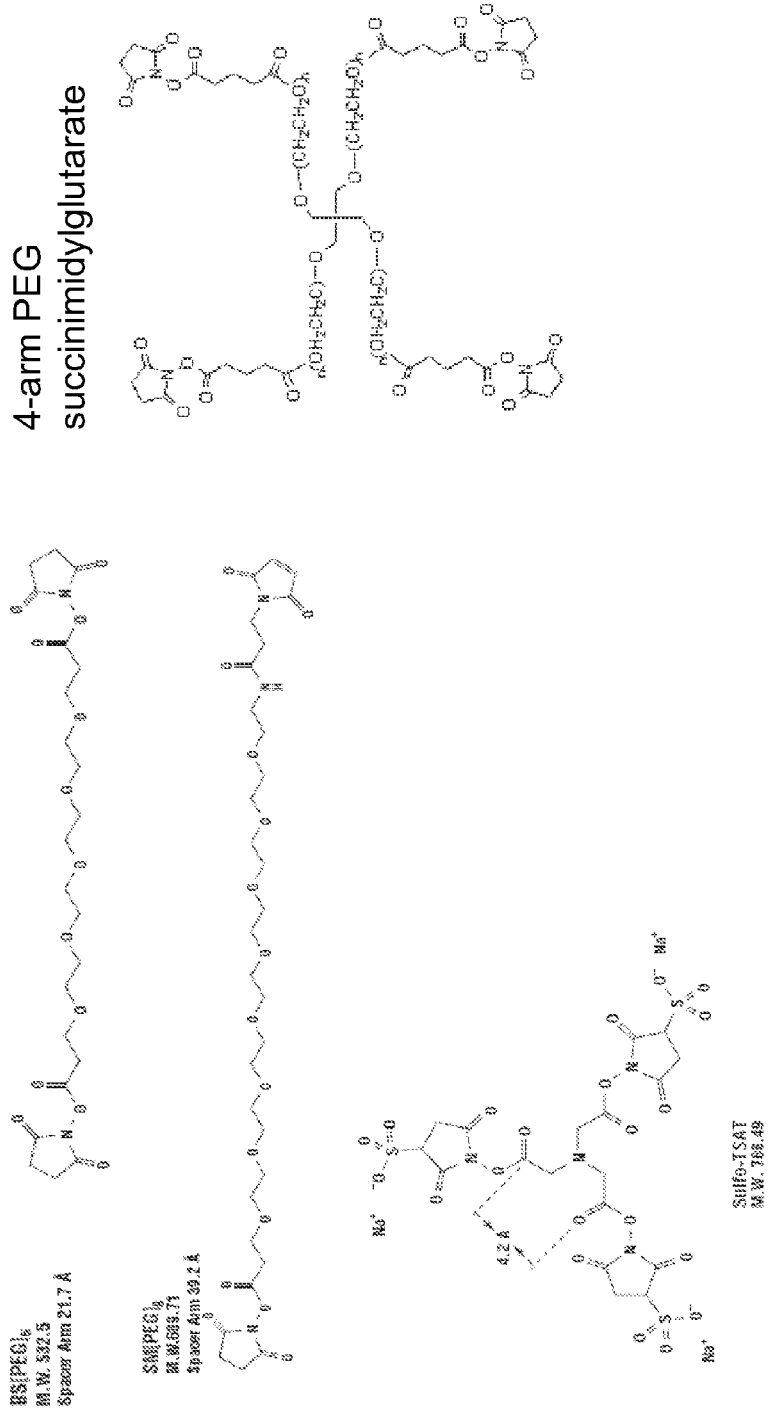
Fig. 23: Examples of Cross-linking components

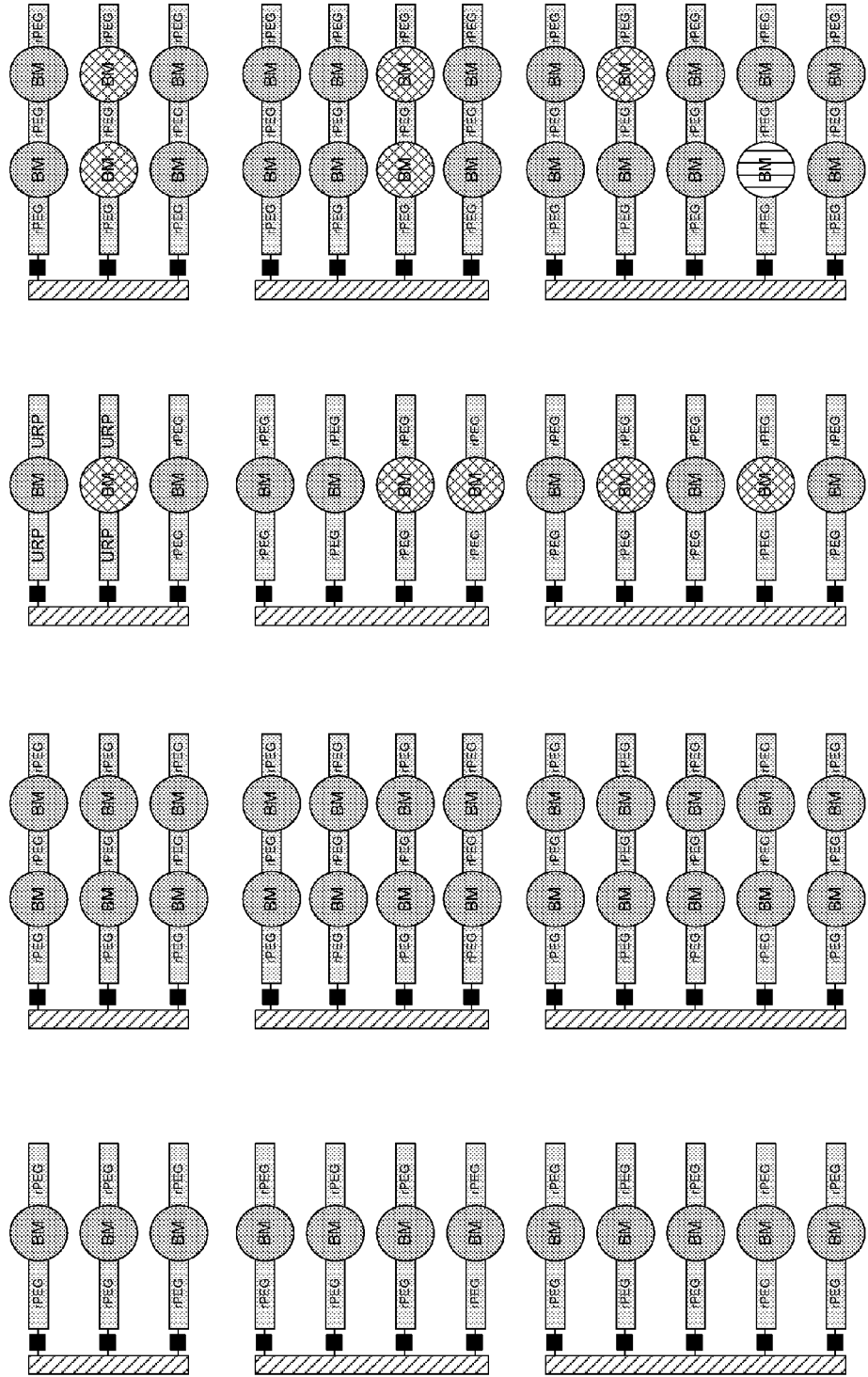
Fig. 24: Examples of crosslinked accessory polypeptides

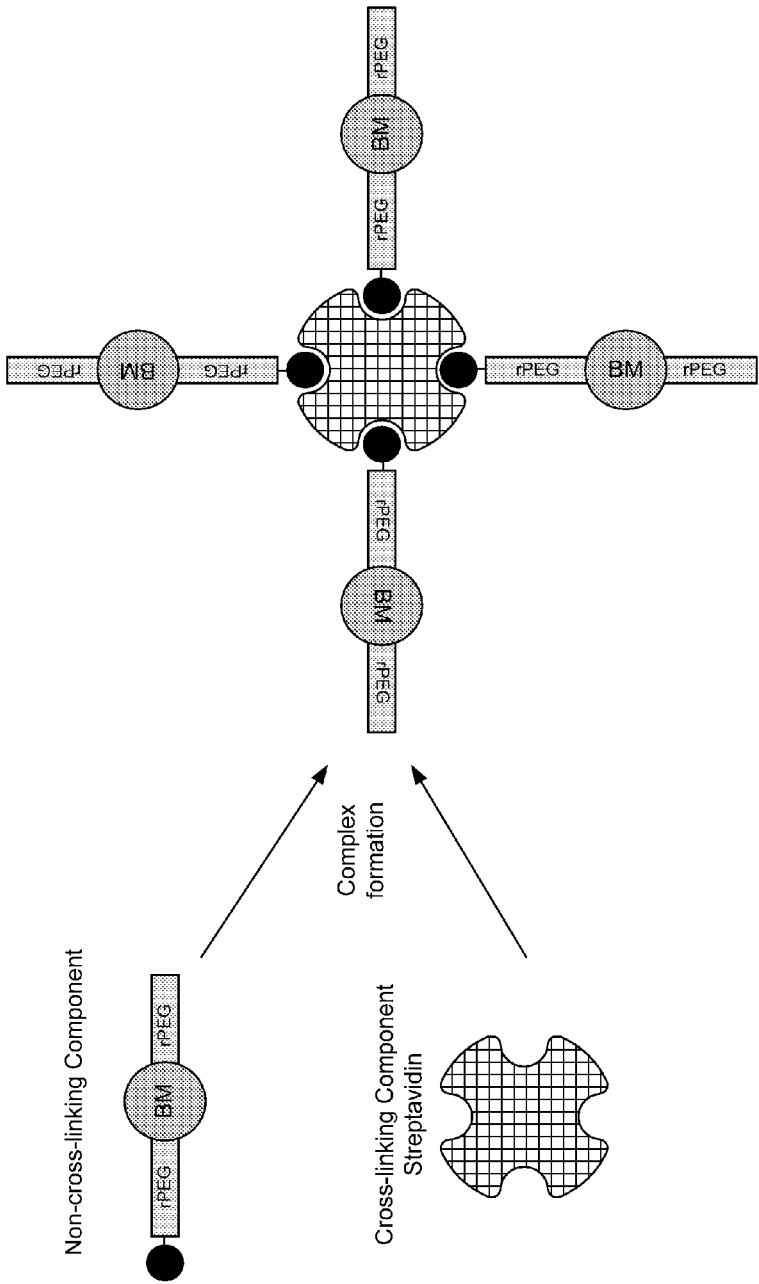

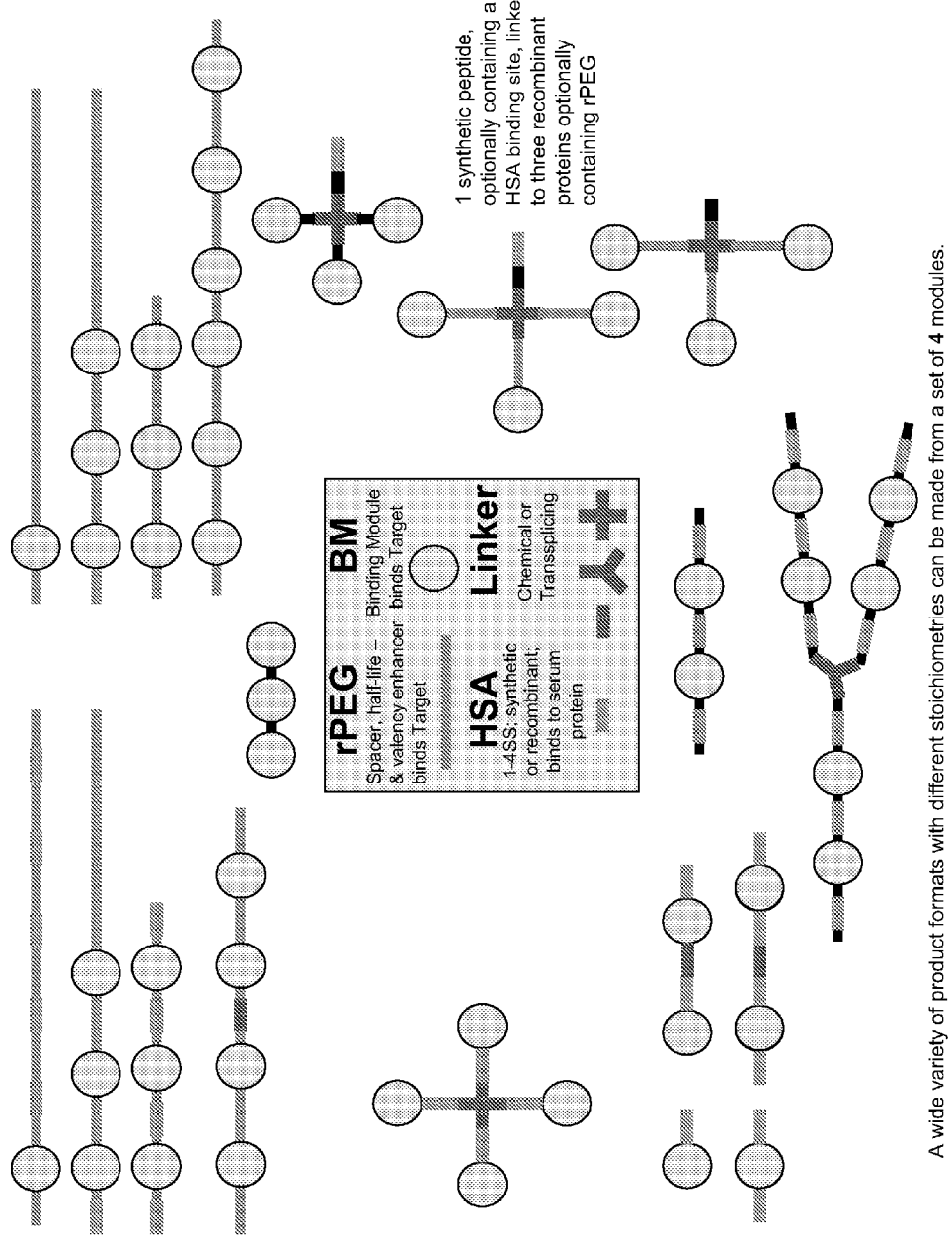
Fig. 26: Examples of combinations of 1-4 Product Modules

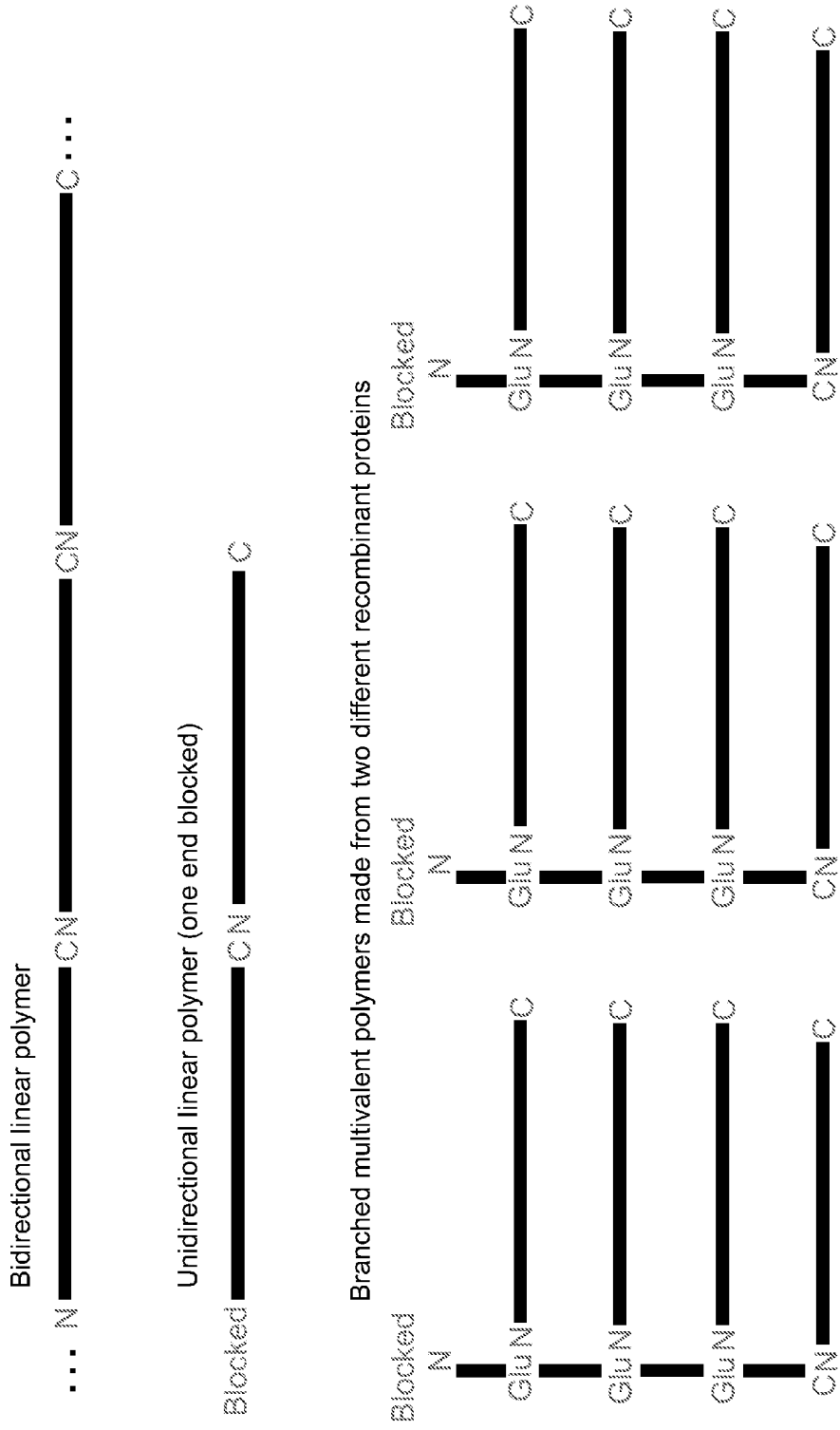

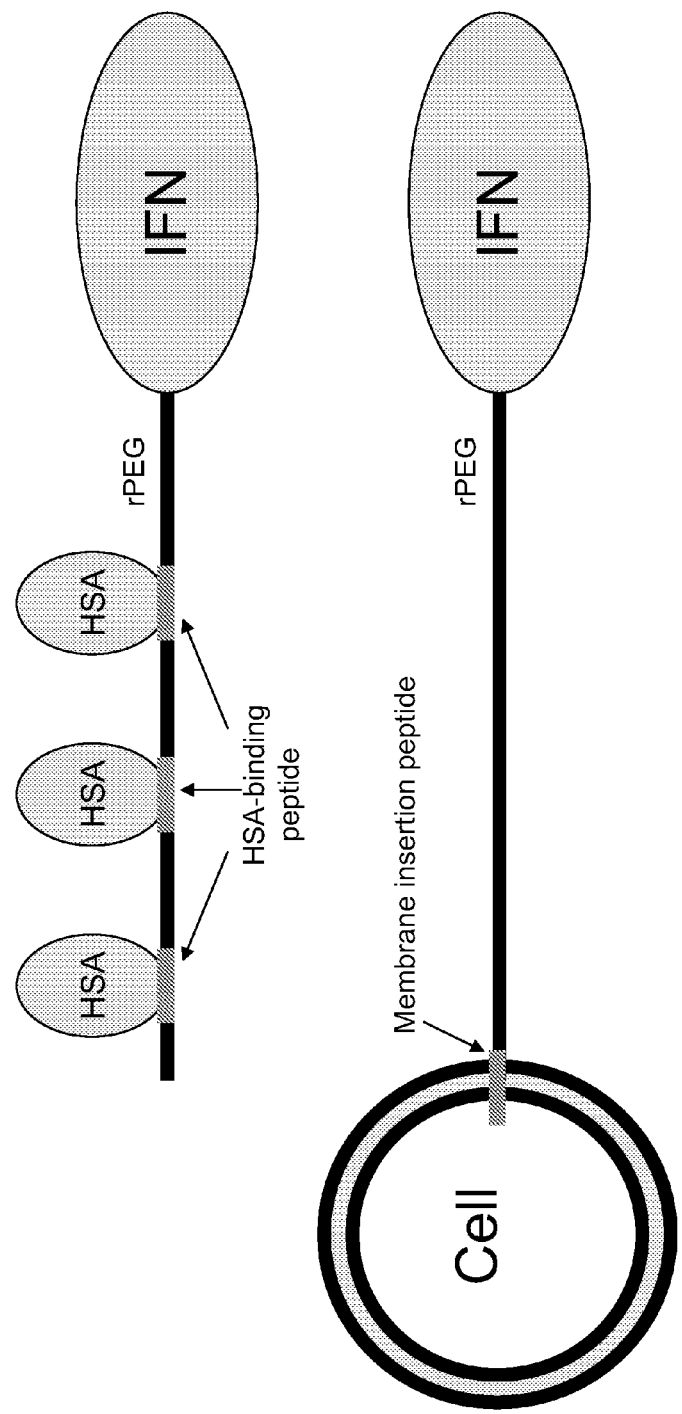

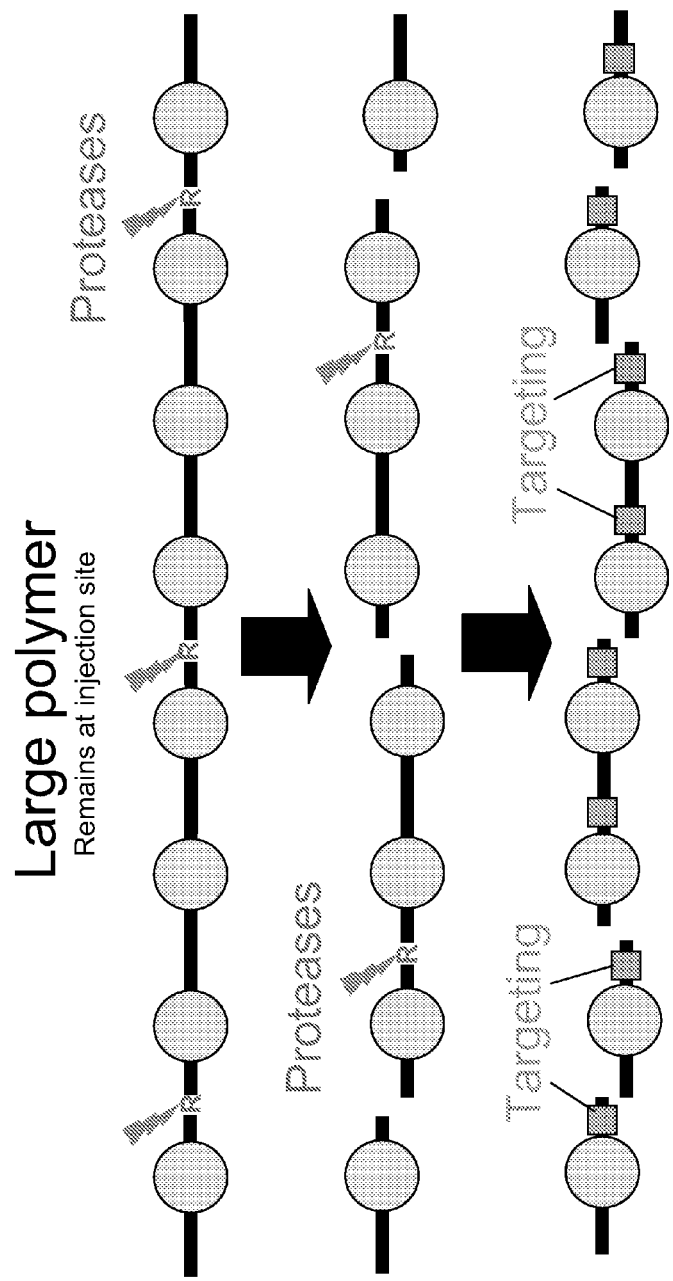
Fig. 29: Accessory Proteins with Protease-cleavable Sites

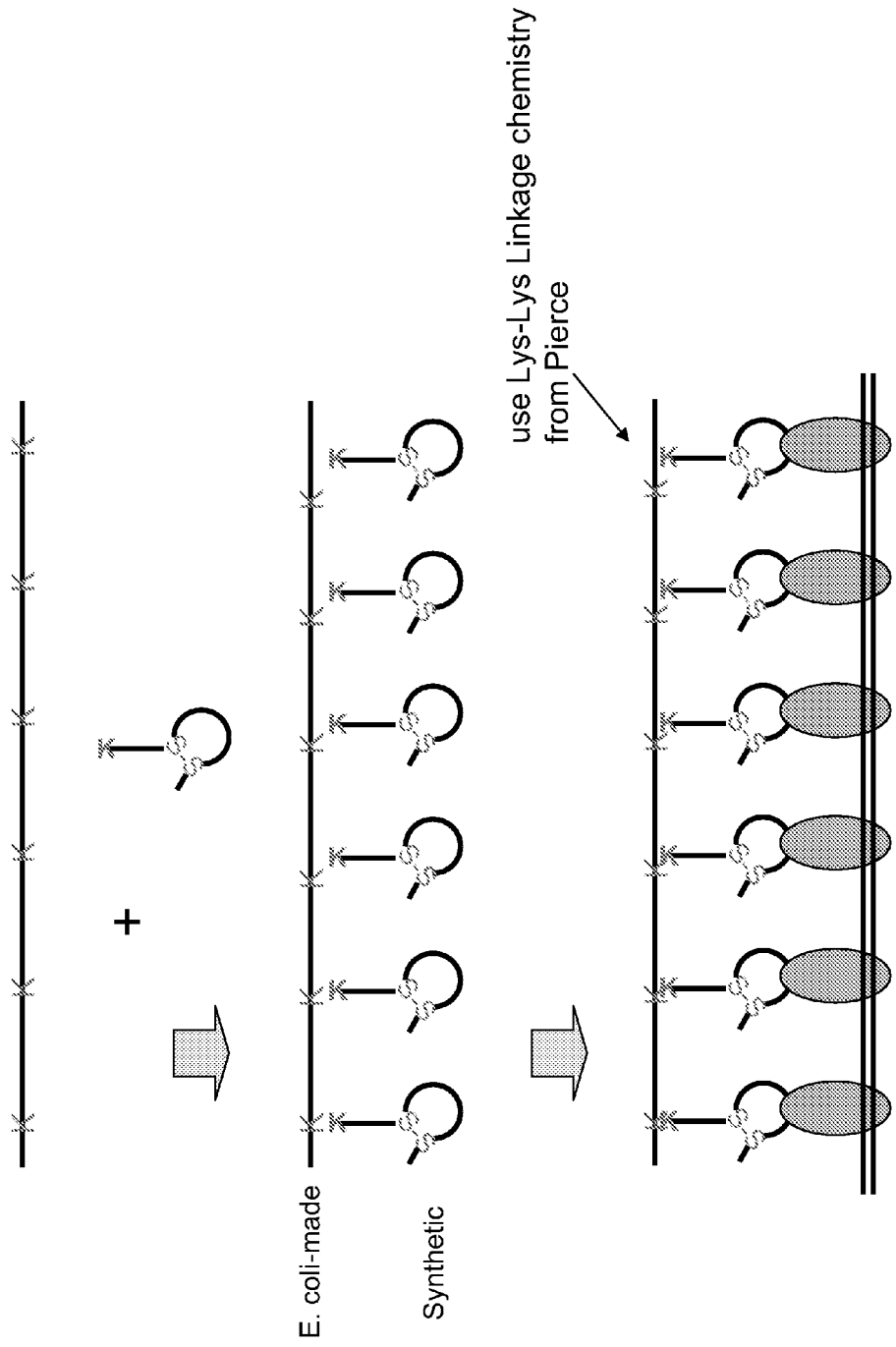

single chain Fc
2-disulfide Hinge single chain Fc
1-disulfide Hinge single chain Fc
1-disulfide Hinge single chain Fc
no-disulfide Hinge rPEG Options: No extension, any linker, rPEG or natural sequence

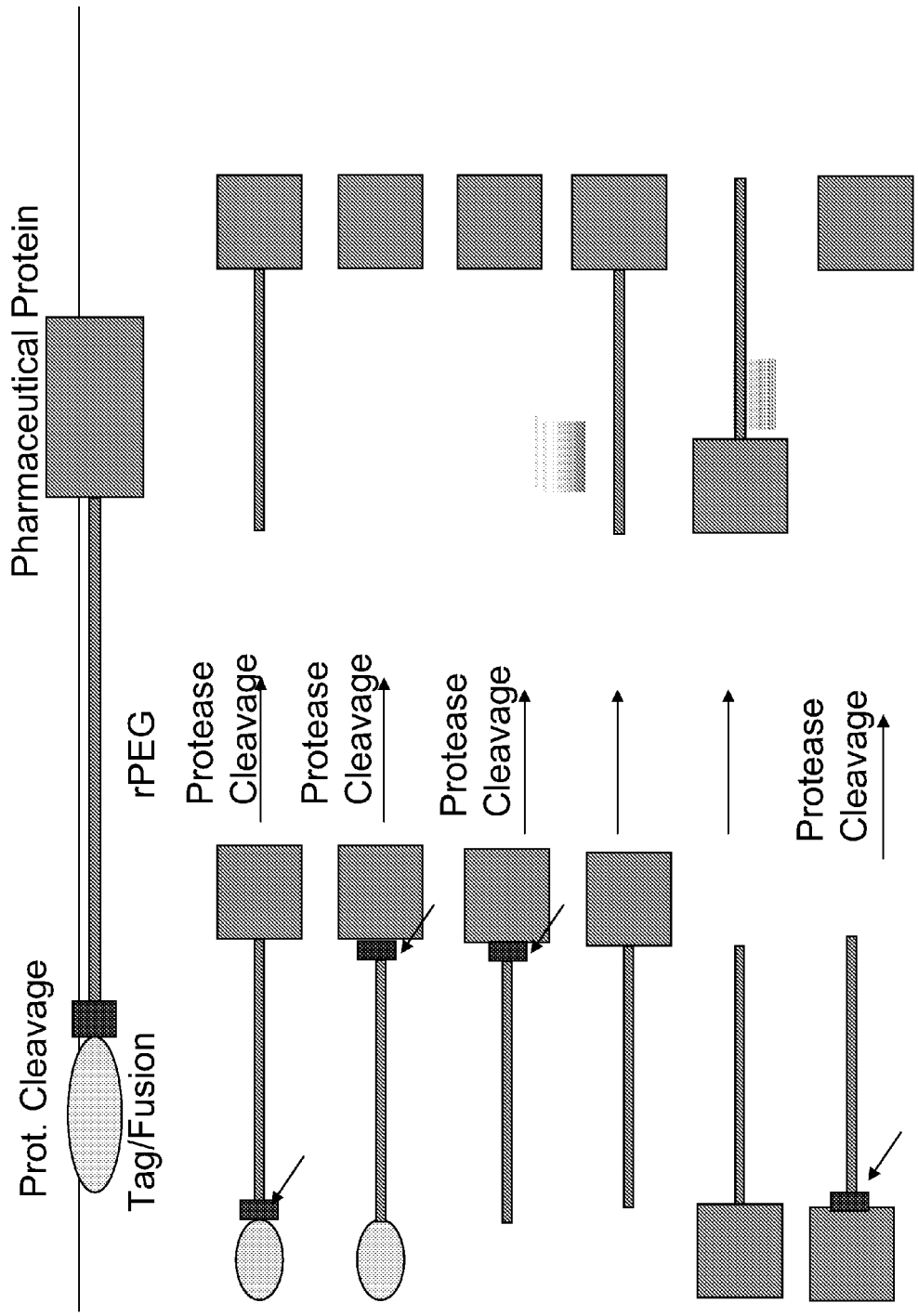

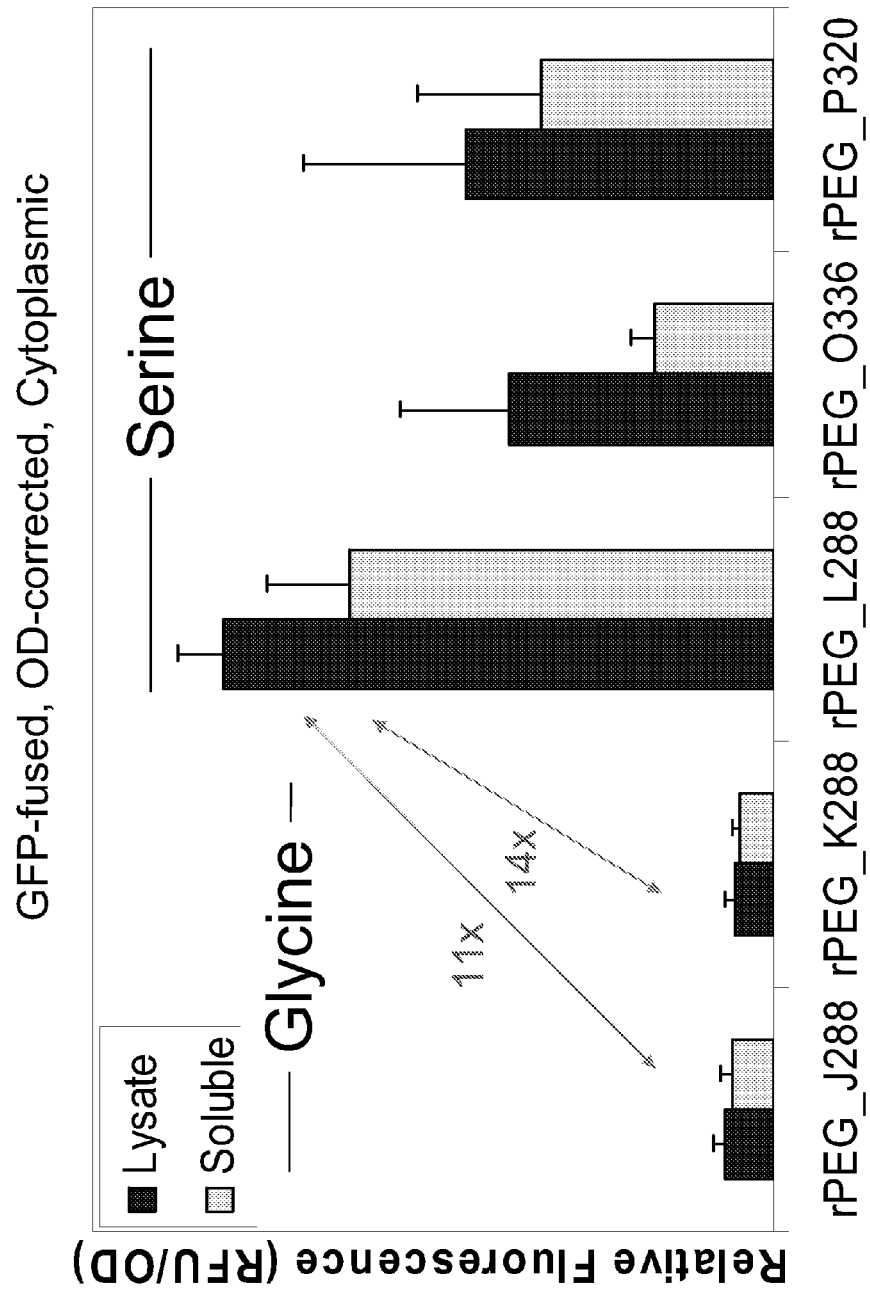

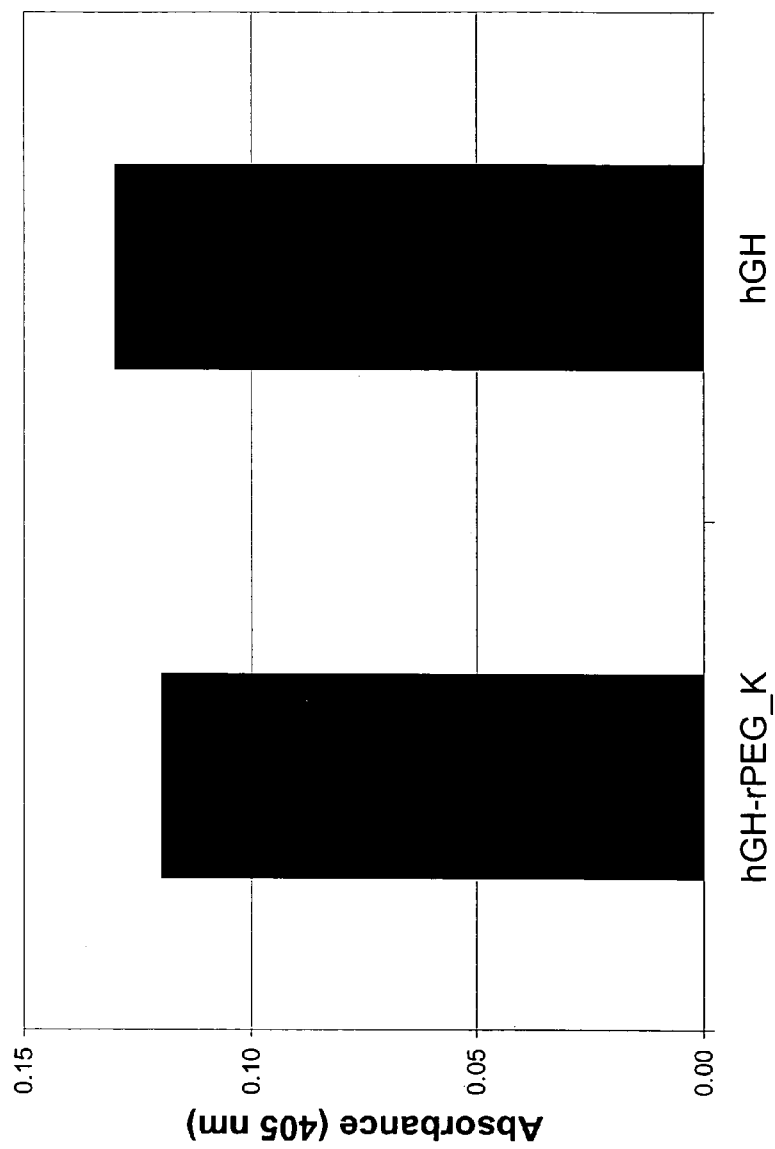
Fig. 34: Activity of accessory-modified hGH polypeptide

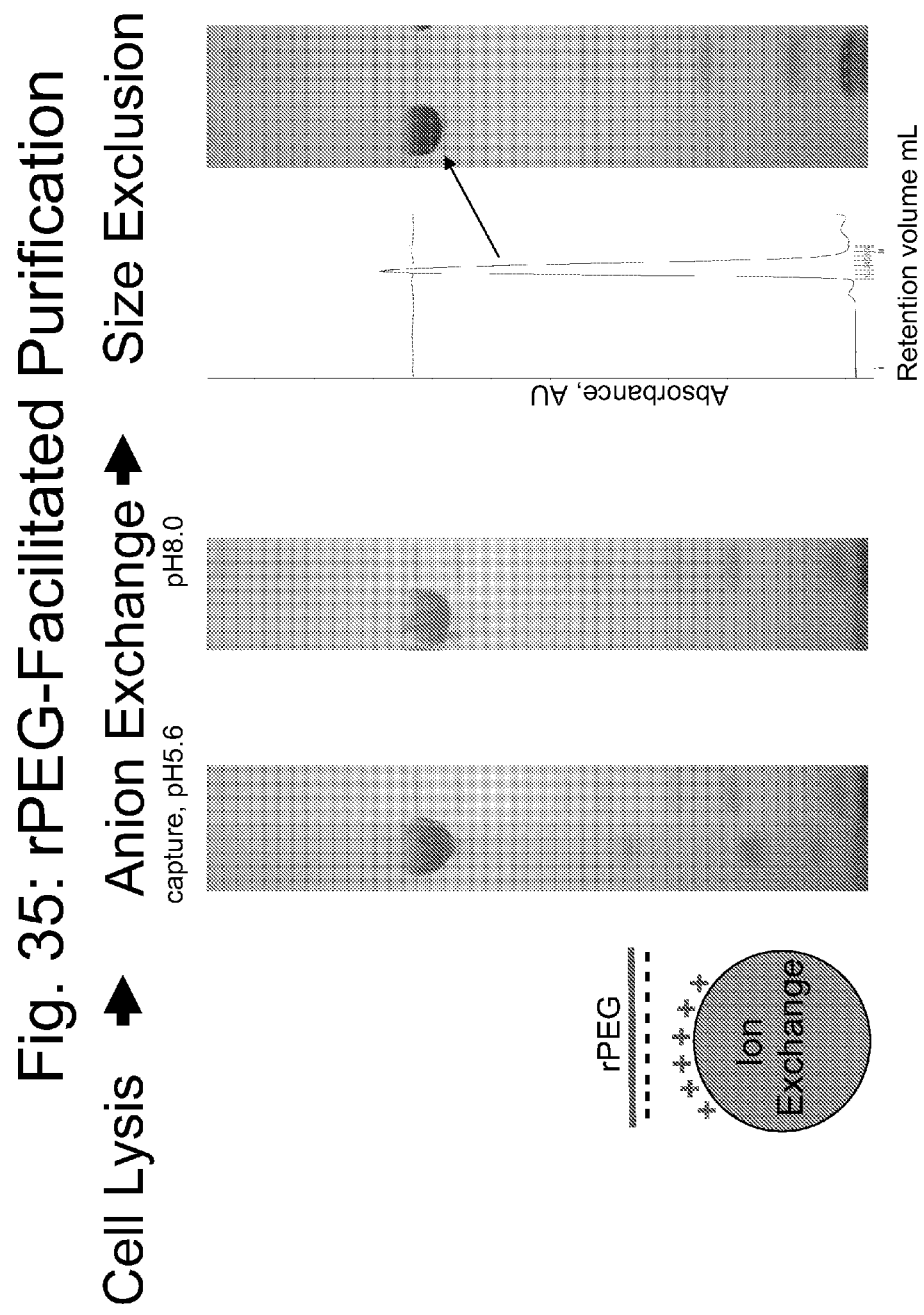

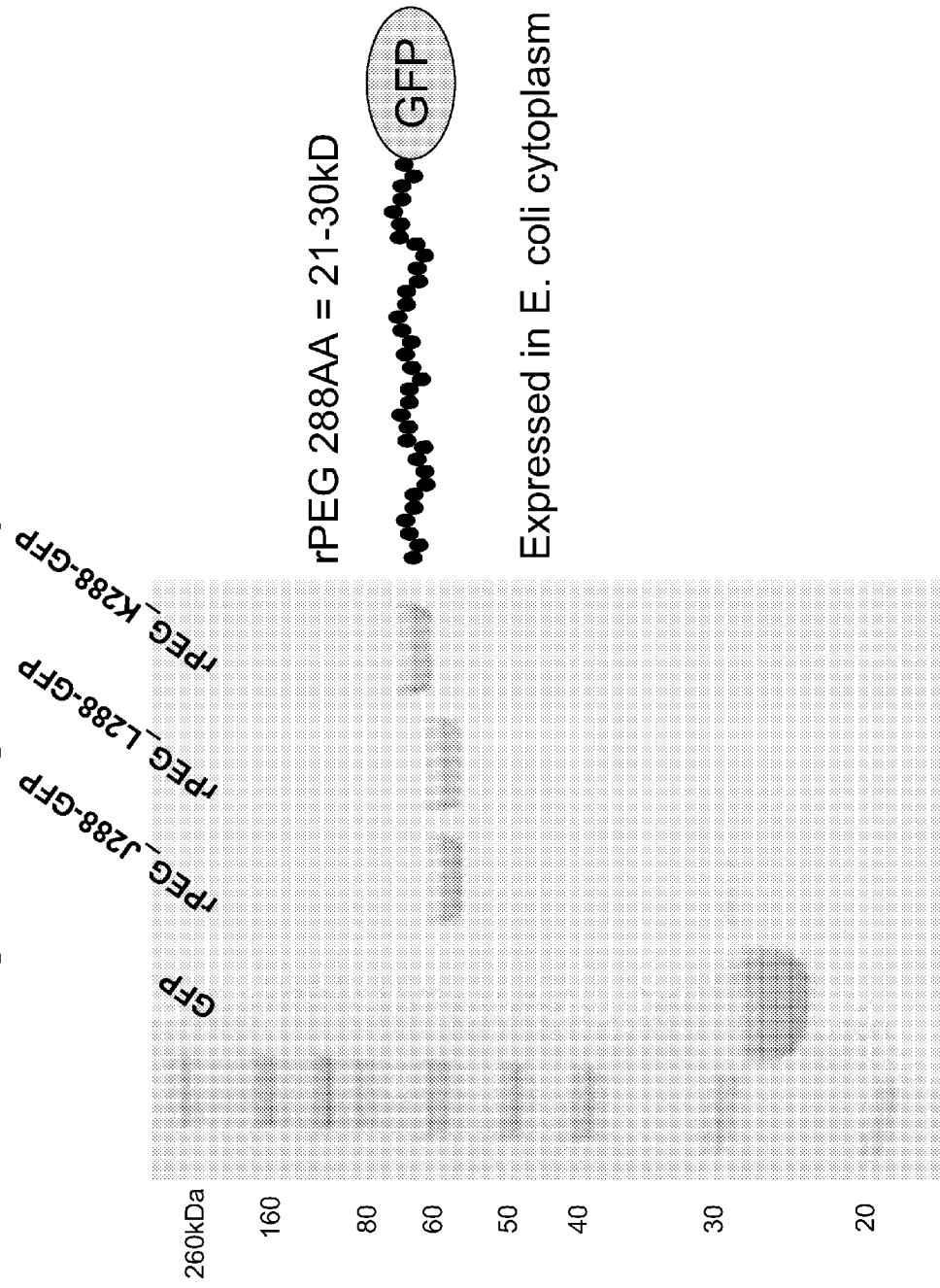
Fig. 36: Single Band by SDS-PAGE

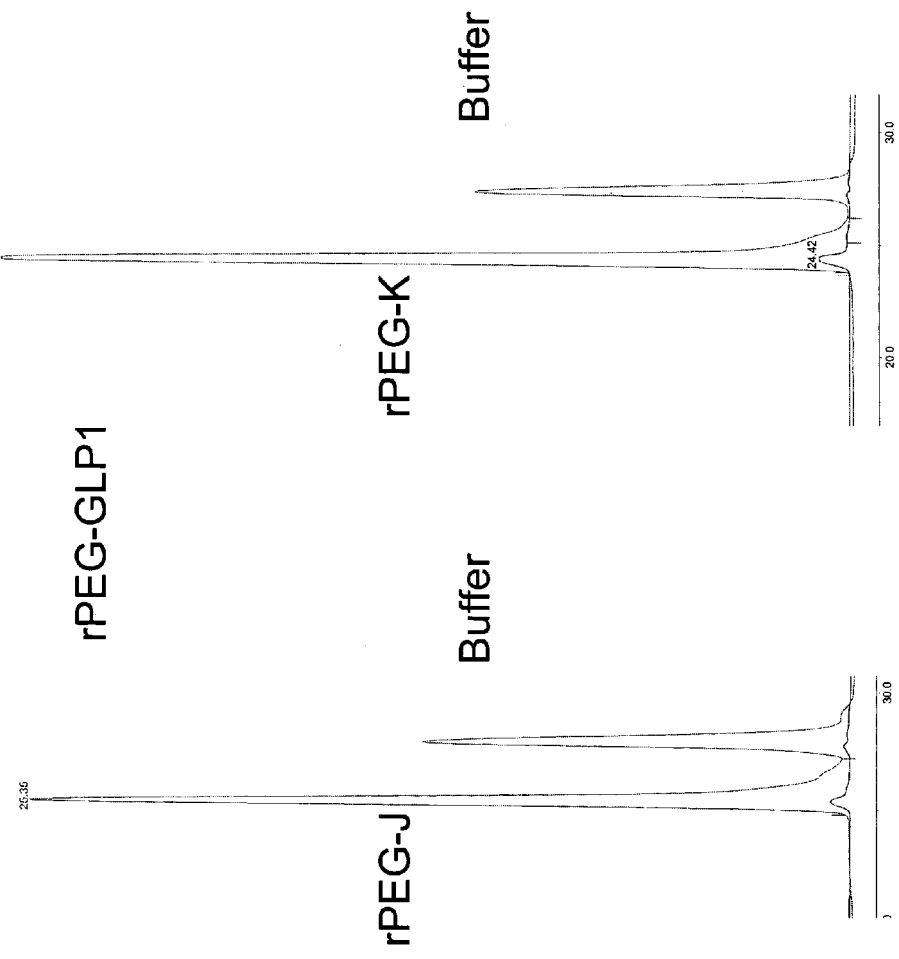
Fig. 37: Single Band by Analytical SEC

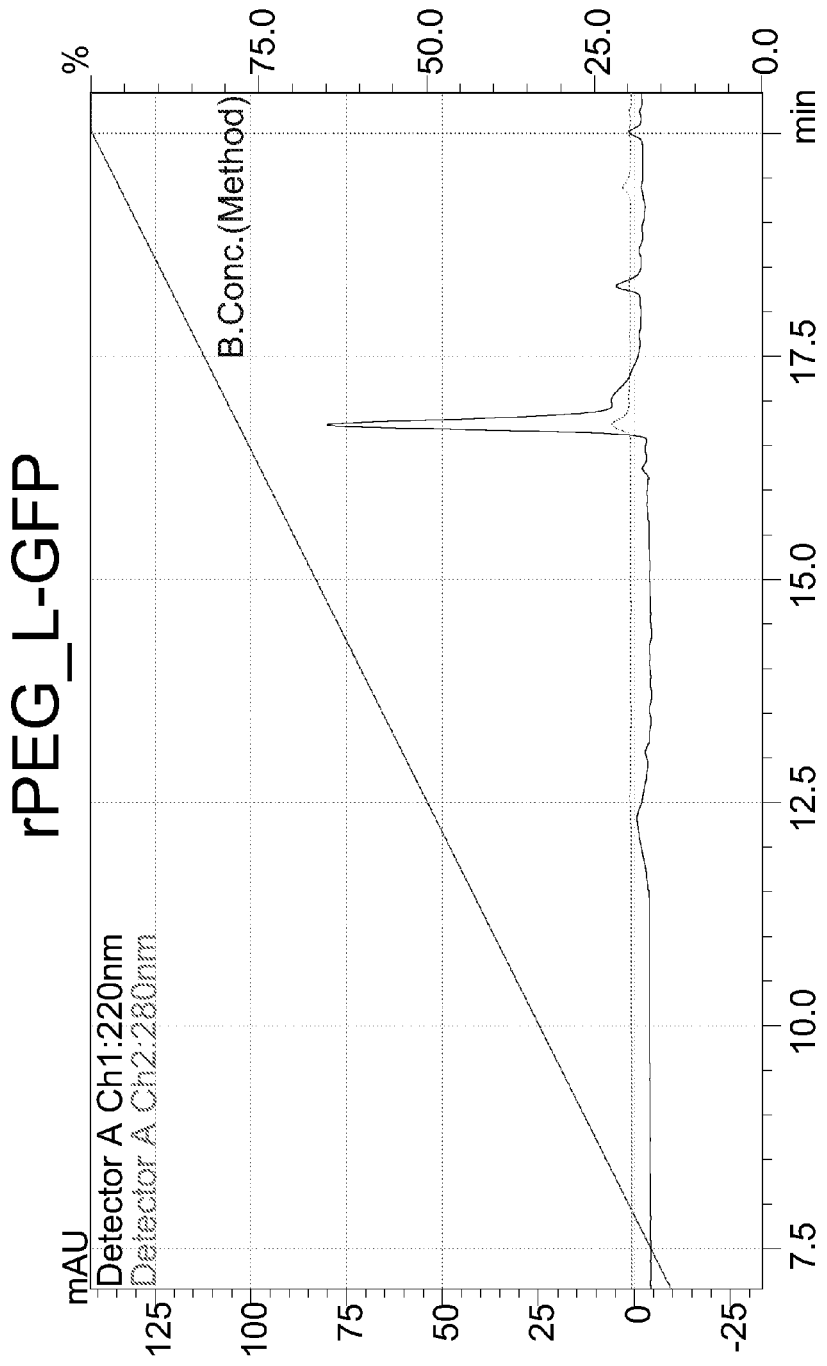
Fig. 38: Single Band by Analytical Reverse Phase HPLC

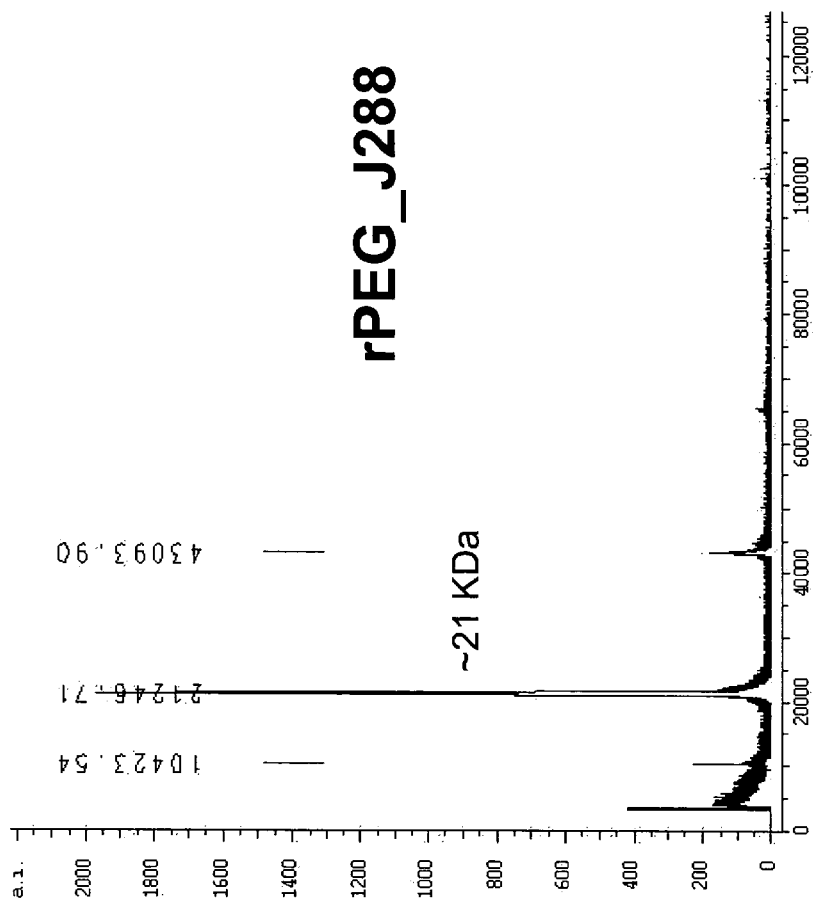
Fig. 39: Single Band by Mass Spectrometry

Fig. 40: No Binding to Other Proteins
Binding of serum Antibodies to rPEG
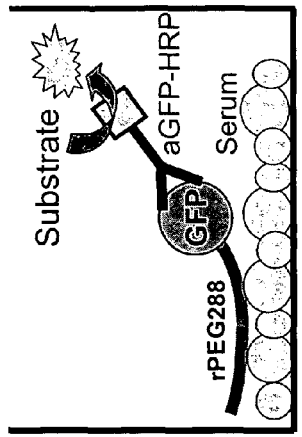
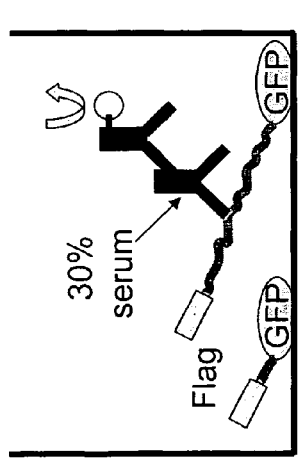
Binding of non-Ab serum proteins to rPEG
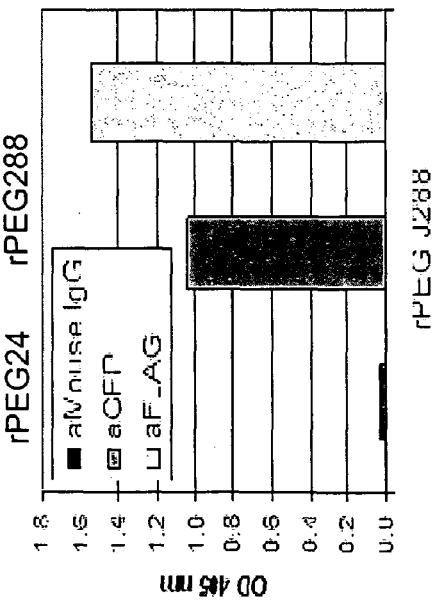
No serum proteins bind to rPEG

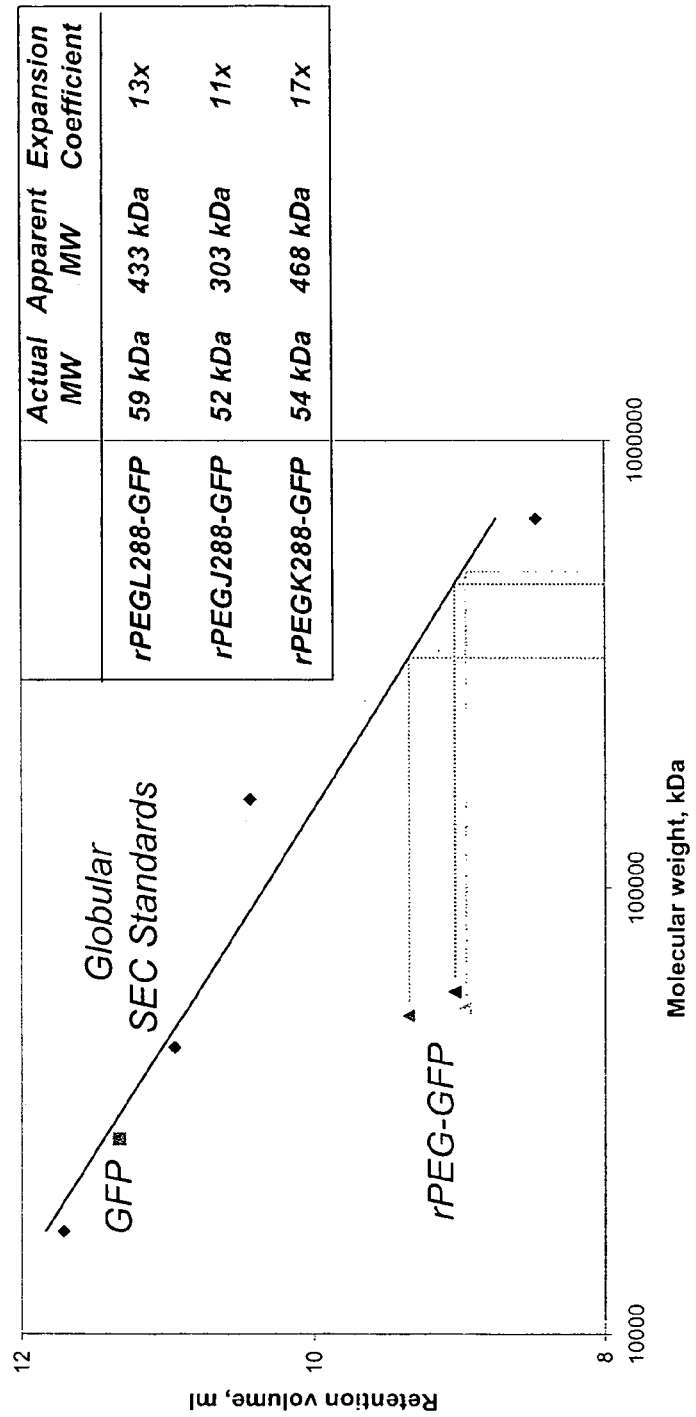
Fig. 41: rPEG Increases Apparent MW

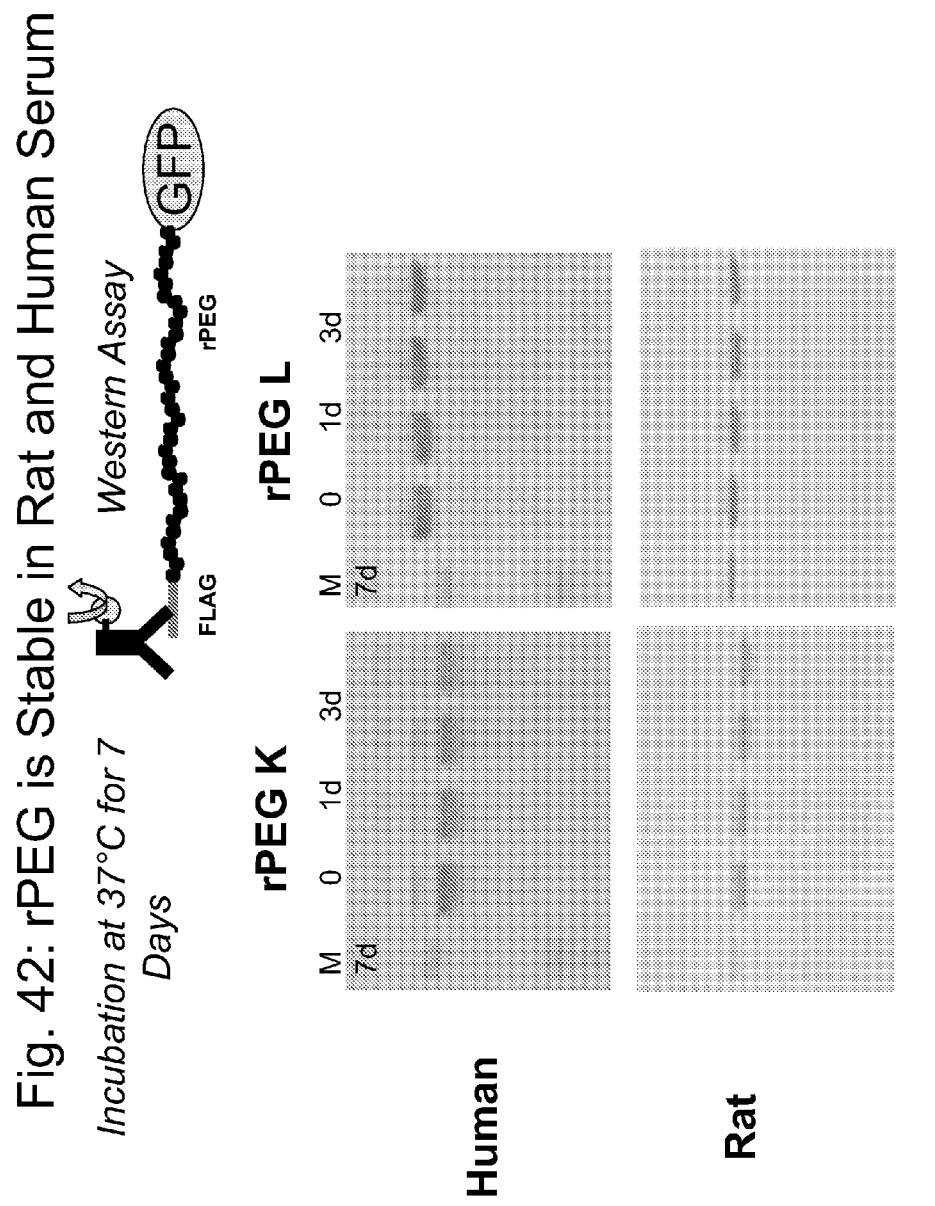

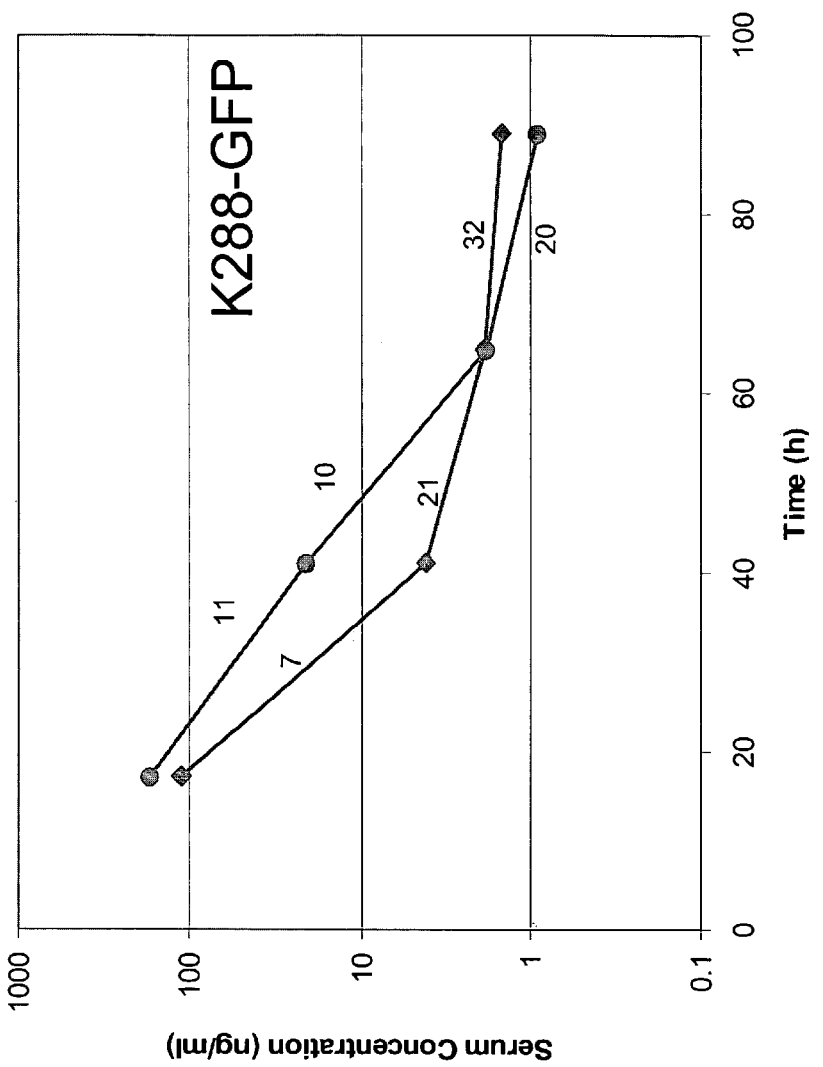

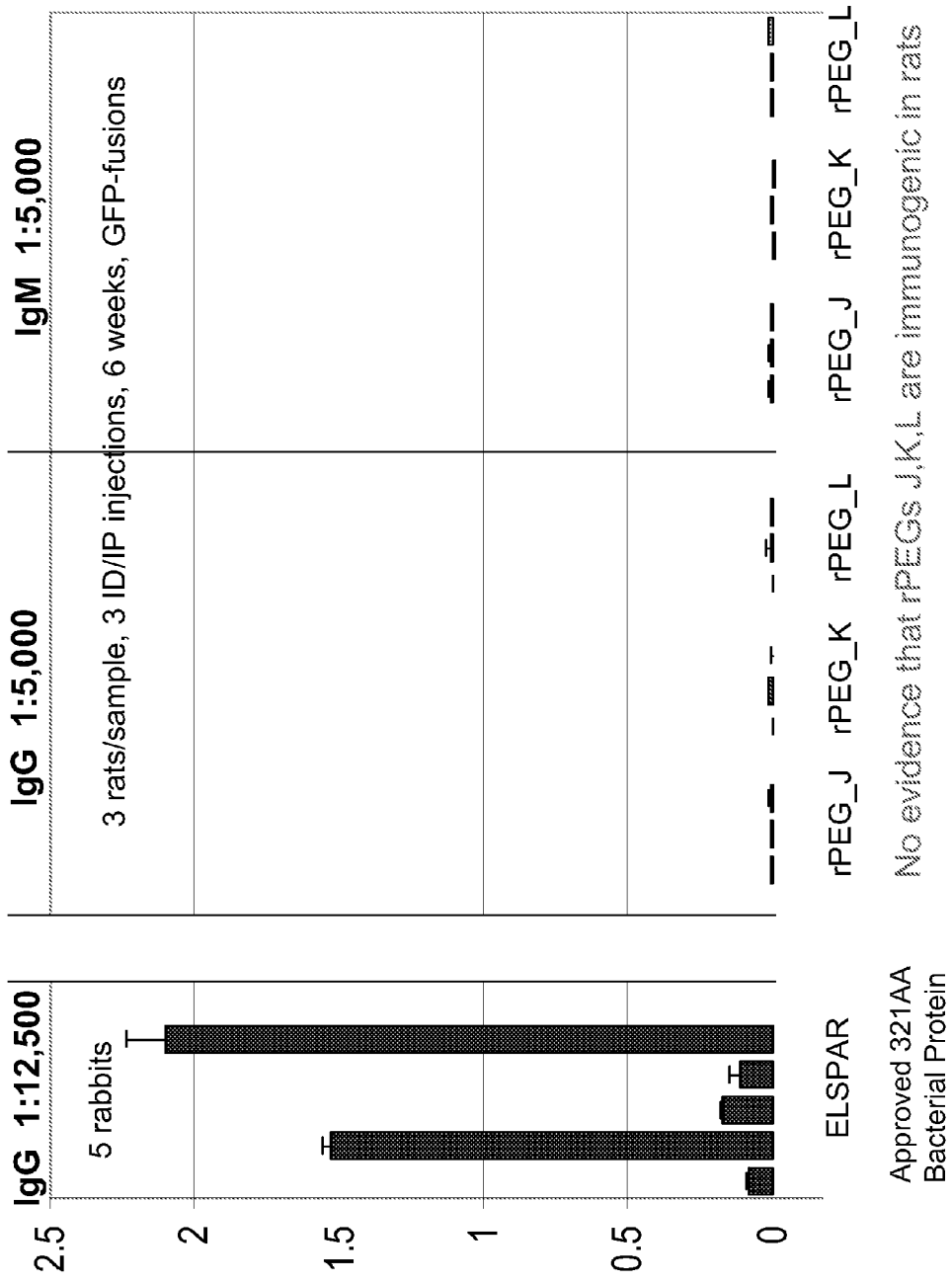

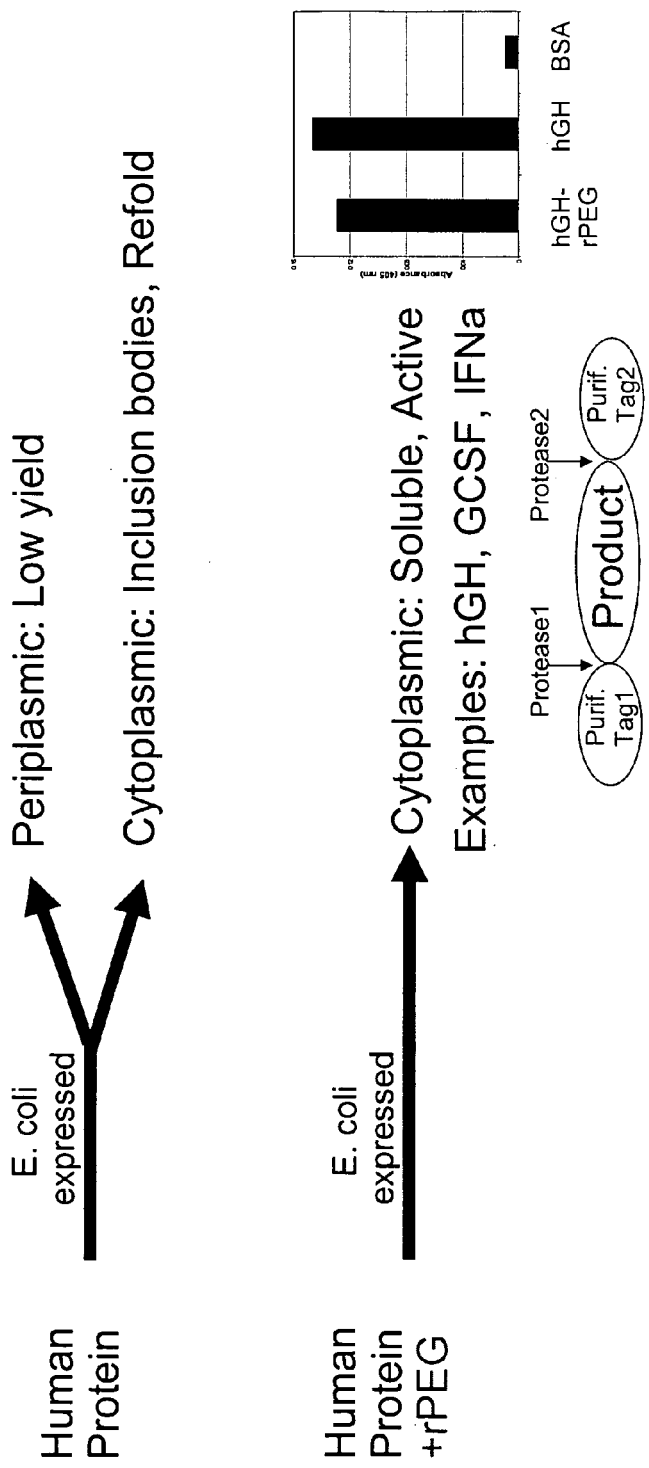
Fig. 45: Manufacturing Advantage of rPEG
rPEG enables cytoplasmic expression of active protein, that otherwise would form inclusion bodies

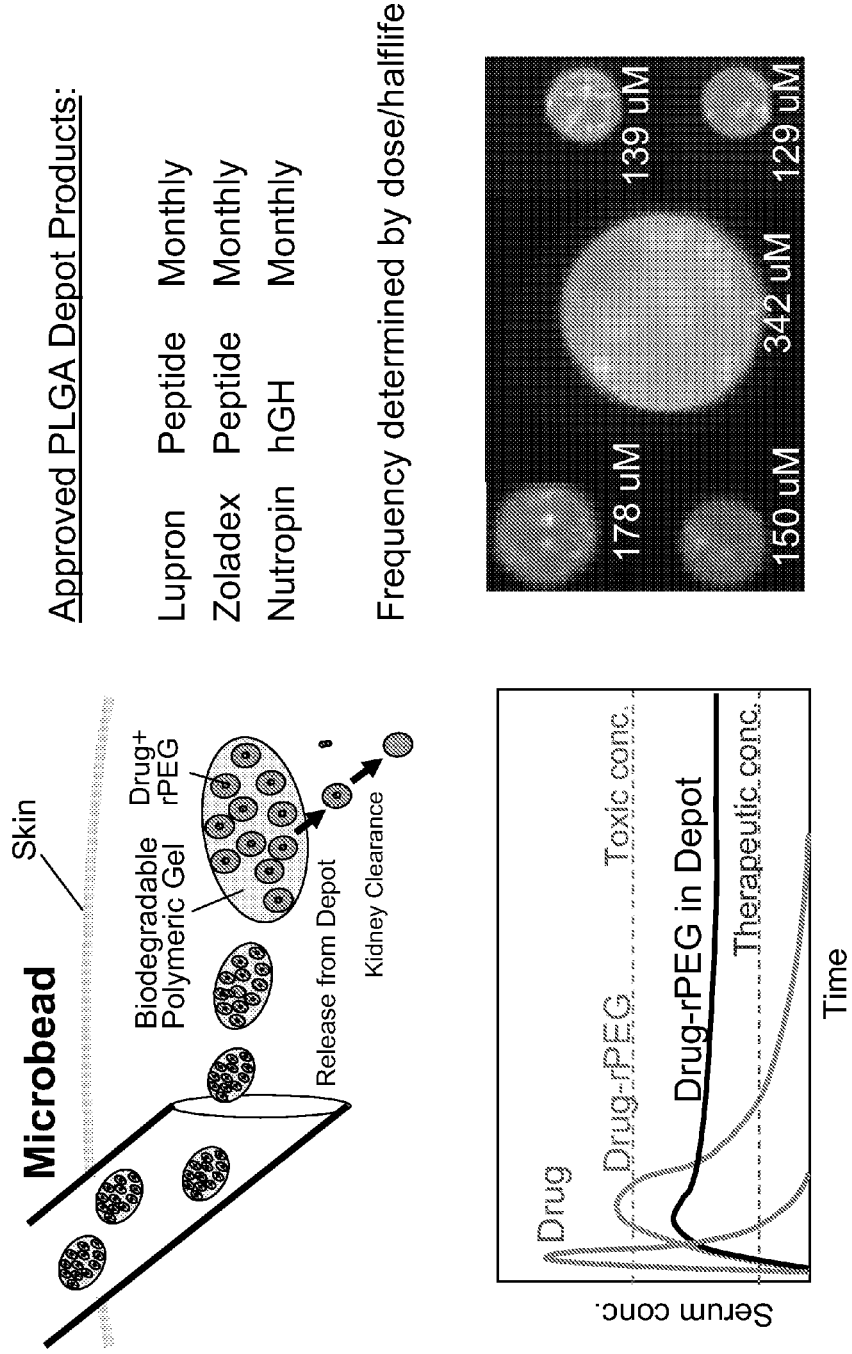
Fig. 46: Sustained Release of Modified Polypeptides

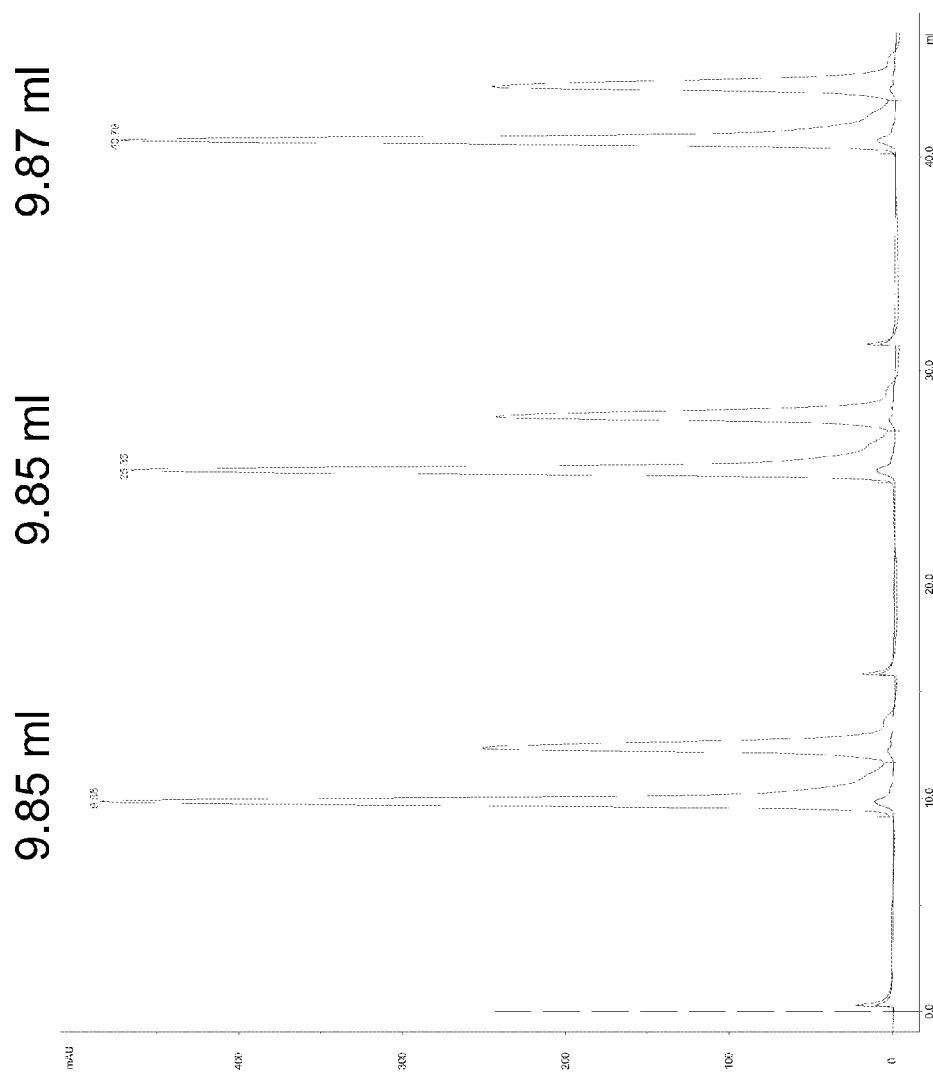
Fig. 47: GLP1-rPEGJ

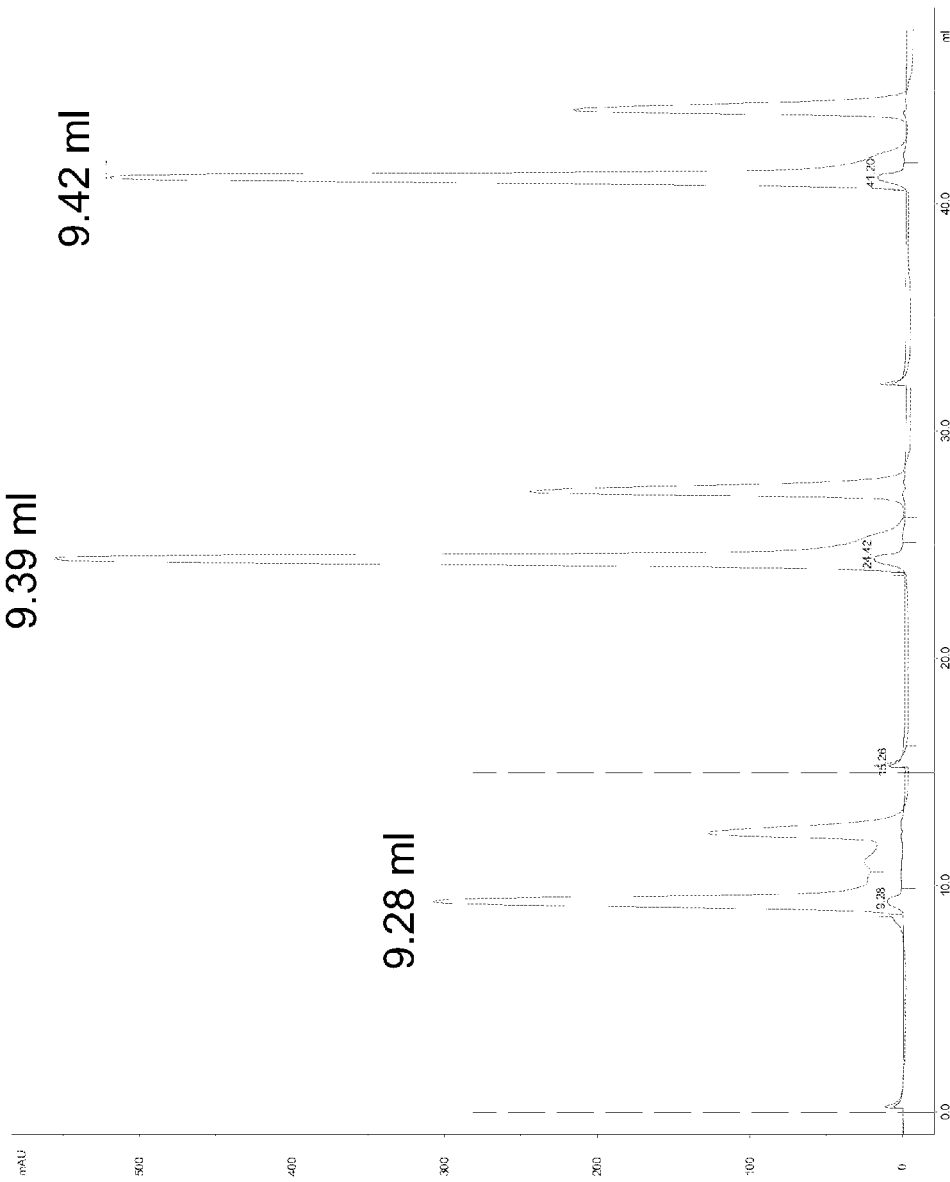

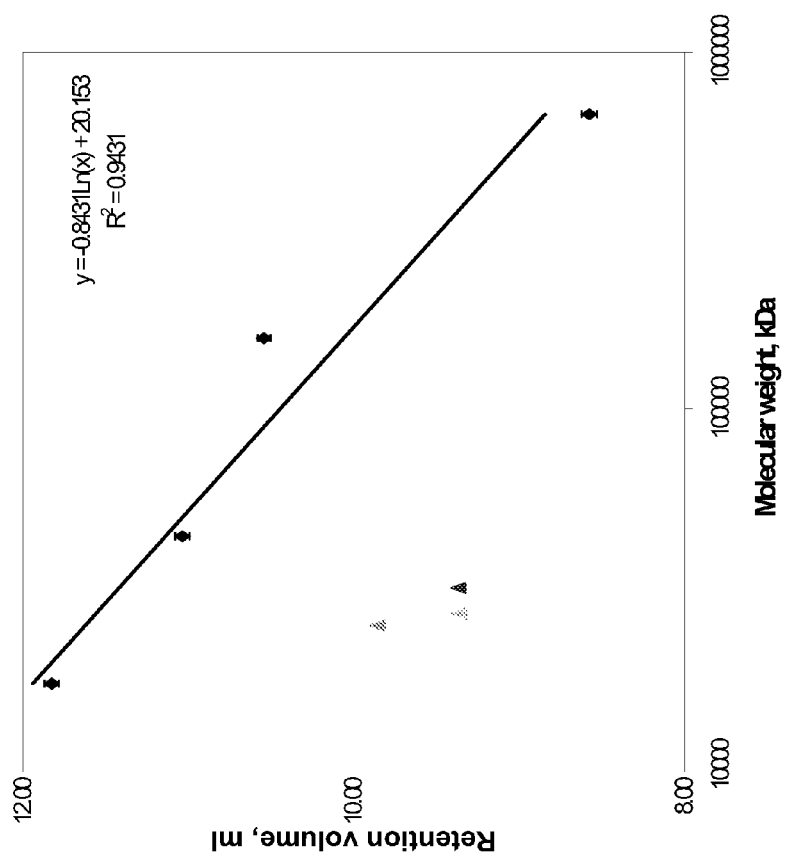
Fig. 49: SEC: Apparent MW of GLP1-rPEG fusions

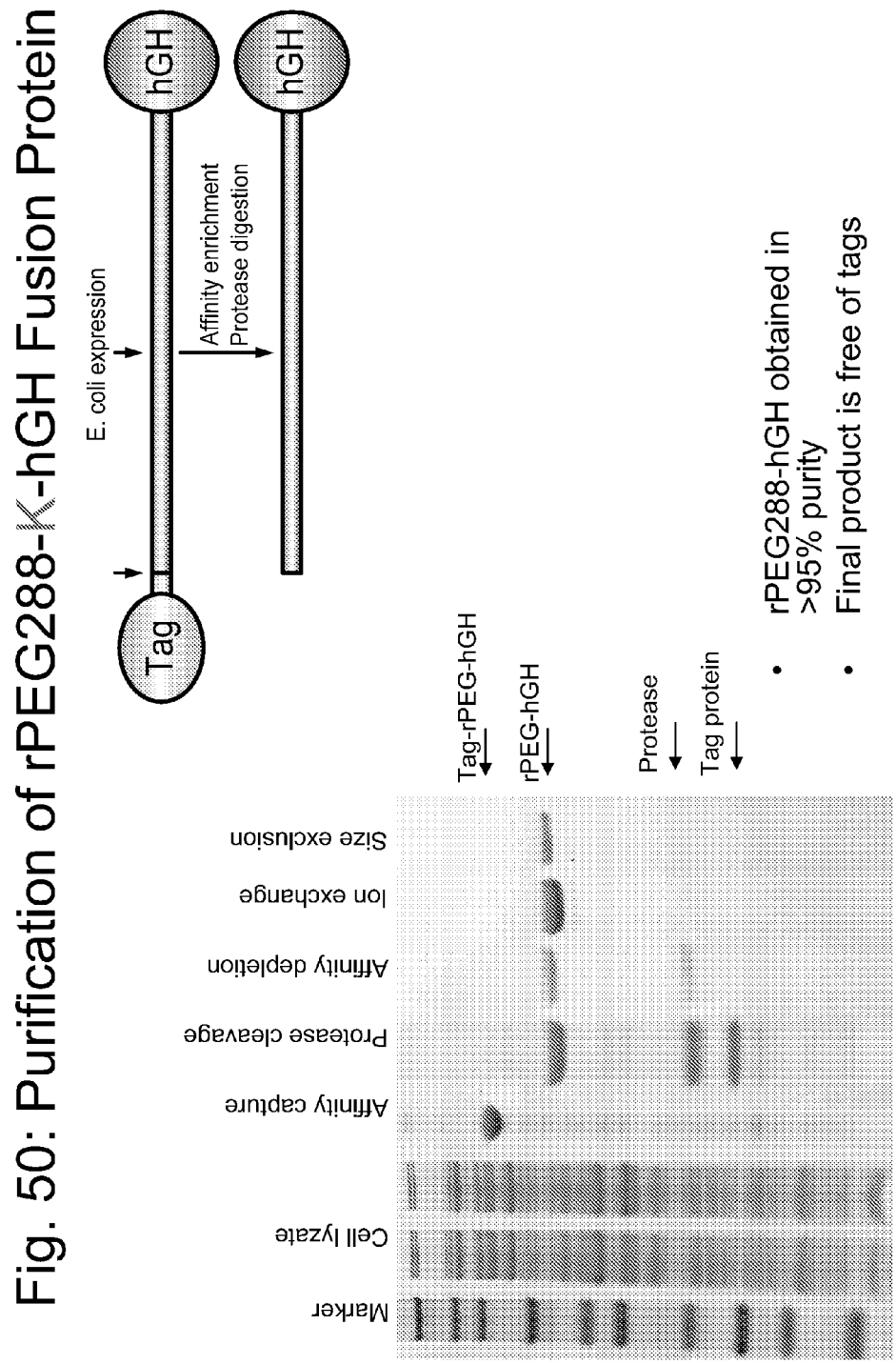

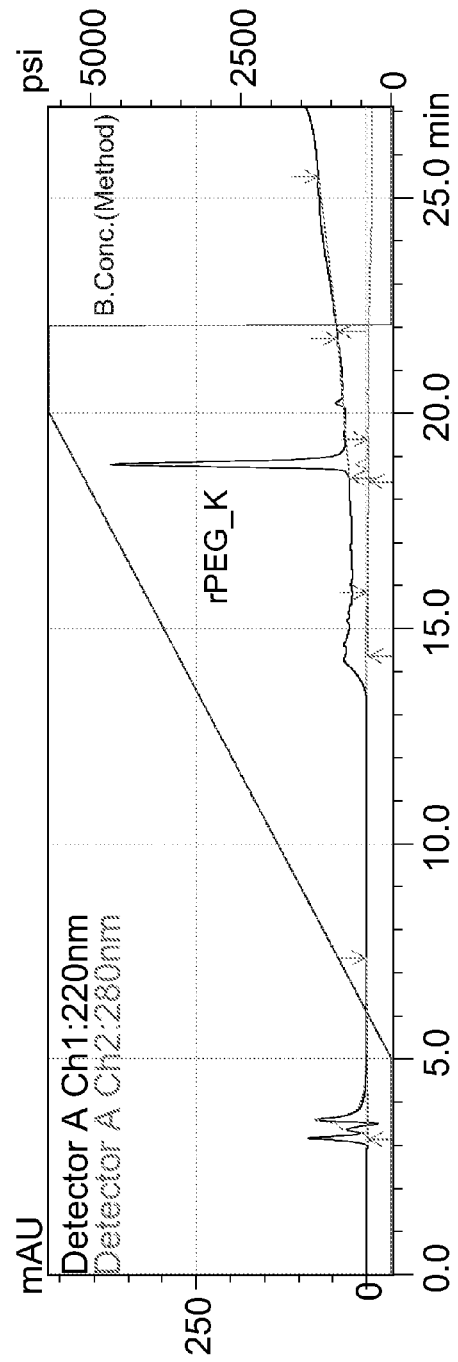
Fig. 51: Single Band by RP-HPLC

Whole Antibody
(IgG1,2,3,4, IgE,IgA,IgD,IgM)

Dimer of scFv Fragments

Single Chain Diabody

Single Chain Fc Fragment

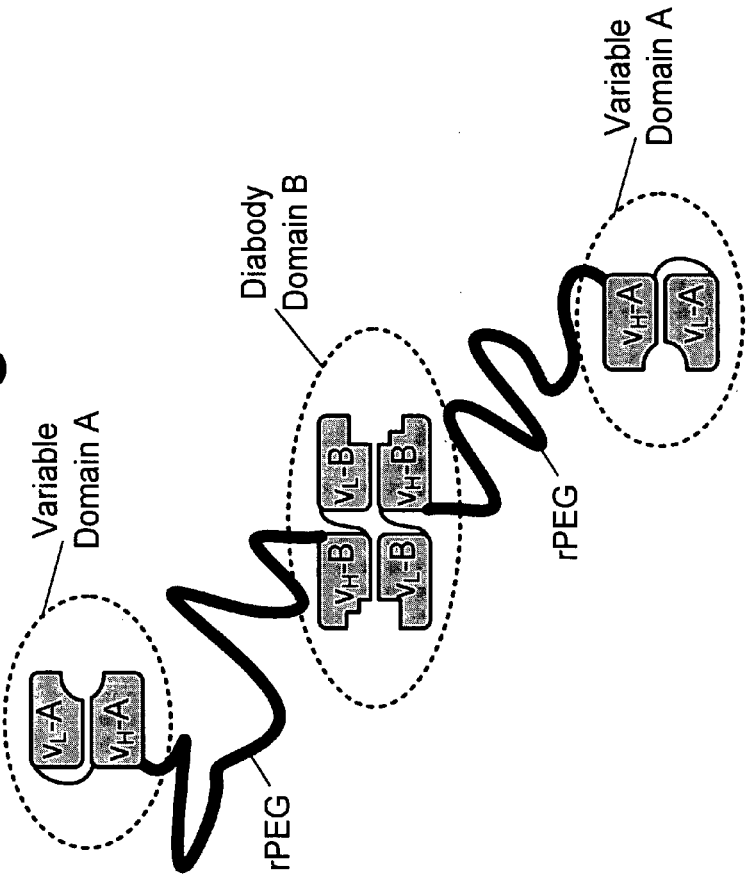
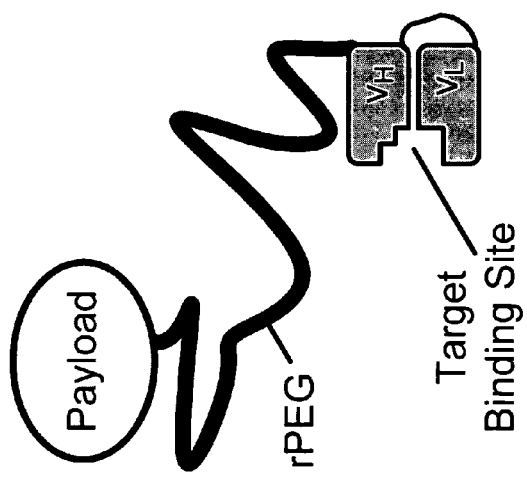
Fig. 58b
Fig. 58a

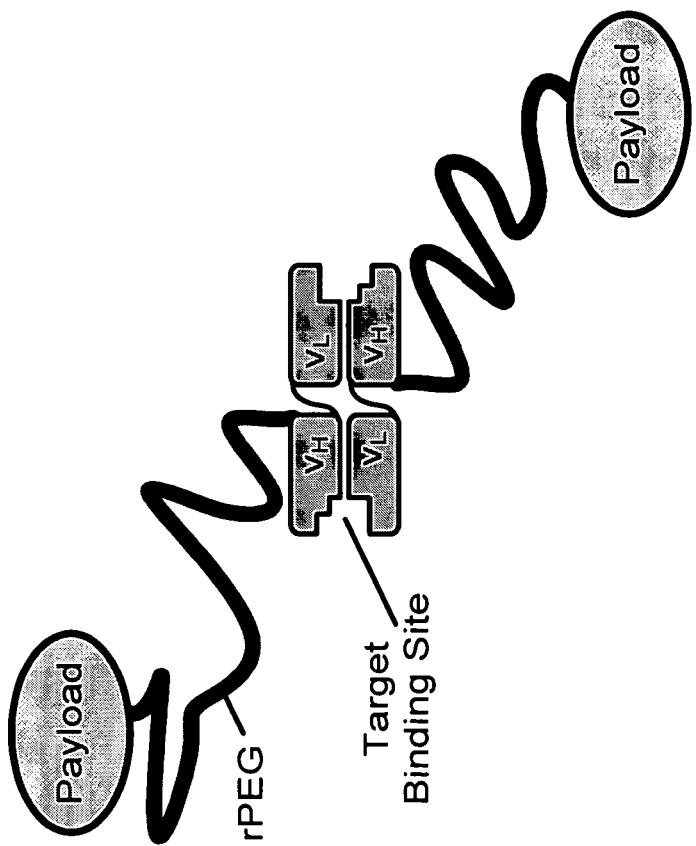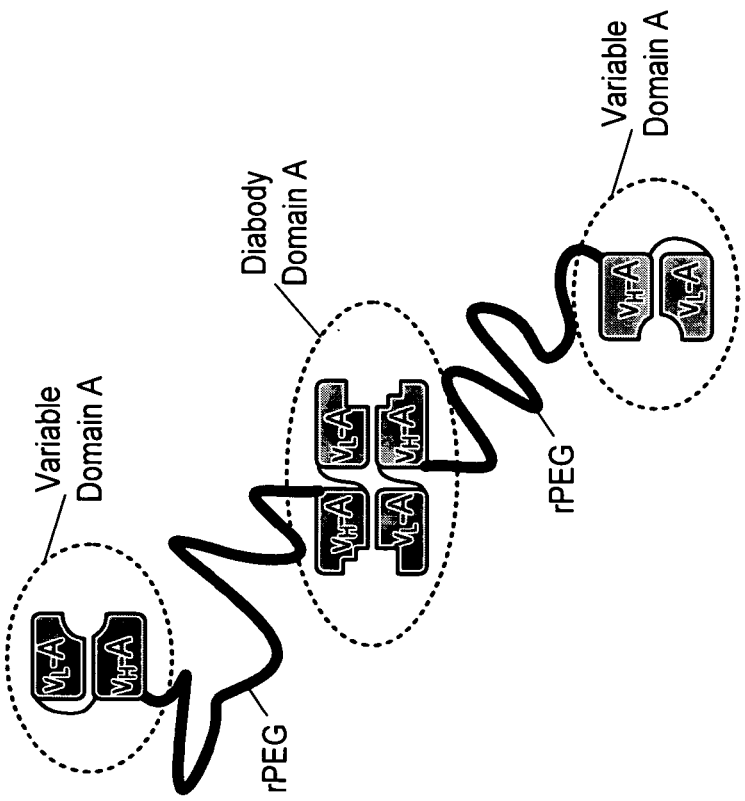

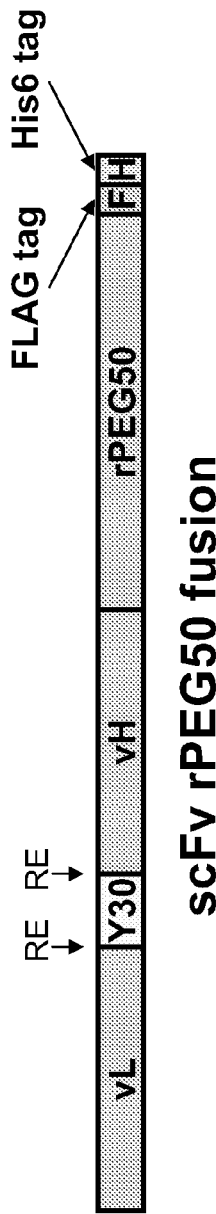

Fig. 64a scFv rPEG50 fusion

Fig. 64b Anti-Her2 scFv rPEG50 sequence

MEGDIQMTQSPSSLSASVGDRVTITCRASQDVNTAVAWYQQKPGKAPKLLIYSASFLYSGVPSRFS
GSRSGTDFTLTISSLQPEDFATYYCQQHYTTPPTFGQGTKVEIKTGSGEGSGEGGGEGSEGEGSG
EGGEGEGSSGTEVQLVESGGGLVQPGGSLRLSCAASGFNIKDTYIHWVRQAPGKGLEWVARIYPTNG
YTRYADSVKGRFTISADTSKNTAYLQMNSLRAEDTAVYYCSRWGGDGFYAMDYWGQGTLVTVSGGE
GSGEGSGEGSGEGGEGEGSEGGSEGSGEGEGSGEGGSGEGSEGEGGSGEGSGEGSEGSEGGSEGSG
EGSGEGEGSEGGSEGGEGEGSGEGSGEGSEGEGGSEGSEGGSEGSGEGEGGSGEGSGEGEGGSGEGSE
GGGEGSGEGEGGSEGSEGGSGEGSGEGSEGGSEGSGEGGSEGSEGSGEGSGEGGSEGSEGEGEGS
GSGEGEGGSEGGSEGGSEGGSGEGSGEGSEGEGGSGEGSGEGSGEGSGEGSGEGSEGEGGSGEGSEGE
GSEGSGEGGSEGSGEGGSGEGSGEGSGEGGSGEGSGEGSGEGSGEGSGEGSEGGSGEGSGEGSGEGGS
EGSEGGSEGGSEGGSEGSGEGSGEGSGEGSGEGSGEGSGEGSGEGSGEGSEGEGGSGEGSGEGGS
EGEGSGGSEGEGGSEGSGEGGGEGSGEGSGEGSEGDYKDDDDKGGSHHHHHH

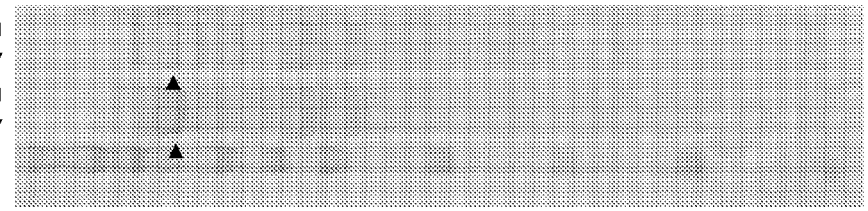

Anti-EGFR scFv rPEG50 sequence

MEDILLLTQSPVILSVSPGERVSFSCRASQSIGTNIHWYQQRTNGSPRLLIKYASESISGIPSRFSG
SGSGTDFTLSINSVESEDIADYYCQQNNNWPTTFGAGTKLELKTGSGEGGSEGGGEGSEGEGSGE
GGEGEGSGTQVQLKQSGPGLIVQPSQSLSITCTVSGFSLTNYGVHWVRQSPGKGLEWLGVIWSGGNT
DYNTPFTSRLSINKDNSKSQVFFKMNSLQSNDTAIYYCARALTYYDYEFAYWGQGTLVTVSGGEGS
GEGSEGEGSGEGEGGSEGGSGEGEGSEGGSEGEGEGGSEGGSEGEGGSEGEGSEGGSEGEGSEG
SEGEGSGEGEGSEGEGGSGEGEGSGEGEGSGEGGSEGGSEGGSEGGSEGEGSEGGSEGEGGSEGG
GEGSEGEGSGEGSGEGEGGSEGSGEGEGSEGSGEGEGSGEGGSEGGSEGSEGGSEGGSEGGSEGS
GEGEGSEGGEGSGEGEGSEGSGEGGSEGGSGEGEGSGEGGSEGGSGEGEGSGEGGSEGSEGSEG
EGGSEGGSEGEGGSEGSGEGEGSGEGEGSEGEGGSEGSGEGEGSGEGGSEGGSEGGSEGEGGSEG
SEGGSGEGSGEGSGEGGGGSEGGGSEGSEGGSEGSEGGSEGSEGGSGEGEGSGEGSEGGSEGGSEG
EGSEGGSGEGGSGEGGGEGSEGGEGSGEGEGGSEGSEGGSGEGEGSGEGGSEGGEGGSEGG
BGSEGGSEGGGEGSEGEGSEGGGSEGDYKDDDDKGGSHHHHHH

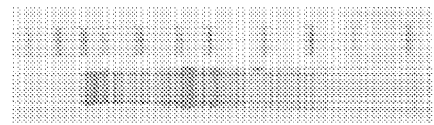

Fig. 65a scFv rPEG50 fusion

Fig. 65b Anti-Her2 diabody rPEG50 sequence with 3 amino acid linker

MEGDIHMEDIQMTQSPSSLSASVGDRVTITCRASQDVNTAVAWYQQKPGKAPKLLIYSASFLYSGVPSRFSGSRSGTDF
TLTISSLQPEDFATYYCQQHYTTPPTFGQGTKVEIKSGEEVQLVESGGGLVQPGGSLRLSCAASGFNIKDTYIHWVRQAP
GKGLEWVARIYPTNGYTRYADSVKGRFTISADTSKNTAYLQMNSLRAEDTAVYYCSRWGGDGFYAMDYWGQGTLVTV
SGGEGSGEGSGEGEGSGEGEGSEGGSSEGEGSGEGGSEGEGSEGGSEGSGEGGSEGSEGGSEGSEGGSEGEGGSEGEGSE
GEGSGEGEGSEGGSEGEGSSEGGSSEGSGEGSSGEGGSSEGGSEGSGEGGSEGSGEGSSEGGSEGSGEGGSEGSSEGGG
SEGSSEGEGSGEGSSEGEGSEGGSSGEGGSEGSGEGEGSGEGGSEGGSEGEGGSGEGSEGGGSSEGSGEGGSEGGSSGE
GSEEGSSEGGSSEGEGGSEGEGSSEGSSEGEGSEGEGSSEGGSSEGSGEGSGEGGSEGSSEGGSEGEGSGEGGSSGEGS
EGEGSSEGGSEGGEGGSEGEGSEGGSEGEGGSSEGGSSEGGSEGSGEGGSEGSSGEGGSEGSSEGSSEGGSGEGSSGEG
GSEGGEGSSEGEGSSEGEGEGGSEGSSEGEGGGSSEGEGSSEGEGGSEGSEGGSEGGSEGSSEGGSEGGEGSEGGGSHH
HHHH

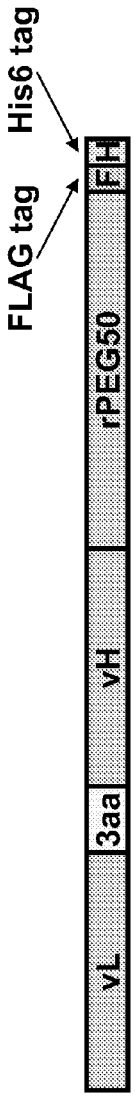

```
M  D  K  T  H  T  C  P  P  C  P  A  P  E  L  L  G  G  P  S
ATGGATAAAACTCATACTTGCCCTCCTTGTCCAGCTCCGGAACTGCTGGGCGGTCCGTCT

V  F  L  F  P  P  K  P  K  D  T  L  M  I  S  R  T  P  E  V
GTTTTCCTGTTCCCACCAAAACCAAAGGACACCCTGATGATTTCCCGTACTCCTGAGGTA

T  C  V  V  V  D  V  S  H  E  D  P  E  V  K  F  N  W  Y  V
ACCTGCGTAGTTGTAGACGTTCTCACGAGGATCCGGAAGTAAAATCAACTGGTACGTG

D  G  V  E  V  H  N  A  K  T  K  P  R  E  E  Q  Y  N  S  T
GATGGCGTTGAGGTGCATAACGCTAAAACCAAACCGCGCGAGGAGCAATATAATTCCACC

Y  R  V  V  S  V  L  T  V  L  H  Q  D  N  L  N  G  K  E  Y
TACCGTGTTGTGTCTGTTCTGACCGTCCTGCACCAAGATTGGCTGAACGGCAAAGAATAC

K  C  K  V  S  N  K  A  L  P  A  P  I  E  K  T  I  S  K  A
AAGTGTAAAGTGTCCAACAAAGCCCTGCCAGCCCCGATCGAGAAAACTATTTCTAAGGCG

K  G  Q  P  R  E  P  Q  V  Y  T  L  P  P  S  R  D  E  L  T
AAAGGCCAGCCGCGCGAACCACAAGTATATACCGCTGCCCCGTCTCGCGATGAACTGACC

K  N  Q  V  S  L  T  C  L  V  K  G  F  Y  P  S  D  I  A  V
AAGAACCAAGTTTCCCTGACCTGCCTGGTGAAGGGTTTCTACCCATCGATATCGCCGTC

E  W  E  S  N  G  Q  P  E  N  N  Y  K  T  T  P  P  V  L  D
GAGTGGGAATCCAATGGTCAGCCGGAGAACAATTATAAAACTATCCCACCGGTTCTGGAC

S  D  G  S  F  F  L  Y  S  K  L  T  V  D  K  S  R  W  Q  Q
TCTGACGGTTCCTTCTTTCTGTATTCCAAGCTGACCGTTGATAAAAGCCGTTGGCAGCAG

G  N  V  F  S  C  S  V  M  H  E  A  L  H  N  H  Y  T  Q  K
GGCAACGTGTTCTCTTGCTCTGTGATGCATGAAGCACTGCACAACCATTACACCCAGAAA

S  L  S  P  G  K
AGCCTGTCCCCTGGTCGGGGGTAAG
```

Fig. 69

MSKGEELFTGVVPILVELDGDVNGHKFSVSGEGEGDATYGKLTLKFICTTGKLPVPWPTLVTTFSYGVQCFS
RYPDHMKRHDFFKSAMPEGYVQERTISFKDDGNYKTRAEVKFEGDTLVNRIELKGIDFKEDGNILGHKLEYN
YNSHNVYITADKQKNGIKANFKIRHNIEDGSVQLADHYQQNTPIGDGPVLLPDNHYLSTQSALSKDPNEKRDH
MVLLEFVTAAGIGEGSGEGEGEGGEGSEGEGSEGGEGSEGGGEGSEGEGSEGGSGEGEGSEGEGSEGGSGEGE
GSGEGSEGEGSEGSGEGGEGGEGSEGEGSEGGSGEGEGSEGEGSEGGSGEGEGSEGEGSEGGSGEGEGSEGE
GGSEGGSEGEGSEGSGEGGEGGEGSEGEGSEGGSGEGEGSEGEGSEGGSGEGEGSEGEGSEGGSGEGEGSEG
GEGSEGSGEGEGGEGSEGEGSEGGSGEGEGSEGEGSEGGSGEGEGSEGEGSEGGSGEGEGSEGEGSEGGSEG
SGEGGSEGSGEGEGGEGSEGEGSEGGSGEGEGSEGEGSEGGSGEGEGSEGEGSEGGSGEGEGSEGEGSEGGE
GGSEGGSEGEGSEGSGEGGEGGEGSEGEGSEGGSGEGEGSEGEGSEGGSGEGEGSEGEGSEGSGEGEGSEGE
GGSEGEGSEGSGEGGEGGGEGGEGSEGEGSEGGSGEGEGSEGEGSEGGSGEGEGSEGEGSEGGSGEGEGSEGGE
GEGSEGSEGGSEGSGEGGEGGGEGGEGSEGEGSEGGSGEGEGSEGEGSEGGSGEGEGSEG

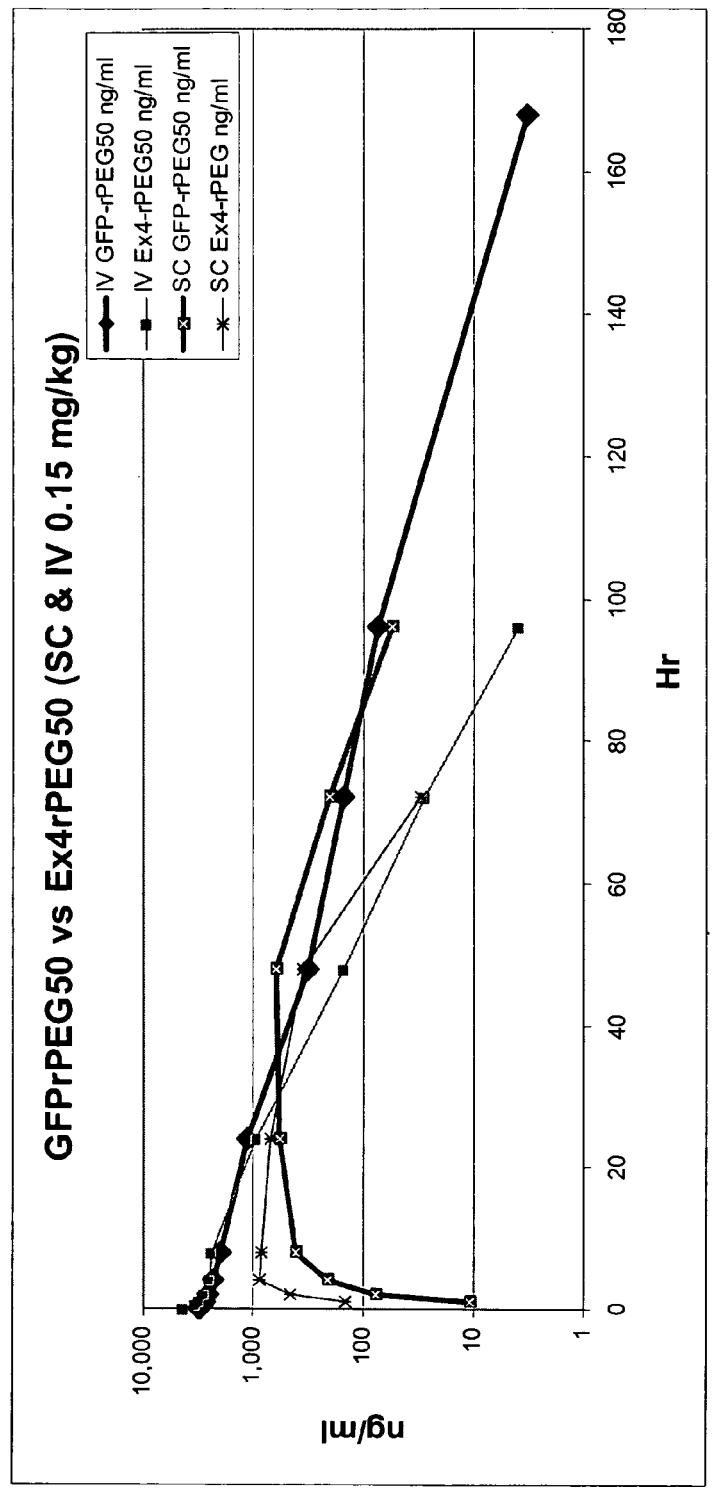

Fig. 71a

MANTPVSGNLKVEFYNSNPSDTTNSINPQFKVTNTGSSAIDLSKLTLRYYYTVDGQKDQTFWADHAAIIGSNGSYNGITSNVKGT
FVKMSSSTNNADTYLEISFTGGTLEPGAHVQIQGRFAKNDWSNYTQSNDYSFKSASQFVEWDQVTAYLNGVLVWGKEPGGSV
VGSGSGSENLYFQHGEGTFTSDLSKQMEEEAVRLFIEWLKNGGPSSGAPPPSGGEGSGEGSGEGSGEGSGEGSGEGSGE
GEGSEGSEGEGGSGEGSGEGEGSGEGSGEGSGEGSEGSGEGEGSGEGSGEGEGSGEGSEGEGSGEGSGEGSGEGE
GSGEGEGSGEGGSGEGSGEGEGSGEGSGEGEGSGEGSGEGSGEGSEGEGSGEGSEGEGSGEGSGEGSEGEGSGEGGS
EGSEGEGGSGEGSGEGSGEGSGEGSGEGEGSGEGSGEGEGSGEGSGEGSEGEGSGEGSGEGSGEGSEGSGEGEGSGEGE
GSGEGSGEGEGGSGEGSGEGSGEGSGEGSEGEGSGEGSGEGEGGSGEGSGEGSGEGSEGEGSGEGSEGEGSGEGSG
EGEGSEGSGEGGSGEGSGEGSEGEGGSGEGEGGEGSGEGSGEGSEGSGEGSEGEGSEGEGSGEGSGEGSGEGSEGEGS
GEGSEG

Fig. 71b

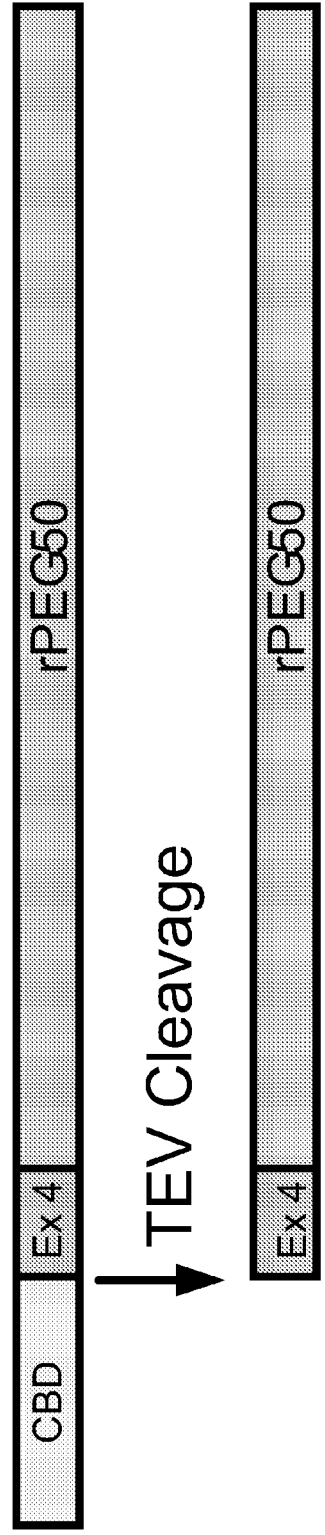

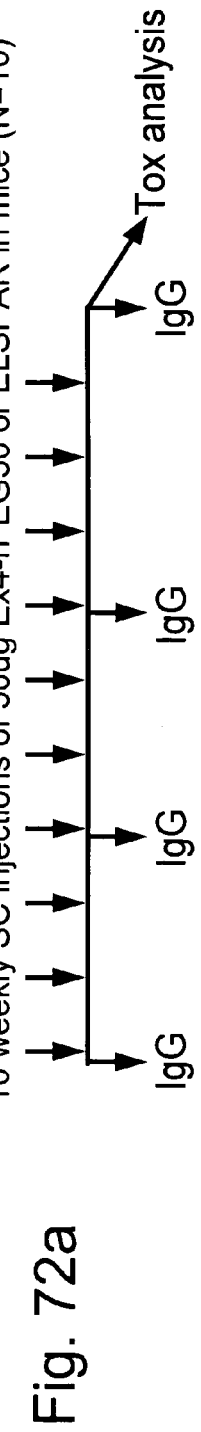
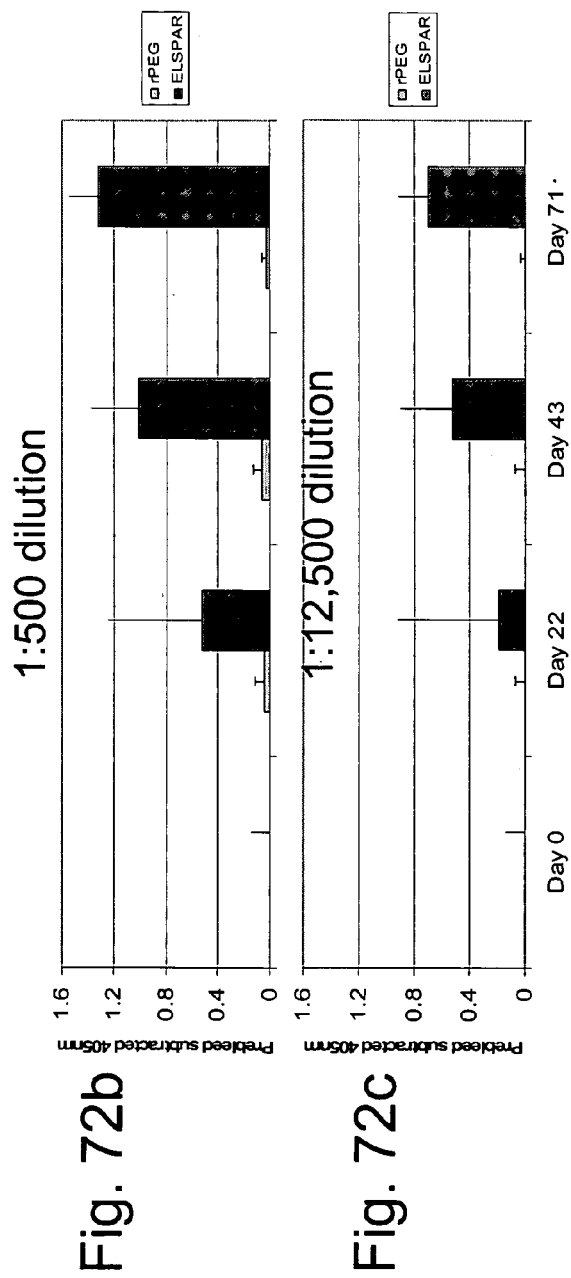
Fig. 72a
Fig. 72b
Fig. 72c

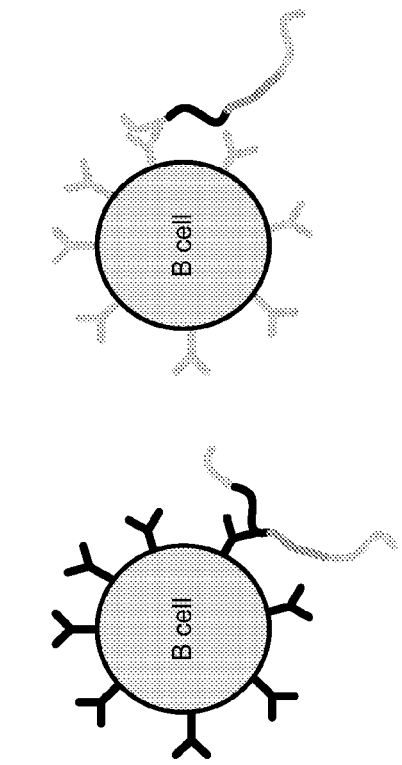
Fig. 74a
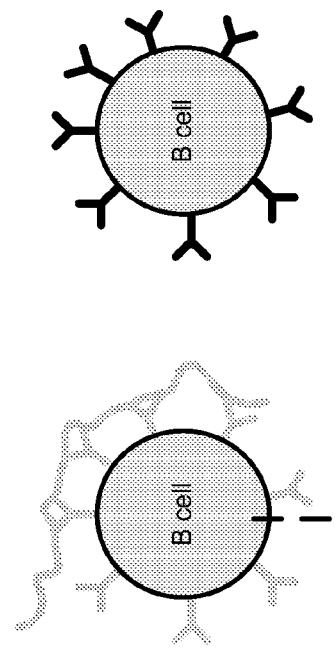
Fig. 74b

Fig. 75 input sequence: ABCDABCDABDEACAD
segment length: 4

| | | 1 | 2 | 3 | 4 | 5 | 6 | 7 | 8 | 9 | 10 | 11 | 12 |
|---|---|---|---|---|---|---|---|---|---|---|---|---|---|
| | | ABCD | BCDA | CDAB | DABC | ABCD | BCDA | CDAB | DABD | ABDE | BDEA | DEAC | EACA |
| 1 | ABCD | 1 | | | | 1 | | | | | | | |
| 2 | BCDA | | 1 | | | | 1 | | | | | | |
| 3 | CDAB | | | 1 | | | | 1 | | | | | |
| 4 | DABC | | | | 1 | | | | | | | | |
| 5 | ABCD | 1 | | | | 1 | | | | | | | |
| 6 | BCDA | | 1 | | | | 1 | | | | | | |
| 7 | CDAB | | | 1 | | | | 1 | | | | | |
| 8 | DABD | | | | | | | | 1 | | | | |
| 9 | ABDE | | | | | | | | | 1 | | | |
| 10 | BDEA | | | | | | | | | | 1 | | |
| 11 | DEAC | | | | | | | | | | | 1 | |
| 12 | EACA | | | | | | | | | | | | 1 |
| | Sum | 2 | 2 | 2 | 1 | 2 | 2 | 2 | 1 | 1 | 1 | 1 | 1 |
| | Max | 2 | | | | | | | | | | | |

- Monomers:
  - GEGGSGEGGE  GEGGEGSSGE  1x
  - GEGGSEGGE   GEGGEGGSE   1x
  - GEGGGEGSE   GEGSEGGGE   1x
  - GEGGSEGSE   GEGSEGGSE   3x
  - GEGGSEGSE   GEGSEGGSE   3x

Fig. 80

GEGGSEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEG
GSEGSEGGSEGGEGGSEGGSEGEGSEGGSEGGEGSEGGSEGEGSEGGSEGGSE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
SGEGSEGGSEGGEGSEGGSEGEGSEGGSEGGEGSEGGSEGEGSEGGSEGGSE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
SGEGSEGGSEGGEGGSEGGSEGEGSEGGSEGGEGSEGGSEGEGSEGGSEGGSE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
GSEGSEGGSEGGEGGSEGGSEGEGSEGGSEGGEGSEGGSEGEGSEGGSEGGSE

GEGGSEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGE
GSEGGSEGGEGGSEGGSEGEGSEGGSEGGEGSEGGSEGEGSEGGSEGEGGSE

GEGGSEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGEG
SGEGSEGGSEGGEGGSEGGSEGEGSEGGSEGGEGSEGGSEGEGSEGGSEGGSE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
SGEGSEGGSEGGEGGSEGGSEGEGSEGGSEGGEGSEGGSEGEGSEGGSEGGGE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
SGEGSEGGSEGGEGGSEGGSEGEGSEGGSEGGEGSEGGSEGEGSEGGSEGGSE

GEGGSEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGEG
SGEGSEGGSEGGEGGSGEGSEGEGSEGGSEGGEGSEGGSEGEGSEGGSEGGGE

GEGGSEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGEG
SGEGSEGGSEGGEGGSGEGSEGEGSEGGSEGGEGSEGGSEGEGSEGGSEGGSE

GEGGSEGEGSEGGSEGGEGSEGGSEGEGGSEGEGSEGGSEGGEGSEGGSEGEGSEGGSEGGEGSEGGSEGEGSEGGSEGGEGSEGGSEGEGSEGGSEGGEGSEG
SGEGSEGGSEGGEGGSEGGSEGEGSEGGSEGGEGSEGGSEGEGSEGGSEGGSE

Fig. 81

MDYKDDDDKGSPGEGSGEGSEGEGSEGSEGSGEGSGEGEGSEGSGEGEGSEGSGEGE
GGEGSGEGGSEGEGGSEGEGGSEGEGSEGSEGGSEGEGSEGSEGGSEGEGSEGSEGS
GEGEGSEGGSEGEGSEGSEGSEGSEGEGGSEGEGSEGSGEGEGSEGSGEGSEGSGEGEG
SEGGSEGEGGSSEGEGSEGGEGSGEGSEGSEGEGSEGSEGSEGEGSEGSGEGGSEGS
EGEGGSEGEGSEGGEGSGEGEGSEGSGEGSEGSGEGSEGSEGGSEGEGSGEGEGG
SEGSEGEGSGEGGSEGSEGEGGSEGEGSEGSEGSEGEGGSEGEGGSEGEGGSEGSE
GEGGSGEGEGSGEGSEGSGEGSEGEGGSEGSEGSGEGEGSGEGEGGSEGSGEGSEGSE
GSGEGEGSEGGEGGSEGEGSEGEGGSEGSGEGSEGGSGEGEGSEGSGEGEGSEGGSEG
EGGSEGEGSEGGSEGEGSEGSEGGEGSEGSGEGEGSSEGEGGSEGSGEGSGEGGSE
GGEGSEGGSEGEGSEGGSEGEGSEGGEGGEGSEGSGEGEGGSGEGEGSGEGEGSEGS
KGEELFTGVVPILVELDGDVNGHKFSVSGEGEGDATYGKLTLKFICTTGKLPVPWPTLV
TTFSYGVQCFSRYPDHMKRHDFFKSAMPEGYVQERTISFKDDGNYKTRAEVKFEGDTLV
NRIELKGIDFKEDGNILGHKLEYNYNSHNVYITADKQKNGIKANFKIRHNIEDGSVQLA
DHYQQNTPIGDGPVLLPDNHYLSTQSALSKDPNEKRDHMVLLEFVTAAGITHGMDELYK

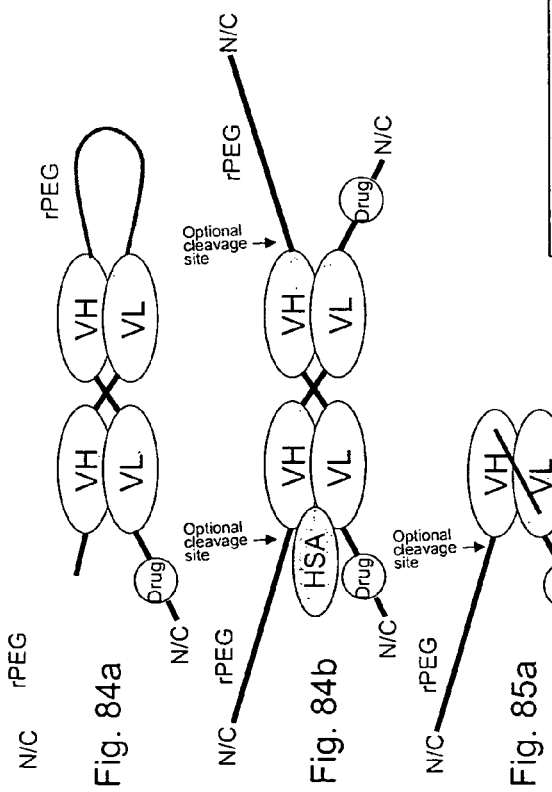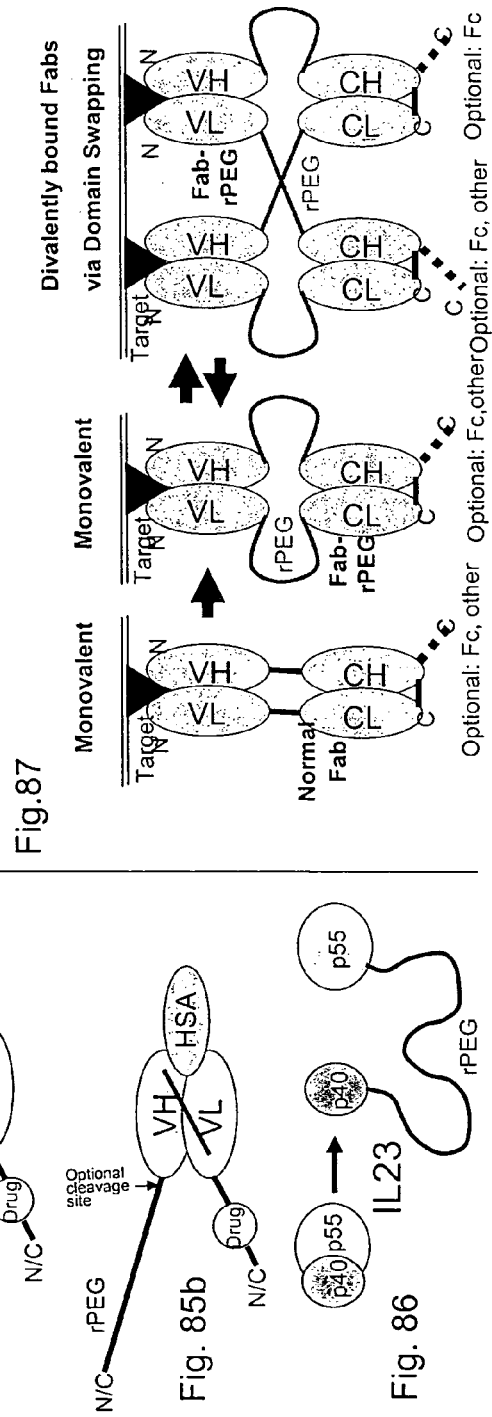

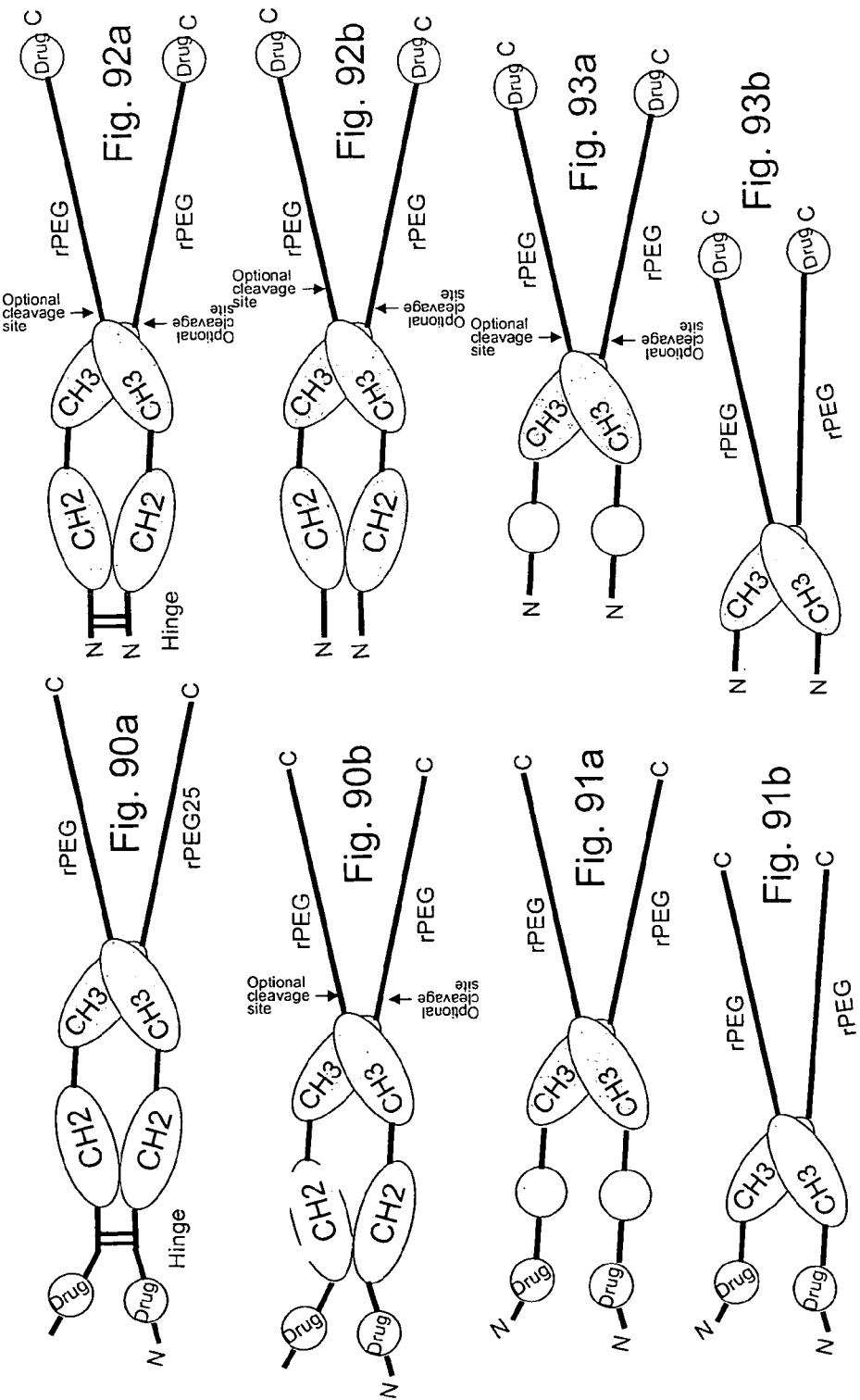

Trap-like High Affinity Formats with Long Halflife

If rPEG product is pre-loaded with (approved) ligand, no peak dose toxicity should occur

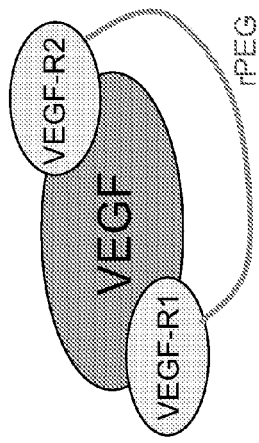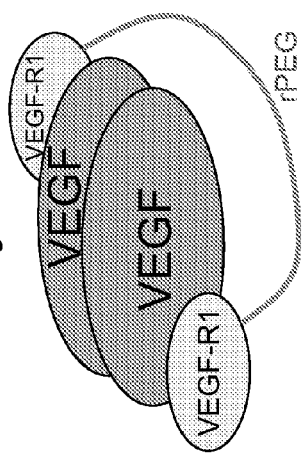

Product is an Inactive Pro-Drug Which is activated by serum protease

Activated Drug has long halflife

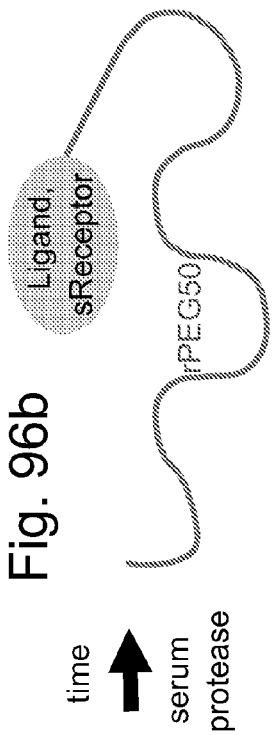

Fig. 96a

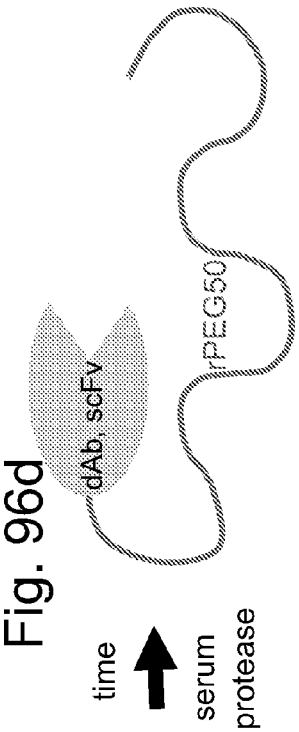

Fig. 96b

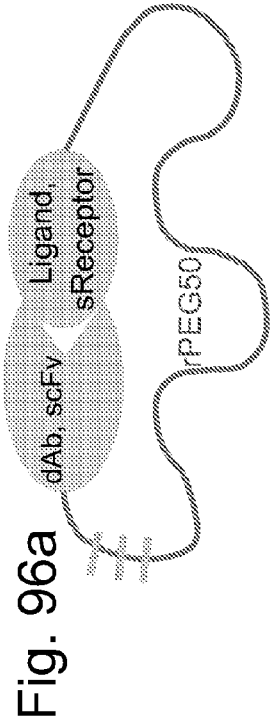

Fig. 96c

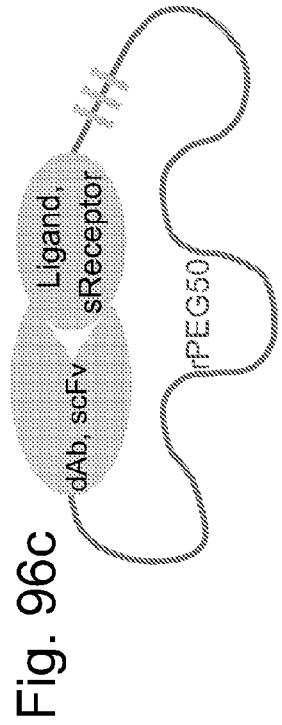

Fig. 96d

Options:
- No cleavage sites
- Protease sites (1-N) for in vivo cleavage in patient's blood
- Protease sites for in vitro cleavage (after purification, before injection)
- Plus or minus Association Sequence (ie peptide like SKVILF, RARADADA or Leu-zipper coiled coil, or domains.

Product is an Inactive Pro-Drug
Which is activated by serum protease

Activated Drug has long halflife

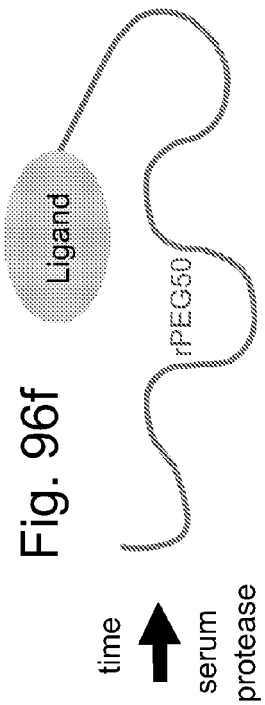

Fig. 96e

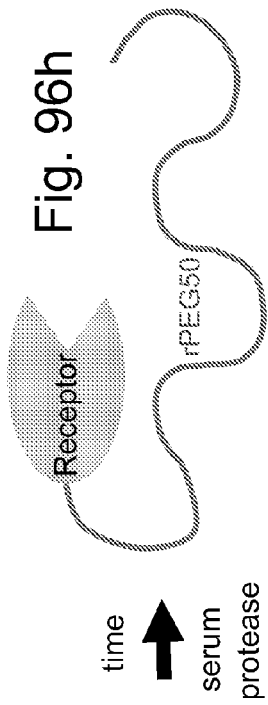

Fig. 96f

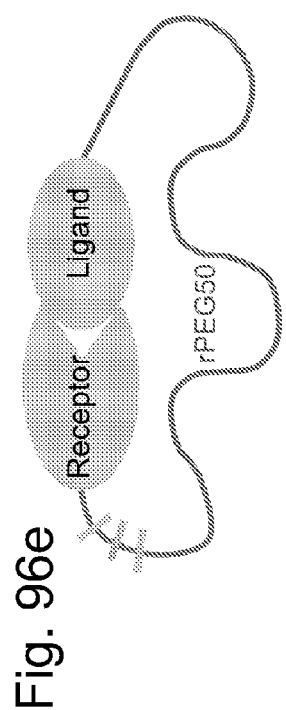

Fig. 96g

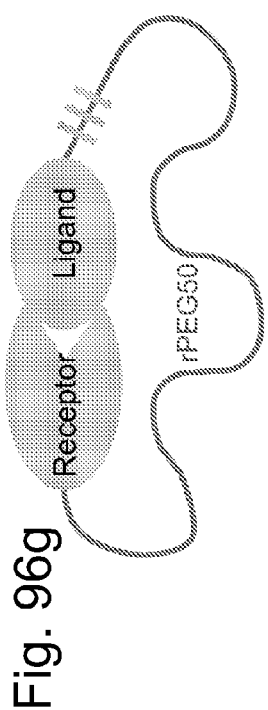

Fig. 96h

Options:
- No cleavage sites
- Protease sites (1-N) for in vivo cleavage in patient's blood
- Protease sites for in vitro cleavage (after purification, before injection)
- Plus or minus Association Sequence (ie peptide like SKVILF, RARADADA or Leu-zipper coiled coil, or domains.

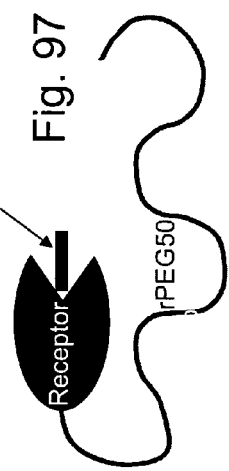
Fig. 97
(Synthetic) peptide, Added to recombinant product (receptor-rPEG) to prevent peak dose toxicity or receptor-mediated clearance
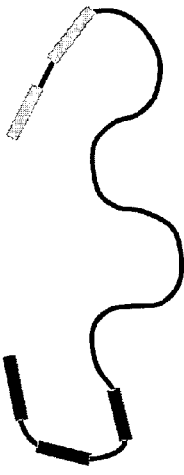
Fig. 98
rPEG product with multiple peptides with the same activity
rPEG product with multiple peptides having different activities, with one or more copies of the peptide per activity.

Fig. 99 The Pro-Drug-rPEG Format Yields a Constant Effective Concentration, Preventing Peak Dose Toxicity

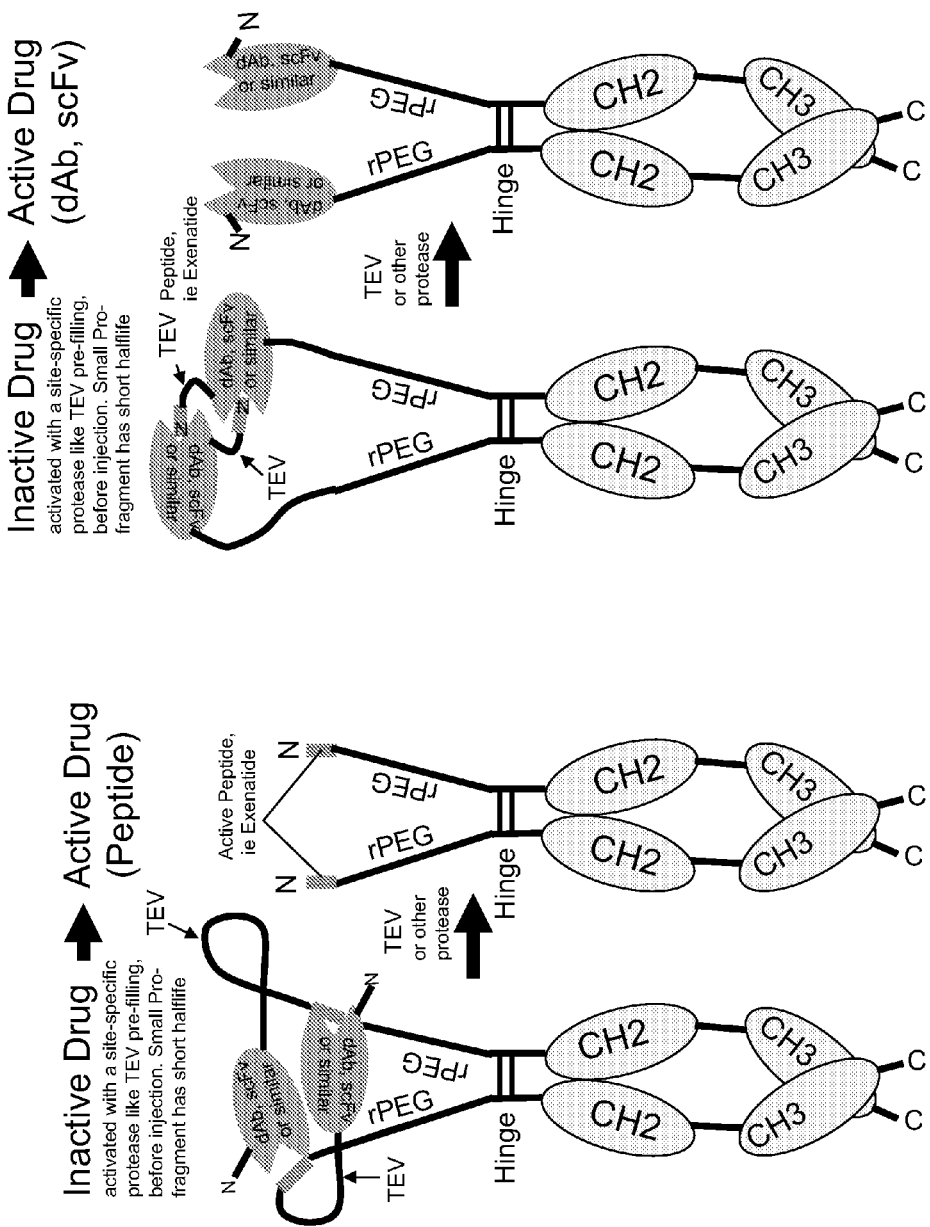

SEQUENCE LISTING

```
<160> NUMBER OF SEQ ID NOS: 524

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 1

His His His His His His
1               5

<210> SEQ ID NO 2
<211> LENGTH: 60
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 2 to 10
      "Gly Gly Glu Gly Gly Ser" repeating units

<400> SEQUENCE: 2

Gly Gly Glu Gly Gly Ser Gly Gly Glu Gly Gly Ser Gly Gly Glu Gly
1               5                   10                  15

Gly Ser Gly Gly Glu Gly Gly Ser Gly Gly Glu Gly Gly Ser Gly Gly
            20                  25                  30

Glu Gly Gly Ser Gly Gly Glu Gly Gly Ser Gly Gly Glu Gly Gly Ser
        35                  40                  45

Gly Gly Glu Gly Gly Ser Gly Gly Glu Gly Gly Ser
    50                  55                  60

<210> SEQ ID NO 3
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1 to 10
      "Gly Glu Gly Gly Gly Glu Gly Gly Glu" repeating units

<400> SEQUENCE: 3

Gly Glu Gly Gly Gly Glu Gly Gly Glu Gly Gly Gly Gly Glu Gly
1               5                   10                  15

Gly Glu Gly Glu Gly Gly Gly Glu Gly Gly Gly Glu Gly Gly Gly
            20                  25                  30

Glu Gly Gly Glu Gly Glu Gly Gly Gly Glu Gly Gly Gly Glu Gly
        35                  40                  45

Gly Gly Glu Gly Gly Glu Gly Glu Gly Gly Gly Glu Gly Gly Gly
    50                  55                  60

Glu Gly Gly Gly Glu Gly Gly Glu Gly Glu Gly Gly Gly Glu Gly
65                  70                  75                  80

Glu Gly Glu Gly Gly Gly Glu Gly Gly Glu
                85                  90

<210> SEQ ID NO 4
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 10, 15, 20 or 50
      "Ser" repeating residues

<400> SEQUENCE: 4

Ser Ser Ser Ser Ser Ser Ser Ser Ser Ser Ser Ser Ser Ser Ser Ser
1               5                   10                  15

Ser Ser Ser Ser Ser Ser Ser Ser Ser Ser Ser Ser Ser Ser Ser Ser
            20                  25                  30

Ser Ser Ser Ser Ser Ser Ser Ser Ser Ser Ser Ser Ser Ser Ser Ser
        35                  40                  45

Ser Ser
```

```
                  50

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Glu Gly Gly Ser Gly Gly Glu Gly Gly Ser Gly Gly Glu Gly
1               5                   10                  15

Gly Ser

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Glu Gly Gly Glu Gly Gly Glu Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ser Ser Ser Ser Ser Ser Ser Ser Ser
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 8

Ser Lys Val Ile Leu Phe Glu
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Arg Ala Asp Ala Asp Ala
1               5
```

<210> SEQ ID NO 10
<211> LENGTH: 224
<212> TYPE: PRT
<213> ORGANISM: Homo sapiens

<400> SEQUENCE: 10

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Ile Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Glu Gly Ser Gly Glu Gly Ser Glu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Glu Gly Gly Ser Glu Gly Ser Glu
1               5

<210> SEQ ID NO 13

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Glu Gly Ser Glu Gly Ser Gly Glu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Glu Gly Ser Glu Gly Gly Ser Glu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Glu Gly Ser Gly Glu Gly Gly Glu
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Glu Gly Gly Ser Glu Gly Gly Glu
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Glu Gly Gly Gly Glu Gly Ser Glu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Gly Glu Gly Gly Glu Gly Ser Gly Glu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Glu Gly Gly Glu Gly Gly Ser Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Glu Gly Ser Glu Gly Gly Gly Glu
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Glu
<220> FEATURE:
<221> NAME/KEY: MOD_RES
<222> LOCATION: (9)..(9)
<223> OTHER INFORMATION: Ser or Glu
<220> FEATURE:
<221> NAME/KEY: MOD_RES
<222> LOCATION: (11)..(11)
<223> OTHER INFORMATION: Ser or Glu

<400> SEQUENCE: 21

Gly Xaa Glu Gly Ser Gly Glu Gly Xaa Gly Xaa Glu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Glu
<220> FEATURE:
<221> NAME/KEY: MOD_RES
<222> LOCATION: (9)..(9)
<223> OTHER INFORMATION: Ser or Glu
<220> FEATURE:
<221> NAME/KEY: MOD_RES
<222> LOCATION: (11)..(11)
<223> OTHER INFORMATION: Ser or Glu

<400> SEQUENCE: 22
```

```
Gly Xaa Glu Gly Gly Ser Glu Gly Xaa Gly Xaa Glu
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Glu

<400> SEQUENCE: 23

```
Gly Xaa Glu Gly Ser Gly Glu Gly Gly Ser Gly Glu
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Glu

<400> SEQUENCE: 24

```
Gly Xaa Glu Gly Gly Ser Glu Gly Gly Ser Gly Glu
1               5                   10
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Glu
<220> FEATURE:
<221> NAME/KEY: MOD_RES
<222> LOCATION: (9)..(9)
<223> OTHER INFORMATION: Ser or Glu
<220> FEATURE:
<221> NAME/KEY: MOD_RES
<222> LOCATION: (11)..(11)
<223> OTHER INFORMATION: Ser or Glu

<400> SEQUENCE: 25

```
Gly Ser Gly Glu Gly Xaa Glu Gly Xaa Gly Xaa Glu
1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Glu
<220> FEATURE:

```
<221> NAME/KEY: MOD_RES
<222> LOCATION: (9)..(9)
<223> OTHER INFORMATION: Ser or Glu
<220> FEATURE:
<221> NAME/KEY: MOD_RES
<222> LOCATION: (11)..(11)
<223> OTHER INFORMATION: Ser or Glu

<400> SEQUENCE: 26

Gly Gly Ser Glu Gly Xaa Glu Gly Xaa Gly Xaa Glu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Glu

<400> SEQUENCE: 27

Gly Ser Gly Glu Gly Xaa Glu Gly Gly Ser Gly Glu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Glu

<400> SEQUENCE: 28

Gly Gly Ser Glu Gly Xaa Glu Gly Gly Ser Gly Glu
1               5                   10

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Glu, Thr or Pro
<220> FEATURE:
<221> NAME/KEY: MOD_RES
<222> LOCATION: (4)..(4)
<223> OTHER INFORMATION: Asp, Glu, Thr or Pro
<220> FEATURE:
<221> NAME/KEY: MOD_RES
<222> LOCATION: (6)..(6)
<223> OTHER INFORMATION: Asp, Glu, Thr or Pro
<220> FEATURE:
<221> NAME/KEY: MOD_RES
<222> LOCATION: (8)..(8)
<223> OTHER INFORMATION: Asp, Glu, Thr or Pro
<220> FEATURE:
<221> NAME/KEY: MOD_RES
<222> LOCATION: (10)..(10)
<223> OTHER INFORMATION: Asp, Glu, Thr or Pro
<220> FEATURE:
<221> NAME/KEY: MOD_RES
```

```
<222> LOCATION: (12)..(12)
<223> OTHER INFORMATION: Asp, Glu, Thr or Pro
<220> FEATURE:
<221> NAME/KEY: MOD_RES
<222> LOCATION: (14)..(14)
<223> OTHER INFORMATION: Asp, Glu, Thr or Pro
<220> FEATURE:
<221> NAME/KEY: MOD_RES
<222> LOCATION: (16)..(16)
<223> OTHER INFORMATION: Asp, Glu, Thr or Pro
<220> FEATURE:
<221> NAME/KEY: MOD_RES
<222> LOCATION: (18)..(18)
<223> OTHER INFORMATION: Asp, Glu, Thr or Pro
<220> FEATURE:
<221> NAME/KEY: MOD_RES
<222> LOCATION: (20)..(20)
<223> OTHER INFORMATION: Asp, Glu, Thr or Pro

<400> SEQUENCE: 29

Gly Xaa Gly Xaa Gly Xaa Gly Xaa Gly Xaa Gly Xaa Gly Xaa Gly Xaa
1               5                   10                  15

Gly Xaa Gly Xaa
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Glu, Thr or Pro
<220> FEATURE:
<221> NAME/KEY: MOD_RES
<222> LOCATION: (4)..(4)
<223> OTHER INFORMATION: Asp, Glu, Thr or Pro
<220> FEATURE:
<221> NAME/KEY: MOD_RES
<222> LOCATION: (6)..(6)
<223> OTHER INFORMATION: Asp, Glu, Thr or Pro
<220> FEATURE:
<221> NAME/KEY: MOD_RES
<222> LOCATION: (8)..(8)
<223> OTHER INFORMATION: Asp, Glu, Thr or Pro
<220> FEATURE:
<221> NAME/KEY: MOD_RES
<222> LOCATION: (10)..(10)
<223> OTHER INFORMATION: Asp, Glu, Thr or Pro
<220> FEATURE:
<221> NAME/KEY: MOD_RES
<222> LOCATION: (12)..(12)
<223> OTHER INFORMATION: Asp, Glu, Thr or Pro
<220> FEATURE:
<221> NAME/KEY: MOD_RES
<222> LOCATION: (14)..(14)
<223> OTHER INFORMATION: Asp, Glu, Thr or Pro
<220> FEATURE:
<221> NAME/KEY: MOD_RES
<222> LOCATION: (16)..(16)
<223> OTHER INFORMATION: Asp, Glu, Thr or Pro
<220> FEATURE:
<221> NAME/KEY: MOD_RES
<222> LOCATION: (18)..(18)
<223> OTHER INFORMATION: Asp, Glu, Thr or Pro
<220> FEATURE:
<221> NAME/KEY: MOD_RES
<222> LOCATION: (20)..(20)
<223> OTHER INFORMATION: Asp, Glu, Thr or Pro

<400> SEQUENCE: 30

Ser Xaa Ser Xaa Ser Xaa Ser Xaa Ser Xaa Ser Xaa Ser Xaa Ser Xaa
```

Ser Xaa Ser Xaa
        20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Thr or Pro
<220> FEATURE:
<221> NAME/KEY: MOD_RES
<222> LOCATION: (6)..(6)
<223> OTHER INFORMATION: Asp, Glu, Thr or Pro
<220> FEATURE:
<221> NAME/KEY: MOD_RES
<222> LOCATION: (9)..(9)
<223> OTHER INFORMATION: Asp, Glu, Thr or Pro
<220> FEATURE:
<221> NAME/KEY: MOD_RES
<222> LOCATION: (12)..(12)
<223> OTHER INFORMATION: Asp, Glu, Thr or Pro
<220> FEATURE:
<221> NAME/KEY: MOD_RES
<222> LOCATION: (15)..(15)
<223> OTHER INFORMATION: Asp, Glu, Thr or Pro
<220> FEATURE:
<221> NAME/KEY: MOD_RES
<222> LOCATION: (18)..(18)
<223> OTHER INFORMATION: Asp, Glu, Thr or Pro
<220> FEATURE:
<221> NAME/KEY: MOD_RES
<222> LOCATION: (21)..(21)
<223> OTHER INFORMATION: Asp, Glu, Thr or Pro

<400> SEQUENCE: 31

Gly Gly Xaa Gly Gly Xaa Gly Gly Xaa Gly Gly Xaa Gly Gly Xaa Gly
1               5                   10                  15

Gly Xaa Gly Gly Xaa
        20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Thr or Pro
<220> FEATURE:
<221> NAME/KEY: MOD_RES
<222> LOCATION: (6)..(6)
<223> OTHER INFORMATION: Asp, Glu, Thr or Pro
<220> FEATURE:
<221> NAME/KEY: MOD_RES
<222> LOCATION: (9)..(9)
<223> OTHER INFORMATION: Asp, Glu, Thr or Pro
<220> FEATURE:
<221> NAME/KEY: MOD_RES
<222> LOCATION: (12)..(12)
<223> OTHER INFORMATION: Asp, Glu, Thr or Pro
<220> FEATURE:
<221> NAME/KEY: MOD_RES
<222> LOCATION: (15)..(15)
<223> OTHER INFORMATION: Asp, Glu, Thr or Pro
<220> FEATURE:

```
<221> NAME/KEY: MOD_RES
<222> LOCATION: (18)..(18)
<223> OTHER INFORMATION: Asp, Glu, Thr or Pro
<220> FEATURE:
<221> NAME/KEY: MOD_RES
<222> LOCATION: (21)..(21)
<223> OTHER INFORMATION: Asp, Glu, Thr or Pro

<400> SEQUENCE: 32

Ser Ser Xaa Ser Ser Xaa Ser Ser Xaa Ser Ser Xaa Ser Ser Xaa Ser
1               5                   10                  15

Ser Xaa Ser Ser Xaa
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Glu, Thr or Pro
<220> FEATURE:
<221> NAME/KEY: MOD_RES
<222> LOCATION: (8)..(8)
<223> OTHER INFORMATION: Asp, Glu, Thr or Pro
<220> FEATURE:
<221> NAME/KEY: MOD_RES
<222> LOCATION: (12)..(12)
<223> OTHER INFORMATION: Asp, Glu, Thr or Pro
<220> FEATURE:
<221> NAME/KEY: MOD_RES
<222> LOCATION: (16)..(16)
<223> OTHER INFORMATION: Asp, Glu, Thr or Pro
<220> FEATURE:
<221> NAME/KEY: MOD_RES
<222> LOCATION: (20)..(20)
<223> OTHER INFORMATION: Asp, Glu, Thr or Pro

<400> SEQUENCE: 33

Gly Gly Gly Xaa Gly Gly Gly Xaa Gly Gly Gly Xaa Gly Gly Gly Xaa
1               5                   10                  15

Gly Gly Gly Xaa
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Glu, Thr or Pro
<220> FEATURE:
<221> NAME/KEY: MOD_RES
<222> LOCATION: (8)..(8)
<223> OTHER INFORMATION: Asp, Glu, Thr or Pro
<220> FEATURE:
<221> NAME/KEY: MOD_RES
<222> LOCATION: (12)..(12)
<223> OTHER INFORMATION: Asp, Glu, Thr or Pro
<220> FEATURE:
<221> NAME/KEY: MOD_RES
<222> LOCATION: (16)..(16)
<223> OTHER INFORMATION: Asp, Glu, Thr or Pro
<220> FEATURE:
<221> NAME/KEY: MOD_RES
```

```
<222> LOCATION: (20)..(20)
<223> OTHER INFORMATION: Asp, Glu, Thr or Pro

<400> SEQUENCE: 34

Ser Ser Ser Xaa Ser Ser Ser Xaa Ser Ser Ser Xaa Ser Ser Ser Xaa
1               5                   10                  15

Ser Ser Ser Xaa
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Glu, Thr or Pro
<220> FEATURE:
<221> NAME/KEY: MOD_RES
<222> LOCATION: (10)..(10)
<223> OTHER INFORMATION: Asp, Glu, Thr or Pro
<220> FEATURE:
<221> NAME/KEY: MOD_RES
<222> LOCATION: (15)..(15)
<223> OTHER INFORMATION: Asp, Glu, Thr or Pro
<220> FEATURE:
<221> NAME/KEY: MOD_RES
<222> LOCATION: (20)..(20)
<223> OTHER INFORMATION: Asp, Glu, Thr or Pro

<400> SEQUENCE: 35

Gly Gly Gly Gly Xaa Gly Gly Gly Gly Xaa Gly Gly Gly Gly Xaa Gly
1               5                   10                  15

Gly Gly Gly Xaa
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Glu, Thr or Pro
<220> FEATURE:
<221> NAME/KEY: MOD_RES
<222> LOCATION: (10)..(10)
<223> OTHER INFORMATION: Asp, Glu, Thr or Pro
<220> FEATURE:
<221> NAME/KEY: MOD_RES
<222> LOCATION: (15)..(15)
<223> OTHER INFORMATION: Asp, Glu, Thr or Pro
<220> FEATURE:
<221> NAME/KEY: MOD_RES
<222> LOCATION: (20)..(20)
<223> OTHER INFORMATION: Asp, Glu, Thr or Pro

<400> SEQUENCE: 36

Ser Ser Ser Ser Xaa Ser Ser Ser Ser Xaa Ser Ser Ser Ser Xaa Ser
1               5                   10                  15

Ser Ser Ser Xaa
            20

<210> SEQ ID NO 37
```

```
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 1 to 20
      "Gly" repeating residues
<220> FEATURE:
<221> NAME/KEY: MOD_RES
<222> LOCATION: (21)..(21)
<223> OTHER INFORMATION: Asp, Glu, Thr or Pro
<220> FEATURE:
<221> NAME/KEY: MOD_RES
<222> LOCATION: (22)..(41)
<223> OTHER INFORMATION: This region may encompass 1 to 20
      "Gly" repeating residues
<220> FEATURE:
<221> NAME/KEY: MOD_RES
<222> LOCATION: (42)..(42)
<223> OTHER INFORMATION: Asp, Glu, Thr or Pro
<220> FEATURE:
<221> NAME/KEY: MOD_RES
<222> LOCATION: (43)..(62)
<223> OTHER INFORMATION: This region may encompass 1 to 20
      "Gly" repeating residues
<220> FEATURE:
<221> NAME/KEY: MOD_RES
<222> LOCATION: (63)..(63)
<223> OTHER INFORMATION: Asp, Glu, Thr or Pro
<220> FEATURE:
<221> NAME/KEY: MOD_RES
<222> LOCATION: (64)..(83)
<223> OTHER INFORMATION: This region may encompass 1 to 20
      "Gly" repeating residues
<220> FEATURE:
<221> NAME/KEY: MOD_RES
<222> LOCATION: (84)..(84)
<223> OTHER INFORMATION: Asp, Glu, Thr or Pro
<220> FEATURE:
<221> NAME/KEY: MOD_RES
<222> LOCATION: (85)..(104)
<223> OTHER INFORMATION: This region may encompass 1 to 20
      "Gly" repeating residues
<220> FEATURE:
<221> NAME/KEY: MOD_RES
<222> LOCATION: (105)..(105)
<223> OTHER INFORMATION: Asp, Glu, Thr or Pro
<220> FEATURE:
<221> NAME/KEY: MOD_RES
<222> LOCATION: (106)..(125)
<223> OTHER INFORMATION: This region may encompass 1 to 20
      "Gly" repeating residues
<220> FEATURE:
<221> NAME/KEY: MOD_RES
<222> LOCATION: (126)..(126)
<223> OTHER INFORMATION: Asp, Glu, Thr or Pro
<220> FEATURE:
<221> NAME/KEY: MOD_RES
<222> LOCATION: (127)..(146)
<223> OTHER INFORMATION: This region may encompass 1 to 20
      "Gly" repeating residues
<220> FEATURE:
<221> NAME/KEY: MOD_RES
<222> LOCATION: (147)..(147)
<223> OTHER INFORMATION: Asp, Glu, Thr or Pro
<220> FEATURE:
<221> NAME/KEY: MOD_RES
<222> LOCATION: (148)..(167)
<223> OTHER INFORMATION: This region may encompass 1 to 20
      "Gly" repeating residues
<220> FEATURE:
<221> NAME/KEY: MOD_RES
<222> LOCATION: (168)..(168)
<223> OTHER INFORMATION: Asp, Glu, Thr or Pro
<220> FEATURE:
```

```
<221> NAME/KEY: MOD_RES
<222> LOCATION: (169)..(188)
<223> OTHER INFORMATION: This region may encompass 1 to 20
      "Gly" repeating residues
<220> FEATURE:
<221> NAME/KEY: MOD_RES
<222> LOCATION: (189)..(189)
<223> OTHER INFORMATION: Asp, Glu, Thr or Pro
<220> FEATURE:
<221> NAME/KEY: MOD_RES
<222> LOCATION: (190)..(209)
<223> OTHER INFORMATION: This region may encompass 1 to 20
      "Gly" repeating residues
<220> FEATURE:
<221> NAME/KEY: MOD_RES
<222> LOCATION: (210)..(210)
<223> OTHER INFORMATION: Asp, Glu, Thr or Pro

<400> SEQUENCE: 37

Gly Gly Gly Gly Gly Gly Gly Gly Gly Gly Gly Gly Gly Gly Gly
1               5                   10                  15

Gly Gly Gly Gly Xaa Gly Gly Gly Gly Gly Gly Gly Gly Gly Gly
            20                  25                  30

Gly Gly Gly Gly Gly Gly Gly Gly Xaa Gly Gly Gly Gly Gly Gly
        35                  40                  45

Gly Gly Gly Gly Gly Gly Gly Gly Gly Gly Gly Gly Gly Xaa Gly
    50                  55                  60

Gly Gly Gly Gly Gly Gly Gly Gly Gly Gly Gly Gly Gly Gly Gly
65                  70                  75                  80

Gly Gly Gly Xaa Gly Gly Gly Gly Gly Gly Gly Gly Gly Gly Gly
                85                  90                  95

Gly Gly Gly Gly Gly Gly Gly Gly Xaa Gly Gly Gly Gly Gly Gly
            100                 105                 110

Gly Gly Gly Gly Gly Gly Gly Gly Gly Gly Gly Xaa Gly Gly
        115                 120                 125

Gly Gly Gly Gly Gly Gly Gly Gly Gly Gly Gly Gly Gly Gly Gly
    130                 135                 140

Gly Gly Xaa Gly Gly Gly Gly Gly Gly Gly Gly Gly Gly Gly Gly
145                 150                 155                 160

Gly Gly Gly Gly Gly Gly Xaa Gly Gly Gly Gly Gly Gly Gly Gly
                165                 170                 175

Gly Gly Gly Gly Gly Gly Gly Gly Gly Gly Gly Xaa Gly Gly Gly
            180                 185                 190

Gly Gly Gly Gly Gly Gly Gly Gly Gly Gly Gly Gly Gly Gly Gly
        195                 200                 205

Gly Xaa
    210

<210> SEQ ID NO 38
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Asp, Glu, Thr or Pro
<220> FEATURE:
<221> NAME/KEY: MOD_RES
<222> LOCATION: (22)..(41)
<223> OTHER INFORMATION: This region may encompass 1 to 20
      "Ser" repeating residues
```

```
<220> FEATURE:
<221> NAME/KEY: MOD_RES
<222> LOCATION: (42)..(42)
<223> OTHER INFORMATION: Asp, Glu, Thr or Pro
<220> FEATURE:
<221> NAME/KEY: MOD_RES
<222> LOCATION: (43)..(62)
<223> OTHER INFORMATION: This region may encompass 1 to 20
      "Ser" repeating residues
<220> FEATURE:
<221> NAME/KEY: MOD_RES
<222> LOCATION: (63)..(63)
<223> OTHER INFORMATION: Asp, Glu, Thr or Pro
<220> FEATURE:
<221> NAME/KEY: MOD_RES
<222> LOCATION: (64)..(83)
<223> OTHER INFORMATION: This region may encompass 1 to 20
      "Ser" repeating residues
<220> FEATURE:
<221> NAME/KEY: MOD_RES
<222> LOCATION: (84)..(84)
<223> OTHER INFORMATION: Asp, Glu, Thr or Pro
<220> FEATURE:
<221> NAME/KEY: MOD_RES
<222> LOCATION: (85)..(104)
<223> OTHER INFORMATION: This region may encompass 1 to 20
      "Ser" repeating residues
<220> FEATURE:
<221> NAME/KEY: MOD_RES
<222> LOCATION: (105)..(105)
<223> OTHER INFORMATION: Asp, Glu, Thr or Pro
<220> FEATURE:
<221> NAME/KEY: MOD_RES
<222> LOCATION: (106)..(125)
<223> OTHER INFORMATION: This region may encompass 1 to 20
      "Ser" repeating residues
<220> FEATURE:
<221> NAME/KEY: MOD_RES
<222> LOCATION: (126)..(126)
<223> OTHER INFORMATION: Asp, Glu, Thr or Pro
<220> FEATURE:
<221> NAME/KEY: MOD_RES
<222> LOCATION: (127)..(146)
<223> OTHER INFORMATION: This region may encompass 1 to 20
      "Ser" repeating residues
<220> FEATURE:
<221> NAME/KEY: MOD_RES
<222> LOCATION: (147)..(147)
<223> OTHER INFORMATION: Asp, Glu, Thr or Pro
<220> FEATURE:
<221> NAME/KEY: MOD_RES
<222> LOCATION: (148)..(167)
<223> OTHER INFORMATION: This region may encompass 1 to 20
      "Ser" repeating residues
<220> FEATURE:
<221> NAME/KEY: MOD_RES
<222> LOCATION: (168)..(168)
<223> OTHER INFORMATION: Asp, Glu, Thr or Pro
<220> FEATURE:
<221> NAME/KEY: MOD_RES
<222> LOCATION: (169)..(187)
<223> OTHER INFORMATION: This region may encompass 1 to 20
      "Ser" repeating residues
<220> FEATURE:
<221> NAME/KEY: MOD_RES
<222> LOCATION: (189)..(189)
<223> OTHER INFORMATION: Asp, Glu, Thr or Pro
<220> FEATURE:
<221> NAME/KEY: MOD_RES
<222> LOCATION: (190)..(209)
<223> OTHER INFORMATION: This region may encompass 1 to 20
      "Ser" repeating residues
<220> FEATURE:
<221> NAME/KEY: MOD_RES
<222> LOCATION: (210)..(210)
<223> OTHER INFORMATION: Asp, Glu, Thr or Pro

<400> SEQUENCE: 38
```

```
Ser Ser Ser Ser Ser Ser Ser Ser Ser Ser Ser Ser Ser Ser Ser
1               5                   10                  15

Ser Ser Ser Ser Xaa Ser Ser Ser Ser Ser Ser Ser Ser Ser Ser
                20                  25                  30

Ser Ser Ser Ser Ser Ser Ser Ser Xaa Ser Ser Ser Ser Ser Ser
        35                  40                  45

Ser Ser Ser Ser Ser Ser Ser Ser Ser Ser Ser Ser Xaa Ser Ser
    50                  55                  60

Ser Ser Ser Ser Ser Ser Ser Ser Ser Ser Ser Ser Ser Ser Ser
65                  70                  75                  80

Ser Ser Ser Xaa Ser Ser Ser Ser Ser Ser Ser Ser Ser Ser Ser
                85                  90                  95

Ser Ser Ser Ser Ser Ser Ser Xaa Ser Ser Ser Ser Ser Ser Ser
                100                 105                 110

Ser Ser Ser Ser Ser Ser Ser Ser Ser Ser Ser Xaa Ser Ser Ser
            115                 120                 125

Ser Ser Ser Ser Ser Ser Ser Ser Ser Ser Ser Ser Ser Ser Ser
        130                 135                 140

Ser Ser Xaa Ser Ser Ser Ser Ser Ser Ser Ser Ser Ser Ser Ser
145                 150                 155                 160

Ser Ser Ser Ser Ser Ser Xaa Ser Ser Ser Ser Ser Ser Ser Ser
                165                 170                 175

Ser Ser Ser Ser Ser Ser Ser Ser Ser Ser Xaa Ser Ser Ser Ser
            180                 185                 190

Ser Ser Ser Ser Ser Ser Ser Ser Ser Ser Ser Ser Ser Ser Ser
        195                 200                 205

Ser Xaa
    210

<210> SEQ ID NO 39
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Ser Gly Ser Ser Glu Ser Ser Gly Ser Ser Glu Ser Ser Gly Ser
1               5                   10                  15

Ser Glu Ser Ser Gly Ser Ser Glu Ser Ser Gly Ser Ser Glu Ser Ser
                20                  25                  30

Gly Ser Ser Glu Ser Ser Gly Ser Ser Glu Ser Ser Gly Ser Ser Glu
        35                  40                  45

Ser Ser Gly Ser Ser Glu Ser Ser Gly Ser Ser Glu Ser Ser Gly Ser
    50                  55                  60

Ser Glu Ser Ser Gly Ser Ser Glu Ser Ser Gly Ser Ser Glu Ser Ser
65                  70                  75                  80

Gly Ser Ser Glu Ser Ser Gly Ser Ser Glu Ser Ser Gly Ser Ser Glu
                85                  90                  95

Ser Ser Gly Ser Ser Glu Ser Ser Gly Ser Ser Glu Ser Ser Gly Ser
                100                 105                 110

Ser Glu Ser Ser Gly Ser Ser Glu Ser Ser Gly Ser Ser Glu Ser Ser
            115                 120                 125

Gly Ser Ser Glu Ser Ser Gly Ser Ser Glu Ser Ser Gly Ser Ser Glu
        130                 135                 140
```

Ser Ser Gly Ser Ser Glu Ser Gly Ser Ser Glu Ser Ser Gly Ser
145                 150                 155                 160

Ser Glu Ser Ser Gly Ser Ser Glu Ser Ser Gly Ser Ser Glu Ser Ser
            165                 170                 175

Gly Ser Ser Glu Ser Ser Gly Ser Ser Glu Ser Ser Gly Ser Ser Glu
                180                 185                 190

Ser Ser Gly Ser Ser Glu Ser Ser Gly Ser Ser Glu Ser Ser Gly Ser
        195                 200                 205

Ser Glu Ser Ser Gly Ser Ser Glu Ser Ser Gly Ser Ser Glu Ser Ser
    210                 215                 220

Gly Ser Ser Glu Ser Ser Gly Ser Ser Glu Ser Ser Gly Ser Ser Glu
225                 230                 235                 240

Ser Ser Gly Ser Ser Glu Ser Ser Gly Ser Ser Glu Ser Ser Gly Ser
                245                 250                 255

Ser Glu Ser Ser Gly Ser Ser Glu Ser Ser Gly Ser Ser Glu Ser Ser
            260                 265                 270

Gly Ser Ser Glu Ser Ser Gly Ser Ser Glu Ser Ser Gly Ser Ser Glu
                275                 280                 285

<210> SEQ ID NO 40
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Ser Glu Ser Ser Ser Glu Ser Ser Ser Glu Ser Ser Ser Glu Ser
1               5                   10                  15

Ser Ser Glu Ser Ser Ser Glu Ser Ser Ser Glu Ser Ser Ser Glu
            20                  25                  30

Ser Ser Ser Glu Ser Ser Ser Glu Ser Ser Ser Glu Ser Ser Ser Glu
                35                  40                  45

Ser Ser Glu Ser Ser Ser Glu Ser Ser Ser Glu Ser Ser Ser Glu Ser
    50                  55                  60

Ser Ser Glu Ser Ser Ser Glu Ser Ser Glu Ser Ser Ser Ser Glu
65                  70                  75                  80

Ser Ser Glu Ser Ser Ser Glu Ser Ser Ser Glu Ser Ser Ser Glu
                85                  90                  95

Ser Ser Glu Ser Ser Ser Glu Ser Ser Ser Glu Ser Ser Ser Glu Ser
            100                 105                 110

Ser Ser Glu Ser Ser Ser Glu Ser Ser Glu Ser Ser Ser Ser Glu
                115                 120                 125

Ser Ser Ser Glu Ser Ser Glu Ser Ser Ser Glu Ser Ser Ser Glu
        130                 135                 140

Ser Ser Glu Ser Ser Ser Glu Ser Ser Ser Glu Ser Ser Ser Glu Ser
145                 150                 155                 160

Ser Ser Ser Glu Ser Ser Ser Glu Ser Ser Glu Ser Ser Ser Glu
                165                 170                 175

Ser Ser Ser Glu Ser Ser Ser Glu Ser Ser Ser Glu Ser Ser Ser Glu
                180                 185                 190

Ser Ser Glu Ser Ser Ser Glu Ser Ser Ser Glu Ser Ser Glu Ser
        195                 200                 205

Ser Ser Glu Ser Ser Ser Glu Ser Ser Glu Ser Ser Ser Ser Glu

```
                210                 215                 220
Ser Ser Ser Glu Ser Ser Glu Ser Ser Ser Glu Ser Ser Ser Glu
225                 230                 235                 240

Ser Ser Glu Ser Ser Ser Glu Ser Ser Glu Ser Ser Ser Glu Ser
                245                 250                 255

Ser Ser Ser Glu Ser Ser Glu Ser Ser Glu Ser Ser Ser Glu
                260                 265                 270

Ser Ser Ser Glu Ser Ser Glu Ser Ser Ser Glu Ser Ser Ser Glu
            275                 280                 285
```

<210> SEQ ID NO 41
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gly Glu Gly Gly Gly Glu Gly Gly Glu Gly Gly Gly Gly Glu Gly
1               5                   10                  15

Gly Glu Gly Glu Gly Gly Gly Glu Gly Gly Gly Gly Glu Gly Gly
                20                  25                  30

Glu Gly Gly Glu Gly Glu Gly Gly Glu Gly Gly Glu Gly Glu Gly
            35                  40                  45

Gly Gly Glu Gly Gly Glu Gly Glu Gly Gly Glu Gly Gly Glu Gly
        50                  55                  60

Glu Gly Gly Glu Gly Gly Gly Glu Gly Gly Glu Gly Gly Glu Gly
65                  70                  75                  80

Glu Gly Glu Gly Gly Gly Gly Glu Gly Glu Gly Gly Gly Gly Glu
                85                  90                  95

Gly Gly Glu Gly Glu Gly Gly Gly Glu Gly Gly Glu Gly Gly Gly
                100                 105                 110

Gly Glu Gly Gly Glu Gly Gly Gly Gly Glu Gly Gly Glu Gly Glu
        115                 120                 125

Gly Gly Gly Glu Gly Gly Glu Gly Glu Gly Gly Glu Gly Gly Glu
    130                 135                 140

Gly Glu Gly Gly Gly Glu Gly Gly Glu Gly Gly Gly Gly Glu Gly
145                 150                 155                 160

Gly Glu Gly Glu Gly Gly Gly Glu Gly Gly Glu Gly Gly Gly Gly
                165                 170                 175

Glu Gly Gly Glu Gly Gly Gly Gly Glu Gly Gly Glu Gly Glu Gly
            180                 185                 190

Gly Gly Glu Gly Gly Glu Gly Gly Gly Glu Gly Gly Glu Gly Gly
        195                 200                 205

Glu Gly Gly Gly Glu Gly Gly Glu Gly Glu Gly Gly Glu Gly Gly
    210                 215                 220

Glu Gly Glu Gly Gly Gly Gly Glu Gly Glu Gly Gly Gly Gly Glu
225                 230                 235                 240

Gly Gly Glu Gly Glu Gly Gly Gly Glu Gly Gly Glu Gly Gly Gly
                245                 250                 255

Gly Glu Gly Gly Glu Gly Gly Gly Gly Glu Gly Gly Glu Gly Glu
            260                 265                 270

Gly Gly Gly Glu Gly Gly Glu Gly Glu Gly Gly Gly Glu Gly Glu
        275                 280                 285
```

```
Gly Glu Gly Gly Gly Glu Gly Glu Gly Glu Gly Gly Gly Glu Gly
    290                 295                 300
Gly Glu Gly Glu Gly Gly Gly Glu Gly Glu Gly Glu Gly Gly Gly
305                 310                 315                 320
Glu Gly Gly Glu
```

```
<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Ser Glu
1               5
```

```
<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Ser Glu
1
```

```
<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Glu Glu Glu Glu
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Gly
1               5
```

```
<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ser Ser Ser Ser
1               5
```

```
<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ala Ala Ala Ala
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Glu Ser Ser Ser Glu Ser Ser Glu
1               5

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Ser Glu Ser Ser Ser Ser Glu Ser Ser Ser Glu
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ser Ser Glu Ser Ser Ser Ser Glu Ser Ser Ser Ser Glu
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ser Ser Ser Glu Ser Ser Ser Ser Ser Ser Glu
1               5                   10

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Ser Ser Ser Glu
1

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Ser Ser Ser Glu
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ser Ser Ser Ser Glu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Ser Ser Ser Ser Glu
1               5

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Glu Gly Glu Ser Glu Gly Glu Gly Glu Gly Glu Ser Glu Gly Glu
1               5                   10                  15

Gly Glu Ser Gly Glu
            20

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Gly Gly Gly Gly Gly Gly Gly Gly Glu Glu Glu Glu Glu Glu
1               5                   10                  15

Glu Glu Glu Glu Gly Gly Gly Gly Gly Gly Gly Gly Gly Glu Glu
            20                  25                  30

```
Glu Glu Glu Glu Glu Glu Glu Glu
        35                  40

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Glu Glu
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Glu Gly Gly Ser
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Gly Gly Ser Gly Gly
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Glu Gly Gly Ser Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Ser Gly Gly Glu
1               5

<210> SEQ ID NO 63
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 63

Ser Gly Gly Glu Gly Gly
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ser Gly Gly Glu Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Glu Glu Gly Ser Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ser Ser Gly Glu Glu
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Ser Glu Gly Glu
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Ser Gly Glu Glu Gly
1               5
```

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Glu Glu Gly Gly Gly Ser Ser Ser Gly Glu Gly Gly Ser Ser Ser
1               5                   10                  15

Gly Ser Glu Glu
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Ser Gly Gly Ser Ser Glu Gly Ser Ser Glu Glu Ser Gly Ser Ser
1               5                   10                  15

Glu Gly Ser Glu
            20

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Glu Glu Ser Ser Ser Gly Gly Gly
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Glu Ser Ser Gly Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Ser Gly Ser Glu
1               5

<210> SEQ ID NO 74
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Glu Ser Gly Ser
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Ser Gly Gly Ser Glu
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Ser Gly Glu Glu Ser Gly
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Ser Gly Pro Glu Ser Gly
1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Gly Glu Gly Glu Gly Glu Gly Glu Gly Glu
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ser Gly Ser Gly Ser Gly Ser Gly Ser Gly Ser Gly Ser
```

```
1               5                   10
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ser Glu Ser Glu Ser Glu Ser Glu Ser Glu Ser Glu Ser Glu Ser Glu
1               5                   10                  15

Ser
```

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Asp Asp Asp Glu Glu
1               5
```

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Asp Asp Asp Gly Gly
1               5
```

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Asp Asp Asp Lys Lys
1               5
```

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Asp Asp Asp Pro Pro
1               5
```

<210> SEQ ID NO 85
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 85

Asp Asp Asp Arg Arg
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Asp Asp Ser Ser
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Asp Asp Thr Thr
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Glu Glu Asp Asp
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Glu Glu Gly Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Glu Glu Lys Lys
1               5
```

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Glu Glu Glu Pro Pro
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Glu Glu Glu Arg Arg
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Glu Glu Glu Ser Ser
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Glu Glu Glu Thr Thr
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Gly Gly Asp Asp
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 96

Gly Gly Gly Glu Glu
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Lys Lys
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Pro Pro
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Arg Arg
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Lys Lys Asp Asp
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Lys Lys Glu Glu
1               5

<210> SEQ ID NO 102
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 102

Lys Lys Lys Gly Gly
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Lys Lys Pro Pro
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Lys Lys Arg Arg
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Lys Lys Ser Ser
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Lys Lys Thr Thr
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Pro Pro Asp Asp
1               5
```

```
<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Pro Pro Glu Glu
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Pro Pro Gly Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Pro Pro Lys Lys
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Pro Pro Pro Arg Arg
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Pro Pro Pro Ser Ser
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 113

Pro Pro Pro Thr Thr
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Arg Arg Asp Asp
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Arg Arg Glu Glu
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Arg Arg Gly Gly
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Arg Arg Lys Lys
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Arg Arg Pro Pro
1               5

<210> SEQ ID NO 119
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Arg Arg Ser Ser
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Arg Arg Thr Thr
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ser Ser Asp Asp
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ser Ser Glu Glu
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Ser Ser Gly Gly
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Ser Ser Lys Lys
```

```
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Ser Ser Pro Pro
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ser Ser Arg Arg
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Ser Ser Thr Thr
1               5

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Thr Thr Asp Asp
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Thr Thr Glu Glu
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 130

Thr Thr Thr Gly Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Thr Thr Lys Lys
1               5

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Thr Thr Pro Pro
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Thr Thr Arg Arg
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Thr Thr Ser Ser
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Asp Asp Asp Glu Glu Glu
1               5

<210> SEQ ID NO 136

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Asp Asp Asp Gly Gly Gly
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Asp Asp Asp Lys Lys Lys
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Asp Asp Asp Pro Pro Pro
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Asp Asp Asp Arg Arg Arg
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Asp Asp Asp Ser Ser Ser
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141
```

```
Asp Asp Asp Asp Thr Thr Thr
1               5
```

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Glu Glu Glu Glu Asp Asp Asp
1               5
```

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Glu Glu Glu Glu Gly Gly Gly
1               5
```

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Glu Glu Glu Glu Lys Lys Lys
1               5
```

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Glu Glu Glu Glu Pro Pro Pro
1               5
```

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Glu Glu Glu Glu Arg Arg Arg
1               5
```

<210> SEQ ID NO 147
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 147

Glu Glu Glu Glu Ser Ser Ser
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Glu Glu Glu Glu Thr Thr Thr
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Lys Lys Lys Asp Asp Asp
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Lys Lys Lys Lys Glu Glu Glu
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Lys Lys Lys Lys Gly Gly Gly
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Lys Lys Lys Lys Pro Pro Pro
1               5
```

```
<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Lys Lys Lys Arg Arg Arg
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Lys Lys Lys Ser Ser Ser Ser
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Lys Lys Lys Lys Thr Thr Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Pro Pro Pro Asp Asp Asp
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Pro Pro Pro Pro Glu Glu Glu
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Pro Pro Pro Pro Gly Gly Gly
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Pro Pro Lys Lys Lys Lys
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Pro Pro Pro Pro Arg Arg Arg
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Pro Pro Pro Pro Ser Ser Ser
1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Pro Pro Thr Thr Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Arg Arg Arg Asp Asp Asp
1               5

<210> SEQ ID NO 164
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 164

Arg Arg Arg Arg Glu Glu Glu
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Arg Arg Arg Gly Gly Gly
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Arg Arg Arg Lys Lys Lys
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Arg Arg Arg Pro Pro Pro
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Arg Arg Arg Ser Ser Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Arg Arg Arg Thr Thr Thr
1               5
```

```
<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Ser Ser Ser Asp Asp Asp
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ser Ser Ser Glu Glu Glu
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ser Ser Ser Gly Gly Gly
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Ser Ser Ser Lys Lys Lys
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Ser Ser Ser Pro Pro Pro
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 175

Ser Ser Ser Ser Arg Arg Arg
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Ser Ser Ser Thr Thr Thr
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Thr Thr Thr Thr Asp Asp Asp
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Thr Thr Thr Thr Glu Glu Glu
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Thr Thr Thr Gly Gly Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Thr Thr Thr Thr Lys Lys Lys
1               5

<210> SEQ ID NO 181
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 181

Thr Thr Thr Thr Pro Pro Pro
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Thr Thr Thr Arg Arg Arg
1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Thr Thr Thr Ser Ser Ser
1               5

<210> SEQ ID NO 184
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Asp Glu Glu
1

<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Asp Gly Gly
1

<210> SEQ ID NO 186
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Asp Lys Lys
1
```

<210> SEQ ID NO 187
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Asp Pro Pro
1

<210> SEQ ID NO 188
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Asp Arg Arg
1

<210> SEQ ID NO 189
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Asp Ser Ser
1

<210> SEQ ID NO 190
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Asp Thr Thr
1

<210> SEQ ID NO 191
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Glu Asp Asp
1

<210> SEQ ID NO 192
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 192

Glu Glu Gly Gly
1

<210> SEQ ID NO 193
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Glu Glu Lys Lys
1

<210> SEQ ID NO 194
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Glu Pro Pro
1

<210> SEQ ID NO 195
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Glu Glu Arg Arg
1

<210> SEQ ID NO 196
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Glu Ser Ser
1

<210> SEQ ID NO 197
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Glu Thr Thr
1

<210> SEQ ID NO 198
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Gly Asp Asp
1

<210> SEQ ID NO 199
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Gly Glu Glu
1

<210> SEQ ID NO 200
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Gly Lys Lys
1

<210> SEQ ID NO 201
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Pro Pro
1

<210> SEQ ID NO 202
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gly Arg Arg
1

<210> SEQ ID NO 203
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Ser Ser
```

```
<210> SEQ ID NO 204
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Gly Thr Thr
1

<210> SEQ ID NO 205
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Lys Lys Asp Asp
1

<210> SEQ ID NO 206
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Lys Glu Glu
1

<210> SEQ ID NO 207
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys Lys Gly Gly
1

<210> SEQ ID NO 208
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Lys Pro Pro
1

<210> SEQ ID NO 209
<211> LENGTH: 4
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 209

Lys Lys Arg Arg
1

<210> SEQ ID NO 210
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Lys Lys Ser Ser
1

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Lys Lys Thr Thr
1

<210> SEQ ID NO 212
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Pro Pro Asp Asp
1

<210> SEQ ID NO 213
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Pro Pro Glu Glu
1

<210> SEQ ID NO 214
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Pro Pro Gly Gly
1

<210> SEQ ID NO 215

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Pro Pro Lys Lys
1

<210> SEQ ID NO 216
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Pro Pro Arg Arg
1

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Pro Pro Ser Ser
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Pro Pro Thr Thr
1

<210> SEQ ID NO 219
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Arg Asp Asp
1

<210> SEQ ID NO 220
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220
```

```
Arg Arg Glu Glu
1

<210> SEQ ID NO 221
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Arg Gly Gly
1

<210> SEQ ID NO 222
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Arg Lys Lys
1

<210> SEQ ID NO 223
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Arg Pro Pro
1

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Arg Ser Ser
1

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Arg Arg Thr Thr
1

<210> SEQ ID NO 226
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 226

Ser Ser Asp Asp
1

<210> SEQ ID NO 227
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Ser Glu Glu
1

<210> SEQ ID NO 228
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Ser Gly Gly
1

<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Ser Lys Lys
1

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Ser Pro Pro
1

<210> SEQ ID NO 231
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Ser Arg Arg
1
```

```
<210> SEQ ID NO 232
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Ser Thr Thr
1

<210> SEQ ID NO 233
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Thr Thr Asp Asp
1

<210> SEQ ID NO 234
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Thr Glu Glu
1

<210> SEQ ID NO 235
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Thr Thr Gly Gly
1

<210> SEQ ID NO 236
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Thr Thr Lys Lys
1

<210> SEQ ID NO 237
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237
```

Thr Thr Pro Pro
1

<210> SEQ ID NO 238
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Thr Thr Arg Arg
1

<210> SEQ ID NO 239
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Thr Thr Ser Ser
1

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Gly Ser Ser
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Gly Gly Thr Thr
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Asp Asp Glu Glu Glu
1               5

<210> SEQ ID NO 243
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 243

Asp Asp Gly Gly Gly
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Asp Lys Lys Lys
1               5

<210> SEQ ID NO 245
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Asp Pro Pro Pro
1               5

<210> SEQ ID NO 246
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Asp Arg Arg Arg
1               5

<210> SEQ ID NO 247
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Asp Ser Ser Ser
1               5

<210> SEQ ID NO 248
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Asp Thr Thr Thr
1               5
```

-continued

<210> SEQ ID NO 249
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Glu Glu Asp Asp Asp
1               5

<210> SEQ ID NO 250
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Glu Gly Gly Gly
1               5

<210> SEQ ID NO 251
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Glu Lys Lys Lys
1               5

<210> SEQ ID NO 252
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Glu Pro Pro Pro
1               5

<210> SEQ ID NO 253
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Glu Arg Arg Arg
1               5

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 254

Glu Glu Ser Ser Ser
1               5

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Glu Thr Thr Thr
1               5

<210> SEQ ID NO 256
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Gly Asp Asp Asp
1               5

<210> SEQ ID NO 257
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Gly Glu Glu Glu
1               5

<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Gly Lys Lys Lys
1               5

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Gly Pro Pro Pro
1               5

<210> SEQ ID NO 260
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 260

Gly Gly Arg Arg Arg
1               5

<210> SEQ ID NO 261
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Gly Ser Ser Ser
1               5

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Gly Thr Thr Thr
1               5

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Lys Asp Asp Asp
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Lys Lys Glu Glu Glu
1               5

<210> SEQ ID NO 265
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Lys Lys Gly Gly Gly
1               5
```

<210> SEQ ID NO 266
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Lys Lys Pro Pro Pro
1               5

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Lys Arg Arg Arg
1               5

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Lys Lys Ser Ser Ser
1               5

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Lys Lys Thr Thr Thr
1               5

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Pro Pro Asp Asp Asp
1               5

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Pro Pro Glu Glu Glu
1               5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Pro Pro Gly Gly Gly
1               5

<210> SEQ ID NO 273
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Pro Pro Lys Lys Lys
1               5

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Pro Pro Arg Arg Arg
1               5

<210> SEQ ID NO 275
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Pro Pro Ser Ser Ser
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Pro Pro Thr Thr Thr
1               5

<210> SEQ ID NO 277
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Arg Asp Asp Asp
1               5

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Arg Glu Glu Glu
1               5

<210> SEQ ID NO 279
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Arg Arg Gly Gly Gly
1               5

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Arg Arg Lys Lys Lys
1               5

<210> SEQ ID NO 281
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Arg Pro Pro Pro
1               5

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Arg Arg Ser Ser Ser
```

```
1               5

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Arg Arg Thr Thr Thr
1               5

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ser Ser Asp Asp Asp
1               5

<210> SEQ ID NO 285
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ser Ser Glu Glu Glu
1               5

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ser Ser Gly Gly Gly
1               5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Ser Lys Lys Lys
1               5

<210> SEQ ID NO 288
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 288

Ser Ser Pro Pro Pro
1               5

<210> SEQ ID NO 289
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ser Ser Arg Arg Arg
1               5

<210> SEQ ID NO 290
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Ser Thr Thr Thr
1               5

<210> SEQ ID NO 291
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Thr Thr Asp Asp Asp
1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Thr Thr Glu Glu Glu
1               5

<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Thr Thr Gly Gly Gly
1               5

<210> SEQ ID NO 294

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Thr Thr Lys Lys Lys
1               5

<210> SEQ ID NO 295
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Thr Thr Pro Pro Pro
1               5

<210> SEQ ID NO 296
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Thr Arg Arg Arg
1               5

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Thr Thr Ser Ser Ser
1               5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Asp Asp Glu Glu Glu
1               5

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299
```

```
Asp Asp Asp Gly Gly Gly
1               5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp Asp Asp Lys Lys Lys
1               5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Asp Asp Pro Pro Pro
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Asp Asp Arg Arg Arg
1               5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asp Asp Asp Ser Ser Ser
1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asp Asp Asp Thr Thr Thr
1               5

<210> SEQ ID NO 305
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 305

Glu Glu Glu Asp Asp Asp
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Glu Glu Glu Gly Gly Gly
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Glu Glu Glu Lys Lys Lys
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Glu Glu Pro Pro Pro
1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Glu Glu Arg Arg Arg
1               5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Glu Glu Glu Ser Ser Ser
1               5
```

-continued

```
<210> SEQ ID NO 311
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Glu Glu Glu Thr Thr Thr
1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Gly Gly Asp Asp Asp
1               5

<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Gly Gly Glu Glu Glu
1               5

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Gly Gly Lys Lys Lys
1               5

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Gly Gly Pro Pro Pro
1               5

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316
```

```
Gly Gly Gly Arg Arg Arg
1               5

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Gly Gly Ser Ser Ser
1               5

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gly Gly Gly Thr Thr Thr
1               5

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Lys Lys Lys Asp Asp Asp
1               5

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Lys Lys Lys Glu Glu Glu
1               5

<210> SEQ ID NO 321
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Lys Lys Lys Gly Gly Gly
1               5

<210> SEQ ID NO 322
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 322

Lys Lys Lys Pro Pro Pro
1               5

<210> SEQ ID NO 323
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Lys Lys Lys Arg Arg Arg
1               5

<210> SEQ ID NO 324
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Lys Lys Lys Ser Ser Ser
1               5

<210> SEQ ID NO 325
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Lys Lys Lys Thr Thr Thr
1               5

<210> SEQ ID NO 326
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Pro Pro Pro Asp Asp Asp
1               5

<210> SEQ ID NO 327
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Pro Pro Pro Glu Glu Glu
1               5
```

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Pro Pro Pro Gly Gly Gly
1               5

<210> SEQ ID NO 329
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Pro Pro Pro Lys Lys Lys
1               5

<210> SEQ ID NO 330
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Pro Pro Pro Arg Arg Arg
1               5

<210> SEQ ID NO 331
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Pro Pro Pro Ser Ser Ser
1               5

<210> SEQ ID NO 332
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Pro Pro Pro Thr Thr Thr
1               5

<210> SEQ ID NO 333
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 333

Arg Arg Arg Asp Asp Asp
1               5

<210> SEQ ID NO 334
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Arg Arg Glu Glu Glu
1               5

<210> SEQ ID NO 335
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Arg Arg Arg Gly Gly Gly
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Arg Arg Arg Lys Lys Lys
1               5

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Arg Arg Pro Pro Pro
1               5

<210> SEQ ID NO 338
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Arg Arg Arg Ser Ser Ser
1               5

<210> SEQ ID NO 339
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 339

Arg Arg Arg Thr Thr Thr
1               5

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ser Ser Ser Asp Asp Asp
1               5

<210> SEQ ID NO 341
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ser Ser Ser Glu Glu Glu
1               5

<210> SEQ ID NO 342
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ser Ser Ser Gly Gly Gly
1               5

<210> SEQ ID NO 343
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ser Ser Ser Lys Lys Lys
1               5

<210> SEQ ID NO 344
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ser Ser Ser Pro Pro Pro
1               5
```

```
<210> SEQ ID NO 345
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ser Ser Ser Arg Arg Arg
1               5

<210> SEQ ID NO 346
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ser Ser Ser Thr Thr Thr
1               5

<210> SEQ ID NO 347
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Thr Thr Thr Asp Asp Asp
1               5

<210> SEQ ID NO 348
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Thr Thr Thr Glu Glu Glu
1               5

<210> SEQ ID NO 349
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Thr Thr Thr Gly Gly Gly
1               5

<210> SEQ ID NO 350
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 350

Thr Thr Thr Lys Lys Lys
1               5

<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Thr Thr Thr Pro Pro Pro
1               5

<210> SEQ ID NO 352
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Thr Thr Thr Arg Arg Arg
1               5

<210> SEQ ID NO 353
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Thr Thr Thr Ser Ser Ser
1               5

<210> SEQ ID NO 354
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gly Gly Gly Gly Asp Asp Asp
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Gly Gly Gly Gly Glu Glu Glu
1               5

<210> SEQ ID NO 356
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Gly Gly Gly Lys Lys Lys
1               5

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Gly Gly Gly Pro Pro Pro
1               5

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Gly Gly Gly Arg Arg Arg
1               5

<210> SEQ ID NO 359
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gly Gly Gly Gly Ser Ser Ser
1               5

<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Gly Gly Gly Thr Thr Thr
1               5

<210> SEQ ID NO 361
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Pro Pro Pro Pro Thr Thr Thr
```

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Ser Ser Glu Ser Ser Glu Ser Ser Ser Ser Glu
1               5                   10

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Gly Glu Gly Glu Gly Gly Gly Glu
1               5

<210> SEQ ID NO 364
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Ser Glu Ser Ser Ser Ser Glu Ser Ser Glu Ser Glu Ser
1               5                   10                  15

Ser Ser Ser Glu Ser Ser Ser Glu
            20

<210> SEQ ID NO 365
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ser Ser Ser Ser Glu Ser Ser Ser Ser Glu Ser Ser Ser Ser Glu
1               5                   10                  15

<210> SEQ ID NO 366
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ser Ser Ser Ser Ser Glu Ser Ser Ser Ser Glu Ser Ser Ser Ser
1               5                   10                  15

Ser Glu

<210> SEQ ID NO 367

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ser Ser Ser Ser Ser Ser Glu Ser Ser Ser Ser Ser Ser Glu
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ser Ser Ser Ser Ser Ser Glu Ser Ser Ser Ser Glu
1               5                   10

<210> SEQ ID NO 369
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ser Ser Ser Ser Ser Ser Glu Ser Ser Ser Glu Ser Ser Ser Ser
1               5                   10                  15

Ser Ser Glu Ser Ser Ser Ser Glu
            20

<210> SEQ ID NO 370
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ser Gly Gly Gly Gly Gly Gly Gly Gly Gly Arg Gly Ala Gly Gly
1               5                   10                  15

<210> SEQ ID NO 371
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Thr Gly Ser Gly Asn Gly Ser Gly Gly Gly Gly Gly Gly Gly Ser Gly
1               5                   10                  15

Gly

<210> SEQ ID NO 372
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 372

Gly Gly Ser Gly Gly Gly Gly Ser Gly Gly Gly Gly
1               5                   10

<210> SEQ ID NO 373
<211> LENGTH: 37
<212> TYPE: PRT
<213> ORGANISM: Homo sapiens

<400> SEQUENCE: 373

Gly Pro Gly Gly Gly Gly Pro Gly Gly Gly Gly Pro Gly Gly
1               5                   10                  15

Gly Gly Pro Gly Gly Gly Gly Gly Pro Gly Gly Gly Gly
            20                  25                  30

Gly Pro Gly Gly Gly
        35

<210> SEQ ID NO 374
<211> LENGTH: 33
<212> TYPE: PRT
<213> ORGANISM: Homo sapiens

<400> SEQUENCE: 374

Gly Ala Gly Gly Gly Gly Gly Gly Gly Gly Gly Gly Gly Ser
1               5                   10                  15

Gly Gly Gly Gly Gly Gly Gly Ala Gly Ala Gly Ala Gly Ala
            20                  25                  30

Gly

<210> SEQ ID NO 375
<211> LENGTH: 32
<212> TYPE: PRT
<213> ORGANISM: Homo sapiens

<400> SEQUENCE: 375

Gly Gly Gly Ser Gly Ser Gly Gly Ala Gly Gly Ser Gly Gly Gly
1               5                   10                  15

Ser Gly Ser Gly Gly Gly Gly Gly Ala Gly Gly Gly Gly Gly
            20                  25                  30

<210> SEQ ID NO 376
<211> LENGTH: 27
<212> TYPE: PRT
<213> ORGANISM: Homo sapiens

<400> SEQUENCE: 376

Gly Asp Gly Gly Gly Ala Gly Gly Gly Gly Gly Gly Gly Ser Gly
1               5                   10                  15

Gly Gly Gly Ser Gly Gly Gly Gly Gly Gly Gly
            20                  25

<210> SEQ ID NO 377
<211> LENGTH: 25
<212> TYPE: PRT
<213> ORGANISM: Homo sapiens

<400> SEQUENCE: 377

Gly Ser Gly Ser Gly Ser Gly Gly Gly Gly Gly Gly Gly Gly Gly
1               5                   10                  15

```
Gly Gly Ser Gly Gly Gly Gly Gly
        20                  25

<210> SEQ ID NO 378
<211> LENGTH: 23
<212> TYPE: PRT
<213> ORGANISM: Homo sapiens

<400> SEQUENCE: 378

Gly Gly Gly Arg Gly Gly Arg Gly Gly Arg Gly Gly Gly Arg
1               5                   10                  15

Gly Gly Gly Arg Gly Gly Gly
            20

<210> SEQ ID NO 379
<211> LENGTH: 21
<212> TYPE: PRT
<213> ORGANISM: Homo sapiens

<400> SEQUENCE: 379

Gly Ser Gly Gly Ser Gly Gly Ser Gly Gly Gly Pro Gly Pro Gly Pro
1               5                   10                  15

Gly Gly Gly Gly Gly
            20

<210> SEQ ID NO 380
<211> LENGTH: 18
<212> TYPE: PRT
<213> ORGANISM: Homo sapiens

<400> SEQUENCE: 380

Gly Glu Gly Gly Gly Gly Gly Gly Glu Gly Gly Gly Ala Gly Gly Gly
1               5                   10                  15

Ser Gly

<210> SEQ ID NO 381
<211> LENGTH: 12
<212> TYPE: PRT
<213> ORGANISM: Homo sapiens

<400> SEQUENCE: 381

Gly Gly Gly Gly Gly Gly Gly Gly Asp Gly Gly Gly
1               5                   10

<210> SEQ ID NO 382
<211> LENGTH: 46
<212> TYPE: PRT
<213> ORGANISM: Homo sapiens

<400> SEQUENCE: 382

Gly Gly Gly Ser Gly Ser Gly Gly Ala Gly Gly Ser Gly Gly Gly
1               5                   10                  15

Ser Gly Ser Gly Gly Gly Gly Gly Ala Gly Gly Gly Gly Gly
            20                  25                  30

Ser Ser Gly Gly Gly Ser Gly Thr Ala Gly Gly His Ser Gly
        35                  40                  45

<210> SEQ ID NO 383
<211> LENGTH: 35
<212> TYPE: PRT
<213> ORGANISM: Homo sapiens
```

```
<400> SEQUENCE: 383

Gly Gly Ser Gly Ala Gly Gly Gly Gly Gly Gly Gly Gly Gly
1               5                   10                  15

Ser Gly Ser Gly Gly Gly Gly Ser Thr Gly Gly Gly Gly Thr Ala
            20                  25                  30

Gly Gly Gly
        35

<210> SEQ ID NO 384
<211> LENGTH: 32
<212> TYPE: PRT
<213> ORGANISM: Homo sapiens

<400> SEQUENCE: 384

Gly His Pro Gly Ser Gly Ser Gly Gly Gly Gly Gly Gly
1               5                   10                  15

Gly Gly Gly Gly Gly Ser Gly Gly Gly Gly Gly Ala Pro Gly Gly
            20                  25                  30

<210> SEQ ID NO 385
<211> LENGTH: 31
<212> TYPE: PRT
<213> ORGANISM: Homo sapiens

<400> SEQUENCE: 385

Gly Gly Gly Gly Ser Gly Gly Gly Gly Gly Gly Gly Gly Gly
1               5                   10                  15

Gly Gly Gly Ser Gly Ser Thr Gly Gly Gly Ser Gly Ala Gly
            20                  25                  30

<210> SEQ ID NO 386
<211> LENGTH: 31
<212> TYPE: PRT
<213> ORGANISM: Homo sapiens

<400> SEQUENCE: 386

Gly Gly Arg Gly Arg Gly Gly Arg Gly Arg Gly Ser Arg Gly Arg Gly
1               5                   10                  15

Gly Gly Gly Thr Arg Gly Arg Gly Arg Gly Arg Gly Arg Gly
            20                  25                  30

<210> SEQ ID NO 387
<211> LENGTH: 30
<212> TYPE: PRT
<213> ORGANISM: Homo sapiens

<400> SEQUENCE: 387

Gly Ser Gly Gly Ser Gly Gly Ser Gly Gly Pro Gly Pro Gly Pro
1               5                   10                  15

Gly Gly Gly Gly Gly Pro Ser Gly Ser Gly Ser Gly Pro Gly
            20                  25                  30

<210> SEQ ID NO 388
<211> LENGTH: 29
<212> TYPE: PRT
<213> ORGANISM: Homo sapiens

<400> SEQUENCE: 388

Gly Gly Gly Gly Gly Gly Gly Gly Gly Arg Gly Gly Gly
1               5                   10                  15

Arg Gly Gly Gly Arg Gly Gly Gly Gly Glu Gly Gly Gly
```

```
                20                  25

<210> SEQ ID NO 389
<211> LENGTH: 28
<212> TYPE: PRT
<213> ORGANISM: Homo sapiens

<400> SEQUENCE: 389

Gly Gly Gly Gly Thr Gly Ser Ser Gly Ser Gly Ser Gly Gly
1               5                   10                  15

Gly Ser Gly Gly Gly Gly Gly Gly Gly Ser Ser Gly
                20                  25

<210> SEQ ID NO 390
<211> LENGTH: 27
<212> TYPE: PRT
<213> ORGANISM: Homo sapiens

<400> SEQUENCE: 390

Gly Gly Gly Gly Gly Gly Gly Ser Gly Gly Gly Gly Ser Gly Gly
1               5                   10                  15

Gly Gly Ser Gly Gly Gly Arg Gly Ala Gly Gly
                20                  25

<210> SEQ ID NO 391
<211> LENGTH: 27
<212> TYPE: PRT
<213> ORGANISM: Homo sapiens

<400> SEQUENCE: 391

Gly Gly Gly Ala Ala Gly Ala Gly Gly Gly Ser Gly Ala Gly Gly
1               5                   10                  15

Gly Ser Gly Gly Ser Gly Gly Arg Gly Thr Gly
                20                  25

<210> SEQ ID NO 392
<211> LENGTH: 27
<212> TYPE: PRT
<213> ORGANISM: Homo sapiens

<400> SEQUENCE: 392

Gly Ala Gly Gly Gly Arg Gly Gly Ala Gly Gly Glu Gly Ala
1               5                   10                  15

Ser Gly Ala Glu Gly Gly Gly Gly Ala Gly Gly
                20                  25

<210> SEQ ID NO 393
<211> LENGTH: 26
<212> TYPE: PRT
<213> ORGANISM: Homo sapiens

<400> SEQUENCE: 393

Gly Gly Gly Gly Gly Gly Gly Gly Gly Gly Gly Gly Gly Gly
1               5                   10                  15

Gly Gly Gly Gly Gly Gly Gly Glu Ala Gly
                20                  25

<210> SEQ ID NO 394
<211> LENGTH: 26
<212> TYPE: PRT
<213> ORGANISM: Homo sapiens

<400> SEQUENCE: 394
```

```
Gly Gly Gly Gly Gly Ser Ala Gly Gly Ser Ser Gly Gly Gly
1               5                   10                  15

Pro Gly Gly Gly Gly Gly Ala Gly Gly
            20                  25

<210> SEQ ID NO 395
<211> LENGTH: 25
<212> TYPE: PRT
<213> ORGANISM: Homo sapiens

<400> SEQUENCE: 395

Gly Gly Gly Gly Gly Pro Gly Gly Gly Gly Gly Pro Gly Gly
1               5                   10                  15

Gly Gly Gly Pro Gly Gly Gly Gly Gly
            20                  25

<210> SEQ ID NO 396
<211> LENGTH: 25
<212> TYPE: PRT
<213> ORGANISM: Homo sapiens

<400> SEQUENCE: 396

Gly Arg Gly Gly Ala Gly Ser Gly Ala Gly Ser Gly Ala Ala Gly
1               5                   10                  15

Gly Thr Gly Ser Ser Gly Gly Gly Gly
            20                  25

<210> SEQ ID NO 397
<211> LENGTH: 25
<212> TYPE: PRT
<213> ORGANISM: Homo sapiens

<400> SEQUENCE: 397

Gly Gly Gly Gly Gly Gly Gly Gly Gly Ser Gly Gly Ser Gly
1               5                   10                  15

Gly Gly Gly Gly Gly Gly Gly Gly Gly
            20                  25

<210> SEQ ID NO 398
<211> LENGTH: 25
<212> TYPE: PRT
<213> ORGANISM: Homo sapiens

<400> SEQUENCE: 398

Gly Gly Ser Gly Gly Gly Arg Gly Gly Ala Ser Gly Pro Gly Ser Gly
1               5                   10                  15

Ser Gly Gly Pro Gly Gly Pro Ala Gly
            20                  25

<210> SEQ ID NO 399
<211> LENGTH: 25
<212> TYPE: PRT
<213> ORGANISM: Homo sapiens

<400> SEQUENCE: 399

Gly Gly His His Gly Asp Arg Gly Gly Arg Gly Gly Arg Gly Gly
1               5                   10                  15

Arg Gly Gly Arg Gly Gly Arg Ala Gly
            20                  25

<210> SEQ ID NO 400
```

```
<211> LENGTH: 25
<212> TYPE: PRT
<213> ORGANISM: Homo sapiens

<400> SEQUENCE: 400

Gly Ser Arg Gly Gly Gly Gly Gly Gly Gly Gly Gly Gly Gly Gly
1               5                   10                  15

Gly Gly Gly Ala Gly Ala Gly Gly Gly
            20                  25

<210> SEQ ID NO 401
<211> LENGTH: 24
<212> TYPE: PRT
<213> ORGANISM: Homo sapiens

<400> SEQUENCE: 401

Gly Gly Arg Gly Gly Arg Gly Pro Gly Glu Pro Gly Arg Gly Arg
1               5                   10                  15

Ala Gly Gly Ala Glu Gly Arg Gly
            20

<210> SEQ ID NO 402
<211> LENGTH: 24
<212> TYPE: PRT
<213> ORGANISM: Homo sapiens

<400> SEQUENCE: 402

Gly Gly Gly Gly Gly Asp Ala Gly Ser Gly Asp Ala Gly Ala
1               5                   10                  15

Gly Gly Arg Ala Gly Arg Ala Gly
            20

<210> SEQ ID NO 403
<211> LENGTH: 23
<212> TYPE: PRT
<213> ORGANISM: Homo sapiens

<400> SEQUENCE: 403

Gly Gly Ser Gly Gly Gly Gly Gly Ser Ser Gly Gly Arg Gly Ser
1               5                   10                  15

Gly Gly Gly Ser Ser Gly Gly
            20

<210> SEQ ID NO 404
<211> LENGTH: 23
<212> TYPE: PRT
<213> ORGANISM: Homo sapiens

<400> SEQUENCE: 404

Gly Ser Gly Pro Gly Thr Gly Gly Gly Ser Gly Ser Gly Gly
1               5                   10                  15

Gly Gly Gly Ser Gly Gly Gly
            20

<210> SEQ ID NO 405
<211> LENGTH: 23
<212> TYPE: PRT
<213> ORGANISM: Homo sapiens

<400> SEQUENCE: 405

Gly Ala Arg Gly Gly Gly Ser Gly Gly Gly Gly Gly Gly Gly
1               5                   10                  15
```

Gly Gly Gly Gly Gly Pro Gly
        20

<210> SEQ ID NO 406
<211> LENGTH: 23
<212> TYPE: PRT
<213> ORGANISM: Homo sapiens

<400> SEQUENCE: 406

Gly Gly Gly Gly Gly Gly Gly Gly Gly Gly Gly Gly Gly Gly
1               5                   10                  15

Gly Gly Gly Gly Gly Asp Gly
        20

<210> SEQ ID NO 407
<211> LENGTH: 23
<212> TYPE: PRT
<213> ORGANISM: Homo sapiens

<400> SEQUENCE: 407

Gly Gly Thr Arg Gly Gly Thr Arg Gly Gly Thr Arg Gly Gly Asp Arg
1               5                   10                  15

Gly Arg Gly Arg Gly Ala Gly
        20

<210> SEQ ID NO 408
<211> LENGTH: 23
<212> TYPE: PRT
<213> ORGANISM: Homo sapiens

<400> SEQUENCE: 408

Gly Ala Gly Gly Gly Gly Gly Gly Gly Gly Gly Gly Gly Gly
1               5                   10                  15

Ala Gly Gly Gly Gly Gly Gly
        20

<210> SEQ ID NO 409
<211> LENGTH: 22
<212> TYPE: PRT
<213> ORGANISM: Homo sapiens

<400> SEQUENCE: 409

Gly Arg Gly Arg Gly Gly Gly Gly Gly Gly Gly Gly Gly Gly
1               5                   10                  15

Gly Arg Gly Gly Gly Gly
        20

<210> SEQ ID NO 410
<211> LENGTH: 22
<212> TYPE: PRT
<213> ORGANISM: Homo sapiens

<400> SEQUENCE: 410

Gly Arg Gly Arg Gly Arg Gly Arg Gly Arg Gly Arg Gly Arg Gly Arg
1               5                   10                  15

Gly Arg Gly Gly Ala Gly
        20

<210> SEQ ID NO 411
<211> LENGTH: 22
<212> TYPE: PRT
<213> ORGANISM: Homo sapiens

```
<400> SEQUENCE: 411

Gly Ala Gly Gly Gly Gly Gly Gly Gly Gly Gly Gly Gly Gly Gly
1               5                   10                  15

Gly Gly Gly Gly Gly Gly
            20

<210> SEQ ID NO 412
<211> LENGTH: 22
<212> TYPE: PRT
<213> ORGANISM: Homo sapiens

<400> SEQUENCE: 412

Gly Gly Gly Ser Gly Gly Gly His Ser Gly Gly Ser Gly Gly Gly His
1               5                   10                  15

Ser Gly Gly Ser Gly Gly
            20

<210> SEQ ID NO 413
<211> LENGTH: 22
<212> TYPE: PRT
<213> ORGANISM: Homo sapiens

<400> SEQUENCE: 413

Gly Ala Gly Ala Gly Gly Gly Gly Gly Gly Gly Ala Gly Gly
1               5                   10                  15

Gly Ser Ala Gly Ser Gly
            20

<210> SEQ ID NO 414
<211> LENGTH: 22
<212> TYPE: PRT
<213> ORGANISM: Homo sapiens

<400> SEQUENCE: 414

Gly Gly Pro Gly Thr Gly Ser Gly Gly Gly Ala Gly Thr Gly Gly
1               5                   10                  15

Gly Ala Gly Gly Pro Gly
            20

<210> SEQ ID NO 415
<211> LENGTH: 22
<212> TYPE: PRT
<213> ORGANISM: Homo sapiens

<400> SEQUENCE: 415

Gly Gly Gly Gly Gly Gly Gly Gly Ala Gly Gly Ala Gly Gly Ala
1               5                   10                  15

Gly Ser Ala Gly Gly Gly
            20

<210> SEQ ID NO 416
<211> LENGTH: 21
<212> TYPE: PRT
<213> ORGANISM: Homo sapiens

<400> SEQUENCE: 416

Gly Gly Asp Gly Gly Gly Ser Ala Gly Gly Ala Gly Gly Gly Ser
1               5                   10                  15

Gly Gly Gly Ala Gly
            20
```

```
<210> SEQ ID NO 417
<211> LENGTH: 21
<212> TYPE: PRT
<213> ORGANISM: Homo sapiens

<400> SEQUENCE: 417

Gly Gly Gly Gly Gly Ser Gly Gly Gly Gly Gly Gly Gly Gly
1               5                   10                  15

Gly Gly Gly Gly Gly
            20

<210> SEQ ID NO 418
<211> LENGTH: 21
<212> TYPE: PRT
<213> ORGANISM: Homo sapiens

<400> SEQUENCE: 418

Gly Pro Gly Ala Gly Ala Gly Ser Gly Ala Gly Gly Ser Ser Gly Gly
1               5                   10                  15

Gly Gly Gly Pro Gly
            20

<210> SEQ ID NO 419
<211> LENGTH: 21
<212> TYPE: PRT
<213> ORGANISM: Homo sapiens

<400> SEQUENCE: 419

Gly Gly Gly Gly Gly Gly Gly Gly Gly Ser Ser Gly Gly Gly
1               5                   10                  15

Gly Ser Ser Gly Gly
            20

<210> SEQ ID NO 420
<211> LENGTH: 21
<212> TYPE: PRT
<213> ORGANISM: Homo sapiens

<400> SEQUENCE: 420

Gly Ser Gly Ser Gly Pro Gly Pro Gly Ser Gly Pro Gly Ser Gly Pro
1               5                   10                  15

Gly His Gly Ser Gly
            20

<210> SEQ ID NO 421
<211> LENGTH: 21
<212> TYPE: PRT
<213> ORGANISM: Homo sapiens

<400> SEQUENCE: 421

Gly Pro Gly Pro Gly Pro Gly Pro Gly Pro Gly Pro Gly Pro Gly Pro
1               5                   10                  15

Gly Pro Gly Pro Gly
            20

<210> SEQ ID NO 422
<211> LENGTH: 21
<212> TYPE: PRT
<213> ORGANISM: Homo sapiens

<400> SEQUENCE: 422

Gly Ala Gly Ser Gly Gly Gly Gly Ala Ala Gly Ala Gly Ala Gly Ser
1               5                   10                  15
```

Ala Gly Gly Gly Gly
        20

<210> SEQ ID NO 423
<211> LENGTH: 21
<212> TYPE: PRT
<213> ORGANISM: Homo sapiens

<400> SEQUENCE: 423

Gly Gly Gly Gly Gly Gly Gly Ser Gly Gly Gly Gly Gly Ser Gly
1               5                   10                  15

Gly Gly Gly Gly Gly
        20

<210> SEQ ID NO 424
<211> LENGTH: 21
<212> TYPE: PRT
<213> ORGANISM: Homo sapiens

<400> SEQUENCE: 424

Gly Arg Gly Arg Gly Arg Gly Arg Gly Arg Gly Arg Gly Arg Gly Arg
1               5                   10                  15

Gly Arg Gly Arg Gly
        20

<210> SEQ ID NO 425
<211> LENGTH: 21
<212> TYPE: PRT
<213> ORGANISM: Homo sapiens

<400> SEQUENCE: 425

Gly Gly Gly Gly Gly Gly Gly Ser Gly Gly Ser Gly Gly Gly Gly
1               5                   10                  15

Ser Gly Gly Gly Gly
        20

<210> SEQ ID NO 426
<211> LENGTH: 21
<212> TYPE: PRT
<213> ORGANISM: Homo sapiens

<400> SEQUENCE: 426

Gly Gly Glu Glu Gly Gly Ala Ser Gly Gly Pro Gly Ala Gly Ser
1               5                   10                  15

Gly Ser Ala Gly Gly
        20

<210> SEQ ID NO 427
<211> LENGTH: 21
<212> TYPE: PRT
<213> ORGANISM: Homo sapiens

<400> SEQUENCE: 427

Gly Gly Gly Gly Gly Gly Gly Gly Asp Gly Gly Gly Arg Arg Gly Arg
1               5                   10                  15

Gly Arg Gly Arg Gly
        20

<210> SEQ ID NO 428
<211> LENGTH: 20
<212> TYPE: PRT
<213> ORGANISM: Homo sapiens

```
<400> SEQUENCE: 428

Gly Gly Pro Gly Pro Gly Gly Gly Ala Gly Gly Pro Gly Gly
1               5                   10                  15

Ala Gly Ala Gly
            20

<210> SEQ ID NO 429
<211> LENGTH: 20
<212> TYPE: PRT
<213> ORGANISM: Homo sapiens

<400> SEQUENCE: 429

Gly Thr Gly Gly Gly Gly Ser Thr Gly Gly Gly Gly Gly Gly
1               5                   10                  15

Ser Gly His Gly
            20

<210> SEQ ID NO 430
<211> LENGTH: 20
<212> TYPE: PRT
<213> ORGANISM: Homo sapiens

<400> SEQUENCE: 430

Gly Pro Ala Gly Ala Gly Gly Gly Gly Gly Gly Gly Gly Gly
1               5                   10                  15

Gly Gly Gly Gly
            20

<210> SEQ ID NO 431
<211> LENGTH: 20
<212> TYPE: PRT
<213> ORGANISM: Homo sapiens

<400> SEQUENCE: 431

Gly Gly Thr Gly Gly Ser Ser Gly Ser Ser Gly Ser Gly Ser Gly Gly
1               5                   10                  15

Gly Arg Arg Gly
            20

<210> SEQ ID NO 432
<211> LENGTH: 20
<212> TYPE: PRT
<213> ORGANISM: Homo sapiens

<400> SEQUENCE: 432

Gly Ser Gly Thr Gly Thr Thr Gly Ser Ser Gly Ala Gly Gly Pro Gly
1               5                   10                  15

Thr Pro Gly Gly
            20

<210> SEQ ID NO 433
<211> LENGTH: 20
<212> TYPE: PRT
<213> ORGANISM: Homo sapiens

<400> SEQUENCE: 433

Gly Gly Ser Gly Gly Gly Ala Ala Gly Gly Ala Gly Gly Ala Gly
1               5                   10                  15

Ala Gly Ala Gly
            20
```

<210> SEQ ID NO 434
<211> LENGTH: 20
<212> TYPE: PRT
<213> ORGANISM: Homo sapiens

<400> SEQUENCE: 434

Gly Ser Ser Gly Gly Gly Gly Gly Ala Gly Ala Ala Gly Gly Ala
1               5                   10                  15

Gly Gly Ala Gly
            20

<210> SEQ ID NO 435
<211> LENGTH: 20
<212> TYPE: PRT
<213> ORGANISM: Homo sapiens

<400> SEQUENCE: 435

Gly Pro Gly Pro Ser Gly Gly Pro Gly Gly Gly Gly Gly Gly Gly
1               5                   10                  15

Gly Gly Gly Gly
            20

<210> SEQ ID NO 436
<211> LENGTH: 20
<212> TYPE: PRT
<213> ORGANISM: Homo sapiens

<400> SEQUENCE: 436

Gly Gly Gly Gly Gly Gly Gly Gly Gly Gly Gly Gly Gly Ala Ala
1               5                   10                  15

Gly Ala Gly Gly
            20

<210> SEQ ID NO 437
<211> LENGTH: 20
<212> TYPE: PRT
<213> ORGANISM: Homo sapiens

<400> SEQUENCE: 437

Gly Ser Ala Gly Gly Ser Ser Gly Ala Ala Gly Ala Ala Gly Gly
1               5                   10                  15

Ala Gly Ala Gly
            20

<210> SEQ ID NO 438
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser Ser Asp" repeating units

<400> SEQUENCE: 438

Ser Ser Asp Ser Ser Asp Ser Ser Asp Ser Ser Asp Ser Ser Asp Ser
1               5                   10                  15

Ser Asp Ser Ser Asp Ser Ser Asp Ser Ser Asp Ser Ser Asp Ser Ser
                20                  25                  30

Asp Ser Ser Asp Ser Ser Asp Ser Ser Asp Ser Ser Asp Ser Ser Asp
        35                  40                  45

```
Ser Ser Asp Ser Ser Asp Ser Ser Asp Ser Ser Asp Ser
 50                  55                  60
Ser Asp Ser Ser Asp Ser Ser Asp Ser Ser Asp Ser Ser
 65                  70                  75                  80
Asp Ser Ser Asp Ser Ser Asp Ser Ser Asp Ser Ser Asp
                     85                  90                  95
Ser Ser Asp Ser Ser Asp Ser Ser Asp Ser Ser Asp Ser
                    100                 105                 110
Ser Asp Ser Ser Asp Ser Ser Asp Ser Ser Asp Ser Ser
                    115                 120                 125
Asp Ser Ser Asp Ser Ser Asp Ser Ser Asp Ser Ser Asp
 130                 135                 140
Ser Ser Asp Ser Ser Asp Ser Ser Asp Ser Ser Asp Ser
145                  150                 155                 160
Ser Asp Ser Ser Asp Ser Ser Asp Ser Ser Asp Ser Ser
                    165                 170                 175
Asp Ser Ser Asp Ser Ser Asp Ser Ser Asp Ser Ser Asp
                    180                 185                 190
Ser Ser Asp Ser Ser Asp Ser Ser Asp Ser Ser Asp Ser
                    195                 200                 205
Ser Asp Ser Ser Asp Ser Ser Asp Ser Ser Asp Ser Ser
                    210                 215                 220
Asp Ser Ser Asp Ser Ser Asp Ser Ser Asp Ser Ser Asp
225                  230                 235                 240
Ser Ser Asp Ser Ser Asp Ser Ser Asp Ser Ser Asp Ser
                    245                 250                 255
Ser Asp Ser Ser Asp Ser Ser Asp Ser Ser Asp Ser Ser
                    260                 265                 270
Asp Ser Ser Asp Ser Ser Asp Ser Ser Asp Ser Ser Asp
                    275                 280                 285
Ser Ser Asp Ser Ser Asp Ser Ser Asp Ser Ser Asp Ser
                    290                 295                 300
Ser Asp Ser Ser Asp Ser Ser Asp Ser Ser Asp Ser Ser
305                  310                 315                 320
Asp Ser Ser Asp Ser Ser Asp Ser Ser Asp Ser Ser Asp
                    325                 330                 335
Ser Ser Asp Ser Ser Asp Ser Ser Asp Ser Ser Asp Ser
                    340                 345                 350
Ser Asp Ser Ser Asp Ser Ser Asp Ser Ser Asp Ser Ser
                    355                 360                 365
Asp Ser Ser Asp Ser Ser Asp Ser Ser Asp Ser Ser Asp
 370                 375                 380
Ser Ser Asp Ser Ser Asp Ser Ser Asp Ser Ser Asp Ser
385                  390                 395                 400
Ser Asp Ser Ser Asp Ser Ser Asp Ser Ser Asp Ser Ser
                    405                 410                 415
Asp Ser Ser Asp Ser Ser Asp Ser Ser Asp Ser Ser Asp
                    420                 425                 430
Ser Ser Asp Ser Ser Asp Ser Ser Asp Ser Ser Asp Ser
                    435                 440                 445
Ser Asp Ser Ser Asp Ser Ser Asp Ser Ser Asp Ser Ser
 450                 455                 460
Asp Ser Ser Asp Ser Ser Asp Ser Ser Asp Ser Ser Asp
```

```
                465                 470                 475                 480
Ser Ser Asp Ser Ser Asp Ser Asp Ser Asp Ser Ser Asp Ser Ser Asp Ser
                    485                 490                 495

Ser Asp Ser Ser Asp Ser Ser Asp Ser Ser Asp Ser Ser Asp Ser Ser
            500                 505                 510

Asp Ser Ser Asp Ser Ser Asp Ser Ser Asp Ser Ser Asp Ser Ser Asp
            515                 520                 525

Ser Ser Asp Ser Ser Asp Ser Ser Asp Ser Ser Asp Ser Ser Asp Ser
        530                 535                 540

Ser Asp Ser Ser Asp Ser Ser Asp Ser Ser Asp Ser Ser Asp Ser Ser
545                 550                 555                 560

Asp Ser Ser Asp Ser Ser Asp Ser Ser Asp Ser Ser Asp Ser Ser Asp
            565                 570                 575

Ser Ser Asp Ser Ser Asp Ser Ser Asp Ser Ser Asp Ser Ser Asp Ser
            580                 585                 590

Ser Asp Ser Ser Asp Ser Ser Asp
        595                 600
```

<210> SEQ ID NO 439
<211> LENGTH: 1200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser Ser Asp Ser Ser Asn" repeating units

<400> SEQUENCE: 439

```
Ser Ser Asp Ser Ser Asn Ser Ser Asp Ser Ser Asn Ser Ser Asp Ser
1               5                   10                  15

Ser Asn Ser Ser Asp Ser Ser Asn Ser Ser Asp Ser Ser Asn Ser Ser
            20                  25                  30

Asp Ser Ser Asn Ser Ser Asp Ser Ser Asn Ser Ser Asp Ser Ser Asn
        35                  40                  45

Ser Ser Asp Ser Ser Asn Ser Ser Asp Ser Ser Asn Ser Ser Asp Ser
    50                  55                  60

Ser Asn Ser Ser Asp Ser Ser Asn Ser Ser Asp Ser Ser Asn Ser Ser
65                  70                  75                  80

Asp Ser Ser Asn Ser Ser Asp Ser Ser Asn Ser Ser Asp Ser Ser Asn
            85                  90                  95

Ser Ser Asp Ser Ser Asn Ser Ser Asp Ser Ser Asn Ser Ser Asp Ser
            100                 105                 110

Ser Asn Ser Ser Asp Ser Ser Asn Ser Ser Asp Ser Ser Asn Ser Ser
        115                 120                 125

Asp Ser Ser Asn Ser Ser Asp Ser Ser Asn Ser Ser Asp Ser Ser Asn
        130                 135                 140

Ser Ser Asp Ser Ser Asn Ser Ser Asp Ser Ser Asn Ser Ser Asp Ser
145                 150                 155                 160

Ser Asn Ser Ser Asp Ser Ser Asn Ser Ser Asp Ser Ser Asn Ser Ser
            165                 170                 175

Asp Ser Ser Asn Ser Ser Asp Ser Ser Asn Ser Ser Asp Ser Ser Asn
            180                 185                 190

Ser Ser Asp Ser Ser Asn Ser Ser Asp Ser Ser Asn Ser Ser Asp Ser
        195                 200                 205
```

```
Ser Asn Ser Ser Asp Ser Ser Asn Ser Ser Asp Ser Ser Asn Ser Ser
    210                 215                 220
Asp Ser Ser Asn Ser Ser Asp Ser Ser Asn Ser Ser Asp Ser Ser Asn
225                 230                 235                 240
Ser Ser Asp Ser Ser Asn Ser Ser Asp Ser Ser Asn Ser Ser Asp Ser
            245                 250                 255
Ser Asn Ser Ser Asp Ser Ser Asn Ser Ser Asp Ser Ser Asn Ser Ser
        260                 265                 270
Asp Ser Ser Asn Ser Ser Asp Ser Ser Asn Ser Ser Asp Ser Ser Asn
    275                 280                 285
Ser Ser Asp Ser Ser Asn Ser Ser Asp Ser Ser Asn Ser Ser Asp Ser
290                 295                 300
Ser Asn Ser Ser Asp Ser Ser Asn Ser Ser Asp Ser Ser Asn Ser Ser
305                 310                 315                 320
Asp Ser Ser Asn Ser Ser Asp Ser Ser Asn Ser Ser Asp Ser Ser Asn
            325                 330                 335
Ser Ser Asp Ser Ser Asn Ser Ser Asp Ser Ser Asn Ser Ser Asp Ser
        340                 345                 350
Ser Asn Ser Ser Asp Ser Ser Asn Ser Ser Asp Ser Ser Asn Ser Ser
    355                 360                 365
Asp Ser Ser Asn Ser Ser Asp Ser Ser Asn Ser Ser Asp Ser Ser Asn
370                 375                 380
Ser Ser Asp Ser Ser Asn Ser Ser Asp Ser Ser Asn Ser Ser Asp Ser
385                 390                 395                 400
Ser Asn Ser Ser Asp Ser Ser Asn Ser Ser Asp Ser Ser Asn Ser Ser
            405                 410                 415
Asp Ser Ser Asn Ser Ser Asp Ser Ser Asn Ser Ser Asp Ser Ser Asn
        420                 425                 430
Ser Ser Asp Ser Ser Asn Ser Ser Asp Ser Ser Asn Ser Ser Asp Ser
    435                 440                 445
Ser Asn Ser Ser Asp Ser Ser Asn Ser Ser Asp Ser Ser Asn Ser Ser
450                 455                 460
Asp Ser Ser Asn Ser Ser Asp Ser Ser Asn Ser Ser Asp Ser Ser Asn
465                 470                 475                 480
Ser Ser Asp Ser Ser Asn Ser Ser Asp Ser Ser Asn Ser Ser Asp Ser
            485                 490                 495
Ser Asn Ser Ser Asp Ser Ser Asn Ser Ser Asp Ser Ser Asn Ser Ser
        500                 505                 510
Asp Ser Ser Asn Ser Ser Asp Ser Ser Asn Ser Ser Asp Ser Ser Asn
    515                 520                 525
Ser Ser Asp Ser Ser Asn Ser Ser Asp Ser Ser Asn Ser Ser Asp Ser
530                 535                 540
Ser Asn Ser Ser Asp Ser Ser Asn Ser Ser Asp Ser Ser Asn Ser Ser
545                 550                 555                 560
Asp Ser Ser Asn Ser Ser Asp Ser Ser Asn Ser Ser Asp Ser Ser Asn
            565                 570                 575
Ser Ser Asp Ser Ser Asn Ser Ser Asp Ser Ser Asn Ser Ser Asp Ser
        580                 585                 590
Ser Asn Ser Ser Asp Ser Ser Asn Ser Ser Asp Ser Ser Asn Ser Ser
    595                 600                 605
Asp Ser Ser Asn Ser Ser Asp Ser Ser Asn Ser Ser Asp Ser Ser Asn
610                 615                 620

Ser Ser Asp Ser Ser Asn Ser Ser Asp Ser Ser Asn Ser Ser Asp Ser
```

```
               625                 630                 635                 640
Ser Asn Ser Ser Asp Ser Ser Asn Ser Ser Asp Ser Ser Asn Ser Ser
                    645                 650                 655
Asp Ser Ser Asn Ser Ser Asp Ser Ser Asn Ser Ser Asp Ser Ser Asn
                    660                 665                 670
Ser Ser Asp Ser Ser Asn Ser Ser Asp Ser Ser Asn Ser Ser Asp Ser
                    675                 680                 685
Ser Asn Ser Ser Asp Ser Ser Asn Ser Ser Asp Ser Ser Asn Ser Ser
                    690                 695                 700
Asp Ser Ser Asn Ser Ser Asp Ser Ser Asn Ser Ser Asp Ser Ser Asn
705                 710                 715                 720
Ser Ser Asp Ser Ser Asn Ser Ser Asp Ser Ser Asn Ser Ser Asp Ser
                    725                 730                 735
Ser Asn Ser Ser Asp Ser Ser Asn Ser Ser Asp Ser Ser Asn Ser Ser
                    740                 745                 750
Asp Ser Ser Asn Ser Ser Asp Ser Ser Asn Ser Ser Asp Ser Ser Asn
                    755                 760                 765
Ser Ser Asp Ser Ser Asn Ser Ser Asp Ser Ser Asn Ser Ser Asp Ser
                    770                 775                 780
Ser Asn Ser Ser Asp Ser Ser Asn Ser Ser Asp Ser Ser Asn Ser Ser
785                 790                 795                 800
Asp Ser Ser Asn Ser Ser Asp Ser Ser Asn Ser Ser Asp Ser Ser Asn
                    805                 810                 815
Ser Ser Asp Ser Ser Asn Ser Ser Asp Ser Ser Asn Ser Ser Asp Ser
                    820                 825                 830
Ser Asn Ser Ser Asp Ser Ser Asn Ser Ser Asp Ser Ser Asn Ser Ser
                    835                 840                 845
Asp Ser Ser Asn Ser Ser Asp Ser Ser Asn Ser Ser Asp Ser Ser Asn
                    850                 855                 860
Ser Ser Asp Ser Ser Asn Ser Ser Asp Ser Ser Asn Ser Ser Asp Ser
865                 870                 875                 880
Ser Asn Ser Ser Asp Ser Ser Asn Ser Ser Asp Ser Ser Asn Ser Ser
                    885                 890                 895
Asp Ser Ser Asn Ser Ser Asp Ser Ser Asn Ser Ser Asp Ser Ser Asn
                    900                 905                 910
Ser Ser Asp Ser Ser Asn Ser Ser Asp Ser Ser Asn Ser Ser Asp Ser
                    915                 920                 925
Ser Asn Ser Ser Asp Ser Ser Asn Ser Ser Asp Ser Ser Asn Ser Ser
                    930                 935                 940
Asp Ser Ser Asn Ser Ser Asp Ser Ser Asn Ser Ser Asp Ser Ser Asn
945                 950                 955                 960
Ser Ser Asp Ser Ser Asn Ser Ser Asp Ser Ser Asn Ser Ser Asp Ser
                    965                 970                 975
Ser Asn Ser Ser Asp Ser Ser Asn Ser Ser Asp Ser Ser Asn Ser Ser
                    980                 985                 990
Asp Ser Ser Asn Ser Ser Asp Ser  Ser Asn Ser Ser Asp  Ser Ser Asn
        995                 1000                1005
Ser Ser  Asp Ser Ser Asn Ser  Ser Asp Ser Ser Asn  Ser Ser Asp
   1010                1015                1020
Ser Ser  Asn Ser Ser Asp Ser  Ser Asn Ser Ser Asp  Ser Ser Asn
   1025                1030                1035
Ser Ser  Asp Ser Ser Asn Ser  Ser Asp Ser Ser Asn  Ser Ser Asp
   1040                1045                1050
```

```
Ser Ser Asn Ser Ser Asp Ser  Ser Asn Ser Ser Asp  Ser Ser Asn
    1055             1060              1065

Ser Ser Asp Ser Ser Asn Ser  Ser Asp Ser Ser Asn  Ser Ser Asp
    1070             1075              1080

Ser Ser Asn Ser Ser Asp Ser  Ser Asn Ser Ser Asp  Ser Ser Asn
    1085             1090              1095

Ser Ser Asp Ser Ser Asn Ser  Ser Asp Ser Ser Asn  Ser Ser Asp
    1100             1105              1110

Ser Ser Asn Ser Ser Asp Ser  Ser Asn Ser Ser Asp  Ser Ser Asn
    1115             1120              1125

Ser Ser Asp Ser Ser Asn Ser  Ser Asp Ser Ser Asn  Ser Ser Asp
    1130             1135              1140

Ser Ser Asn Ser Ser Asp Ser  Ser Asn Ser Ser Asp  Ser Ser Asn
    1145             1150              1155

Ser Ser Asp Ser Ser Asn Ser  Ser Asp Ser Ser Asn  Ser Ser Asp
    1160             1165              1170

Ser Ser Asn Ser Ser Asp Ser  Ser Asn Ser Ser Asp  Ser Ser Asn
    1175             1180              1185

Ser Ser Asp Ser Ser Asn Ser  Ser Asp Ser Ser Asn
    1190             1195              1200

<210> SEQ ID NO 440
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 4 to 200
      "Ser Ser Glu" repeating units

<400> SEQUENCE: 440

Ser Ser Glu Ser Ser Glu Ser  Ser Glu Ser Ser Glu  Ser Ser Glu
1                5                    10                   15

Ser Glu Ser Ser Glu Ser Ser  Glu Ser Ser Glu Ser  Ser Glu Ser
        20                   25                   30

Glu Ser Ser Glu Ser Ser Glu  Ser Ser Glu Ser Ser  Glu Ser Ser
            35                   40                   45

Ser Ser Glu Ser Ser Glu Ser  Ser Glu Ser Ser Glu  Ser Ser Glu
    50                   55                   60

Ser Glu Ser Ser Glu Ser Ser  Glu Ser Ser Glu Ser  Ser Glu Ser
65                   70                   75                   80

Glu Ser Ser Glu Ser Ser Glu  Ser Ser Glu Ser Ser  Glu Ser Ser Glu
            85                   90                   95

Ser Ser Glu Ser Ser Glu Ser  Ser Glu Ser Ser Glu  Ser Ser Glu Ser
            100                  105                  110

Ser Glu Ser Ser Glu Ser Ser  Glu Ser Ser Glu Ser  Ser Glu Ser Ser
            115                  120                  125

Glu Ser Ser Glu Ser Ser Glu  Ser Ser Glu Ser Ser  Glu Ser Ser Glu
            130                  135                  140

Ser Ser Glu Ser Ser Glu Ser  Ser Glu Ser Ser Glu  Ser Ser Glu Ser
145                  150                  155                  160

Ser Glu Ser Ser Glu Ser Ser  Glu Ser Ser Glu Ser  Ser Glu Ser Ser
                165                  170                  175

Glu Ser Ser Glu Ser Ser Glu  Ser Ser Glu Ser Ser  Glu Ser Ser Glu
```

```
            180                 185                 190
Ser Ser Glu Ser Ser Glu Ser Glu Ser Glu Ser Ser Glu Ser
        195                 200                 205
Ser Glu Ser Ser Glu Ser Ser Glu Ser Ser Glu Ser Ser Ser
        210                 215                 220
Glu Ser Ser Glu Ser Ser Glu Ser Ser Glu Ser Ser Ser Glu
225                 230                 235                 240
Ser Ser Glu Ser Ser Glu Ser Ser Glu Ser Ser Glu Ser Ser
                245                 250                 255
Ser Glu Ser Ser Glu Ser Ser Glu Ser Ser Glu Ser Ser Ser
        260                 265                 270
Glu Ser Ser Glu Ser Ser Glu Ser Ser Glu Ser Ser Ser Glu
        275                 280                 285
Ser Ser Glu Ser Ser Ser Glu Ser Ser Glu Ser Ser Glu Ser
        290                 295                 300
Ser Glu Ser Ser Glu Ser Ser Glu Ser Ser Glu Ser Ser Ser
305                 310                 315                 320
Glu Ser Ser Glu Ser Ser Glu Ser Ser Glu Ser Ser Ser Glu
                325                 330                 335
Ser Ser Glu Ser Ser Ser Glu Ser Ser Glu Ser Ser Glu Ser
                340                 345                 350
Ser Glu Ser Ser Glu Ser Ser Glu Ser Ser Glu Ser Ser Ser
        355                 360                 365
Glu Ser Ser Glu Ser Ser Glu Ser Ser Glu Ser Ser Ser Glu
        370                 375                 380
Ser Ser Glu Ser Ser Ser Glu Ser Ser Glu Ser Ser Glu Ser
385                 390                 395                 400
Ser Glu Ser Ser Glu Ser Ser Glu Ser Ser Glu Ser Ser Ser
                405                 410                 415
Glu Ser Ser Glu Ser Ser Glu Ser Ser Glu Ser Ser Ser Glu
                420                 425                 430
Ser Ser Glu Ser Ser Ser Glu Ser Ser Glu Ser Ser Glu Ser
        435                 440                 445
Ser Glu Ser Ser Glu Ser Ser Glu Ser Ser Glu Ser Ser Ser
        450                 455                 460
Glu Ser Ser Glu Ser Ser Glu Ser Ser Glu Ser Ser Ser Glu
465                 470                 475                 480
Ser Ser Glu Ser Ser Glu Ser Ser Glu Ser Ser Glu Ser Ser
                485                 490                 495
Ser Glu Ser Ser Glu Ser Ser Glu Ser Ser Glu Ser Ser Ser
        500                 505                 510
Glu Ser Ser Glu Ser Ser Glu Ser Ser Glu Ser Ser Ser Glu
        515                 520                 525
Ser Ser Glu Ser Ser Glu Ser Ser Glu Ser Ser Glu Ser Ser
        530                 535                 540
Ser Glu Ser Ser Glu Ser Ser Glu Ser Ser Glu Ser Ser Ser
545                 550                 555                 560
Glu Ser Ser Glu Ser Ser Glu Ser Ser Glu Ser Ser Ser Glu
                565                 570                 575
Ser Ser Glu Ser Ser Glu Ser Ser Glu Ser Ser Glu Ser Ser
                580                 585                 590
Ser Glu Ser Ser Glu Ser Ser Glu
        595                 600
```

```
<210> SEQ ID NO 441
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ser, Asp, Glu, Thr or Pro
<220> FEATURE:
<221> NAME/KEY: MOD_RES
<222> LOCATION: (4)..(4)
<223> OTHER INFORMATION: Ser, Asp, Glu, Thr or Pro
<220> FEATURE:
<221> NAME/KEY: MOD_RES
<222> LOCATION: (6)..(6)
<223> OTHER INFORMATION: Ser, Asp, Glu, Thr or Pro
<220> FEATURE:
<221> NAME/KEY: MOD_RES
<222> LOCATION: (8)..(8)
<223> OTHER INFORMATION: Ser, Asp, Glu, Thr or Pro
<220> FEATURE:
<221> NAME/KEY: MOD_RES
<222> LOCATION: (10)..(10)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (14)..(14)
<223> OTHER INFORMATION: Ser, Asp, Glu, Thr or Pro
<220> FEATURE:
<221> NAME/KEY: MOD_RES
<222> LOCATION: (16)..(16)
<223> OTHER INFORMATION: Ser, Asp, Glu, Thr or Pro
<220> FEATURE:
<221> NAME/KEY: MOD_RES
<222> LOCATION: (18)..(18)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (22)..(22)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (26)..(26)
<223> OTHER INFORMATION: Ser, Asp, Glu, Thr or Pro
<220> FEATURE:
<221> NAME/KEY: MOD_RES
<222> LOCATION: (28)..(28)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (32)..(32)
<223> OTHER INFORMATION: Ser, Asp, Glu, Thr or Pro
<220> FEATURE:
<221> NAME/KEY: MOD_RES
<222> LOCATION: (34)..(34)
<223> OTHER INFORMATION: Ser, Asp, Glu, Thr or Pro
<220> FEATURE:
<221> NAME/KEY: MOD_RES
```

<222> LOCATION: (36)..(36)
<223> OTHER INFORMATION: Ser, Asp, Glu, Thr or Pro
<220> FEATURE:
<221> NAME/KEY: MOD_RES
<222> LOCATION: (38)..(38)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro

<400> SEQUENCE: 441

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa Gly Xaa
            20                  25                  30

Gly Xaa Gly Xaa Gly Xaa Gly Xaa
        35                  40

<210> SEQ ID NO 442
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Asp, Glu, Thr or Pro
<220> FEATURE:
<221> NAME/KEY: MOD_RES
<222> LOCATION: (6)..(6)
<223> OTHER INFORMATION: Ser, Asp, Glu, Thr or Pro
<220> FEATURE:
<221> NAME/KEY: MOD_RES
<222> LOCATION: (9)..(9)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (15)..(15)
<223> OTHER INFORMATION: Ser, Asp, Glu, Thr or Pro
<220> FEATURE:
<221> NAME/KEY: MOD_RES
<222> LOCATION: (18)..(18)
<223> OTHER INFORMATION: Ser, Asp, Glu, Thr or Pro
<220> FEATURE:
<221> NAME/KEY: MOD_RES
<222> LOCATION: (21)..(21)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (27)..(27)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (33)..(33)
<223> OTHER INFORMATION: Ser, Asp, Glu, Thr or Pro
<220> FEATURE:
<221> NAME/KEY: MOD_RES
<222> LOCATION: (36)..(36)
<223> OTHER INFORMATION: Ser, Asp, Glu, Thr or Pro
<220> FEATURE:

```
<221> NAME/KEY: MOD_RES
<222> LOCATION: (39)..(39)
<223> OTHER INFORMATION: Ser, Asp, Glu, Thr or Pro

<400> SEQUENCE: 442

Gly Gly Xaa Gly Gly Xaa Gly Gly Xaa Gly Gly Xaa Gly Gly Xaa Gly
1               5                   10                  15

Gly Xaa Gly Gly Xaa Gly Gly Xaa Gly Gly Xaa Gly Gly Xaa Gly Gly
            20                  25                  30

Xaa Gly Gly Xaa Gly Gly Xaa
        35

<210> SEQ ID NO 443
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Ser, Asp, Glu, Thr or Pro
<220> FEATURE:
<221> NAME/KEY: MOD_RES
<222> LOCATION: (8)..(8)
<223> OTHER INFORMATION: Ser, Asp, Glu, Thr or Pro
<220> FEATURE:
<221> NAME/KEY: MOD_RES
<222> LOCATION: (12)..(12)
<223> OTHER INFORMATION: Ser, Asp, Glu, Thr or Pro
<220> FEATURE:
<221> NAME/KEY: MOD_RES
<222> LOCATION: (16)..(16)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (24)..(24)
<223> OTHER INFORMATION: Ser, Asp, Glu, Thr or Pro
<220> FEATURE:
<221> NAME/KEY: MOD_RES
<222> LOCATION: (28)..(28)
<223> OTHER INFORMATION: Ser, Asp, Glu, Thr or Pro
<220> FEATURE:
<221> NAME/KEY: MOD_RES
<222> LOCATION: (32)..(32)
<223> OTHER INFORMATION: Ser, Asp, Glu, Thr or Pro
<220> FEATURE:
<221> NAME/KEY: MOD_RES
<222> LOCATION: (36)..(36)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro

<400> SEQUENCE: 443

Gly Gly Gly Xaa Gly Gly Gly Xaa Gly Gly Gly Xaa Gly Gly Gly Xaa
1               5                   10                  15

Gly Gly Gly Xaa Gly Gly Gly Xaa Gly Gly Gly Xaa Gly Gly Gly Xaa
            20                  25                  30

Gly Gly Gly Xaa Gly Gly Gly Xaa
        35                  40

<210> SEQ ID NO 444
<211> LENGTH: 40
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Ser, Asp, Glu, Thr or Pro
<220> FEATURE:
<221> NAME/KEY: MOD_RES
<222> LOCATION: (10)..(10)
<223> OTHER INFORMATION: Ser, Asp, Glu, Thr or Pro
<220> FEATURE:
<221> NAME/KEY: MOD_RES
<222> LOCATION: (15)..(15)
<223> OTHER INFORMATION: Ser, Asp, Glu, Thr or Pro
<220> FEATURE:
<221> NAME/KEY: MOD_RES
<222> LOCATION: (20)..(20)
<223> OTHER INFORMATION: Ser, Asp, Glu, Thr or Pro
<220> FEATURE:
<221> NAME/KEY: MOD_RES
<222> LOCATION: (25)..(25)
<223> OTHER INFORMATION: Ser, Asp, Glu, Thr or Pro
<220> FEATURE:
<221> NAME/KEY: MOD_RES
<222> LOCATION: (30)..(30)
<223> OTHER INFORMATION: Ser, Asp, Glu, Thr or Pro
<220> FEATURE:
<221> NAME/KEY: MOD_RES
<222> LOCATION: (35)..(35)
<223> OTHER INFORMATION: Ser, Asp, Glu, Thr or Pro
<220> FEATURE:
<221> NAME/KEY: MOD_RES
<222> LOCATION: (40)..(40)
<223> OTHER INFORMATION: Ser, Asp, Glu, Thr or Pro

<400> SEQUENCE: 444

Gly Gly Gly Gly Xaa Gly Gly Gly Gly Xaa Gly Gly Gly Gly Xaa Gly
1               5                   10                  15

Gly Gly Gly Xaa Gly Gly Gly Gly Xaa Gly Gly Gly Gly Xaa Gly Gly
            20                  25                  30

Gly Gly Xaa Gly Gly Gly Gly Xaa
        35                  40

<210> SEQ ID NO 445
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Ser, Asp, Glu, Thr or Pro
<220> FEATURE:
<221> NAME/KEY: MOD_RES
<222> LOCATION: (22)..(41)
<223> OTHER INFORMATION: This region may encompass 1 to 20
      "Gly" repeating residues
<220> FEATURE:
<221> NAME/KEY: MOD_RES
<222> LOCATION: (42)..(42)
<223> OTHER INFORMATION: Ser, Asp, Glu, Thr or Pro
<220> FEATURE:
<221> NAME/KEY: MOD_RES
<222> LOCATION: (43)..(62)
<223> OTHER INFORMATION: This region may encompass 1 to 20
      "Gly" repeating residues
<220> FEATURE:
<221> NAME/KEY: MOD_RES
<222> LOCATION: (63)..(63)
<223> OTHER INFORMATION: Ser, Asp, Glu, Thr or Pro
<220> FEATURE:
```

```
<221> NAME/KEY: MOD_RES
<222> LOCATION: (64)..(83)
<223> OTHER INFORMATION: This region may encompass 1 to 20
      "Gly" repeating residues
<220> FEATURE:
<221> NAME/KEY: MOD_RES
<222> LOCATION: (84)..(84)
<223> OTHER INFORMATION: Ser, Asp, Glu, Thr or Pro
<220> FEATURE:
<221> NAME/KEY: MOD_RES
<222> LOCATION: (85)..(104)
<223> OTHER INFORMATION: This region may encompass 1 to 20
      "Gly" repeating residues
<220> FEATURE:
<221> NAME/KEY: MOD_RES
<222> LOCATION: (105)..(105)
<223> OTHER INFORMATION: Ser, Asp, Glu, Thr or Pro
<220> FEATURE:
<221> NAME/KEY: MOD_RES
<222> LOCATION: (106)..(125)
<223> OTHER INFORMATION: This region may encompass 1 to 20
      "Gly" repeating residues
<220> FEATURE:
<221> NAME/KEY: MOD_RES
<222> LOCATION: (126)..(126)
<223> OTHER INFORMATION: Ser, Asp, Glu, Thr or Pro
<220> FEATURE:
<221> NAME/KEY: MOD_RES
<222> LOCATION: (127)..(146)
<223> OTHER INFORMATION: This region may encompass 1 to 20
      "Gly" repeating residues
<220> FEATURE:
<221> NAME/KEY: MOD_RES
<222> LOCATION: (147)..(147)
<223> OTHER INFORMATION: Ser, Asp, Glu, Thr or Pro
<220> FEATURE:
<221> NAME/KEY: MOD_RES
<222> LOCATION: (148)..(167)
<223> OTHER INFORMATION: This region may encompass 1 to 20
      "Gly" repeating residues
<220> FEATURE:
<221> NAME/KEY: MOD_RES
<222> LOCATION: (168)..(168)
<223> OTHER INFORMATION: Ser, Asp, Glu, Thr or Pro
<220> FEATURE:
<221> NAME/KEY: MOD_RES
<222> LOCATION: (169)..(187)
<223> OTHER INFORMATION: This region may encompass 1 to 20
      "Gly" repeating residues
<220> FEATURE:
<221> NAME/KEY: MOD_RES
<222> LOCATION: (189)..(189)
<223> OTHER INFORMATION: Ser, Asp, Glu, Thr or Pro
<220> FEATURE:
<221> NAME/KEY: MOD_RES
<222> LOCATION: (190)..(209)
<223> OTHER INFORMATION: This region may encompass 1 to 20
      "Gly" repeating residues
<220> FEATURE:
<221> NAME/KEY: MOD_RES
<222> LOCATION: (210)..(210)
<223> OTHER INFORMATION: Ser, Asp, Glu, Thr or Pro
<220> FEATURE:
<221> NAME/KEY: MOD_RES
<222> LOCATION: (211)..(230)
<223> OTHER INFORMATION: This region may encompass 1 to 20
      "Gly" repeating residues
<220> FEATURE:
<221> NAME/KEY: MOD_RES
<222> LOCATION: (231)..(231)
<223> OTHER INFORMATION: Ser, Asp, Glu, Thr or Pro
<220> FEATURE:
<221> NAME/KEY: MOD_RES
<222> LOCATION: (232)..(251)
<223> OTHER INFORMATION: This region may encompass 1 to 20
      "Gly" repeating residues
<220> FEATURE:
<221> NAME/KEY: MOD_RES
<222> LOCATION: (252)..(252)
```

<223> OTHER INFORMATION: Ser, Asp, Glu, Thr or Pro
<220> FEATURE:
<221> NAME/KEY: MOD_RES
<222> LOCATION: (253)..(272)
<223> OTHER INFORMATION: This region may encompass 1 to 20
      "Gly" repeating residues
<220> FEATURE:
<221> NAME/KEY: MOD_RES
<222> LOCATION: (273)..(273)
<223> OTHER INFORMATION: Ser, Asp, Glu, Thr or Pro
<220> FEATURE:
<221> NAME/KEY: MOD_RES
<222> LOCATION: (274)..(293)
<223> OTHER INFORMATION: This region may encompass 1 to 20
      "Gly" repeating residues
<220> FEATURE:
<221> NAME/KEY: MOD_RES
<222> LOCATION: (294)..(294)
<223> OTHER INFORMATION: Ser, Asp, Glu, Thr or Pro
<220> FEATURE:
<221> NAME/KEY: MOD_RES
<222> LOCATION: (295)..(314)
<223> OTHER INFORMATION: This region may encompass 1 to 20
      "Gly" repeating residues
<220> FEATURE:
<221> NAME/KEY: MOD_RES
<222> LOCATION: (315)..(315)
<223> OTHER INFORMATION: Ser, Asp, Glu, Thr or Pro

<400> SEQUENCE: 445

Gly Gly Gly Gly Gly Gly Gly Gly Gly Gly Gly Gly Gly Gly Gly
 1               5                  10                  15

Gly Gly Gly Gly Xaa Gly Gly Gly Gly Gly Gly Gly Gly Gly Gly
            20                  25                  30

Gly Gly Gly Gly Gly Gly Gly Gly Xaa Gly Gly Gly Gly Gly Gly
        35                  40                  45

Gly Gly Gly Gly Gly Gly Gly Gly Gly Gly Gly Gly Xaa Gly
    50                  55                  60

Gly Gly Gly Gly Gly Gly Gly Gly Gly Gly Gly Gly Gly Gly Gly
65                  70                  75                  80

Gly Gly Gly Xaa Gly Gly Gly Gly Gly Gly Gly Gly Gly Gly Gly
                85                  90                  95

Gly Gly Gly Gly Gly Gly Gly Xaa Gly Gly Gly Gly Gly Gly Gly
            100                 105                 110

Gly Gly Gly Gly Gly Gly Gly Gly Gly Gly Gly Xaa Gly Gly
        115                 120                 125

Gly Gly Gly Gly Gly Gly Gly Gly Gly Gly Gly Gly Gly Gly Gly
    130                 135                 140

Gly Gly Xaa Gly Gly Gly Gly Gly Gly Gly Gly Gly Gly Gly Gly
145                 150                 155                 160

Gly Gly Gly Gly Gly Gly Gly Xaa Gly Gly Gly Gly Gly Gly Gly
                165                 170                 175

Gly Gly Gly Gly Gly Gly Gly Gly Gly Gly Gly Xaa Gly Gly
            180                 185                 190

Gly Gly Gly Gly Gly Gly Gly Gly Gly Gly Gly Gly Gly Gly Gly
        195                 200                 205

Gly Xaa Gly Gly Gly Gly Gly Gly Gly Gly Gly Gly Gly Gly
    210                 215                 220

Gly Gly Gly Gly Gly Gly Xaa Gly Gly Gly Gly Gly Gly Gly
225                 230                 235                 240

Gly Gly Gly Gly Gly Gly Gly Gly Gly Gly Xaa Gly Gly Gly Gly
                245                 250                 255

```
Gly Gly Gly Gly Gly Gly Gly Gly Gly Gly Gly Gly
            260                 265                 270

Xaa Gly Gly Gly Gly Gly Gly Gly Gly Gly Gly Gly Gly
        275                 280                 285

Gly Gly Gly Gly Gly Xaa Gly Gly Gly Gly Gly Gly Gly
    290                 295                 300

Gly Gly Gly Gly Gly Gly Gly Gly Gly Xaa
305                 310                 315

<210> SEQ ID NO 446
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Lys Cys Lys Lys
1

<210> SEQ ID NO 447
<211> LENGTH: 4
<212> TYPE: PRT
<213> ORGANISM: Homo sapiens

<400> SEQUENCE: 447

Asp Asp Asp Lys
1

<210> SEQ ID NO 448
<211> LENGTH: 4
<212> TYPE: PRT
<213> ORGANISM: Homo sapiens

<400> SEQUENCE: 448

Ile Asp Gly Arg
1

<210> SEQ ID NO 449
<211> LENGTH: 6
<212> TYPE: PRT
<213> ORGANISM: Homo sapiens

<400> SEQUENCE: 449

Leu Val Pro Arg Gly Ser
1               5

<210> SEQ ID NO 450
<211> LENGTH: 8
<212> TYPE: PRT
<213> ORGANISM: Homo sapiens

<400> SEQUENCE: 450

Leu Glu Val Leu Phe Gln Gly Pro
1               5

<210> SEQ ID NO 451
<211> LENGTH: 7
<212> TYPE: PRT
<213> ORGANISM: Homo sapiens

<400> SEQUENCE: 451

Glu Gln Leu Tyr Phe Gln Gly
```

1               5

<210> SEQ ID NO 452
<211> LENGTH: 7
<212> TYPE: PRT
<213> ORGANISM: Homo sapiens

<400> SEQUENCE: 452

Glu Thr Leu Phe Gln Gly Pro
1               5

<210> SEQ ID NO 453
<211> LENGTH: 5
<212> TYPE: PRT
<213> ORGANISM: Homo sapiens

<400> SEQUENCE: 453

Leu Pro Glu Thr Gly
1               5

<210> SEQ ID NO 454
<211> LENGTH: 191
<212> TYPE: PRT
<213> ORGANISM: Homo sapiens

<400> SEQUENCE: 454

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 455
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Gly Gly Ser Gly Gly Glu Gly Gly Ser Gly Gly Glu Gly Gly Ser Gly
1               5                   10                  15

Gly Glu Gly Gly Ser Gly Gly Glu Gly Gly Ser Gly Gly Glu Gly Gly
            20                  25                  30

Ser Gly Gly Glu Gly Gly Ser Gly Gly Glu Gly Gly Ser Gly Gly Glu
        35                  40                  45

Gly Gly Ser Gly Gly Glu Gly Gly Ser Gly Gly Glu Gly Gly Ser Gly
    50                  55                  60

Gly Glu Gly Gly Ser Gly Gly Glu Gly Gly Ser Gly Gly Glu Gly Gly
65                  70                  75                  80

Ser Gly Gly Glu Gly Gly Ser Gly Gly Glu Gly Gly Ser Gly Gly Glu
            85                  90                  95

Gly Gly Ser Gly Gly Glu Gly Gly Ser Gly Gly Glu Gly Gly Ser Gly
        100                 105                 110

Gly Glu Gly Gly Ser Gly Gly Glu Gly Gly Ser Gly Gly Glu Gly Gly
    115                 120                 125

Ser Gly Gly Glu Gly Gly Ser Gly Gly Glu Gly Gly Ser Gly Gly Glu
130                 135                 140

Gly Gly Ser Gly Gly Glu Gly Gly Ser Gly Gly Glu Gly Gly Ser Gly
145                 150                 155                 160

Gly Glu Gly Gly Ser Gly Gly Glu Gly Gly Ser Gly Gly Glu Gly Gly
            165                 170                 175

Ser Gly Gly Glu Gly Gly Ser Gly Gly Glu Gly Gly Ser Gly Gly Glu
        180                 185                 190

Gly Gly Ser Gly Gly Glu Gly Gly Ser Gly Gly Glu Gly Gly Ser Gly
    195                 200                 205

Gly Glu Gly Gly Ser Gly Gly Glu Gly Gly Ser Gly Gly Glu Gly Gly
210                 215                 220

Ser Gly Gly Glu Gly Gly Ser Gly Gly Glu Gly Gly Ser Gly Gly Glu
225                 230                 235                 240

Gly Gly Ser Gly Gly Glu Gly Gly Ser Gly Gly Glu Gly Gly Ser Gly
            245                 250                 255

Gly Glu Gly Gly Ser Gly Gly Glu Gly Gly Ser Gly Gly Glu Gly Gly
        260                 265                 270

Ser Gly Gly Glu Gly Gly Ser Gly Gly Glu Gly Gly Ser Gly Gly Glu
    275                 280                 285

<210> SEQ ID NO 456
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
aggtagtggw ggwgarggwg gwtcyggwgg agaagg                                    36

<210> SEQ ID NO 457
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
acctccttct ccwccrgawc cwccytcwcc wccact                                    36

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
aggttcgtct tcactcgagg gtac                                          24

<210> SEQ ID NO 459
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
cctcgagtga agacga                                                   16

<210> SEQ ID NO 460
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Ser Ser Ser Glu Ser Ser Glu Ser Ser Ser Glu Ser Ser Ser Glu
1               5                   10                  15

Ser Ser Glu Ser Ser Ser Glu Ser Ser Glu Ser Ser Glu Ser
            20                  25                  30

Ser Ser Ser Glu Ser Ser Glu Ser Ser Glu Ser Ser Ser Glu
        35                  40                  45

Ser Ser Ser Glu Ser Ser Glu Ser Ser Ser Glu Ser Ser Ser Glu
    50                  55                  60

Ser Ser Glu Ser Ser Ser Glu Ser Ser Ser Glu Ser Ser Glu Ser
65                  70                  75                  80

Ser Ser Ser Glu Ser Ser Glu Ser Ser Glu Ser Ser Ser Glu
            85                  90                  95

Ser Ser Ser Glu Ser Ser Glu Ser Ser Glu Ser Ser Ser Glu
        100                 105                 110

Ser Ser Glu Ser Ser Ser Ser Glu Ser Ser Ser Glu Ser Ser Glu Ser
            115                 120                 125

Ser Ser Ser Glu Ser Ser Glu Ser Ser Glu Ser Ser Ser Glu
    130                 135                 140

Ser Ser Ser Glu Ser Ser Glu Ser Ser Glu Ser Ser Ser Glu
145                 150                 155                 160

Ser Ser Glu Ser Ser Ser Ser Glu Ser Ser Glu Ser Ser Glu Ser
            165                 170                 175

Ser Ser Ser Glu Ser Ser Glu Ser Ser Glu Ser Ser Ser Glu
        180                 185                 190

Ser Ser Ser Glu Ser Ser Glu Ser Ser Ser Glu Ser Ser Ser Glu
    195                 200                 205

Ser Ser Glu Ser Ser Ser Ser Glu Ser Ser Glu Ser Ser Glu Ser
        210                 215                 220

Ser Ser Ser Glu Ser Ser Glu Ser Ser Glu Ser Ser Ser Glu
225                 230                 235                 240

Ser Ser Ser Glu Ser Ser Glu Ser Ser Glu Ser Ser Ser Glu
                245                 250                 255

Ser Ser Glu Ser Ser Ser Glu Ser Ser Glu Ser Ser Glu Ser
            260                 265                 270

Ser Ser Ser Glu Ser Ser Glu Ser Ser Glu Ser Ser Ser Glu
        275                 280                 285

<210> SEQ ID NO 461
<211> LENGTH: 36
<212> TYPE: PRT
<213> ORGANISM: Artificial Sequence
<220> FEATURE:
<223> OTHER INFORMATION: Description of Artificial Sequence: Synthetic peptide

<400> SEQUENCE: 461

Ser Ser Ser Glu Ser Ser Glu Ser Ser Ser Glu Ser Ser Glu
1               5                   10                  15

Ser Ser Glu Ser Ser Ser Glu Ser Ser Glu Ser Ser Glu Ser
            20                  25                  30

Ser Ser Ser Glu
        35

<210> SEQ ID NO 462
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 462

Ser Ser Glu Ser Ser Glu Ser Ser Ser Ser Glu Ser
1               5                   10

<210> SEQ ID NO 463
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 463
ttctagtgar tcyagygart cyagytcyag ygaatc                           36

<210> SEQ ID NO 464
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 464
agaagattcr ctrgarctrg aytcrctrga ytcact                           36

<210> SEQ ID NO 465
<211> LENGTH: 24
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 465
ttcttcgtct tcactcgagg gtac                                              24

<210> SEQ ID NO 466
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

```
Gly Glu Gly Gly Gly Glu Gly Gly Gly Glu Gly Gly Gly Glu Gly
1               5                   10                  15
Gly Glu Gly Gly Glu Gly Gly Glu Gly Gly Gly Glu Gly Gly Gly
                20                  25                  30
Glu Gly Gly Gly Glu Gly Gly Gly Glu Gly Gly Gly Glu Gly Gly
            35                  40                  45
Gly Gly Glu Gly Gly Gly Glu Gly Gly Gly Glu Gly Gly Glu Gly
        50                  55                  60
Glu Gly Gly Gly Glu Gly Gly Gly Glu Gly Gly Gly Glu Gly Gly
65                  70                  75                  80
Glu Gly Gly Gly Glu Gly Gly Gly Glu Gly Gly Gly Glu Gly Glu
                85                  90                  95
Gly Gly Glu Gly Gly Gly Glu Gly Gly Gly Glu Gly Gly Glu Gly
            100                 105                 110
Gly Glu Gly Gly Glu Gly Gly Glu Gly Gly Gly Glu Gly Gly Glu
        115                 120                 125
Gly Gly Gly Glu Gly Gly Gly Glu Gly Gly Gly Glu Gly Gly Glu
    130                 135                 140
Gly Glu Gly Gly Gly Glu Gly Gly Glu Gly Glu Gly Gly Glu Gly
145                 150                 155                 160
Gly Glu Gly Glu Gly Gly Gly Glu Gly Gly Glu Gly Glu Gly Gly
                165                 170                 175
Glu Gly Gly Glu Gly Glu Gly Gly Glu Gly Gly Glu Gly Glu Gly
            180                 185                 190
Gly Gly Glu Gly Gly Gly Glu Gly Gly Gly Gly Glu Gly Gly Glu
        195                 200                 205
Glu Gly Gly Gly Glu Gly Gly Glu Gly Gly Glu Gly Glu Gly Gly
    210                 215                 220
Glu Gly Glu Gly Gly Gly Glu Gly Gly Glu Gly Gly Gly Gly Glu
225                 230                 235                 240
Gly Gly Glu Gly Glu Gly Gly Gly Glu Gly Gly Glu Gly Gly Gly
                245                 250                 255
Gly Glu Gly Gly Glu Gly Glu Gly Gly Glu Gly Gly Glu Gly Glu
            260                 265                 270
Gly Gly Gly Glu Gly Gly Glu Gly Gly Gly Gly Glu Gly Gly Glu
        275                 280                 285
```

<210> SEQ ID NO 467
<211> LENGTH: 27
<212> TYPE: DNA
<213> ORGANISM: Artificial Sequence
<220> FEATURE:
<223> OTHER INFORMATION: Description of Artificial Sequence: Synthetic

```
                primer

<400> SEQUENCE: 467
aggtgaaggw garggwggwg gwgaagg                                              27

<210> SEQ ID NO 468
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
acctccttcw ccwccwccyt cwccttc                                              27

<210> SEQ ID NO 469
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid

<400> SEQUENCE: 469

Glu Asn Leu Tyr Phe Gln Xaa
1               5

<210> SEQ ID NO 470
<211> LENGTH: 165
<212> TYPE: PRT
<213> ORGANISM: Homo sapiens

<400> SEQUENCE: 470

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 471
<211> LENGTH: 174
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 471

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 472
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gly Ser Gly Gly Glu Gly Gly Ser Gly Gly Glu Gly Gly Ser Gly Gly
1               5                   10                  15

Glu Gly Gly Ser Gly Gly Glu Gly Gly Ser Gly Gly Glu Gly Gly Ser
            20                  25                  30

Gly Gly Glu Gly Gly Ser Gly Gly Glu Gly Gly Ser Gly Gly Glu Gly
        35                  40                  45

Gly Ser Gly Gly Glu Gly Gly Ser Gly Gly Glu Gly Gly Ser Gly Gly
    50                  55                  60

Glu Gly Gly Ser Gly Gly Glu Gly Gly Ser Gly Gly Glu Gly Gly Ser
65                  70                  75                  80

Gly Gly Glu Gly Gly Ser Gly Gly Glu Gly Gly Ser Gly Gly Glu Gly
                85                  90                  95

Gly Ser Gly Gly Glu Gly Gly Ser Gly Gly Glu Gly Gly Ser Gly Gly
            100                 105                 110

Glu Gly Gly Ser Gly Gly Glu Gly Gly Ser Gly Gly Glu Gly Gly Ser
        115                 120                 125

Gly Gly Glu Gly Gly Ser Gly Gly Glu Gly Gly Ser Gly Gly Glu Gly
    130                 135                 140

Gly Ser Gly Gly Glu Gly Gly Ser Gly Gly Glu Gly Gly Ser Gly Gly

```
                145                 150                 155                 160
Glu Gly Gly Ser Gly Gly Glu Gly Gly Ser Gly Gly Glu Gly Gly Ser
                    165                 170                 175

Gly Gly Glu Gly Gly Ser Gly Gly Glu Gly Gly Ser Gly Gly Glu Gly
                180                 185                 190

Gly Ser Gly Gly Glu Gly Gly Ser Gly Gly Glu Gly Gly Ser Gly Gly
            195                 200                 205

Glu Gly Gly Ser Gly Gly Glu Gly Gly Ser Gly Gly Glu Gly Gly Ser
        210                 215                 220

Gly Gly Glu Gly Gly Ser Gly Gly Glu Gly Gly Ser Gly Gly Glu Gly
225                 230                 235                 240

Gly Ser Gly Gly Glu Gly Gly Ser Gly Gly Glu Gly Gly Ser Gly Gly
            245                 250                 255

Glu Gly Gly Ser Gly Gly Glu Gly Gly Ser Gly Gly Glu Gly Gly Ser
        260                 265                 270

Gly Gly Glu Gly Gly Ser Gly Gly Glu Gly Gly Ser Gly Gly Glu Gly
    275                 280                 285

<210> SEQ ID NO 473
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Gly Glu Gly Glu Gly Gly Gly Glu Gly Gly Glu Gly Gly Gly Gly Gly
1               5                   10                  15

Glu Gly Gly Glu Gly Gly Gly Gly Gly Glu Gly Gly Glu Gly Glu Gly
                20                  25                  30

Gly Gly Glu Gly Gly Glu Gly Glu Gly Gly Glu Gly Gly Glu Glu Gly
            35                  40                  45

Glu Gly Gly Glu Gly Gly Gly Glu Gly Gly Gly Gly Glu Gly Gly Gly
        50                  55                  60

Glu Gly Glu Gly Gly Gly Glu Gly Gly Gly Glu Gly Glu Gly Gly Glu
65                  70                  75                  80

Gly Gly Glu Gly Glu Gly Gly Glu Gly Gly Glu Gly Glu Gly Gly Gly
                85                  90                  95

Gly Glu Gly Gly Glu Gly Gly Gly Gly Glu Gly Gly Glu Gly Gly Glu
            100                 105                 110

Gly Gly Gly Glu Gly Gly Gly Gly Glu Gly Gly Glu Gly Gly Gly Glu
        115                 120                 125

Gly Glu Gly Gly Gly Glu Gly Gly Glu Gly Gly Gly Gly Glu Gly Gly
    130                 135                 140

Gly Glu Gly Gly Gly Gly Gly Glu Gly Gly Gly Gly Glu Gly Gly Gly
145                 150                 155                 160

Glu Gly Gly Glu Gly Gly Gly Gly Glu Gly Gly Gly Gly Glu Gly Gly
                165                 170                 175

Gly Gly Glu Gly Gly Glu Gly Glu Gly Gly Gly Gly Glu Gly Gly Gly
            180                 185                 190

Glu Gly Gly Gly Glu Gly Gly Glu Gly Glu Gly Gly Gly Glu Gly Gly
        195                 200                 205

Glu Gly Glu Gly Gly Gly Glu Gly Gly Glu Gly Glu Gly Gly Gly Glu
    210                 215                 220
```

```
Gly Gly Glu Gly Glu Gly Gly Glu Gly Glu Gly Gly Glu Gly Gly
225                 230                 235                 240

Gly Glu Gly Gly Glu Gly Gly Glu Gly Glu Gly Gly Glu Gly Glu
                245                 250                 255

Gly Gly Glu Gly Gly Glu Gly Gly Glu Gly Glu Gly Gly Glu Glu
            260                 265                 270

Gly Glu Gly Gly Gly Glu Gly Gly Glu Gly Glu Gly Gly Glu Gly
        275                 280                 285

<210> SEQ ID NO 474
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Ser Ser Glu Ser Ser Glu Ser Ser Ser Glu Ser Ser Ser Glu Ser
1               5                   10                  15

Ser Glu Ser Ser Ser Ser Glu Ser Ser Ser Glu Ser Ser Glu Ser
                20                  25                  30

Ser Ser Glu Ser Ser Ser Glu Ser Ser Glu Ser Ser Ser Glu Ser
            35                  40                  45

Ser Ser Glu Ser Ser Glu Ser Ser Ser Glu Ser Ser Ser Glu Ser
        50                  55                  60

Ser Glu Ser Ser Ser Ser Glu Ser Ser Ser Glu Ser Ser Glu Ser
65                  70                  75                  80

Ser Ser Glu Ser Ser Ser Glu Ser Ser Glu Ser Ser Ser Glu Ser
                85                  90                  95

Ser Ser Glu Ser Ser Glu Ser Ser Ser Glu Ser Ser Ser Glu Ser
            100                 105                 110

Ser Glu Ser Ser Ser Ser Glu Ser Ser Ser Glu Ser Ser Glu Ser
        115                 120                 125

Ser Ser Glu Ser Ser Ser Glu Ser Ser Glu Ser Ser Ser Glu Ser
130                 135                 140

Ser Ser Glu Ser Ser Glu Ser Ser Ser Glu Ser Ser Ser Glu Ser
145                 150                 155                 160

Ser Glu Ser Ser Ser Ser Glu Ser Ser Ser Glu Ser Ser Glu Ser
                165                 170                 175

Ser Ser Glu Ser Ser Ser Glu Ser Ser Glu Ser Ser Ser Glu Ser
            180                 185                 190

Ser Ser Glu Ser Ser Glu Ser Ser Ser Glu Ser Ser Ser Glu Ser
        195                 200                 205

Ser Glu Ser Ser Ser Ser Glu Ser Ser Ser Glu Ser Ser Glu Ser
        210                 215                 220

Ser Ser Glu Ser Ser Ser Glu Ser Ser Glu Ser Ser Ser Glu Ser
225                 230                 235                 240

Ser Ser Glu Ser Ser Glu Ser Ser Ser Glu Ser Ser Ser Glu Ser
                245                 250                 255

Ser Glu Ser Ser Ser Ser Glu Ser Ser Ser Glu Ser Ser Glu Ser
            260                 265                 270

Ser Ser Glu Ser Ser Ser Glu Ser Ser Glu Ser Ser Ser Glu Ser
        275                 280                 285

<210> SEQ ID NO 475
```

<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Ser Ser Ser Ser Ser Glu Ser Ser Ser Ser Ser Glu Ser Ser Ser
1               5                   10                  15

Ser Ser Ser Glu Ser Ser Ser Ser Ser Glu Ser Ser Ser Ser Ser
                20                  25                  30

Ser Glu Ser Ser Ser Ser Ser Glu Ser Ser Ser Ser Ser Ser Glu
        35                  40                  45

Ser Ser Ser Ser Ser Glu Ser Ser Ser Ser Ser Glu Ser Ser Ser
    50                  55                  60

Ser Ser Ser Ser Glu Ser Ser Ser Ser Ser Glu Ser Ser Ser Ser
65                  70                  75                  80

Ser Ser Glu Ser Ser Ser Ser Ser Glu Ser Ser Ser Ser Ser Ser
            85                  90                  95

Glu Ser Ser Ser Ser Ser Glu Ser Ser Ser Ser Ser Glu Ser Ser
                100                 105                 110

Ser Ser Ser Ser Glu Ser Ser Ser Ser Ser Glu Ser Ser Ser Ser
        115                 120                 125

Ser Ser Ser Glu Ser Ser Ser Ser Ser Glu Ser Ser Ser Ser Ser
    130                 135                 140

Ser Glu Ser Ser Ser Ser Ser Glu Ser Ser Ser Ser Ser Ser Glu
145                 150                 155                 160

Ser Ser Ser Ser Ser Glu Ser Ser Ser Ser Ser Glu Ser Ser Ser
                165                 170                 175

Ser Ser Ser Ser Glu Ser Ser Ser Ser Ser Glu Ser Ser Ser Ser
        180                 185                 190

Ser Ser Glu Ser Ser Ser Ser Ser Glu Ser Ser Ser Ser Ser Ser
    195                 200                 205

Glu Ser Ser Ser Ser Ser Glu Ser Ser Ser Ser Ser Glu Ser Ser
210                 215                 220

Ser Ser Ser Ser Ser Glu Ser Ser Ser Ser Ser Glu Ser Ser Ser
225                 230                 235                 240

Ser Ser Ser Glu Ser Ser Ser Ser Ser Glu Ser Ser Ser Ser Ser
                245                 250                 255

Ser Glu Ser Ser Ser Ser Ser Glu Ser Ser Ser Ser Ser Ser Glu
        260                 265                 270

Ser Ser Ser Ser Ser Glu Ser Ser Ser Ser Ser Glu Ser Ser Ser
    275                 280                 285

Ser Ser Ser Ser Glu Ser Ser Ser Ser Ser Glu Ser Ser Ser Ser
290                 295                 300

Ser Ser Glu Ser Ser Ser Ser Ser Glu Ser Ser Ser Ser Ser Ser
305                 310                 315                 320

Glu Ser Ser Ser Ser Ser Ser Glu Ser Ser Ser Ser Ser Glu Ser
                325                 330                 335

<210> SEQ ID NO 476
<211> LENGTH: 320
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 476

Ser Ser Ser Glu Ser Ser Ser Glu Ser Ser Ser Glu Ser Ser Ser Ser
1               5                   10                  15

Ser Ser Glu Ser Ser Ser Ser Glu Ser Ser Ser Ser Glu Ser Ser Ser
            20                  25                  30

Ser Glu Ser Ser Ser Ser Glu Ser Ser Ser Ser Glu Ser Ser Ser Ser
        35                  40                  45

Glu Ser Ser Ser Ser Glu Ser Ser Ser Ser Glu Ser Ser Ser Ser Glu
    50                  55                  60

Ser Ser Ser Ser Glu Ser Ser Ser Ser Glu Ser Ser Ser Ser Glu Ser
65                  70                  75                  80

Ser Ser Ser Glu Ser Ser Ser Ser Glu Ser Ser Ser Ser Glu Ser Ser
                85                  90                  95

Ser Ser Glu Ser Ser Ser Ser Glu Ser Ser Ser Ser Glu Ser Ser Ser
            100                 105                 110

Ser Glu Ser Ser Ser Ser Glu Ser Ser Ser Ser Glu Ser Ser Ser Ser
        115                 120                 125

Glu Ser Ser Ser Ser Glu Ser Ser Ser Ser Glu Ser Ser Ser Ser Glu
    130                 135                 140

Ser Ser Ser Ser Glu Ser Ser Ser Ser Glu Ser Ser Ser Ser Glu Ser
145                 150                 155                 160

Ser Ser Ser Glu Ser Ser Ser Ser Glu Ser Ser Ser Ser Glu Ser Ser
                165                 170                 175

Ser Ser Glu Ser Ser Ser Ser Glu Ser Ser Ser Ser Glu Ser Ser Ser
            180                 185                 190

Ser Glu Ser Ser Ser Ser Glu Ser Ser Ser Ser Glu Ser Ser Ser Ser
        195                 200                 205

Glu Ser Ser Ser Ser Glu Ser Ser Ser Ser Glu Ser Ser Ser Ser Glu
    210                 215                 220

Ser Ser Ser Ser Glu Ser Ser Ser Ser Glu Ser Ser Ser Ser Glu Ser
225                 230                 235                 240

Ser Ser Ser Glu Ser Ser Ser Ser Glu Ser Ser Ser Ser Glu Ser Ser
                245                 250                 255

Ser Ser Glu Ser Ser Ser Ser Glu Ser Ser Ser Ser Glu Ser Ser Ser
            260                 265                 270

Ser Glu Ser Ser Ser Ser Glu Ser Ser Ser Ser Glu Ser Ser Ser Ser
        275                 280                 285

Glu Ser Ser Ser Ser Glu Ser Ser Ser Ser Glu Ser Ser Ser Ser Glu
    290                 295                 300

Ser Ser Ser Ser Glu Ser Ser Ser Ser Glu Ser Ser Ser Ser Glu Ser
305                 310                 315                 320

<210> SEQ ID NO 477
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Gly Glu Gly Ser Gly Glu Gly Ser Glu Gly Glu Gly Ser Glu Gly Ser
1               5                   10                  15

Gly Glu Gly Glu Gly Ser Glu Gly Ser Gly Glu Gly Glu Gly Gly Ser

```
            20                  25                  30

Glu Gly Ser Glu Gly Glu Gly Ser Glu Gly Ser Glu Gly Glu Gly
        35                  40                  45

Gly Ser Glu Gly Ser Gly Glu Gly Ser Gly Glu Gly Ser Glu Gly
        50                  55                  60

Glu Gly Gly Ser Glu Gly Ser Glu Gly Glu Gly Ser Glu Gly Ser
65                  70                  75                  80

Glu Gly Glu Gly Ser Glu Gly Ser Glu Gly Glu Gly Gly Ser Glu
                85                  90                  95

Gly Ser Glu Gly Glu Gly Ser Gly Glu Gly Ser Glu Gly Gly Gly
            100                 105                 110

Glu Gly Gly Ser Glu Gly Glu Gly Ser Glu Gly Ser Glu Gly Glu
            115                 120                 125

Gly Ser Gly Glu Gly Ser Glu Gly Glu Gly Ser Glu Gly Ser Glu
            130                 135                 140

Gly Glu Gly Ser Gly Glu Gly Ser Glu Gly Glu Gly Ser Glu Gly Ser
145                 150                 155                 160

Gly Glu Gly Glu Gly Ser Glu Gly Ser Gly Glu Gly Glu Gly Ser
                165                 170                 175

Glu Gly Ser Glu Gly Glu Gly Ser Glu Gly Ser Glu Gly Glu Gly
            180                 185                 190

Gly Glu Gly Ser Gly Glu Gly Glu Gly Ser Glu Gly Ser Glu Gly
            195                 200                 205

Glu Gly Gly Gly Glu Gly Ser Glu Gly Glu Gly Ser Glu Gly Gly
            210                 215                 220

Glu Gly Glu Gly Ser Glu Gly Gly Ser Glu Gly Glu Gly Ser Glu
225                 230                 235                 240

Gly Gly Glu Gly Glu Gly Ser Glu Gly Gly Ser Glu Gly Glu Gly Ser
                245                 250                 255

Glu Gly Gly Ser Glu Gly Glu Gly Ser Glu Gly Gly Ser Glu Gly Glu
            260                 265                 270

Gly Ser Glu Gly Ser Gly Glu Gly Glu Gly Ser Glu Gly Ser Gly Glu
        275                 280                 285

<210> SEQ ID NO 478
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Gly Glu Gly Ser Gly Glu Gly Ser Glu Gly Glu Gly Ser Glu Gly Ser
1               5                   10                  15

Gly Glu Gly Glu Gly Ser Glu Gly Gly Ser Glu Gly Glu Gly Ser Glu
            20                  25                  30

Gly Ser Glu Gly Glu Gly Ser Glu Gly Ser Glu Gly Glu Gly Glu Gly
        35                  40                  45

Gly Glu Gly Ser Gly Glu Gly Glu Gly Ser Gly Glu Gly Ser Glu Gly
        50                  55                  60

Glu Gly Gly Glu Gly Ser Glu Gly Glu Gly Gly Ser Glu Gly Gly Ser
65                  70                  75                  80

Glu Gly Glu Gly Gly Ser Glu Gly Ser Glu Gly Glu Gly Gly Glu Gly
                85                  90                  95
```

```
Ser Gly Glu Gly Glu Ser Glu Gly Ser Gly Glu Gly Ser
            100                 105                 110

Gly Glu Gly Ser Glu Gly Glu Gly Ser Glu Gly Ser Gly Gly Glu
            115                 120                 125

Gly Ser Glu Gly Ser Gly Glu Gly Gly Ser Glu Gly Ser Glu
            130                 135                 140

Gly Glu Gly Ser Gly Glu Gly Ser Gly Glu Gly Ser Glu Gly Ser
145                 150                 155                 160

Gly Gly Glu Gly Glu Ser Glu Gly Ser Gly Gly Glu Gly Ser
                165                 170                 175

Glu Gly Ser Glu Gly Glu Gly Ser Glu Gly Ser Glu Gly Glu Gly
            180                 185                 190

Gly Ser Glu Gly Ser Glu Gly Glu Gly Ser Gly Glu Gly Ser Glu Gly
            195                 200                 205

Glu Gly Gly Ser Glu Gly Ser Glu Gly Glu Gly Ser Glu Gly Ser
            210                 215                 220

Glu Gly Glu Gly Ser Glu Gly Ser Gly Glu Gly Gly Ser Glu
225                 230                 235                 240

Gly Ser Glu Gly Glu Gly Ser Gly Glu Gly Ser Glu Gly Gly Gly
                245                 250                 255

Glu Gly Gly Ser Glu Gly Glu Gly Ser Glu Gly Ser Glu Gly Glu
            260                 265                 270

Gly Ser Gly Glu Gly Ser Glu Gly Ser Gly Glu Ser Gly Glu
            275                 280                 285

<210> SEQ ID NO 479
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Ser Glu Gly Glu Ser Glu Glu Ser Ser Glu Ser Gly Gly Glu Ser Ser
1               5                   10                  15

Ser Gly Gly Gly Ser Glu Glu Ser Ser Glu Glu Gly Ser Gly Gly Gly
                20                  25                  30

Ser Glu Gly Glu Gly Glu Glu Ser Ser Gly Ser Glu Gly Gly Gly
            35                  40                  45

Ser Gly Glu Gly Ser Glu Gly Gly Ser Glu Gly Ser Glu Ser
            50                  55                  60

Ser Glu Gly Glu Ser Glu Glu Ser Ser Glu Gly Gly Glu Ser Ser
65                  70                  75                  80

Ser Gly Gly Gly Ser Glu Glu Ser Ser Glu Glu Gly Ser Gly Gly Gly
                85                  90                  95

Ser Gly Glu Ser Gly Ser Gly Ser Ser Gly Ser Glu Ser Glu Gly Gly
            100                 105                 110

Ser Glu Gly Glu Ser Glu Glu Ser Ser Gly Gly Gly Ser Glu Gly
            115                 120                 125

Ser Glu Gly Glu Ser Glu Glu Ser Ser Glu Ser Gly Gly Glu Ser Ser
            130                 135                 140

Ser Gly Gly Gly Ser Glu Glu Ser Ser Glu Glu Gly Ser Gly Gly Gly
145                 150                 155                 160

Ser Glu Glu Glu Ser Gly Glu Gly Ser Gly Glu Gly Ser Glu Gly Ser
                165                 170                 175
```

Ser Gly Glu Gly Ser Glu Ser Ser Gly Ser Glu Gly Gly
        180             185             190

Ser Gly Gly Ser Gly Gly Glu Ser Glu Ser Ser Gly Ser
        195             200             205

Ser Gly Ser Glu Ser Glu Gly Gly Ser Glu Gly Glu Ser
        210             215             220

Ser Gly Gly Gly Ser Glu Gly Ser Ser Glu Gly Gly Ser
225             230             235             240

Ser Glu Glu Gly Ser Glu Gly Ser Gly Gly Glu Gly Glu Ser
                245             250             255

Ser Glu Gly Glu Ser Gly Gly Gly Ser Gly Gly Glu Gly Ser
        260             265             270

<210> SEQ ID NO 480
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Ser Glu Gly Glu Ser Glu Gly Ser Ser Glu Ser Gly Gly Glu Ser Ser
1               5                   10                  15

Ser Gly Gly Gly Ser Glu Gly Ser Ser Glu Glu Gly Ser Gly Gly Gly
                20                  25                  30

Ser Glu Gly Glu Ser Glu Gly Ser Ser Glu Ser Gly Gly Glu Ser Ser
        35                  40                  45

Ser Gly Gly Gly Ser Glu Gly Ser Ser Glu Gly Gly Ser Gly Gly Gly
        50                  55                  60

Ser Gly Glu Ser Gly Ser Gly Ser Ser Gly Glu Ser Gly Gly Gly
65                  70                  75                  80

Ser Glu Gly Glu Ser Glu Gly Ser Ser Gly Gly Gly Ser Glu Gly
                85                  90                  95

Ser Glu Ser Glu Gly Glu Gly Ser Glu Gly Gly Ser Gly Glu Gly
                100             105                 110

Ser Gly Glu Gly Gly Gly Glu Ser Ser Glu Gly Glu Ser Glu Ser
        115                 120                 125

Ser Gly Glu Ser Gly Ser Gly Ser Ser Gly Ser Glu Gly Gly
        130                 135                 140

Ser Glu Gly Glu Ser Glu Ser Ser Gly Gly Gly Ser Glu Gly
145                 150                 155                 160

Ser Gly Glu Ser Gly Ser Gly Ser Ser Gly Ser Glu Gly Gly
                165                 170                 175

Ser Glu Gly Glu Ser Glu Ser Ser Gly Gly Gly Ser Glu Gly
                180                 185                 190

Ser Gly Glu Ser Gly Ser Gly Ser Ser Gly Ser Glu Gly Gly
                195                 200                 205

Ser Glu Gly Glu Ser Glu Ser Ser Gly Gly Gly Gly Ser Glu Gly
        210                 215                 220

Ser Ser Glu Glu Ser Gly Ser Ser Glu Gly Gly Ser Gly Gly Ser
225                 230                 235                 240

Ser Gly Gly Glu Ser Glu Glu Ser Ser Glu Gly Glu Ser Gly Gly Gly
                245                 250                 255

Ser Gly Gly Gly Ser Glu Gly Ser
                260

260

<210> SEQ ID NO 481
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Ser Glu Gly Glu Ser Glu Glu Ser Ser Glu Ser Gly Gly Glu Ser Ser
1               5                   10                  15

Ser Gly Gly Gly Ser Glu Glu Ser Glu Glu Gly Ser Gly Gly Gly
            20                  25                  30

Ser Glu Gly Glu Gly Glu Glu Ser Ser Gly Ser Glu Gly Gly Gly
        35                  40                  45

Ser Gly Glu Gly Ser Gly Gly Ser Glu Gly Ser Glu Glu Gly Ser
    50                  55                  60

Ser Glu Gly Glu Ser Glu Glu Ser Ser Glu Ser Gly Gly Glu Ser Ser
65              70                  75                  80

Ser Gly Gly Gly Ser Glu Glu Ser Ser Glu Glu Gly Ser Gly Gly Gly
            85                  90                  95

Ser Gly Glu Ser Gly Ser Gly Ser Ser Gly Ser Glu Ser Glu Gly Gly
            100                 105                 110

Ser Glu Gly Glu Ser Glu Glu Ser Gly Gly Gly Ser Glu Gly Gly
        115                 120                 125

Ser Gly Glu Ser Gly Ser Gly Ser Ser Gly Ser Glu Ser Glu Gly Gly
        130                 135                 140

Ser Glu Gly Glu Ser Glu Glu Ser Ser Gly Gly Gly Ser Glu Gly Gly
145                 150                 155                 160

Ser Glu Ser Glu Gly Glu Glu Gly Ser Glu Glu Gly Ser Gly Glu Gly
                165                 170                 175

Ser Gly Glu Gly Gly Gly Gly Ser Ser Glu Gly Glu Ser Glu Ser
            180                 185                 190

Ser Glu Gly Glu Ser Glu Ser Ser Gly Ser Gly Gly Glu Ser Ser
            195                 200                 205

Ser Gly Gly Gly Ser Glu Ser Ser Glu Gly Ser Gly Gly Gly
            210                 215                 220

Ser Ser Glu Glu Ser Gly Gly Ser Glu Glu Gly Ser Gly Gly Ser
225                 230                 235                 240

Ser Gly Gly Glu Ser Glu Glu Ser Ser Gly Glu Ser Gly Gly Gly
                245                 250                 255

Ser Gly Gly Gly Ser Glu Gly Ser
            260

<210> SEQ ID NO 482
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Ser Glu Gly Glu Ser Glu Glu Ser Ser Glu Ser Gly Gly Glu Ser Ser
1               5                   10                  15

Ser Gly Gly Gly Ser Glu Glu Ser Ser Glu Glu Gly Ser Gly Gly Gly

```
            20                  25                  30
Ser Gly Glu Ser Gly Ser Gly Ser Gly Ser Glu Ser Gly Gly
        35                  40                  45
Ser Glu Gly Glu Ser Glu Gly Ser Ser Gly Gly Gly Ser Glu Gly
    50                  55                  60
Ser Gly Glu Gly Glu Ser Glu Gly Ser Ser Glu Gly Glu Ser Ser
65                  70                  75                  80
Ser Gly Gly Gly Ser Glu Glu Ser Ser Glu Glu Gly Ser Gly Gly
                85                  90                  95
Ser Glu Glu Gly Ser Gly Glu Ser Ser Gly Gly Ser Glu Ser Glu Gly
            100                 105                 110
Ser Gly Gly Glu Ser Glu Gly Gly Ser Gly Glu Gly Gly Glu Gly
            115                 120                 125
Ser Gly Glu Ser Gly Ser Gly Ser Ser Gly Ser Glu Ser Glu Gly Gly
            130                 135                 140
Ser Glu Gly Glu Ser Glu Gly Ser Ser Gly Gly Gly Ser Glu Gly
145                 150                 155                 160
Ser Ser Glu Glu Ser Gly Gly Ser Ser Glu Glu Gly Ser Gly Gly
                165                 170                 175
Ser Glu Ser Gly Glu Glu Ser Gly Ser Gly Glu Glu Ser Glu Gly Gly
            180                 185                 190
Ser Gly Gly Ser Gly Gly Glu Gly Ser Gly Glu Ser Gly Ser Gly Ser
            195                 200                 205
Ser Gly Ser Glu Ser Glu Gly Gly Ser Glu Gly Glu Ser Glu Ser
        210                 215                 220
Ser Gly Gly Gly Ser Gly Gly Ser Ser Gly Gly Gly Glu Glu Ser
225                 230                 235                 240
Ser Glu Gly Glu Gly Gly Glu Ser Ser Glu Gly Ser Gly Gly Ser
                245                 250                 255
Ser Glu Glu Gly Ser Gly Glu Gly
            260

<210> SEQ ID NO 483
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Ser Gly Glu Gly Ser Glu Gly Glu Gly Gly Glu Gly Ser Glu Gly
1               5                   10                  15

Glu Gly Ser Gly Glu Gly Gly Glu Gly Glu Gly Ser
            20                  25

<210> SEQ ID NO 484
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(864)

<400> SEQUENCE: 484 tct agt gag tcc agt gaa tcc agc tcc agc gaa tct tct agt gaa tcc      48
```

```
Ser Ser Glu Ser Ser Glu Ser Ser Ser Glu Ser Ser Ser Glu Ser
1               5                   10                  15 agc gag tct agc tct agc gaa tct tct agt gag tcc agt gag tcc agt        96
Ser Glu Ser Ser Ser Glu Ser Ser Ser Glu Ser Ser Ser Glu Ser Ser
                20                  25                  30 tcc agt gaa tct tct agt gag tcc agt gaa tct agc tcc agt gaa tct       144
Ser Ser Glu Ser Ser Ser Glu Ser Ser Glu Ser Ser Ser Ser Glu Ser
            35                  40                  45 tct agt gag tct agc gaa tct agc tcc agc gaa tct tct agt gaa tcc       192
Ser Ser Glu Ser Ser Glu Ser Ser Ser Glu Ser Ser Ser Ser Glu Ser
        50                  55                  60 agc gaa tcc agc tct agt gaa tct tct agt gaa tct agc gag tcc agc       240
Ser Glu Ser Ser Ser Glu Ser Ser Ser Glu Ser Ser Glu Ser Ser Ser
65                  70                  75                  80 tcc agt gaa tct tct agt gag tcc agt gag tcc agt tct agt gaa tct       288
Ser Ser Glu Ser Ser Ser Glu Ser Ser Glu Ser Ser Ser Ser Glu Ser
                85                  90                  95 tct agt gaa tct agt gag tcc agc tcc agc gaa tct tct agt gaa tct       336
Ser Ser Glu Ser Ser Glu Ser Ser Ser Glu Ser Ser Ser Ser Glu Ser
                100                 105                 110 agc gag tcc agt tcc agt gaa tct tct agt gaa tct agt gaa tct agc       384
Ser Glu Ser Ser Ser Ser Glu Ser Ser Ser Glu Ser Ser Glu Ser Ser
            115                 120                 125 tct agc gaa tct tct agt gag tcc agc gaa tcc agt tct agt gaa tct       432
Ser Ser Glu Ser Ser Ser Glu Ser Ser Glu Ser Ser Ser Ser Glu Ser
        130                 135                 140 tct agt gag tcc agc gag tcc agc tct agt gaa tct tct agt gaa tcc       480
Ser Ser Glu Ser Ser Glu Ser Ser Ser Ser Glu Ser Ser Ser Glu Ser
145                 150                 155                 160 agc gag tcc agt tcc agt gaa tct tct agt gaa tct agt gag tcc agt       528
Ser Glu Ser Ser Ser Ser Glu Ser Ser Ser Glu Ser Ser Glu Ser Ser
                165                 170                 175 tct agt gaa tct tct agt gag tcc agc gag tcc agc tct agt gaa tct       576
Ser Ser Glu Ser Ser Ser Glu Ser Ser Glu Ser Ser Ser Ser Glu Ser
            180                 185                 190 tct agt gaa tcc agc gag tcc agt tcc agt gaa tct tct agt gaa tct       624
Ser Ser Glu Ser Ser Glu Ser Ser Ser Ser Glu Ser Ser Ser Glu Ser
        195                 200                 205 agt gag tcc agt tct agt gaa tct tct agt gaa tct agt gag tcc agt       672
Ser Glu Ser Ser Ser Ser Glu Ser Ser Ser Glu Ser Ser Glu Ser Ser
210                 215                 220 tcc agt gaa tct tct agt gaa tct agt gaa tcc agt tct agc gaa tct       720
Ser Ser Glu Ser Ser Ser Glu Ser Ser Glu Ser Ser Ser Ser Glu Ser
225                 230                 235                 240 tct agt gag tcc agt gag tcc agc tct agt gaa tct tct agt gaa tcc       768
Ser Ser Glu Ser Ser Glu Ser Ser Ser Ser Glu Ser Ser Ser Glu Ser
            245                 250                 255 agc gaa tcc agc tct agc gaa tct tct agt gag tcc agc gag tct agt       816
Ser Glu Ser Ser Ser Ser Glu Ser Ser Ser Glu Ser Ser Glu Ser Ser
        260                 265                 270 tcc agt gaa tct tct agt gaa tcc agc gaa tct agc tcc agc gaa tct       864
Ser Ser Glu Ser Ser Ser Glu Ser Ser Glu Ser Ser Ser Ser Glu Ser
    275                 280                 285

<210> SEQ ID NO 485
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 485

Ser Ser Glu Ser Ser Glu Ser Ser Glu Ser Ser Ser Glu Ser
1               5                   10                  15

Ser Glu Ser Ser Ser Glu Ser Ser Ser Glu Ser Ser Glu Ser
            20                  25                  30

Ser Ser Glu Ser Ser Ser Glu Ser Ser Glu Ser Ser Glu Ser
        35                  40                  45

Ser Ser Glu Ser Ser Glu Ser Ser Ser Glu Ser Ser Glu Ser
        50                  55                  60

Ser Glu Ser Ser Ser Glu Ser Ser Glu Ser Ser Glu Ser Ser
65                  70                  75                  80

Ser Ser Glu Ser Ser Ser Glu Ser Ser Glu Ser Ser Glu Ser
                85                  90                  95

Ser Ser Glu Ser Ser Glu Ser Ser Glu Ser Ser Glu Ser Ser
            100                 105                 110

Ser Glu Ser Ser Ser Glu Ser Ser Ser Glu Ser Ser Glu Ser
        115                 120                 125

Ser Ser Glu Ser Ser Ser Glu Ser Ser Glu Ser Ser Glu Ser
        130                 135                 140

Ser Ser Glu Ser Ser Glu Ser Ser Ser Glu Ser Ser Glu Ser
145                 150                 155                 160

Ser Glu Ser Ser Ser Glu Ser Ser Ser Glu Ser Ser Glu Ser
                165                 170                 175

Ser Ser Glu Ser Ser Glu Ser Ser Glu Ser Ser Ser Glu Ser
            180                 185                 190

Ser Ser Glu Ser Ser Glu Ser Ser Ser Glu Ser Ser Glu Ser
        195                 200                 205

Ser Glu Ser Ser Ser Glu Ser Ser Ser Glu Ser Ser Glu Ser Ser
        210                 215                 220

Ser Ser Glu Ser Ser Glu Ser Ser Glu Ser Ser Ser Glu Ser
225                 230                 235                 240

Ser Ser Glu Ser Ser Glu Ser Ser Ser Glu Ser Ser Glu Ser
            245                 250                 255

Ser Glu Ser Ser Ser Glu Ser Ser Ser Glu Ser Ser Glu Ser
        260                 265                 270

Ser Ser Glu Ser Ser Glu Ser Ser Glu Ser Ser Ser Glu Ser
        275                 280                 285

<210> SEQ ID NO 486
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Glu Gly Glu Gly Glu Gly Glu Gly Glu Gly Glu Gly Glu Gly Glu
1               5                   10                  15

Gly Glu Gly Glu Gly Glu Gly Glu Gly Glu
            20                  25

<210> SEQ ID NO 487
<211> LENGTH: 26
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 487

Gly Glu Gly Gly Gly Glu Gly Gly Gly Glu Gly Gly Gly Glu Gly
1               5                   10                  15

Gly Glu Gly Gly Gly Glu Gly Gly Glu Gly Gly
            20                  25

<210> SEQ ID NO 488
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gly Gly Ser Gly Gly Glu Gly Gly Ser Gly Gly Glu Gly Gly Ser Gly
1               5                   10                  15

Gly Glu Gly Gly Ser Gly Gly Glu Gly Gly Ser
            20                  25

<210> SEQ ID NO 489
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Ser Glu Ser Ser Ser Glu Ser Ser Glu Ser Glu Ser Ser Ser Glu Ser
1               5                   10                  15

Ser Glu Ser Glu Ser Ser Ser Glu Ser Ser Glu Ser Glu
            20                  25

<210> SEQ ID NO 490
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gly Gly Gly Gly Gly Gly Gly Gly Gly Gly Gly Gly Gly
1               5                   10

<210> SEQ ID NO 491
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gly Gly Ser Gly Gly Ser Gly Gly Ser Gly Gly Glu Gly Gly Ser Gly
1               5                   10                  15

Gly Ser Gly Gly Ser Gly Gly Glu
            20

<210> SEQ ID NO 492
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Gly Gly Ser Gly Gly Glu Gly Ser Gly Gly Glu Gly Gly Ser Gly
1               5                   10                  15

Gly Glu Gly Gly Ser Gly Gly Glu
            20

<210> SEQ ID NO 493
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gly Glu Gly Gly Gly Glu Gly Gly Glu Gly Glu Gly Gly Glu Gly
1               5                   10                  15

Gly Glu Gly Glu Gly Gly Gly Glu
            20

<210> SEQ ID NO 494
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Gly Glu Gly Glu Gly Glu Gly Glu Gly Glu Gly Glu Gly Glu Gly Glu
1               5                   10                  15

Gly Glu

<210> SEQ ID NO 495
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Glu Glu Glu Glu Glu Glu Glu Glu Glu Glu Glu Glu Glu
1               5                   10

<210> SEQ ID NO 496
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Ser Ser Ser Ser Ser Glu Ser Ser Ser Ser Glu Ser Ser Ser Ser
1               5                   10                  15

Ser Glu Ser Ser Ser Ser
            20
```

<210> SEQ ID NO 497
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 497

Ser Ser Ser Glu Ser Ser Glu Ser Ser Ser Glu Ser Ser Ser Glu
1               5                   10                  15

Ser Ser Glu Ser Ser Ser Ser Glu
            20

<210> SEQ ID NO 498
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 498

Ser Ser Ser Ser Ser Glu Ser Ser Ser Ser Glu Ser Ser Ser Ser
1               5                   10                  15

Ser Glu

<210> SEQ ID NO 499
<211> LENGTH: 864
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(864)

<400> SEQUENCE: 499 ggt ggt tct ggt ggt gaa ggt ggt tct ggt ggt gaa ggt ggt tct ggt      48
Gly Gly Ser Gly Gly Glu Gly Gly Ser Gly Gly Glu Gly Gly Ser Gly
1               5                   10                  15 ggt gaa ggt ggt tct ggt ggt gaa ggt ggt tct ggt ggt gaa ggt ggt      96
Gly Glu Gly Gly Ser Gly Gly Glu Gly Gly Ser Gly Gly Glu Gly Gly
            20                  25                  30 tct ggt ggt gaa ggt ggt tct ggt ggt gaa ggt ggt tct ggt ggt gaa     144
Ser Gly Gly Glu Gly Gly Ser Gly Gly Glu Gly Gly Ser Gly Gly Glu
        35                  40                  45 ggt ggt tct ggt ggt gaa ggt ggt tct ggt ggt gaa ggt ggt tct ggt     192
Gly Gly Ser Gly Gly Glu Gly Gly Ser Gly Gly Glu Gly Gly Ser Gly
    50                  55                  60 ggt gaa ggt ggt tct ggt ggt gaa ggt ggt tct ggt ggt gaa ggt ggt     240
Gly Glu Gly Gly Ser Gly Gly Glu Gly Gly Ser Gly Gly Glu Gly Gly
65                  70                  75                  80 tct ggt ggt gaa ggt ggt tct ggt ggt gaa ggt ggt tct ggt ggt gaa     288
Ser Gly Gly Glu Gly Gly Ser Gly Gly Glu Gly Gly Ser Gly Gly Glu
                85                  90                  95 ggt ggt tct ggt ggt gaa ggt ggt tct ggt ggt gaa ggt ggt tct ggt     336
Gly Gly Ser Gly Gly Glu Gly Gly Ser Gly Gly Glu Gly Gly Ser Gly
            100                 105                 110 ggt gaa ggt ggt tct ggt ggt gaa ggt ggt tct ggt ggt gaa ggt ggt     384
Gly Glu Gly Gly Ser Gly Gly Glu Gly Gly Ser Gly Gly Glu Gly Gly
        115                 120                 125

| | | |
|---|---|---|
| tct ggt ggt gaa ggt ggt tct ggt ggt gaa ggt ggt tct ggt ggt gaa<br>Ser Gly Gly Glu Gly Gly Ser Gly Gly Glu Gly Gly Ser Gly Gly Glu<br>130       135       140 | | 432 |
| ggt ggt tct ggt ggt gaa ggt ggt tct ggt ggt gaa ggt ggt tct ggt<br>Gly Gly Ser Gly Gly Glu Gly Gly Ser Gly Gly Glu Gly Gly Ser Gly<br>145      150       155       160 | | 480 |
| ggt gaa ggt ggt tct ggt ggt gaa ggt ggt tct ggt ggt gaa ggt ggt<br>Gly Glu Gly Gly Ser Gly Gly Glu Gly Gly Ser Gly Gly Glu Gly Gly<br>      165       170       175 | | 528 |
| tct ggt ggt gaa ggt ggt tct ggt ggt gaa ggt ggt tct ggt ggt gaa<br>Ser Gly Gly Glu Gly Gly Ser Gly Gly Glu Gly Gly Ser Gly Gly Glu<br>180       185       190 | | 576 |
| ggt ggt tct ggt ggt gaa ggt ggt tct ggt ggt gaa ggt ggt tct ggt<br>Gly Gly Ser Gly Gly Glu Gly Gly Ser Gly Gly Glu Gly Gly Ser Gly<br>195      200       205 | | 624 |
| ggt gaa ggt ggt tct ggt ggt gaa ggt ggt tct ggt ggt gaa ggt ggt<br>Gly Glu Gly Gly Ser Gly Gly Glu Gly Gly Ser Gly Gly Glu Gly Gly<br>210       215       220 | | 672 |
| tct ggt ggt gaa ggt ggt tct ggt ggt gaa ggt ggt tct ggt ggt gaa<br>Ser Gly Gly Glu Gly Gly Ser Gly Gly Glu Gly Gly Ser Gly Gly Glu<br>225       230       235       240 | | 720 |
| ggt ggt tct ggt ggt gaa ggt ggt tct ggt ggt gaa ggt ggt tct ggt<br>Gly Gly Ser Gly Gly Glu Gly Gly Ser Gly Gly Glu Gly Gly Ser Gly<br>      245       250       255 | | 768 |
| ggt gaa ggt ggt tct ggt ggt gaa ggt ggt tct ggt ggt gaa ggt ggt<br>Gly Glu Gly Gly Ser Gly Gly Glu Gly Gly Ser Gly Gly Glu Gly Gly<br>      260       265       270 | | 816 |
| tct ggt ggt gaa ggt ggt tct ggt ggt gaa ggt ggt tct ggt ggt gaa<br>Ser Gly Gly Glu Gly Gly Ser Gly Gly Glu Gly Gly Ser Gly Gly Glu<br>275       280       285 | | 864 |

<210> SEQ ID NO 500
<211> LENGTH: 288
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 500

Gly Gly Ser Gly Gly Glu Gly Gly Ser Gly Gly Glu Gly Gly Ser Gly
1       5       10       15

Gly Glu Gly Gly Ser Gly Gly Glu Gly Gly Ser Gly Gly Glu Gly Gly
      20       25       30

Ser Gly Gly Glu Gly Gly Ser Gly Gly Glu Gly Gly Ser Gly Gly Glu
      35       40       45

Gly Gly Ser Gly Gly Glu Gly Gly Ser Gly Gly Glu Gly Gly Ser Gly
 50       55       60

Gly Glu Gly Gly Ser Gly Gly Glu Gly Gly Ser Gly Gly Glu Gly Gly
65       70       75       80

Ser Gly Gly Glu Gly Gly Ser Gly Gly Glu Gly Gly Ser Gly Gly Glu
      85       90       95

Gly Gly Ser Gly Gly Glu Gly Gly Ser Gly Gly Glu Gly Gly Ser Gly
      100       105       110

Gly Glu Gly Gly Ser Gly Gly Glu Gly Gly Ser Gly Gly Glu Gly Gly
      115       120       125

Ser Gly Gly Glu Gly Gly Ser Gly Gly Glu Gly Gly Ser Gly Gly Glu
      130       135       140

Gly Gly Ser Gly Gly Glu Gly Gly Ser Gly Gly Glu Gly Gly Ser Gly

```
                145                 150                 155                 160
Gly Glu Gly Gly Ser Gly Gly Glu Gly Gly Ser Gly Gly Gly
                165                 170                 175

Ser Gly Gly Glu Gly Gly Ser Gly Gly Glu Gly Gly Ser Gly Gly Glu
            180                 185                 190

Gly Gly Ser Gly Gly Glu Gly Gly Ser Gly Gly Glu Gly Gly Ser Gly
        195                 200                 205

Gly Glu Gly Gly Ser Gly Gly Glu Gly Gly Ser Gly Gly Glu Gly Gly
    210                 215                 220

Ser Gly Gly Glu Gly Gly Ser Gly Gly Glu Gly Gly Ser Gly Gly Glu
225                 230                 235                 240

Gly Gly Ser Gly Gly Glu Gly Gly Ser Gly Gly Glu Gly Gly Ser Gly
            245                 250                 255

Gly Glu Gly Gly Ser Gly Gly Glu Gly Gly Ser Gly Gly Glu Gly Gly
        260                 265                 270

Ser Gly Gly Glu Gly Gly Ser Gly Gly Glu Gly Gly Ser Gly Gly Glu
    275                 280                 285

<210> SEQ ID NO 501
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(39)
<220> FEATURE:
<221> NAME/KEY: CDS
<222> LOCATION: (58)..(126)

<400> SEQUENCE: 501 atg gat tat aaa gac gat gac gat aaa ggg tct cca ggt tagtaaccta       49
Met Asp Tyr Lys Asp Asp Asp Asp Lys Gly Ser Pro Gly
1               5                   10 ggtgatag gga ggt tcg tct tca ctc gag ggt acc cat cac cat cac cat     99
         Gly Gly Ser Ser Ser Leu Glu Gly Thr His His His His His
                 15                  20                  25 cac gag ctc gta ccg gta gaa aaa atg                                 126
His Glu Leu Val Pro Val Glu Lys Met
        30                  35

<210> SEQ ID NO 502
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Met Asp Tyr Lys Asp Asp Asp Asp Lys Gly Ser Pro Gly
1               5                   10

<210> SEQ ID NO 503
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503
```

```
Gly Gly Ser Ser Ser Leu Glu Gly Thr His His His His His Glu
1               5                   10                  15

Leu Val Pro Val Glu Lys Met
            20
```

<210> SEQ ID NO 504
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

```
Lys Lys Lys Lys Lys Lys
1               5
```

<210> SEQ ID NO 505
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

```
Met Glu Gly Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Thr Gly
            100                 105                 110

Ser Gly Glu Gly Ser Glu Gly Glu Gly Gly Glu Gly Ser Glu Gly
        115                 120                 125

Glu Gly Ser Gly Glu Gly Glu Gly Glu Gly Ser Gly Thr Glu Val
    130                 135                 140

Gln Leu Val Glu Ser Gly Gly Leu Val Gln Pro Gly Gly Ser Leu
145                 150                 155                 160

Arg Leu Ser Cys Ala Ala Ser Gly Phe Asn Ile Lys Asp Thr Tyr Ile
                165                 170                 175

His Trp Val Arg Gln Ala Pro Gly Lys Gly Leu Glu Trp Val Ala Arg
            180                 185                 190

Ile Tyr Pro Thr Asn Gly Tyr Thr Arg Tyr Ala Asp Ser Val Lys Gly
        195                 200                 205

Arg Phe Thr Ile Ser Ala Asp Thr Ser Lys Asn Thr Ala Tyr Leu Gln
    210                 215                 220

Met Asn Ser Leu Arg Ala Glu Asp Thr Ala Val Tyr Tyr Cys Ser Arg
225                 230                 235                 240

Trp Gly Gly Asp Gly Phe Tyr Ala Met Asp Tyr Trp Gly Gln Gly Thr
                245                 250                 255
```

-continued

```
Leu Val Thr Val Ser Gly Glu Gly Ser Gly Gly Ser Gly
            260                 265                 270

Glu Gly Ser Glu Gly Ser Gly Glu Gly Ser Gly Ser Gly
        275                 280                 285

Glu Gly Glu Gly Ser Glu Gly Ser Glu Gly Ser Glu Gly
        290                 295                 300

Ser Gly Glu Gly Glu Gly Glu Gly Ser Glu Gly Gly Ser
305                 310                 315                 320

Gly Glu Gly Ser Glu Gly Glu Gly Gly Glu Gly Ser Gly Glu
                325                 330                 335

Gly Ser Gly Glu Gly Gly Glu Gly Ser Glu Gly Ser Glu
        340                 345                 350

Gly Glu Gly Gly Ser Glu Gly Glu Gly Gly Ser Glu Gly Ser
        355                 360                 365

Gly Glu Gly Glu Gly Ser Glu Gly Gly Ser Glu Gly Glu Gly Ser Glu
        370                 375                 380

Gly Gly Ser Glu Gly Glu Gly Ser Glu Gly Ser Gly Glu Gly
385                 390                 395                 400

Ser Glu Gly Ser Gly Glu Gly Glu Gly Ser Glu Gly Ser Gly Glu Gly
                405                 410                 415

Glu Gly Ser Glu Gly Ser Gly Glu Gly Glu Gly Ser Glu Gly Gly Ser
                420                 425                 430

Glu Gly Glu Gly Gly Ser Glu Gly Ser Glu Gly Glu Gly Ser Gly Glu
                435                 440                 445

Gly Ser Gly Glu Gly Glu Gly Ser Glu Gly Ser Gly Glu Gly Gly
450                 455                 460

Gly Glu Gly Ser Glu Gly Glu Gly Ser Gly Glu Gly Ser Glu Gly Glu
465                 470                 475                 480

Gly Gly Ser Glu Gly Ser Glu Gly Glu Gly Gly Ser Glu Gly Ser Glu
                485                 490                 495

Gly Glu Gly Gly Glu Gly Ser Gly Glu Gly Gly Glu Gly Ser Gly Ser
                500                 505                 510

Gly Glu Gly Glu Gly Ser Gly Glu Gly Ser Gly Glu Gly Ser Glu
        515                 520                 525

Gly Ser Gly Glu Gly Glu Gly Ser Gly Gly Ser Gly Glu Gly Glu Gly
        530                 535                 540

Gly Ser Glu Gly Ser Glu Gly Glu Gly Ser Gly Glu Gly Ser Glu Gly
545                 550                 555                 560

Glu Gly Ser Glu Gly Ser Gly Glu Gly Glu Gly Ser Gly Ser Gly
                565                 570                 575

Glu Gly Glu Gly Gly Ser Glu Gly Ser Glu Gly Glu Gly Ser Glu
        580                 585                 590

Gly Ser Glu Gly Glu Gly Gly Ser Glu Gly Ser Glu Gly Gly Gly
        595                 600                 605

Glu Gly Ser Gly Glu Gly Glu Gly Ser Glu Gly Glu Gly Glu
        610                 615                 620

Gly Ser Gly Glu Gly Ser Glu Gly Glu Gly Ser Glu Gly Ser Gly Glu
625                 630                 635                 640

Gly Glu Gly Ser Glu Gly Ser Gly Glu Gly Glu Gly Ser Glu Gly
                645                 650                 655

Ser Glu Gly Glu Gly Ser Glu Gly Ser Gly Glu Gly Glu Gly Glu
                660                 665                 670
```

```
Gly Ser Gly Glu Gly Glu Gly Ser Gly Glu Gly Ser Glu Gly Gly
            675                 680                 685
Gly Gly Glu Gly Ser Gly Glu Gly Ser Gly Ser Gly Glu Gly
        690                 695                 700
Glu Gly Ser Glu Gly Ser Gly Glu Gly Glu Gly Ser Glu Gly Gly Ser
705                 710                 715                 720
Glu Gly Glu Gly Gly Ser Glu Gly Ser Glu Gly Gly Ser Glu Gly
                725                 730                 735
Gly Ser Glu Gly Glu Gly Ser Glu Gly Ser Glu Gly Gly Ser
        740                 745                 750
Glu Gly Ser Gly Glu Gly Glu Gly Ser Glu Gly Ser Gly Glu Gly Glu
        755                 760                 765
Gly Ser Gly Glu Gly Ser Glu Gly Gly Gly Ser Glu Gly Gly Glu
        770                 775                 780
Gly Glu Gly Ser Glu Gly Gly Ser Gly Glu Gly Ser Glu Gly Gly
785                 790                 795                 800
Ser Glu Gly Glu Gly Gly Glu Gly Ser Gly Glu Gly Gly Gly
                805                 810                 815
Glu Gly Ser Glu Gly Glu Gly Ser Glu Gly Ser Gly Glu Gly Glu Gly
                820                 825                 830
Ser Gly Glu Gly Ser Glu Gly Asp Tyr Lys Asp Asp Asp Lys Gly
        835                 840                 845
Gly Ser His His His His His His
    850                 855

<210> SEQ ID NO 506
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Met Glu Asp Ile Leu Leu Thr Gln Ser Pro Val Ile Leu Ser Val Ser
1               5                   10                  15
Pro Gly Glu Arg Val Ser Phe Ser Cys Arg Ala Ser Gln Ser Ile Gly
            20                  25                  30
Thr Asn Ile His Trp Tyr Gln Gln Arg Thr Asn Gly Ser Pro Arg Leu
        35                  40                  45
Leu Ile Lys Tyr Ala Ser Glu Ser Ile Ser Gly Ile Pro Ser Arg Phe
    50                  55                  60
Ser Gly Ser Gly Ser Gly Thr Asp Phe Thr Leu Ser Ile Asn Ser Val
65                  70                  75                  80
Glu Ser Glu Asp Ile Ala Asp Tyr Tyr Cys Gln Gln Asn Asn Asn Trp
                85                  90                  95
Pro Thr Thr Phe Gly Ala Gly Thr Lys Leu Glu Leu Lys Thr Gly Ser
            100                 105                 110
Gly Glu Gly Ser Glu Gly Glu Gly Gly Glu Gly Ser Glu Gly Glu
        115                 120                 125
Gly Ser Gly Glu Gly Glu Gly Glu Gly Ser Gly Thr Gln Val Gln
        130                 135                 140
Leu Lys Gln Ser Gly Pro Gly Leu Val Gln Pro Ser Gln Ser Leu Ser
145                 150                 155                 160
Ile Thr Cys Thr Val Ser Gly Phe Ser Leu Thr Asn Tyr Gly Val His
                165                 170                 175
```

-continued

```
Trp Val Arg Gln Ser Pro Gly Lys Gly Leu Glu Trp Leu Gly Val Ile
            180                 185                 190

Trp Ser Gly Gly Asn Thr Asp Tyr Asn Thr Pro Phe Thr Ser Arg Leu
            195                 200                 205

Ser Ile Asn Lys Asp Asn Ser Lys Ser Gln Val Phe Phe Lys Met Asn
210                 215                 220

Ser Leu Gln Ser Asn Asp Thr Ala Ile Tyr Tyr Cys Ala Arg Ala Leu
225                 230                 235                 240

Thr Tyr Tyr Asp Tyr Glu Phe Ala Tyr Trp Gly Gln Gly Thr Leu Val
            245                 250                 255

Thr Val Ser Gly Gly Glu Gly Ser Gly Glu Gly Ser Glu Gly Glu Gly
            260                 265                 270

Ser Glu Gly Ser Gly Glu Gly Glu Gly Ser Glu Gly Ser Gly Glu Gly
            275                 280                 285

Glu Gly Gly Ser Glu Gly Ser Glu Gly Glu Gly Ser Glu Gly Ser Gly
            290                 295                 300

Glu Gly Glu Gly Gly Glu Gly Ser Gly Glu Gly Glu Gly Ser Gly Glu
305                 310                 315                 320

Gly Ser Glu Gly Glu Gly Gly Glu Gly Ser Glu Gly Glu Gly Glu Ser
            325                 330                 335

Gly Glu Gly Gly Glu Gly Glu Gly Ser Glu Gly Gly Ser Glu Gly Glu
            340                 345                 350

Gly Gly Ser Glu Gly Glu Gly Gly Ser Glu Gly Ser Gly Glu
            355                 360                 365

Gly Glu Gly Ser Glu Gly Ser Glu Gly Glu Gly Ser Glu Gly Gly
            370                 375                 380

Ser Glu Gly Glu Gly Ser Glu Gly Ser Gly Glu Gly Gly Ser Glu
385                 390                 395                 400

Gly Ser Gly Glu Gly Glu Gly Ser Glu Gly Ser Gly Glu Gly Glu Gly
            405                 410                 415

Ser Glu Gly Ser Gly Glu Gly Glu Gly Ser Glu Gly Ser Gly Glu Gly
            420                 425                 430

Glu Gly Gly Ser Glu Gly Ser Glu Gly Glu Gly Ser Glu Gly Gly Ser
            435                 440                 445

Glu Gly Glu Gly Gly Ser Glu Gly Ser Glu Gly Glu Gly Gly Gly Glu
450                 455                 460

Gly Ser Glu Gly Glu Gly Ser Glu Gly Gly Ser Glu Gly Glu Gly Gly
465                 470                 475                 480

Ser Glu Gly Ser Gly Glu Gly Gly Gly Ser Glu Gly Ser Glu Gly Glu
            485                 490                 495

Gly Gly Glu Gly Ser Glu Gly Glu Gly Ser Glu Gly Ser Glu Gly Glu
            500                 505                 510

Gly Glu Gly Ser Gly Glu Gly Ser Glu Gly Glu Gly Ser Glu Gly Ser
            515                 520                 525

Gly Glu Gly Glu Gly Ser Glu Gly Ser Gly Glu Gly Glu Gly Gly Ser
            530                 535                 540

Glu Gly Ser Glu Gly Glu Gly Ser Gly Glu Gly Ser Glu Gly Glu Gly
545                 550                 555                 560

Ser Glu Gly Ser Gly Glu Gly Glu Gly Ser Glu Gly Ser Gly Glu Gly
            565                 570                 575

Glu Gly Gly Ser Glu Gly Ser Glu Gly Glu Gly Gly Ser Glu Gly Ser
            580                 585                 590
```

```
Glu Gly Glu Gly Ser Glu Gly Ser Gly Gly Glu Gly
            595                 600                 605
Ser Gly Glu Gly Glu Gly Ser Glu Gly Ser Gly Glu Gly Ser
        610                 615                 620
Gly Glu Gly Ser Glu Gly Gly Ser Glu Ser Gly Glu Gly Glu
625                 630                 635                 640
Gly Ser Glu Gly Ser Gly Gly Glu Gly Gly Ser Glu Gly Ser Glu
            645                 650                 655
Gly Glu Gly Ser Glu Gly Ser Gly Gly Glu Gly Gly Ser
            660                 665                 670
Gly Glu Gly Glu Gly Ser Gly Glu Gly Ser Glu Gly Gly Gly
        675                 680                 685
Glu Gly Ser Glu Gly Glu Gly Ser Glu Gly Ser Glu Gly Glu Gly
            690                 695                 700
Ser Glu Gly Ser Gly Glu Gly Gly Ser Glu Gly Ser Glu Gly
705                 710                 715                 720
Glu Gly Gly Ser Glu Gly Ser Gly Glu Gly Ser Glu Gly Gly Ser
            725                 730                 735
Glu Gly Glu Gly Ser Glu Gly Gly Ser Glu Gly Glu Gly Ser Glu Gly
            740                 745                 750
Ser Gly Glu Gly Glu Gly Ser Glu Gly Ser Gly Glu Gly Glu Gly Ser
755                 760                 765
Gly Glu Gly Ser Glu Gly Glu Gly Ser Glu Gly Glu Gly Glu
        770                 775                 780
Gly Ser Glu Gly Ser Glu Gly Glu Gly Ser Glu Gly Gly Ser Glu
785                 790                 795                 800
Gly Glu Gly Gly Glu Gly Ser Gly Glu Gly Glu Gly Gly Glu Gly
            805                 810                 815
Ser Glu Gly Glu Gly Ser Glu Gly Ser Gly Glu Gly Glu Ser Gly
            820                 825                 830
Glu Gly Ser Glu Gly Asp Tyr Lys Asp Asp Asp Lys Gly Gly Ser
            835                 840                 845
His His His His His His
        850

<210> SEQ ID NO 507
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Met Glu Gly Asp Ile His Met Glu Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95
```

```
Gln Gln His Tyr Thr Thr Pro Pro Thr Phe Gly Gln Gly Thr Lys Val
                100                 105                 110
Glu Ile Lys Ser Gly Glu Gly Val Gln Leu Val Glu Ser Gly Gly Gly
        115                 120                 125
Leu Val Gln Pro Gly Gly Ser Leu Arg Leu Ser Cys Ala Ala Ser Gly
130                 135                 140
Phe Asn Ile Lys Asp Thr Tyr Ile His Trp Val Arg Gln Ala Pro Gly
145                 150                 155                 160
Lys Gly Leu Glu Trp Val Ala Arg Ile Tyr Pro Thr Asn Gly Tyr Thr
                165                 170                 175
Arg Tyr Ala Asp Ser Val Lys Gly Arg Phe Thr Ile Ser Ala Asp Thr
            180                 185                 190
Ser Lys Asn Thr Ala Tyr Leu Gln Met Asn Ser Leu Arg Ala Glu Asp
        195                 200                 205
Thr Ala Val Tyr Tyr Cys Ser Arg Trp Gly Gly Asp Gly Phe Tyr Ala
210                 215                 220
Met Asp Tyr Trp Gly Gln Gly Thr Leu Val Thr Val Ser Gly Gly Glu
225                 230                 235                 240
Gly Ser Gly Glu Gly Ser Glu Gly Glu Gly Ser Glu Gly Ser Gly Glu
                245                 250                 255
Gly Glu Gly Ser Glu Gly Ser Gly Glu Gly Gly Ser Glu Gly
                260                 265                 270
Ser Glu Gly Glu Gly Ser Glu Gly Ser Gly Glu Gly Glu Gly Gly Glu
            275                 280                 285
Gly Ser Gly Glu Gly Glu Gly Ser Gly Glu Gly Ser Glu Gly Glu Gly
        290                 295                 300
Gly Gly Glu Gly Ser Glu Gly Glu Gly Ser Gly Glu Gly Gly Glu Gly
305                 310                 315                 320
Glu Gly Ser Glu Gly Gly Ser Gly Glu Gly Gly Ser Glu Gly Gly
                325                 330                 335
Glu Gly Glu Gly Ser Glu Gly Ser Gly Glu Gly Gly Ser Glu Gly
            340                 345                 350
Gly Ser Glu Gly Glu Gly Ser Glu Gly Gly Ser Glu Gly Glu Gly Ser
        355                 360                 365
Glu Gly Ser Gly Glu Gly Glu Gly Ser Glu Gly Ser Gly Glu Gly Glu
    370                 375                 380
Gly Ser Glu Gly Ser Gly Glu Gly Glu Gly Ser Glu Gly Ser Gly Glu
385                 390                 395                 400
Gly Glu Gly Ser Glu Gly Gly Ser Glu Gly Glu Gly Ser Glu Gly Gly
                405                 410                 415
Ser Glu Gly Glu Gly Ser Gly Glu Gly Ser Glu Gly Glu Gly Gly Ser
            420                 425                 430
Glu Gly Ser Glu Gly Glu Gly Gly Glu Gly Ser Glu Gly Glu Gly
        435                 440                 445
Ser Gly Glu Gly Ser Glu Gly Gly Gly Ser Glu Gly Ser Glu Gly
        450                 455                 460
Glu Gly Glu Gly Ser Glu Gly Ser Gly Glu Gly Gly Glu Gly Ser Gly
465                 470                 475                 480
Glu Gly Glu Gly Ser Glu Gly Ser Gly Glu Gly Gly Ser Gly Glu
            485                 490                 495
Gly Ser Glu Gly Glu Gly Ser Gly Ser Gly Glu Gly Glu Gly Ser
        500                 505                 510
```

Glu Gly Ser Gly Glu Gly Glu Gly Ser Gly Glu Ser Gly Glu
            515                 520                 525

Gly Ser Gly Glu Gly Ser Gly Glu Gly Ser Glu Gly Ser Gly Glu
        530                 535                 540

Gly Glu Gly Ser Glu Gly Ser Gly Glu Gly Glu Gly Ser Glu Gly
545                 550                 555                 560

Ser Glu Gly Glu Gly Gly Ser Glu Gly Ser Glu Gly Glu Gly Ser
            565                 570                 575

Glu Gly Ser Glu Gly Glu Gly Gly Ser Gly Glu Gly Glu Gly Gly
        580                 585                 590

Ser Glu Gly Ser Gly Glu Gly Glu Gly Ser Gly Glu Gly Ser Glu Gly
        595                 600                 605

Glu Gly Ser Glu Gly Ser Gly Glu Gly Glu Gly Ser Glu Gly Ser Gly
            610                 615                 620

Glu Gly Glu Gly Gly Ser Glu Gly Ser Glu Gly Gly Ser Glu Gly
625                 630                 635                 640

Ser Gly Glu Gly Glu Gly Glu Gly Gly Ser Gly Glu Gly Glu Gly Ser
            645                 650                 655

Gly Glu Gly Ser Glu Gly Glu Gly Gly Gly Glu Gly Ser Glu Gly Glu
        660                 665                 670

Gly Ser Glu Gly Ser Gly Glu Gly Gly Ser Glu Gly Ser Gly Glu
            675                 680                 685

Gly Glu Gly Ser Glu Gly Gly Ser Glu Gly Glu Gly Ser Glu Gly
        690                 695                 700

Ser Glu Gly Glu Gly Ser Glu Gly Gly Ser Glu Gly Glu Gly Ser Glu
705                 710                 715                 720

Gly Gly Ser Glu Gly Glu Gly Ser Glu Gly Ser Gly Glu Gly Glu Gly
            725                 730                 735

Ser Glu Gly Ser Gly Glu Gly Glu Gly Ser Gly Glu Gly Ser Glu Gly
        740                 745                 750

Glu Gly Gly Ser Glu Gly Gly Gly Glu Gly Ser Glu Gly Gly Ser
            755                 760                 765

Glu Gly Glu Gly Ser Glu Gly Gly Ser Glu Gly Gly Gly Glu Gly
        770                 775                 780

Ser Gly Glu Gly Glu Gly Gly Glu Gly Ser Glu Gly Glu Gly Ser
785                 790                 795                 800

Glu Gly Ser Gly Glu Gly Glu Gly Ser Gly Glu Gly Ser Gly Asp
            805                 810                 815

Tyr Lys Asp Asp Asp Asp Lys Gly Gly Ser His His His His His
            820                 825                 830

<210> SEQ ID NO 508
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(684)

<400> SEQUENCE: 508 atg gat aaa act cat act tgc cct cct tgt cca gcg ccc gaa ctg ctg      48
Met Asp Lys Thr His Thr Cys Pro Pro Cys Pro Ala Pro Glu Leu Leu
1               5                   10                  15 ggt ggc ccg tct gtt ttc ctg ttc cca cca aaa cca aaa gac acc ctg      96

-continued

```
Gly Gly Pro Ser Val Phe Leu Phe Pro Pro Lys Pro Lys Asp Thr Leu
             20                  25                  30 atg att tcc cgt act cct gag gta acc tgt gta gtt gta gac gtt tct      144
Met Ile Ser Arg Thr Pro Glu Val Thr Cys Val Val Val Asp Val Ser
             35                  40                  45 cac gaa gat ccg gaa gtt aaa ttc aac tgg tac gtg gat ggt gtt gag      192
His Glu Asp Pro Glu Val Lys Phe Asn Trp Tyr Val Asp Gly Val Glu
 50                  55                  60 gtg cat aac gct aaa acc aaa ccg cgc gag gag caa tat aat tcc acc      240
Val His Asn Ala Lys Thr Lys Pro Arg Glu Glu Gln Tyr Asn Ser Thr
 65                  70                  75                  80 tac cgt gtt gtg tct gtt ctg acc gtc ctg cac caa gat tgg ctg aac      288
Tyr Arg Val Val Ser Val Leu Thr Val Leu His Gln Asp Trp Leu Asn
                 85                  90                  95 ggc aaa gaa tac aag tgt aaa gtg tcc aac aaa gcc ctg cca gcg ccg      336
Gly Lys Glu Tyr Lys Cys Lys Val Ser Asn Lys Ala Leu Pro Ala Pro
            100                 105                 110 atc gag aaa act att tct aag gcg aaa ggc cag ccg cgc gaa cca caa      384
Ile Glu Lys Thr Ile Ser Lys Ala Lys Gly Gln Pro Arg Glu Pro Gln
            115                 120                 125 gta tat acc ctg ccg ccg tcc cgt gat gaa ctg acc aag aac caa gtt      432
Val Tyr Thr Leu Pro Pro Ser Arg Asp Glu Leu Thr Lys Asn Gln Val
130                 135                 140 tcc ctg acc tgc ctg gtg aag ggt ttc tac cca tct gat atc gcc gtc      480
Ser Leu Thr Cys Leu Val Lys Gly Phe Tyr Pro Ser Asp Ile Ala Val
145                 150                 155                 160 gag tgg gaa tcc aac ggt cag ccg gag aac aat tat aaa act atc cca      528
Glu Trp Glu Ser Asn Gly Gln Pro Glu Asn Asn Tyr Lys Thr Ile Pro
                165                 170                 175 ccg gtt ctg gac tct gac ggc tcc ttc ttt ctg tat tcc aag ctg acc      576
Pro Val Leu Asp Ser Asp Gly Ser Phe Phe Leu Tyr Ser Lys Leu Thr
            180                 185                 190 gtt gat aaa agc cgt tgg cag cag ggc aac gtt ttc tct tgc tct gta      624
Val Asp Lys Ser Arg Trp Gln Gln Gly Asn Val Phe Ser Cys Ser Val
            195                 200                 205 atg cat gaa gca ctg cac aac cat tac acc cag aaa agc ctg tcc ctg      672
Met His Glu Ala Leu His Asn His Tyr Thr Gln Lys Ser Leu Ser Leu
            210                 215                 220 tcg ccg ggt aag                                                      684
Ser Pro Gly Lys
225
```

<210> SEQ ID NO 509
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

```
Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
             35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
```

```
                65                  70                  75                  80
Tyr Arg Val Val Ser Val Leu Thr Val Leu His Gln Asp Trp Leu Asn
                    85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
                115                 120                 125

Val Tyr Thr Leu Pro Pro Ser Arg Asp Glu Leu Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Ile Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Lys
225

<210> SEQ ID NO 510
<211> LENGTH: 806
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190
```

```
Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Gly Glu Gly Ser Gly Glu Gly Ser Gly Glu
225                 230                 235                 240

Gly Ser Glu Gly Ser Gly Gly Gly Gly Ser Gly Ser Gly Glu
                245                 250                 255

Gly Glu Gly Gly Ser Gly Ser Glu Gly Gly Ser Glu Gly Ser
            260                 265                 270

Gly Glu Gly Glu Gly Glu Gly Ser Gly Glu Gly Glu Gly Ser Gly
            275                 280                 285

Glu Gly Ser Glu Gly Glu Gly Gly Glu Gly Ser Glu Gly Glu Gly
290                 295                 300

Ser Gly Glu Gly Glu Gly Glu Gly Ser Glu Gly Ser Glu Gly
305                 310                 315                 320

Glu Gly Gly Ser Glu Gly Gly Gly Glu Gly Ser Glu Gly Ser Gly
            325                 330                 335

Glu Gly Glu Gly Ser Glu Gly Gly Ser Glu Gly Glu Gly Ser Glu Gly
            340                 345                 350

Gly Ser Glu Gly Glu Gly Ser Glu Gly Ser Gly Glu Gly Glu Gly Ser
            355                 360                 365

Glu Gly Ser Gly Glu Gly Glu Gly Ser Gly Glu Ser Gly Glu Glu
            370                 375                 380

Gly Ser Glu Gly Ser Gly Glu Gly Glu Gly Ser Glu Gly Gly Ser Glu
385                 390                 395                 400

Gly Glu Gly Gly Ser Glu Gly Ser Glu Gly Glu Gly Ser Gly Glu Gly
                405                 410                 415

Ser Glu Gly Glu Gly Gly Ser Glu Gly Ser Glu Gly Glu Gly Gly
                420                 425                 430

Glu Gly Ser Glu Gly Glu Gly Ser Gly Glu Gly Ser Glu Gly Glu Gly
            435                 440                 445

Gly Ser Glu Gly Ser Gly Glu Gly Gly Ser Glu Gly Ser Glu Gly
450                 455                 460

Glu Gly Gly Glu Gly Ser Gly Glu Gly Glu Gly Ser Glu Gly Ser Gly
465                 470                 475                 480

Glu Gly Glu Gly Ser Gly Glu Gly Glu Gly Ser Glu Gly Ser Glu Gly
                485                 490                 495

Ser Gly Glu Gly Glu Gly Ser Glu Gly Ser Gly Glu Gly Glu Gly Gly
            500                 505                 510

Ser Glu Gly Ser Glu Gly Glu Gly Ser Gly Glu Gly Ser Gly Glu Glu
            515                 520                 525

Gly Ser Glu Gly Ser Gly Glu Gly Glu Gly Glu Gly Ser Gly Glu
            530                 535                 540

Gly Glu Gly Gly Ser Glu Gly Ser Glu Gly Glu Gly Gly Ser Glu Gly
545                 550                 555                 560

Ser Glu Gly Glu Gly Gly Ser Glu Gly Ser Glu Gly Glu Gly Gly Glu
                565                 570                 575

Gly Ser Gly Glu Gly Glu Gly Ser Gly Ser Gly Glu Glu Gly
            580                 585                 590

Ser Gly Glu Gly Ser Glu Gly Glu Gly Ser Gly Ser Gly Glu Gly
            595                 600                 605

Glu Gly Ser Glu Gly Ser Gly Glu Gly Glu Gly Gly Ser Glu Gly Ser
```

```
                610             615             620

Glu Gly Glu Gly Ser Glu Gly Ser Gly Glu Gly Gly Glu Gly
625                 630             635                 640

Ser Gly Glu Gly Glu Gly Ser Gly Glu Gly Ser Gly Glu Gly Gly Gly
                645             650                 655

Gly Glu Gly Ser Glu Gly Gly Ser Glu Gly Ser Gly Glu Gly Glu
                660             665                 670

Gly Ser Glu Gly Ser Gly Glu Gly Gly Ser Glu Gly Gly Ser Glu
                675             680                 685

Gly Glu Gly Gly Ser Glu Gly Ser Glu Gly Glu Gly Ser Glu Gly Gly
690                 695             700

Ser Glu Gly Glu Gly Ser Gly Gly Ser Glu Gly Glu Gly Ser Glu
705                 710             715                 720

Gly Ser Gly Glu Gly Glu Gly Ser Glu Gly Ser Gly Glu Gly Glu Gly
                725             730                 735

Ser Gly Glu Gly Ser Glu Gly Glu Gly Ser Glu Gly Gly Glu Gly
                740             745                 750

Glu Gly Ser Glu Gly Gly Ser Glu Gly Glu Gly Ser Glu Gly Gly Ser
                755             760                 765

Glu Gly Glu Gly Gly Glu Gly Ser Gly Glu Gly Glu Gly Gly Glu
                770             775                 780

Gly Ser Glu Gly Glu Gly Ser Gly Glu Gly Ser Gly Glu Gly Ser
785                 790             795                 800

Gly Glu Gly Ser Glu Gly
                805

<210> SEQ ID NO 511
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Met Ala Asn Thr Pro Val Ser Gly Asn Leu Lys Val Glu Phe Tyr Asn
1               5                   10                  15

Ser Asn Pro Ser Asp Thr Thr Asn Ser Ile Asn Pro Gln Phe Lys Val
                20                  25                  30

Thr Asn Thr Gly Ser Ser Ala Ile Asp Leu Ser Lys Leu Thr Leu Arg
            35                  40                  45

Tyr Tyr Tyr Thr Val Asp Gly Gln Lys Asp Gln Thr Phe Trp Ala Asp
        50                  55                  60

His Ala Ala Ile Ile Gly Ser Asn Gly Ser Tyr Asn Gly Ile Thr Ser
65                  70                  75                  80

Asn Val Lys Gly Thr Phe Val Lys Met Ser Ser Ser Thr Asn Asn Ala
                85                  90                  95

Asp Thr Tyr Leu Glu Ile Ser Phe Thr Gly Gly Thr Leu Glu Pro Gly
                100                 105                 110

Ala His Val Gln Ile Gln Gly Arg Phe Ala Lys Asn Asp Trp Ser Asn
            115                 120                 125

Tyr Thr Gln Ser Asn Asp Tyr Ser Phe Lys Ser Ala Ser Gln Phe Val
        130                 135                 140

Glu Trp Asp Gln Val Thr Ala Tyr Leu Asn Gly Val Leu Val Trp Gly
145                 150                 155                 160
```

-continued

```
Lys Glu Pro Gly Gly Ser Val Val Gly Ser Gly Ser Glu Asn
            165                 170                 175
Leu Tyr Phe Gln His Gly Glu Gly Thr Phe Thr Ser Asp Leu Ser Lys
        180                 185                 190
Gln Met Glu Glu Glu Ala Val Arg Leu Phe Ile Glu Trp Leu Lys Asn
        195                 200                 205
Gly Gly Pro Ser Ser Gly Ala Pro Pro Ser Gly Glu Gly Ser
        210                 215                 220
Gly Glu Gly Ser Glu Gly Gly Ser Glu Gly Glu Gly Gly Glu
225                 230                 235                 240
Gly Ser Glu Gly Ser Glu Gly Glu Gly Gly Ser Glu Gly Ser Glu
            245                 250                 255
Gly Glu Gly Ser Glu Gly Ser Gly Glu Gly Glu Gly Glu Gly Ser
            260                 265                 270
Gly Glu Gly Glu Gly Ser Gly Glu Gly Ser Glu Gly Gly Gly
        275                 280                 285
Glu Gly Ser Glu Gly Glu Gly Ser Gly Glu Gly Glu Gly Glu Gly
        290                 295                 300
Ser Glu Gly Gly Ser Glu Gly Glu Gly Ser Glu Gly Gly Glu Gly
305                 310                 315                 320
Glu Gly Ser Glu Gly Ser Gly Glu Gly Glu Gly Ser Glu Gly Gly Ser
            325                 330                 335
Glu Gly Glu Gly Ser Glu Gly Gly Ser Glu Gly Gly Ser Glu Gly
            340                 345                 350
Ser Gly Glu Gly Glu Gly Ser Glu Gly Ser Glu Gly Glu Gly Ser
            355                 360                 365
Glu Gly Ser Gly Glu Gly Glu Gly Ser Glu Gly Ser Gly Glu Gly Glu
        370                 375                 380
Gly Ser Glu Gly Gly Ser Gly Glu Gly Gly Ser Glu Gly Ser Glu
385                 390                 395                 400
Gly Glu Gly Ser Gly Glu Gly Ser Glu Gly Glu Gly Ser Glu Gly
            405                 410                 415
Ser Glu Gly Glu Gly Gly Gly Glu Gly Ser Glu Gly Glu Gly Ser Gly
            420                 425                 430
Glu Gly Ser Glu Gly Glu Gly Gly Ser Glu Gly Ser Glu Gly Glu Gly
        435                 440                 445
Gly Ser Glu Gly Ser Glu Gly Gly Gly Glu Gly Ser Gly Glu Gly
        450                 455                 460
Glu Gly Ser Glu Gly Ser Gly Glu Gly Glu Gly Ser Gly Glu Gly Ser
465                 470                 475                 480
Glu Gly Glu Gly Ser Gly Glu Gly Ser Gly Glu Gly Glu Gly Ser Glu Gly
            485                 490                 495
Ser Gly Glu Gly Glu Gly Gly Ser Glu Gly Ser Gly Glu Gly Ser
            500                 505                 510
Gly Glu Gly Ser Glu Gly Glu Gly Ser Glu Gly Ser Gly Glu Gly Glu
        515                 520                 525
Gly Ser Glu Gly Ser Gly Glu Gly Gly Ser Glu Gly Ser Glu
        530                 535                 540
Gly Glu Gly Gly Ser Gly Glu Gly Gly Ser Gly Ser Glu Gly
545                 550                 555                 560
Ser Glu Gly Glu Gly Gly Glu Gly Ser Gly Glu Gly Gly Ser Glu
            565                 570                 575
Gly Ser Gly Glu Gly Glu Gly Ser Gly Glu Gly Ser Glu Gly Glu Gly
```

```
                    580                 585                 590
Ser Glu Gly Ser Gly Glu Gly Glu Gly Ser Glu Gly Ser Gly Glu Gly
                595                 600                 605

Glu Gly Gly Ser Glu Gly Ser Glu Gly Glu Gly Ser Glu Gly Ser Gly
            610                 615                 620

Glu Gly Glu Gly Gly Glu Gly Ser Gly Glu Gly Glu Gly Ser Gly Glu
625                 630                 635                 640

Gly Ser Glu Gly Glu Gly Gly Glu Gly Ser Glu Gly Glu Gly Gly Ser
                645                 650                 655

Glu Gly Ser Gly Glu Gly Glu Gly Ser Glu Gly Ser Gly Glu Gly Glu
            660                 665                 670

Gly Ser Glu Gly Gly Ser Glu Gly Glu Gly Ser Glu Gly Ser Glu Glu
            675                 680                 685

Gly Glu Gly Ser Glu Gly Gly Ser Glu Gly Glu Gly Ser Glu Gly Gly
            690                 695                 700

Ser Glu Gly Glu Gly Ser Glu Gly Ser Gly Glu Gly Glu Gly Ser Glu
705                 710                 715                 720

Gly Ser Gly Glu Gly Glu Gly Ser Gly Glu Gly Ser Glu Gly Glu Gly
                725                 730                 735

Gly Ser Glu Gly Gly Glu Gly Glu Gly Ser Glu Gly Gly Ser Glu Gly
            740                 745                 750

Glu Gly Ser Gly Glu Gly Ser Glu Gly Glu Gly Glu Gly Glu Ser Gly
            755                 760                 765

Glu Gly Glu Gly Gly Ser Glu Gly Ser Glu Gly Glu Gly Gly Ser Glu
            770                 775                 780

Ser Gly Glu Gly Glu Gly Ser Gly Glu Gly Ser Glu Gly
785                 790                 795

<210> SEQ ID NO 512
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Gly Glu Gly Ser Gly Glu Gly Ser Gly Glu Gly Gly Ser Glu Gly
1               5                   10                  15

Gly Glu Gly Glu Gly Gly Ser Glu Gly Ser Glu Gly Glu Gly Ser Glu
            20                  25                  30

Gly Gly Ser Glu Gly Glu Gly Ser Gly Glu Gly Ser Glu Glu Gly Gly
        35                  40                  45

Gly Ser Glu Gly Glu Gly Gly Glu Gly Ser Glu Gly Ser Glu Gly Gly
        50                  55                  60

Glu Gly Ser Gly Glu Gly Ser Glu Gly Glu Gly Gly Ser Glu Gly Ser
65                  70                  75                  80

Glu Gly Glu Gly Ser Glu Gly Gly Gly Glu Gly Glu Gly Ser Gly Glu
                85                  90                  95

Gly Ser Glu Gly Glu Gly Gly Ser Glu Gly Ser Glu Gly Glu Gly Ser
            100                 105                 110

Gly Glu Gly Ser Glu Gly Glu Gly Ser Glu Gly Gly Glu Gly Gly Glu
            115                 120                 125

Gly Gly Ser Glu Gly Ser Glu Gly Glu Gly Ser Glu Gly Gly Ser Glu
        130                 135                 140
```

<210> SEQ ID NO 513
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 513

Gly Glu Gly Gly Ser Glu Gly Ser Gly Glu Gly Ser Gly Gly
1               5                   10                  15

Gly Glu Gly Gly Gly Ser Gly Glu Gly Ser Glu Gly Glu Gly Ser
            20                  25                  30

Glu Gly Ser Glu Gly Glu Gly Ser Glu Gly Ser Glu Gly Glu Gly
        35                  40                  45

Gly Ser Glu Gly Glu Gly Glu Gly Ser Glu Gly Ser Glu Gly
    50                  55                  60

Glu Gly Ser Gly Gly Ser Glu Gly Glu Gly Ser Gly Glu Gly Ser
65                  70                  75                  80

Glu Gly Glu Gly Gly Ser Gly Gly Glu Gly Glu Gly Gly Ser Glu
                85                  90                  95

Gly Ser Glu Gly Glu Gly Ser Glu Gly Ser Glu Gly Glu Gly Ser
            100                 105                 110

Gly Glu Gly Ser Glu Gly Glu Gly Ser Gly Glu Gly Glu Gly Glu
        115                 120                 125

Gly Gly Ser Glu Gly Ser Glu Gly Glu Gly Ser Glu Gly Gly Ser Glu
    130                 135                 140

<210> SEQ ID NO 514
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 514

Gly Glu Gly Gly Ser Glu Gly Ser Gly Glu Gly Ser Glu Gly Gly
1               5                   10                  15

Gly Glu Gly Glu Gly Ser Gly Glu Gly Ser Glu Gly Glu Gly Ser
            20                  25                  30

Glu Gly Ser Glu Gly Glu Gly Ser Glu Gly Ser Glu Gly Glu Gly
        35                  40                  45

Gly Ser Glu Gly Gly Gly Gly Gly Ser Glu Gly Ser Glu Gly Gly
    50                  55                  60

Glu Gly Ser Glu Gly Gly Ser Glu Gly Glu Gly Ser Gly Glu Gly Ser
65                  70                  75                  80

Glu Gly Glu Gly Gly Ser Gly Gly Glu Gly Glu Gly Gly Ser Glu
                85                  90                  95

Gly Ser Glu Gly Glu Gly Ser Glu Gly Ser Glu Gly Glu Gly Ser
            100                 105                 110

Gly Glu Gly Ser Glu Gly Glu Gly Ser Gly Glu Gly Glu Gly Glu
        115                 120                 125

Gly Gly Ser Glu Gly Ser Glu Gly Glu Gly Ser Glu Gly Gly Ser Glu
    130                 135                 140

<210> SEQ ID NO 515
<211> LENGTH: 144

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Gly Glu Gly Ser Gly Glu Gly Ser Glu Gly Gly Ser Glu Gly Gly
1               5                   10                  15

Gly Glu Gly Glu Gly Gly Ser Glu Gly Ser Gly Glu Gly Ser Glu
                20                  25                  30

Gly Gly Ser Glu Gly Gly Ser Gly Glu Gly Ser Glu Gly Glu Gly
            35                  40                  45

Gly Ser Glu Gly Gly Glu Gly Gly Ser Glu Gly Ser Glu Gly Gly
        50                  55                  60

Glu Gly Ser Glu Gly Gly Ser Gly Glu Gly Gly Ser Glu Gly Ser
65                  70                  75                  80

Glu Gly Glu Gly Ser Glu Gly Gly Glu Gly Glu Gly Ser Gly Glu
                85                  90                  95

Gly Ser Glu Gly Glu Gly Gly Ser Glu Gly Ser Glu Gly Glu Ser
            100                 105                 110

Gly Glu Gly Ser Glu Gly Gly Ser Glu Gly Gly Ser Gly Glu Glu
        115                 120                 125

Gly Gly Ser Glu Gly Ser Glu Gly Glu Gly Ser Glu Gly Ser Glu
    130                 135                 140

<210> SEQ ID NO 516
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Gly Glu Gly Gly Ser Glu Gly Ser Glu Gly Glu Gly Ser Gly Gly
1               5                   10                  15

Gly Glu Gly Glu Gly Ser Gly Glu Gly Ser Gly Glu Gly Gly Ser
                20                  25                  30

Glu Gly Ser Glu Gly Gly Gly Ser Gly Glu Gly Ser Glu Gly Gly
            35                  40                  45

Gly Ser Glu Gly Gly Glu Gly Glu Gly Ser Gly Ser Glu Gly Gly
        50                  55                  60

Glu Gly Ser Glu Gly Gly Ser Glu Gly Glu Gly Ser Gly Glu Gly
65                  70                  75                  80

Ser Gly Ser Glu Gly Ser Gly Glu Gly Ser Gly Glu Gly Gly Glu
                85                  90                  95

Gly Gly Ser Glu Gly Gly Glu Gly Gly Gly Ser Gly Glu Gly Ser
            100                 105                 110

Gly Glu Gly Ser Glu Gly Glu Gly Ser Glu Gly Ser Gly Glu Glu
        115                 120                 125

Gly Gly Ser Glu Gly Ser Glu Gly Glu Gly Ser Gly Glu Gly Glu
    130                 135                 140

<210> SEQ ID NO 517
<211> LENGTH: 144
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 517

Gly Glu Gly Ser Gly Glu Gly Ser Gly Glu Gly Gly Ser Glu Gly Gly
1               5                   10                  15

Ser Glu Gly Glu Gly Gly Glu Gly Ser Gly Glu Gly Glu Gly Ser Gly
                20                  25                  30

Glu Gly Ser Glu Gly Glu Gly Ser Gly Glu Gly Ser Glu Gly Glu Gly
            35                  40                  45

Gly Ser Glu Gly Gly Glu Gly Glu Gly Ser Glu Gly Ser Glu Gly Gly
        50                  55                  60

Glu Gly Ser Glu Gly Gly Ser Glu Gly Glu Gly Ser Glu Gly Gly Ser
65                  70                  75                  80

Glu Gly Glu Gly Ser Glu Gly Ser Gly Glu Gly Glu Gly Ser Glu Gly
                85                  90                  95

Gly Ser Glu Gly Glu Gly Gly Ser Gly Glu Gly Ser Glu Gly Glu Gly
            100                 105                 110

Ser Gly Glu Gly Ser Gly Ser Glu Gly Gly Ser Glu Gly Glu Gly Glu
        115                 120                 125

Gly Gly Gly Glu Gly Ser Glu Gly Ser Gly Glu Gly Gly Gly Gly Glu
    130                 135                 140

<210> SEQ ID NO 518
<211> LENGTH: 144
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 518

Gly Glu Gly Gly Ser Glu Gly Ser Gly Glu Gly Ser Gly Gly Gly Gly
1               5                   10                  15

Gly Glu Gly Glu Gly Ser Gly Glu Gly Ser Gly Glu Gly Glu Gly Ser
                20                  25                  30

Glu Gly Ser Glu Gly Glu Gly Ser Gly Glu Gly Ser Glu Gly Glu Gly
            35                  40                  45

Gly Ser Glu Gly Gly Glu Gly Glu Gly Ser Glu Gly Ser Glu Gly Gly
        50                  55                  60

Glu Gly Ser Glu Gly Gly Ser Glu Gly Glu Gly Ser Glu Gly Gly Ser
65                  70                  75                  80

Glu Gly Glu Gly Gly Ser Glu Gly Gly Gly Gly Glu Gly Gly Ser Glu
                85                  90                  95

Gly Ser Glu Gly Glu Gly Ser Glu Gly Gly Ser Glu Gly Glu Gly Ser
            100                 105                 110

Gly Glu Gly Ser Glu Gly Glu Gly Ser Glu Gly Glu Gly Glu Gly Glu
        115                 120                 125

Gly Gly Ser Glu Gly Ser Glu Gly Glu Gly Glu Gly Glu Gly Ser Glu
    130                 135                 140

<210> SEQ ID NO 519
<211> LENGTH: 144
<212> TYPE: PRT
<213> ORGANISM: Artificial Sequence
<220> FEATURE:
<223> OTHER INFORMATION: Description of Artificial Sequence: Synthetic
polypeptide -continued

<400> SEQUENCE: 519

Gly Glu Gly Ser Gly Glu Gly Ser Gly Glu Gly Gly Ser Glu Gly
1               5                   10                  15

Ser Glu Gly Glu Gly Gly Glu Gly Ser Glu Gly Glu Gly Ser Gly
                20                  25                  30

Glu Gly Ser Glu Gly Gly Ser Glu Gly Gly Ser Glu Gly Glu Gly
                35                  40                  45

Gly Ser Glu Gly Gly Gly Glu Gly Ser Glu Gly Ser Gly Glu Gly
            50                  55                  60

Glu Gly Ser Glu Gly Gly Ser Glu Gly Glu Gly Ser Glu Gly Gly Ser
65                  70                  75                  80

Glu Gly Glu Gly Ser Glu Gly Ser Glu Gly Gly Ser Glu Gly
                85                  90                  95

Gly Ser Glu Gly Glu Gly Gly Ser Glu Gly Ser Glu Gly Ser Glu Gly
                    100                 105                 110

Ser Gly Glu Gly Ser Gly Ser Glu Gly Ser Glu Gly Gly Glu Gly
                115                 120                 125

Gly Gly Gly Glu Gly Ser Glu Gly Gly Ser Glu Gly Ser Gly Gly Glu
        130                 135                 140

<210> SEQ ID NO 520
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Gly Glu Gly Gly Ser Glu Gly Ser Glu Gly Gly Ser Glu Gly Gly
1               5                   10                  15

Gly Glu Gly Glu Gly Ser Gly Glu Ser Gly Glu Gly Glu Gly Ser
                20                  25                  30

Glu Gly Ser Glu Gly Gly Ser Glu Gly Ser Glu Gly Glu Gly Glu Gly
                35                  40                  45

Gly Ser Glu Gly Gly Glu Gly Gly Ser Glu Gly Ser Glu Gly Gly
            50                  55                  60

Glu Gly Ser Glu Gly Gly Ser Glu Gly Glu Gly Ser Glu Gly Gly Ser
65                  70                  75                  80

Glu Gly Glu Gly Gly Ser Gly Glu Gly Glu Gly Gly Ser Glu
                85                  90                  95

Gly Ser Glu Gly Glu Gly Ser Gly Ser Glu Gly Glu Gly Gly Ser
                    100                 105                 110

Gly Glu Gly Ser Glu Gly Glu Gly Ser Gly Gly Glu Gly Glu
                115                 120                 125

Gly Gly Ser Glu Gly Ser Glu Gly Gly Glu Gly Gly Ser Glu
        130                 135                 140

<210> SEQ ID NO 521
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Gly Glu Gly Gly Ser Glu Gly Ser Glu Gly Gly Gly Ser Glu Gly Gly

-continued

```
                1               5                      10                      15
Gly Glu Gly Glu Gly Ser Gly Glu Gly Ser Glu Gly Glu Gly Gly Ser
                        20                      25                      30
Glu Gly Ser Glu Gly Glu Gly Ser Glu Gly Gly Ser Glu Gly Glu Gly
                        35                      40                      45
Gly Ser Glu Gly Gly Glu Gly Gly Ser Gly Glu Gly Ser Glu Gly
            50                      55                      60
Glu Gly Ser Glu Gly Gly Ser Glu Gly Gly Ser Gly Glu Gly Ser
65                      70                      75                      80
Glu Gly Glu Gly Gly Ser Glu Gly Gly Glu Gly Gly Ser Glu
                85                      90                      95
Gly Ser Glu Gly Glu Gly Ser Glu Gly Gly Ser Glu Gly Glu Gly Ser
                    100                     105                     110
Gly Glu Gly Ser Glu Gly Glu Gly Gly Ser Glu Gly Gly Glu Gly Glu
                    115                     120                     125
Gly Gly Ser Glu Gly Ser Glu Gly Gly Gly Ser Glu Gly Gly Ser Glu
                    130                     135                     140
```

<210> SEQ ID NO 522
<211> LENGTH: 826
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 522

```
Met Asp Tyr Lys Asp Asp Asp Lys Gly Ser Pro Gly Glu Gly Ser
1               5                       10                      15
Gly Glu Gly Ser Glu Gly Glu Gly Ser Glu Gly Ser Gly Glu Gly Glu
                        20                      25                      30
Gly Ser Glu Gly Ser Gly Glu Gly Gly Gly Ser Glu Gly Ser Glu
                        35                      40                      45
Gly Glu Gly Ser Glu Gly Ser Gly Glu Gly Gly Gly Glu Gly Ser
            50                      55                      60
Gly Glu Gly Glu Gly Ser Gly Glu Gly Ser Glu Gly Gly Gly Gly
65                      70                      75                      80
Glu Gly Ser Glu Gly Glu Gly Ser Gly Glu Gly Gly Glu Gly Glu Gly
                85                      90                      95
Ser Glu Gly Gly Ser Glu Gly Glu Gly Gly Ser Glu Gly Glu Gly
                    100                     105                     110
Glu Gly Ser Glu Gly Ser Gly Glu Gly Gly Glu Gly Gly Gly Ser
                    115                     120                     125
Glu Gly Glu Gly Ser Gly Gly Ser Glu Gly Glu Gly Ser Glu Gly
                    130                     135                     140
Ser Gly Glu Gly Glu Gly Ser Glu Gly Ser Gly Glu Gly Glu Gly Ser
145                     150                     155                     160
Glu Gly Ser Gly Glu Gly Gly Glu Gly Ser Glu Gly Glu Gly Glu
                    165                     170                     175
Gly Ser Glu Gly Gly Ser Glu Gly Glu Gly Gly Ser Glu Gly Ser Glu
                    180                     185                     190
Gly Glu Gly Ser Gly Glu Gly Ser Glu Gly Glu Gly Gly Ser Glu Gly
                    195                     200                     205
Ser Glu Gly Glu Gly Gly Gly Glu Gly Ser Glu Gly Glu Gly Ser Gly
                    210                     215                     220
```

-continued

Glu Gly Ser Glu Gly Glu Gly Ser Glu Gly Glu Gly
225                 230                 235                 240

Gly Ser Glu Gly Ser Glu Gly Glu Gly Glu Gly Ser Gly Glu Gly
                245                 250                 255

Glu Gly Ser Glu Gly Ser Gly Glu Gly Glu Gly Ser Gly Glu Ser
                260                 265                 270

Glu Gly Glu Gly Ser Glu Gly Ser Gly Glu Gly Glu Gly Ser Glu Gly
                275                 280                 285

Ser Gly Glu Gly Glu Gly Ser Glu Gly Ser Gly Glu Gly Glu Gly Ser
290                 295                 300

Gly Glu Gly Ser Glu Gly Glu Gly Ser Glu Gly Ser Gly Glu Gly Glu
305                 310                 315                 320

Gly Ser Glu Gly Ser Gly Glu Gly Glu Gly Ser Glu Gly Ser Glu
                325                 330                 335

Gly Glu Gly Gly Ser Glu Gly Ser Glu Gly Glu Gly Ser Glu Gly
                340                 345                 350

Ser Glu Gly Glu Gly Gly Glu Gly Ser Gly Glu Gly Glu Gly Ser Glu
                355                 360                 365

Gly Ser Gly Glu Gly Glu Gly Ser Gly Glu Gly Ser Glu Gly Glu Gly
                370                 375                 380

Ser Glu Gly Ser Gly Glu Gly Glu Gly Ser Glu Gly Ser Gly Glu Gly
385                 390                 395                 400

Glu Gly Gly Ser Glu Gly Ser Glu Gly Glu Gly Ser Gly Ser Gly
                405                 410                 415

Glu Gly Glu Gly Gly Glu Gly Ser Gly Glu Gly Glu Gly Ser Gly Glu
                420                 425                 430

Gly Ser Glu Gly Glu Gly Gly Glu Gly Ser Glu Gly Glu Gly Ser
                435                 440                 445

Glu Gly Ser Gly Glu Gly Glu Gly Ser Glu Gly Ser Gly Glu Gly Glu
                450                 455                 460

Gly Ser Glu Gly Gly Ser Glu Gly Glu Gly Ser Glu Gly Ser Glu
465                 470                 475                 480

Gly Glu Gly Ser Glu Gly Gly Ser Glu Gly Glu Gly Ser Glu Gly Gly
                485                 490                 495

Ser Glu Gly Glu Gly Ser Gly Ser Gly Glu Gly Glu Gly Ser Glu
                500                 505                 510

Gly Ser Gly Glu Gly Glu Gly Ser Gly Glu Gly Ser Glu Gly Glu Gly
                515                 520                 525

Gly Ser Glu Gly Gly Glu Gly Gly Ser Gly Gly Ser Glu Gly
                530                 535                 540

Glu Gly Ser Glu Gly Gly Ser Glu Gly Glu Gly Glu Gly Ser Gly
545                 550                 555                 560

Glu Gly Glu Gly Gly Glu Gly Ser Glu Gly Glu Gly Ser Glu Gly
                565                 570                 575

Ser Gly Glu Gly Glu Gly Ser Gly Glu Gly Ser Glu Gly Ser Lys Gly
                580                 585                 590

Glu Glu Leu Phe Thr Gly Val Val Pro Ile Leu Val Glu Leu Asp Gly
                595                 600                 605

Asp Val Asn Gly His Lys Phe Ser Val Ser Gly Glu Gly Glu Gly Asp
                610                 615                 620

Ala Thr Tyr Gly Lys Leu Thr Leu Lys Phe Ile Cys Thr Thr Gly Lys
625                 630                 635                 640

Leu Pro Val Pro Trp Pro Thr Leu Val Thr Thr Phe Ser Tyr Gly Val

```
                    645                 650                 655
Gln Cys Phe Ser Arg Tyr Pro Asp His Met Lys Arg His Asp Phe Phe
                660                 665                 670

Lys Ser Ala Met Pro Glu Gly Tyr Val Gln Glu Arg Thr Ile Ser Phe
                675                 680                 685

Lys Asp Asp Gly Asn Tyr Lys Thr Arg Ala Glu Val Lys Phe Glu Gly
            690                 695                 700

Asp Thr Leu Val Asn Arg Ile Glu Leu Lys Gly Ile Asp Phe Lys Glu
705                 710                 715                 720

Asp Gly Asn Ile Leu Gly His Lys Leu Glu Tyr Asn Tyr Asn Ser His
                725                 730                 735

Asn Val Tyr Ile Thr Ala Asp Lys Gln Lys Asn Gly Ile Lys Ala Asn
                740                 745                 750

Phe Lys Ile Arg His Asn Ile Glu Asp Gly Ser Val Gln Leu Ala Asp
                755                 760                 765

His Tyr Gln Gln Asn Thr Pro Ile Gly Asp Gly Pro Val Leu Leu Pro
            770                 775                 780

Asp Asn His Tyr Leu Ser Thr Gln Ser Ala Leu Ser Lys Asp Pro Asn
785                 790                 795                 800

Glu Lys Arg Asp His Met Val Leu Leu Glu Phe Val Thr Ala Ala Gly
                805                 810                 815

Ile Thr His Gly Met Asp Glu Leu Tyr Lys
                820                 825

<210> SEQ ID NO 523
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ser Lys Val Ile Leu Phe
1               5

<210> SEQ ID NO 524
<211> LENGTH: 7
<212> TYPE: PRT
<213> ORGANISM: Homo sapiens

<400> SEQUENCE: 524

Glu Asn Leu Tyr Phe Gln Gly
1               5
```

COMPOSITIONS COMPRISING MODIFIED BIOLOGICALLY ACTIVE POLYPEPTIDES

CROSS-REFERENCE TO RELATED APPLICATIONS

This application claims the priority benefit of U.S. Provisional Application Ser. Nos. 60/956,109 filed on Aug. 15, 2007, 60/981,073 filed Oct. 18, 2007, and 60/986,569 filed Nov. 8, 2007, all of which are hereby incorporated herein by reference in their entirety.

FEDERALLY SPONSORED WORK

The work in this application was partly funded by SBIR grants 1R43GM079873-01 and 2R44GM079873-02 awarded by the National Institutes of Health. The government may have certain rights in the invention.

STATEMENT REGARDING FEDERALLY SUPPORTED RESEARCH

This invention was made with government support under SBIR grant 1R43GM079873-01 and 2R44GM079873-02 awarded by the National Institutes of Health. The government has certain rights in the invention.

BACKGROUND OF THE INVENTION

Recombinant proteins have become very attractive candidates for the development of novel therapeutics. However, production of protein pharmaceuticals requires significant optimization of processes to obtain sufficient yields of specific biologically active polypeptides. It is well established that the expression of recombinant proteins in the cytoplasm of *Escherichia coli*, in particular mammalian recombinant proteins, frequently results in the formation of insoluble aggregates known as inclusion bodies. High cell density fermentation and purification of the recombinant protein from inclusion bodies of *E. coli* are two major bottlenecks for the cost effective production of therapeutic proteins (Panda, A. K, 2003, Adv. Biochem. Eng. Biotechnol., 85, 43). Similarly, for research purposes, where hundreds of proteins may need to be screened for various activities, the expression of soluble, active protein is desirable, thereby avoiding the step of first purifying inclusion bodies and then having to denature and refold protein each separately.

Examples of the many pharmaceutically important proteins that form insoluble inclusion bodies when expressed in the cytoplasmic space of *E. coli* include human Growth Hormone (hGH) (Patra, A. K. et al., 2000, Protein Expr. Purif, 18, 182; Khan, R. H, et al., 1998, Biotechnol. Prog., 14, 722), human Granulocyte-Colony Stimulating Factor (G-CSF) (Zaveckas, M. et al. 2007, J Chromatogr B Analyt Technol Biomed Life Sci. 852, 409; Lee, A. Y. et al., 2003, Biotechnol Lett., 25, 205,) and Interferon alpha (IFN-alpha; Valente, C. A. et al., 2006, Protein. Expr. Purif. 45, 226). Furthermore, the immunoglobulin domains of antibodies and their fragments, including domain antibody fragments (dAb), Fv fragments, single-chain Fv fragments (scFv), Fab fragments, Fab'2 fragments, and many non-antibody proteins (such as FnIII domains) generally form inclusion bodies upon expression in the cytoplasm of bacterial hosts (Kou, G., et al., 2007, Protein Expr Purif. 52, 131; Cao, P., et al. 2006, Appl Microbiol Biotechnol., 73, 151; Chen, L. H et al., 2006, Protein Expr Purif.; 46, 495).

Human proteins typically fold using a hydrophobic core comprising a large number of hydrophobic amino acids. Research has shown that proteins can aggregate and form inclusion bodies, especially when genes from one organism are expressed in another expression host, such that the protein's native binding partners are absent, so that folding help is unavailable and hydrophobic patches remain exposed. This is especially true when large evolutionary distances are crossed: a cDNA isolated from a eukaryote for example, when expressed as a recombinant gene in a prokaryote, has a high risk of aggregating and forming an inclusion body. While the cDNA may properly code for a translatable mRNA, the protein that results will emerge in a foreign microenvironment. This often results in misfolded, inactive protein that generally accumulates as aggregates if the concentration is high enough. Other effectors, such as the internal microenvironment of a prokaryotic cell (pH, osmolarity) may differ from that of the original source of the gene and affect protein folding. Mechanisms for folding a protein may also be host-dependent and thus be absent in a heterologous host, and hydrophobic residues that normally would remain buried as part of the hydrophobic core instead remain exposed and available for interaction with hydrophobic sites on other proteins. Processing systems for the cleavage and removal of internal peptides of the expressed protein may also be absent in bacteria. In addition, the fine controls that may keep the concentration of a protein low will also be missing in a prokaryotic cell, and over-expression can result in filling a cell with protein that, even if it were properly folded, would precipitate by saturating its environment.

The recovery of biologically active products from the aggregated state found in inclusion bodies is typically accomplished by unfolding with chaotropic agents or acids, followed by dilution or dialysis into optimized refolding buffers. However, many polypeptides (especially structurally complex oligomeric proteins and those containing multiple disulfide bonds) do not easily adopt an active conformation following chemical denaturation. Small changes in primary structure can affect solubility, presumably by altering folding pathways (Mitraki, A. et al. (1989) Bio/Technology 7, 690; Baneyx, F, et. al. 2004 Nat Biotechnol, 22, 1399; Ventura, S. 2005 Microb Cell Fact, 4, 11). In order to reduce the formation of insoluble aggregates during high-density fermentation, some groups have linked heterologous fusion proteins to the protein of interest. Examples of such fusion sequences are Glutathione-S-Transferase (GST), Protein Disulfide Isomerase (PDI), Thioredoxin (TRX), Maltose Binding Protein (MBP), His6 tag (SEQ ID NO: 1), Chitin Binding Domain (CBD) and Cellulose Binding Domain (CBD) (Sahadev, S. et al. 2007, Mol. Cell. Biochem.; Dysom, M. R. et al. 2004, BMC Biotechnol, 14, 32). In summary, these approaches were found to be protein-specific, as they do not work for all proteins.

While various fusion proteins have been designed to improve folding, chemical PEGylation of proteins has also been reported to enhance protein solubility, reduce aggregation, reduce immunogenicity, and reduce proteolysis. Nonetheless, the proper folding of overproduced polypeptides remains problematic within the highly concentrated and viscous environment of the cell cytoplasm, where aggregation occurs in a concentration-dependent manner. Another approach for the expression of mammalian proteins in bacterial hosts avoids leader peptides and expresses the active protein directly in the cytoplasm of the host. However, this process tends to result in aggregation and inclusion body formation.

One widely used approach for the expression of mammalian proteins in active form in bacteria is to direct the protein into the non-reducing environment of the periplasmic space of bacterial hosts such as *E. coli*, typically using signal- or leader-peptides to direct secretion. Secretion into the periplasm (and rarely into the media) appears to mimic the native eukaryotic process of protein secretion, folding and disulfide formation and often results in active protein. This approach has many profound drawbacks. The periplasm tends to give low yields; the process is generally limited to smaller proteins; the process tends to be protein-specific; and also that the procedures for extracting periplasmic proteins are not as robust as extraction from the cytoplasm, which contributes to low yields. For these reasons, expression of proteins in the periplasm of bacteria is not applicable to most pharmaceutical proteins, which are typically commercially expressed in yeast or mammalian cell lines.

Another approach that has been tried to make mammalian proteins express in the cytoplasm of bacteria without forming inclusion bodies is to over-express folding-helper proteins, like the molecular chaperones which play a role in a wide range of biotechnological applications (Mogk et al. 2002 Chembiochem 3, 807). To date, several different families of chaperones have been reported. All are characterized by their ability to bind unfolded or partially unfolded proteins and release correctly folded proteins into the cytoplasm of bacteria. A well-characterized example is the heat-shock family of proteins (Hsp), which are designated according to their relative molecular weight, as described by Buchner, J., Faseb J. 1996 10, 10 and by Beissinger, M. and Buchner, 1998. J. Biol. Chem. 379, 245. While many bacterial and eukaryotic chaperonins have been tried for over-expression of proteins in bacteria and to a lesser extent mammalian cells, this approach has generally had little or no effect and this is less often practiced for expression optimization.

Many therapeutic proteins suffer from a number of drawbacks including short half-life, high serum clearance, and high immunogenicity. Sustained-release, or depot, formulations of protein therapeutics offer a strategy to decrease the frequency of protein injections and thus reduce the chance of undesired immune response and also increase patient compliance. The active pharmaceutical ingredient (API) is typically encapsulated in a matrix made of a biodegradable polymer, which then allows slow release of the API upon administration to a patient. Drugs administered as sustained-release formulations may also exhibit a less dramatic burst in bioavailability following injection ('bolus effect') compared to drug alone. This is very important as all drugs have a defined therapeutic window. At concentrations higher than the therapeutic window, the drug is toxic, whereas at concentrations below the therapeutic window, the drug no longer exhibits its biological or therapeutic effect. Depot formulations can provide a way to increase the period a drug is present in this therapeutic window.

Once the drug is released, however, the half-life of peptide or protein therapeutics remains relatively short. Improvements to therapeutic properties of proteins, in particular plasma clearance and immunogenicity, by attaching non-proteinaceous polymers to the proteins, have previously been described (Kochendoerfer, G. (2003) *Expert Opin Biol Ther,* 3: 1253-61), (Greenwald, R. B., et al. (2003) *Adv Drug Deliv Rev,* 55: 217-50), (Harris, J. M., et al. (2003) *Nat Rev Drug Discov,* 2: 214-21).

Therapeutic antibodies are typically administered bi-weekly or monthly but currently similar regimens for other therapeutic proteins still need to be developed. Recently, PLGA microspheres containing insulin modified with PEG (5 kDa) have been described as a controlled release formulation, but due to the short half-life of insulin, weekly injection intervals may still be required (Hinds, K. D., et al. (2005) J Control Release, 104:447-60).

SUMMARY OF THE INVENTION

There remains a significant need for methods and compositions that improve biological properties such as serum half-life and provide more constant dosing of proteins to a patient and a longer time interval between treatments. There also exists a significant need for methods and compositions for production of biologically active proteins and for improving their solubility to effect large scale production utilizing host cells, such as prokaryotes.

In one embodiment, the present invention provides a method of producing a biologically active polypeptide. The method typically involves the steps of a) providing a polynucleotide sequence coding for a modified polypeptide comprising the biologically active polypeptide linked with an accessory polypeptide such that expression of the modified polypeptide in a host cell yields a higher quantity of soluble form of biologically active polypeptide, as compared to expression of the biologically active polypeptide by itself (e.g., free from said accessory polypeptide; and b) causing the modified polypeptide to be expressed in said host cell, thereby producing the biologically active polypeptide. In one embodiment, the expression of the soluble, active form of a biologically active polypeptide is about 1%, 5%, 25%, 50%, 75%, 95% or 99% of the total of that protein. In one embodiment, the expression of the modified polypeptide in a host cell yields at least about 2-fold more soluble form of biologically active polypeptide as compared to expression of the biologically active polypeptide by itself. In another embodiment, the biologically active polypeptide is linked to the accessory polypeptide via a proteinase cleaveage site. Where desired, the cleaveage site can be selected from the group consisting of TEV protease, enterokinase, Factor Xa, thrombin, PreScission™ protease, 3C protease, sortase A, and granzyme B. In some embodiments, the expression of the modified polypeptide in a host cell yields at least about 2-fold, 5-fold, 10-fold, 30-fold, or 100-fold, or more soluble form of biologically active polypeptide.

The present invention also provides a host cell for expressing the modified polynucleotide sequence. The host cell is typically prokaryotic including but not limited to *E. Coli*, and it may also be eurkaryotic such as yeast cells and also mammalian cells (e.g. CHO cells).

The present invention also provides a genetic vehicle comprising the subject polynucleotide sequence that encodes a biologically active polypeptide linked with or without an accessory polypeptide.

Further provided by the present invention is a composition comprising soluble form of a biologically active polypeptide linked with an accessory polypeptide, wherein said accessory polypeptide when linked with the biologically active polypeptide increases solubility of the biologically active polypeptide in a cytosolic fraction of a host cell in which the linked biologically active polypeptide is expressed. Where desired, the biologically active polypeptide is linked via a protease cleavage site to the accessory polypeptide. The cleaveage site can be selected from the group consisting of TEV protease, enterokinase, Factor Xa, thrombin, PreScission™ protease, 3C protease, sortase A, and granzyme B.

The accessory polypeptide used in the subject methods or compositions can be characterized in whole or in part by the following. In one embodiment, the subject accessory polypeptide provides an average net positive charge density of the modified biologically active polypeptide of about +0.025, +0.05, +0.075, +0.1, +0.2, +0.3, +0.4, +0.5, +0.6, +0.7, +0.8, +0.9 or even +1.0 charges per amino acid residue. In another embodiment, the subject accessory polypeptide provides an average net negative charge density of the modified biologically active polypeptide of about −0.25, −0.5, −0.075, −0.1, −0.2, −0.3, −0.4, −0.5, −0.6, −0.7, −0.8, −0.9 or even −1.0 average net charges per amino acid residue. In one embodiment, the subject accessory polypeptide provides a net positive charge of the modified biologically active polypeptide of about +3, +4, +5, +6, +7, +8, +9, +10, +12, +14+16+18+20, +25, +30, +35, +40, +50 or more. In one embodiment, the subject accessory polypeptide provides a net negative charge of the modified biologically active polypeptide of about −3, 4, −5, −6, −7, −8, −9, −10, −12, −14, −16, −18, −20, −25, −30, −35, 40, −50 or more.

In yet another embodiment, the accessory polypeptides of the invention may comprise more than about 10, 30, 50 or 100 aminoacids. In one embodiment, the accessory polypeptide comprises at least 40 contiguous amino acids and is substantially incapable of non-specific binding to a serum protein. In some embodiments, the sum of glycine (G), aspartate (D), alanine (A), serine (S), threonine (T), glutamate (E) and proline (P) and lysin (K) residues contained in the accessory polypeptide, constitutes more than about 80% of the total amino acids of the accessory polypeptide; and/or at least 50% of the amino acids in the accessory polypeptide are devoid of secondary structure as determined by the Chou-Fasman algorithm. In a related embodiment, the accessory polypeptide comprises at least 40 contiguous amino acids and the accessory polypeptide has an in vitro serum half-life greater than about 4 hours, 5 hours, 10 hours, 15 hours or 24 hours. Further wherein (a) the sum of glycine (G), aspartate (D), alanine (A), serine (S), threonine (T), glutamate (E) and proline (P) and lysine (K) residues contained in the accessory polypeptide, constitutes more than about 80% of the total amino acids of the accessory polypeptide; and/or (b) at least 50% of the amino acids in the accessory polypeptide are devoid of secondary structure as determined by Chou-Fasman algorithm. In some embodiments the set of amino acids from which the 80% (or 50, 60, 70 or 90%) of the total amino acids are chosen is G/S/E/D, G/S/K/R, G/S/E/D/K/R, or G/A/S/T/Q.

In some embodiments, an accessory polypeptide comprises at least 50% glycine residues (i.e., 50% of all residues are glycine). Alternatively, an accessory polypeptide may comprise less than 50% glycine residues. In some embodiments, accessory polypeptides comprise at least 50% serine residues. Other embodiments provide for accessory polypeptides comprising at least 50% serine and glycine residues. Further embodiments provide for accessory polypeptides which comprise at least 5% glutamic acid, or alternatively at least 10, 20 or 30% glutamic acid.

In one embodiment, an accessory polypeptide may also be characterized in that (a) it consists of three types of amino acids, and each type being selected from a group consisting of alanine (A), aspartic acid (D), glutamic acid (E), glycine (G), histidine (H), lysine (K), asparagine (N), proline (P), glutamine (Q), arginine (R), serine (S), threonine (T) and tyrosine (Y); and (b) it comprises 10, 25, 50, 100 or more amino acids. In a related embodiment, the accessory polypeptide consists of three types of amino acids, each type being selected from the group consisting of D, E, G, K, P, R, S, and T. The accessory polypeptide may also consist of three types of amino acids, each type being selected from the group consisting of E, G, and S.

The invention also provides for an accessory polypeptide characterized in that: (i) it consists of three types of amino acids, two of which are serine (S) and glycine (G) and the other type being selected from the group consisting of aspartic acid (D), glutamic acid (E), lysine (K), proline (P), Arginine (R), Glycine (G), Threonine (T), alanine (A), histidine (H), asparagine (N), tyrosine (Y), leucine (L), valine (V), tryptophan (W), methionine (M), phenylalanine (F), isoleucine (I), and cysteine (C); and (ii) it comprises ten or more amino acid residues, of which 50% or more are serine or glycine.

In another embodiment, the accessory polypeptide is characterized in that: (a) it consists of two types of amino acids, one of which is glycine (G) and the other type is selected from the group consisting of aspartic acid (D), glutamic acid (E), lysine (K), proline (P), Arginine (R), Serine (S), Threonine (T), alanine (A), histidine (H), asparagine (N), tyrosine (Y), leucine (L), valine (V), tryptophan (W), methionine (M), phenylalanine (F), isoleucine (I), and cysteine (C); and (b) it comprises ten or more amino acid residues, of which 50% or less are glycine.

Alternatively, the accessory polypeptide consists of two types of amino acids, wherein 50% or less of the total amino acids are selected from the group consisting of A, S, T, D, E, K and H.

In still another embodiment, the accessory polypeptide is characterized in that: (a) it comprises 50 or more amino acids; (b) it consists of two types of amino acids, and (c) 50% or less of the total amino acids are selected from the group consisting of A, S, T, D, E, K and H.

Accessory polypeptides may comprise 1, 2, 5 or 10 or more repeating motifs, each of which may comprise two to five hundred amino acids. In some cases, repeating motifs consist of two or three or more different types of amino acids. Multiple accessory polypeptides may be used. Accessory polypeptide may also comprise charged amino acids.

In some embodiments, the accessory polypeptide comprises an amino acid sequence (GGEGGS)$_n$ (SEQ ID NO: 2), wherein n is an integer of 2, 3, 4, 5, 6, 7, 8, 9, 10 or greater. In other embodiments, the accessory polypeptide comprises an amino acid sequence (GES)n, wherein G, E, and S can be in any order and n is an integer of 2, 3, 4, 5, 6, 7, 8, 9, 10 or greater. Alternatively, the accessory polypeptide comprises an amino acid sequence (GGSGGE)n, wherein G, E, and S can be in any order and n is an integer of 2, 3, 4, 5, 6, 7, 8, 9, 10 or greater. In yet another embodiment, the accessory polypeptide comprises an amino acid sequence (GEGGGEGGE)n (SEQ ID NO: 3), wherein n is an integer of 1, 2, 3, 4, 5, 6, 7, 8, 9, 10 or greater. In yet another embodiment, the accessory sequence comprises an minor acid sequence (GE)n, wherein G and E can be in any order and n is an integer of 1, 2, 3, 4, 5, 6, 7, 8, 9, 10 or greater.

In some embodiments, the accessory polypeptide comprises an amino acid sequence (S)n (SEQ ID NO: 4), wherein n is an integer of 10, 15 20, 50 or greater. In other embodiments, the accessory polypeptide comprises an amino acid sequence (SSSSSSE)n, wherein E and S can be in any order and n is an integer of 2, 3, 4, 5, 6, 7, 8, 9, 10 or greater In other embodiments, the accessory polypeptide comprises an amino acid sequence (SSSSE)n, wherein E and S can be in any order and n is an integer of 2, 3, 4, 5, 6, 7, 8, 9, 10 or greater. In yet other embodiments, the accessory polypeptide comprises an amino acid sequence (SESSSESSE)n, wherein E and S can be in any order and n is an integer of 2, 3, 4, 5, 6, 7, 8, 9, 10 or greater. In some embodiments, the accessory polypeptide comprises an amino acid sequence (SSESSSSESSSE)n, wherein E and S can be in any order and n is an integer of 3 or greater. In other embodiments, the accessory polypeptide comprises an amino acid sequence (SSSESSSSSESSSSE)n, wherein E, and S can be in any order and n is an integer of 3 or greater. In still other embodiments, the accessory polypeptide comprises an amino acid sequence (SSSSESSSSSSESSSSSE)n, wherein E and S can be in any order and n is an integer of 3 or greater.

In some embodiments the accessory polypeptide is not composed of repeating units of a peptide motif of 3, 4, 5, 6 or 7 amino acids, or is not composed of repeating units of any single polypeptide motif. In some embodiments the accessory polypeptide is composed of more than 2, 5, 10, or 20 different repeating motifs of a fixed length. In some embodiments the accessory polypeptide is composed of more than 2, 5, 10, or 20 different repeating motifs of any length.

Additionally, the invention describes a method of making a pharmaceutical composition, comprising: (a) providing a modified polypeptide; (b) mixing said modified polypeptide with a polymer matrix.

The biologically active polypeptide produced by the subject methods or present in the subject composition can be human growth hormone (hGH), glucagon-like peptide-1 (GLP-1), exenatide, pramlitide, uricase, granulocyte-colony stimulating factor (G-CSF), interferon-alpha, interferon-beta, interferon-gamma, insulin, interleukin 1 receptor antagonist (IL-1RA), erythropoietin or tumor necrosis factor-alpha (TFN-alpha).

The present invention relates to a pharmaceutical composition comprising (a) a slow release agent, and (b) a modified polypeptide comprising a biologically active polypeptide linked to an accessory polypeptide. The modified polypeptide may yield an apparent molecular weight factor of greater than 1. The apparent molecular weight factor may be determined as the apparent molecular weight of the modified polypeptide as measured by size exclusion chromatography relative to the predicted molecular weight of the modified polypeptide. In one embodiment, the apparent molecular weight factor of the modified polypeptide is greater than 3. In another embodiment, the apparent molecular weight factor of the modified polypeptide is greater than 5. In yet another embodiment, the apparent molecular weight factor of the modified polypeptide is greater than 7. In still another embodiment, the apparent molecular weight factor of the modified polypeptide is greater than 9.

The accessory polypeptide can increase the serum half-life of a biologically active polypeptide. Alternatively, accessory polypeptides can increase the protease resistance of a biologically active polypeptide. In other cases, accessory polypeptides can increase the solubility of a biologically active polypeptide. In other cases, accessory polypeptides can decrease the immunogenicity of a biologically active polypeptide. The accessory polypeptides of the invention may comprise more than about 10, 30, 50 or 100 aminoacids. In some embodiments, the biologically active polypeptide can be human growth hormone (hGH), glucagon-like peptide-1 (GLP-1), exenatide, pramlitide, uricase, granulocyte-colony stimulating factor (G-CSF), interferon-alpha, interferon-beta, interferon-gamma, insulin, interleukin 1 receptor antagonist (IL-1RA), erythropoietin or tumor necrosis factor-alpha (TNF-alpha).

In one embodiment, the accessory polypeptide comprises at least 40 contiguous amino acids and is substantially incapable of non-specific binding to a serum protein. In some embodiments, the sum of glycine (G), aspartate (D), alanine (A), serine (S), threonine (T), glutamate (E) and proline (P) residues contained in the accessory polypeptide, constitutes more than about 80% of the total amino acids of the accessory polypeptide; and/or at least 50% of the amino acids in the accessory polypeptide are devoid of secondary structure as determined by the Chou-Fasman algorithm. In a related embodiment, the accessory polypeptide comprises at least 40 contiguous amino acids and the accessory polypeptide has an in vitro serum half-life greater than about 4 hours, 5 hours, 10 hours, 15 hours or 24 hours. Further wherein (a) the sum of glycine (G), aspartate (D), alanine (A), serine (S), threonine (T), glutamate (E) and proline (P) residues contained in the accessory polypeptide, constitutes more than about 80% of the total amino acids of the accessory polypeptide; and/or (b) at least 50% of the amino acids in the accessory polypeptide are devoid of secondary structure as determined by Chou-Fasman algorithm.

In some embodiments, an accessory polypeptide comprises at least 50% glycine residues (i.e., 50% of all residues are glycine). Alternatively, an accessory polypeptide may comprise less than 50% glycine residues. In some embodiments, accessory polypeptides comprise at least 50% serine residues. Other embodiments provide for accessory polypeptides comprising at least 50% serine and glycine residues. Further embodiments provide for accessory polypeptides which comprise at least 5% glutamic acid, or alternatively at least 10, 20 or 30% glutamic acid.

In one embodiment, an accessory polypeptide may also be characterized in that (a) it consists of three types of amino acids, and each type being selected from a group consisting of alanine (A), aspartic acid (D), glutamic acid (E), glycine (G), histidine (H), lysine (K), asparagine (N), proline (P), glutamine (Q), arginine (R), serine (S), threonine (T) and tyrosine (Y); and (b) it comprises 10, 25, 50, 100 or more amino acids. In a related embodiment, the accessory polypeptide consists of three types of amino acids, each type being selected from the group consisting of D, E, G, K, P, R, S, and T. The accessory polypeptide may also consist of three types of amino acids, each type being selected from the group consisting of E, G, and S.

The invention also provides for an accessory polypeptide characterized in that: (i) it consists of three types of amino acids, two of which are serine (S) and glycine (G) and the other type being selected from the group consisting of aspartic acid (D), glutamic acid (E), lysine (K), proline (P), Arginine (R), Glycine (G), Threonine (T), alanine (A), histidine (H), asparagine (N), tyrosine (Y), leucine (L), valine (V), tryptophan (W), methionine (M), phenylalanine (F), isoleucine (I), and cysteine (C); and (ii) it comprises ten or more amino acid residues, of which 50% or more are serine or glycine.

In another embodiment, the accessory polypeptide is characterized in that: (a) it consists of two types of amino acids, one of which is glycine (G) and the other type is selected from the group consisting of aspartic acid (D), glutamic acid (E), lysine (K), proline (P), Arginine (R), Serine (S), Threonine (T), alanine (A), histidine (H), asparagine (N), tyrosine (Y), leucine (L), valine (V), tryptophan (W), methionine (M), phenylalanine (F), isoleucine (I), and cysteine (C); and (b) it comprises ten or more amino acid residues, of which 50% or less are glycine.

Alternatively, the accessory polypeptide consists of two types of amino acids, wherein 50% or less of the total amino acids are selected from the group consisting of A, S, T, D, E, and H.

In still another embodiment, the accessory polypeptide is characterized in that: (a) it comprises 50 or more amino acids; (b) it consists of two types of amino acids, and (c) 50% or less of the total amino acids are selected from the group consisting of A, S, T, D, E, and H.

Accessory polypeptides may comprise 1, 2, 5 or 10 or more repeating motifs, each of which may comprise two to five hundred amino acids. In some cases, repeating motifs consist of two or three or more different types of amino acids. Multiple accessory polypeptides may be used. Accessory polypeptide may also comprise charged amino acids.

In some embodiments, the accessory polypeptide comprises an amino acid sequence (GGEGGS)n (SEQ ID NO: 2), wherein n is an integer of 2, 3, 4, 5, 6, 7, 8, 9, 10 or greater. In other embodiments, the accessory polypeptide comprises an amino acid sequence (GES)n, wherein G, E, and S can be in any order and n is an integer of 2, 3, 4, 5, 6, 7, 8, 9, 10 or greater. Alternatively, the accessory polypeptide comprises an amino acid sequence (GGSGGE)n, wherein G, E, and S can be in any order and n is an integer of 2, 3, 4, 5, 6, 7, 8, 9, 10 or greater. In yet another embodiment, the accessory polypeptide comprises an amino acid sequence (GEGGGEGGE)n (SEQ ID NO: 3), wherein n is an integer of 1, 2, 3, 4, 5, 6, 7, 8, 9, 10 or greater. In yet another embodiment, the accessory sequence comprises an minor acid sequence (GE)n, wherein G and E can be in any order and n is an integer of 1, 2, 3, 4, 5, 6, 7, 8, 9, 10 or greater. In some embodiments, the accessory polypeptide comprises an amino acid sequence (S)n (SEQ ID NO: 4), wherein n is an integer of 10, 15 20, 50 or greater. In other embodiments, the accessory polypeptide comprises an amino acid sequence (SSSSSSE)n, wherein E and S can be in any order and n is an integer of 2, 3, 4, 5, 6, 7, 8, 9, 10 or greater In other embodiments, the accessory polypeptide comprises an amino acid sequence (SSSSE)n, wherein E and S can be in any order and n is an integer of 2, 3, 4, 5, 6, 7, 8, 9, 10 or greater. In yet other embodiments, the accessory polypeptide comprises an amino acid sequence (SESSSESSE)n, wherein E and S can be in any order and n is an integer of 2, 3, 4, 5, 6, 7, 8, 9, 10 or greater. In some embodiments, the accessory polypeptide comprises an amino acid sequence (SSESSSSESSSE)n, wherein E and S can be in any order and n is an integer of 3 or greater. In other embodiments, the accessory polypeptide comprises an amino acid sequence (SSSESSSSSESSSSE)n, wherein E, and S can be in any order and n is an integer of 3 or greater. In still other embodiments, the accessory polypeptide comprises an amino acid sequence (SSSSESSSSSSESSSSSE)n, wherein E and S can be in any order and n is an integer of 3 or greater.

In some embodiments the accessory polypeptide is not composed of repeating units of a peptide motif of 3, 4, 5, 6 or 7 amino acids, or is not composed of repeating units of any single polypeptide motif. In some embodiments the accessory polypeptide is composed of more than 2, 5, 10, or 20 different repeating motifs of a fixed length. In some embodiments the accessory polypeptide is composed of more than 2, 5, 10, or 20 different repeating motifs of any length.

A slow release agent may include a polymeric matrix. In some embodiments, the polymeric matrix is charged. In specific embodiments, the polymeric matrix may be poly-d,l-lactide (PLA), poly-(d,l-lactide-co-glycolide) (PLGA), PLGA-PEG copolymers, alginate, dextran and/or chitosan. A slow release agent may also be packaged including a transdermal patch.

The present invention also provides a method of producing modified polypeptides, comprising: a) providing a polynucleotide sequence encoding the modified polypeptide; b) causing said modified polypeptide to be expressed in a host cell, thereby producing said modified polypeptide. A genetic vehicle comprising a nucleic acid sequence encoding the modified polypeptide is also provided, as well as host cells expressing the modified polypeptides of the invention.

Additionally, the invention describes a method of making a pharmaceutical composition, comprising: (a) providing a modified polypeptide; (b) mixing said modified polypeptide with a polymer matrix.

Pharmaceutical compositions of the inventions may comprise a) a slow release agent, by a modified polypeptide comprising a biologically active polypeptide linked to a PEG group of greater than 5 kD in size.

In yet other embodiments the accessory polypeptide substantially lacks secondary structure. In still other embodiments, the accessory polypeptide exhibits a two-fold longer serum half-life as compared to a corresponding polypeptide lacking the accessory polypeptide. The biologically active polypeptide and the accessory polypeptide may be linked via a peptide bond.

In some embodiments, the modified polypeptide further comprises at least one depot module. The depot module is at least 10 amino acids in length, preferably at least 100 amino acids in length. Positively charged depot modules (e.g., lysine rich or arginine rich polypeptides) may be useful in conjunction with a negatively charged polymer. Negatively charged depot modules may be useful in conjunction with a positively charged polymer. A depot module including poly-His sequences may be used in conjunction with a chelating hydrogel. In some cases, the depot module can be protease sensitive, e.g., and without limitation, sensitive to serum proteases or other proteases. Multiple and/or different depot modules may be employed. Any combination of depot module, biologically active polypeptides and accessory polypeptides may be potentially used to produce a sustained-release therapeutic. In a particular embodiment, the slow release agent is a depot module linked to the modified polypeptide.

Additionally, a genetic vehicle comprising a nucleic acid sequence encoding an API of the invention is provided. In another embodiment, a host cell is described expressing the polypeptides.

The present invention relates to accessory polypeptides that may be used to modify the properties of biologically active polypeptides. In one embodiment, the invention provides for an isolated polypeptide comprising a biologically active polypeptide and an accessory polypeptide, wherein the accessory polypeptide is characterized in that it (i) consists of three types of amino acids, and each type being selected from a group consisting of alanine (A), aspartic acid (D), glutamic acid (E), glycine (G), histidine (H), lysine (K), asparagine (N), proline (P), glutamine (Q), arginine (R), serine (S), threonine (T) and tyrosine (Y); and (ii) it comprises ten or more amino acids. In a related embodiment, the accessory polypeptide consists of three types of amino acids, and each type being selected from a group consisting of D, E, G, K, P, R, S, and T. In another related embodiment, the accessory polypeptide consists of three types of amino acids, and each type being selected from a group consisting of E, S, G, R, and A. In another related embodiment, the accessory polypeptide consists of three types of amino acids, and each type being selected from a group consisting of E, S, G, R, and A. In yet another embodiment, the accessory polypeptide consists of three types of amino acids, and each type being selected from a group consisting of E, G, and S. The isolated polypeptide may be a therapeutic polypeptide.

The invention also provides for isolated polypeptides comprising a biologically active polypeptide and an accessory polypeptide, wherein the accessory polypeptide is characterized in that: (i) is poly-serine, and (ii) it comprises ten or more amino acids. In a related embodiment, the isolated polypeptide (i) consists of two types of amino acids, the majority of which are serine, and (ii) it comprises ten or more amino acids.

In another embodiment, the accessory polypeptide consists of two types of amino acids, one of which is glycine (G) and the other type is selected from the group consisting of aspartic acid (D), glutamic acid (E), lysine (K), proline (P), Arginine (R), Serine (S), Threonine (T), alanine (A), histidine (H), asparagine (N), tyrosine (Y), leucine (L), valine (V), tryptophan (W), methionine (M), phenylalanine (F), isoleucine (I), and cysteine (C); and (ii) it comprises ten or more amino acid residues, of which 50% or less are glycine.

The invention also provides for isolated polypeptides comprising a biologically active polypeptide and an accessory polypeptide, wherein the accessory polypeptide is characterized in that: (i) it consists of two types of amino acids, one of which is serine (S) and the other type is selected from the group consisting of aspartic acid (D), glutamic acid (E), lysine (K), proline (P), Arginine (R), Glycine (G), Threonine (T), alanine (A), histidine (H), asparagine (N), tyrosine (Y), leucine (L), valine (V), tryptophan (W), methionine (M), phenylalanine (F), isoleucine (I), and cysteine (C); and (ii) it comprises ten or more amino acid residues, of which 50% or more are serine.

Alternatively, the invention describes an isolated polypeptide comprising a biologically active polypeptide and an accessory polypeptide, wherein the accessory polypeptide is characterized in that: (i) it comprises ten or more amino acids; (ii) it consists of two types of amino acids, wherein 50% or less of the total amino acids are selected from the group consisting of A, S, T, D, E, and H.

In yet another embodiment, the invention describes an isolated polypeptide comprising a biologically active polypeptide and an accessory polypeptide, wherein the accessory polypeptide is characterized in that: (i) it comprises ten or more amino acids; (ii) it consists of two types of amino acids, 50% or less of the total amino acids are selected from the group consisting of A, G, T, D, E, and H.

In some embodiments, an isolated polypeptide is provided comprising a biologically active polypeptide and an accessory polypeptide, wherein the accessory polypeptide is characterized in that: (i) it consists of two types of amino acids, one of which is selected from the group consisting of P, R, L, V, Y, W, M, F, I, K, and C; and (ii) it comprises ten or more amino acids.

In other embodiments, an isolated polypeptide is provided comprising a biologically active polypeptide and an accessory polypeptide, wherein the accessory polypeptide comprises at least 10 amino acids in length and consists of two different types of amino acids represented in equal numbers. Alternatively, the two different types of amino acids are represented in 1:2, 2:3, or 3:4 ratio. The accessory polypeptide may additionally comprise four or more repeating motifs, each of which comprises two to five hundred amino acids and is made of two different types of amino acids. The repeating motif may comprise more than 8 amino acids, and in some embodiments four or more of the repeating motifs are identical. The four or more repeating motifs may comprise different amino acid sequences. In a related embodiment, the accessory polypeptide comprises at least ten repeating motifs.

Yet other embodiments provide biologically active polypeptides modified with accessory polypeptides which substantially lack secondary structure. Alternatively, the apparent molecular weight of the isolated polypeptides is greater than that of a corresponding polypeptide lacking the accessory polypeptide. In a particular embodiment, the apparent molecular weight of the accessory polypeptide is at least 3 times greater than its actual molecular weight. In still other embodiments, the accessory polypeptide exhibits a two-fold longer serum half-life as compared to a corresponding polypeptide lacking the accessory polypeptide. The biologically active polypeptide and the accessory polypeptide may be linked via a peptide bond.

In some embodiments, the accessory polypeptide comprises an amino acid sequence (GGEGGS)n (SEQ ID NO: 5), wherein n is an integer of 3 or greater. In other embodiments, the accessory polypeptide comprises an amino acid sequence (GES)n, wherein G, E, and S can be in any order and n is an integer of 3 or greater. Alternatively, the accessory polypeptide comprises an amino acid sequence (GGSGGE)n, wherein G, E, and S can be in any order and n is an integer of 3 or greater. In yet another embodiment, the accessory polypeptide comprises an amino acid sequence (GGEGGEG-GES)n (SEQ ID NO: 6), wherein n is an integer of 1 or greater. In yet another embodiment, the accessory sequence comprises an amino acid sequence (GE)n, wherein G and E can be in any order.

In some embodiments, the accessory polypeptide comprises an amino acid sequence (S)n (SEQ ID NO: 7), wherein n is an integer of 10 or greater. In other embodiments, the accessory polypeptide comprises an amino acid sequence (SSSSSSE)n, wherein E and S can be in any order and n is an integer of 2 or greater In yet other embodiments, the accessory polypeptide comprises an amino acid sequence (SESSSESSE)n, wherein E and S can be in any order and n is an integer of 3 or greater. In some embodiments, the accessory polypeptide comprises an amino acid sequence (SSESSSSESSSE)n, wherein E and S can be in any order and n is an integer of 3 or greater. In other embodiments, the accessory polypeptide comprises an amino acid sequence (SSSESSSSSESSSSE)n, wherein E, and S can be in any order and n is an integer of 3 or greater. In still other embodiments, the accessory polypeptide comprises an amino acid sequence (SSSSESSSSSSESSSSSE)n, wherein E and S can be in any order and n is an integer of 3 or greater.

The present invention also provides a method of producing an isolated polypeptide, comprising: a). providing a polynucleotide sequence encoding the isolated polypeptide of any one of claims 1, 6, 7, 8, or 9; b) causing said polypeptide to be expressed in a host cell, thereby producing said polypeptide.

Additionally, a genetic vehicle comprising a nucleic acid sequence encoding the isolated polypeptides of the invention is provided. In another embodiment, a host cell is described expressing the subject polypeptides. Libraries of subject polypeptides are also envisioned. In a particular embodiment, libraries of polypeptides are displayed on phage particles.

INCORPORATION BY REFERENCE

All publications and patent applications mentioned in this specification are herein incorporated by reference to the same extent as if each individual-publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an illustrative representation of an accessory polypeptide modifying a biologically active protein.

FIGS. 2 and 3 show possible modules for inclusion in modified polypeptides of the invention: accessory polypeptide(s), biologically active polypeptide(s), optional depot module(s) and optional polymeric matrix or matrices.

FIG. 4 shows examples of various product configurations. Modules may be used several times in the same product, for example to increase affinity of the biologically active protein for its target, to increase half-life by extending the rPEG module, or to modify the properties of the depot formulation.

FIG. 5 presents a specific example of a tetrameric modified polypeptide comprising a depot module that allows for site-specific biotinylation. The addition of streptavidin induces the formation of highly stable, yet non-covalent, modified polypeptide tetramers. Multivalent polypeptides can also be created by combining multiple modules into a single protein chain or by chemically linking multiple protein chains containing a specific module.

FIG. 6 illustrates a lysine- or arginine-rich depot module (depicted as rectangles) which may be incorporated into the polymer matrix of an alginate microsphere. The matrix module is depicted as larger circles. The lysine- or arginine-rich depot will carry a net positive charge at physiological pH and this property can be exploited to bind the modified polypeptide to the negatively charged alginate polymer. Binding may occur in a multivalent fashion.

FIG. 7 illustrates a divalent cation chelating hydrogel (matrix module) exemplified by the divalent cation $Cu^{2+}$ bound to the polymer. The polyhistidine depot module (rectangular module) binds with high affinity to the $Cu^{2+}$ cations.

FIG. 8 depicts a protease sensitive multimeric modified polypeptide. The depot module (depicted by a rectangle) connects individual modified polypeptide units in an extended polymer. The depot module is designed such that it is specifically sensitive to serum proteases. Protease cleavage of the depot module releases individual active modified polypeptides.

FIG. 9 shows the design of the expression vector pCWO150. FIG. 9 discloses the "6× His-tag" and "H6" sequence as SEQ ID NO: 1.

FIG. 10 shows the design and construction of the accessory polypeptide rPEG(L288) fused to GFP. FIG. 10 discloses the "H6" sequence as SEQ ID NO: 1.

FIG. 11 shows the amino acid (SEQ ID NO: 485) and nucleotide sequence (SEQ ID NO: 484) of the rPEG_L288 polypeptide.

FIG. 12 shows the design of hGH-rPEG(L288) and GLP-1-rPEG(L288) constructs.

FIG. 13 shows examples biologically active proteins conjugated to accessory polypeptides (SEQ ID NOS 486-489, respectively, in order of appearance).

FIGS. 14 and 15 describe exemplary guidelines for sequence optimization of accessory polypeptides. FIG. 15 discloses SEQ ID NOS 490-498, respectively, in order or appearance.

FIG. 16 describes the construction of a vector comprising the rPEG_J288 accessory polypeptide sequence fused to GFP. FIG. 16 discloses the "116" sequences as SEQ ID NO: 1.

FIG. 17 shows the amino acid (SEQ ID NO: 500) and nucleotide sequence (SEQ ID NO: 499) of the rPEG_J288 polypeptide.

FIG. 18 shows the design of a stuffer vector suitable for use in the present invention. FIG. 18 discloses the amino acid sequences as SEQ ID NOS 502 and 503, respectively, the nucleotide sequence as SEQ ID NO: 501 and the "6× His-tag" as SEQ ID NO: 1.

FIG. 19 shows the purification of rPEG_J288-modified GFP.

FIG. 20 shows the determination of serum stability of rPEG_J288-modified GFP.

FIG. 21 shows the interaction of an accessory-modified polypeptide with a cellular target.

FIG. 22 illustrates the concept of crosslinked accessory polypeptides.

FIG. 23 describes examples of crosslinking components.

FIG. 24 lists several examples of crosslinked accessory polypeptides.

FIG. 25 shows an example wherein streptavidin is used as a linker.

FIG. 26 describes different modalities of constructing crosslinked accessory polypeptides.

FIG. 27 identifies illustrates several possible formats of crosslinked accessory polypeptides.

FIG. 28 describes accessory polypeptides additionally modified with binding domains or other groups FIG. 29 illustrates the concept of slow-release accessory polypeptides.

FIG. 30 shows universal accessory polypeptides. FIG. 30 discloses the "KKKKKK" sequences as SEQ ID NO: 504.

FIG. 32 illustrates various configurations of modified polypeptides comprising affinity tags, solubility tags and/or protease cleavage sites.

FIG. 33 illustrates improved expression levels of modified polypeptides using specific accessory polypeptides.

FIG. 34 illustrates shows activity of an accessory-modified hGH polypeptide relative to unmodified hGH.

FIG. 35 shows purification of accessory-modified polypeptides by anion exchange and size exclusion chromatography.

FIG. 36 shows pure product obtained by purification of rPEG-modified GFP as confirmed by SDS-PAGE.

FIG. 37 shows the purity of rPEG-linked GLP1 as ascertained by analytical size exclusion chromatography.

FIG. 38 shows the purity of rPEG_L288-GFP modified polypeptide as observed by analytical reverse-phase HPLC.

FIG. 39 Mass spectrometry of rPEG_J288-GFP

FIG. 40 demonstrates that little nonspecific binding is observed between modified polypeptides and serum proteins.

FIG. 41 describes the increase in apparent molecular weight observed upon linking a biologically active polypeptide to an accessory polypeptide.

FIG. 42 shows the stability of modified polypeptides in rat and human serum.

FIG. 43 illustrates a PK profile of rPEG_K288-GFP polypeptide in rat serum.

FIG. 44 describes shows the relative lack of immunogenicity of rPEG polypeptides as determined in animal experiments for rPEG_J288-GFP, rPEG_K288-GFP and rPEG_L288-GFP.

FIG. 45 illustrates the advantage of expressing biologically active polypeptides linked to accessory polypeptides.

FIG. 46 illustrates sustained release of accessory-modified polypeptides.

FIG. 47 shows the purity of rPEG_J288-GLP1 polypeptide as determined by size exclusion chromatography (multiple injections per run).

FIG. 48 shows the purity of rPEG_K288-GLP1 polypeptide as determined by size exclusion chromatography (multiple injections per run).

FIG. 49 describes the increase in apparent molecular weight observed upon linking a biologically active polypeptide (GLP1) to rPEG_J288, rPEG_K288, and rPEG_L288 accessory polypeptides.

FIG. 50 shows the products obtained through protease cleavage of a polypeptide comprising an affinity tag, an accessory polypeptide and hGH as a biologically active polypeptide (rPEG_K288-hGH). The protease removes the Tag, while leaving a final product which is hGH linked to the rPEG_K288 accessory polypeptide.

FIG. 51 shows the purity of rPEG_K288-hGH after protease cleavage and further purification.

FIG. 53a shows a scFv-Fc fusion protein: FIG. 53b shows a dAb-Fc fusion protein. FIG. 53c shows a scFv-scFv-Fc fusion protein, which is tetravalent.

FIG. 58: Structure of AFBTs. 58a: Monovalent AFBT; 58b: Structure of a bispecific AFBT FIG. 60a: Multivalent AFBT containing antibody fragments derived from two parent antibodies;

FIG. 60b: Structure of an AFBT comprising a diabody and a payload

FIG. 64: Construction, sequence, and expression of scFv-rPEG50 fusion proteins. 64a: Cartoon of the protein architecture (FIG. 64a discloses the "His6 tag" sequence as SEQ ID NO: 1); 64b: sequence (SEQ ID NO: 505) of an AFBT with specificity for Her-2; 64c: SDS/PAGE showing the expression of scFv-rPEG50 fusion proteins; 64d: sequence (SEQ ID NO: 506) of an AFBT with specificity for EGFR.

FIG. 65: Construction, sequence, and expression of a diabody-rPEG50 fusion proteins, aHer203-rPEG. 65a: Cartoon of the protein architecture (FIG. 65a discloses the "His6 tag" as SEQ ID NO: 1); 65b: protein sequence (SEQ ID NO: 507); 65c: SDS/PAGE demonstrating the expression of fusion protein in the cytosol of E. coli.

FIG. 69: Amino acid sequence (SEQ ID NO: 510) of GFP-rPEG50. The sequence of GFP is underlined.

FIG. 70: Pharmacokinetics of GFP-rPEG50 and Ex4-rPEG50 in cynomologos monkeys.

FIG. 71a: Amino acid sequence (SEQ ID NO: 511) of the CDB-Ex4-rPEG50 fusion protein. FIG. 71b: Illustration of the process used to liberate Ex4-rPEG50 from the fusion sequence shown in FIG. 14a.

FIG. 72: Immunogenicity of Ex4-rPEG50 in mice. FIG. 72a illustrates the time course of injections and blood sample analyses. FIG. 72b shows ELISA analyses of blood samples at 1:500 dilution. FIG. 72c shows ELISA analyses of blood samples at 1:12,500 dilution.

FIG. 74: Comparison of the interaction of repetitive and non-repetitive URPs with B cells. FIG. 74a shows a repetitive URP that is composed of multiple identical sequence repeats. Such a repetitive URP can form multivalent contacts with B cells that recognize the repeating sequence, which can trigger B cell proliferation. FIG. 74b shows a non-repetitive URP that is composed of multiple different subsequences. Each subsequence can be recognized by a particular subset of B-cells with cognate specificity. However, an individual molecule of a non-repetitive URP can only form one or few interactions with any particular B cell, which is unlikely to trigger proliferation.

FIG. 75: Algorithm to assess the repetitivness of an amino acid sequence.

FIG. 78: Amino acid sequences (SEQ ID NOS 15, 18, 16, 19, 17, 20, 11, 13, 12 and 14, respectively, in order of appearance) that were used to construct rPEG_Y. The figure also indicates the relative concentrations of oligonucleotides that were used to construct the segment libraries.

FIG. 79: Assembly of URP segments from synthetic oligonucleotides.

FIG. 80: Examples of URP_Y144 sequences (SEQ ID NOS 512-521, respectively, in order or appearance).

FIG. 81: Amino acid sequence (SEQ ID NO: 522) encoded by plasmid pCW0279. The open reading frame encodes a fusion protein of Flag-URP_Y576-GFP. The amino acid sequence of URP_Y576 is underlined.

FIG. 84*a* A Diabody is formed when the single chain linker between the VH and VL domain is shorter than about 10-20 AA, preventing the formation of a single chain Fv fragment. A diabody has two protein chains and can have an rPEG at one or both C-terminal ends, and/or at one or both N-terminal ends. The diabody has two binding sites, of which zero, one or two may bind to a pharmaceutical target, or to a halflife target (ie HSA, IgG, Red Blood Cells, Collagen, etc) or to no target.

FIG. 84*b* The diabody may contain zero, one or more drug modules located at the N-terminal or C-terminal end of zero, one or both protein chains.

FIG. 85*a* shows a single chain Fv fragment, to which a drug module (like IFNa, hGH, etc) can be fused at one or both of the N- and/or C-terminal ends. The scFv has one binding site, which may or may not bind to a pharmaceutical target, or to a halflife target (ie HSA (see FIG. 85*b*), IgG, Red Blood Cells, etc)

FIG. 86 shows the use of rPEG to associate two proteins that belong to the same complex. The affinity between such proteins is often insufficient to keep them associated, but the addition of rPEG stabilizes their interaction and reduces their tendency to form polymers.

FIG. 87 shows a Fab fragment binding to a cell-surface target; the H chain may be fused to Fc (like in whole antibodies) or to a wide variety of other proteins, domains and peptides. Extension of the length of the natural linkers from the usual 2-6-amino acids to 4, 5, 6, 7, 8, 9, 10, 11, 1, 13, 14, 15, 16, 17, 18, 19, 20, 21, 22, 24, 26, 28, 30, 35, 40, 45, 50, 60, 70, 80, 100 or more amino acids, between the VH and the CH domains, and between the VL and the CL domains, increases the ability of one Fab to crosslink to another Fab by domain swapping, thereby forming a binding complex with higher valency, resulting in higher apparent affinity (avidity). The linker may be rPEG or a different composition. This 'Extended Linker' format allows binding with increased affinity specifically at sites with a higher density of target, such as (partially) tumor-specific antigen on tumor cells.

FIG. 90*a* shows an antibody Fc fragment, with a hinge region, (optionally) fused to a drug module (e.g. IFNa, hGH, etc.) on one end and (optionally) fused to rPEG on the other end. The sequence between CH2 and CH3 mediates binding to FcRn, the neonatal Fc receptor, unless that function is removed by mutation. FIG. 90*b* shows a similar construct but without the hinge region.

FIG. 91*a* shows a protein construct comprising a paired pair of CH3 domains; zero, one or both of these chains may be fused to rPEG on the N-terminal and/or C-terminal end, and to zero, one or more drug modules at the other end. The FcRn binding sequence can either be retained or deleted; retention should yield a longer serum halflife.

FIG. 91*b* shows a similar protein, but CH2 was fully removed so that the binding of the Fc to the FcRn receptor is no longer functional, reducing halflife.

FIG. 92*a* shows a protein that is a full Fc, including a hinge, CH2 and CH3 domains, fused at the c-terminus to an rPEG, with the drug/pharmacophore located at the C-terminus.

FIG. 92*b* shows a full Fc, but without a hinge fused at the c-terminus to an rPEG, with the drug/pharmacophore located at the C-terminus; these molecules can chain swap, potentially resulting in hetero-dimers.

FIG. 93*a* shows a partial Fc, without hinge and with a CH2 that is truncated but retains FcRn binding and with the drug/pharmacophore located at the C-terminus.

FIG. 93*b* shows a partial Fc, without hinge and CH2, but retaining CH3 and with the drug/pharmacophore located at the C-terminus. This does not bind FcRn but can dimerize via the CH3 domain.

As shown in FIG. 94, some pro-drug formats do not need a cleavage or other activation site. A single protein chain can contain two (or more) drug modules separated by rPEG; these modules can be the same (of a single type) or of two or more different types. All drug modules are receptor or all are ligand. This rPEG containing product is complexed with a second, complementary protein to form a receptor-ligand-receptor interaction. In this format the ligand is likely to be dimeric or multimeric, but can also be monomeric, especially if the two drug modules are different. Both modules bind to a third protein. X and Y can be the same or different, and X and Y can be the drug module or bind to the drug module. In each case in FIG. 94, X and Y (and rPEG) comprise one protein chain, and the molecule they bind to is a separate molecule, typically protein or small molecule. It is possible to have more than two binding proteins combined in a single protein chain. The idea is that the complex of a large rPEG-containing protein and a non-rPEG containing protein is inactive when injected, but over 2-24 hours the smaller, non-rPEG-containing protein leaves the complex and is excreted via the kidney, thereby activating the drug module(s). The benefit of this format is that is reduces or removes the initial spike in drug concentration and the associated safety issues, and that the complex minimizes the receptor-mediated clearance while it is complexed, thereby extending the serum secretion halflife.

FIG. 95 shows an rPEGs flanked on both sides by a VEGF-receptors. Since VEGF is dimeric, this can be the same receptor on both sides of the rPEG, or a different receptor (preferably VEGF-R1 and VEGF-R2, but VEGFR3 can also be used.

FIG. 96 shows products that are either manufactured (cleaved before injection) or administered as an inactive pro-drug (cleaved after injection, in the blood). The inactivation of the drug is mediated by a binding protein that is linked to the drug by rPEG, so that all three modules are manufactured as a single protein chain. If the drug is a receptor, then the binding protein is a ligand (peptide or protein) of that receptor; if the drug is an antibody fragment, then the binding site is a peptide or protein ligand. In these examples, the drug is activated by protease cleavage of a site between the two binding domains, called X and Y. If Protein Y is the active product, then Y must retain the rPEG and the protease cleavage site must be (between X and Y, but) close to X. If Protein X is the active product, then X must retain the rPEG and the cleavage site must be close to Y. There can be one or multiple cleavage sites, as shown by the blue crossbars. The drug module can be a receptor, a ligand, one or more Ig domains, an antibody fragment, a peptide, a microprotein, an epitope for an antibody. The protein that binds to the drug module can be a binding protein, a receptor, a ligand, one or more Ig domains, an antibody fragment, a peptide, a microprotein, an epitope for an antibody. FIG. 96 discloses the "SVILF" sequence as SEQ ID NO: 524 and the "RARADADA" sequence as SEQ ID NO: 9.

FIG. 97 shows how an inactive pro-drug can be created by adding a binding peptide to a drug module. The peptide must neutralize the target binding capacity of the drug and the peptide is gradually cleared from the blood at a higher rate than the rPEG-containing drug. Such a peptide can be natural but more typically it would be obtained by phage panning of random peptide libraries against the drug module. The peptide would preferably be made synthetically, but it can be recombinant.

FIG. 98 shows a single-chain protein drug containing multiple bio-active peptides, which can be at the same end of rPEG or at opposite ends of rPEG. These peptides can have the same activity or different activities. The purpose of having multiple peptides in a single chain is to increase their effective potency through binding avidity, without complicating manufacturing.

FIG. 102a shows an alternative format for a Pro-drug containing an Fc fragment. The format is similar as described in FIG. 101, with the addition (at the N-terminus) of an inhibitory sequence (in blue) that binds to and inhibits the drug sequence (in red). As before, the drug is separated from the inhibitory sequence by a cleavage site. The N-terminal inhibitory binding sequence is followed by a cleavage site, which is followed by the drug sequence (in red). Before cleavage, the drug is bound to the inhibitory sequence and thus inactive (pro-drug). After cleavage, the inhibitory binding sequence (blue) is gradually released and cleared, gradually increasing the amount of time that the drug (red) is active.

FIG. 102b. shows an alternative Pro-drug format containing an Fc fragment. The formats is similar to the format described in FIG. 101, again with the addition of an inhibitory binding sequence (peptide or domain, shown in red, typically positioned in or near the rPEG) which is separated from the drug (shown in blue) by a cleavage site. Before cleavage, the drug is bound to the inhibitory sequence and thus inactive (pro-drug). After cleavage, the inhibitory binding sequence (blue) is gradually released and cleared, gradually increasing the amount of time that the drug (blue) is active.

DETAILED DESCRIPTION OF THE INVENTION

Figure 31A:
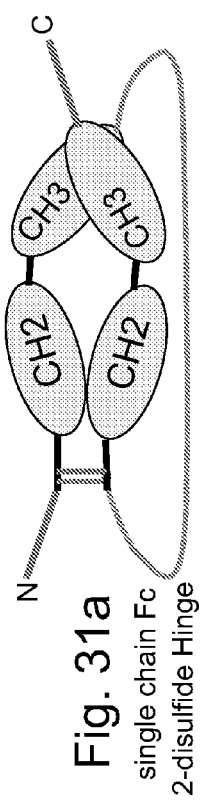
FIG. 31 shows an antibody Fc fragment from human IgG1, but this could also be from IgG2, IgG3, IgG4, IgA, IgD or IgE. This Fc can have a native hinge from IgG1, IgG2, IgG3, IgG4, IgA, IgD or IgE. There is natural diversity in the number of hinge disulfides, but this can also be created by mutation, deletion, or truncation of the hinge, especially the cysteine residues. The variants that are useful have either three disulfides (not shown), two disulfides, one disulfide (choice of first one or second natural one of IgG1) or no disulfides.
Figure 31B:
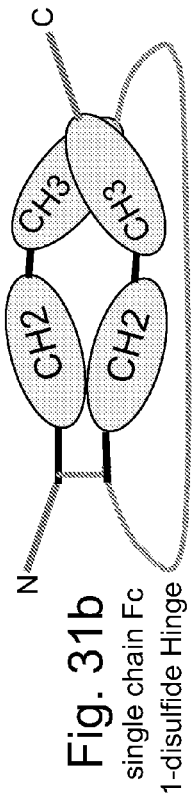
Figure 31C:
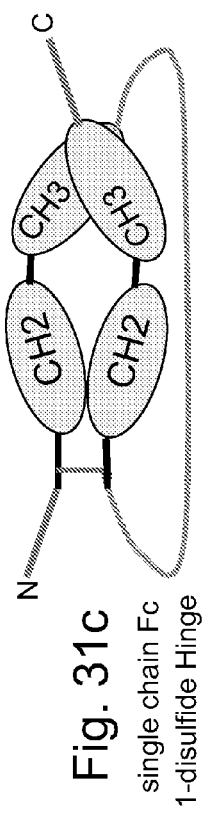
Figure 31D:
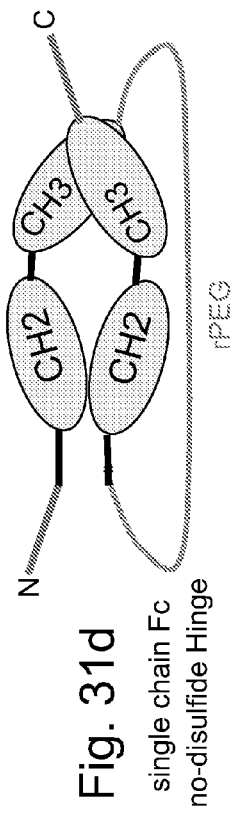

The present invention makes use of the unexpected discovery that biologically active polypeptides modified with accessory polypeptides may have the property of remaining soluble in the cytoplasm and folding into their active form, in conditions in which a biologically active polypeptide without such a modification would aggregate and form inclusion bodies. The methods of the invention may be useful for, among other applications, high throughput screening of proteins in the design phase, the manufacturing of proteins that currently require periplasmic expression, and for manufacturing of proteins that are difficult to refold from aggregates such as including inclusion bodies. The invention discloses methods of designing accessory protein sequences, recombinant DNA molecules encoding modified polypeptide, expression vectors for such polypeptides, host cells for expression of such polypeptides and purification processes. For example, the fusion of a long hydrophilic polypeptide sequence to proteins, which may include peptides, proteins, antibodies, and vaccines, and may be eukaryotic or mammalian proteins, results in a soluble fusion protein showing improved folding in the cytoplasm in active form.

Accessory polypeptides of the invention may be linked to pharmaceutical proteins including GCSF, growth hormone, interferon alpha and to antibody fragments. These four proteins or classes of proteins typically form inclusion bodies when expressed in the cytoplasm of E. coli. However, when linked to a long hydrophilic accessory polypeptide sequence, the folding properties of the biologically active polypeptides may be greatly improved, leading to a greatly increased fraction able to fold correctly into active protein within the cell, as opposed to immediate and irreversible aggregation into inclusion bodies which typically occurs for eukaryotic proteins in the absence of an accessory protein. Accessory polypeptides may additionally comprise affinity tags for protein purification by ion exchange, alone or in combination with other known purification tags, such as chitin binding domain, cellulose binding domain, MBP, GST or His-tags.

This and other aspects of the invention will be described in further detail below.

General Techniques:

The practice of the present invention employs, unless otherwise indicated, conventional techniques of immunology, biochemistry, chemistry; molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

DEFINITIONS

As used in the specification and claims, the singular form "a", "an" and "the" include plural references unless the context clearly dictates otherwise. For example, the term "a cell" includes a plurality of cells, including mixtures thereof.

The terms "polypeptide", "peptide", "amino acid sequence" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation; or any other manipulation, such as conjugation with a labeling component. As used herein the term "amino acid" refers to either natural and/or unnatural or synthetic amino acids, including but not limited to glycine and both the D or L optical isomers, and amino acid analogs and peptidomimetics. Standard single or three letter codes are used to designate amino acids.

The term "biologically active polypeptide" refers to a polypeptide of any length that exhibits binding specificity to a given target or targets, which can be a therapeutic target and/or an accessory target, such as for cell-, tissue- or organ targeting. Alternatively, or in addition, it refers to a polypeptide that exhibits a desired biological characteristic when used in vitro or in vivo. By way of example, biologically active polypeptides include functional therapeutics or in vivo diagnostic proteins that bind to therapeutic or diagnostic targets. The term "biologically active polypeptide" and "Binding Module" or "BM" are used interchangeably herein. Biologically active polypeptides can be, for example, and without limitation, linear or cyclic peptides, cysteine-constrained peptides, microproteins, scaffold proteins like fibronectin, ankyrins, crystalline, streptavidin, antibody fragments, domain antibodies, peptidic hormones, growth factors, cytokines, or any type of protein domain, human or non-human, natural or non-natural, and they may be based on a natural scaffold or not based on a natural scaffold (i.e. engineered or selected), or based on combinations or fragments of any of the above. Optionally, the biologically active polypeptide can be engineered by adding, removing or replacing one or multiple amino acids in order to enhance their binding properties, their stability, or other desired properties. Binding modules can be obtained from natural proteins, by design or by genetic package display, including phage display, cellular display, ribosomal display or other display methods, for example. Binding modules may bind to the same copy of the same target, which results in avidity, or they may bind to different copies of the same target (which can result in avidity if these copies are somehow connected or linked, such as by a cell membrane), or they may bind to two unrelated targets (which yields avidity if these targets are somehow linked, such as by a membrane). Binding modules can be identified by screening or otherwise analyzing random libraries of peptides or proteins.

"Recombinant PEG", "rPEG" or "rPEG polypeptides" or "recombinant PK Enhancing Group" are general terms encompassing a class of polypeptides that can be used to modify biologically active polypeptides, whereby the modification results in a desirable change in biological properties such as serum half-life or in vivo clearance. In general, rPEG polypeptides lack binding specificity to the same given target bound by the biologically active polypeptide. In some aspects, rPEG is a functional analog of PEG that, may mimic some, but not necessarily all, well-known properties of PEG. Such properties, described in more detail below, include enhanced ability to increase hydrodynamic radius, increased resistance to proteases, decreased immunogenicity and decreased specific activity. While rPEG molecules may share broad structural and functional features with PEG, such as linearity or lack of tertiary structure, strict chemical similarity with PEG is not a necessary feature of rPEG.

"Accessory polypeptide" or "accessory protein" refers to a polypeptide which, when used in conjunction with a biologically active polypeptide, e.g. by way of linking to the biologically active polypeptide, renders a desirable change in biological properties of the entire linked polypeptide. Non-limiting examples of accessory polypeptides include rPEGs and any other polypeptides capable of increasing hydrodynamic radius, extending serum half-life, and/or modifying in vivo clearance rate. When desired, an accessory polypeptide causes a small increase in predicated molecular weight, but a much larger increase in apparent molecular weight. Although the different names emphasize different features, they refer to the same module and can be used interchangeably.

The terms "modified polypeptide" and "accessory-modified polypeptide" are used interchangeably to refer to biologically active polypeptides which have been modified with the accessory polypeptides of the invention. These terms may also refer to slow release or other types or formulations comprising biologically active polypeptides modified with accessory polypeptides according to the invention.

A "repetitive sequence" or "repetitive motif" are used interchangeably herein and refer to an amino acid sequence that can be described as an oligomer of repeating peptide sequences ("repeats"), forming direct repeats, or inverted repeats or alternating repeats of multiple sequence motifs. These repeating oligomer sequences can be identical or homologous to each other, but there can also be multiple repeated motifs. Repetitive sequences are characterized by a very low information content. A repetitive sequence is not a required feature of an accessory polypeptide and in some cases a non-repetitive sequence will in fact be preferred.

Amino acids can be characterized based on their hydrophobicity. A number of scales have been developed. An example is a scale developed by Levitt, M et al. (see Levitt, M (1976) J Mol Biol 104, 59, #3233, which is listed in Hopp, T P, et al. (1981) Proc Natl Acad Sci USA 78, 3824, #3232). Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

As used herein, the term "cell surface proteins" refers to the plasma membrane components of a cell. It encompasses integral and peripheral membrane proteins, glycoproteins, polysaccharides and lipids that constitute the plasma membrane. An integral membrane protein is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface via covalent or noncovalent interaction directly or indirectly with other membrane components.

The terms "membrane", "cytosolic", "nuclear" and "secreted" as applied to cellular-proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

"Non-naturally occurring" as applied to a protein means that the protein contains at least one amino acid that is different from the corresponding wildtype or native protein. Non-natural sequences can be determined by performing BLAST search using, e.g., the lowest smallest sum probability where the comparison window is the length of the sequence of interest (the queried) and when compared to the non-redundant ("nr") database of Genbank using BLAST 2.0. The BLAST 2.0 algorithm, which is described in Altschul et al. (1990) J. Mol. Biol. 215:403-410, respectively. Software for performing BLAST analyses is publicly available through the National Center for Biotechnology Information.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

As used herein, the term "isolated" means separated from constituents, cellular and otherwise, with which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. In general, a polypeptide made by recombinant means and expressed in a host cell is considered to be "isolated".

"Conjugated", "linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature).

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

"Heterologous" means derived from a genotypically distinct entity from the rest of the entity to which it is being compared. For example, a glycine rich sequence removed from its native coding sequence and operatively linked to a coding sequence other than the native sequence is a heterologous glycine rich sequence. The term "heterologous" as applied to a polynucleotide, a polypeptide, means that the polynucleotide or polypeptide is derived from a genotypically distinct entity from that of the rest of the entity to which it is being compared.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that can potentially be expressed in a host cell.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

The "target" as used in the context of accessory polypeptides is a biochemical molecule or structure to which the biologically active polypeptide can bind and where the binding event results in a desired biological activity. The target can be a protein ligand or receptor that is inhibited, activated or otherwise acted upon by the t protein. Examples of targets are hormones, cytokines, antibodies or antibody fragments, cell surface receptors, kinases, growth factors and other biochemical structures with biological activity.

"Serum degradation resistance"—Proteins can be eliminated by degradation in the blood, which typically involves proteases in the serum or plasma. The serum degradation resistance is measured by combining the protein with human (or mouse, rat, monkey, as appropriate) serum or plasma, typically for a range of days (ie 0.25, 0.5, 1, 2, 4, 8, 16 days) at 37 C. The samples for these timepoints are then run on a Western assay and the protein is detected with an antibody. The antibody can be to a tag in the protein. If the protein shows a single band on the western, where the protein's size is identical to that of the injected protein, then no degradation has occurred. The timepoint where 50% of the protein is degraded, as judged by Western Blots or equivalent techniques, is the serum degradation half-life or "serum half-life" of the protein.

"Apparent Molecular Weight Factor" or "Apparent Molecular Weight" are related terms referring to a measure of the relative increase or decrease in apparent molecular weight exhibited by a particular amino acid sequence. The Apparent Molecular Weight is determined using a size exclusion column that can be calibrated using globular protein standards and is measured in "apparent kD" units. The Apparent Molecular Weight Factor is measured as the ratio between the apparent molecular weight, as determined on a size exclusion column calibrated with globular proteins and the actual molecular weight, (i.e., predicted by adding based on amino acid composition the calculated molecular weight of each type of amino acid in the amino acid composition). For example, a 20 kD poly-Glycine sequence has an apparent molecular weight of 200 kD by size exclusion chromatography, corresponding to an Apparent Molecular Weight Factor of 10×. The 'Specific Hydrodynamic Radius' is the hydrodynamic radius per unit molecular weight (kD), is a measure for the performance of a halflife extender, which is measured as the serum secretion halflife per unit mass (hours per kD). Both of these measurements are correlated with the 'Apparent Molecular Weight Factor', which is a more intuitive measure.

The "hydrodynamic radius" of a protein affects its rate of diffusion in aqueous solution as well as its ability to migrate in gels of macromolecules. The hydrodynamic radius of a protein is determined by its molecular weight as well as by its structure, including shape and compactness. Most proteins have globular structures, which is the most compact three-dimensional structure a protein can have with the smallest hydrodynamic radius. Some proteins adopt a random and open, unstructured, or 'linear' conformation and as a result have a much larger hydrodynamic radius compared to typical globular proteins of similar molecular weight.

"Physiological conditions" refer to a set of conditions including temperature, salt concentration, pH that mimic those conditions of a living subject. A host of physiologically relevant conditions for use in in vitro assays have been established. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al. (1989) supra and hence is not detailed herein. Physiologically relevant temperature ranges from about 25° C. to about 38° C., and preferably from about 30° C. to about 37° C.

A "reactive group" is a chemical structure that can be coupled to a second reactive group. Examples for reactive groups are amino groups, carboxyl groups, sulfhydryl groups, hydroxyl groups, aldehyde groups, azide groups. Some reactive groups can be activated to facilitate coupling with a second reactive group. Examples for activation are the reaction of a carboxyl group with carbodiimide, the conversion of a carboxyl group into an activated ester, or the conversion of a carboxyl group into an azide function.

A "crosslinking component" includes a chemical structure that comprises one or more reactive groups. These reactive groups can be identical in their chemical structure allowing the direct construction of cross-linked accessory polypeptides. Cross-linking components can contain reactive groups that have been blocked by protecting groups. This allows one to conjugate several different non-cross-linking components to one cross-linking component in controlled consecutive reactions. Cross-linking components can contain multiple reactive groups that differ in their structure and that can be selectively conjugated with different non-cross-linking components. Proteins that contain multiple high-affinity binding sites can also serve as cross-linking agents. Examples are streptavidin, which can bind up to four molecules of a biotinylated non-cross-linking component. Branched multifunctional polyethylene glycol (PEG) molecules can serve as cross-linking components. A variety of reagents with two to eight functional groups and various lengths of PEG as well as various reactive groups are commercially available. Suppliers include NOF America Corporation and SunBio.

"Non-crosslinking components" include chemical structures that comprise reactive groups which allow conjugation to a cross-linking component. Non-cross-linking components can contain a variety of modules, including one or more biologically active polypeptides and/or one or more accessory polypeptides. In addition, non-crosslinking components can contain affinity tags that facilitate purification and/or detection, such as Flag-tag, E-tag, Myc-tag, HA-tag, His6-tag (SEQ ID NO: 1), Green Fluorescent protein, etc.

A "crosslinked rPEG polypeptide", "crosslinked accessory polypeptide", "crosslinked rPEG", "CL-rPEG polypeptide", "CL-rPEG" are terms referring to conjugates of one or more non-crosslinking components with a crosslinking component.

"Controlled release agent", "slow release agent", "depot formulation" or "sustained release agent" are used interchangeably to refer to an agent capable of extending the duration of release of a modified polypeptide of the invention relative to the duration of release when the modified polypeptide is administered in the absence of agent. Different embodiments of the present invention may have different release rates, resulting in different therapeutic amounts.

"vL domain" refers to the variable domain of the light chain of an antibody.

"vH domain" refers to the variable domain of the heavy chain of an antibody.

A "variable fragment" (Fv) refers to a portion of an antibody which comprises two non-covalently associated VL and VH domains.

A "single chain variable fragment" (scFv) refers to a portion of an antibody which comprises one vH linked via a non-natural peptide linker to one vL domain, as a single chain. scFvs can have the structure vH-linker-vL or vL-linker-vH where the linker can be any peptide sequence comprising various numbers of amino acids. A scFv preferentially occurs under physiological conditions as a monomeric structure which requires a peptide linker of preferably more than 12 amino acids.

Disulfide-stabilized Fv fragments of antibodies (dFv) refer to molecules in which the $V_H$-$V_L$ heterodimer is stabilized by an interchain disulfide bond engineered between structurally conserved framework positions distant from complementarity-determining regions (CDRs). This method of stabilization is applicable for the stabilization of many antibody Fvs.

A "variable domain" refers to the domain that forms the antigen binding site of an antibody. Variable domains can be vH or vL; Differences, between the variable domains, are located on three loops known as hypervariable regions (HV-1, HV-2 and HV-3) or CDR1, CDR2 and CDR3. CDRs are supported within the variable domains by conserved framework regions.

A "domain antibody" (dAb) refers to a portion of an antibody that is capable of binding the target as a monomer. Domain antibodies correspond to the variable regions of either the heavy (VH) or light (VL) chains of antibodies. dAbs do not generally require a second variable domain (vH or vL) for target binding. dAbs can be generated by phage display or other in vitro methods. Alternatively, dAb domain can be obtained from immunized camelids or sharks or other species that generate antibodies that lack a light chain.

A "diabody" refers to a recombinant antibody that has two Fv heads, each consisting of a $V_H$ domain from one polypeptide paired with the VI domain from another polypeptide. A diabody typically contains two vH-vL (or vL-vH) chains. Diabody can be constructed by joining the vL and vH domains of an antibody by a peptide linker. The peptide linker lengths comprise various numbers of amino acids, preferably between 2 and 12 amino acids. A diabody can be monospecific or bispecific.

A "triabody" refers to a recombinant antibody that has three Fv heads, each consisting of a $V_H$ domain from one polypeptide paired with the VL domain from a neighboring polypeptide. A triabody contains three vH-vL (or vL-vH) chains. Triabody can be constructed by joining the vL and vH domains of an antibody by a peptide linker. The peptide linker lengths comprise various numbers of amino acids, preferably between 0 and 2 amino acids. A triabody can be monospecific, bispecific or trispecific.

A "tetrabody" comprises four vH-vL (or vL-vH) chains. Tetrabodies can be constructed by joining the vL and vH domains of an antibody by a peptide linker. The peptide linker lengths comprise various numbers of amino acids, preferably between 0 and 2 amino acids. Tetrabodies can be obtained by truncating various numbers of amino acids, preferably between 1 to 10 amino acids, from the joined ends of the vL and vH domains.

A "Fab fragment" refers to a region on an antibody which binds to antigens. A Fab fragment is composed of one constant and one variable domain of each of the heavy and the light chain. These domains shape the paratope—the antigen binding site—at the amino terminal end of the monomer. The two variable domains bind the epitope on their specific antigens. A Fab fragment can be linked by a disulfide bond at the C-terminus. Fab fragments can be generated in vitro. The enzyme papain can be used to cleave an immunoglobulin monomer into two Fab fragments and an Fc fragment. The enzyme pepsin cleaves below the hinge region, so a F(ab')2 fragment and a Fc fragment is formed. The variable regions of the heavy and light chains can be fused together to form a single chain variable fragment (scFv), which retains the original specificity of the parent immunoglobulin The term "antibody fragment" is used herein to include all of the fragments described in the present invention including any antigen binding unit as defined in details below, such as dAb, Fv, Fab, and Fc in any form. Antibody fragments can comprise additional domains of an antibody. An antibody fragment also encompasses a complete or full antibody.

The term "parent antibody" is used herein to refer to the antibody upon which the construction of an antibody fragment is based.

An "antibody fragment based therapeutic" (AFBT) refers to any therapeutic agent or pharmaceutical composition that is based on an antibody fragment as described herein. AFBTs can comprise multiple antibody fragments that can be derived from multiple different parent antibodies. Multispecific AFBTs may comprise multiple antibody fragments with specificity against multiple different epitopes. These epitopes can be part of the same target antigen or on multiple different target antigens. Bispecific AFBTs may comprise binding sites (generally two or more, but may be one) with two different binding specificities.

The terms "antigen", "target antigen" or "immunogen" are used interchangeably herein to refer to the structure or binding determinant that an antibody fragment or an antibody fragment-based therapeutic binds to or has specificity against.

The terms "domain reassortment" and "domain swapping" are used interchangeably herein to refer to a process that changes the valency of an antibody fragment or an antibody fragment based therapeutic. For example, single chain variable fragments (scFv) can reassort to form dimers, trimers etc, as well as diabodies, triabodies, tetrabodies, and the like. Fabs can exchange whole chains with other Fabs or even whole antibodies, potentially yielding mismatched chains that result in loss of one or both binding activities. The formation of light chain dimers, called Bence-Jones Protein, is another example. Another example of reassortment is heavy chain reassortment between IgG4 antibodies, which do not have a disulfide-bonded hinge that prevents such exchange, which can lead to bispecific IgG4 antibodies. The rate of domain reassortment is dependent on the reaction conditions such as salt concentration, pH, temperature, and the presence of target antigen.

The term "payload" as used herein refers to a protein or peptide sequence that has biological or therapeutic activity, equivalent to the pharmacophore of small molecules. Examples of payloads include, but are not limited to, cytokines, enzymes and growth factors. Payloads can comprise genetically fused or chemically conjugated moieties. Examples for such chemically conjugated moieties include, but are not limited to, chemotherapeutic agents, antiviral compounds, or contrast agents. These conjugated moieties can be joined to the rest of the AFBT via a linker which may be cleavable or non-cleavable.

"Collagen binding domain" (CBD) refers to a protein domain that binds to or has specificity against collagen. CBDs can be specific for any particular types of collagen such as collagen I. Alternatively, CBDs may bind to a variety of collagen types. An example is fibronectin in which four protein domains are sufficient for collagen binding.

The term "repetitiveness" used in the context of a polypeptide, for example, an accessory polypeptide PEG, refers to the degree of internal homology in a peptide sequence. A repetitive sequence may contain multiple identical or homologos copies of an amino acid sequence. Repetitiveness can be measured by analyzing the frequency of identical subsequences. For instance, a polypeptide sequence of interest may be divided into n-mer sub-sequences and the number of identical subsequences can be counted. Highly repetitive sequences contain a large fraction of identical subsequences.

"Total charge density" as used herein is calculated by adding the number of negatively charged amino acids with the number of positively charged amino acids, and dividing the sum by the total number of amino acids in a polypeptide. For example: hIgG1 Fc sequence: (MDKTHTCPPCPAPELLG-GPSVFLFPPKPKDTLMISRTPEVTCV-VVDVSHEDPEVK FNWYVDGVEVHNAKTKPRE-EQYNSTYRVVSVLTVLHQDWLNGKEYKCKVSNK ALPAPIEK-TISKAKGQPREPQVYTLPPSRDELTKN-QVSLTCLVKGFYPSDIAVEWE SNGQPENNYKTIPPV-LDSDGSFFLYSKLTVDKSRWQQGNVFSCSVMHEAL HNHY TQKSLSL (SEQ ID NO: 10)) Number of negatively charged residues: 24; Number of positively charged residues: 22; Total number of residues: 224; Total charge density of Fc alone: (22+24)/224=46/224=20.5%

"Net charge density" as used herein is calculated by subtracting the number of positively charged amino acids from the number of negatively charged amino acids, and dividing the difference by the total number of amino acids in a polypeptide. For example: hIgG1 Fc sequence: (MDKTH-TCPPCPAPELLGGPSVFLFPPKP-KDTLMISRTPEVTCVVVDVSHEDPEVK FNW-YVDGVEVHNAKTKPREEQYNSTYRVVS VLTVLHQDWLNGKEYKCKVSNK ALPAPIEK-TISKAKGQPREPQVYTLPPSRDELTKN-QVSLTCLVKGFYPSDIAVEWE SNGQPENNYKTIPPV-LDSDGSFPLYSKLTVDKSRWQQGNVFSCSVMHEAL HNHY TQKSLSL (SEQ ID NO: 10)) Number of negatively charged residues: 24; Number of positively charged residues: 22; Total number of residues: 224; Net charge density of Fc alone: (24-22)/224=2/224=0.9%.

"Predicted solubility" as used herein is calculated by adding the net charge of folded protein to the total charge of an unstructured protein (e.g. rPEG), and dividing the sum by the total number of amino acids in the protein. For example, the predicted solubility of Fc-rPEG50 is (−2+192)/(224+576) =190/800=23.75%

Design of Accessory Polypeptides for Improving Solubility During Expression of Biologically Active Polypeptides.

Expression of soluble modified biologically active polypeptides may be optimized by modifying the net charge density of the modified polypeptide. In some cases, the net charge density is above +0.1 or below −0.1 charges/residue. In other cases, the charge density is above +0.2 or below −0.2 charges per residue. Charge density may be controlled by modifying the content of charged amino acids such as arginine, lysine, glutamic acid and aspartic acid within accessory polypeptides linked to the biologically active polypeptide. If desired, the accessory polypeptide may be composed exclusively of a short stretch of charged residues. Alternatively, the accessory polypeptide may comprise charged residues separated by other residues such as serine or glycine, which may lead to better expression or purification behavior. Higher expression may be obtained. Use of serine may lead to higher expression levels.

The net charge that is required for the accessory protein to make a fusion protein soluble and fold in the cytoplasm depends on the biologically active polypeptide, specifically its size and net charge. The net charge of the modified polypeptide may be positive or negative. In some applications, accessory polypeptide sequences rich in negative amino acids such as glutamic acid or aspartic acid may be desirable. In other applications, accessory polypeptide sequences rich in positive amino acids such as lysine or arginine may be preferred. The use of both positively and negatively charged amino acids may lead to charge neutralization, which could potentially neutralize the advantage of the invention. For example, accessory proteins of 288 amino acids with 16%, 25% or 33% negatively charged residues may provide up to 96 total charges, which is sufficient to achieve a charge density of 0.1 for a neutral fusion protein of up to 960 amino acids, or a non-fusion protein of 672 amino acids. In one specific example, an accessory polypeptide comprising 33% glutamic acid residues might be used to make even very large and difficult to express proteins soluble.

To impart solubility on the binding protein, the net positive or negative charge of the accessory polypeptide may be greater than 5, 10, 15 or 20 or even greater than 30, 40, 50, 60, 70, 80, 90 or 100. Charges can be concentrated in a short sequence of 5, 10, 15, 20, 25, 30, 40, 50 amino acids, or can be spaced out over a longer sequence of 60, 80, 100, 150, 200, 250, 300, 400, or 500 or more amino acids. The sequence of a negative accessory polypeptide may contain over 5, 10, 15, 25, 30, 40, 50, 60, 70, 80, 90 or 100 percent of glutamic or aspartic acid, while a positive accessory polypeptide may contain over 5, 10, 15, 20, 25, 30, 40, 50, 60, 70, 80, 90 or 100 percent of arginine or lysine. Non-charged residues may be used such as the relatively hydrophilic residues Serine and Glycine.

Additional Considerations in the Design of Accessory Polypeptides:

One aspect of the present invention is the design of accessory polypeptides, e.g., rPEG accessory polypeptides and the like for the modification of biologically active polypeptides (FIG. 1). The accessory polypeptides are particularly useful for generating recombinant proteins of therapeutic and/or diagnostic value.

A variety of accessory polypeptide sequences can be designed and these may be rich in glycine and/or serine, as well as other amino acids such as glutamate, aspartate, alanine or proline. Accessory polypeptide sequences may be rich in hydrophilic amino acids and contain a low percentage of hydrophobic or aromatic amino acids. Accessory polypeptide sequences can be designed to have at least 30, 40, 50, 60, 70, 80, 90 or 100% glycine and/or serine residues. In some cases, accessory polypeptide sequences contain at least 50, 55, 60, 65% glycine and/or serine. In other cases, accessory polypeptide sequences may contain at least 70, 75, 80, 85, 90% glycine and/or serine residues.

The compositions of the present invention will typically contain accessory polypeptide sequences consisting of a total of at least 40 amino acids. However, the products can contain multiple accessory polypeptide sequences and some or all of these individual accessory polypeptide sequences may be shorter than 40 amino acids as long as the combined length of all accessory polypeptide sequences of a product is at least 40 amino acids. In some embodiments, the combined length of accessory polypeptide sequences that are attached to a protein can be 20, 25, 35, 50, 60, 70, 80, 90, 100, 120, 140, 160, 180, 200, 250, 300, 350, 400, 500, 600, 700, 800, 900 or more than 1000 or 2000 amino acids. In some modified biologically active polypeptides the combined length of accessory polypeptide sequences exceeds 60, 70, 80, 90 or more amino acids. In other modified polypeptides the combined length of accessory polypeptide sequences exceeds 100, 120, 140, 160 or 180 amino acids, and even 200, 250, 300, 350, 400, 5000, 600, 700, 800 or even more than 1000 amino acids.

One or several accessory polypeptide sequences can be fused to a biologically active polypeptide, for example to the N- or C-terminus of the biologically active polypeptide or inserted into loops of a polypeptide of interest to give the resulting modified polypeptide improved properties relative to the unmodified polypeptide. Fusion of accessory sequences to a (therapeutic) protein leads to a significant increase in the hydrodynamic radius of the resulting fusion protein relative to the unmodified protein, which can be detected by ultracentrifugation, size exclusion chromatography, or light scattering, for example.

Accessory polypeptide sequences can be designed to avoid one or more types of amino acids to yield a desired property. For instance, one can design accessory polypeptide sequences to contain few or none of the following amino acids: cysteine (to avoid disulfide formation and oxidation), methionine (to avoid oxidation), asparagine and glutamine (to avoid desamidation) and aspartate. Accessory polypeptide sequences can be designed to contain proline residues that tend to reduce sensitivity to proteolytic degradation.

Accessory polypeptide sequences can be designed such as to optimize protein production. This can be achieved by avoiding or minimizing repetitiveness of the encoding DNA. Accessory polypeptide sequences such as poly-glycine or poly-serine may have very desirable pharmaceutical properties but their manufacturing can be difficult due to the high GC-content of DNA sequences encoding for poly-glycine and due to the presence of repeating DNA sequences that can lead to recombination.

Accessory polypeptides, including simple sequences composed of short, repeated motifs rich in sequences rich in G, S and E, may cause relatively high antibody titers of >1,000 in multiple species despite the absence of T-cell epitopes in these sequences. This may be caused be the repetitive nature of the accessory polypeptides, as it has been shown that immunogens with repeated epitopes, including protein aggregates, cross-linked immunogens, and repetitive carbohydrates are highly immunogenic. (Johansson, J., et al. (2007) Vaccine, 25: 1676-82, Yankai, Z., et al. (2006) Biochem Biophys Res Commun, 345: 1365-71, Hsu, C. T., et al. (2000) Cancer Res, 60: 3701-5). B-cells displaying pentavalent IgM molecules are stimulated by repetitive immunogens even if the monovalent binding affinity of an immunogen for the IgM is very low, such as at micromolar concentrations (FIG. 74). Simultaneous binding of linked repeats to multiple linked IgM domains located on the same molecule or on the same cell may cause a large (thousand, million or perhaps even billion-fold) increase in the apparent (effective) affinity of the interaction, which may stimulate B-cells. To avoid this type of effect, accessory polypeptides may be screened for immunogenicity (as well as for effects on halflife and other properties) in multiple species of animals (such as rats, rabbits, mice, or guinea pigs. Multiple injections may be performed, with pharmacokinetic properties being measured in the same animals before and after immunization). In addition, accessory polypeptide sequences may be designed to be non-repetitive (comprising only 1 identical copy of each sequence motif) or to have a minimal number of copies of each sequence motif. Accessory polypeptide sequences that are less-repetitive may comprise binding sites for different IgMs, but they may be less able to bind multivalently to the same IgM molecule or to the same B-cell, since each B-cell generally secretes only one type of IgM and each IgM typically only has one type of binding site. This mechanism is illustrated in FIGS. 74a and b. In some embodiments, accessory polypeptides may contain exclusively sequences that occur at 1, 2, 3, 4, 5 or so copies per accessory polypeptide. Polypeptides with a lower number of repeats, may have a lower expected avidity may be less likely to induce a substantial immune response. Such sequences may comprise multiple types of amino acids, such as two types (for example, G and E or S and E), three types of amino acids (like G, E and S) or even four or more. Such accessory polypeptides may also comprise, for example, 30-80% glycine, 10-40% serine and 15-50% glutamate of the total amino acid composition. Such sequences may provide an optimal balance of desired properties such as expression level, serum and *E. coli* protease resistance, solubility, aggregation, and immunogenicity.

FIG. 74 compares the interactions of a repetitive (74*a*) and a non repetitive accessory polypeptide sequence (74*b*) with B cells that recognize epitopes in said sequences. A repetitive sequence will be recognized by few B cells in an organism as it contains a relatively small number of different epitopes. However, a repetitive sequence can form multivalent contacts with these few B cells and as a consequence it can stimulate their proliferation as illustrated in FIG. 74*a*. A non repetitive sequence can make contacts with many different B cells as it contains many different epitopes. However, each individual B cell can only make one or a small number of contacts with an individual non-repetitive accessory polypeptide ("nrURP") due to the lack of repetitiveness as illustrated in FIG. 74*b*. As a result, non-repetitive accessory polypeptides may have a much lower tendency to stimulate proliferation of B cells and thus an immune response.

An additional advantage of non-repetitive accessory polypeptides relative to repetitive accessory polypeptides is that non-repetitive accessory polypeptides form weaker contacts with antibodies relative to repetitive accessory polypeptides. Antibodies are multivalent molecules. For instance, IgGs have two identical binding sites and IgMs contain 10 identical binding sites. Thus antibodies against repetitive sequences can form multivalent contacts with such repetitive sequences with high avidity, which can affect the potency and/or elimination of such repetitive sequences. In contrast, antibodies against non-repetitive accessory polypeptides tend to form mostly monovalent interactions with antibodies as said non-repetitive accessory polypeptides contain few repeats of each epitope.

Repetitiveness describes the degree of internal homology in a peptide sequence. In the extreme case a repetitive sequence can contain multiple identical copies of an amino acid sequence. Repetitiveness can be measured by analyzing the frequency of identical subsequences. For instance one can divide a sequence of interest into n-mer subsequences and count the number of identical or homologos subsequences. Highly repetitive sequences will contain a large fraction of identical or homologossubsequences.

The repetitiveness of a gene can be measured by computer algorithms. An example is illustrated in FIG. 75. Based on the query sequence on can perform a pair wise comparison of all subsequences of a particular length. These subsequences can be compared for identity or homology. The example in FIG. 75 compares subsequences of 4 amino acids for identity. In the example, most 4-mer subsequences occur just once in the query sequence and 3 4mer subsequences occur twice. One can average the repetitiveness in a gene. The length of the subsequences can be adjusted. Where desired, the length of the subsequences can reflect the length of sequence epitopes that can be recognized by the immune system. Thus analysis of subsequences of 4-15 amino acids can be performed. Genes encoding non-repetitive accessory polypeptides can be assembled from oligonucleotides using standard techniques of gene synthesis. The gene design can be performed using algorithms that optimize codon usage and amino acid composition. In addition, one can avoid amino acid sequences that are protease sensitive or that are known to be epitopes that can be easily recognized by the human immune system. Computer algorithms can be applied during sequence design to minimize the repetitive of the resulting amino acid sequences. One can evaluate the repetitiveness of large numbers of gene designs that match preset criteria such as amino acid composition, codon usage, avoidance of protease sensitive subsequence, avoidance of epitopes, and chose the least repetitive sequences for synthesis and subsequent evaluation.

An alternative approach to the design of non-repetitive accessory polypeptide genes is to analyze the sequences of existing collections of non-repetitive accessory polypeptides that show high level expression, low aggregation tendency, high solubility, and good resistance to proteases. A computer algorithm can design non-repetitive accessory polypeptide sequences based on such pre-existing non-repetitive accessory polypeptide sequences by re-assembly of sequence fragments. The algorithm generates a collection of subsequences from these non-repetitive accessory polypeptide sequences and evaluates multiple ways to assembly non-repetitive accessory polypeptide sequences from such subsequences. These assembled sequences can be evaluated for repetitiveness to identify a non-repetitive accessory polypeptide sequence that is only composed of subsequences of previously identified non-repetitive accessory polypeptides.

Figure 77:
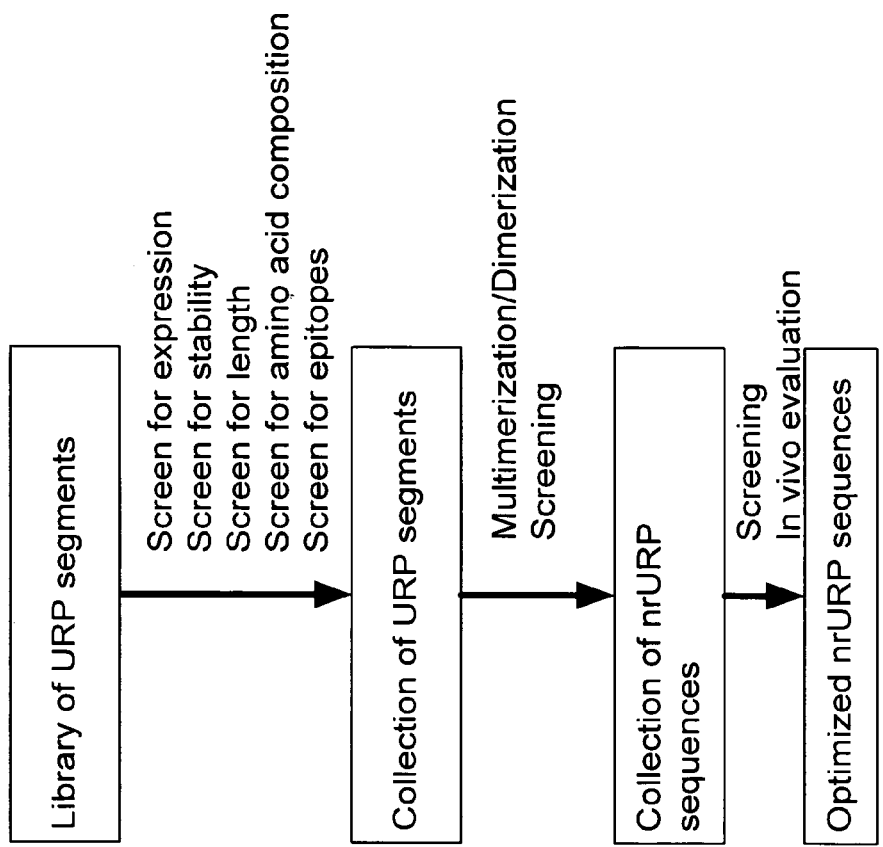
FIG. 77: Construction of nrURPs from libraries of URP segments.

Non-repetitive accessory polypeptide-encoding genes can be assembled from libraries of short accessory polypeptide segments as illustrated in FIG. 77. One can first generate large libraries of accessory polypeptide segments. Such libraries can be assembled from partially randomized oligonucleotides. The randomization scheme can be optimized to control amino acid choices for each position as well as codon usage. One may clone the library of accessory polypeptide segments into an expression vector. Alternatively, one may clone the library of accessory polypeptide segments into an expression vector fused to an indicator gene like GFP. Subsequently, one can screen library members for a number of properties such as level of expression, protease stability, binding to antiserum. One can determine the amino acid sequence of the library members to identify segments that have a particularly desirable amino acid composition, segment length, or to identify segments that have a low frequency of internal repeats. Subsequently, one can assemble non-repetitive accessory polypeptide sequences from collections of accessory polypeptide segments by random dimerization or multimerization. Dimerization or multimerization can be achieved by ligation or PCR assembly. This process results in a library non-repetitive accessory polypeptide sequences that can be evaluated for a number of properties to identify the non-repetitive accessory polypeptide sequences with the best properties. One can repeat the process of dimerization or multimerization to further increase the length of non-repetitive accessory polypeptide sequences.

In a specific embodiment, an accessory polypeptide comprises a mixture of the following 8 amino acid motifs: GEGSGEGSE (SEQ ID NO: 11), GEGGSEGSE (SEQ ID NO: 12), GEGSEGSGE (SEQ ID NO: 13), GEGSEGGSE (SEQ ID NO: 14), GEGSGEGGE (SEQ ID NO: 15), GEGGSEGGE (SEQ ID NO: 16), GEGGGEGSE (SEQ ID NO: 17), GEGGEGSGE (SEQ ID NO: 18), GEGGEGGSE (SEQ ID NO: 19), or GEGSEGGGE (SEQ ID NO: 20). This design has an average of 33% E and 11-22% Serine content, depending on the ratio of the numbers of motifs relative to each other. In another specific embodiment, an accessory polypeptide comprises a mixture of the following 12 amino acid motifs: GXEGSGEGXGXE (SEQ ID NO: 21), GXEGGSEGXGXE (SEQ ID NO: 22), GXEGSGEGGSGE (SEQ ID NO: 23), GXEGGSEGGSGE (SEQ ID NO: 24), GSGEGXEGXGXE (SEQ ID NO: 25), GGSEGXEGXGXE (SEQ ID NO: 26), GSGEGXEGGSGE (SEQ ID NO: 27) or GGSEGX- EGGSGE (SEQ ID NO: 28), where X represents either S or E with equal likelihood. This design has an average of 25% E and around 1% S, depending on the specific ratios chosen. Suitable specific ratios may be 1:1:1:1:1:1:1:1 ratio or any other ratio, and may be to fine-tune the composition.

Accessory polypeptide sequences can be designed to be highly repetitive, less repetitive or non-repetitive at the amino acid level. For example, highly repetitive accessory polypeptide sequences may contain only a small number of overlapping 9-mer peptide sequences and in this way the risk of eliciting an immune reaction can be reduced.

Examples of single-amino-acid-type accessory polypeptide sequences are: poly-glycine, poly-glutamic acid, poly-aspartic acid, poly-serine, poly-threonine, wherein the length is at least 20 residues. Examples of accessory polypeptides with two types of amino acids are (GX)n (SEQ ID NO: 29), (SX)n (SEQ ID NO: 30), where G is glycine and S is serine, and X is aspartic acid, glutamic acid, threonine, or proline and n is at least 10. Another example is (GGX)n (SEQ ID NO: 31) or (SSX)n (SEQ ID NO: 32), where X is aspartic acid, glutamic acid, threonine, or proline and n is at least 7. Another example is (GGGX)n (SEQ ID NO: 33) or (SSSX)n (SEQ ID NO: 34), where X is aspartic acid, glutamic acid, threonine, or proline and n is at least 5. Another example is (GGGGX)n (SEQ ID NO: 35) or (SSSSX)n (SEQ ID NO: 36), where X is aspartic acid, glutamic acid, threonine, or proline and n is at least 4. Other examples are (GzX)n (SEQ ID NO: 37) and (SzX)n (SEQ ID NO: 38) and where X is aspartic acid, glutamic acid, threonine, or proline, n is at least 10, and z is between 1 and 20.

The number of these repeats can be any number between 5 and 300 or more. Products of the invention may contain accessory polypeptide sequences that are semi-random sequences. Examples are semi-random sequences containing at least 30, 40, 50, 60 or 70% glycine in which the glycines are well dispersed and in which the total concentration of tryptophan, phenylalanine, tyrosine, valine, leucine, and isoleucine is less then 70, 60, 50, 40, 30, 20, or 10% when combined. A preferred semi-random accessory polypeptide sequence contains at least 40% glycine and the total concentration of tryptophan, phenylalanine, tyrosine, valine, leucine, and isoleucine is less than 10%. A more preferred random accessory polypeptide sequence contains at least 50% glycine and the total concentration of tryptophan, phenylalanine, tyrosine, valine, leucine, and isoleucine is less then 5%. Accessory polypeptide sequences can be designed by combining the sequences of two or more shorter accessory polypeptide sequences or fragments of accessory polypeptide sequences. Such a combination allows one to better modulate the pharmaceutical properties of the product containing the accessory polypeptide sequences and it allows one to reduce the repetitiveness of the DNA sequences encoding the accessory polypeptide sequences, which can improve expression and reduce recombination of the accessory polypeptide sequences-encoding sequences.

Where high level of solubility is desired, a high fraction of charged residues, preferably >25% glutamate (E) with the rest being mostly glycine or serine may be employed. High-level expression favors 10-50% serine (E), since serine has 6 codons which generally yields a much higher expression level than glycine (4 codons). There is generally a trade-off in solubility and rapid clearance when utilizing high glutmate content in a sequence. Where desired, a glutamate content of less than 50%, preferably less than 30%, is used to provide desired solubility and to avoid rapid clearance in animals.

Non-Glycine Residues can be Selected to Optimize Properties

Of particular interest are accessory polypeptide sequences that are rich in glycine and/or serine. The sequences of non-gly, non-ser residues in these gly-rich or ser-rich sequences can be selected to optimize the properties of the protein. For instance, one can optimize the sequences of accessory polypeptides to enhance the selectivity of the biologically active polypeptide for a particular tissue. Such tissue-selective accessory polypeptide sequences can be obtained by generating libraries of random or semi-random accessory polypeptide sequences, injecting them into animals or patients, and determining sequences with the desired tissue selectivity in tissue samples. Sequence determination can be performed by mass spectrometry. Using similar methods one can select accessory polypeptide sequences that facilitate oral, buccal, intestinal, nasal, thecal, peritoneal, pulmonary, rectal, or dermal uptake. Of particular interest are accessory polypeptide sequences that contain regions that are relatively rich in the positively charged amino acids arginine or lysine which favor cellular uptake or transport through membranes; such accessory polypeptides may be useful for intracellular delivery of proteins.

As described in more detail below, accessory polypeptide sequences can be designed to contain one or several protease-sensitive sequences. Such accessory polypeptide sequences can be cleaved once the product of the invention has reached its target location. This cleavage may trigger an increase in potency of the pharmaceutically active domain (pro-drug activation) or it may enhance binding of the cleavage product to a receptor. This is currently not possible for antibodies. However, in the case of PEGylated or accessory protein modified biologically active polypeptides, it is possible to provide a cleavage site for a foreign protease such as Tomato Etch Virus Protease or a similar site-specific, non-human protease. If the protease site is between the accessory protein and the therapeutic protein, or close to the therapeutic protein, then the injection of the protease will remove the accessory protein tail from the drug resulting in a shorter halflife and removal from the patient's system. The concentration of the drug in the serum will drop 10-100-fold, effectively terminating treatment. This would be desirable, for example, if treatment needs to be stopped suddenly, such as due to an infection during treatment with a TNF-inhibitory microprotein (such as TNFa-Receptor-rPEG). An example would be to add a protease to the treatment regime that cleaves off the accessory protein, thereby sharply reducing the halflife of the active, TNF-inhibitory part of the protein which is then rapidly cleared. This approach would allow the infection to be controlled.

Accessory polypeptide sequences can also be designed to carry excess negative charges by introducing aspartic acid or glutamic acid residues. Of particular interest are accessory polypeptide that contain 8, 10, 15, 20, 25, 30, 40 or even 50% glutamic acid and less than 2% lysine or arginine. Such accessory polypeptides carry a high net negative charge and as a result they have a tendency to adopt open conformations due to electrostatic repulsion between individual negative charges of the peptide. Such a net negative charge leads to an effective increase in their hydrodynamic radius and as a result it can lead to reduced kidney clearance of such molecules. Thus, one can modulate the effective net charge and hydrodynamic radius of an accessory polypeptide sequence by controlling the frequency and distribution of negatively charged amino acids in the accessory polypeptide sequences. Most tissues and surfaces in a human or animal have a net negative charge. By designing accessory polypeptide sequences to have a net negative charge one can minimize non-specific interactions between the accessory polypeptide-therapeutic protein and various surfaces such as blood vessels, healthy tissues, or various receptors.

Other accessory polypeptides useful in the present invention exhibit one or more following features.

The accessory polypeptide can be characterized by enhanced hydrodynamic radius, wherein the accessory polypeptide increases the Apparent Molecular Weight Factor of the biologically active polypeptide to which it is linked. Because the Apparent Molecular Weight Factor is a predictor of serum secretion half-life (assuming the predicted molecular weight is constant), accessory polypeptides with higher Apparent Molecular Weight Factor are expected to show longer serum half-lives. In some embodiments, Apparent Molecular Weight Factors for accessory polypeptides can be greater than 3, 5, 7 or even 9. The Apparent Molecular Weight Factor can be measured by a variety of methods including but not limited to ultrafiltration through membranes with controlled pore sizes, or by size exclusion gel filtration (SEC). The Apparent Molecular Weight Factor can be affected by the concentration of salts and other solutes. It should generally be measured under conditions that are similar to physiological conditions, such as in blood or saline.

The accessory polypeptide can also be characterized by the effect wherein upon its incorporation into a biologically active polypeptide, the biologically active polypeptide exhibits a longer serum half-life as compared to the corresponding protein that lacks the accessory polypeptide. (Methods of ascertaining serum half-life are known in the art (see e.g., Alvarez, P., et al. (2004) *J Biol Chem*, 279: 3375-81). One can readily determine whether the resulting protein has a longer serum half-life as compared to the unmodified protein by practicing any methods available in the art or exemplified herein.

The accessory polypeptide can also increase the solubility of the protein to which it is attached. For example, whereas human Interferon-alpha, human Growth Hormone and human G-CSF typically form inclusion bodies when expressed in the cytoplasm of *E. coli*, attachment of an accessory polypeptide (such as $(SSGSSE)_{48}$ (SEQ ID NO: 39) or $(SSESSSESSSE)_{24}$ (SEQ ID NO: 40), $(GEGGGEGGE)_{36}$ (SEQ ID NO: 41), or others) increases the solubility of the expressed polypeptide such that it no longer forms inclusion bodies but remains soluble in the cytoplasm from where it can be easily purified in active form and at high expression levels and efficiency, avoiding the need for refolding from inclusion bodies.

Accessory polypeptides can have a high degree of conformational flexibility under physiological conditions and they tend to have large hydrodynamic radii (Stokes' radius) compared to globular proteins of similar molecular weight, leading to a large 'specific volume' (volume per unit mass). Thus, the accessory polypeptide can behave like denatured peptide sequences lacking well defined secondary and tertiary structures under physiological conditions. Denatured conformation describes the state of a peptide in solution that is characterized by a large conformational freedom of the peptide backbone. Most peptides and proteins adopt a denatured conformation in the presence of high concentrations of denaturants or at elevated temperature. Peptides in denatured conformation have characteristic CD spectra and they are characterized by a lack of long range interactions as determined by NMR. "Denatured conformation" and "unfolded conformation" are used synonymously herein. A variety of methods have been established in the art to discern the presence or absence of secondary and tertiary structures of a given polypeptide. For example, the secondary structure of a polypeptide can be determined by CD spectroscopy in the "far-UV" spectral region (190-250 nm). Secondary structure elements, such as alpha-helix, beta-sheet, and random coil structures each give rise to a characteristic shape and magnitude of CD spectra. Secondary structure can also be ascertained via certain computer programs or algorithms such as the Chou-Fasman algorithm (Chou, P. Y., et al. (1974) *Biochemistry*, 13: 222-45). For a given accessory sequence, the algorithm can predict whether there exists some or no secondary structure at all. In many cases, accessory sequences will have spectra that resemble denatured sequences due to their low degree of secondary and tertiary structure. In other cases, accessory sequences can adopt secondary structure, especially helices such as alpha-helices, or sheets such as beta-sheets. While unstructured amino acid polymers are generally preferred for the present invention, it is possible to use amino acid sequences that adopt some secondary structure, especially alpha-helices and to a lesser extent beta-sheets. Tertiary structure is generally undesirable due to its low specific hydrodynamic radius. Sequences with secondary structure are likely to have a lower hydrodynamic radius than sequences with less secondary structure, but they may still be useful. If the accessory sequence adopts tertiary structure (such as in protein domains), the hydrodynamic radius is expected to be even smaller. Whereas polyglycine has the highest ratio of hydrodynamic radius to mass (glycine is only 70D), globular proteins have the smallest ratio of hydrodynamic radius to mass. An exception is the inclusion in the accessory polypeptide of peptides with 0, 1, 2, 3 or 4 disulfides and varying degrees of secondary and tertiary structure) that bind to serum-exposed targets and increase the serum secretion halflife by a different mechanism.

The accessory polypeptides can be sequences with low immunogenicity. Low immunogenicity can be a direct result of the conformational flexibility of accessory sequences. Many antibodies recognize so-called conformational epitopes in protein antigens. Conformational epitopes are formed by regions of the protein surface that are composed of multiple discontinuous amino acid sequences of the protein antigen. The precise folding of the protein brings these sequences into a well-defined special configuration that can be recognized by antibodies. Preferred accessory polypeptides are designed to avoid formation of conformational epitopes. For example, of particular interest are accessory sequences having a low tendency to adapt compactly folded conformations in aqueous solution. In particular, low immunogenicity can be achieved by choosing sequences that resist antigen processing in antigen presenting cells, choosing sequences that do not bind MHC well and/or by choosing sequences that are derived from human sequences. Accessory polypeptide sequences can also reduce the immunogenicity of the biologically active polypeptide.

The accessory polypeptides can be sequences with a high degree of protease resistance. Protease resistance can also be a result of the conformational flexibility of accessory sequences, e.g., due to their high entropy. Protease resistance can be designed by avoiding known protease recognition sites for both endo- and exo-proteases, and by including a high glycine content. Alternatively, protease resistant sequences can be selected by phage display or related techniques from random or semi-random sequence libraries. Where desired for special applications, such as slow release from a depot protein, serum protease cleavage sites can be built into an accessory polypeptide. In such cases, the compositions of the present invention may dissolve or degrade (or may be intended to dissolve or degrade) during use. In general, degradation attributable to biodegradability involves the degradation of a polymer into its constituents (including, without limitation, the modified polypeptides and resulting degradation products). The degradation rate of a polymer often depends in part on a variety of factors, including the identity of any constituents that form the polymer (such as a protease sensitive site), the ratio of any substituents, and how the composition is formed or treated (e.g. whether substituents are protected). Of interest, however, are also accessory sequences with high stability (e.g., long serum half-life, less prone to cleavage by proteases present in bodily fluid) in blood or in the bodily tissue that is relevant for the application. Accessory polypeptides can also improve the protease resistance of a protein as they shield it from protease attack. An example of a natural unstructured, repetitive sequence composed of 3 amino acids is the linker in the pIII protein of M13 phage, which has the repeat (GGGSE)n (SEQ ID NO: 42) and is known to be exceptionally stable to a vast array of proteases. An accessory protein with the motif (GGGSE)n (SEQ ID NO: 42) is predicted to be very useful. For long sequences, one may prefer (GGSE)n, (SEQ ID NO: 43) to achieve higher solubility which may be needed at the increased length.

Accessory polypeptides with good solubility in water, blood and other bodily fluids under physiological conditions are also desirable to facilitate bioavailability. Such sequences can be obtained by designing sequences that are rich in hydrophilic amino acids such as glycine, serine, aspartate, glutamate, lysine, arginine, threonine and that contain few hydrophobic amino acids such as tryptophan, phenylalanine, tyrosine, leucine, isoleucine, valine, methionine. As a result of their amino acid composition, accessory polypeptides have a low tendency to form aggregates in aqueous formulations and the fusion of an accessory polypeptide to other proteins or peptides tends to enhance their solubility and reduce their tendency to form aggregates, which is a separate mechanism to reduce immunogenicity.

The accessory polypeptide can, in some cases, display enhanced non-specific binding to tissues or serum proteins (FIG. 28), which can function to prolong their serum half-life. Serum protein binding can be measured using a variety of methods. Examples for binding assays are ELISA, Biacore, Kinexa, or Forte Bio. Since most animal tissue surfaces have a (net) weak negative charge, proteins with a net negative charge show less non-specific tissue binding than proteins with a net positive charge. Creating a net weak negative charge by the addition of negative charges or by the deletion of positive charges can make a protein bind more specifically or at least reduce non-specific binding.

However, if the net negative charge (or the net charge density) is too high, it can result in non-specific binding to surfaces with local patches of positive charge, such as parts or proteins that bind to extracellular matrix, or to DNA or RNA (e.g. VEGF, histones). In contrast, creating a protein with net positive charge by the addition of positive charges (such as K, R) or by the deletion of negative charges can make a protein bind non-specifically to tissues, which results in an extension of halflife.

The charge type and density of the accessory polypeptide itself can be modified. The negatively charged amino acids are E, D, (C) and the positively charged amino acids are R, K, (H). Changes generally involve exchanging one negatively charged residue for another, such as E for D or vice versa. In some instances, E is preferred, because D can isomerize leading to chemical instability that is undesirable for manufacturing. Changes in charge type, from positive charge to negative charge or vice versa, involve replacing K or R with E or D (positive replaced by a negative). Changes in charge also include replacing a non- or weakly charged amino acid (A, C, F, G, H, I, L, M, N, P, Q, S, T, V, W, Y) with a charged amino acid (E, D, K, R) or vice versa. "Charge density" is the number of charged amino acids as a percentage of total residues. Changing the charge density involves increasing or reducing the number of negatively charged amino acids (specifically E, D) or positively charged amino acids (K, R) as a percentage of total amino acids. In contrast, the 'net charge density' is the sum of all positively charged amino acids minus the sum of all negatively charged amino acids ("net charge") as a percentage of the total number of residues.

The "net charge" and the "net charge density (net charge per AA)" can influence the solubility of the accessory polypeptide and of the accessory-modified polypeptide, as well as its ability to bind to other molecules. The accessory polypeptide can modify the charge type and density of fusion proteins, which can enhance serum halflife and can be exploited to enhance desirable interactions or to reduce non-desirable interactions of the fusion protein with other proteins or materials.

The accessory polypeptide can, in some cases, display enhanced non-specific binding to tissues or serum proteins, which can function to prolong their serum half-life. This can be measured as an extension of serum halflife compared to an accessory sequence that does not show non-specific binding, or it can be shown by ELISA as a weak binding affinity for proteins a high density of the opposite charge.

Accessory polypeptides can consist partially or entirely of a single amino acid, such as (E(n, (G)n or (S)n (also referred to as poly-E, EEEEE (SEQ ID NO: 44), poly-G, GGGGG (SEQ ID NO: 45), or poly-S, SSSSS (SEQ ID NO: 46)), or even a homo-polymer of one of A, C, D, F, H, I, K, L, M, N, P, Q, R, S, T, V, W, Y; ie AAAAA (SEQ ID NO: 47)). The best single amino acid motifs (E, G, S) are immunologically the least complex (only one type of 9 amino acid peptide can be created), but each has some drawbacks. Glycine is weakly hydrophobic and poly-G has limited solubility. An advantage of glycine is its high entropy. In some instances, serine may be preferred over glycine because the corresponding DNA sequence is likely to have a more balanced GC-ratio and generally provides a higher expression level, likely due to its 6 codons. The four charged amino acids, including Glutamic acid (E), have the highest solubility of the 20 natural amino acids, followed by Glycine and Serine. However, at a high negative net charge density the proteins start binding non-specifically to positively charged proteins and surfaces, such as VEGF (basic exons that bind ECM), histones, DNA/RNA-binding proteins and also to bone. Others have reported that a long string of poly-E causes a reduced halflife, instead of the desired extended halflife.

Serine and poly-Serine offer high solubility without a risk of aggregation and with the best codon use and expression level. The six codons for serine offer a balanced GC content, but more importantly, they allow poly-S or S-rich sequences to be encoded by exceptionally diverse DNA sequences that offer a greater degree of codon usage optimization and expression level optimization than other amino acids such as poly-E or poly-G (FIGS. 14 and 15).

The accessory polypeptides can be of any length necessary to effect the functional changes described above. The length of an accessory sequence that only contains 1, 2, 3 or more types of amino acids can have a lower limit of 10, 12, 14, 16, 18, 20, 25, 30, 35, 40, 45, 50, 60, 70, 80, 90 or 100 amino acids and an upper limit of 30, 40, 50, 60, 70, 80, 90, 100, 125, 150, 175, 200, 250, 300, 350, 400, 500, 600 or even 1000 amino acids.

The amino acid composition of the accessory polypeptide can be chosen such that the desirable properties of the resulting polypeptide are maximized. For example, for the extension of serum half-life a high ratio of apparent molecular weight to predicted molecular weight is preferred. The unstructured accessory polypeptides that offer more hydrodynamic radius for the same mass are constructed with amino acids that do not support structures such as alpha helices or beta-sheets. According to the rating of amino acid residues by the Chou-Fasman algorithm, residues A, D, E, Q, I, L, K, M, F, W, V support alpha-helical structure and residues C, Q, I, L, M, F, T, W, Y, V support beta-sheet structures. The amino acids that the Chou-Fasman algorithm considers most unstructured, because they are turn-forming, are, in order from most to least unstructured: G, N, P, D, S, C, Y, K. On balance, the residues that least support structure are G, N, P, S.

To achieve better fine tuning of the properties of the polymer, especially solubility and charge density, accessory polypeptides composed of two or three amino acids are generally preferred over those composed of a single amino acid. Accessory polypeptides that are composed of two or three types of amino acids are preferred because they offer the best balance of immunological simplicity (yielding only a small number of different 9-mer peptides can bind MHC complexes or 8-mer peptides that form epitopes for antibody binding), with the optimization of solubility, protease resistance, charge type and density, absence of structure, entropy, and non-specific binding to tissues (which can be undesirable but can also be used as a half-life mechanism). In general, the larger the number of non-human 8-mer or 9-mer peptides that can be created from the accessory protein sequence, the higher the risk of immunogenicity. Accordingly, in some aspects the accessory polypeptide comprises a small number of different 8-mer or 9-mer, and wherein all or most of these peptide sequences occur in the human proteome, preferably with many copies.

Where desired, a blend of two or three amino acids types can be optimized for obtaining the desired balance of properties. The 20 natural amino acids (AA) can be separated into groups with related properties. Residues E, D (and to a lesser extent C) are negatively charged at physiological (neutral) pH, and residues K, R and to a lesser extent H are positively charged at neutral pH. The presence of charged residues E, D, K and R may be desirable for maximizing the water solubility of long polypeptides. For some biological applications it is desirable to have a high but equal or similar frequency of negative and positive residues that result in an uncharged, or nearly uncharged polypeptide that has high charge density but low net charge, such, polypeptides tend to have low tendency for non-specific interactions with receptors that bind charged polymers such as heparin. For some biological applications, a single charge type (negative) which (unlike D) is chemically stable; thus favoring E (glutamate). The question is what the percentage of amino acids should be E, and whether the majority of non-charges amino acids should be G or S. and whether the sequence should be highly repetitive or less repetitive.

A high frequency of negatively charged residues E, D is likely to make the polymer bind to molecules with a large number of positive charges, like DNA binding proteins, histones and other R, K-rich sequences. A high frequency of positively charged residues K, R is likely to make the polymer bind to surfaces with a large number of negative charges, which includes most cell surfaces. Binding to cell surfaces is generally not desirable but a low degree of such non-specific binding may be useful to increase the half-life. The polar, hydrophilic amino acids N, Q, S, T, K, R, H, D, E, and additionally the amino acids C or Y can be useful in making accessory polypeptides that are relatively water soluble. Q and N can be glycosylation sites, offering a separate mechanism for increasing the hydrodynamic radius and thereby halflife. Non-polar, hydrophobic residues such as A, V, L, I, P, Y, F, W, M, C are less useful when creating a sequence with high water solubility, but it may be desirable to incorporate one or more of these residues at a low frequency, such that they constitute less than 10-20% of total. For example, a limited number of substitutions of hydrophobic residues can increase half-life by increasing non-specific binding to serum-exposed sites. Similarly, free thiols from cysteine residues may function as a mechanism for half-life extension by binding to other free thiols, such as the free thiol in human serum albumin. Also, these less-preferred amino acids can be used to create peptides that bind to serum-exposed proteins, thereby adding a second halflife extension mechanism, other than hydrodynamic radius, to the accessory protein.

Glycine is a preferred residue that can be used in accessory polypeptides due to its high ratio of hydrodynamic radius to mass, or apparent molecular weight to predicated molecular weight. Glycine does not have a side chain and thus is the smallest residue, at 70 Da. Because of its small size it provides maximal rotational freedom and maximum entropy. This makes it difficult for proteins to bind to sequences with higher frequencies of glycine, and glycine-rich sequences are highly protease resistant.

Residues C, W, N, Q, S, T, Y, K, R, H, D, E can form hydrogen bonds with other residues and thereby support structure (intermolecular hydrogen bonds) and binding to other proteins (intermolecular hydrogen bonds). These can be excluded in places where structure is not desired, or included if some degree of binding (specific or non-specific) is required for extension of half-life. The sulfur-containing residues C and M are typically avoided in accessory polypeptides, but cysteine can be included to provide half-life via its free thiol and can also be used in cyclic peptides as low-immunogenicity binding elements to extend half-life by binding to serum-exposed proteins or to obtain tissue targeting or modulated biodistribution by binding to tissue specific sites.

In one embodiment, the accessory polypeptide contains no or minimal repetitive sequence. IgM is pentavalent and exhibits propensity for recognizing repetitive sequences. Even low affinity contacts with IgM may lead to significant apparent affinity (avidity) due to the pentavalency of IgM. One way to build sequences with a reduced degree of repetition and reduced likelihood of IgM binding is to use repeat sequences that are long (ie 7, 8, 9, 10, 12, 14, 16, 20, 30, 40, 50, 70, 100, 150, 200 amino acids in repeat length). Examples of sequences with reduced repetition are (SESSSESSE)n (SEQ ID NO: 48), (SSESSSSESSSE)n (SEQ ID NO: 49), (SSSESSSSSESSSSE)n (SEQ ID NO: 50), or (SSSSESSSSSSE)n (SEQ ID NO: 51), whereas the repetitive sequences with similar overall composition would be (SSE)n, (SSSE)n (SEQ ID NO: 52), (SSSSE)n (SEQ ID NO: 53), (SSSSSE)n (SEQ ID NO: 54) or (SSSSSSE)n (SEQ ID NO: 55). Another approach involves the use of multiple motifs and/or variations of one or more motif intermixed in the same accessory polypeptide (such as sequence variations of motifs, spacing variations and variations in the sequences that separate the motifs). Another aspect of the present invention provides for the use of long, fully human or humanized sequences that are mostly non-repetitive and have the desired amino acid composition. In a related embodiment, other types of amino acids or motifs based on other types of amino acids can be interspersed. An example would be: GEGESEG-EGEGESEGEGESGE (SEQ ID NO: 56).

Accessory Polypeptide Sequences Containing Three Different Types of Aminoacids:

In one embodiment, the accessory polypeptide comprises a sequence containing three different types of aminoacids. The advantage of three amino acids compared to one or two is the increased ability to fine-tune the properties of the resulting polymer for the intended commercial applications.

One particular embodiment of the present invention provides a non-repetitive sequence containing three different types of aminoacids. A further embodiment of the invention provides a non-repetitive sequence containing three different types of aminoacids, wherein the aminoacids are chosen from the group consisting of A, D, E, G, H, K, N, P, Q, R, S, T and Y. Exemplary sequences for this embodiment are shown in Table 1. In a preferred embodiment, the aminoacids are chosen from the group consisting of D, E, G, K, P, R, S and T. In a more preferred embodiment, the aminoacids are chosen from the group consisting of E, S, G, R and A. In the most preferred embodiment, the aminoacids are E, G and S, In such proteins, the preferred composition is to have G ranging from 30-70% (best: 50-60%), E ranging from 20-40% (best 25-30%) and S ranging from 10-25%, and preferably with only 1, 2, 3, 4 or 5 copies (repeats) of each sequence with more than 9-15 AA.

In a separate embodiment, the accessory polypeptide comprises a sequence containing repeated sequence motifs, wherein each repeated sequence motif contains three different types of aminoacids, wherein the aminoacids are chosen from the group consisting of A, D, E, G, H, K, N, P, Q, R, S, T and Y. Exemplary sequences for this embodiment are shown in Table 1. In one embodiment, the aminoacids are chosen from the group consisting of D, E, G, K, P, R, S and T. In another embodiment, the aminoacids are chosen from the group consisting of E, S, G, R and A. In yet another embodiment, the aminoacids are E, G and S (in any order).

In a related embodiment, the accessory polypeptide of the invention contains three different types of aminoacids organized in repetitive sequence motifs, wherein each repeated sequence motif is longer than three consecutive aminoacids. Exemplary sequences for this embodiment are shown in Table 1. Repetitive sequence motifs can be direct or inverted and 1, 2, 3, 4 or more different types of motifs can occur separately or intermixed in the same protein. The repeats can be perfect or imperfect, having 1, 2, 3, 4, 5 or more mismatched residues, and the repeats can be contiguous or dispersed, meaning they are separated by other, unrelated sequences that are not comprised of the same motif. In some embodiments, repetitive sequences constitute a majority of the accessory polypeptide, while non-repetitive sequences predominate in other embodiments. In one particular embodiment, a repetitive sequence contains interspersed single amino acids which break the strictly repetitive nature of the sequence. Exemplary sequences for this embodiment are shown in Table 1. In another related embodiment, the accessory polypeptide contains primarily three types of aminoacids, organized in repetitive or non-repetitive sequences, together with a smaller number of aminoacids of a different type, wherein the said three types of aminoacid make up for more than 50%, 60%, 70%, 80%, 90%, 95%, 98% or >99% of the entire sequence.

Another example of a sequence comprising multiple types of repeated motifs is GGGGGGGGGG-GEEEEEEEEEEGGGGGGGGGGEEEEEEEEEE (SEQ ID NO: 57). Other preferred examples are sequences with various combinations of 2,3,4,5 or more motifs, wherein the motifs are chosen from E, S, G, GE, GS, SE, GES, GSE, ESG, EGS, SGE, and SEG, leading to compositions (E)n, (S)n, (G)n, (GE)n, (GS)n, (SE)n, (GES)n, (GSE)n, (ESG)n, (EGS)n, (SGE)n, and (SEG) as well as many additional sequences.

The composition of amino acids in the motif or in the polymeric sequence can be balanced (for example, 50% G and 50% E; or 33% G, 33% E and 33% S, and other similar examples) or unbalanced (ie 75% 5 and 25% E).

The accessory sequence repeats can be located at the N-terminus of the protein, at the C-terminus of the protein or 1, 2, 3, 4, 5, 6, 10, 20, 30 or more amino acid residues away from the N-terminus or C-terminus. The polyamino acid can also lie between two protein domains.

The number of repeats of a motif in a polyamino acid can have a lower limit of 4, 5, 6, 7, 8, 9, 10, 12, 14, 16, 18, 20 25, 30, 35, 40, 45, 50, 60, 70, 80, 90, 100 and an upper limit of 10, 12, 14, 16, 18, 20, 25, 30, 35, 40, 45, 50, 60, 70, 80, 90, 100, 150, 200, 250, 300, 400, 500, or even 600.

A repeated motif can have a major amino acid type and a minor amino acid type. For a given repeated motif, there are more residues of the major amino acid type than of the minor type. For example, in the accessory polypeptide (GGGEE)n (SEQ ID NO: 58), G is the major and E is the minor amino acid type. These sequences are by definition not balanced. In such motifs, it is possible to have 2, 3, 4 or more types of major amino acids. In a preferred embodiment, the major amino acids are G, E, S, and the minor amino acids are A, D, E, F, G, H, I, K, L, M, N, P, Q, R, S, T, V, W, Y, with the additional limitation that the same amino acid type cannot be in both the major and minor groups present in the motif. In such motifs, it is also possible to have two or more types of minor amino acids; an example is (GGEGGS)n (SEQ ID NO: 59), wherein G is the major type and E and S are the minor types of amino acids. Other examples are (EGGSGG)n (SEQ ID NO: 60), (GEGGSG)n (SEQ ID NO: 61), (GGSGGE)n (SEQ ID NO: 62), (SGGEGG)n (SEQ ID NO: 63), (GSGGEG)n (SEQ ID NO: 64), (GEEGSS)n (SEQ ID NO: 65), (GSSGEE)n (SEQ ID NO: 66), (SGSEGE)n (SEQ ID NO: 67), (SSGEEG)n (SEQ ID NO: 68).

Irrespective of the particular sequence, the total number of amino acid residues in an accessory sequence has a lower limit of 10, 12, 14, 16, 18, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 120, 140, 160, 180, 200, 250, or 300 amino acids and an upper limit of 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 350, 400, 450, 500, 550, or even more than 600, 700, 800, 900 or 1000 amino acids. These numbers can refer to the length of a single contiguous sequence, or to the cumulative length total for multiple sequences comprised of multiple motifs that occur non-contiguously, meaning these repeats are dispersed and are separated by other sequences including repeats of a different motif.

TABLE 1

Accessory polypeptide sequences containing three different types of aminoacids.

| | | | | | |
|---|---|---|---|---|---|
| (DEG)n, | (DEK)n, | (DEP)n, | (DER)n, | (DES)n, | (DET)n, |
| (DGK)n, | (DGP)n, | (DGR)n, | (DGS)n, | (DET)n, | (DKP)n, |
| (DKR)n, | (DKS)n, | (DKT)n, | (DPR)n, | (DPS)n, | (DPT)n, |
| (DRK)n, | (DRS)n, | (DSE)n, | (DSP)n, | (DTE)n, | (DTG)n, |
| (DTK)n, | (DTP)n, | (DTR)n, | (DTS)n, | (EGD)n, | (EGK)n, |
| (EGP)n, | (EGR)n, | (EGS)n, | (EGT)n, | (EKD)n, | (EKG)n, |
| (EKP)n, | (EKR)n, | (EKS)n, | (EKT)n, | (EPD)n, | (EPG)n, |
| (EPK)n, | (EPR)n, | (EPS)n, | (EPT)n, | (ERD)n, | (ERG)n, |
| (ERK)n, | (ERP)n, | (ERS)n, | (ERT)n, | (ESD)n, | (ESG)n, |
| (ESK)n, | (ESP)n, | (ESR)n, | (EST)n, | (ETD)n, | (ETG)n, |
| (ETK)n, | (ETP)n, | (ETR)n, | (ETS)n, | (GKD)n, | (GKE)n, |

TABLE 1-continued

Accessory polypeptide sequences containing three different types of aminoacids.

(GKP)n, (GKR)n, (GKS)n, (GKT)n, (GPK)n, (GPD)n,
(GPE)n, (GPR)n, (GPS)n, (GPT)n, (GRD)n, (GRE)n,
(GRK)n, (DRP)n, (DRS)n, (DRT)n, (GSD)n, (GSE)n,
(GSK)n, (GSP)n, (GST)n, (GTE)n, (GTD)n, (GTK)n,
(GTP)n, (GTR)n, (GTS)n, (KPD)n, (KPE)n, (KPG)n,
(KPR)n, (KPS)n, (KPT)n, (KRD)n, (KRE)n, (KRG)n,
(KRP)n, (KRS)n, (KRT)n, (KSD)n, (KSE)n, (KSG)n,
(KSP)n, (KSR)n, (KST)n, (KTD)n, (KTE)n, (KTG)n,
(KTP)n, (KTR)n, (KTS)n, (PRD)n, (PRE)n, (PRG)n,
(PRK)n, (PRS)n, (PRT)n, (PSD)n, (PSE)n, (PSG)n,
(PSK)n, (PSP)n, (PSR)n, (PST)n, (PTD)n, (PTE)n,
(PTG)n, (PTK)n, (PTR)n, (PTS)n, (RSD)n, (RSE)n,
(RSG)n, (RSK)n, (RSP)n, (RST)n, (RTD)n, (RTE)n,
(RTG)n, (RTK)n, (RTP)n, (RTS)n, (SED)n, (SEG)n,
(SEK)n, (SEP)n, (SER)n, (SET)n, (STD)n, (STE)n,
(STG)n, (STK)n, (STP)n, (STR)n.

. . . EEEGGGSSSGEGGSSSGSEE . . . (SEQ ID NO: 69)
. . . ESGGSSEGSSEESGSSEGSE . . . (SEQ ID NO: 70)

(EEESSSGGG)n (SEQ ID NO: 71),
(EESSGG)n (SEQ ID NO: 72),
(ESGSE)n (SEQ ID NO: 73), (EESGS)n (SEQ ID NO: 74),
(ESGGSE)n (SEQ ID NO: 75)

(ESG)n(E)(ESG)n (SEQ ID NO: 76)

(ESG)n(P)(ESG)n (SEQ ID NO: 77)

Accessory Polypeptides Containing Two Different Types of Amino Acids:

In one embodiment, the accessory polypeptide comprises a sequence containing two different types of aminoacids.

In a particular embodiment, the accessory polypeptide comprises a sequence containing two different types of aminoacids, wherein one of the aminoacids is glycine and the other is D, E, K, P, R, S, T, A, H, N, Y, L, V, W, M, F, I or C. A more specific embodiment provides an accessory polypeptide comprising a sequence containing two different types of aminoacids, wherein one of the aminoacids is glycine, and wherein glycine makes up 0%, half or less than half of the entire sequence. In related embodiments, the accessory polypeptide comprises 10%, 20%, 30%, 40%, 50%, 60%, 70%, 80%, 90% or even 100% glycine residues.

In different embodiment, the accessory polypeptide comprises a sequence containing two different types of aminoacids, wherein one of the aminoacids is serine and the other is D, E, K, P, R, G, T, A, H, N, Y, L, V, W, M, F, I or C. A more specific embodiment provides an accessory polypeptide comprising a sequence containing two different types of aminoacids, wherein one of the aminoacids is serine, and wherein serine makes up 0%, half or less than half of the entire sequence. In related embodiments, the accessory polypeptide comprises 10%, 20%, 30%, 40%, 50%, 60%, 70%, 80%, 90% or even 100% serine residues.

In a related embodiment, the accessory polypeptide comprises two different types of amino acids, wherein the amino acids are represented in equal or about equal amounts (1:1 ratio). In related embodiments, the two types of amino acids are represented in 1:2, 1:3, 2:3, 3:4 ratios. Example sequences are shown in Table 2.

An alternative embodiment of the present invention provides an accessory polypeptide comprising a sequence containing two different types of aminoacids, wherein half or less than half of the total amino acids are A, T, G, D, E or H.

An alternative embodiment of the present invention provides an accessory polypeptide comprising a sequence containing two different types of aminoacids, wherein half or more of the amino acids are G and half or less than half of the total amino acids are A, S, T, D, E or H.

Another embodiment of the present invention provides an accessory polypeptide comprising a sequence containing two different types of aminoacids, wherein half or more of the amino acids are S and half or less than half of the total amino acids are A, T, G, D, E or H.

Another embodiment of the present invention provides an accessory polypeptide comprising a sequence containing two different types of aminoacids, wherein half or less than half of the total amino acids are P, R, L, V, Y, W, M, F, I, K or C.

Accessory polypeptides are also envisioned comprising repeating sequence motifs, wherein the sequence motifs can consist of 2, 3, 4, 5, 6, 7, 8, 9 or more aminoacids.

The composition of amino acids in the motif or in the polymeric sequence can be balanced (for example, 50% S and 50% E), or unbalanced (i.e., 75% S and 25% E).

The accessory polypeptide repeats can be located at the N-terminus of the protein, at the C-terminus of the protein or 1, 2, 3, 4, 5, 6, 10, 20, 30 or more amino acid residues away from the N-terminus or C-terminus. The polyamino acid can also lie between two protein domains.

The number of repeats of a motif in a polyamino acid can have a lower limit of 4, 5, 6, 7, 8, 9, 10, 12, 14, 16, 18, 20 25, 30, 35, 40, 45, 50, 60, 70, 80, 90, 100 and an upper limit of 10, 12, 14, 16, 18, 20, 25, 30, 35, 40, 45, 50, 60, 70, 80, 90, 100, 150, 200, 250, 300, 400, 500, or even 600.

The total number of amino acid residues in a accessory polypeptide can have a lower limit of 20, 21, 22, 23, 24, 25, 26, 27, 28, 29, 30, 31, 32, 34, 35, 36, 37, 38, 39, 40, 45, 50, 55, 60, 65, 70, 75, 80, 85, 90, 95, 100, 120, 140, 160, 180, 200, 250, or 300 amino acids and an upper limit of 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 350, 400, 450, 500, 550, or even more than 600, 700, 800, 900 or 1000 amino acids. This number can refer to the length of a single contiguous sequence, or to the cumulative length total for multiple sequences that occur non-contiguously, meaning these repeats are dispersed and are separated by other sequences including repeats of a different motif.

Possible motifs comprising two amino acids are AD, AE, AF, AG, AH, AI, AK, AL, AM, AN, AP, AQ, AR, AS, AT, AV, AW, AY, DA, DE, DF, DG, DH, DI, DK, DL, DM, DN, DP, DQ, DR, DS, DT, DV, DW, DY, EA, ED, EF, EG, EH, EI, EK, EL, EM, EN, EP, EQ, ER, ES, ET, EV, EW, EY, FA, FD, FE, FG, FH, FI, FK, FL, FM, FN, FP, FQ, FR, FS, FT, FV, FW, FY, GA, GD, GE, GF, GH, GI, GK, GL, GM, GN, GP, GQ, GR, GS, GT, GV, GW, GY, HA, HD, HE, HF, HG, HI, HK, HL, HM, HN, HP, HQ, HR, HS, HT, HV, HW, HY, IA, ID, IE, IF, IG, IH, IK, IL, IM, IN, IP, IQ, IR, IS, IT, IV, IW, IY, KA, KD, KE, KF, KG, KH, KI, KL, KM, KN, KP, KQ, KR, KS, KT, KV, KW, KY, LA, LD, LE, LF, LG, LH, LI, LK, LM, LN, LP, LQ, LR, LS, LT, LV, LW, LY, MA, MD, ME, MF, MG, MH, MI, MK, ML, MN, MP, MQ, MR, MS, MT, MV, MW, MY, NA, ND, NE, NF, NG, NH, NI, NK, NL, NM, NN, NP, NQ, NR, NS, NT, NV, NR, NY, PA, PD, PE, PF, PG, PH, PI, PK, PL, PM, PN, PQ, PR, PS, PT, PV, PW, PY, QA, QD, QE, QF, QG, QH, QI, QK, QL, QM, QN, QP, QR, QS, QT, QV, QW, QY, RA, RD, RE, RF, RG, RH, R1, RK, RL, RM, RN, RP, RQ, RR, RS, RT, RV, RW, RY, SA, SD, SE, SF, SG, SH, SI, SK, SL, SM, SN, SP, SQ, SR, SS, ST, SV, SW, SY, TA, TD, TE, TF, TG, TH, TI, TK, TL, TM, TN, TP, TQ, TR, TS, TV, TW, TY, VA, VD, VE, VF, VG, VH, VI, VK, VL, VM, VN, VP, VQ, VR, VS, VT, VW, VY, WA, WD, WE, WF, WG, WH, WI, WK, WL, WM, WN, WP, WQ, WR, WS, WT, WV, WY, YA, YD, YE, YF, YG, YH, YI, YK, YL, YM, YN, YP, YQ, YR, YS, YT, YV, YW. Of these, the preferred 2 amino acid motifs are EG and GE (forming the polymer EGEGEGEGEGE (SEQ ID NO: 78) and other variants), GS and SG (forming the polymer GSGSGSGSGSGSGS (SEQ ID NO: 79) and other variants), ES and SE (forming the polymer SESESESESESESES (SEQ ID NO: 80) and other variants). The repeats can also comprise 3, 4, 5, 6 or 7 amino acid residues. It is also possible for the repeats to comprise 8, 9, 10, 11, 12, 13, 14, 15, 16, 17, 18, 19, 20 or even >20 residues. Each such repeat may contain 2, 3, 4, 5 or more types of amino acids, up to the number of residues present in the repeat.

One preferred type of accessory contains only two amino acid types but 50% or more of the residues is one of the preferred residues (A, S, T, D, E, H). In some cases the accessory polypeptide contains only two primary types of amino acids, but at a lower ratio P, R, L, V, Y, W, M, F, I, K or C can be added for optimal fine-tuning of the properties of the accessory polypeptide (see Table 2).

TABLE 2

Accessory polypeptides containing two different types of aminoacids (DE), (DG), (DK), (DP), (DR), (DS), (DT), (ED),
(EG), (EK), (EP), (ER), (ES), (ET), (GD), (GE),
(GK), (GP), (GR), (GS), (GT), (KD), (KE), (KG),
(KP), (KR), (KS), (KT), (PD), (PE), (PG), (PK),
(PR), (PS), (PT), (RD), (RE), (RG), (RK), (RP),
(RS), (RT), (SD), (SE), (SG), (SK), (SP), (SR),
(ST), (TD), (TE), (TG), (TK), (TP), (TR), (TS);

(DEE), (DGG), (DKK), (DPP), (DRR), (DSS), (DTT),
(EDD), (EKK), (EPP), (ERR), (ESS), (ETT), (GDD),
(GEE), (GKK), (GPP), (GRR), (GSS), (GTT), (KDD),
(KEE), (KGG), (KPP), (KRR), (KSS), (KTT), (PDD),
(PEE), (PGG), (PKK), (PRR), (PSS), (PTT), (RDD),
(REE), (RGG), (RKK), (RPP), (RSS), (RTT), (SDD),
(SEE), (SKK), (SPP), (SRR), (STT), (TDD), (TEE),
(TKK), (TPP), (TRR), (TSS);

(DDDEE) (SEQ ID NO: 81), (DDDGG) (SEQ ID NO: 82),
(DDDKK) (SEQ ID NO: 83), (DDDPP) (SEQ ID NO: 84),
(DDDRR) (SEQ ID NO: 85), (DDDSS) (SEQ ID NO: 86),
(DDDTT) (SEQ ID NO: 87), (EEEDD) (SEQ ID NO: 88),
(EEEGG) (SEQ ID NO: 89), (EEEKK) (SEQ ID NO: 90)
(EEEPP) (SEQ ID NO: 91), (EEERR) (SEQ ID NO: 92),
(EEESS) (SEQ ID NO: 93), (EEETT) (SEQ ID NO: 94),
(GGGDD) (SEQ ID NO: 95), (GGGEE) (SEQ ID NO: 96),
(GGGKK) (SEQ ID NO: 97), (GGGPP) (SEQ ID NO: 98),
(GGGRR) (SEQ ID NO: 99), (KKKDD) (SEQ ID NO: 100),
(KKKEE) (SEQ ID NO: 101), (KKKGG) (SEQ ID NO: 102),
(KKKPP) (SEQ ID NO: 103), (KKKRR) (SEQ ID NO: 104),
(KKKSS) (SEQ ID NO: 105), (KKKTT) (SEQ ID NO: 106),
(PPPDD) (SEQ ID NO: 107), (PPPEE) (SEQ ID NO: 108),
(PPPGG) (SEQ ID NO: 109), (PPPKK) (SEQ ID NO: 110),
(PPPRR) (SEQ ID NO: 111), (PPPSS) (SEQ ID NO: 112),
(PPPTT) (SEQ ID NO: 113), (RRRDD) (SEQ ID NO: 114),
(RRREE) (SEQ ID NO: 115), (RRRGG) (SEQ ID NO: 116),
(RRRKK) (SEQ ID NO: 117), (RRRPP) (SEQ ID NO: 118),
(RRRSS) (SEQ ID NO: 119), (RRRTT) (SEQ ID NO: 120),
(SSSDD) (SEQ ID NO: 121), (SSSEE) (SEQ ID NO: 122),
(SSSGG) (SEQ ID NO: 123), (SSSKK) (SEQ ID NO: 124),
(SSSPP) (SEQ ID NO: 125), (SSSRR) (SEQ ID NO: 126),
(SSSTT) (SEQ ID NO: 127), (TTTDD) (SEQ ID NO: 128),
(TTTEE) (SEQ ID NO: 129), (TTTGG) (SEQ ID NO: 130),
(TTTKK) (SEQ ID NO: 131), (TTTPP) (SEQ ID NO: 132),
(TTTRR) (SEQ ID NO: 133), (TTTSS) (SEQ ID NO: 134).

TABLE 2-continued

Accessory polypeptides containing two different types of aminoacids (DDDDEEE) (SEQ ID NO: 135), (DDDDGGG) (SEQ ID NO: 136), (DDDDKKK) (SEQ ID NO: 137), (DDDDPPP), (SEQ ID NO: 138), (DDDDRRR) (SEQ ID NO: 139), (DDDDSSS) (SEQ ID NO: 140), (DDDDTTT) (SEQ ID NO: 141), (EEEEDDD) (SEQ ID NO: 142), (EEEEGGG) (SEQ ID NO: 143), (EEEEKKK) (SEQ ID NO: 144), (EEEEPPP) (SEQ ID NO: 145), (EEEERRR) (SEQ ID NO: 146), (EEEESSS) (SEQ ID NO: 147), (EEEETTT) (SEQ ID NO: 148), (KKKKDDD) (SEQ ID NO: 149), (KKKKEEE) (SEQ ID NO: 150), (KKKKGGG) (SEQ ID NO: 151), (KKKKPPP) (SEQ ID NO: 152), (KKKKRRR) (SEQ ID NO: 153), (KKKKSSS) (SEQ ID NO: 154), (KKKKTTT) (SEQ ID NO: 155), (PPPPDDD) (SEQ ID NO: 156), (PPPPEEE) (SEQ ID NO: 157), (PPPPGGG) (SEQ ID NO: 158), (PPPPKKK) (SEQ ID NO: 159), (PPPPRRR) (SEQ ID NO: 160), (PPPPSSS) (SEQ ID NO: 161), (PPPTTT) (SEQ ID NO: 162), (RRRRDDD) (SEQ ID NO: 163), (RRRREEE) (SEQ ID NO: 164), (RRRRGGG) (SEQ ID NO: 165), (RRRRKKK) (SEQ ID NO: 166), (RRRRPPP) (SEQ ID NO: 167), (RRRRSSS) (SEQ ID NO: 168), (RRRRTTT) (SEQ ID NO: 169), (SSSSDDD) (SEQ ID NO: 170), (SSSSEEE) (SEQ ID NO: 171), (SSSSGGG) (SEQ ID NO: 172), (SSSSKKK) (SEQ ID NO: 173), (SSSSPPP) (SEQ ID NO: 174), (SSSSRRR) (SEQ ID NO: 175), (SSSSTTT) (SEQ ID NO: 176), (TTTTDDD) (SEQ ID NO: 177), (TTTTEEE) (SEQ ID NO: 178), (TTTTGGG) (SEQ ID NO: 179), (TTTTKKK) (SEQ ID NO: 180), (TTTTPPP) (SEQ ID NO: 181), (TTTTRRR) (SEQ ID NO: 182), (TTTTSSS) (SEQ ID NO: 183).

(DE)n, (DG)n, (DK)n, (DP)n, (DR)n, (DS)n, (DT)n,
(ED)n, (EG)n, (EK)n, (EP)n, (ER)n, (ES)n, (ET)n,
(GD)n, (GE)n, (GK)n, (GP)n, (GR)n, (GS)n, (GT)n,
(KD)n, (KE)n, (KG)n, (KP)n, (KR)n, (KS)n, (KT)n,
(PD)n, (PE)n, (PG)n, (PK)n, (PR)n, (PS)n, (PT)n,
(RD)n, (RE)n, (RG)n, (RK)n, (RP)n, (RS)n, (RT)n,
(SD)n, (SE)n, (SG)n, (SK)n, (SP)n, (SR)n, (ST)n,
(TD)n, (TE)n, (TG)n, (TK)n, (TP)n, (TR)n, (TS)n.
(DEE)n, (DGG)n, (DKK)n, (DPP)n, (DRR)n, (DSS)n,
(DTT)n, (EDD)n, (EGG)n, (EKK)n, (EPP)n, (ERR)n,
(ESS)n, (ETT)n, (GDD)n, (GEE)n, (GKK)n, (GPP)n,
(GRR)n, (GSS)n, (GTT)n, (KDD)n, (KEE)n, (KGG)n,
(KPP)n, (KRR)n, (KSS)n, (KTT)n, (PDD)n, (PEE)n,
(PGG)n, (PKK)n, (PRR)n, (PSS)n, (PTT)n, (RDD)n,
(REE)n, (RGG)n, (RKK)n, (RPP)n, (RSS)n, (RTT)n,
(SDD)n, (SEE)n, (SGG)n, (SKK)n, (SPP)n, (SRR)n,
(STT)n, (TDD)n, (TEE)n, (TGG)n, (TKK)n, (TPP)n,
(TRR)n, (TSS)n.

(DDE)n, (DDG)n, (DDK)n, (DDP)n, (DDR)n, (DDS)n,
(DDT)n, (EED)n, (EEG)n, (EEK)n, (EEP)n, (EER)n,
(EES)n, (EET)n, (GGD)n, (GGE)n, (GGK)n, (GGP)n,
(GGR)n, (GGS)n, (GGT)n, (KKD)n, (KKE)n, (KKG)n,
(KKP)n, (KKR)n, (KKS)n, (KKT)n, (PPD)n, (PPE)n,
(PPG)n, (PPK)n, (PPR)n, (PPS)n, (PPT)n, (RRD)n,
(RRE)n, (RRG)n, (RRK)n, (RRP)n, (RRS)n, (RRT)n,
(SSD)n, (SSE)n, (SSG)n, (SSK)n, (SSP)n, (SSR)n,
(SST)n, (TTD)n, (TTE)n, (TTG)n, (TTK)n, (TTP)n,
(TTR)n, (TTS)n.

(DDEE)n (SEQ ID NO: 184), (DDGG)n (SEQ ID NO: 185),
(DDKK)n (SEQ ID NO: 186), (DDPP)n (SEQ ID NO: 187),
(DDRR)n (SEQ ID NO: 188), (DDSS)n (SEQ ID NO: 189),
(DDTT)n (SEQ ID NO: 190), (EEDD)n (SEQ ID NO: 191),
(EEGG)n (SEQ ID NO: 192), (EEKK)n (SEQ ID NO: 193),
(EEPP)n (SEQ ID NO: 194), (EERR)n (SEQ ID NO: 195),
(EESS)n (SEQ ID NO: 196), (EETT)n (SEQ ID NO: 197),
(GGDD)n (SEQ ID NO: 198), (GGEE)n (SEQ ID NO: 199),
(GGKK)n (SEQ ID NO: 200), (GGPP)n (SEQ ID NO: 201),
(GGRR)n (SEQ ID NO: 202), (GGSS)n (SEQ ID NO: 203),
(GGTT)n (SEQ ID NO: 204), (KKDD)n (SEQ ID NO: 205),
(KKEE)n (SEQ ID NO: 206), (KKGG)n (SEQ ID NO: 207),
(KKPP)n (SEQ ID NO: 208), (KKRR)n (SEQ ID NO: 209),
(KKSS)n (SEQ ID NO: 210), (KKTT)n (SEQ ID NO: 211),

TABLE 2-continued

Accessory polypeptides containing two different types of aminoacids (PPDD)n (SEQ ID NO: 212), (PPEE)n (SEQ ID NO: 213), (PPGG)n (SEQ ID NO: 214), (PPKK)n (SEQ ID NO: 215), (PPRR)n (SEQ ID NO: 216), (PPSS)n (SEQ ID NO: 217), (PPTT)n (SEQ ID NO: 218), (RRDD)n (SEQ ID NO: 219), (RREE)n (SEQ ID NO: 220), (RRGG)n (SEQ ID NO: 221), (RRKK)n (SEQ ID NO: 222), (RRPP)n (SEQ ID NO: 223), (RRSS)n (SEQ ID NO: 224), (RRTT)n (SEQ ID NO: 225), (SSDD)n (SEQ ID NO: 226), (SSEE)n (SEQ ID NO: 227), (SSGG)n (SEQ ID NO: 228), (SSKK)n (SEQ ID NO: 229), (SSPP)n (SEQ ID NO: 230), (SSRR)n (SEQ ID NO: 231), (SSTT)n (SEQ ID NO: 232), (TTDD)n (SEQ ID NO: 233), (TTEE)n (SEQ ID NO: 234), (TTGG)n (SEQ ID NO: 235), (TTKK)n (SEQ ID NO: 236), (TTPP)n (SEQ ID NO: 237), (TTRR)n (SEQ ID NO: 238), (TTSS)n (SEQ ID NO: 239), (DDDEE)n (SEQ ID NO: 81), (DDDGG)n (SEQ ID NO: 82), (DDDKK)n (SEQ ID NO: 83), (DDDPP)n (SEQ ID NO: 84), (DDDRR)n (SEQ ID NO: 85), (DDDSS)n (SEQ ID NO: 86), (DDDTT)n (SEQ ID NO: 87), (EEEDD)n (SEQ ID NO: 88), (EEEGG)n (SEQ ID NO: 89), (EEEKK)n (SEQ ID NO: 90), (EEEPP)n (SEQ ID NO: 91), (EEERR)n (SEQ ID NO: 92), (EEESS)n (SEQ ID NO: 93), (EEETT)n (SEQ ID NO: 94), (GGGDD)n (SEQ ID NO: 95), (GGGEE)n (SEQ ID NO: 96), (GGGKK)n (SEQ ID NO: 97), (GGGPP)n (SEQ ID NO: 98), (GGGRR)n (SEQ ID NO: 99), (GGGSS)n (SEQ ID NO: 240), (GGGTT)n (SEQ ID NO: 241), (KKKDD)n (SEQ ID NO: 100), (KKKEE)n (SEQ ID NO: 101), (KKKGG)n (SEQ ID NO: 102), (KKKPP)n (SEQ ID NO: 103), (KKKRR)n (SEQ ID NO: 104), (KKKSS)n (SEQ ID NO: 105), (KKKTT)n (SEQ ID NO: 106), (PPPDD)n (SEQ ID NO: 107), (PPPEE)n (SEQ ID NO: 108), (PPPGG)n (SEQ ID NO: 109), (PPPKK)n (SEQ ID NO: 110), (PPPRR)n (SEQ ID NO: 111), (PPPSS)n (SEQ ID NO: 112), (PPPTT)n (SEQ ID NO: 113), (RRRDD)n (SEQ ID NO: 114), (RRREE)n (SEQ ID NO: 115), (RRRGG)n (SEQ ID NO: 116), (RRRKK)n (SEQ ID NO: 117), (RRRPP)n (SEQ ID NO: 118), (RRRSS)n (SEQ ID NO: 119), (RRRTT)n (SEQ ID NO: 120), (SSSDD)n (SEQ ID NO: 121), (SSSEE)n (SEQ ID NO: 122), (SSSGG)n (SEQ ID NO: 123), (SSSKK)n (SEQ ID NO: 124), (SSSPP)n (SEQ ID NO: 125), (SSSRR)n (SEQ ID NO: 126), (SSSTT)n (SEQ ID NO: 127), (TTTDD)n (SEQ ID NO: 128), (TTTEE)n (SEQ ID NO: 129), (TTTGG)n (SEQ ID NO: 130), (TTTKK)n (SEQ ID NO: 131), (TTTPP)n (SEQ ID NO: 132), (TTTRR)n (SEQ ID NO: 133),(TTTSS)n (SEQ ID NO: 134).
(DDEEE)n (SEQ ID NO: 242), (DDGGG)n (SEQ ID NO: 243), (DDKKK)n (SEQ ID NO: 244), (DDPPP)n (SEQ ID NO: 245), (DDRRR)n (SEQ ID NO: 246), (DDSSS)n (SEQ ID NO: 247), (DDTTT)n (SEQ ID NO: 248), (EEDDD)n (SEQ ID NO: 249), (EEGGG)n (SEQ ID NO: 250), (EEKKK)n (SEQ ID NO: 251), (EEPPP)n (SEQ ID NO: 252), (EERRR)n (SEQ ID NO: 253), (EESSS)n (SEQ ID NO: 254), (EETTT)n (SEQ ID NO: 255), (GGDDD)n (SEQ ID NO: 256), (GGEEE)n (SEQ ID NO: 257), (GGKKK)n (SEQ ID NO: 258), (GGPPP)n (SEQ ID NO: 259), (GGRRR)n (SEQ ID NO: 260),(GGSSS)n (SEQ ID NO: 261), (GGTTT)n (SEQ ID NO: 262), (KKDDD)n (SEQ ID NO: 263), (KKEEE)n (SEQ ID NO: 264), (KKGGG)n (SEQ ID NO: 265), (KKPPP)n (SEQ ID NO: 266), (KKRRR)n (SEQ ID NO: 267), (KKSSS)n (SEQ ID NO: 268), (KKTTT)n (SEQ ID NO: 269), (PPDDD)n (SEQ ID NO: 270),(PPEEE)n (SEQ ID NO: 271), (PPGGG)n (SEQ ID NO: 272), (PPKKK)n (SEQ ID NO: 273), (PPRRR)n (SEQ ID NO: 274), (PPSSS)n (SEQ ID NO: 275),(PPTTT)n (SEQ ID NO: 276), (RRDDD)n (SEQ ID NO: 277), (RREEE)n (SEQ ID NO: 278), (RRGGG)n (SEQ ID NO: 279), (RRKKK)n (SEQ ID NO: 280), (RRPPP)n (SEQ ID NO: 281), (RRSSS)n (SEQ ID NO: 282), (RRTTT)n (SEQ ID NO: 283), (SSDDD)n (SEQ ID NO: 284), (SSEEE)n (SEQ ID NO: 285), (SSGGG)n (SEQ ID NO: 286), (SSPPP)n (SEQ ID NO: 287), (SSKKK)n (SEQ ID NO: 288), (SSRRR)n (SEQ ID NO: 289), (SSTTT)n (SEQ ID NO: 290), (TTDDD)n (SEQ ID NO: 291), (TTEEE)n (SEQ ID NO: 292), (TTGGG)n (SEQ ID NO: 293), (TTKKK)n (SEQ ID NO: 294), (TTPPP)n (SEQ ID NO: 295), (TTRRR)n (SEQ ID NO: 296), (TTSSS)n (SEQ ID NO: 297).
(DDDEEE)n (SEQ ID NO: 298), (DDDGGG)n (SEQ ID NO: 299),(DDDKKK)n (SEQ ID NO: 300), (DDDPPP)n (SEQ ID NO: 301), (DDDRRR)n (SEQ ID NO: 302), (DDDSSS)n (SEQ ID NO: 303), (DDDTTT)n (SEQ ID NO: 304),(EEEDDD)n (SEQ ID NO: 305), (EEEGGG)n (SEQ ID NO: 306), (EEEKKK)n (SEQ ID NO: 307), (EEEPPP)n (SEQ ID NO: 308), (EEERRR)n (SEQ ID NO: 309), (EEESSS)n (SEQ ID NO: 310), (EEETTT)n (SEQ ID NO: 311), (GGGDDD)n (SEQ ID NO: 312), (GGGEEE)n (SEQ ID NO: 313), (GGGKKK)n (SEQ ID NO: 314), (GGGPPP)n (SEQ ID NO: 315), (GGGRRR)n (SEQ ID NO: 316), (GGGSSS)n (SEQ ID NO: 317), (GGGTTT)n (SEQ ID NO: 318), (KKKDDD)n (SEQ ID NO: 319), (KKKEEE)n (SEQ ID NO: 320), (KKKGGG)n (SEQ ID NO: 321), (KKKPPP)n (SEQ ID NO: 322), (KKKRRR)n (SEQ ID NO: 323), (KKKSSS)n (SEQ ID NO: 324), (KKKTTT)n (SEQ ID NO: 325), (PPPDDD)n (SEQ ID NO: 326), (PPPEEE)n (SEQ ID NO: 327), (PPPGGG)n (SEQ ID NO: 328), (PPPKKK)n (SEQ ID NO: 329), (PPPRRR)n (SEQ ID NO: 330), (PPPSSS)n (SEQ ID NO: 331), (PPPTTT)n (SEQ ID NO: 332), (RRRDDD)n (SEQ ID NO: 332), (RRREEE)n (SEQ ID NO: 333), (RRRGGG)n (SEQ ID NO: 334), (RRRKKK)n (SEQ ID NO: 335), (RRRPPP)n (SEQ ID NO: 336), (RRRSSS)n (SEQ ID NO: 337), (RRRTTT)n (SEQ ID NO: 338), (SSSDDD)n (SEQ ID NO: 339), (SSSEEE)n (SEQ ID NO: 340), (SSSGGG)n (SEQ ID NO: 341), (SSSKKK)n (SEQ ID NO: 342), (SSSPPP)n (SEQ ID NO: 343), (SSSRRR)n (SEQ ID NO: 344), (SSSTTT)n (SEQ ID NO: 345), (TTTDDD)n (SEQ ID NO: 346), (TTTEEE)n (SEQ ID NO: 347), (TTTGGG)n (SEQ ID NO: 348), (TTTKKK)n (SEQ ID NO: 349), (TTTPPP)n (SEQ ID NO: 350), (TTTRRR)n (SEQ ID NO: 351), (TTTSSS)n (SEQ ID NO: 352).
(DDDDEEE)n (SEQ ID NO: 135), (DDDDGGG)n (SEQ ID NO: 136), (DDDDKKK)n (SEQ ID NO: 137), (DDDDPPP)n (SEQ ID NO: 138), (DDDDRRR)n (SEQ ID NO: 139), (DDDDSSS)n (SEQ ID NO: 140), (DDDDTTT)n (SEQ ID NO: 141), (EEEEDDD)n (SEQ ID NO: 142), (EEEEGGG)n (SEQ ID NO: 143), (EEEEKKK)n (SEQ ID NO: 144), (EEEEPPP)n (SEQ ID NO: 145),(EEEERRR)n (SEQ ID NO: 146), (EEEESSS)n (SEQ ID NO: 147), (EEEETTT)n (SEQ ID NO: 148), (GGGGDDD)n (SEQ ID NO: 353), (GGGGEEE)n (SEQ ID NO: 354), (GGGGKKK)n (SEQ ID NO: 355), (GGGGPPP)n (SEQ ID NO: 356), (GGGGRRR)n (SEQ ID NO: 357), (GGGGSSS)n (SEQ ID NO: 358), (GGGGTTT)n (SEQ ID NO: 359), (KKKKDDD)n (SEQ ID NO: 149), (KKKKEEE)n (SEQ ID NO: 150), (KKKKGGG)n (SEQ ID NO: 151), (KKKKPPP)n (SEQ ID NO: 152), (KKKKRRR)n(SEQ ID NO: 153), (KKKKSSS)n (SEQ ID NO: 154), (KKKKTTT)n (SEQ ID NO: 155), (PPPPDDD)n (SEQ ID NO: 156), (PPPPEEE)n (SEQ ID NO: 157), (PPPPGGG)n (SEQ ID NO: 158), (PPPKKKK)n (SEQ ID NO: 159), (PPPPRRR)n (SEQ ID NO: 160), (PPPPSSS)n (SEQ ID NO: 161), (PPPPTTT)n (SEQ ID NO: 360), (RRRRDDD)n (SEQ ID NO: 163), (RRRREEE)n (SEQ ID NO: 164), (RRRRGGG)n (SEQ ID NO: 165), (RRRRKKK)n (SEQ ID NO: 166), (RRRRPPP)n (SEQ ID NO: 167), (RRRRSSS)n (SEQ ID NO: 168), (RRRRTTT)n (SEQ ID NO: 169), (SSSSDDD)n (SEQ ID NO: 170), (SSSSEEE)n (SEQ ID NO: 171), (SSSSGGG)n (SEQ ID NO: 172), (SSSSKKK)n (SEQ ID NO: 173), (SSSSPPP)n (SEQ ID NO: 174), (SSSSRRR)n (SEQ ID NO: 175), (SSSSTTT)n (SEQ ID NO: 176), (TTTTDDD)n (SEQ ID NO: 177), (TTTTEEE)n (SEQ ID NO: 178), (TTTTGGG)n (SEQ ID NO: 179), (TTTTKKK)n (SEQ ID NO: 180), (TTTTPPP)n (SEQ ID NO: 181), (TTTTRRR)n (SEQ ID NO: 182), (TTTTSSS)n (SEQ ID NO: 183)

(SSSESSESSSSSE)n (SEQ ID NO: 361), (GGEGEGGGE)n (SEQ ID NO: 362)

Accessory Polypeptide Sequences that are Related to Human Sequences

Accessory polypeptide sequences that are closely related to sequences of human proteins are desirable in some applications as they carry a diminished risk of inducing an immune reaction in patients. Such sequences may be used as accessory polypeptides in some embodiments of the present invention. The relationship of accessory sequences to human sequences can be assessed by determining the abundance of partial sequences of said accessory polypeptide sequences in the human genome. Table 3 shows an example for the occurrence of 8mer partial sequences. Accessory polypeptides can be cleaved into a small number of 8mer sequences as illustrated in Table 3, where the 8mer sequences are underlined. For each 8mer sequence one can perform a data base search to identify the number of matches in a data base of human protein sequences. A similar analysis can be performed for 7mers, 9mers, 10mers, 11mers, or longer oligomers. One can perform database analysis searching for complete matches of these partial sequences or one can search for close homologues. Thus, the stringency of the search can be tuned to allow a ranking of accessory polypeptides for their relationship to human proteins. The data in Table 3 shows several examples of accessory polypepdes which are chosen based on their close relatedness to human proteins. Of particular interest are accessory proteins of sequence (SSSSE)n (SEQ ID NO: 53), (SSSSSSE)n (SEQ ID NO: 55), and (SSSSESSSSSE)n (SEQ ID NO: 51) where all 8mer subsequences can be found in several human proteins.

TABLE 3

Ranking sequences by their relatedness to human protein sequences.

| Repeating unit | 8 mers | SEQ ID NOS | hits in human genome |
|---|---|---|---|
| SSESSSSESSSE (SEQ ID NO: 49) | SSESSSSESSSESSESSSSESSSE | 364 | 4 |
| | SSESSSSESSSESSESSSSESSSE | 364 | 4 |
| | SSESSSSESSSESSESSSSESSSE | 364 | 4 |
| | SSESSSSESSSESSESSSSESSSE | 364 | 10 |
| | SSESSSSESSSESSESSSSESSSE | 364 | 25 |
| | SSESSSSESSSESSESSSSESSSE | 364 | 3 |
| | SSESSSSESSSESSESSSSESSSE | 364 | 5 |
| | SSESSSSESSSESSESSSSESSSE | 364 | 9 |
| | SSESSSSESSSESSESSSSESSSE | 364 | 9 |
| | SSESSSSESSSESSESSSSESSSE | 364 | 12 |
| | SSESSSSESSSESSESSSSESSSE | 364 | 0 |
| | SSESSSSESSSESSESSSSESSSE | 364 | 0 |
| SSSSE (SEQ ID NO: 53) | SSSSESSSSESSSSE | 365 | 10 |
| | SSSSESSSSESSSSE | 365 | 9 |
| | SSSSESSSSESSSSE | 365 | 4 |
| | SSSSESSSSESSSSE | 365 | 4 |
| | SSSSESSSSESSSSE | 365 | 4 |
| SSSSSE (SEQ ID NO: 54) | SSSSSESSSSSESSSSSE | 366 | 14 |
| | SSSSSESSSSSESSSSSE | 366 | 10 |
| | SSSSSESSSSSESSSSSE | 366 | 9 |
| | SSSSSESSSSSESSSSSE | 366 | 25 |
| | SSSSSESSSSSESSSSSE | 366 | 0 |
| | SSSSSESSSSSESSSSSE | 366 | 0 |
| SSSSSSE (SEQ ID NO: 55) | SSSSSSESSSSSSE | 367 | 58 |
| | SSSSSSESSSSSSE | 367 | 14 |
| | SSSSSSESSSSSSE | 367 | 10 |
| | SSSSSSESSSSSSE | 367 | 9 |
| | SSSSSSESSSSSSE | 367 | 25 |
| | SSSSSSESSSSSSE | 367 | 43 |
| | SSSSSSESSSSSSE | 367 | 21 |

TABLE 3-continued

Ranking sequences by their relatedness to human protein sequences.

| Repeating unit | 8 mers | SEQ ID NOS | hits in human genome |
|---|---|---|---|
| SSSSSSESSSSE (SEQ ID NO: 368) | SSSSSSESSSSESSSSSESSSSE | 369 | 58 |
| | SSSSSSESSSSESSSSSESSSSE | 369 | 14 |
| | SSSSSSESSSSESSSSSESSSSE | 369 | 10 |
| | SSSSSSESSSSESSSSSESSSSE | 369 | 9 |
| | SSSSSSESSSSESSSSSESSSSE | 369 | 4 |
| | SSSSSSESSSSESSSSSESSSSE | 369 | 4 |
| | SSSSSSESSSSESSSSSESSSSE | 369 | 4 |
| | SSSSSSESSSSESSSSSESSSSE | 369 | 10 |
| | SSSSSSESSSSESSSSSESSSSE | 369 | 9 |
| | SSSSSSESSSSESSSSSESSSSE | 369 | 25 |
| | SSSSSSESSSSESSSSSESSSSE | 369 | 43 |
| | SSSSSSESSSSESSSSSESSSSE | 369 | 21 |

Unstructured Recombinant Polymers (URPs):

One aspect of the present invention is the use of unstructured recombinant polymers (URPs) as accessory polypeptides. The subject URPs are particularly useful for generating recombinant proteins of therapeutic and/or diagnostic value. The subject URPs exhibit one or more following features.

The subject URPs comprise amino acid sequences that typically share commonality with denatured peptide sequences under physiological conditions. URP sequences typically behave like denatured peptide sequences under physiological conditions. URP sequences lack well defined secondary and tertiary structures under physiological conditions. A variety of methods have been established in the art to ascertain the second and tertiary structures of a given polypeptide. For example, the secondary structure of a polypeptide can be determined by CD spectroscopy in the "far-UV" spectral region (190-250 nm). Alpha-helix, beta-sheet, and random coil structures each give rise to a characteristic shape and magnitude of CD spectra. Secondary structure can also be ascertained via certain computer programs or algorithms such as the Chou-Fasman algorithm (Chou, P. Y., et al. (1974) *Biochemistry*, 13: 22245). For a given URP sequence, the algorithm can predict whether there exists some or no secondary structure at all. In general, URP sequences will have spectra that resemble denatured sequences due to their low degree of secondary and tertiary structure. Where desired, URP sequences can be designed to have predominantly denatured conformations under physiological conditions. URP sequences typically have a high degree of conformational flexibility under physiological conditions and they tend to have large hydrodynamic radii (Stokes' radius) compared to globular proteins of similar molecular weight. As used herein, physiological conditions refer to a set of conditions including temperature, salt concentration, pH that mimic those conditions of a living subject. A host of physioloigcally relevant conditions for use in in vitro assays have been established. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al. (1989) supra and hence is not detailed herein. Physiologically relevant temperature ranges from about 25° C. to about 38° C., and preferably from about 30° C. to about 37° C.

The subject URPs can be sequences with low immunogenicity. Low immunogenicity can be a direct result of the conformational flexibility of URP sequences. Many antibodies recognize so-called conformational epitopes in protein antigens. Conformational epitopes are formed by regions of the protein surface that are composed of multiple discontinuous amino acid sequences of the protein antigen. The precise folding of the protein brings these sequences into a well-defined special configuration that can be recognized by antibodies. Preferred URPs are designed to avoid formation of conformational epitopes. For example, of particular interest are URP sequences having a low tendency to adapt compactly folded conformations in aqueous solution. In particular, low immunogenicity can be achieved by choosing sequences that resist antigen processing in antigen presenting cells, choosing sequences that do not bind MHC well and/or by choosing sequences that are derived from human sequences.

The subject URPs can be sequences with a high degree of protease resistance. Protease resistance can also be a result of the conformational flexibility of URP sequences. Protease resistance can be designed by avoiding known protease recognition sites. Alternatively, protease resistant sequences can be selected by phage display or related techniques from random or semi-random sequence libraries. Where desired for special applications, such as slow release from a depot protein, serum protease cleavage sites can be built into an URP. Of particular interest are URP sequences with high stability (e.g., long serum half-life, less prone to cleavage by proteases present in bodily fluid) in blood.

The subject URP can also be characterized by the effect in that wherein upon incorporation of it into a biologically active polypeptide, the modified polypeptide exhibits a longer serum half-life and/or higher solubility as compared to an unmodified biologically active polypeptide. The subject URP can be of any length necessary to effect (a) extension of serum half-life of a protein comprising the URP; (b) an increase in solubility of the resulting protein; (c) an increased resistance to protease; and/or (d) a reduced immunogenicity of the resulting protein that comprises the URP. Typically, the subject URP has about 30, 40, 50, 60, 70, 80, 90, 100, 150, 200, 300, 400 or more contiguous amino acids. When incorporated into a protein, the URP can be fragmented such that the resulting protein contains multiple URPs, or multiple fragments of URPs. Some or all of these individual URP sequences may be shorter that 40 amino acids as long as the combined length of all URP sequences in the resulting protein is at least 40 amino acids. Preferably, the resulting protein has a combined length of URP sequences exceeding 40, 50, 60, 70, 80, 90, 100, 150, 200 or more amino acids.

URPs may have an isoelectric point (pI) of 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5 or even 13.0.

In general, URP sequences are rich in hydrophilic amino acids and contain a low percentage of hydrophobic or aromatic amino acids. Suitable hydrophilic residues include but are not limited to glycine, serine, aspartate, glutamate, lysine, arginine, and threonine. Hydrophobic residues that are less favored in construction of URPs include tryptophan, phenylalanine, tyrosine, leucine, isoleucine, valine, and methionine. URP sequences can be rich in glycine but URP sequences can also be rich in the amino acids glutamate, aspartate, serine, threonine, alanine or proline. Thus the predominant amino acid may be G, E, D, S, T, A or P. The inclusion of proline residues tends to reduce sensitivity to proteolytic degradation.

The inclusion of hydrophilic residues typically increases URPs' solubility in water and aqueous media under physiological conditions. As a result of their amino acid composition, URP sequences have a low tendency to form aggregates in aqueous formulations and the fusion of URP sequences to other biologically active polypeptides or peptides tends to enhance their solubility and reduce their tendency to form aggregates, which is a separate mechanism to reduce immunogenicity.

URP sequences can be designed to avoid certain amino acids that confer undesirable properties to the biologically active polypeptide. For instance, one can design URP sequences to contain few or none of the following amino acids: cysteine (to avoid disulfide formation and oxidation), methionine (to avoid oxidation), asparagine and glutamine (to avoid desamidation).

Glycine-Rich URPs:

In one embodiment, the subject URP comprises a glycine rich sequence (GRS). For example, glycine can be present predominantly such that it is the most prevalent residues present in the sequence of interest. In another example, URP sequences can be designed such that glycine residues constitute at least about 30%, 35%, 40%, 45%, 50%, 55%, 60%, 65%, 70%, 75%, 80%, 85%, 90%, 95%, 100% of the total amino acids. URPs can also contain 100% glycines. In yet another example, the URPs contain at least 30% glycine and the total concentration of tryptophan, phenylalanine, tyrosine, valine, leucine, and isoleucine is less then 20%. In still another example, the URPs contain at least 40% glycine and the total concentration of tryptophan, phenylalanine, tyrosine, valine, leucine, and isoleucine is less then 10%. In still yet another example, the URPs contain at least about 50% glycine and the total concentration of tryptophan, phenylalanine, tyrosine, valine, leucine, and isoleucine is less then 5%.

The length of GRS can vary between about 5 amino acids and 200 amino acids or more. For example, the length of a single, contiguous GRS can contain 5, 10, 15, 20, 25, 30, 35, 40, 45, 50, 55, 60, 70, 80, 90, 100, 120, 140, 160, 180, 200, 240, 280, 320 or 400 or more amino acids. GRS may comprise glycine residues at both ends.

GRS can also have a significant content of other amino acids, for example Ser, Thr, Ala, or Pro. GRS can contain a significant fraction of negatively charged amino acids including but not limited to Asp and Glu. GRS can contain a significant fraction of positively charged amino acids including but not limited to Arg or Lys. Where desired, URPs can be designed to contain only a single type of amino acid (i.e., Gly or Glu), sometimes only a few types of amino acid, e.g., two to five types of amino acids (e.g., selected from G, E, D, S, T, A and P), in contrast to typical proteins and typical linkers which generally are composed of most of the twenty types of amino acids. URPs may contain negatively charged residues (Asp, Glu) in 30, 25, 20, 15, 12, 10, 9, 8, 7, 6, 5, 4, 3, 2, or 1 percent of the amino acids positions.

Typically, the subject GRS-containing URP has about 30, 40, 50, 60, 70, 80, 90, 100, or more contiguous amino acids. When incorporated into a biologically active polypeptide, the URP can be fragmented such that the resulting modified polypeptide contains multiple URPs, or multiple fragments of URPs. Some or all of these individual URP sequences may be shorter that 40 amino acids as long as the combined length of all URP sequences in the resulting polypeptide is at least 30 amino acids. Preferably, the resulting polypeptide has a combined length of URP sequences exceeding 40, 50, 60, 70, 80, 90, 100, or more amino acids.

The GRS-containing URPs are of particular interest due to, in part, the increased conformational freedom of glycine-containing peptides. Denatured peptides in solution have a high degree of conformational freedom. Most of that conformational freedom is lost upon binding of said peptides to a target like a receptor, an antibody, or a protease. This loss of entropy needs to be offset by the energy of interaction between the peptide and its target. The degree of conformational freedom of a denatured peptide is dependent on its amino acid sequences. Peptides containing many amino acids with small side chains tend to have more conformational freedom than peptides that are composed of amino acids with larger side chains. Peptides containing the amino acid glycine have particularly large degrees of freedom. It has been estimated that glycine-containing peptide bonds have about 3.4 times more entropy in solution as compared to corresponding alanine-containing sequences (D'Aquino, J. A., et al. (1996) *Proteins*, 25: 143-56). This factor increases with the number of glycine residues in a sequence. As a result, such peptides tend to lose more entropy upon binding to targets, which reduces their overall ability to interact with other proteins as well as their ability to adopt defined three-dimensional structures. The large conformational flexibility of glycine-peptide bonds is also evident when analyzing Ramachandran plots of protein structures where glycine peptide bonds occupy areas that are rarely occupied by other peptide bonds (Venkatachalam, C. M., et al. (1969) *Annu Rev Biochem*, 38: 45-82). Stites et al. studied a database of 12,320 residues from 61 nonhomologous, high resolution crystal structures to determine the phi, psi conformational preferences of each of the 20 amino acids. The observed distributions in the native state of proteins are assumed to also reflect the distributions found in the denatured state. The distributions were used to approximate the energy surface for each residue, allowing the calculation of relative conformational entropies for each residue relative to glycine. In the most extreme case, replacement of glycine by proline, conformational entropy changes will stabilize the native state relative to the denatured state by −0.82+/−0.08 kcal/mol at 20° C. (Stites, W. E., et al. (1995) *Proteins*, 22: 132). These observations confirm the special role of glycine among the 20 natural amino acids.

In designing the subject URPs, natural or non-natural sequences can be used. For example, a host of natural sequences containing high glycine content is provided in Table 4, Table 5, Table 6, and Table 7. One skilled in the art may adopt any one of the sequences as an URP, or modify the sequences to achieve the intended properties. Where immunogenicity to the host subject is of concern, it is preferable to design GRS-containing URRs based on glycine rich sequences derived from the host. Preferred GRS-containing URPs are sequences from human proteins or sequences that share substantial homology to the corresponding glycine rich sequences in the reference human proteins.

TABLE 4

Structural analysis of proteins that contain glycine rich sequences

| PDB file | Protein function | Glycine rich sequences |
|---|---|---|
| 1K3V | Porcine Parvovirus capsid | sgggggggggrgagg (SEQ ID NO: 370) |
| 1FPV | Feline Panleukopenia Virus | tgsgngsggggggsgg (SEQ ID NO: 371) |
| 1IJS | CpV strain D, mutant A300d | tgsgngsggggggsgg (SEQ ID NO: 371) |
| 1MVM | Mvm (strain I) virus | ggsggggsgggg (SEQ ID NO: 372) |

TABLE 5

Open reading frames encoding GRS with 300 or more glycine residues

| Accession | Organism | Gly (%) | GRS length | Gene length | Predicted Function |
|---|---|---|---|---|---|
| NP_974499 | *Arabidopsis thaliana* | 64 | 509 | 579 | unknown |
| ZP_00458077 | *Burkholderia cenocopacia* | 66 | 373 | 518 | putative lipoprotein |
| XP_477841 | *Oryza sativa* | 74 | 371 | 422 | unknown |
| NP_910409 | *Oryza sativa* | 75 | 368 | 400 | putative cell-wall precursor |
| NP_610660 | *Drosophila melanogaster* | 66 | 322 | 610 | transposable element |

TABLE 6

Examples of human GRS

| Accession | Gly (%) | GRS length | Gene length | Hydrophobics | Predicted Function |
|---|---|---|---|---|---|
| NP_000217 | 62 | 135 | 622 | yes | keratin 9 |
| NP_631961 | 61 | 73 | 592 | yes | TBP-associated factor 15 isoform 1 |
| NP_476429 | 65 | 70 | 629 | yes | keratin 3 |
| NP_000418 | 70 | 66 | 316 | yes | loricrin, cell envelope |
| NP_056932 | 60 | 66 | 638 | yes | cytokeratin 2 |

TABLE 7

Additional examples of human GRS

| Accession | Sequences | Number of amino acids |
|---|---|---|
| NP_006228 | GPGGGGGPGGGGGPGGGGPGGGGGGPGGGGGG PGGG | 37 |
| NP_787059 | GAGGGGGGGGGGGGGSGGGGGGGGAGAGGAGAG | 33 |
| NP_009060 | GGGSGSGGAGGGSGGGSGSGGGGGGAGGGGGG | 32 |
| NP_031393 | GDGGGAGGGGGGGGSGGGGSGGGGGGG | 27 |
| NP_005850 | GSGSGSGGGGGGGGGGGGGSGGGGGG | 25 |
| NP_061856 | GGGRGGRGGGRGGGGRGGGRGGG | 23 |
| NP_787059 | GAGGGGGGGGGGGGGSGGGGGGGGAGAGGAGAG | 33 |
| NP_009060 | GGGSGSGGAGGGSGGGSGSGGGGGGAGGGGGG | 32 |
| NP_031393 | GDGGGAGGGGGGGGSGGGGSGGGGGGG | 27 |
| NP_115818 | GSGGSGGSGGGPGPGPGGGGG | 21 |
| XP_376532 | GEGGGGGGEGGGAGGGSG | 18 |
| NP_065104 | GGGGGGGGDGGG | 12 |

(Table 7 discloses SEQ ID NOS 373-378, 374-376 and 379-381, respectively, in order of appearance.
GGGSGSGGAGGGSGGGSGSGGGGGGAGGGGGGSSGGGSGTAGGHSG
(SEQ ID NO: 382)

POU domain, class 4, transcription factor 1 [Homo sapiens]
GPGGGGGPGGGGPGGGGPGGGGGGPGGGGGPGGG
(SEQ ID NO: 373)

YEATS domain containing 2 [Homo sapiens]
GGSGAGGGGGGGGGGSGSGGGGSTGGGGGTAGGG
(SEQ ID NO: 383)

AT rich interactive domain 1B (SWI1-like) isoform 3; BRG1-binding protein ELD/OSA1; Eld (eyelid)/Osa protein [Homo sapiens]
GAGGGGGGGGGGGGGSGGGGGGGGAGAGGAGAG
(SEQ ID NO: 374)

AT rich interactive domain 1B (SWI1-like) isoform 2; BRG1-binding protein ELD/OSA1; Eld (eyelid)/Osa protein [Homo sapiens]
GAGGGGGGGGGGGGGSGGGGGGGGAGAGGAGAG
(SEQ ID NO: 374)

AT rich interactive domain 1B (SWI1-like) isoform 1; BRG1-binding protein ELD/OSA1; Eld (eye lid)/Osa protein [Homo sapiens]
GAGGGGGGGGGGGGGSGGGGGGGGAGAGGAGAG
(SEQ ID NO: 374)

purine-rich element binding protein A; purine-rich single-stranded DNA-binding protein alpha; transcriptional activator protein PUR-alpha [Homo sapiens]
GHPGSGSGSGGGGGGGGGGGGSGGGGGGAPGG
(SEQ ID NO: 384)

regulatory factor X1; trans-acting regulatory factor 1; enhancer factor C; MHC class II regulatory factor RFX [Homo sapiens]
GGGGSGGGGGGGGGGGGGSGSTGGGGSGAG
(SEQ ID NO: 385)

bromo domain-containing protein disrupted in leukemia [Homo sapiens
GGRGRGRGRGSRGRGGGGTRGRGRGGGRG

TABLE 7-continued

Additional examples of human GRS (SEQ ID NO: 386)

unknown protein [Homo sapiens]
GSGGSGGSGGGPGPGPGGGGGPSGSGSGPG
(SEQ ID NO: 387)

PREDICTED: hypothetical protein XP_059256 [Homo sapiens]
GGGGGGGGGGGRGGGGRGGGRGGGGEGGG
(SEQ ID NO: 388)

zinc finger protein 281; ZNP-99 transcription factor [Homo sapiens]
GGGGTGSSGGSGSGGGGSGGGGGGGSSG
(SEQ ID NO: 389)

RNA binding protein (autoantigenic, hnRNP-associated with lethal yellow) short isoform; RNA-binding protein (autoantigenic); RNA-binding protein (autoantigenic, hnRNP-associated with lethal yellow) [Homo sapiens]
GDGGGAGGGGGGGSGGGGSGGGGGGG
(SEQ ID NO: 376)

signal recognition particle 68 kDa [Homo sapiens]
GGGGGGGSGGGGSGGGGSGGGRGAGG (SEQ ID NO: 390)

KIAA0265 protein [Homo sapiens]
GGGAAGAGGGGSGAGGGSGGSGGRGTG (SEQ ID NO: 391)

engrailed homolog 2; Engrailed-2 [Homo sapiens]
GAGGGRGGGAGGEGGASGAEGGGGAGG (SEQ ID NO: 392)

RNA binding protein (autoantigenic, hnRNP-associated with lethal yellow) long isoform; RNA-binding protein (autoantigenic); RNA-binding protein (autoantigenic, hnRNP-associated with lethal yellow) [Homo sapiens]
GDGGGAGGGGGGGSGGGGSGGGGGGG (SEQ ID NO: 376)

androgen receptor; dihydrotestosterone receptor [Homo sapiens]
GGGGGGGGGGGGGGGGGGGGGEAG (SEQ ID NO: 393)

homeo box D11; homeo box 4F; Hox-4.6, mouse, homolog of; homeobox protein Hox-D11 [Homo sapiens]
GGGGGGSAGGGSSGGGPGGGGGAGG (SEQ ID NO: 394)

frizzled 8; frizzled (Drosophila) homolog 8 [Homo sapiens]
GGGGGPGGGGGGGPGGGGGPGGGG (SEQ ID NO: 395)

ocular development-associated gene [Homo sapiens]
GRGGAGSGGAGSGAAGGTGSSGGGG (SEQ ID NO: 396)

homeo box B3; homeo box 2G; homeobox protein Hox-B3 [Homo sapiens]
GGGGGGGGGGGSGGSGGGGGGGGG (SEQ ID NO: 397)

chromosome 2 open reading frame 29 [Homo sapiens]
GGSGGGRGGASGPGSGSGGPGGPAG (SEQ ID NO: 398)

DKFZP564F0522 protein [Homo sapiens]
GGHHGDRGGGRGGRGGRGGRGGRAG (SEQ ID NO: 399)

PREDICTED: similar to Homeobox even-skipped homolog protein 2 (EVX-2) [Homo sapiens]
GSRGGGGGGGGGGGGGGGAGAGGG (SEQ ID NO: 400)

ras homolog gene family, member U; Ryu GTPase; Wnt-1 responsive Cdc42 homolog; 2310026M05Rik; GTP-binding protein like 1; CDC42-like GTPase [Homo sapiens]
GGRGGRGPGEPGGRGRAGGAEGRG (SEQ ID NO: 401)

scratch 2 protein; transcriptional repressor scratch 2; scratch (drosophila homolog) 2, zinc TABLE 7-continued Additional examples of human GRS finger protein [Homo sapiens]
GGGGGDAGGSGDAGGAGGRAGRAG (SEQ ID NO: 402)

nucleolar protein family A, member 1; GAR1 protein
[Homo sapiens]
GGGRGGRGGGRGGGRGGGRGGG (SEQ ID NO: 378)

keratin 1; Keratin-1; cytokeratin 1; hair alpha
protein [Homo sapiens]
GGSGGGGGGSSGGRGSGGGSSGG (SEQ ID NO: 403)

hypothetical protein FLJ31413 [Homo sapiens]
GSGPGTGGGGSGSGGGGGSGGG (SEQ ID NO: 404)

one cut domain, family member 2; onecut 2
[Homo sapiens]
GARGGGSGGGGGGGGGGGGPG (SEQ ID NO: 405)

POU domain, class 3, transcription factor 2
[Homo sapiens]
GGGGGGGGGGGGGGGGGGGDG (SEQ ID NO: 406)

PREDICTED: similar to THO complex subunit 4
(Tho4) (RNA and export factor binding protein 1)
(REF1-I) (Ally of AML-1 and LEF-1) (Aly/REF)
[Homo sapiens]
GGTRGGTRGGTRGGDRGRGRGAG (SEQ ID NO: 407)

PREDICTED: similar to THO complex subunit 4 (Tho4)
(RNA and export factor binding protein 1) (REF1-I)
(Ally of AML-1 and LEF-1) (Aly/REF) [Homo sapiens]
GGTRGGTRGGTRGGDRGRGRGAG (SEQ ID NO: 407)

POU domain, class 3, transcription factor 3 [Homo
sapiens]
GAGGGGGGGGGGGGGAGGGGGG (SEQ ID NO: 408)

nucleolar protein family A, member 1; GAR1 protein
[Homo sapiens]
GGGRGGRGGGRGGGRGGGRGGG (SEQ ID NO: 378)

fibrillarin; 34-kD nucleolar scleroderma antigen;
RNA, U3 small nucleolar interacting protein 1
[Homo sapiens]
GRGRGGGGGGGGGGGGRGGGG (SEQ ID NO: 409)

zinc finger protein 579 [Homo sapiens]
GRGRGRGRGRGRGRGRGRGGAG (SEQ ID NO: 410)

calpain, small subunit 1; calcium-activated
neutral proteinase; calpain, small polypeptide;
calpain 4, small subunit (30K); calcium-dependent
protease, small subunit [Homo sapiens]
GAGGGGGGGGGGGGGGGGGGG (SEQ ID NO: 411)

keratin 9 [Homo sapiens]
GGGSGGGHSGGSGGGHSGGSGG (SEQ ID NO: 412)

forkhead box D1; forkhead-related activator 4;
Forkhead, drosophila, homolog-like 8; forkhead
(Drosophila)-like 8 [Homo sapiens]
GAGAGGGGGGGAGGGGSAGSG (SEQ ID NO: 413)

PREDICTED: similar to RIKEN cDNA C230094B15 [Homo
sapiens]
GGPGTGSGGGGAGTGGGAGGPG (SEQ ID NO: 414)

GGGGGGGGGAGGAGGAGSAGGG (SEQ ID NO: 415)

cadherin 22 precursor; ortholog of rat PB-cadherin
[Homo sapiens]
GGDGGGSAGGGAGGGSGGGAG (SEQ ID NO: 416)

AT-binding transcription factor 1; AT motif-
binding factor 1 [Homo sapiens]
GGGGGSGGGGGGGGGGGGG (SEQ ID NO: 417)

eomesodermin; t box, brain, 2; eomesodermin

TABLE 7-continued

Additional examples of human GRS (Xenopus laevis) homolog [Homo sapiens]
GPGAGAGSGAGGSSGGGGGPG (SEQ ID NO: 418)

phosphatidylinositol transfer protein, membrane-
associated 2; PYK2 N-terminal domain-interacting
receptor 3; retinal degeneration B alpha 2
(Drosophila) [Homo sapiens]
GGGGGGGGGGGSSGGGGSSGG (SEQ ID NO: 419)

sperm associated antigen 8 isoform 2; sperm
membrane protein 1 [Homo sapiens]
GSGSGPGPGSGPGSGPGHGSG (SEQ ID NO: 420)

PREDICTED: RNA binding motif protein 27 [Homo
sapiens]
GPGPGPGPGPGPGPGPGPG (SEQ ID NO: 421)

AP1 gamma subunit binding protein 1 isoform 1;
gamma-synergin; adaptor-related protein complex 1
gamma subunit-binding protein 1 [Homo sapiens]
GAGSGGGGAAGAGAGSAGGGG (SEQ ID NO: 422)

AP1 gamma subunit binding protein 1 isoform 2;
gamma-synergin; adaptor-related protein complex 1
gamma subunit-binding protein 1 [Homo sapiens]
GAGSGGGGAAGAGAGSAGGGG (SEQ ID NO: 422)

ankyrin repeat and sterile alpha motif domain
containing 1; ankyrin repeat and SAM domain
containing 1 [Homo sapiens]
GGGGGGGSGGGGGGSGGGGGG (SEQ ID NO: 423)

methyl-CpG binding domain protein 2 isoform 1
[Homo sapiens]
GRGRGRGRGRGRGRGRGRGRG (SEQ ID NO: 424)

triple functional domain (PTPRF interacting)
[Homo sapiens]
GGGGGGGSGGSGGGGGSGGGG (SEQ ID NO: 425)

forkhead box D3 [Homo sapiens
GGEEGGASGGGPGAGSGSAGG (SEQ ID NO: 426)

sperm associated antigen 8 isoform 1; sperm
membrane protein 1 [Homo sapiens]
GSGSGPGPGSGPGSGPGHGSG (SEQ ID NO: 420)

methyl-CpG binding domain protein 2 testis-
specific isoform [Homo sapiens]
GRGRGRGRGRGRGRGRGRG (SEQ ID NO: 424)

cell death regulator aven; programmed cell death
12 [Homo sapiens]
GGGGGGGDGGGRRGRGRGRG (SEQ ID NO: 427)

regulator of nonsense transcripts 1; delta
helicase; up-frameshift mutation 1 homolog (S.
cerevisiae); nonsense mRNA reducing factor 1;
yeast Upf1p homolog [Homo sapiens]
GGPGGPGGGGAGGPGGAGAG (SEQ ID NO: 428)

small conductance calcium-activated potassium
channel protein 2 isoform a; apamin-sensitive
small-conductance Ca2+-activated potassium
channel [Homo sapiens]
GTGGGGSTGGGGGGGSGHG (SEQ ID NO: 429)

SRY (sex determining region Y)-box 1; SRY-related
HMG-box gene 1 [Homo sapiens]
GPAGAGGGGGGGGGGGGG (SEQ ID NO: 430)

transcription factor 20 isoform 2; stromelysin-1
platelet-derived growth factor-responsive element
binding protein; stromelysin 1 PDGF-responsive
element-binding protein; SPRE-binding protein;
nuclear factor SPBP [Homo sapiens]
GGTGGSSGSSGSGSGGGRRG (SEQ ID NO: 431)

TABLE 7-continued

Additional examples of human GRS transcription factor 20 isoform 1; stromelysin-1 platelet-derived growth factor-responsive element binding protein; stromelysin 1 PDGF-responsive element-binding protein; SPRE-binding protein; nuclear factor SPBP [Homo sapiens]
GGTGGSSGSSGSGSGGGRRG (SEQ ID NO: 431)

Ras-interacting protein 1 [Homo sapiens]
GSGTGTTGSSGAGGPGTPGG (SEQ ID NO: 432)

BMP-2 inducible kinase isoform b [Homo sapiens]
GGSGGGAAGGGAGGAGAGAG (SEQ ID NO: 433)

BMP-2 inducible kinase isoform a [Homo sapiens]
GGSGGGAAGGGAGGAGAGAG (SEQ ID NO: 433)

forkhead box C1; forkhead-related activator 3; Forkhead, drosophila, homolog-like 7; forkhead (Drosophila)-like 7; iridogoniodysgenesis type 1 [Homo sapiens]
GSSGGGGGGAGAAGGAGGAG (SEQ ID NO: 434)

splicing factor p54; arginine-rich 54 kDa nuclear protein [Homo sapiens]
GPGPSGGPGGGGGGGGGGGG (SEQ ID NO: 435)

v-maf musculoaponeurotic fibrosarcoma oncogene homolog; Avian musculoaponeurotic fibrosarcoma (MAF) protooncogene; v-mafmusculoaponeurotic fibrosarcoma (avian) oncogene homolog [Homo sapiens]
GGGGGGGGGGGGGGAAGAGG (SEQ ID NO: 436)

small nuclear ribonucleoprotein D1 polypeptide 16 kDa; snRNP core protein D1; Sm-D autoantigen; small nuclear ribonucleoprotein D1 polypeptide (16 kD) [Homo sapiens]
GRGRGRGRGRGRGRGRGRGG (SEQ ID NO: 410)

hypothetical protein H41 [Homo sapiens]
GSAGGSSGAAGAAGGGAGAG (SEQ ID NO: 437)

URPs Containing Non-Glycine Residues (NGR):

The sequences of non-glycine residues in these GRS can be selected to optimize the properties of URPs and hence the biologically active polypeptides that contain the desired URPs. For instance, one can optimize the sequences of URPs to enhance the selectivity of the resulting modified polypeptide for a particular tissue, specific cell type or cell lineage. For example, one can incorporate protein sequences that are not ubiquitously expressed, but rather are differentially expressed in one or more of the body tissues including heart, liver, prostate, lung, kidney, bone marrow, blood, skin, bladder, brain, muscles, nerves, and selected tissues that are affected by diseases such as infectious diseases, autoimmune disease, renal, neronal, cardiac disorders and cancers. One can employ sequences representative of a specific developmental origin, such as those expressed in an embryo or an adult, during ectoderm, endoderm or mesoderm formation in a multi-cellular organism. One can also utilize sequence involved in a specific biological process, including but not limited to cell cycle regulation, cell differentiation, apoptosis, chemotaxis, cell motility and cytoskeletal rearrangement. One can also utilize other non-ubiquitously expressed protein sequences to direct the resulting protein to a specific subcellular locations: extracellular matrix, nucleus, cytoplasm, cytoskeleton, plasma and/or intracellular membranous structures which include but are not limited to coated pits, Golgi apparatus, endoplasmic reticulum, endosome, lysosome, and mitochondria.

A variety of these tissue-specific, cell-type specific, sub-cellular location specific sequences are known and available from numerous protein databases. Such selective URP sequences can be obtained by generating libraries of random or semi-random URP sequences, injecting them into animals or patients, and determining sequences with the desired tissue selectivity in tissue samples. Sequence determination can be performed by mass spectrometry. Using similar methods one can select URP sequences that facilitate oral, buccal, intestinal, nasal, thecal, peritoneal, pulmonary, rectal, or dermal uptake.

Of particular interest are URP sequences that contain regions that are relatively rich in the positively charged amino acids arginine or lysine which favor cellular uptake or transport through membranes. URP sequences can be designed to contain one or several protease-sensitive sequences. Such URP sequences can be cleaved once the product of the invention has reached its target location. This cleavage may trigger an increase in potency of the pharmaceutically active domain (pro-drug activation) or it may enhance binding of the cleavage product to a receptor. URP sequences can be designed to carry excess negative charges by introducing aspartic acid or glutamic acid residues. Of particular interest are URP that contain greater than 5%, greater than 6%, 7%, 8%, 9%, 10%, 15%, 30% or more glutamic acid and less than 2% lysine or arginine. Such URPs carry an excess negative charge and as a result they have a tendency to adopt open conformations due to electrostatic repulsion between individual negative charges of the peptide. Such an excess negative charge leads to an effective increase in their hydrodynamic radius and as a result it can lead to reduced kidney clearance of such molecules. Thus, one can modulate the effective net charge and hydrodynamic radius of a URP sequence by controlling the frequency and distribution of negatively charged amino acids in the URP sequences. Most tissues and surfaces in a human or animal carry excess negative charges. By designing URP sequences to carry excess negative charges one can minimize non-specific interactions between the resulting modified polypeptide comprising the URP and various surfaces such as blood vessels, healthy tissues, or various receptors.

URPs may have a repetitive amino acid sequence of the format (Motif)$_x$ in which a sequence motif forms a direct repeat (ie ABCABCABCABC) or an inverted repeat (ABC-CBAABCCBA) and the number of these repeats can be 2, 3, 4, 5, 6, 7, 8, 9, 10, 12, 14, 16, 18, 20, 22, 24, 26, 28, 30, 35, 40, 50 or more. URPs or the repeats inside URPs often contain only 1, 2, 3, 4, 5 or 6 different types of amino acids. URPs typically consist of repeats of human amino acid sequences that are 4, 5, 6, 7, 8, 9, 10, 11, 12, 13, 14, 15, 16, 17, 18, 19, 20, 22, 24, 26, 28, 30, 32, 34, 36 or more amino acids long, but URPs may also consist of non-human amino acid sequences that are 20, 22, 24, 26, 28, 30, 32, 34 36, 38 40, 42, 44, 46, 48, 50 amino acids long.

URPs Derived from Human Sequences:

URPs can be derived from human sequences. The human genome contains many subsequences that are rich in one particular amino acid. Of particular interest are such amino acid sequences that are rich in a hydrophilic amino acid like serine, threonine, glutamate, aspartate, or glycine. Of particular interest are such subsequences that contain few hydrophobic amino acids. Such subsequences are predicted to be unstructured and highly soluable in aqeuous solution. Such human subsequences can be modified to further improve their utility. For example, dentin sialophosphoprotein contains a 670-amino acid subsequence in which 64% of the residues are serine and most other positions are hydrophilic amino acids such as aspartate, asparagines, and glutamate. The sequence is extremely repetitive and as a result it has a low information content. One can directly use subsequences of such a human protein. Where desired, one can modify the sequence in a way that preserves its overall character but which makes it more suitable for pharmaceutical applications. Examples of sequences that are related to dentin sialophosphoprotein are (SSD)n (SEQ ID NO: 438), (SSDSSN)n (SEQ ID NO: 439), (SSE)n (SEQ ID NO: 440), where n is between about 4 and 200.

The use of sequences from human proteins is particularly desirable in design of URPs with reduced immunogenicity in a human subject. A key step for eliciting an immune response to a foreign protein is the presentation of peptide fragments of said protein by MHC class II receptors. These MHCII-bound fragments can then be detected by T cell receptors, which triggers the proliferation of T helper cells and initiates an immune response. The elimination of T cell epitopes from pharmaceutical proteins has been recognized as a means to reduce the risk of eliciting an immune reaction (Stickler, M., et al. (2003) *J Immunol Methods,* 281: 95-108). MHCII receptors typically interact with an epitope having e.g., a 9-amino acid long region of the displayed peptides. Thus, one can reduce the risk of eliciting an immune response to a protein in patients if all or most of the possible 9mer subsequences of the protein can be found in human proteins and if so, these sequences and repeats of these sequences will not be recognized by the patient as foreign sequences. One can incorporate human sequences into the design of URP sequences by oligomerizing or concatenating human sequences that have suitable amino acid compositions. These can be direct repeats or inverted repeats or mixtures of different repeats. For instance one can oligomerize the sequences shown in table 5. Such oligomers have reduced risk of being immunogenic. However, the junction sequences between the monomer units can still contain T cell epitopes that can trigger an immune reaction. One can further reduce the risk of eliciting an immune response by designing URP sequences based on multiple overlapping human sequences. An URP sequence may be designed as an oligomer based on multiple human sequences such that each 9mer subsequences of the oligomer can be found in a human protein. In these designs, every 9-mer subsequence is a human sequence. For example an URP sequence may be based on three human sequences. It is also possible to design URP sequences based on a single human sequences such that all possible 9mer subsequences in the oligomeric URP sequences occur in the same human protein. Non-oligomeric URP sequences can be designed based on human proteins as well. The primary conditions are that all 9mer sub-sequences can be found in human sequences. The amino acid composition of the sequences preferably contains few hydrophobic residues. Of particular interest are URP sequences that are designed based on human sequences and that contain a large fraction of glycine residues.

Utilizing this or similar scheme, one can design a class of URPs that comprise repeat sequences with low immunogenicity to the host of interest. Host of interest can be any animals, including vertebrates and invertebrates. Preferred hosts are mammals such as primates (e.g. chimpanzees and humans), cetaceans (e.g. whales and dolphins), chiropterans (e.g. bats), perrisodactyls (e.g. horses and rhinoceroses), rodents (e.g. rats), and certain kinds of insectivores such as shrews, moles and hedgehogs. Where human is selected as the host, the URPs typically contain multiple copies of the repeat sequences or units, wherein the majority of segments comprising about 6 to about 15 contiguous amino acids are present in one or more native human proteins. One can also design URPs in which the majority of segments comprising between about 9 to about 15 contiguous amino acids are found in one or more native human proteins. As used herein, majority of the segments refers to more than about 50%, preferably 60%, preferably 70%, preferably 80%, preferably 90%, preferably 100%. Where desired, each of the possible segments between about 6 to 15 amino acids, preferably between about 9 to 15 amino acids within the repeating units are present in one or more native human proteins. The URPs can comprise multiple repeating units or sequences, for example having 2, 3, 4, 5, 6, 7, 8, 9, 10, or more repeating units.

Design of URPs that are Substantially Free of Human T-Cell Epitopes:

URP sequences can be designed to be substantially free of epitopes recognized by human T cells. For instance, one can synthesize a series of semi-random sequences with amino acid compositions that favor denatured, unstructured conformations and evaluate these sequences for the presence of human T cell epitopes and whether they are human sequences. Assays for human T cell epitopes have been described (Stickler, M., et al. (2003) *J Immunol Methods,* 281: 95-108). Of particular interest are peptide sequences that can be oligomerized without generating T cell epitopes or non-human sequences. This can be achieved by testing direct repeats of these sequences for the presence of T-cell epitopes and for the occurrence of 6 to 15-mer and in particular 9-mer subsequences that are not human. An alternative is to evaluate multiple peptide sequences that can be assembled into repeating units as described in the previous section for the assembly of human sequences. Another alternative is to design URP sequences that result in low scores using epitope prediction algorithms like TEPITOPE (Sturniolo, T., et al. (1999) *Nat Biotechnol,* 17: 555-61). Another approach to avoiding T-cell epitopes is to avoid amino acids that can serve as anchor residues during peptide display on MHC, such as M, I, L, V, F. Hydrophobic amino acids and positively charged amino acids can frequently serve as such anchor residues and minimizing their frequency in a URP sequences reduces the chance of generating T-cell epitopes and thus eliciting an immune reaction. The selected URPs generally contain subsequences that are found in at least one human protein, and have a lower content of hydrophobic amino acids.

URP sequences can be designed to optimize protein production. This can be achieved by avoiding or minimizing repetitiveness of the encoding DNA. URP sequences such as poly-glycine may have very desirable pharmaceutical properties but their manufacturing can be difficult due to the high GC-content of DNA sequences encoding for GRS and due to the presence of repeating DNA sequences that can lead to recombination.

As noted above, URP sequences can be designed to be highly repetitive at the amino acid level. As a result the URP sequences have very low information content and the risk of eliciting an immune reaction can be reduced.

Non-limiting examples of URPs containing repeating amino acids are: poly-glycine, poly-glutamic acid, poly-aspartic acid, poly-serine, poly-threonine, $(GX)_n$ (SEQ ID NO: 441) where G is glycine and X is serine, aspartic acid, glutamic acid, threonine, or proline and n is at least 20, $(GGX)_n$ (SEQ ID NO: 442) where X is serine, aspartic acid, glutamic acid, threonine, or proline and n is at least 13, $(GGGX)_n$ (SEQ ID NO: 443) where X is serine, aspartic acid, glutamic acid, threonine, or proline and n is at least 10, $(GGGGX)_n$ (SEQ ID NO: 444) where X is serine, aspartic acid, glutamic acid, threonine, or proline and n is at least 8, $(G_zX)_n$ (SEQ ID NO: 445) where X is serine, aspartic acid, glutamic acid, threonine, or proline, n is at least 15, and z is between 1 and 20.

The number of these repeats can be any number between 10 and 100. Products of the invention may contain URP sequences that are semi-random sequences. Examples are semi-random sequences containing at least 30, 40, 50, 60 or 70% glycine in which the glycines are well dispersed and in which the total concentration of tryptophan, phenylalanine, tyrosine, valine, leucine, and isoleucine is less then 70, 60, 50, 40, 30, 20, or 10% when combined. A preferred semi-random URP sequence contains at least 40% glycine and the total concentration of tryptophan, phenylalanine, tyrosine, valine, leucine, and isoleucine is less then 10%. A more preferred random URP sequence contains at least 50% glycine and the total concentration of tryptophan, phenylalanine, tyrosine, valine, leucine, and isoleucine is less then 5%. URP sequences can be designed by combining the sequences of two or more shorter URP sequences or fragments of URP sequences. Such a combination allows one to better modulate the pharmaceutical properties of the product containing the URP sequences and it allows one to reduce the repetitiveness of the DNA sequences encoding the URP sequences, which can improve expression and reduce recombination of the URP encoding sequences.

URP sequences can be designed and selected to possess several of the following desired properties: a) high genetic stability of the coding sequences in the production host, b) high level of expression, c) low (predicted/calculated) immunogenicity, d) high stability in presence of serum proteases and/or other tissue proteases, e) large hydrodynamic radius under physiological conditions. One exemplary approach to obtain URP sequences that meet multiple criteria is to construct a library of candidate sequences and to identify from the library the suitable subsequences. Libraries can comprise random and/or semi-random sequences. Of particular utility are codon libraries, which is a library of DNA molecules that contains multiple codons for the identical amino acid residue. Codon randomization can be applied to selected amino acid positions of a certain type or to most or all positions. True codon libraries encode only a single amino acid sequence, but they can easily be combined with amino acid libraries, which is a population of DNA molecules encoding a mixture of (related or unrelated) amino acids at the same residue position. Codon libraries allow the identification of genes that have relatively low repetitiveness at the DNA level but that encode highly repetitive amino acid sequences. This is useful because repetitive DNA sequences tend to recombine, leading to instability. One can also construct codon libraries that encode limited amino acid diversity. Such libraries allow introduction of a limited number of amino acids in some positions of the sequence while other positions allow for codon variation but all codons encode the same amino acid. One can synthesize partially random oligonucleotides by incorporating mixtures of nucleotides at the same position during oligonucleotide synthesis. Such partially random oligonucleotides can be fused by overlap PCR or ligation-based approaches. In particular, one can multimerize semi-random oligonucleotides that encode glycine-rich sequences. These oligonucleotides can differ in length and sequences and codon usage. As a result, one obtains a library of candidate URP sequences. Another method to generate libraries is to synthesize a starting sequence and subsequently subject said sequence to partial randomization. This can be done by cultivation of the gene encoding the URP sequences in a mutator strain or by amplification of the encoding gene under mutagenic conditions (Leung, D., et al. (1989) Technique, 1: 11-15). URP sequences with desirable properties can be identified from libraries using a variety of methods. Sequences that have a high degree of genetic stability can be enriched by cultivating the library in a production host. Sequences that are unstable will accumulate mutations, which can be identified by DNA sequencing. Variants of URP sequences that can be expressed at high level can be identified by screening or selection using multiple protocols known to someone skilled in the art. For instance one can cultivate multiple isolates from a library and compare expression levels. Expression levels can be measured by gel analysis, analytical chromatography, or various ELISA-based methods. The determination of expression levels of individual sequence variants can be facilitated by fusing the library of candidate URP sequences to sequence tags like myc-tag, His-tag, HA-tag. Another approach is to fuse the library to an enzyme or other reporter protein like green fluorescent protein. Of particular interest is the fusion of the library to a selectable marker like beta-lactamase or kanamycin-acyl transferase. One can use antibiotic selection to enrich for variants with high level of expression and good genetic stability. Variants with good protease resistance can be identified by screening for intact sequences after incubation with proteases. An effective way to identify protease-resistant URP sequences is bacterial phage display or related display methods. Multiple systems have been described where sequences that undergo rapid proteolysis can be enriched by phage display. These methods can be easily adopted to enrich for protease resistant sequences. For example, one can clone a library of candidate URP sequences between an affinity tag and the pIII protein of M13 phage. The library can then be exposed to proteases or protease-containing biological samples like blood or lysosomal preparations. Phage that contain protease-resistant sequences can be captured after protease treatment by binding to the affinity tag. Sequences that resist degradation by lysosomal preparations are of particular interest because lysosomal degradation is a key step during antigen presentation in dendritic and other antigen presenting cells. Phage display can be utilized to identify candidate URP sequences that do not bind to a particular immune serum in order to identify URP sequences with low immunogenicity. One can immunize animals with a candidate URP sequence or with a library of URP sequences to raise antibodies against the URP sequences in the library. The resulting serum can then be used for phage panning to remove or identify sequences that are recognized by antibodies in the resulting immune serum. Other methods like bacterial display, yeast display, ribosomal display can be utilized to identify variants of URP sequences with desirable properties. Another approach is the identification of URP sequences of interest by mass spectrometry. For instance, one can incubate a library of candidate URP sequences with a protease or biological sample of interest and identify sequences that resist degradation by mass spectrometry. In a similar approach one can identify URP sequences that facilitate oral uptake. One can feed a mixture of candidate URP sequences to animals or humans and identify variants with the highest transfer or uptake efficiency across some tissue barrier (ie dermal, etc) by mass spectrometry. In a similar way, one can identify URP sequences that favor other uptake mechanisms like pulmonary, intranasal, rectal, transdermal delivery. One can also identify URP sequences that favor cellular uptake or URP sequences that resist cellular uptake.

URP sequences can be designed by combining URP sequences or fragments of URP sequences that were designed by any of the methods described above. In addition, one can apply semi-random approaches to optimize sequences that were designed based on the rules described above. Of particular interest is codon optimization with the goal of improving expression of the enhanced polypeptides and to improve the genetic stability of the encoding gene in the production hosts. Codon optimization is of particular importance for URP sequences that are rich in glycine or that have very repetitive amino acid sequences. Codon optimization can be performed using computer programs (Gustafsson, C., et al. (2004) *Trends Biotechnol*, 22: 346-53), some of which minimize ribosomal pausing (Coda Genomics Inc.). When designing URP sequences one can consider a number of properties. One can minimize the repetitiveness in the encoding DNA sequences. In addition, one can avoid or minimize the use of codons that are rarely used by the production host (ie the AGG and AGA arginine codons and one Leucine codon in *E. coli*) DNA sequences that have a high level of glycine tend to have a high GC content that can lead to instability or low expression levels. Thus, when possible it is preferred to choose codons such that the GC-content of URP-encoding sequence is suitable for the production organism that will be used to manufacture the URP.

URP encoding genes can be made in one or more steps, either fully synthetically or by synthesis combined with enzymatic processes, such as restriction enzyme-mediated cloning, PCR and overlap extension. URP accessory polypeptides can be constructed such that the URP accessory polypeptide-encoding gene has low repetitiveness while the encoded amino acid sequence has a high degree of repetitiveness. As a first step, one constructs a library of relatively short URP sequences. This can be a pure codon library such that each library member has the same amino acid sequence but many different coding sequences are possible. To facilitate the identification of well-expressing library members one can construct the library as fusion to a reporter protein. Examples of suitable reporter genes are green fluorescent protein, luciferace, alkaline phosphatase, beta-galactosidase. By screening one can identify short URP sequences that can be expressed in high concentration in the host organism of choice. Subsequently, one can generate a library of random URP dimers and repeat the screen for high level of expression. Dimerization can be performed by ligation, overlap extension or similar cloning techniques. This process of dimerization and subsequent screening can be repeated multiple times until the resulting URP sequence has reached the desired length. Optionally, one can sequence clones in the library to eliminate isolates that contain undesirable sequences. The initial library of short URP sequences can allow some variation in amino acid sequence. For instance one can randomize some codons such that a number of hydrophilic amino acids can occur in said position. During the process of iterative multimerization one can screen library members for other characteristics like solubility or protease resistance in addition to a screen for high-level expression. Instead of dimerizing URP sequences one can also generate longer multimers. This allows one to faster increase the length of URP accessory polypeptides.

Many URP sequences contain particular amino acids at high fraction. Such sequences can be difficult to produce by recombinant techniques as their coding genes can contain repetitive sequences that are subject to recombination. Furthermore, genes that contain particular codons at very high frequencies can limit expression as the respective loaded tRNAs in the production host become limiting. An example is the recombinant production of GRS. Glycine residues are encoded by 4 triplets, GGG, GGC, GGA, and GGT. As a result, genes encoding GRS tend to have high GC-content and tend to be particularly repetitive. An additional challenge can result from codon bias of the production host. In the case of *E. coli*, two glycine codons, GGA and GGG, are rarely used in highly expressed proteins. Thus codon optimization of the gene encoding URP sequences can be very desirable. One can optimize codon usage by employing computer programs that consider codon bias of the production host (Gustafsson, C., et al. (2004) *Trends Biotechnol*, 22: 346-53). As an alternative, one can construct codon libraries where all members of the library encode the same amino acid sequence but where codon usage is varied. Such libraries can be screened for highly expressing and genetically stable members which are particularly suitable for the large-scale production of URP-containing products.

Multivalent Unstructured Recombinant Proteins (MURPs):

As noted above, the subject URPs are particularly useful as accessory polypeptides for the modification of biologically active polypeptides. Accordingly, the present invention provides proteins comprising one or more subject URPs. Such proteins are termed herein Multivalent Unstructured Recombinant Proteins (MURPs).

To construct MURPs, one or more URP sequences can be fused to the N-terminus or C-terminus of a protein or inserted in the middle of the protein, e.g., into loops of a protein or in between modules of the biologically active polypeptide of interest, to give the resulting modified polypeptide improved properties relative to the unmodified protein. The combined length of URP sequences that are attached to a protein can be 40, 50, 60, 70, 80, 90, 100, 150, 200 or more amino acids.

The subject MURPs exhibit one or more improved properties as detailed below.

Improved Half-Life:

Adding a URP sequences to a biologically active polypeptide can improve many properties of that protein. In particular, adding a long URP sequence can significantly increase the serum half-life of the protein. Such URPs typically contain amino acid sequences of at least about 40, 50, 60, 70, 80, 90, 100, 150, 200 or more amino acids.

The URPs can be fragmented such that the resulting protein contains multiple URPs, or multiple fragments of URPs. Some or all of these individual URP sequences may be shorter that 40 amino acids as long as the combined length of all URP sequences in the resulting protein is at least 30 amino acids. Preferably, the resulting protein has a combined length of URP sequences exceeding 40, 50, 60, 70, 80, 90, 100, 150, 200 or more amino acids. In one aspect, the fused URPS can increase the hydrodynamic radius of a protein and thus reduces its clearance from the blood by the kidney. The increase in the hydrodynamic radius of the resulting fusion protein relative to the unmodified protein can be detected by ultracentrifugation, size exclusion chromatography, or light scattering.

Improved Tissue Selectivity:

Increasing the hydrodynamic radius can also lead to reduced penetration into tissues, which can be exploited to minimize side effects of a biologically active polypeptide. It is well documented that hydrophilic polymers have a tendency to accumulate selectively in tumor tissue which is caused by the enhanced permeability and retention (EPR) effect. The underlying cause of the EPR effect is the leaky nature of tumor vasculature (McDonald, D. M., et al. (2002) *Cancer Res*, 62: 5381-5) and the lack of lymphatic drainage in tumor tissues. Therefore, the selectivity of biologically active polypeptides for tumor tissues can be enhanced by adding hydrophilic polymers. As such, the therapeutic index of a given biologically active polypeptide can be increased via incorporating the subject URPS.

Protection from Degradation and Reduced Immunogenicity:

Adding URP sequences can significantly improve the protease resistance of a protein. URP sequences themselves can be designed to be protease resistant and by attaching them to a protein one can shield that protein from the access of degrading enzymes. URP sequences can be added to biologically active polypeptides with the goal of reducing undesirable interactions of the protein with other receptors or surfaces. To achieve this, it can be beneficial to add the URP sequences to the biologically active polypeptide in proximity to the site of the protein that makes such undesirable contacts. In particular, one can add URP sequences to biologically active polypeptides with the goal of reducing their interactions with any component of the immune system to prevent an immune response against the product of the invention. Adding a URP sequence to a biologically active polypeptide can reduce interaction with pre-existing antibodies or B-cell receptors. Furthermore, the addition of URP sequences can reduce the uptake and processing of the product of the invention by antigen presenting cells. Adding one or more URP sequence to a protein is a preferred way of reducing its immunogenicity as it will suppress an immune response in many species allowing one to predict the expected immunogenicity of a product in patients based on animal data. Such species independent testing of immunogenicity is not possible for approaches that are based on the identification and removal of human T cell epitopes or sequences comparison with human sequences.

Interruption of T Cell Epitopes:

URP sequences can be introduced into proteins in order to interrupt T cell epitopes. This is particularly useful for proteins that combine multiple separate functional modules. The formation of T cell epitopes requires that peptide fragments of a protein antigen bind to MHC. MHC molecules interact with a short segment of amino acids typically 9 contiguous residues of the presented peptides. The direct fusion of different binding modules in a protein molecule can lead to T cell epitopes that span two neighboring domains. By separating the functional modules by URP accessory polypeptides prevents the generation of such module-spanning T cell epitopes. The insertion of URP sequences between functional modules can also interfere with proteolytic processing in antigen presenting cells, which will lead to an additional reduction of immunogenicity.

Improved Solubility:

Functional modules of a protein can have limited solubility. In particular, binding modules tend to carry hydrophobic residues on their surface, which can limit their solubility and can lead to aggregation. By spacing or flanking such functional modules with URP accessory polypeptides one can improve the overall solubility of the resulting product. This is in particular true for URP accessory polypeptides that carry a significant percentage of hydrophilic or charged residues. By separating functional modules with soluble URP modules one can reduce intramolecular interactions between these functional modules Improved pH Profile and Homogeneity of Product Charge:

URP sequences can be designed to carry an excess of negative or positive charges. As a result they confer an electrostatic field to any fusion partner which can be utilized to shift the pH profile of an enzyme or a binding interaction. Furthermore, the electrostatic field of a charged URP sequence can increase the homogeneity of pKa values of surface charges of a protein product, which leads to sharpened pH profiles of ligand interactions and to sharpened separations by isoelectric focusing or chromatofocusing.

Improved Purification Properties Due to Sharper Product pKa:

Each amino acid in solution by itself has a single, fixed pKa, which is the pH at which its functional groups are half protonated. In a typical protein you have many types of residues and due to proximity and protein breathing effects, they also change each other's effective pKa in variable ways. Because of this, at a wide range of pH conditions, typical proteins can adopt hundreds of differently ionized species, each with a different molecular weight and net charge, due to large numbers of combinations of charged and neutral amino acid residues. This is referred to as a broad ionization spectrum and makes the analysis (eg by mass spectrometry) and purification of such proteins more difficult.

PEG is uncharged and does not affect the ionization spectrum of the protein it is attached to, leaving it with a broad ionization spectrum. However, an URP with a high content of Gly and Glu in principle exist in only two states: neutral (—COOH) when the pH is below the pKa of Glutamate and negatively charged ($—COO^-$) when the pH is above the pKa of Glutamate. URP accessory polypeptides can form a single, homogeneously ionizated type of molecule and can yield a single mass in mass spectrometry.

Where desired, MURPs can be expressed as a fusion with an URP having a single type of charge (Glu) distributed at constant spacing through the URP accessory polypeptide. One may choose to incorporate 25-50 Glu residues per 20 kD of URP and all of these 25-50 residues would have very similar pKa.

In addition, adding 25-50 negative charges to a small protein like IFN, hGH or GCSF (with only 20 charged residues) will increase the charge homogeneity of the product and sharpen its isoelectric point, which will be very close to the pKa of free glutamate.

The increase in the homogeneity of the charge of the protein population has favorable processing properties, such as in ion exchange, isoelectric focusing, mass spec, etc. compared to traditional PEGylation.

Biologically Active Polypeptides

Suitable polypeptides that can be linked to the accessory polypeptide include all biologically active polypeptides exhibiting a binding specificity to a given target or another desired biological characteristic when used in vitro or in vivo. In particular, any protein of therapeutic or diagnostic interest can be modified by accessory polypeptides. Of particular interest are polypeptides for which modification of certain properties such as serum half-life or in vivo clearance is desirable. Such modification can be envisioned in the context of therapeutic applications, for example if one desires to prolong the half-life of an administered protein therapeutic drug. Modification with accessory polypeptides could also show utility in diagnostic applications, for example to reduce non-specific binding of a diagnostic protein or imaging agent to other molecules Biologically active polypeptides can include, but are not limited to cytokines, chemokines, lymphokines, ligands, receptors, hormones, enzymes, antibodies and antibody fragments, and growth factors. Examples of receptors include TNF type I receptor, IL-1 receptor type II, IL-1 receptor antagonist, IL-4 receptor and any chemically or genetically modified soluble receptors. Examples of enzymes include activated protein C, factor VII, collagenase (e.g., marketed by Advance Biofactures Corporation under the name Santyl); agalsidase-beta (e.g., marketed by Genzyme under the name Fabrazyme); domase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-β), interferon gamma (IFNγ), interferon gamma inducing factor I (IGIF), transforming growth factor beta (TGF-β), RANTES (regulated upon activation, normal T-cell expressed and presumably secreted), macrophage inflammatory proteins (e.g., MIP-1-α and MIP-1-β), Leishmania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT4), neurotrophin-5 (NT-5), glial cell line-derived neurotrophic factor (GDNF), ciliary neurotrophic factor (CNTF), TNF a type II receptor, erythropoietin (EPO), insulin and soluble glycoproteins e.g., gp120 and gp160 glycoproteins. The gp120 glycoprotein is a human immunodeficiency virus (HIV) envelope protein, and the gp160 glycoprotein is a known precursor to the gp120 glycoprotein.

By way of example, the following are several examples of biologically active polypeptides which may be suitable for modification according to the present invention.

In one embodiment, the biologically active polypeptide is GLP-1. GLP-1 is an approximately 30 amino acid polypeptide that is currently being investigated as a possible therapy for diabetes. GLP-1 suppresses glucagon release and increases insulin release. Both responses to GLP-1 result in a decrease in the serum concentration of glucose. GLP-1 is rapidly cleaved by dipeptidyl peptidase-4 in the body and as a result has an extremely short serum half-life, ~2 min. The successful development of GLP-1 as a therapeutic protein requires formulations to increase the serum half life and delivery of the protein. This example describes the preparation of an rPEG-GLP-1 fusion protein based on rPEG (L288) and its encapsulation in a polymer matrix to improve the half-life of GLP-1 for therapeutic use.

In another embodiment, the biologically active polypeptide is nesiritide, human B-type natriuretic peptide (hBNP). Nesiritide can be manufactured in E. coli using recombinant DNA technology. In a specific embodiment, nesiritide consists of a 32 amino acid sequence with a molecular weight of 3464 g/mol.

In yet another embodiment, the biologically active polypeptide is secretin, which is a peptide hormone composed of an amino acid sequence identical to the naturally occurring porcine secretin consisting of 27 amino acids. After intravenous bolus administration of 0.4 mcg/kg of unmodified polypeptide, synthetic human secretin concentration rapidly declines to baseline secretin levels within 90 to 120 minutes. The elimination half-life of synthetic human secretin (not modified with accessory polypeptide) is approximately 45 minutes.

In an alternative embodiment, the biologically active polypeptide is enfuvirtide, a linear 36-amino acid synthetic polypeptide which is an inhibitor of the fusion of HIV-1 with CD4+ cells.

In an additional embodiment, the biologically active polypeptide is bivalirudin, a specific and reversible direct thrombin inhibitor. A more specific embodiment provides for an biologically active polypeptide which is a synthetic, 20 amino acid peptide with a molecular weight of 1280 daltons.

Alternatively, Antihemophilic Factor (AHF) may be selected as the biologically active polypeptide. AHF is a glycoprotein amenable to synthesis in a genetically engineered Chinese Hamster Ovary (CHO) cell line. It is also known as HEMOFIL M™ AHF (Baxter) or Antihemophilic Factor (Human) [AHF (Human)]. The mean in vivo half-life of HEMOFIL M™ AHF is known to be 14.7±5.1 hours (n=61).

In another embodiment, erythropoietin is the biologically active polypeptide. Erythropoietin is a 165 amino acid glycoprotein manufactured by recombinant DNA technology and has the same biological effects as endogenous erythropoietin. In a specific embodiment, erythropoietin has a molecular weight of 30,400 daltons and is produced by mammalian cells into which the human erythropoietin gene has been introduced. The product may contain the identical amino acid sequence of isolated natural erythropoietin. In adult and pediatric patients with chronic renal failure, the elimination half-life of unmodified plasma erythropoietin after intravenous administration is known to range from 4 to 13 hours.

In still another embodiment, the biologically active polypeptide is Reteplase. Reteplase is a non-glycosylated deletion mutein of tissue plasminogen activator (tPA), comprising the kringle 2 and the protease domains of human tPA. Reteplase contains 355 of the 527 amino acids of native tPA (amino acids 1-3 and 176-527). The polypeptide may be produced by recombinant DNA technology in E. coli. and may be isolated as inactive inclusion bodies from E. coli, converted into its active form by an in vitro folding process and purified by chromatographic separation. The molecular weight of unmodified Reteplase is 39,571 daltons. Based on the measurement of thrombolytic activity, the effective half-life of unmodified Reteplase is known to be approximately 15 minutes.

A further embodiment provides for a biologically active polypeptide which is Anakirna, a recombinant, nonglycosylated form of the human interleukin-1 receptor antagonist (IL-IRa). In one case, Anakirna consists of 153 amino acids and has a molecular weight of 17.3 kilodaltons. It may be produced by recombinant DNA technology using an E. coli bacterial expression system. The in vivo half-life of unmodified Anakirna is known to range from 4 to 6 hours.

Becaplermin may also be selected as the biologically active polypeptide. Becaplermin is a recombinant human platelet-derived growth factor (rhPDGF-BB) for topical administration. Becaplermin may be produced by recombinant DNA technology by insertion of the gene for the B chain of platelet derived growth factor (PDGF) into the yeast strain Saccharomyces cerevisiae. One form of Becaplermin has a molecular weight of approximately 25 kD and is a homodimer composed of two identical polypeptide chains that are bound together by disulfide bonds.

The biologically active polypeptide may be Oprelvekin, which is a recombinant form of interleukin eleven (IL-1) that is produced in Escherichia coli (E. coli) by recombinant DNA technology. In one embodiment, the selected biologically active polypeptide has a molecular mass of approximately 19,000 daltons, and is non-glycosylated. The polypeptide is 177 amino acids in length and differs from the 178 amino acid length of native IL-11 only in lacking the amino-terminal proline residue, which is known not to result in measurable differences in bioactivity either in vitro or in vivo. The terminal half-life of unmodified Oprelvekin is known to be approximately 7 hrs.

Yet another embodiment provides for a biologically active polypeptide which is Glucagon, a polypeptide hormone identical to human glucagon that increases blood glucose and relaxes smooth muscles of the gastrointestinal tract. Glucagon may be synthesized in a special non-pathogenic laboratory strain of E. coli bacteria that have been genetically altered by the addition of the gene for glucagon. In a specific embodiment, glucagon is a single-chain polypeptide that contains 29 amino acid residues and has a molecular weight of 3,483. The in vivo half-life is known to be short, ranging from 8 to 18 minutes.

G-CSF may also be chosen as a biologically active polypeptide. Recombinant granulocyte-colony stimulating factor or G-CSF is used following various chemotherapy treatments to stimulate the recovery of white blood cells. The reported half life of recombinant G-CSF is only 3.5 hours.

Alternatively, the biologically active polypeptide can be interferon alpha (IFN alpha). Chemically PEG-modified interferon-alpha 2a is clinically validated for the treatment of hepatitis C. This PEGylated protein requires weekly injection and slow release formulations with longer half-life are desirable.

Additional cellular proteins which may be modified with accessory polypeptides, or to which biologically active polypeptides may be targeted are VEGF, VEGF-R1, VEGF-R2, VEGF-R3, Her-1, Her-2, Her-3, EGF-1, EGF-2, EGF-3, Alpha3, cMet, ICOS, CD40L, LFA-1, c-Met, ICOS, LFA-1, IL-6, B7.1, B7.2, OX40, IL-1b, TACI, IgE, BAFF or BLys, TPO-R, CD19, CD20, CD22, CD33, CD28, IL-1-R1, TNFα, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL10, CXCL11, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/IL23), IL1b, IL1a, IL1ra, IL2, IL3, IL4, IL5, IL6, IL8, IL10, IL12, IL15, IL23, Fas, FasL, Flt3 ligand, 41BB, ACE, ACE-2, KGF, FGF-7, SCF, Netrin1, 2, IFNa, b, g, Caspase-2, 3, 7, 8, 10, ADAM S1, S5, 8, 9, 15, TS1, TS5; Adiponectin, ALCAM, ALK-1, APRIL, Annexin V, Angiogenin, Amphiregulin, Angiopoietin1, 2, 4, B7-1/CD80, B7-2/CD86, B7-H1, B7-H2, B7-H3, Bcl-2, BACE-1, BAK, BCAM, BDNF, bNGF, bECGF, BMP2, 3, 4, 5, 6, 7, 8; CRP, Cadherin-6, 8, 11; Cathepsin A, B, C, D, E, L, S, V, X; CD11a/LFA-1, LFA-3, GP2b3a, GH receptor, RSV F protein, IL-23 (p40, p19), IL-12, CD80, CD86, CD28, CTLA-4, α4β1, α4β7, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, Ws1-1, TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/TNFRSF25, HVEM/TNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/TNFRSF18, Osteoprotegerin/TNFRSF11B, RANK/TNFRSF11A, TRAIL R3/TNFRSF10C, TRAIL/TNFSF10, TRANCE/RANK L/TNFSF11, 4-1BB Ligand/TNFSF9, TWEAK/TNFSF12, CD40 Ligand/TNFSF5, Fas Ligand/TNFSF6, RELT/TNFRSF19L, APRIL/TNFSF13, DcR3/TNFRSF6B, TNF RI/TNFRSF1A, TRAIL R1/TNFRSF10A, TRAIL R4/TNFRSF10D, CD30 Ligand/TNFSF8, GITR Ligand/TNFSF18, TNFSF18, TACI/TNFRSF13B, NGF R/TNFRSF16, OX40 Ligand/TNFSF4, TRAIL R2/TNFRSF10B, TRAIL R3/TNFRSF10C, TWEAK R/TNFRSF12, BAFF/BLyS/TNFSF13, DR6/TNFRSF21, TNF-alpha/TNFSF1A, Pro-TNF-alpha/TNFSF1A, Lymphotoxin beta R/TNFRSF3, Lymphotoxin beta R (LTbR)/Fc Chimera, TNF RV/TNFRSF1A, TNF-beta/TNFSF1B, PGRP-S, TNF RI/TNFRSF1A, TNF RII/TNFRSF1B, EDA-A2, TNF-alpha/TNFSF1A, EDAR, XEDAR, TNF RI/TNFRSF1A.

Of particular interest are human target proteins that are commercially available in purified form as well as proteins that bind to these target proteins. Examples are: 4EBP1, 14-3-3 zeta, 53BP1, 2B4/SLAMF4, CCL21/6Ckine, 4-1BB/TNFRSF9, 8D6A, 4-1BB Ligand/TNFSF9, 8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIIB, Angiopoietin-2, ADAM8, Angiopoietin-3, ADAM9, Angiopoietin-4, ADAM10, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTS5, Annexin A7, ADAMTS1, Annexin A10, ADAMTSL-1/Punctin, Annexin V, Adiponectin/Acrp30, ANP, AEBSF, AP Site, Aggrecan, APAF-1, Agrin, APC, AgRP, APE, AGTR-2, APJ, AIF, APLP-1, Akt, APLP-2, Akt1, Apolipoprotein AI, Akt2, Apolipoprotein B, Akt3, APP, Serum Albumin, APRIL/TNFSF13, ALCAM, ARC, ALK-1, Artemin, ALK-7, Arylsulfatase A/ARSA, Alkaline Phosphatase, ASAH2/N-acylsphingosine Amidohydrolase-2, alpha 2u-Globulin, ASC, alpha-1-Acid Glycoprotein, ASGR1, alpha-Fetoprotein, ASK1, ALS, ATM, Ameloblastin, ATRIP, AMICA/JAML, Aurora A, AMIGO, Aurora B, AMIGO2, Axin-1, AMIGO3, Ax1, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Blk, B7-H4, BMI-1, BACE-1, BMP-1/PCP, BACE-2, BMP-2, Bad, BMP-3, BAFF/TNFSF13B, BMP-3b/GDF-10, BAFF R/TNFRSF13C, BMP-4, Bag-1, BMP-5, BAK, BMP-6, BAMBI/NMA, BMP-7, BARD1, BMP-8, Bax, BMP-9, BCAM, BMP-10, Bcl-10, BMP-15/GDF-9B, Bcl-2, BMPR-IA/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thyl, c-Rel, CD94, CCL6/C10, CD97, C1q R1/CD93, CD151, C1qTNF1, CD160, C1qTNF4, CD163, C1qTNF5, CD164, Complement Component C1r, CD200, Complement Component C1s, CD200 R1, Complement Component C2, CD229/SLAMF3, Complement Component C3a, CD23/Fc epsilon RII, Complement Component C3d, CD2F-10/SLAMF9, Complement Component C5a, CD5L, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1, Cannabinoid R2/CB2/CNR2, Chk2, CAR/NR1I3, CHL-1/L1CAM-2, Carbonic Anhydrase I, Choline Acetyltransferase/ChAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, CINC-1, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-1, Carbonic Anhydrase XIII, CLEC-2, Carbonic Anhydrase XIV, CLECSF13/CLEC4F, Carboxymethyl Lysine, CLECSF8, Carboxypeptidase A1/CPA1, CLF-1, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor II/Thrombin, Caspase-1, Coagulation Factor III/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component C1rLP, beta-Catenin, Complement Component C1qA, Cathepsin 1, Complement Component C1qC, Cathepsin 3, Complement Factor D, Cathepsin 6, Complement Factor I, Cathepsin A, Complement MASP3, Cathepsin B, Connexin 43, Cathepsin C/DPPI, Contactin-1, Cathepsin D, Contactin-2/TAG1, Cathepsin E, Contactin-4, Cathepsin F, Contactin-5, Cathepsin H, Corin, Cathepsin L, Cornulin, Cathepsin O, CORS26/C1qTNF, 3, Cathepsin S, Rat Cortical Stem Cells, Cathepsin V, Cortisol, Cathepsin X/Z/P, COUP-TF I/NR2F1, CBP, COUP-TF II/NR2F2, CCI, COX-1, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-1, CCR10, CRIM1, CD155/PVR, Cripto, CD2, CRISP-2, CD3, CRISP-3, CD4, Crossveinless-2, CD4+/45RA−, CRTAM, CD4+/45RO−, CRTH-2, CD4+/CD62L−/CD44, CRY1, CD4+/CD62L+/CD44, Cryptic, CD5, CSB/ERCC6, CD6, CCL27/CTACK, CD8, CTGF/CCN2, CD8+/45RA−, CTLA4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCR5, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSF5, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISP1, DAN, Dkk-1, DANCE, Dkk-2, DARPP-32, Dkk-3, DAX1/NR0B1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-1, DcTRAIL R2/TNFRSF22, DNA-PKcs, DDR1, DNER, DDR2, Dopa Decarboxylase/DDC, DEC-205, DPCR-1, Decapentaplegic, DPP6, Decorin, DPPA4, Dectin-1/CLEC7A, DPPA5/ESG1, Dectin-2/CLEC6A, DPPII/QPP/DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-1, EphA6, ECE-2, EphA7, ECF-L/CHI3L3, EphA8, ECM-1, EphB1, Ecotin, EphB2, EDA, EphB3, EDA-A2, EphB4, EDAR, EphB6, EDG-1, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-1, Epigen, EMAP-II, Epimorphin/Syntaxin 2, EMMPRIN/CD147, Epiregulin, CXCL5/ENA, EPR-1/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMK1, Engrailed-2, ERR alpha/NR3B I, EN-RAGE, ERR beta/NR3B2, Enteropeptidase/Enterokinase, ERR gamma/NR3B3, CCL11/Eotaxin, Erythropoietin, CCL24/Eotaxin-2, trythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R14, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma RI/CD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/GOS3, FcRH2/IRTA4, FoxD3, FcRH4/IRTA1, FoxJ1, FcRH5/IRTA2, FoxP3, Fc Receptor-like 3/CD16-2, Fpg, FEN-1, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-10, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-1, GABA-A-R alpha 6, GLI-2, GABA-A-R beta 1, GLP/EHMT1, GABA-A-R beta 2, GLP-1 R, GABA-A-R beta 3, Glucagon, GABA-A-R gamma 2, Glucosamine (N-acetyl)-6-Sulfatase/GNS, GABA-B-R2, GluR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, Glut5, Galectin-3 BP, Glutaredoxin 1, Galectin-4, Glycine R, Galectin-7, Glycophorin A, Galectin-8, Glypican 2, Galectin-9, Glypican 3, GalNAc4S-6ST, Glypican 5, GAP-43, Glypican 6, GAPDH, GM-CSF, Gas1, GM-CSF R alpha, Gas6, GMF-beta, GASP-1/WFIKKNRP, gp130, GASP-2/WFIKKN, Glycogen Phosphorylase BB/GPBB, GATA-1, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-1, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-1, GSK-3 alpha, GFR alpha-1/GDNF R alpha-1, GSK-3 beta, GFR alpha-2/GDNF R alpha-2, EZFIT, H2AX, Histidine, H60, HM74A, HAI-1, HMGA2, HAI-2, HMGB1, HAI-2A, TCF-2/HNF-1 beta, HAI-2B, HNF-3 beta/FoxA2, HAND1, HNF4 alpha/NR2A1, HAPLN1, HNF4 gamma/NA2, Airway Trypsin-like Protease/HAT, HO-1/HMOX1/HSP32, HB-EGF, HO-2/HMOX2, CCL14a/HCC-1, HPRG, CCL14b/HCC-3, Hrk, CCL16/HCC-4, HRP-1, alpha HCG, HS6ST2, Hck, HSD-1, HCR/CRAM-AIB, HSD-2, HDGF, HSP10/EPF, Hemoglobin, HSP27, Hepassocin, HSP60, HES-1, HSP70, HES4, HSP90, HGF, HTRA/Protease Do, HGF Activator, HTRA1/PRSS11, HGF R, HTRA2/Omi, HIF-1 alpha, HVEM/TNFRSF14, HIF-2 alpha, Hyaluronan, HIN-1/Secretoglobulin 3A1, 4-Hydroxynonenal, Hip, CCL1/I-309/TCA-3, IL-10, cIAP (pan), IL-10 R alpha, cIAP-1/HIAP-2, IL-10 R beta, cIAP-2/HIAP-1, IL-11, IBSP/Sialoprotein II, IL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/IDS, IL-13 R alpha 2, IFN, IL-15, IFN-alpha, IL-15 R alpha, IFN-alpha 1, IL-16, IFN-alpha 2, IL-17, IFN-alpha 4b, IL-17 R, IFN-alpha A, IL-17 RC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 beta/IL-1 R7, IFN-gamma, IL-19, IFN-gamma R1, IL-20, IFN-gamma R2, IL-20 R alpha, IFN-omega, IL-20 R beta, IgE, IL-21, IGFBP-1, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rP10, IL-27, IGF-1, IL-28A, IGF-I R, IL-28B, IGF-II, IL-29/IFN-lambda 1, IGF-II R, IL-31, IgG, IL-31 RA, IgM, IL-32 alpha, IGSF2, IL-33, IGSF4A/SynCAM, ILT2/CD85j, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, IKK gamma, Insulin, IL-1 alpha/IL-1F1, Insulin R/CD220, IL-1 beta/IL-1F2, Proinsulin, IL-1ra/IL-1F3, Insulysin/IDE, IL-1F5/FIL1 delta, Integrin alpha 2/CD49b, IL-1F6/FIL1 epsilon, Integrin alpha 3/CD49c, IL-1F7/FIL1 zeta, Integrin alpha 3 beta 1/VLA-3, IL-1F8/FIL1 eta, Integrin alpha 4/CD49d, IL-1F9/IL-1 H1, Integrin alpha 5/CD49e, IL-1F10/IL-1HY2, Integrin alpha 5 beta 1, IL-1 RI, Integrin alpha 6/CD49f, IL-1 RII, Integrin alpha 7, IL-1 R3/IL-1 R AcP, Integrin alpha 9, IL-1 R4/ST2, Integrin alpha E/CD103, IL-1 R6/IL-1 R rp2, Integrin alpha L/CD11a, IL-1 R8, Integrin alpha L beta 2, IL-1 R9, Integrin alpha M/CD11b, IL-2, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha X/CD11c, IL-4, Integrin beta I/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/IP-10/CRG-2, IL-7 R alpha/CD127, IRAK1, CXCR1/IL-8 RA, IRAK4, CXCR2/IL-8 RB, IRS-1, CXCL8/IL-8, Islet-1, IL-9, CXCL11/I-TAC, IL-9 R, Jagged 1, JAM4/IGSF5, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KIR/CD158, Kallikrein 5, KIR2DL1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KIR3DL2, Kallikrein 10, Kirrel2, Kallikrein 11, KLF4, Kallikrein 12, KLF5, Kallikrein 13, KLF6, Kallikrein 14, Klotho, Kallikrein 15, Klotho beta, KC, KOR, Keap1, Kremen-1, Kell, Kremen-2, KGF/FGF-7, LAG-3, LINGO-2, LAIR1, Lipin 2, LAIR2, Lipocalin-1, Laminin alpha 4, Lipocalin-2 1NGAL, Laminin gamma 1, 5-Lipoxygenase, Laminin I, LXR alpha/NR1H3, Laminin S, LXR beta/NR1H2, Laminin-1, Livin, Laminin-5, LIX, LAMP, LMIR1/CD300A, Langerin, LMIR2/CD300c, LAR, LMIR3/CD300LF, Latexin, LMIR5/CD300LB, Layilin, LMIR6/CD300LE, LBP, LMO2, LDL R, LOX-1/SR-E1, LECT2, LRH-1/NR5A2, LEDGF, LRIG1, Lefty, LRIG3, Lefty-1, LRP-1, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LIF, Lymphotoxin beta/TNFSF3, LIF R alpha, Lymphotoxin beta R/TNFRSF3, LIGHT/TNFSF14, Lyn, Limitin, Lyp, LIMPII/SR-B2, Lysyl Oxidase Homolog 2, LIN-28, LYVE-1, LINGO-1, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4a, CCL4/MIP-1 beta, MANF, CCL15/MIP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-I, Mash1, MIP-II, Matrilin-2, MIP-III, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, Mcl-1, MKP-3, MCP-6, MLH-1, CCL2/MCP-1, MLK4 alpha, MCP-11, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type II, MMP-10, MD-1, MMP-11, MD-2, MMP-12, CCL22/MDC, MMP-13, MDL-1/CLEC5A, MMP-14, MDM2, MMP-15, MEA-1, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mre11, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-1, MGL2, Musashi-1, MGMT, Musashi-2, MIA, MuSK, MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbs1, Nidogen-1/Entactin, NCAM-1/CD56, Nidogen-2, NCAM-L1, Nitric Oxide, Nectin-1, Nitrotyrosine, Nectin-2/CD112, NKG2A, Nectin-3, NKG2C, Nectin-4, NKG2D, Neogenin, NKp30, Neprilysin/CD10, NKp44, Neprilysin-2/MMEL1/MMEL2, NKp46/NCR1, Nestin, NKp80/KLRF1, NETO2, NKX2.5, Netrin-1, NMDA R, NR1Subunit, Netrin-2, NMDA R, NR2A Subunit, Netrin-4, NMDA R, NR2B Subunit, Netrin-G1a, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkBI, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker O1, Otx2, Oligodendrocyte Marker O4, OV-6, OMgp, OX40/TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig 1, Osteocrin, Olig2, Osteopontin, Olig3, Osteoprotegerin/TNFRSF11B, Oligodendrocyte Marker O1, Otx2, Oligodendrocyte Marker O4, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, RalA/RalB, ROBO3, RalA, ROBO4, RalB, ROR/NR1F1-3 (pan), RANK/TNFRSF11A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RPA2, Ras, RSK (pan), RBP4, RSK1/RSK2, RECK, RSK1, Reg 2/PAP, RSK2, Reg I, RSK3, Reg II, RSK4, Reg III, R-Spondin 1, Reg IIIa, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S100A10, SLITRK5, S100A8, SLPI, S100A9, SMAC/Diablo, S100B, Smad1, S100P, Smad2, SALL1, Smad3, delta-Sarcoglycan, Smad4, Sca-1/Ly6, Smad5, SCD-1, Smad7, SCF, Smad8, SCF R/c-kit, SMC1, SCGF, alpha-Smooth Muscle Actin, SCL/Tal1, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, S or CS1, beta-Secretase, S or CS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX17, Semaphorin 6C, SOX21 Semaphorin 6D, SPARC, Semaphorin 7A, SPARC-like 1, Separase, SP-D, Serine/Threonine Phosphatase Substrate I, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-1, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STAT3, SGK, STAT4, SHBG, STAT5a/b, SHIP, STAT5a, SHP/NR1B2, STAT5b, SHP-1, STAT6, SHP-2, VE-Statin, SIGIRR, Stella/Dppa3, Siglec-2/CD22, STRO-1, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu—Zn SOD, SIGNR4, Superoxide Dismutase-2/Mn-SOD, SIRP beta 1, Superoxide Dismutase-3/EC-SOD, SKI, Survivin, SLAM/CD150, Synapsin I, Sleeping Beauty Transposase, Syndecan-1/CD138, Slit3, Syndecan-2, SLITRK1, Syndecan-3, SLITRK2, Syndecan-4, SLITRK4, TACI/TNFRSF13B, TMEFF1/Tomoregulin-1, TAO2, TMEFF2, TAPP1, TNF-alpha/TNFSF1, CCL17/TARC, TNF-beta/TNFSF1B, Tau, TNF RV/TNFRSF1A, TC2I/R-Ras2, TNF R1V/TNFRSF1B, TCAM-1, TOR, TCCR/WSX-1, TP-1, TC-PTP, TP63/TP73L, TDG, TR, CCL25/TECK, TR alpha/NR1A1, Tenascin C, TRbeta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSF10A, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF11, TGF-beta 3, TfR (Transferrin R), TGF-beta 5, Apo-Transferrin, Latent TGF-beta bp1, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb, TREML1/TLT-1, TGF-beta RIII, TRF-1, Thermolysin, TRF-2, Thioredoxin-1, TRH-degrading Ectoenzyme/TRHDE, Thioredoxin-2, TRIM5, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-1/KIM-1/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-1, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF12, TLR5, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-1, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/Flt4, Vasostatin, Versican, Vav-1, VG5Q, VCAM-1, VHR, VDR/NR111, Vimentin, VEGF, Vitronectin, VEGF-B, VLDLR, VEGF-C, vWF-A2, VEGF-D, Synuclein-alpha, Ku70, WASP, Wnt-7b, WIF-1, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Numerous human ion channels are targets of particular interest. Non-limiting examples include 5-hydroxytryptamine 3 receptor B subunit, 5-hydroxytryptamine 3 receptor precursor, 5-hydroxytryptamine receptor 3 subunit C, AAD14 protein, Acetylcholine receptor protein, alpha subunit precursor, Acetylcholine receptor protein, beta subunit precursor, Acetylcholine receptor protein, delta subunit precursor, Acetylcholine receptor protein, epsilon subunit precursor, Acetylcholine receptor protein, gamma subunit precursor, Acid sensing ion channel 3 splice variant b, Acid sensing ion channel 3 splice variant c, Acid sensing ion channel 4, ADP-ribose pyrophosphatase, mitochondrial precursor, Alpha1A-voltage-dependent calcium channel, Amiloride-sensitive cation channel 1, neuronal, Amiloride-sensitive cation channel 2, neuronal Amiloride-sensitive cation channel 4, isoform 2, Amiloride-sensitive sodium channel, Amiloride-sensitive sodium channel alpha-subunit, Amiloride-sensitive sodium channel beta-subunit, Amiloride-sensitive sodium channel delta-subunit, Amiloride-sensitive sodium channel gamma-subunit, Annexin A7, Apical-like protein, ATP-sensitive inward rectifier potassium channel 1, ATP-sensitive inward rectifier potassium channel 10, ATP-sensitive inward rectifier potassium channel 11, ATP-sensitive inward rectifier potassium channel 14, ATP-sensitive inward rectifier potassium channel 15, ATP-sensitive inward rectifier potassium channel 8, Calcium channel alpha12.2 subunit, Calcium channel alpha12.2 subunit, Calcium channel alpha1E subunit, delta19 delta40 delta46 splice variant, Calcium-activated potassium channel alpha subunit 1, Calcium-activated potassium channel beta subunit 1, Calcium-activated potassium channel beta subunit 2, Calcium-activated potassium channel beta subunit 3, Calcium-dependent chloride channel-1, Cation channel TRPM4B, CDNA FLJ90453 fis, clone NT2RP3001542, highly similar to Potassium channel tetramerisation domain containing 6, CDNA FLJ90663 fis, clone PLACE 1005031, highly similar to Chloride intracellular channel protein 5, CGMP-gated cation channel beta subunit, Chloride channel protein, Chloride channel protein 2, Chloride channel protein 3, Chloride channel protein 4, Chloride channel protein 5, Chloride channel protein 6, Chloride channel protein C1C-Ka, Chloride channel protein C1C-Kb, Chloride channel protein, skeletal muscle, Chloride intracellular channel 6, Chloride intracellular channel protein 3, Chloride intracellular channel protein 4, Chloride intracellular channel protein 5, CHRNA3 protein, Clcn3e protein, CLCNKB protein, CNGA4 protein, Cullin-5, Cyclic GMP gated potassium channel, Cyclic-nucleotide-gated cation channel 4, Cyclic-nucleotide-gated cation channel alpha 3, Cyclic-nucleotide-gated cation channel beta 3, Cyclic-nucleotide-gated olfactory channel, Cystic fibrosis transmembrane conductance regulator, Cytochrome B-245 heavy chain, Dihydropyridine-sensitive L-type, calcium channel alpha-2/delta subunits precursor, FXYD domain-containing ion transport regulator 3 precursor, FXYD domain-containing ion transport regulator 5 precursor, FXYD domain-containing ion transport regulator 6 precursor, FXYD domain-containing ion transport regulator 7 precursor, FXYD domain-containing ion transport regulator 8 precursor, G protein-activated inward rectifier potassium channel 1, G protein-activated inward rectifier potassium channel 2, G protein-activated inward rectifier potassium channel 3, G protein-activated inward rectifier potassium channel 4, Gamma-aminobutyric-acid receptor alpha-1 subunit precursor, Gamma-aminobutyric-acid receptor alpha-2 subunit precursor, Gamma-aminobutyric-acid receptor alpha-3 subunit precursor, Gamma-aminobutyric-acid receptor alpha-4 subunit precursor, Gamma-aminobutyric-acid receptor alpha-5 subunit precursor, Gamma-aminobutyric-acid receptor alpha-6 subunit precursor, Gamma-aminobutyric-acid receptor beta-1 subunit precursor, Gamma-aminobutyric-acid receptor beta-2 subunit precursor, Gamma-aminobutyric-acid receptor beta-3 subunit precursor, Gamma-aminobutyric-acid receptor delta subunit precursor, Gamma-aminobutyric-acid receptor epsilon subunit precursor, Gamma-aminobutyric-acid receptor gamma-1 subunit precursor, Gamma-aminobutyric-acid receptor gamma-3 subunit precursor, Gamma-aminobutyric-acid receptor pi subunit precursor, Gamma-aminobutyric-acid receptor rho-1 subunit precursor, Gamma-aminobutyric-acid receptor rho-2 subunit precursor, Gamma-aminobutyric-acid receptor theta subunit precursor, GluR6 kainate receptor, Glutamate receptor 1 precursor, Glutamate receptor 2 precursor, Glutamate receptor 3 precursor, Glutamate receptor 4 precursor, Glutamate receptor 7, Glutamate receptor B, Glutamate receptor delta-1 subunit precursor, Glutamate receptor, ionotropic kainate 1 precursor, Glutamate receptor, ionotropic kainate 2 precursor, Glutamate receptor, ionotropic kainate 3 precursor, Glutamate receptor, ionotropic kainate 4 precursor, Glutamate receptor, ionotropic kainate 5 precursor, Glutamate [NMDA] receptor subunit 3A precursor, Glutamate [NMDA] receptor subunit 3B precursor, Glutamate [NMDA] receptor subunit epsilon 1 precursor, Glutamate [NMDA] receptor subunit epsilon 2 precursor, Glutamate [NMDA] receptor subunit epsilon 4 precursor, Glutamate [NMDA] receptor subunit zeta 1 precursor, Glycine receptor alpha-1 chain precursor, Glycine receptor alpha-2 chain precursor, Glycine receptor alpha-3 chain precursor, Glycine receptor beta chain precursor, H/ACA ribonucleoprotein complex subunit 1, High affinity immunoglobulin epsilon receptor beta-subunit, Hypothetical protein DKFZp313I0334, Hypothetical protein DKFZp761M1724, Hypothetical protein FLJ12242; Hypothetical protein FLJ14389, Hypothetical protein FLJ14798, Hypothetical protein FLJ14995, Hypothetical protein FLJ16180, Hypothetical protein FLJ16802, Hypothetical protein FLJ32069, Hypothetical protein FLJ37401, Hypothetical protein FLJ38750, Hypothetical protein FLJ40162, Hypothetical protein FLJ41415, Hypothetical protein FLJ90576, Hypothetical protein FLJ90590, Hypothetical protein FLJ90622, Hypothetical protein KCTD15, Hypothetical protein MGC15619, Inositol 1,4,5-trisphosphate receptor type 1, Inositol 1,4,5-trisphosphate receptor type 2, Inositol 1,4,5-trisphosphate receptor type 3, Intermediate conductance calcium-activated potassium channel protein 4, Inward rectifier potassium channel 13, Inward rectifier potassium channel 16, Inward rectifier potassium channel 4, Inward rectifying K(+) channel negative regulator Kir2.2v, Kainate receptor subunit KA2a, KCNH5 protein, KCTD17 protein, KCTD2 protein, Keratinocytes associated transmembrane protein 1, Kv channel-interacting protein 4, Melastatin 1, Membrane protein MLC1, MGC15619 protein, Mucolipin-1, Mucolipin-2, Mucolipin-3, Multidrug resistance-associated protein 4, N-methyl-D-aspartate receptor 2C subunit precursor, NADPH oxidase homolog 1, Nav1.5, Neuronal acetylcholine receptor protein, alpha-10 subunit precursor, Neuronal acetylcholine receptor protein, alpha-2 subunit precursor, Neuronal acetylcholine receptor protein, alpha-3 subunit precursor, Neuronal acetylcholine receptor protein, alpha-4 subunit precursor, Neuronal acetylcholine receptor protein, alpha-5 subunit precursor, Neuronal acetylcholine receptor protein, alpha-6 subunit precursor, Neuronal acetylcholine receptor protein, alpha-7 subunit precursor, Neuronal acetylcholine receptor protein, alpha-9 subunit precursor, Neuronal acetylcholine receptor protein, beta-2 subunit precursor, Neuronal acetylcholine receptor protein, beta-3 subunit precursor, Neuronal acetylcholine receptor protein, beta-4 subunit precursor, Neuronal voltage-dependent calcium channel alpha 2D subunit, P2X purinoceptor 1, P2X purinoceptor 2, P2X purinoceptor 3, P2X purinoceptor 4, P2X purinoceptor 5, P2X purinoceptor 6, P2X purinoceptor 7, Pancreatic potassium channel TALK-1b, Pancreatic potassium channel TALK-1c, Pancreatic potassium channel TALK-1d, Phospholemman precursor, Plasmolipin, Polycystic kidney disease 2 related protein, Polycystic kidney disease 2-like 1 protein, Polycystic kidney disease 2-like 2 protein, Polycystic kidney disease and receptor for egg jelly related protein precursor, Polycystin-2, Potassium channel regulator, Potassium channel subfamily K member 1, Potassium channel subfamily K member 10, Potassium channel subfamily K member 12, Potassium channel subfamily K member 13, Potassium channel subfamily K member 15, Potassium channel subfamily K member 16, Potassium channel subfamily K member 17, Potassium channel subfamily K member 2, Potassium channel subfamily K member 3, Potassium channel subfamily K member 4, Potassium channel subfamily K member 5, Potassium channel subfamily K member 6, Potassium channel subfamily K member 7, Potassium channel subfamily K member 9, Potassium channel tetramerisation domain containing 3, Potassium channel tetramerisation domain containing protein 12, Potassium channel tetramerisation domain containing protein 14, Potassium channel tetramerisation domain containing protein 2, Potassium channel tetramerisation domain containing protein 4, Potassium channel tetramerisation domain containing protein 5, Potassium channel tetramerization domain containing 10, Potassium channel tetramerization domain containing protein 13, Potassium channel tetramerization domain-containing 1, Potassium voltage-gated channel subfamily A member 1, Potassium voltage-gated channel subfamily A member 2, Potassium voltage-gated channel subfamily A member 4, Potassium voltage-gated channel subfamily A member 5, Potassium voltage-gated channel subfamily A member 6, Potassium voltage-gated channel subfamily B member 1, Potassium voltage-gated channel subfamily B member 2, Potassium voltage-gated channel subfamily C member 1, Potassium voltage-gated channel subfamily C member 3, Potassium voltage-gated channel subfamily C member 4, Potassium voltage-gated channel subfamily D member 1, Potassium voltage-gated channel subfamily D member 2, Potassium voltage-gated channel subfamily D member 3, Potassium voltage-gated channel subfamily E member 1, Potassium voltage-gated channel subfamily E member 2, Potassium voltage-gated channel subfamily E member 3, Potassium voltage-gated channel subfamily E member 4, Potassium voltage-gated channel subfamily F member 1, Potassium voltage-gated channel subfamily G member 1, Potassium voltage-gated channel subfamily G member 2, Potassium voltage-gated channel subfamily G member 3, Potassium voltage-gated channel subfamily G member 4, Potassium voltage-gated channel subfamily H member 1, Potassium voltage-gated channel subfamily H member 2, Potassium voltage-gated channel subfamily H member 3, Potassium voltage-gated channel subfamily H member 4, Potassium voltage-gated channel subfamily H member 5, Potassium voltage-gated channel subfamily H member 6, Potassium voltage-gated channel subfamily H member 7, Potassium voltage-gated channel subfamily H member 8, Potassium voltage-gated channel subfamily KQT member 1, Potassium voltage-gated channel subfamily KQT member 2, Potassium voltage-gated channel subfamily KQT member 3, Potassium voltage-gated channel subfamily KQT member 4, Potassium voltage-gated channel subfamily KQT member 5, Potassium voltage-gated channel subfamily S member 1, Potassium voltage-gated channel subfamily S member 2, Potassium voltage-gated channel subfamily S member 3, Potassium voltage-gated channel subfamily V member 2, Potassium voltage-gated channel, subfamily H, member 7, isoform 2, Potassium/sodium hyperpolarization-activated cyclic nucleotide-gated channel 1, Potassium/sodium hyperpolarization-activated cyclic nucleotide-gated channel 2, Potassium/sodium hyperpolarization-activated cyclic nucleotide-gated channel 3, Potassium/sodium hyperpolarization-activated cyclic nucleotide-gated channel 4, Probable mitochondrial import receptor subunit TOM40 homolog, Purinergic receptor P2x5, isoform A, Putative 4 repeat voltage-gated ion channel, Putative chloride channel protein 7, Putative GluR6 kainate receptor, Putative ion channel protein CATSPER2 variant 1, Putative ion channel protein CATSPER2 variant 2, Putative ion channel protein CATSPER2 variant 3, Putative regulator of potassium channels protein variant 1, Putative tyrosine-protein phosphatase TPTE, Ryanodine receptor 1, Ryanodine receptor 2, Ryanodine receptor 3, SH3 KBP I binding protein 1, Short transient receptor potential channel 1, Short transient receptor potential channel 4, Short transient potential channel 5, Short transient receptor potential channel 6, Short transient receptor potential channel 7, Small conductance calcium-activated potassium channel protein 1, Small conductance calcium-activated potassium channel protein 2, isoform b, Small conductance calcium-activated potassium channel protein 3, isoform b, Small-conductance calcium-activated potassium channel SK2, Small-conductance calcium-activated potassium channel SK3, Sodium channel, Sodium channel beta-1 subunit precursor, Sodium channel protein type II alpha subunit, Sodium channel protein type III alpha subunit, Sodium channel protein type IV alpha subunit, Sodium channel protein type IX alpha subunit, Sodium channel protein type V alpha subunit, Sodium channel protein type VII alpha subunit, Sodium channel protein type VIII alpha subunit, Sodium channel protein type X alpha subunit, Sodium channel protein type XI alpha subunit, Sodium- and chloride-activated ATP-sensitive potassium channel, Sodium/potassium-transporting ATPase gamma chain, Sperm-associated cation channel 1, Sperm-associated cation channel 2, isoform 4, Syntaxin-1B1, Transient receptor potential cation channel subfamily A member 1, Transient receptor potential cation channel subfamily M member 2, Transient receptor potential cation channel subfamily M member 3, Transient receptor potential cation channel subfamily M member 6, Transient receptor potential cation channel subfamily M member 7, Transient receptor potential cation channel subfamily V member 1, Transient receptor potential cation channel subfamily V member 2, Transient receptor potential cation channel subfamily V member 3, Transient receptor potential cation channel subfamily V member 4, Transient receptor potential cation channel subfamily V member 5, Transient receptor potential cation channel subfamily V member 6, Transient receptor potential channel 4 epsilon splice variant, Transient receptor potential channel 4 zeta splice variant, Transient receptor potential channel 7 gamma splice variant, Tumor necrosis factor, alpha-induced protein 1, endothelial, Two-pore calcium channel protein 2, VDAC4 protein, Voltage gated potassium channel Kv3.2b, Voltage gated sodium channel beta1B subunit, Voltage-dependent anion channel, Voltage-dependent anion channel 2, Voltage-dependent anion-selective channel protein 1, Voltage-dependent anion-selective channel protein 2, Voltage-dependent anion-selective channel protein 3, Voltage-dependent calcium channel gamma-1 subunit, Voltage-dependent calcium channel gamma-2 subunit, Voltage-dependent calcium channel gamma-3 subunit, Voltage-dependent calcium channel gamma-4 subunit, Voltage-dependent calcium channel gamma-5 subunit, Voltage-dependent calcium channel gamma-6 subunit, Voltage-dependent calcium channel gamma-7 subunit, Voltage-dependent calcium channel gamma-8 subunit, Voltage-dependent L-type calcium channel alpha-1C subunit, Voltage-dependent L-type calcium channel alpha-1D subunit, Voltage-dependent L-type calcium channel alpha-1S subunit, Voltage-dependent L-type calcium channel beta-1 subunit, Voltage-dependent L-type calcium channel beta-2 subunit, Voltage-dependent L-type calcium channel beta-3 subunit, Voltage-dependent L-type calcium channel beta-4 subunit, Voltage-dependent N-type calcium channel alpha-1B subunit, Voltage-dependent P/Q-type calcium channel alpha-1A subunit, Voltage-dependent R-type calcium channel alpha-1E subunit, Voltage-dependent T-type calcium channel alpha-1G subunit, Voltage-dependent T-type calcium channel alpha-1H subunit, Voltage-dependent T-type calcium channel alpha-1I subunit, Voltage-gated L-type calcium channel alpha-1 subunit, Voltage-gated potassium channel beta-1 subunit, Voltage-gated potassium channel beta-2 subunit, Voltage-gated potassium channel beta-3 subunit, Voltage-gated potassium channel KCNA7. The Nav1.x family of human voltage-gated sodium channels also a particularly promising target. This family includes, for example, channels Nav1.6 and Nav1.8.

Many of the microproteins used as scaffolds in this application have native activity against G-Protein Coupled Receptors (GPCRs) and offer ideal starting points to create novel GPCR modulators (including agonists, antagonists and modulators of any property of the GPCR). Exemplary GPCRs include but are not limited to Class A Rhodopsin like receptors such as Muscatinic (Musc.) acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykinin, C5a anaphylatoxin, Finet-leu-phe, APJ like, Interleukin-8 type A, Interleukin-8 type B, Interleukin-8 type others, C—C Chemokine type 1 through type 11 and other types, C—X—C Chemokine (types 2 through 6 and others), C—X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P (NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory II fam 1 through 13), Prostaglandin (prostaglandin E2 subtype EP1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY14, 6, 11 GPR91, Purinoceptor P2RY5, 8, 9, 10 GPR35, 92, 174, Purinoceptor P2RY12-14 GPR87 (UDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (TIR), Class D Fungal pheromone, Fungal pheromone A-Factor like (STE2, STE3), Fungal pheromone B like (BAR, BBR, RCB, PRA), Class E cAMP receptors, Ocular albinism proteins, Frizzled/Smoothened family, frizzled Group A (Fz 1&2&4&5&7-9), frizzled Group B (Fz 3 & 6), frizzled Group C (other), Vomeronasal receptors, Nematode chemoreceptors, Insect odorant receptors, and Class Z Archaeal/bacterial/fungal opsins.

Of particular utility is the fusion of accessory sequences to any of the following active polypeptides: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex' recombinant human luteinizing hormone, domase alfa, trafermin, ziconotide, taltirelin, dibotermin alfa, atosiban, becaplermin, eptifibatide, Zemaira, CTC-111, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexiganan acetate, ADI-PEG-20, LDI-200, degarelix, cintredekin besudotox, Favld, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-1 (injectable, vascular disease), BDM-E, rotigaptide, ETC-216, P-113, MBI-594AN, duramycin (inhaled, cystic fibrosis), SCV-07, OP145, Endostatin, Angiostatin, ABT-510, Bowman Birk Inhibitor Concentrate, XMP-629, 99 mTc-Hynic-Annexin V, kahalalideF, CTCE-9908, teverelix (extended release), ozarelix, romidepsin, BAY-504798, interleukin-4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DM1, ovarian cancer immunotherapeutic vaccine, SB-249553, Oncovax-CL, OncoVax-P, BLP-25, CerVax-16, multi-epitope peptide melanoma vaccine (MART-1, gp 100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune iseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FAR-404, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, Cyto-Fab, P-9808, VT-111, icrocaptide, telbermin (dermatological, diabetic foot ulcer), rupintrivir, reticulose, rGRF, PIA, alpha-galactosidase A, ACE-011, ALTU-140, CGX-1160, angiotensin therapeutic vaccine, D4F, ETC-642, APP-018, rhMBL, SCV-07 (oral, tuberculosis), DRF-7295, ABT-828, ErbB2-specific immunotoxin (anticancer), DT3881L-3, TST-10088, PRO-1762, Combotox, cholecystokinin-B/gastrin-receptor binding peptides, 111In-hEGF, AE-37, trastuzumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV-4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1; AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, G1-5005, ACC-001, TTS-CD3, vascular-targeted TNF (solid tumors), desmopressin (buccal controlled-release), onercept, TP-9201.

Non-Repetitive URPs (nrURPs)

The present invention also encompasses non-repetitive URPs (nrURPs). nrURPs are amino acid sequences that are composed mainly of small hydrophilic amino acids and that have a low tendency to form secondary structure in vivo. nrURPs possess the characteristics of URPs including the lack of well defined secondary and tertiary structures under physiological conditions, contributing to their conformational flexibility; high degree of protease resistance; ability to increase the half-life and/or solubility of a biologically active polypeptide upon incorporation of the URP sequences into the biologically active polypeptide. A particular property of nrURPs is their low degree of internal repetitiveness. nrURPs comprise multiple different peptide subsequences. These subsequences have URP-like amino acid composition but differ from each other in their amino acid sequence and length.

nrURPs tend to have improved solubility as compared to repetitive URPs (rURPs) with similar amino acid composition. In general, repetitive amino acid sequences have a tendency to aggregate as exemplified by natural repetitive sequences such as collagens and leucine zippers. Repetitive sequences can form higher order structures such that identical subsequences from similar contacts resulting in crystalline or pseudocrystalline structures. nrURPs have a much lower tendency to form such pseudo-crystalline structures as they contain multiple different subsequences that prevent the formation of any repetitive higher order structure. The low tendency of non-repetitive sequences to aggregate enables the design URPs with a relatively low frequency of charged amino acids that would be likely to aggregate in repetitive URPs. The low aggregation tendency of nrURPs facilitates the formulation of nrURP-comprising pharmaceutical preparations in particular enabling preparations containing extremely high drug concentrations exceeding 100 mg/ml.

(a) nrURPs Have Low Immunogenicity

The interactions of a repetitive and a non-repetitive URP sequence with B cells that recognize epitopes in said sequences are compared and illustrated in FIG. 74. A rURP is recognized by few B cells in an organism as it contains a relatively small number of different epitopes. However, a rURP can form multivalent contacts with these few B cells and as a consequence it can stimulate B cell proliferation as illustrated in FIG. 74*a*. In contrast, a nrURP can make contacts with many different B cells as it contains many different epitopes. However, each individual B cell can only make one or a small number of contacts with an individual nrURP due to the lack of repetitiveness as illustrated in FIG. 74*b*. As a result, nrURPs have a much lower tendency to stimulate proliferation of B cells and thus an immune response.

An additional advantage of nrURPs relative to rURPs is that nrURPs form weaker contacts with antibodies relative to rURPs. Antibodies are multivalent molecules. For instance, IgGs have two identical binding sites and IgMs contain 10 identical binding sites. Thus antibodies against repetitive sequences can form multivalent contacts with such repetitive sequences with high avidity, which can affect the potency and/or elimination of such repetitive sequences. In contrast, antibodies against nrURPs form mainly monovalent interactions with antibodies as said nrURPs contain few repeats of each epitope.

(b) Detection of Repetitiveness

The repetitiveness of a gene can be measured by computer algorithms. An example is illustrated in FIG. 75. Based on the query sequence, a pair wise comparison of all subsequences of a particular length can be performed. These subsequences can be compared for identity or homology. The example in FIG. 75 compares subsequences of 4 amino acids for identity. In the example, most 4-mer subsequences occur once in the query sequence and 3 4-mer subsequences occur twice. The repetitiveness in a gene can be averaged. The length of the subsequences can be adjusted. The length of the subsequences reflects the length of sequence epitopes that can be recognized by the immune system. Thus analysis of subsequences of 4-15 amino acids may be most useful.

(c) Design of nrURP Sequences

Genes encoding nrURPs can be assembled from oligonucleotides using standard techniques of gene synthesis. The gene design can be performed using algorithms that optimize codon usage and amino acid composition. In addition, one can avoid amino acid sequences that are protease sensitive or that are known to contain epitopes that can be easily recognized by the human immune system. Computer algorithms can be applied during sequence design to minimize the repetitiveness of the resulting amino acid sequences. One can evaluate the repetitiveness of large numbers of gene designs that match preset criteria such as amino acid composition, codon usage, avoidance of protease sensitive subsequence, avoidance of epitopes, and chose the least repetitive sequences for synthesis and subsequent evaluation.

Figure 76:
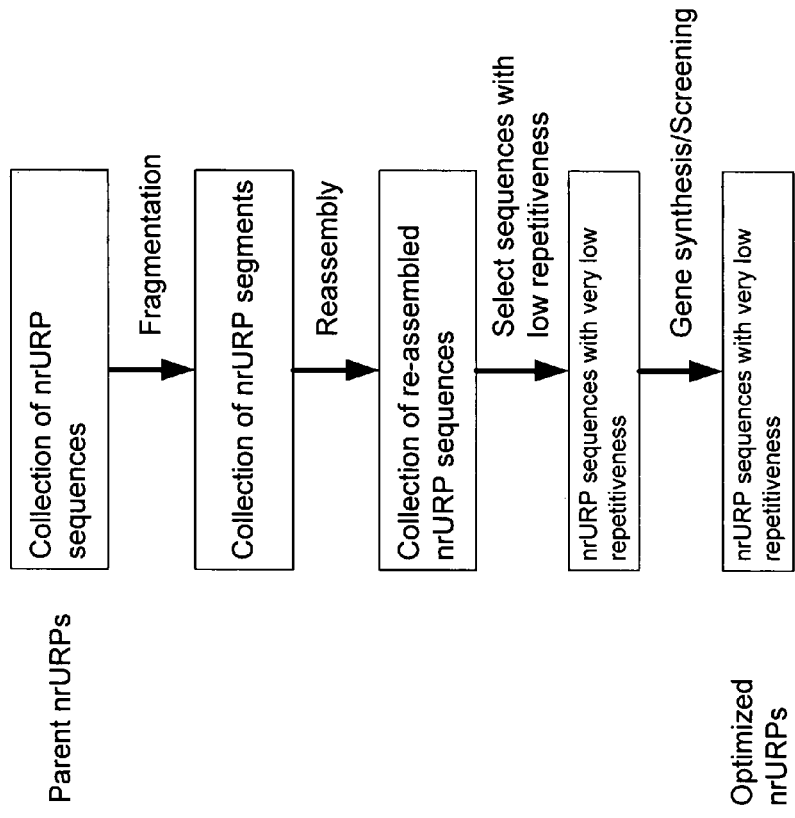
FIG. 76: Computer algorithm to design nrURPs with very low repetitiveness.

An alternative approach to the design of nrURP genes is to analyze the sequences of existing collections of nrURPs that show high level expression, low aggregation tendency, high solubility, and good resistance to proteases. A computer algorithm can design nrURP sequences based on such pre-existing nrURP sequences by re-assembly of sequence fragments as illustrated in FIG. 76. The algorithm generates a collection of subsequences from these nrURP sequences and then evaluates multiple ways to assembly nrURP sequences from such subsequences. These assembled sequences can be evaluated for repetitiveness to identify nrURP sequences that are only composed of subsequences of previously identified nrURPs but that have reduced repetitiveness compared to all parent nrURPs.

(d) Construction of nrURP Sequences from Libraries nrURP-encoding genes can be assembled from libraries of short URP segments as illustrated in FIG. 77. One can first generate large libraries of URP segments. Such libraries can be assembled from partially randomized oligonucleotides. The randomization scheme can be optimized to control amino acid choices for each position as well as codon usage and sequence length. In one embodiment, the library of URP segments is cloned into an expression vector. In another embodiment, the library of URP segments is cloned into an expression vector fused to an indicator gene like GFP. Subsequently, one can screen library members for a number of properties such as level of expression, protease stability, binding to serum proteins. One can screen URP segments for binding to antiserum to eliminate segment with high affinity for said serum. In particular one can screen library members to identify and avoid binding to antisera with reactivity to URP sequences. The amino acid sequence of the library members can be determined to identify segments that have a particularly desirable amino acid composition, segment length, or to identify segments that have a low frequency of internal repeats. Subsequently, nrURP sequences may be assembled from the collections of URP segments by random dimerization or multimerization. Dimerization or multimerization can be achieved by ligation or PCR assembly. This process results in a library of nrURP sequences that can be evaluated for a number of properties to identify the nrURP sequences with the most desirable properties. The process of dimerization or multimerization can be repeated to further increase the length of nrURP sequences.

Design of Crosslinked Accessory Polypeptides

The present invention also relates to polypeptides with enhanced properties (such as increased hydrodynamic radius or extended serum half-life) comprising crosslinked accessory polypeptides. A crosslinked accessory polypeptide can be generated by conjugating one or more non-cross-linking components and one or more cross-linking components.

The advantage of this approach is that one can use an accessory polypeptide of moderate length, which is highly expressed, to efficiently generate larger molecules with desired properties. For example, using chemical coupling one can create a molecule comprising five 200 amino acid long units much more efficiently than a single 1000 amino acid long polypeptide expressed as a single protein.

Any number of non-crosslinking components, such as 2, 3, 4, 5, 6, 7, 8, 9, 10 or more components can be linked together. These components can be identical or of 2, 3, 4, 5, 6, 7, 8, 9 or 10 or more different kinds. In a preferred embodiment, each component has a determined binding specificity, which can be the same for each component or of 2, 3, 4, 5, 6, 7, 8, 9, or 10 or more different types. The sequences of the non-crosslinking components can also be the same or may comprise 1-10 different sequences.

A preferred embodiment of the present invention provides for reacting 1, 2, 3, 4, 5, 6, 7, 8 or more copies of a monoreactive non-crosslinking component with one copy of a multireactive cross-linking component, which optionally contains polyethyleneglycol, an accessory polypeptide or another water-soluble polymer, resulting in a pre-defined polymer containing exactly (for example) four copies of the non-crosslinking component, each copy being linked to the cross-linking agent. The noh-crosslinking component may optionally comprise a domain with binding specificity.

A variety of linkage chemistries can be used for conjugation. In a preferred embodiment, standard amino-carboxyl coupling, and especially linking via the amino group of a lysine group or of the N-terminus, or linking via the carboxyl group of glutamate or of the C-terminus, is especially useful for cross-linking of crosslinked accessory polypeptides.

In some embodiments, the cross-linking component can be a synthetic polypeptide. For example, such a polypeptide may comprise 5 carboxy residues (i.e. 4 glutamates plus the C-terminal carboxy), optionally spaced by sequences inserted between the carboxyl groups ('linkage peptide'). The amino-terminus of this linkage peptide can be blocked, for example by amidation, to prevent the formation of additional variants (FIG. 27). The second reactive group is the amino-terminus of the protein that contains accessory polypeptides. Optionally, one can reserve one or more lysines for coupling to the carboxyls in the linkage peptide. After exhaustive chemical linkage, one can obtain a homogeneous single product, which is a molecule that contains 5 accessory polypeptides (optionally containing binding domains), as well as the linkage peptide. A variation is to have the linkage peptide contain the amino groups and use carboxyls on the other protein, which typically carries the binding domain.

In addition to such branched structures, it is also possible to create linear polymers of 2, 3, 4, 5, 6, 7, 8 or more separately expressed polypeptides by linking the amino-terminus of one protein to the carboxy-terminus of another protein. Again, these polypeptides may be the same or different, as described above.

The preferred linkage is amino-to-carboxy. The amino group that is used for coupling is located on the recombinant protein if the carboxyl group that is used is located on the chemical crosslinker. Alternatively, the amino group that is used for coupling is located on the chemical cross-linker if the carboxyl group that is used is located on the recombinant protein.

The number of coupling sites that is used on the crosslinker determines whether the product will contain 1, 2, 3, 4, 5, 6, 7, 8, 9 or 10 or more recombinant proteins, each typically containing 1, 2, 3, 4, 5 or more binding domains. The crosslinking component is typically a small, FDA-approved chemical but can also be a recombinant polypeptide and optionally contains at least 0, 1, 2, 3, 4, 5, 6, 7, 8, 9, 10, 20, 30, 40, 50, 75, 100 units of a repeated motif, and at most 10, 20, 30, 40, 50, 75, 100, 150, 200, 250, 300, 350, 400, 450 or 500 units of a repeated motif.

Using protection groups that can be differentially removed by different conditions, it is possible to have several conjugation steps that each add a different protein to the conjugate. This allows the creation of conjugates with multiple different protein chains in a pre-designed stoichiometry. Conjugation of divalent crosslinker with two protein chains having one linkable position (like an N-terminus) creates dimers. Crosslinking of proteins with two linkage sites creates a linear polymer. Crosslinking of a trivalent crosslinker with a protein containing linkage sites at both ends creates a dendrimer (FIG. 26).

In some embodiments, non-crosslinking components may comprise one or more biologically active polypeptides with affinity to a target receptor. These biologically active polypeptides can bind to different target receptors, allowing the generation of crosslinked accessory polypeptides that bind several copies of several different target receptors. Alternatively, non-crosslinking components can comprise multiple biologically active polypeptides that bind several different epitopes of the same target receptor. The resulting crosslinked accessory polypeptide can bind multiple copies of a target receptor while making multiple binding contacts with each target receptor resulting in very high avidity. Another option is to use non-crosslinking components that contain multiple identical binding elements in order to construct crosslinked accessory polypeptides with a very large number of identical binding sites.

In other embodiments, non-crosslinking components may comprise one or multiple accessory polypeptide modules. These rPEG modules give the resulting crosslinked accessory polypeptide a large hydrodynamic radius and thus low rate of kidney elimination. In addition, the accessory polypeptide modules increase the mobility of various domains within the resulting crosslinked accessory polypeptide. This can have multiple applications. For instance, the conformational mobility can allow a crosslinked accessory polypeptide to bind to multiple target receptors on a target like a cell, tissue, or infective agent, even when said target receptors are not located in close proximity to each other. Accessory polypeptide modules can also serve to modulate tissue distribution of a crosslinked accessory polypeptide. For instance, one can include accessory polypeptide modules into a crosslinked accessory polypeptide to limit penetration of said crosslinked accessory polypeptide into healthy tissues that are characterized by intact vasculature with low permeability for large proteins.

In yet other embodiments, non-cross-linking components can contain binding elements that increase the serum halflife of the resulting crosslinked accessory polypeptides. Such binding elements can bind to one or multiple serum components like HSA, IgG, red blood cells, or other serum component that is found in high abundance.

In still other embodiments, non-cross-linking components can be conjugated to one or more small molecule drug molecules. Examples for useful drug molecules are doxorubicin, melphalan, paclitaxel, maytansines, duocarmycines, calicheamycin, auristatin and other cytotoxic, cytostatic, antiinfective drugs.

In some embodiments, non-cross-linking components can comprise affinity tags. Examples for useful affinity tags are Flag, HA-tag, hexa-histidine (SEQ ID NO: 1). These affinity tags facilitate the purification of the non-cross-linking components as well as the resulting crosslinked accessory polypeptides. In addition, affinity tags facilitate the detection of crosslinked accessory polypeptides in biological samples. In particular, affinity tags are useful to monitor the serum halflife and/or the tissue distribution of a crosslinked accessory polypeptide in a patient or in animals.

In other embodiments, non-cross-linking components can comprise protease sites that allow the slow release of binding domains, active drugs, or other subsequences with biological activity.

Of particular utility are non-cross-linking components that are free of lysine residues. Such sequences contain a single amino group at their N-terminus, which can be utilized for conjugation to the cross-linking component. Non-cross-linking components that contain a single free cysteine residue are also of utility as there are many chemistries available that allow the controlled conjugation to the side chain of free cysteine residues. Another approach is to utilize the C-terminal carboxyl group of the non-cross-linking component as reactive group.

Many molecules that comprise multiple reactive groups can serve as useful cross-linking components. Many useful cross-linking agents are commercially available from companies like Sigma-Aldrich, or Pierce. Of particular utility are cross-linking components that are available in activated form and can be directly used for conjugation. Examples are shown in FIG. 22. Cross-linking components can comprise multiple reactive groups with similar or identical chemical structure (FIG. 23). Such reactive groups can be simultaneously activated and coupled to multiple identical non-cross-linking components resulting in the direct formation of homomultimeric products. Examples for cross-linking components with multiple similar reactive groups are citric acid, EDTA, TSAT. Of particular interest are branched PEG molecules containing multiple identical reactive groups.

There are a large number of specific chemical products that work based on the following small number of basic reaction schemes, all of which are described in detail at www-.piercenet.com. Examples of useful crosslinking agents are imidoesters, active halogens, maleimide, pyridyl disulfide, and NHS-esters. Homobifunctional crosslinking agents have two identical reactive groups and are often used in a one step chemical crosslinking procedure. Examples are BS3 (a non-cleavable water-soluble DSS analog), BSOCOES (base-reversible), DMA (Dimethyl adipimidate-2HCl), DMP (Dimethyl pimelimidate-2HCl), DMS (Dimethyl suberimidate-2HCl), DSG (5-carbon analog of DSS), DSP (Lomant's reagent), DSS (non-cleavable), DST (cleavable by oxidizing agents), DTBP (Dimethyl 3,3'-dithiobispropionimidate-2HCl), DTSSP, EGS, Sulfo-EGS, THPP, TSAT, DFDNB (1,5-Difluoro-2,4-dinitrobenzene) is especially useful for crosslinking between small spacial distances (Komblatt, J. A. and Lake, D. F. (1980). Cross-linking of cytochrome oxidase subunits with difluorodinitrobenzene. Can J. Biochem. 58, 219-224).

Sulfhydryl-reactive homobifunctional crosslinking agents are homobifunctional protein crosslinkers that react with sulfhydryls and are often based on maleimides, which react with —SH groups at pH 6.5-7.5, forming stable thioether linkages. BM[PEO]3 is an 8-atom polyether spacer that reduces potential for conjugate precipitation in sulfydryl-to-sulfhydryl cross-linking applications. BM[PEO]4 is similar but with an 11-atom spacer. BMB is a non-cleavable crosslinker with a four-carbon spacer. BMDB makes a linkage that can be cleaved with periodate. BMH is a widely used homobifunctional sulfhydryl-reactive crosslinker. BMOE has an especially short linker. DPDPB and DTME are cleavable crosslinkers. HVBS does not have the hydrolysis potential of meleimides. TMEA is another option. Hetero-bifunctional crosslinking agents have two different reactive groups. Examples are NHS-esters and amines/hydrazines via EDC activation, AEDP, ASBA (photoreactive, iodinatable), EDC (water-soluble carbodiimide). Amine-Sulfhydryl reactive bifunctional crosslinkers are AMAS, APDP, BMPS, EMCA, EMCS, GMBS, KMUA, LC-SMCC, LC-SPDP, MBS, SBAP, SIA (extra short), SIAB, SMCC, SMPB, SMPH, SMPT, SPDP, Sulfo-EMCS, Sulfo-GMBS, Sulfo-KMUS, Sulfo-LC-SMPT, Sulfo-LC-SPDP, Sulfo-MBS, Sulfo-SIAB, Sulfo-SMCC, Sulfo-SMPB. Amino-group reactive heterobifunctional crosslinking agents are ANB-NOS, MSA, NHS-ASA, SADP, SAED, SAND, SANPAH, SASD, SFAD, Sulfo-HSAB, Sulfo-NHS-LC-ASA, Sulfo-SADP, Sulfo-SANPAH, TFCS. Arginine-reactive crosslinking agents are, for example APG, which reacts specifically with arginines at pH 7-8.

Polypeptides can be designed to serve as cross-linking components. Such polypeptides can be generated by chemical synthesis or using recombinant techniques. Examples are polypeptides that contain multiple aspartate or glutamate residues. The side chains of these residues as well as the C-terminal carboxyl group can be used for coupling to the non-crosslinking component. By adding one or several amino acids between the aspartate or glutamate residues one can control the distance between reactive groups, which can affect the efficiency of conjugation as well as the overall properties of the resulting crosslinked accessory polypeptide. Of particular utility are polypeptides that contain multiple aspartate or glutamate residues and that carry a protection group at their N-terminal amino group. Examples for suitable protection schemes are acetylation, succinylation, and other modifications that reduce the reactivity of the N-terminal amino group of the peptide.

Of particular utility as cross-linking components are dendrimeric constructs. Many dendrimeric structures are known in the art and they can be designed to contain a large number of reactive groups. Examples of crosslinked accessory polypeptides are illustrated in FIG. 24.

Additional Modifications of Accessory Polypeptides

An additional mechanism may be incorporated into the design of accessory polypeptides as well as crosslinked accessory polypeptidesis mediated by peptides with binding affinity to serum-exposed molecules. By binding to such a target, the halflife of the polypeptide of the present invention is further increased. For example, a crosslinked accessory polypeptide may comprise a non-crosslinking unit that comprises a polypeptide with binding affinity to a serum-exposed target. Alternatively, an accessory polypeptide may comprise a sequence coding for a polypeptide with such binding affinity. Preferred serum-exposed targets that peptides or protein domains can be made to bind to for halflife extension are (human, mouse, rat, monkey) serum albumin, Immunoglobulins such as IgG (IgG1, 2, 3, 4), IgM, IgA, IgE as well as red blood cells (RBC), or endothelial cells. Accessory polypeptides may also comprise, by way of example, sequences that target the extracellular matrix, insert into membranes, or other targeting peptides and domains (FIG. 28)

In another embodiment, accessory polypeptides or crosslinked accessory polypeptides may comprise several biologically active polypeptides separated as well as sequences that comprise specific cleavage sites for serum proteases (FIG. 29). Following administration or exposure to serum, serum proteases act on the cleavage sites leading to gradual proteolysis and release of biologically active polypeptides or accessory polypeptides into the blood.

Accessory polypeptides or crosslinked accessory polypeptides may also be modified postsynthetically. In one embodiment, accessory polypeptides are expressed comprising one or more lysine residues (FIG. 30). Following expression, the polypeptides are reacted with a Lys-reactive moiety that is attached to at least one second functional unit, which may be for example a biologically active polypeptide. In a related embodiment, the functional unit is a polypeptide with binding affinity for serum-exposed targets, such as serum albumin, Immunoglobulins such as IgG (IgG1, 2, 3, 4), IgM, IgA, IgE as well as red blood cells (RBC) or endothelial cells.

Accessory Polypeptides Linked to an Antigen-Binding Unit

The present invention embodies an accessory polypeptide linked to an antigen-binding unit. The term "antigen-binding units" collectively refers to immunoglobulin molecules and any form of immunologically active portions of immunoglobulin molecules, i.e., molecules that contain an antigen-binding site which specifically binds or immunoreacts with an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. An antibody binding unit can be broadly divided into "single-chain" ("Sc") and "non-single-chain" ("Nsc") types, which include, but not limited to, Fv, scFv, dFv, dAb, diabody, triabody, tetrabody, domain Ab, Fab fragment, Fab', (Fab')$_2$, bispecific Ab and multispecific Ab.

Also encompassed within the term "antigen binding unit" are immunoglobulin molecules of a variety of species origins including invertebrates and vertebrates. The term "human" as applies to an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

"Non-single-chain antigen-binding unit" are heteromultimers comprising a light-chain polypeptide and a heavy-chain polypeptide. Examples of the non-single-chain antigen-binding unit include but are not limited to (i) a ccFv fragment, which is a dimeric protein composed of VL and VH regions, which dimerize via the pairwise affinity of the first and second heterodimerization sequences fused in-frame with the VL and VH regions; (ii) any other monovalent and multivalent molecules comprising at least one ccFv fragment; (iii) an Fab fragment consisting of the VL, VH, CL and CH1 domains; (iv) an Fd fragment consisting of the VH and CH1 domains; (v) an Fv fragment consisting of the VL and VH domains of a single arm of an antibody; (vi) an F(ab')2 fragment, a bivalent fragment comprising two Fab fragments linked by a disulfide bridge at the hinge region; (vii) a diabody; and (viii) any other non-single-chain antigen-binding units that have been described and known in the art.

As noted above, a non-single-chain antigen-binding unit can be either "monovalent" or "multivalent." Whereas the former has one binding site per antigen-binding unit, the latter contains multiple binding sites capable of binding to more than one antigen of the same or different kind. Depending on the number of binding sites, a non-single-chain antigen-binding unit may be bivalent (having two antigen-binding sites), trivalent (having three antigen-binding sites), tetravalent (having four antigen-binding sites), and so on. Multivalent non-single-chain antigen-binding unit can be further classified on the basis of their binding specificities. A "monospecific" non-single-chain antigen-binding unit is a molecule capable of binding to one or more antigens of the same kind. A "multispecific" non-single-chain antigen-binding unit is a molecule having binding specificities for at least two different antigens. While such molecules normally will only bind two distinct antigens, antibodies with additional specificities such as trispecific antibodies are encompassed by the present invention.

"Single-chain antigen-binding unit" refers to monomeric antigen-binding unit. Although the two domains of the Fv fragment are coded for by separate genes, a synthetic linker can be made that enables them to be made as a single protein chain (i.e. single chain Fv ("scFv") as described in Bird et al. (1988) Science 242:423-426 and Huston et al. (1988) PNAS 85:5879-5883) by recombinant methods. Other single-chain antigen-binding units include antigen-binding molecules stabilized by the subject heterodimerization sequences, and dAb fragments (Ward et al. (1989) Nature 341:544-546) which consist of a VH domain and an isolated complimentarity determining region (CDR). A preferred single-chain antigen-binding unit contains VL and VH regions that are linked together and stabilized by a pair of subject heterodimerization sequences. The scFvs can be assembled in any order, for example, VH—(first heterodimerization sequence)-(second heterodimerization sequence)—VL or V.sub.L—(first heterodimerization sequence)-(second heterodimerization sequence)—VH.

An antigen-binding unit specifically binds to or immunoreactive with an antigen if it binds with greater affinity or avidity than it binds to other reference antigens including polypeptides or other substances. The antigen-binding unit may be directly attached to the outer surface of the host cell, or may be indirectly attached to the host cell via a host cell bound genetic package such as phage particle.

The accessory polypeptide which is linked to an antigen-binding unit includes, but is not limited to, rPEGs, nrPEGs, and any other polypeptides capable of increasing hydrodynamic radius, extending serum half-life, and/or modifying in vivo clearance rate. When desired, an accessory polypeptide causes a small increase in predicated molecular weight, but a much larger increase in apparent molecular weight.

Figure 82:
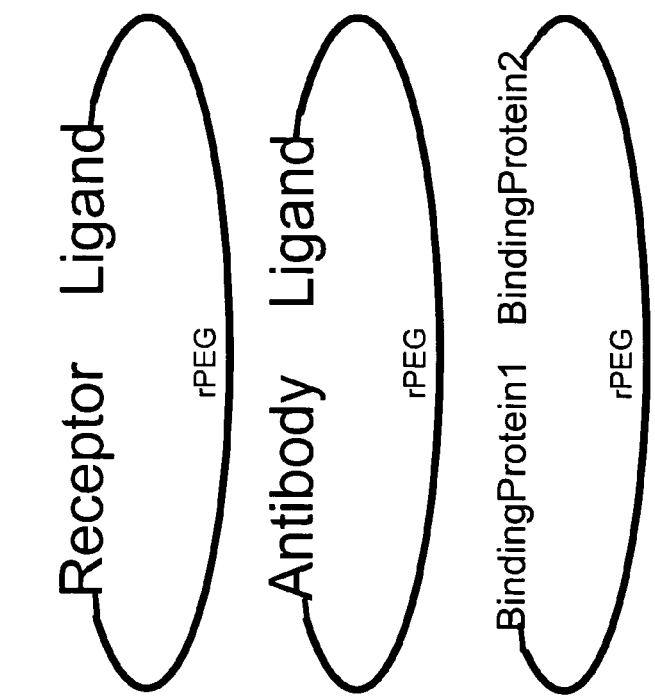
FIG. 82 shows general ways of making 'rPEG linked binding pairs', which have the advantage of no initial activity and therefore no burst release effect (increasing the dose that can be administered without causing toxicity) and reduced initial receptor-mediated clearance. The general binding pairs can be receptor-ligand, antibody-ligand, or generally binding protein 1-binding protein 2. The construct can have a cleavage site, which can be cleaved before injection, after injection (in serum by proteases) and can be located such that the rPEG stays with the therapeutic product end (active protein), which can be either the ligand, the receptor or the antibody.

Another embodiment of the present invention includes an accessory polypeptide such as rPEG linked at both ends to a binding pair. Such binding pair generically consists of a binding protein 1 and a binding protein 2, linked via rPEG. Examples of such binding pair include but are not limited to a receptor-ligand pair, an antibody-antigen pair, or any two polypeptides that are capable of interacting with each other. FIG. 82 shows the general ways of making such rPEG linked binding pairs, which have the advantage of no initial activity and therefore no burst release effect (increasing the dose that can be administered without causing toxicity) and reduced initial receptor-mediated clearance. The general binding pairs can be receptor-ligand, antibody-ligand, or generally binding protein 1-binding protein 2. The construct can have a cleavage site, which can be cleaved before injection, after injection (in serum by proteases) and can be located such that the rPEG stays with the therapeutic product end (active protein), which can be the ligand, the receptor or the antibody.

Antibody Fragment-Based Therapeutics (AFBT)

Another embodiment of the present invention includes an antibody fragment-based therapeutic (AFBT). AFBTs comprise at least one antigen-binding unit or antibody fragment and one accessory polypeptide such as a rPEG domain. An AFBT may also comprise one or more payloads, which include moieties that have biological activities such as cytokines, enzymes and growth factors, as well as agents that may have therapeutic potentials such as cytotoxic agents, chemotherapeutic agents, antiviral compounds, or contrast agents. An AFBT may also include additional domains, for example, multimerization domains such as an Fc region or leucine zipper. FIG. 58a shows an example of an AFBT that illustrates the main components of an AFBT. The antibody fragment provides an AFBT with specificity for a target antigen (also generically illustrated in FIG. 21). The rPEG domain provides a variety of benefits to the antibody fragment as well as to the payload. These benefits include, but are not limited to, prolonged half-life in vivo, increased solubility, increased thermal stability, increased protease stability, improved protein folding, reduced chain reassortment, reduced immunogenicity of the payload, and avoidance of preexisting immune responses to chemical PEG. The rPEG domain also facilitates production and purification. The high solubility of the rPEG domain renders AFBTs high solubility that can be formulated at high concentration with a low tendency to form aggregates. It should be understood that an AFBT may contain additional components not illustrated in particular in this figure.

vH/vL Domain-Based Structures

Figure 52:
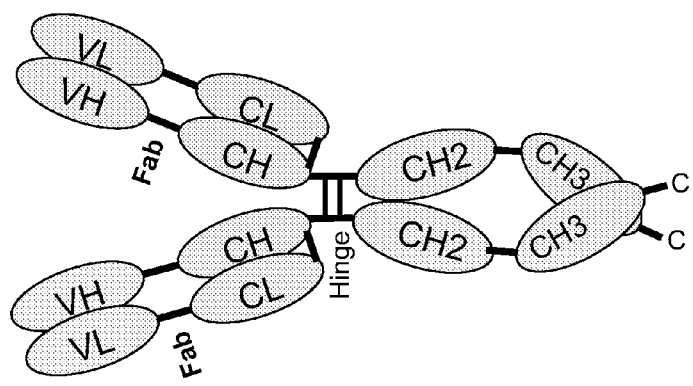
FIG. 52 shows the structure of a whole IgG1, but IgG2, IgG3, IgG4, IgE, IgD, IgA and IgM can similarly be used as starting points. A dAb-dAb-Fc fusion protein is also useful because of its tetravalency; it is not shown.
Figure 53:
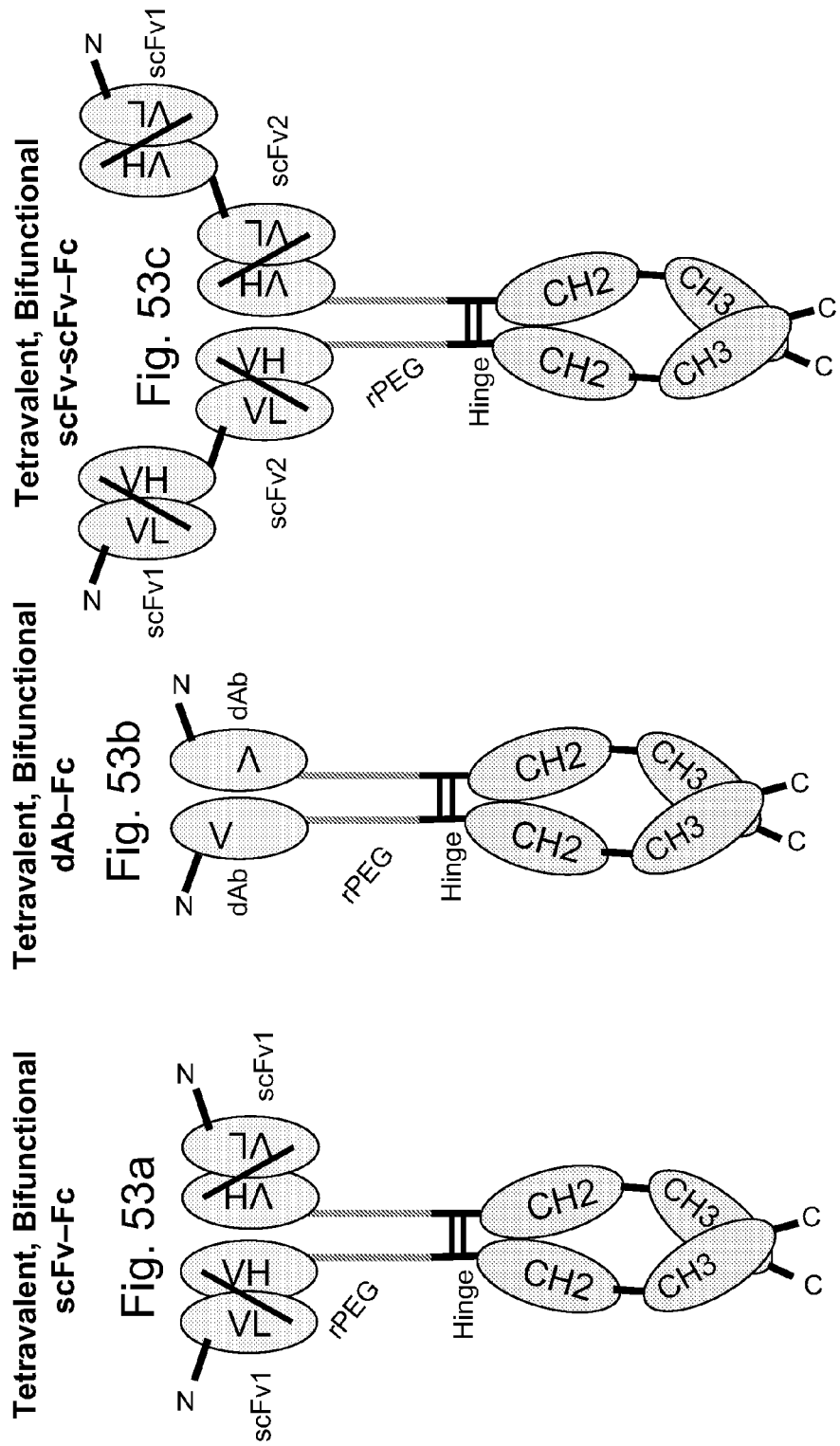
FIG. 53 Constructs are shown with rPEG separating the Fc and antigen binding domains, and the Fc at the C-terminus: (dAb/scFv)-rPEG-Fc and (dAb/scFv)-(dAb/scFv)-rPEG-Fc. However, formats with a different order of the same elements are also useful, like rPEG-Fc-(dAb/scFv), rPEG-Fc-(dAb/scFv)-(dAb/scFv), Fc-rPEG-(dAb/scFv), Fc-rPEG-(dAb/scFv)-(dAb/scFv), Fc-(dAb/scFv)-rPEG, Fc-(dAb/scFv)-(dAb/scFv)-rPEG, dAb/scFv)-Fc-rPEG, and (dAb/scFv)-(dAb/scFv)-Fc-rPEG. One can also mix scFv and dabs, like dAb-scFv or scFv-dAb or combine two scFvs or two dAbs of different target specificities: scFv1-scFv2 or dAb1-dAb2.
Figure 54:
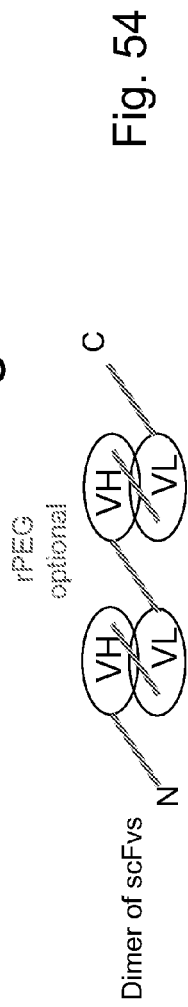
FIG. 54 shows a dimer of a scFv fragment. Both heterodimers and homodimers can be constructed.
Figure 55:
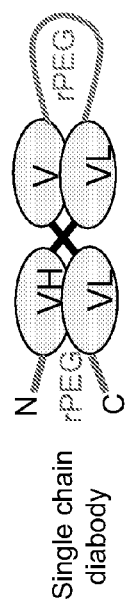
FIG. 55 single chain diabody

In one embodiment of the present invention, an AFBT also comprises one or more antibody-derived immunoglobulin (Ig) domains or fragments, including a single-chain variable fragment (scFv). scFv consists of a vH domain linked to a vL domain via a peptide linker between the vH and vL domains. The linker in the scFv is chosen such that it forms a single molecular species, which includes a scFv, diabody, triabody, or tetrabody (FIGS. 53, 54, 55), as compared to the full-length, i.e. whole antibody (FIG. 52). Typically the valency of the resulting AFBT is between one and four although a higher valency is not excluded. Designs that predominantly form a single, homgeneous species are preferred. An Fv fragment may include a disulfide bond between contacting vH and vL domains to reduce the risk of domain reassortment. The fraction of the desired species that may be achieved ranges from less than 1% to 100% of the antibody fragment mix. The primary controls are the linker length, which directs the format, and the rPEG, which reduces antibody fragment chain reassortment. A preferred embodiment includes the formation of monomeric scFv from a single vH-vL chain employing linkers of at least 12 amino acids. More preferred embodiments include a linker length of at least 15, at least 20, at least 30, at least 50, at least 100, at least 200, or at least 288 amino acids. Of particular utility are vH-vL chains that preferentially form diabodies, which require linkers of less than 10-20 amino acids, preferably 1, 2, 3, 4, 5, 6, 7, 8, 9 or 10 amino acids (FIG. 84). A diabody has two protein chains and can have an rPEG at one or both C-terminal ends, and/or at one or both N-terminal ends. The diabody has two binding sites, of which zero, one or two may bind to a pharmaceutical target, or to a halflife target (e.g. HSA, IgG, Red Blood Cells, Collagen, etc) or to no target. The diabody may contain zero, one or more drug modules located at the N-terminal or C-terminal end of zero, one or both protein chains. AFBTs containing diabodies have increased molecular weight due to their dimeric structure, which slows down renal elimination. In one embodiment, the degree of antibody fragment chain reassortment from one species to another species is less than 50%, 40%, 30%, 20% or 10% of the mass of protein per day or per week at a fixed temperature (e.g. 4° C., 25° C. or 37° C.), preferably less than 5%, 2%, 1% or 0.1%.

In another embodiment, the AFBTs include triabodies, which contain three polypeptide chains, each containing a vH and a vL domain connected via a linker of less than 10 amino acids, preferably less than 5 amino acids. The frequency of triabodies can be increased by eliminating one or a few amino acids from one or both joining ends of the vH and vL domains, shortening the connecting sequence so that triabodies are favorably formed. The number of residues removed from one or both of the fused ends of the antibodies can range from 1 to 10 amino acids.

In yet another embodiment, the AFBTs include tetrabodies, which contain four polypeptide chains, each having one vH domain and a vL domain connected via a short linker of less than 5 amino acids, or as a result of removal of 1 to 10 residues from one or both of the fused ends of the antibody. The number of amino acids to eliminate from one or both joining ends of the vH and vL domains can be adjusted to ensure the most desirable outcome.

Figure 57:
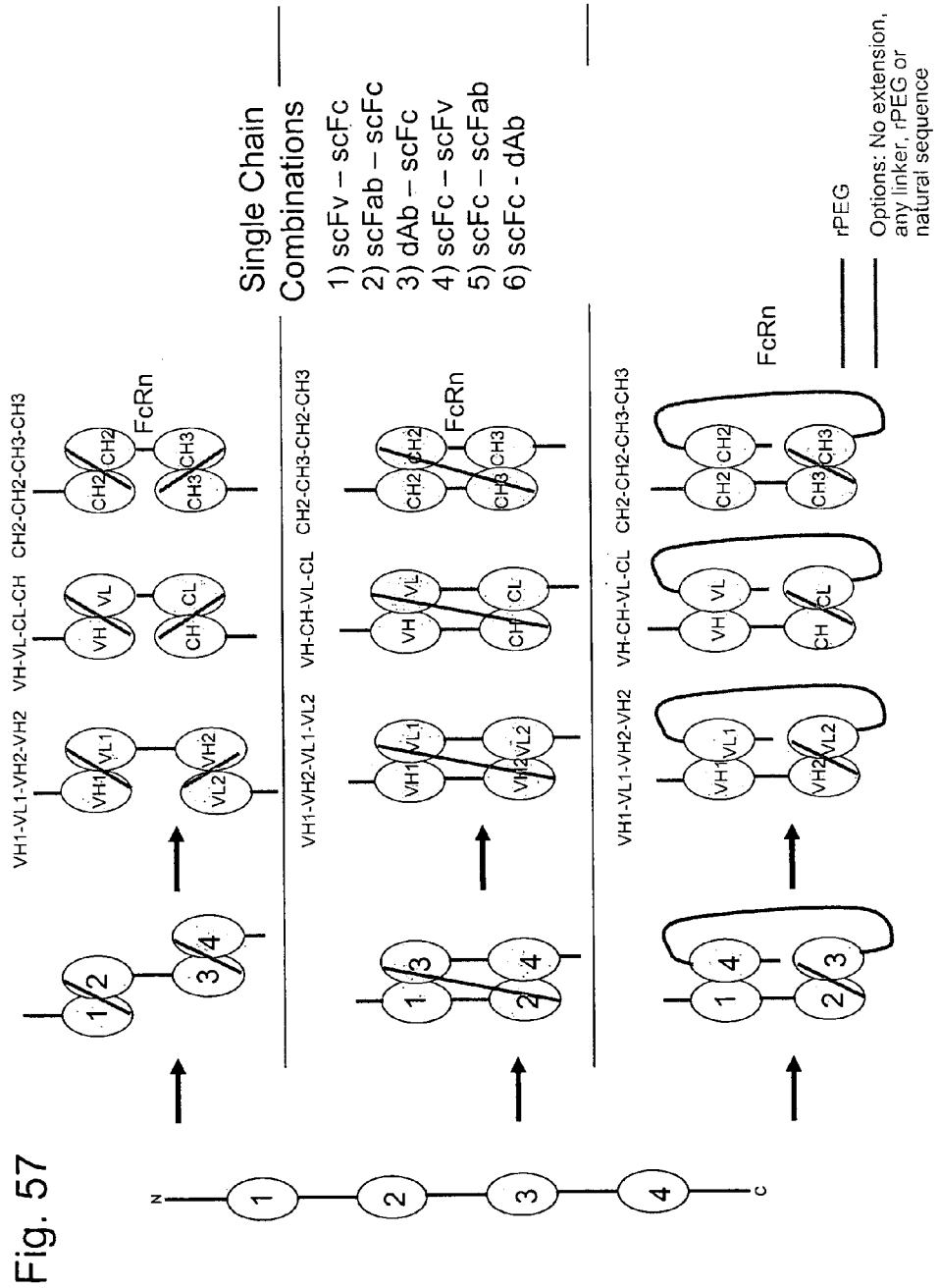
FIG. 57 Products consisting of a single copy of a protein chain

Examples of various types of single chain (scFv) combination consisting of a single copy of a polypeptide chain include but are not limited to scFv-scFv, scFab-scFc, dAb-scFc, scFc-scFc, scFc-scFab, and scFc-dAb (FIG. 57). A scFv fragment can be fused at one or both of the N- and/or C-terminal ends to a drug module such as IFNa, hGH, etc (FIG. 85). The scFv has one binding site, which may or may not bind to a pharmaceutical target, or to a halflife target, e.g. HSA (FIG. 85b), IgG, red blood cells, etc.

AFBTs that contain Ig domains can have a variety of architectures. Constructs of particular utility include, but are not limited to, the following: vL-linker-vH-rPEG, vH-linker-vL-rPEG, vL-linker-vH-rPEG-payload, vH-linker-vL-rPEG-payload, vL-linker-vH-payload-rPEG, vH-linker-vL-payload-rPEG, rPEG-vL-linker-vH, rPEG-vH-linker-vL, payload-rPEG-vL-linker-vH, payload-rPEG-vH-linker-vL, rPEG-payload-vL-linker-vH, rPEG-payload-vH-linker-vL. These AFBTs can contain additional domains that can be inserted between domains or anywhere into an rPEG domain. There can also be several payload modules.

The linker sequence joining vH and vL can be optimized to achieve optimal protein folding and stability as well as high level expression and a large fraction of the desired species. A preferred embodiment includes linker sequences that are rich (e.g. greater than 50%) in glycine and other small hydrophilic amino acids such as serine, threonine, glutamic acid, aspartic acid, lysine, arginine, and alanine. rPEG is particularly suitable as a linker between vH and vL domains. Linkers with improved properties can be obtained by selection or screening of libraries.

scFv with rPEG Linkers

In yet another embodiment, scFv contain rPEG sequences as the linker between the vH and vL domains. A preferred embodiment includes rPEG linkers that contain a significant negative net charge, which results in improved solubility and folding of the scFv domains. Preferred embodiments contain linkers with at least 15, at least 20, at least 30, at least 50, at least 100, at least 200, or at least 288 residues.

Methods to Generate Stable Antibody Fragments of AFBTs

The present invention also relates to methods of generating and engineering an antigen binding unit of an AFBT. Many methods are known to generate antibodies with specificity for a target antigen. Examples include monoclonal antibodies, in particular in transgenic animals that produce human antibodies; phage display of Fab or scFv libraries; ribosomal display; and humanization of monoclonal antibodies. Multiple methods to engineer the stability of scFvs have also been described [Worn, A., et al. (2001) *J Mol Biol*, 305: 989]. It has been shown that adding a disulfide bond between the vH and vL domains of scFv can lead to significant stabilization [Dooley, H, et al. (1998) *Biotechnol Appl Biochem* 28 (Pt 1), 77, #2802]. An alternative is the introduction of consensus mutations. The amino acid frequencies at various positions in antibody framework residues have been analyzed. It has been shown that the Boltzmann equation can predict the stabilizing effect of some consensus mutations [Steipe, B, et al. (1994) *J Mol Biol* 240, 188, #2026]. A combinatorial approach that allows the simultaneous introduction of multiple consensus mutations into single chain antibody fragments has been described [Roberge, M., et al. (2006) *Protein Eng Des Sel*, 19: 141]. Producing more stable antibody fragments has resulted in improved in vivo targeting [Worn, A., et al. (2000) *J Biol Chem*, 275: 2795].

Some scFv have been expressed in soluble form in the cytosol of *E. coli*. In general, disulfide bonds are not formed in the cytosol but they can form spontaneously after cell lysis [Tavladoraki, P., et al. (1999) *Eur J Biochem*, 262: 617]. In general, cytosolic expression of an antibody is well correlated with the antibody stability [Worn, A., et al. (2001) *J Mol Biol*, 305: 989]. Mutant libraries of antibody fragments can be subjected to selection for improved cytosolic expression [Martineau, P., et al. (1998) *J Mol Biol*, 280: 117]. Redox engineered strains of *E. coli* can be used to improve cytosolic expression of Fab fragments [Levy, R., et al. (2007) *J Immunol Methods*, 321: 164]. The culture conditions have been optimized to improve the expression of soluble scFv in the cytosol of *E. coli* resulting in expression levels of up to 35 mg/L of culture [Padiolleau-Lefevre, S., et al. (2007) *Mol Immunol*, 44: 1888]. Another approach to improve the cytosolic expression of scFvs is the screening or selection of genomic libraries with the goal to identify chaperones or other factors that facilitate expression. This approach has been evaluated using lambda phage. Disulfide bonds in scFv have been removed successfully to form intrabodies. Variants of such intrabodies can be identified that result in improved cytosolic expression [der Maur, A. A., et al. (2002) *J Biol Chem*, 277: 45075]. However, disulfide bonds are important for the overall stability of most antibody fragments and in most cases intrabodies have been of limited utility.

Complementary Determining Regions (CDR) Grafting

The binding interactions between antibodies or antibody fragments and their targets are mainly determined by the complementary determining regions (CDRs). It has been shown that CDRs can be grafted between the variable domains of different antibodies [Jones, P. T., et al. (1986) *Nature*, 321: 522]. In many cases other residues in the antibody framework need to be grafted in addition to CDR residues in order to retain antigen binding. CDR grafting can be useful to improve the stability of an antibody by grafting CDRs from a less stable variable domain to a more stable variable domain. An example is the grafting of CDRs from a fluorescein-binding scFv into a well-expressed scFv that is used as a 'scaffold', resulting in improved expression and increased folding stability [Jung, S., et al. (1997) *Protein Eng*, 10: 959]. Further examples of CDR grafting into antibody fragments are described in [Leong, S. R., et al. (2001) *Cytokine*, 16: 106] and [Werther, W. A., et al. (1996) *J Immunol*, 157: 4986]. CDR grafting can be employed to reduce the immunogenicity of antibodies in patients by grafting CDRs from murine antibodies to human framework residues [Winter, G., et al. (1993) *Trends Pharmacol Sci*, 14: 139].

Affinity of the Antigen Binding Unit of AFBT

The present invention also embodies the methods of improving the affinity of the antigen binding unit of an AFBT. Multiple approaches have been described that allow the identification of antibodies and antibody fragments with improved affinity. For instance Pastan prepared mini libraries of 1000-10000 clones focused on hot spots that are naturally prone to hypermutation. Phage panning gave variants with 15-55 fold improvement [Chowdhury, P S, et al. (1999) *Nat Biotechnol* 17, 568, #2800]. Phage display and other display methods can be utilized to identify variants of antibody fragments with improved affinity. Different vectors are available for phage display [Corisdeo, S., et al. (2004) *Protein Expr Purif*, 34: 270]. Residues that are involved in antigen binding can be identified using alanine scanning mutagenesis. Subsequently, these positions can be targeted for mutagenesis to identify variants with improved affinity [Leong, S. R., et al. (2001) *Cytokine*, 16: 106]. Another strategy is CDR walking mutagenesis that can result in the identification of antibody fragments with high target-binding affinity [Yang, W. P., et al. (1995) *Mol Biol*, 254: 392]. Improved affinity can result in improved tumor-selectivity of antibody fragments [Adams, G. P., et al. (1998) *Cancer Res*, 58: 485]. High affinity can restrict the tumor penetration of scFvs [Adams, G. P., et al. (2001) *Cancer Res*, 61: 4750] [Graff, C. P., et al. (2003) *Cancer Res*, 63: 1288]. Antibody fragments with improved affinity can be identified using yeast display in combination with FACS sorting [Boder, E. T., et al. (2000) *Proc Natl Acad Sci USA*, 97: 10701].

Various IgG Domains

AFBTs may contain a variety of immunoglobulin domains. These domains can affect protein expression, multimerization, and can serve as effectors. The following non-exhaustive list, which provides examples for illustrating the variety of Ig domains, is applicable for fusions to any antibody isotype including IgG1, IgG2, IgG3, IgG4, IgE, IgM, IgA, and IgD from any species including humans. Sites for fusion of rPEG to immunoglobulin-family sequences include but are not limited to the following:

N-terminal to the CL1 domain, before the interchain cysteine

N-terminal to the CL1 domain, after the interchain cysteine

C-terminal to the CL1 domain, before the interchain cysteine

C-terminal to the CL1 domain, after the interchain cysteine

N-terminal to the CH1 domain, before the interchain cysteine

N-terminal to the CH1 domain, after the interchain cysteine

C-terminal to the CH1 domain, before the interchain cysteine
C-terminal to the CH1 domain, before the hinge cysteine(s)
C-terminal to the CH1 domain, after the hinge cysteine(s)
N-terminal to the hinge cysteine(s)
C-terminal to the hinge cysteine(s), before CH2
N-terminal to the CH2 domain
C-terminal to the CH2 domain
N-terminal to the CH3 domain
C-terminal to the CH3 domain
N-terminal to the CH4 domain
C-terminal to the CH4 domain
N-terminal to peptides derived from CDRH1-3 and/or CDRL1-3 (lambda and kappa)
N-terminal to peptides derived from CDRH1-3 and/or CDRL1-3 (lambda and kappa)

Fab Domain Based AFBTs

Figure 56:
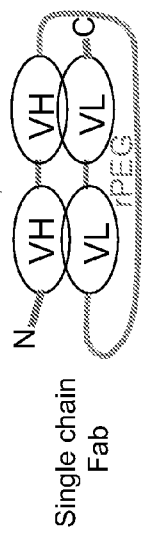
FIG. 56 shows an example of a single chain Fc fragment. Optionally, biologically active proteins can be fused to either terminus of this construct.

Still another embodiment of the present invention includes a Fab domain-based AFBT (FIG. 56). Fab domains comprise two peptide chains, each of which is derived from the heavy and light chains of an antibody. rPEGs and payloads and other domains can be fused to either chain of a Fab fragment. Alternatively, rPEGs and payloads can be fused to both chains of a Fab. Fab domains can be designed to facilitate the dimerization of the resulting proteins such that the final protein contains four peptide chains. The following is a list of AFBTs that comprise at least one Fab domain:

| Light chain | Heavy chain |
| --- | --- |
| vL-CL-rPEG | vH-CH1 |
| vL-CL-rPEG-payload | vH-CH1 |
| vL-CL-payload-rPEG | vH-CH1 |
| rPEG-vL-CL | vH-CH1 |
| payload-rPEG-vL-CL | vH-CH1 |
| rPEG-payload-vL-CL | vH-CH1 |
| vL-CL-rPEG | vH-CH1-rPEG |
| vL-CL-rPEG-payload | vH-CH1-rPEG |
| vL-CL-payload-rPEG | vH-CH1-rPEG |
| rPEG-vL-CL | vH-CH1-rPEG |
| payload-rPEG-vL-CL | vH-CH1-rPEG |
| rPEG-payload-vL-CL | vH-CH1-rPEG |
| vL-CL-rPEG | vH-CH1-rPEG-payload |
| vL-CL-rPEG-payload | vH-CH1-rPEG-payload |
| vL-CL-payload-rPEG | vH-CH1-rPEG-payload |
| rPEG-vL-CL | vH-CH1-rPEG-payload |
| payload-rPEG-vL-CL | vH-CH1-rPEG-payload |
| rPEG-payload-vL-CL | vH-CH1-rPEG-payload |
| vL-CL-rPEG | vH-CH1-payload-rPEG |
| vL-CL-rPEG-payload | vH-CH1-payload-rPEG |
| vL-CL-payload-rPEG | vH-CH1-payload-rPEG |
| rPEG-vL-CL | vH-CH1-payload-rPEG |
| payload-rPEG-vL-CL | vH-CH1-payload-rPEG |
| rPEG-payload-vL-CL | vH-CH1-payload-rPEG |
| vL-CL-rPEG | rPEG-vH-CH1 |
| vL-CL-rPEG-payload | rPEG-vH-CH1 |
| vL-CL-payload-rPEG | rPEG-vH-CH1 |
| rPEG-vL-CL | rPEG-vH-CH1 |
| payload-rPEG-vL-CL | rPEG-vH-CH1 |
| rPEG-payload-vL-CL | rPEG-vH-CH1 |
| vL-CL-rPEG | payload-rPEG-vH-CH1 |
| vL-CL-rPEG-payload | payload-rPEG-vH-CH1 |
| vL-CL-payload-rPEG | payload-rPEG-vH-CH1 |
| rPEG-vL-CL | payload-rPEG-vH-CH1 |
| payload-rPEG-vL-CL | payload-rPEG-vH-CH1 |
| rPEG-payload-vL-CL | payload-rPEG-vH-CH1 |
| vL-CL-rPEG | rPEG-payload-vH-CH1 |
| vL-CL-rPEG-payload | rPEG-payload-vH-CH1 |
| vL-CL-payload-rPEG | rPEG-payload-vH-CH1 |
| rPEG-vL-CL | rPEG-payload-vH-CH1 |
| payload-rPEG-vL-CL | rPEG-payload-vH-CH1 |
| rPEG-payload-vL-CL | rPEG-payload-vH-CH1 |

Full Length Antibodies rPEGs and payloads and other domains can be fused to the light chain or heavy chain of an antibody, or to both chains of an antibody. The following table illustrates a few examples of AFBTs that are based on full-length antibodies:

| Light chain | Heavy chain |
| --- | --- |
| Light chain-rPEG | Heavy chain |
| Light chain-rPEG-payload | Heavy chain |
| Light chain-payload-rPEG | Heavy chain |
| rPEG-Light chain | Heavy chain |
| payload-rPEG-Light chain | Heavy chain |
| rPEG-payload-Light chain | Heavy chain |
| Light chain-rPEG | Heavy chain-rPEG |
| Light chain-rPEG-payload | Heavy chain-rPEG |
| Light chain-payload-rPEG | Heavy chain-rPEG |
| rPEG-Light chain | Heavy chain-rPEG |
| payload-rPEG-Light chain | Heavy chain-rPEG |
| rPEG-payload-Light chain | Heavy chain-rPEG |
| Light chain-rPEG | Heavy chain-rPEG-payload |
| Light chain-rPEG-payload | Heavy chain-rPEG-payload |
| Light chain-payload-rPEG | Heavy chain-rPEG-payload |
| rPEG-Light chain | Heavy chain-rPEG-payload |
| payload-rPEG-Light chain | Heavy chain-rPEG-payload |
| rPEG-payload-Light chain | Heavy chain-rPEG-payload |
| Light chain-rPEG | rPEG-Heavy chain |
| Light chain-rPEG-payload | rPEG-Heavy chain |
| Light chain-payload-rPEG | rPEG-Heavy chain |
| rPEG-Light chain | rPEG-Heavy chain |
| payload-rPEG-Light chain | rPEG-Heavy chain |
| rPEG-payload-Light chain | rPEG-Heavy chain |
| Light chain-rPEG | payload-rPEG-Heavy chain |
| Light chain-rPEG-payload | payload-rPEG-Heavy chain |
| Light chain-payload-rPEG | payload-rPEG-Heavy chain |
| rPEG-Light chain | payload-rPEG-Heavy chain |
| payload-rPEG-Light chain | payload-rPEG-Heavy chain |
| rPEG-payload-Light chain | payload-rPEG-Heavy chain |
| Light chain-rPEG | rPEG-payload-Heavy chain |
| Light chain-rPEG-payload | rPEG-payload-Heavy chain |
| Light chain-payload-rPEG | rPEG-payload-Heavy chain |
| rPEG-Light chain | rPEG-payload-Heavy chain |
| payload-rPEG-Light chain | rPEG-payload-Heavy chain |
| rPEG-payload-Light chain | rPEG-payload-Heavy chain |

Figure 103E:
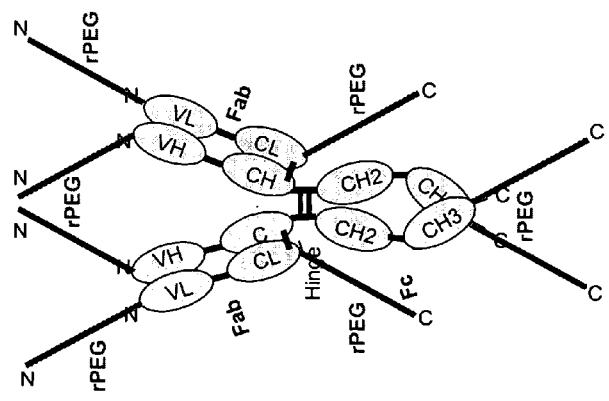
FIG. 103e shows the Preferred Fusion Sites for rPEG to Domains and Fragments of an Antibody (IgG1, 2, 3, 4, IgE, IgA, IgD, IgM). Fusion sites for N-terminal and/or C-terminal addition of rPEG are shown with red arrows or red lines.
Figure 103B:
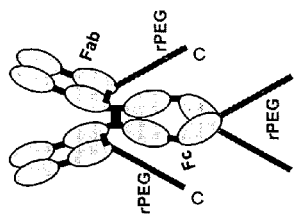
FIG. 103a-d shows the preferred fusion Sites for rPEG to an intact, Whole Antibody (incl. IgG1, 2, 3, 4, IgE, IgA, IgD, IgM). These sites indicated are preferred because they are at the boundary of structured sequences, such as domains, hinges, etc, without disturbing the folding of these functional domains. rPEG can thus be added in 1, 2, 3, 4, 5, 6, 7 or even 8 different locations to an antibody (and more than 8 for IgM and IgG3) and a single antibody can have 1, 2, 3, 4, 5, 6, 7, 8 or more rPEGs in diverse locations and in any combination of the 8 locations shown.
Figure 103C:
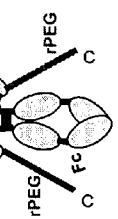
Figure 103D:
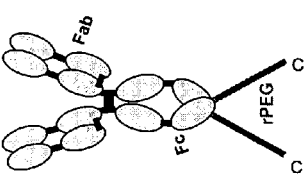
Figure 103A:
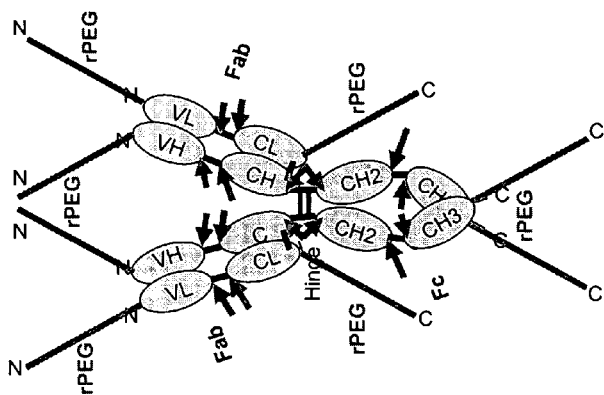

Certain sites on a full-length antibody or an antibody fragment as defined herein are preferred fusion sites for rPEG to a full-length antibody (including IgG1, 2, 3, 4, IgE, IgA, IgD, and IgM) or an antibody fragment. These preferred sites are at the boundary of structured sequences, such as domains, hinges, etc., without disturbing the folding of these functional domains. rPEG can be added in 1, 2, 3, 4, 5, 6, 7 or even 8 different locations to an antibody (and more than 8 for IgM and IgG3) and a single antibody can have 1, 2, 3, 4, 5, 6, 7, 8 or more rPEGs in diverse locations and in any combination of the 8 locations shown in FIG. 103. FIG. 103e shows the preferred fusion sites for rPEG to domains and fragments of an antibody.

Domain Antibody-Based AFBTs

In yet another embodiment, rPEGs and payloads and other domains can be fused to a domain antibody (dAb). In order to generate domain antibodies with suitable binding properties, one can use the naturally monomeric vH domains (called vHH) found in the immune repertoire of camelids and sharks that naturally lacks a light chain. [Hamers-Casterman, C., et al. (1993) *Nature,* 363: 446]. Alternatively, one can engineer the vH-vL interface of a human vH or vL domain in order to improve solubility and reduce dimerization and aggregation. Such mutations carry the risk of increasing immunogenicity of the resulting domain antibody. The present invention describes fusing human vH or vL Ig domains to rPEG, which improves solubility and folding, reduces aggregation, and yet does not induce immune response triggered by the mutagenesis of human framework residues. Examples of AFBTs which are based on dAb domains include, but are not limited to, dAb-rPEG, dAb-rPEG-payload, dAb-payload-rPEG, rPEG-dAb, payload-rPEG-dAb, rPEG-payload-dAb. dAb domain can be derived from the vH or vL domain of an antibody molecule.

Multispecific AFBTs

Figure 59:
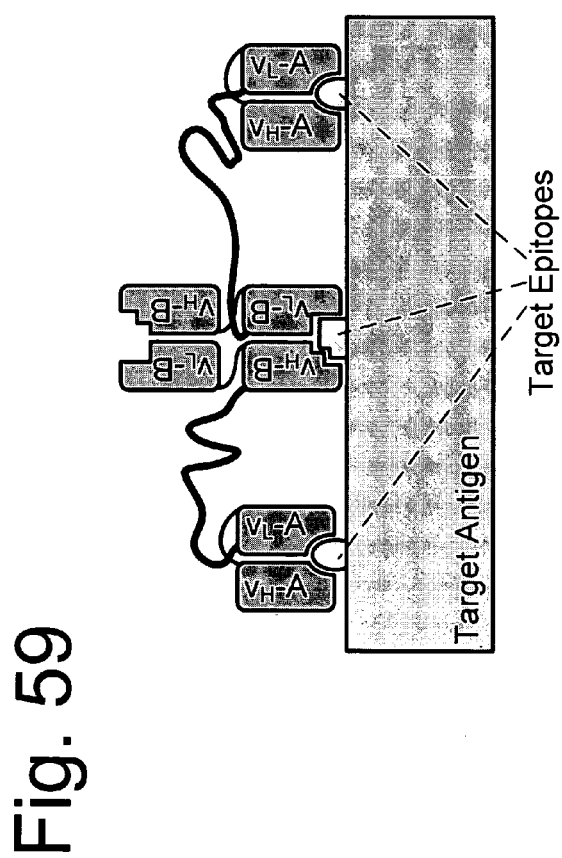
FIG. 59: Multivalent binding of an AFBT to a target antigen

The present invention also embodies AFBTs that comprise fragments derived from multiple different antibodies with different binding specificities. An example is shown in FIG. 58b. Such AFBTs combine the binding specificities of two or more parent antibodies. Parent antibodies can be chosen such that the resulting AFBT binds to multiple different target antigens. Alternatively, the parent antibodies can bind to different epitopes of the same target antigen. AFBTs bind the target very tightly if they can form multivalent interactions by binding to multiple sites on the same target antigen as illustrated in FIG. 59. Multispecific AFBTs can form multimers of the same protein chain. For instance, FIG. 58b illustrates a multispecific AFBT that is a dimer of two polypeptide chains that contains two binding sites based on the vH-vL chain A and two additional binding sites based on the vH-vL chain B. One skilled in the art can appreciate the possibility of generating a multispecific AFBT containing many different combinations of binding domains or binding modules. In addition to different variable domains, multivalent AFBTs may include one or more payload domains, rPEG modules and other protein domains that can be chosen to enhance therapeutic utility or production and purification. One embodiment includes multispecific AFBTs that interact with multiple target antigens that are related to the same disease symptoms, the same pathogen or cause of pathogenesis, or the same physiological pathway or process. Examples of such multispecific AFBTs include but are not limited to multispecific AFBTs that block multiple cytokines which are involved in a related biological process. A preferred embodiment includes multispecific AFBTs that block multiple growth factors that are involved in angiogenesis such as VEGF, PDGF, and PIGF. FIG. 95 shows an rPEGs flanked on both sides by a VEGF-receptors. Since VEGF is dimeric, it can be the same receptor on both sides of the rPEG, or a different receptor, preferably VEGF-R1 and VEGF-R2, but VEGFR3 may also be used. Another preferred embodiment includes multispecific AFBTs that block multiple cytokines that are involved in inflammatory diseases such as TNF-α, IL-1, IL-6, IL12, IL-13, IL17, and IL-23. Yet another preferred embodiment includes multispecific AFBTs that bind multiple tumor antigens such as Her1, Her2, Her3, EGFR, TF antigen, CEA, A33, PSMA, MUC1, av/p3 integrin, αv/β5 integrin, and α5/β1 integrin. Still another preferred embodiment includes multispecific AFBTs that bind multiple antigens that are related to an infectious disease. Said multispecific AFBTs can form multivalent interactions with an infectious agent resulting in improved therapeutic efficacy. Multispecific AFBTs can be engineered to comprise a binding site for a tumor antigen and a second binding site for an antigen on an immune cell. Examples include AFBTs that bind tumor antigens and CD3 or CD16, which can recruit and activate natural killer (NK) cells. To further increase potency, a cytokine domain such as IL-2 can be included to activate immune cells in the vicinity of the tumor cells.

AFBTs Containing Multiple Fragments of the Same Antibody

AFBTs can be engineered such that each polypeptide chain contains multiple variable fragments of the same parent antibody. These fragments can be identical in their sequence or they can be engineered to facilitate proper domain assembly. An example is illustrated in FIG. 60a. This AFBT contains a diabody domain and a monovalent scFv domain based on the same parent antibody. As a result, the AFBT assembles into a dimeric structure that contains a total of 4 equivalent target binding sites. Such multivalent AFBTs can have improved potency due to avidity.

Bispecific AFBTs Based on Diabodies

AFBTs can be constructed to combine one diabody and a variable domain and at least one rPEG domain. The constructs form dimers and contain a total of 4 antigen binding sites. FIG. 58b illustrates an example of a bispecific AFBT. The variable domains A in such a construct can be scFv domains or dAb domains. The variable domains A can be at the C-terminal side of the diabody domain B. Alternatively, the variable domains A can be at the N-terminal side of the diabody domain B. Bispecific AFBTs can contain additional rPEG domains or other domains such as hormones, cytokines or enzymes. If the variable domain in a bispecific AFBT is a scFv domain, the scFv domain can have the configuration vH-linker-vL or the configuration vL-linker-vH.

In a preferred embodiment, a bispecific AFBT comprises a diabody B and a scFv A, in which the diabody and scFv domains are optimized to reduce incorrect pairing of the 4 Ig domains in these constructs. The domains can be optimized such that $v_L$-A and $v_H$-A as well as $v_L$-B and $v_H$-B form tighter interactions than the incorrect pairings VL-A and $v_H$-B and $v_L$-B and $v_H$-A. This can be accomplished by choosing frameworks of both vH and vL domains such that the vH/vL contact surface of scFv domain A has significant structural differences form the vH/vL contact surface of diabody domain B. One can further enhance these differences by engineering the vH/vL contact regions of scFv domain A and diabody domain B to minimize the chance of undesired contacts. For instance, one can engineer charge differences such that an ion pair is formed for correct vH/vL pairing but the same ion pair can not be formed during incorrect pairings of vH and vL domains in the bispecific AFBT. Another approach is to introduce hydrogen bonding partners into the desired vH/vL contact surfaces that can not be formed in incorrect pairings of vH and vL domains. Yet another approach is to alter the shape of the contact vL/vH contact surfaces such that incorrect vL/vH pairings are destabilized.

Bispecific AFBTs based on diabodies are of particular utility as they contain two rPEG domains per divalent complex, which results in reduced kidney filtration and improved in vivo half-life. AFBTs can be engineered to contain a diabody domain and two additional variable domains per polypeptide chain. Such a protein can form dimeric complexes that comprise a total of 6 antigen binding sites. Further variable fragments or payload domains can be added to increase potency.

Dimeric AFBTs Containing Payloads

FIG. 60b illustrates a dimeric AFBT that contains a diabody domain and a payload domain. Such proteins form dimeric complexes such that each complex contains two target binding sites, two rPEGs, and two payload domains. Additional protein domains can be added to increase utility. Having two rPEGs per protein complex reduces kidney filtration and increases in vivo half-life. Having two payload domains increases potency. The target binding sites of the diabody domain can be engineered to further increase in vivo half-life by binding to a component of blood such as red blood cells, human serum albumin, IgG, collagen or other protein or cell in the blood.

Combining Antibody Fragments and Payloads

The present invention also embodies AFBTs which comprise one or more payloads. One preferred embodiment includes payloads that are protein domains and can be directly fused to the other domains comprising an AFBT. Examples of such payload domains include, but are not limited to, cytokines, hormones, growth factors, and enzymes. Such AFBTs combine the specificity of antibodies with the efficacy of the payload while the rPEG domain provides half-life and facilitates production and formulation. Another preferred embodiment includes AFBTs that combine an antibody fragment with specificity for a particular tissue and a payload that exerts its activity in the same tissue. One example includes antibody fragments with specificity for a tumor in combination with cytostatic or cytotoxic payloads. Another example comprises antibody fragments with specificity for infected cells or infectious agents in combination with anti-infective payloads. Yet another useful combination comprises antibody fragments with specificity against inflamed tissues in combination with payloads that have anti-inflammatory activity. Antibodies that can be linked to an accessory polypeptide include, but are not limited to, abciximab, adalimumab, alemtuzumab, basiliximab, bevacizumab, cetuximab, daclizumab, eculizumab, efalizumab, ibritumomab, tiuxetan, infliximab, muromonab-CD3, natalizumab, omalizumab, palivizumab, panitumumab, ranibizumab, gemtuzumab ozogamicin, rituximab, tositumomab, trastuzumab, and any antibody fragments specific for antigens including complement C5, CBL, CD147, IL8, gp120, VLA4, CD11a, CD18, VEGF, CD40L, anti-Id, ICAM1, CD2, EGFR, TGF-β2, TNFα, E-selectin, FactII, Her2/neu, F gp, CD11/18, CD14, CD80, ICAM3, CD4, CD23, β2-integrin, α4β7, CD52, CD22, HLA-DR, CD64 (FcR), TCR α β, CD3, Hep B, CD125, EpCAM, gpIIbIIIa, IgE, CD20, IL5, IL4, CD25, CD33, HLA, F gp, and VNRintegrin.

Enzymes can be used as payloads for tumor-specific AFBTs. Enzymes can be chosen in order to eliminate a required nutrient or metabolite from the tumor environment, such as asparaginase, arginase, histidinase, or methioninase. Alternatively, one can utilize enzymes that exert cytotoxic activity. An example includes AFBTs that comprise a tumor specific antibody fragment and RNAse which induces apoptosis upon internalization into cells.

Payloads that are useful in anti-cancer, anti-microbial, and/or anti-inflammatory therapeutics include toxins such as *Pseudomonas* exotoxin, ricin, botulinum toxin, and other plant or bacterial toxins. Other biological toxins include, but are not limited to, abrin, aerolysin, botulinin toxin A, B, C1, C2, D, E, F, b-bungarotoxin, Caeruleotoxin, Cereolysin, Cholera toxin, *Clostridium difficile* enterotoxin A and B, *Clostridium perfringens* lecithinase, *Clostridium perfringens* kappa toxin, *Clostridium perfringens* perfringolysin O, *Clostridium perfringens* enterotoxin, *Clostridium perfringens* beta toxin, *Clostridium perfringens* delta toxin, *Clostridium perfiringens* epsilon toxin, Conotoxin, Crotoxin, *Diphtheria* toxin, Listeriolysin, Leucocidin, Modeccin, Nematocyst toxins, Notexin, Pertussis toxin, Pneumolysin, *Pseudomonas aeruginosa* toxin A, Saxitoxin, Shiga toxin, *Shigella dysenteriae* neurotoxin, Streptolysin O, *Staphylococcus* enterotoxins B and F, Streptolysin S, Taipoxin, Tetanus toxin, Tetrodotoxin, Viscuminm, Volkensin, and *Yersinia pestis* murine toxin.

Figure 61:
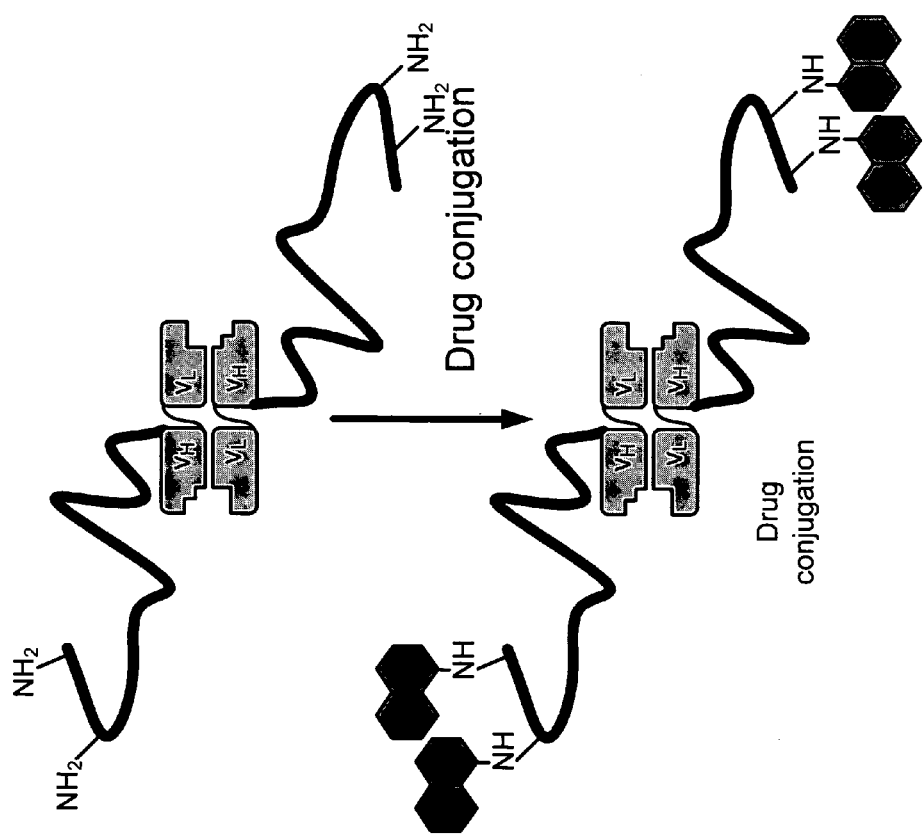
FIG. 61: Preparation of a semisynthetic AFBT

Payloads can be chosen to eliminate a toxic metabolite. Examples are urate oxidase for the treatment of gout and phenylalanine ammonia lyase for the treatment of phenylketonuria. Payloads can also comprise chemically conjugated small molecules. Such payloads can be conjugated to an AFBT resulting in a semisyhetic AFBT. The protein portion of a semisynthetic AFBT can be engineered to facilitate controlled chemical conjugation via exhaustive coupling as illustrated in FIG. 61. The protein portion can be engineered to have a defined number of coupling sites. This enables the use of coupling reagent in excess to the concentration of coupling sites such that coupling efficiency can be close to completion, which results in a defined coupling product: Useful coupling sites can be amino groups. The protein portion of such semisynthetic AFBTs can be engineered such that all or most lysine residues in the antibody fragments are replaced with other residues that are compatible with folding and target binding. In many proteins one can replace lysine residues with arginine, glutamate, aspartate, serine, threonine or another amino acid. Designated coupling sites can be incorporated into the rPEG domain or into any other protein portion of the protein. In addition, the N-terminus of each protein chain can serve as a conjugation site. Cysteine residues can also serve as conjugation sites. Example payloads that can be conjugated to AFBTs include cytotoxic drugs such as doxorubicin, auristatin, maytansine and related molecules that can be fused to AFBTs with tumor-specific antibody fragments. Other payloads of interest for conjugation include antiviral compounds, imaging reagents, and chelating agents that can be labeled with radionuclides to generate imaging agents or AFBTs for radiotherapy.

Thiols in rPEG Tail

Another embodiment of the present invention includes AFBTs comprising rPEG sequences that contain one or multiple cysteine residues. These cysteine side chains can form disulfide bridges with other proteins after injection into a patient. These disulfide bridges can result in increased in vivo half-life. In other embodiments disulfide bond formation can result in prolonged retention of AFBTs at the injection site resulting in a slow-release PK profile. AFBTs that contain free cysteins can also be engineered for improved bioavailability for oral, intranasal, and intradermal administered AFBTs. This can be achieved by forming disulfide bridges with proteins at the surface of epithelial cells resulting in enhanced uptake of the AFBT.

RGD-Peptides in rPEG

AFBTs may also contain one or multiple RGD sequences or related sequences that are known to interact with integrins as well as components of the extracellular matrix. These RGD-related sequences can be flanked by cysteine residues to result in disulfide-mediated cyclization. Alternatively, the RGD-related sequences can be flanked by additional amino acids that can be selected to enhance the affinity and/or specificity of interaction with a particular integrin. One preferred embodiment includes AFBTs that contain RGD sequences and interact with integrins $\alpha_v\beta_3$, $\alpha_v\beta_5$, $\alpha_5\beta_1$, that are overexpressed on a variety of tumor cells.

Antibody Fragments that Increase Half-Life

The present invention also embodies AFBTs that contain antibody fragments that increase the in vivo half-life of the AFBTs. This can be achieved by incorporating antibody fragments that bind to targets that have long in vivo half-lives. Examples of such targets that increase the in vivo half-life include but are not limited to serum proteins, in particular, serum albumin, immunoglobulins, and other highly abundant proteins. AFBTs can also incorporate antibody fragments with specificity for blood cells or vessel walls. Of particular interest are red blood cells (RBCs), which are extremely abundant, have an average life span of approximately 4 months, and are characterized by minimal metabolic activity. AFBTs can be engineered to bind any protein on the surface of an RBC. A preferred embodiment includes AFBTs that bind to glycophorin A, which is expressed in high abundance on the surface of RBCs. AFBTs can be engineered to bind to any cell surface target that can be in contact with an AFBT in vivo resulting in a prolonged retention of the AFBT. Another embodiment includes AFBTs that bind to components of the extracellular matrix (ECM). The ECM contains many proteins including, but not limited to, agrin, alpha elstin, amisyn, bestrophin, collagens, contactin 1, CRIPT, drebrin, entactin, fetuin A, HAS3, HCAP-G, syndecan, KAL1, 1 Afadin, laminins, Mint3, MMP24, NCAM, neurocan, nidogen 2, optimedin, procollagen type IIA, PSCDBP, reelin, SIRP, synaptotagmin, synCAM, syndecan, syntrophin, TAG1, tenascin C, and zyxin. Yet another embodiment includes AFBTs which comprise antibody fragments that bind the FcRn receptor, which results in recycling of endocytosed AFBTs. Examples include antibody fragments that show pH-dependent binding to FcRn such that the antibody fragment binds FcRn with low affinity at around neutral pH but binds with high affinity at lower pH, e.g. pH 5, which is within the range of pH predominantly found in lysosomal compartments. AFBTs that provide increased half-life are illustrated in FIGS. 58a and 60b. It should be noted that many other configurations can be designed that comprise a payload domain and an antibody fragment that provides half-life extension.

Figure 83A:
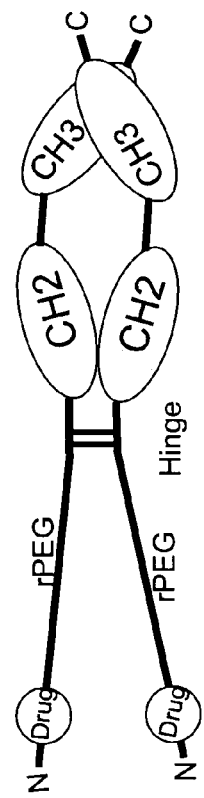
FIG. 83*a* shows a construct with a drug module at the N-terminus, followed by rPEG, fused to an antibody Fc fragment, including the hinge. The Fc fragments provides long halflife and the rPEG allows the Fc fragment to be expressed in the *E. coli* cytoplasm in soluble and active form.
Figure 83B:
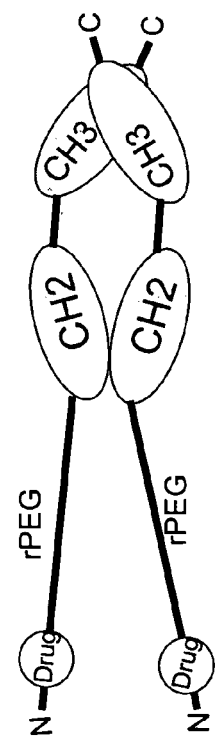
FIG. 83*b* shows a construct with a drug module at the N-terminus, followed by rPEG, fused to an antibody Fc fragment, but without the hinge. The Fc fragments provides long halflife and the rPEG allows the Fc fragment to be expressed in the *E. coli* cytoplasm in soluble and active form.

The present invention also embodies fusion proteins comprising an Fc fragment fused to an rPEG. FIG. 83 shows a construct with a drug module at the N-terminus, followed by rPEG, fused to an antibody Fc fragment, with or without the hinge. The Fc fragment provides a long halflife and the rPEG allows the Fc fragment to be expressed in the E. coli cytoplasm in a soluble and active form. In another embodiment, an antibody Fc fragment, with or without a hinge region, is optionally fused to a drug module (e.g. IFNa, hGH, etc.) on one end and optionally fused to rPEG on the other end. The sequence between CH2 and CH3 mediates binding to FcRn, the neonatal Fc receptor (FIG. 90). Yet another embodiment includes a protein construct comprising a pair of CH3 domains (FIG. 91). Zero, one or both of the two polypeptide chains may be fused to rPEG on the N-terminal and/or C-terminal end, and fused to zero, one or more drug modules at the other end. The FcRn binding sequence can either be retained or deleted. Retention of the FcRn binding sequence yields a longer serum halflife. Still another embodiment describes a protein that is a full Fc, including CH2 and CH3 domains (with or without a hinge), fused at the C-terminus to an rPEG with the drug/pharmacophore located at the C-terminus (FIG. 92). There molecules are capable of polypeptide chain swapping, resulting in heterodimers. Yet another embodiment describes a partial Fc without a hinge and with a CH2 domain that is truncated but retains FcRn binding and with a drug/pharmacophore located at the C-terminus (FIG. 93a). FIG. 93b illustrates a partial Fc without hinge and CH2 domain, but retaining the CH3 domain and having a drug/pharmacophore located at the C-terminus. Such Fc fragment does not bind FcRn but can dimerize via the CH3 domain.

Figure 101:
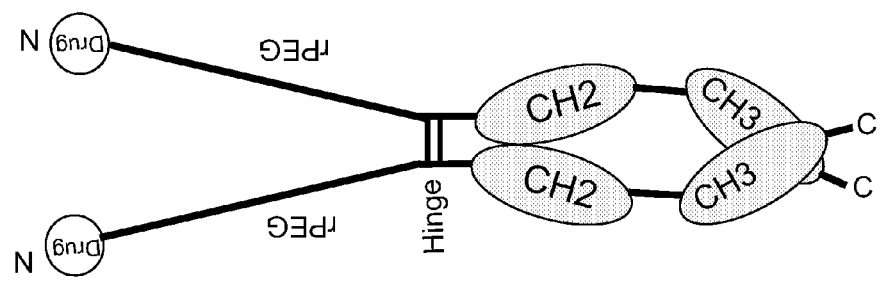
FIG. 101 shows an N-terminal drug module followed by rPEG and a C-terminal Fc fragment (with hinge). This is a useful format for halflife extension of drug modules that can still be manufactured in the E. coli cytoplasm.
Figure 104:
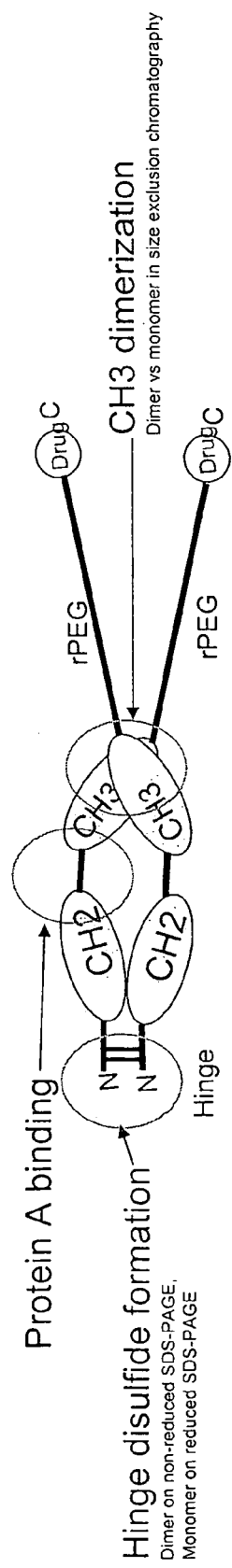
FIG. 104 shows assays for correct folding of Fc fragments.

Still another embodiment employs an N-terminal drug module followed by rPEG and a C-terminal Fc fragment with hinge (FIG. 101). This is a useful format for halflife extension of drug modules that can be manufactured in the E. coli cytoplasm. An alternative format for a pro-drug containing an Fc fragment is described herein (FIG. 102). The format is similar to that described in FIG. 101, with the addition of an inhibitory sequence that binds to and inhibits the drug sequence. The drug is separated from the inhibitory sequence by a cleavage site. The N-terminal inhibitory binding sequence is followed by a cleavage site, which is followed by the drug sequence. Before cleavage, the pro-drug is bound to the inhibitory sequence and thus it is inactive. Upon cleavage, the inhibitory binding sequence is gradually released and cleared, gradually increasing the amount of time that the drug is active. Assays for assessing correct folding of an Fc fragment fused to an rPEG, including SDS-PAGE on hinge disulfide formation and size exclusion chromatography on CH3 dimerization, are depicted in FIG. 104.

Antibody Fragments that Result in Slow Release

AFBTs can be engineered to release slowly from the injection site resulting in long-term drug exposure. One embodiment of the present invention includes the incorporation of an antibody fragment that binds to a molecule expressed in high abundance at the injection site. For example, such antibody fragments may bind to target antigens including but not limited to collagen, hyaluronic acid, heparan sulfate, laminins, elastins, chondroitine sulfate, keratane sulfate, fibronectin, and integrins. By engineering the affinity and/or avidity of the antibody fragment for its target antigen, the rate of AFBT release from the injection site can be controlled. Another embodiment includes the introduction of one or several protease sites that can be cleaved by proteases at the injection site in order to control the rate of AFBT release at the injection site.

Antibody Fragments that Affect Tissue Distribution

The present invention also includes AFBTs that incorporate antibody fragments that bind to a target antigen present in a particular cell or tissue or a particular set of tissues. These constructs can increase the therapeutic window of an active drug by achieving a local tissue-specific accumulation of the AFBT. Examples include AFBTs that contain antibody fragments with specificity for tumor antigens that are overexpressed in tumor tissues or tumor microenvironment including tumor vasculature. One can chose tumor antigens that are effectively internalized by cells as targets for AFBTs that include a payload with intracellular activity. For instance, AFBTs comprise an antibody fragment with specificity for a tumor antigen capable of being internalized upon binding and a cytotoxic payload. Other examples include AFBTs with specificity for viral targets.

Collagen Binding Domains (CBDs)

Another embodiment of the present invention includes the use of CBDs as domains in AFBTs and other protein drugs. Collagen is highly abundant in many tissues in particular in the extracellular space. Protein pharmaceuticals that comprise CBDs can bind to collagen at the injection site or in the vicinity of the injection site, forming a depot from which the AFBT is then slowly released. The release rate can be controlled by introducing protease sites or by choosing CBDs with a suitable affinity to collagen. By choosing a CBD with low affinity to collagen, the rate of release of the AFBT is increased. Alternatively, the rate of AFBT release can be slowed down by including CBDs that bind to collagen with very high affinity or by including multiple CBDs into an AFBT to achieve avidity. CBD sequences can be obtained from naturally occurring CBDs. Examples of proteins that bind to collagen and comprise CBDs include, but are not limited to, integrins, in particular $\alpha_1\beta_1$ integrin, $\alpha_2\beta_1$ integrin, $\alpha_\nu\beta_3$ integrin, angiogenesis inhibitor, collagen V, C-proteinase, decorin, fibronectin, interleukin-2, matrix metalloproteases 1, 2, 9, and 13, phosphophoryn, thrombospondin, biglycan, bilirubin, BM40/SPARC, MRP8, MRP-14, calin from leeches, DDR1, DDR2, fibromodulin, Gla protein, glycoprotein 46, heat shock protein 47, lumican, myelin associated glycoprotein, platelet receptors, *staphylococcus aureous* surface molecules and other microbial adhesion molecules, syndecan-1, tenascin-C, vitronectin, von Willebrand factor, and factor XII. Additional examples of proteins that bind collagen and contain CBDs are listed in [Di Lullo, G. A., et al. (2002) *J Biol Chem*, 277: 4223]. CBDs from natural proteins can be further engineered to increase their therapeutic utility and improve their stability. Immunogenicity of the CBD-containing proteins can be reduced by removing epitopes recognized by B and/or T cells. CBD sequences can also be optimized to maximize protein production and/or to improve protein solubility.

HSA-Binding Peptides in Tail

AFBTs comprising peptide sequences that increase in vivo half-life can also be achieved by utilizing peptide sequences that bind to a serum protein or to the surface of a blood cell. Examples include peptide sequences that bind to human serum albumin (HSA). Such sequences can be obtained by phage display of random peptide sequences or similar selection of screening approaches. AFBTs can contain one or more, either identical or different, copies of such peptide sequences.

Target Antigens

Yet another embodiment of the invention encompasses an antibody fragment that binds to a target antigen which is of therapeutic or diagnostic relevance. FIG. 87 illustrates a Fab fragment binding to a cell-surface target. Extension of the length of the natural linkers from the usual 2-6 amino acids to 4 to 100 or more amino acids, between the VH and the CH domains, and between the VL and the CL domains, increases the ability of one Fab to crosslink to another Fab by domain swapping, thereby forming a binding complex with higher valency, resulting in higher apparent affinity (avidity). The linker may be an rPEG or a different composition. The extended linker format allows binding with increased affinity specifically at sites with a higher density of target. The antibody fragment of an AFBT can bind to a blood component to increase the half-life of the AFPT in circulation. The antibody fragment of the AFBT can also bind to a receptor that facilitates lysosomal recycling. An example is the FcRn receptor that can re-export proteins after lysosomal uptake. Of particular interest are antibody fragments that bind with spacially or temporally-dependent affinity to a receptor that can facilitate lysosomal recycling such that the antibody fragment binds with high affinity under conditions found in a lysosome but it binds with lower affinity to the same receptor under conditions found on the cell surface. The antibody fragment of an AFBT can bind to a target antigen that is predominantly found in a disease-relevant tissue. As a result such AFBTs can accumulate in a particular disease relevant tissue. Examples include AFBTs that bind to tumor tissue or virally-infected tissues. The antibody fragment of an AFBT can bind to a target antigen that facilitates cellular internalization in a disease-relevant tissue. Antibody fragments of an AFBT can also bind to a target antigen that facilitates uptake of the AFBT into a particular compartment of the body, for example, target antigens that facilitate oral, intranasal, mucosal, or lung uptake of an AFBT, and target antigens that facilitate the transport of the AFBT across the blood brain barrier. Examples of target antigents that are of particular interest include, but are not limited to, IL1, IL4, IL6, Il12, IL13, IL17, IL23, CD22, BAFF, and TNFα.

Advantages of rPEG in AFBTs

AFBTs combine valuable properties of rPEG and antibody fragments. The rPEG portion of an AFBT results in a low overall immunogenicity of an AFBT. This is achieved by sterical shielding of the antibody fragment and other potentially immunogenic portions of an AFBT by rPEG. rPEGs are highly flexible and as a result they lack conformational epitopes. Due to their high hydrophilicity and high entropy, rPEGs have a very low inherent immunogenic potential.

The rPEG portions of an AFBT also result in a stabilization of other AFBT domains. Due to their hydrophilic nature, rPEG domains reduce aggregation of AFBTs. This greatly simplifies the formulation development for AFBTs. In addition, steric shielding by rPEG protects other portions of AFBTs from proteolysis. This is of particular importance for payloads and antibody fragments that are prone to proteolytic degradation.

Another advantage of using AFBT over a full length antibody is the minization or elimination of undesirable effector function associated with a full length antibody. Full length antibody molecules have a number of effector functions such as antibody-dependent cell-mediated cytotoxicity (ADCC) as well as complement activation (CDC) that significantly limit their therapeutic use for indications where effector function is undesirable. For instance, many indications require an agent that binds and sequesters a molecule such as a cytokine or hormone. In general it is not desirable to utilize antibodies for such indications as their effector functions results in undesirable toxicity. Much of the antibody dependent effector function is mediated through the Fc portion. In many embodiments described herein, the AFBTs utilize the variable domains of antibodies that are responsible for target binding while replacing the Fc portion that is responsible for effector function. AFBTs can be engineered to bind and activate cell surface receptors such as death receptors DR4 and DR5. Activation can be achieved by receptor multimerization. Although full length antibodies are able to activate such receptors, they also induce toxicity caused by antibody binding to healthy cells that express the same target receptor. AFBTs can activate cell surface receptors without eliciting effector function that would cause toxicity.

Yet another advantage of rPEG is that it helps associate the two proteins that belong to the same complex, as illustrated in FIG. 86. The affinity between such proteins is often insufficient to keep them associated, but the addition of rPEG stabilizes their interaction and reduces their tendency to form polymers.

Manufacture/Production of AFBTs

The present invention also relates to the production of the AFBTs. The rPEG domain in AFBTs facilitates protein folding and reduces protein aggregation. This property facilitates microbial production of AFBTs. Most antibody fragments described in the literature require refolding from inclusion bodies or secretion into the periplasmic space, which results in low production yields. In contrast, most AFBTs can be produced in soluble form at high concentration in the cytosol of microbial expression hosts. A preferred expression host for AFBTs is *E. coli* (FIG. 45). However, the properties of AFBTs make them suitable for expression in most microbial as well as eukaryotic expression systems. The N-terminal sequence of AFBTs can be optimized to control posttranslational processing. In particular the amino acid following the start codon can determine the subsequent processing of the N-terminal methionine [Hirel, P. H., et al. (1989) *Proc Natl Acad Sci USA,* 86: 8247]. One embodiment includes N-terminal sequences that result in uniform products. By choosing gly, ala, pro, ser, thr, or val as amino acid following the N-terminal met, efficient processing and removal of the N-terminal met can be achieved. Another embodiment includes his, gin, glu, phe, met, lys, tyr, trp, or arg as amino acid following the N-terminal met, which prevents removal of the N-terminal met and results in homogeneous products. AFBTs also facilitate refolding under conditions of high protein concentration where most unmodified proteins yield aggregates. The advantage of rPEG during manufacturing of AFBTs is crucial as AFBTs contain multiple protein domains that have a tendency to form aggregates. Such protein domains can be separated by rPEG sequences in the AFBTs to minimize aggregation between individual protein domains during folding.

Generation and Production of Disease-Associated and/or Patient-Specific AFBTs

Figure 68:
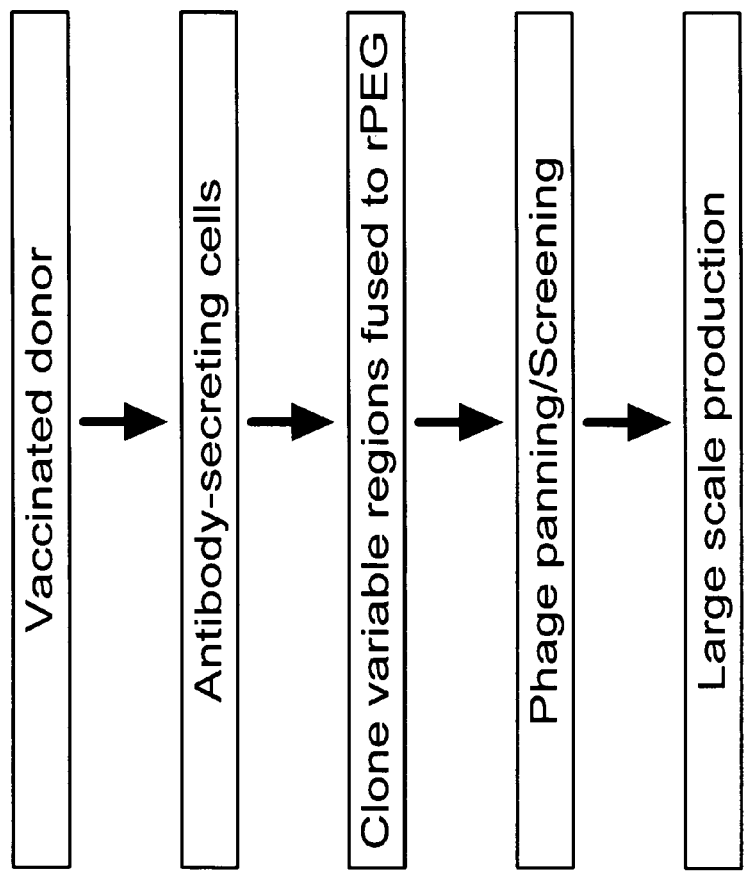
FIG. 68: Flow chart of the discovery process for AFBTs from antisera

The present invention also embodies the generation and production of disease-associated AFBTs, i.e. antibody fragments fused to an accessory polypeptide such as rPEG. Antibody genes can be directly isolated from infected or otherwise exposed patients [Wrammert, J., et al. (2008) Nature]. Various formats of antibody fragments fused to rPEG can be rapidly generated from such antibody genes. The resulting fusion proteins can be produced and purified using standardized protocols, enabling rapid generation of the disease-associated AFBTs. An example of the process is illustrated in FIG. 68. The rapid discovery process enables discovery and preparation of specific treatments in response to an acute disease outbreak such as a bacterial or viral infection. The rapid generation of fusion proteins between antibody fragments and rPEG also enables one to produce patient-specific treatments, which encompass but are not limited to isolation of immune cells from a patient; cloning of disease-specific antibody genes from the immune cells; construction and subsequent manufacturing of antibody fragment-rPEG fusions (i.e. disease-associated AFBTs); and treatment of the patient with the disease.

Polyclonal and Multiclonal AFBTs

The present invention also relates to a pharmaceutical composition comprising more than one AFBT. Such composition of AFBT mixture may have improved performance relative to the individual AFBTs. AFBT-based product can be multiclonal such that they contain two, three, or more defined AFBTs. Alternatively, AFBTs can be polyclonal containing multiple AFBTs. Such polyclonal AFBTs can be generated by cloning antibody fragments from a source that is enriched for antibodies or antibody fragments with a useful specificity. One example is cloning of antibody fragment repertoires from an infected patient. Another example includes display libraries that have been enriched by panning against a target of interest.

rPEG Fusion Products

In one embodiment, an rPEG sequence is genetically fused to the N- or C-terminus of the human growth hormone (hGH) or human growth hormone receptor (hGH-R) gene under control of appropriate transcription and translation sequences for high level protein expression in a biological system (e.g. *Escherichia coli, Pichia pastoris*, CHO—S, etc). Protein expression is induced using standard techniques well known in the art for the expression system employed and purified using standard procedures (e.g. ion exchange chromatography, size exclusion chromatography, affinity chromatography, differential precipitation, phase extraction, etc). The purified protein can then be administered to human patients for therapeutic treatment of indications including, but not limited to: adult growth hormone deficiency, pediatric growth hormone deficiency, Turner syndrome, chronic renal failure, idiopathic short stature, post-transplant growth failure, hypophosphatemic rickets, inflammatory bowel disease, Noonan syndrome, pediatric Coeliac disease, AIDS wasting, obesity, aging, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the human growth hormone fragment 176-191 or 177-191 gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: adult growth hormone deficiency, pediatric growth hormone deficiency, Turner syndrome, chronic renal failure, idiopathic short stature, post-transplant growth failure, hypophosphatemic rickets, inflammatory bowel disease, Noonan syndrome, pediatric Coeliac disease, AIDS wasting, obesity, aging, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the exenatide gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of the following indications: type II diabetes, or other indications for which the unmodified protein has been shown to provide therapeutic benefit. The addition of the rPEG sequence confers the properties of extended serum half-life, improved patient exposure/ efficacy, and/or improved manufacturing efficiency. Due to the sensitivity of the N-terminus of exenatide to maintaining in vivo efficacy, special considerations may be required to maintain the native N-terminal structure upon recombinant expression and purification, and preferred embodiments would comprise fusions of rPEG to the C-terminus of the exenatide sequence. N-terminal leader sequences which can be cleaved by proteases either in vitro or in vivo can be employed to improve manufacturing yield and/or improve delivery of active molecules in vivo. An alternative strategy would comprise mutating the internal methionine of exenatide to a compatible amino acid (eg leucine, which is present at the homologous position in the GLP-1 sequence) and use cyanogen bromide or similar chemical methods to remove the N-terminal leader sequence to generate the native exenatide N-terminus.

In one embodiment, an rPEG sequence is genetically fused to the N- or C-terminus of the GLP-1 gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of the following indications: type II diabetes, or other indications for which the unmodified protein has been shown to provide therapeutic benefit. The addition of the rPEG sequence confers the properties of extended serum half-life, improved patient exposure/ efficacy, and/or improved manufacturing efficiency. Due to the sensitivity of the N-terminus of GLP-1 to maintaining in vivo efficacy, special considerations may be required to maintain the native N-terminal structure upon recombinant expression and purification, and preferred embodiments would comprise fusions of rPEG to the C-terminus of the GLP-1 sequence. N-terminal leader sequences which can be cleaved by proteases either in vitro or in vivo can be employed to improve manufacturing yield and/or improve delivery of active molecules in vivo.

In one embodiment, an rPEG sequence is genetically fused to the N- or C-terminus of the IL1-RA gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: rheumatoid arthritis, psoriatic arthritis, psoriasis, inflammatory bowel disease, Crohn's disease, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the interferon alpha, beta, or gamma gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: hairy cell leukemia, AIDS-related Kaposi's syndrome, pH chromosome positive CML, chronic hepatitis C, condylomata acuminate, chronic hepatitis B, malignant melanoma, follicular lymphoma, multiple sclerosis, non-Hodgkins lymphoma, osteopetrosis, chronic granulomatous disease-associated infections, pulmonary multi-drug resistant tuberculosis, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the G-CSF gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: chemotherapy-induced febrile neutropenia, bone-marrow transplantation, congenital neutropenia, cyclic neutropenia, idiopathic neutropenia, AIDS-associated neutropenia, myelodysplastic syndrome, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the FGF21 gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: diabetes, obesity, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the calcitonin gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: postmenopausal osteoporosis, Paget's disease, hypercalcemia or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the parathyroid hormone (PTH) gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of the following indications: osteoporosis, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the human chorionic gonadotropin (hCG) gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: infertiliy, Kaposi's sarcoma, asthma, artheriopathy, thalassemia, osteopenia, glaucoma, obesity, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the Fuzeon (enfurvitide) gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of the following indications: HIV-1 infection, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the leptin or leptin receptor gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: breast cancer, osteoarthritis, osteoporosis, septic arthritis, obesity, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the TNF Binding protein 1 (TNF-BP1; p55) gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: rheumatoid arthritis, psoriatic arthritis, psoriasis, inflammatory bowel disease, Crohn's disease, or other indications for which the unmodified protein has been shown to provide therapeutic benefit. The addition of the rPEG sequence confers the properties of extended serum half-life, improved patient exposure/efficacy, and/or improved manufacturing efficiency.

In one embodiment, an rPEG sequence is genetically fused to the N- or C-terminus of the glucagon gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: type II diabetes, juvenile diabetes, or other indications for which the unmodified protein has been shown to provide therapeutic benefit. The addition of the rPEG sequence confers the properties of extended serum half-life, improved patient exposure/efficacy, and/or improved manufacturing efficiency. Due to the sensitivity of the N-terminus of glucagon to maintaining in vivo efficacy, special considerations may be required to maintain the native N-terminal structure upon recombinant expression and purification, and preferred embodiments would comprise fusions of rPEG to the C-terminus of the GLP-1 sequence. N-terminal leader sequences which can be cleaved by proteases either in vitro or in vivo can be employed to improve manufacturing yield and/or improve delivery of active molecules in vivo.

In one embodiment, an rPEG sequence is genetically fused to the N- or C-terminus of the IGF-1 gene under control of appropriate transcription and translation sequences for high level protein expression in a biological system (e.g. *Escherichia coli, Pichia pastoris*, CHO—S, etc). Protein expression is induced using standard techniques for the expression system employed and purified using standard procedures (e.g. ion exchange chromatography, size exclusion chromatography, affinity chromatography, differential precipitation, phase extraction, etc) well known to those skilled in the art. The purified protein can then be administered to human patients for therapeutic treatment of indications including, but not limited to: IGF-1 deficiency, hGH deficiency caused by gene deletion or anti-GH antibody formation, or other indications for which the unmodified protein has been shown to provide therapeutic benefit. The addition of the rPEG sequence confers the properties of extended serum half-life, improved patient exposure/efficacy, and/or improved manufacturing efficiency.

Depot Modules

The compositions of the present invention may optionally include a depot module. The depot module may be a naturally occurring polypeptide, an artificial polypeptide or one selected by phage display. In one embodiment, the depot module will bind directly to the polymeric matrix referred to below. The depot module can be incorporated at any position within the modified polypeptide and can be present once or in multiple copies as indicated in FIGS. 2 and 3.

The depot module can be attached to the modified polypeptide in a variety of ways. For example, in one embodiment (FIG. 4), the modified polypeptide comprises repeating units as follows: accessory polypeptide-biologically active polypeptide-depot module, biologically active polypeptide-accessory polypeptide-depot module, depot module-accessory polypeptide-biologically active polypeptide, or depot module-biologically active polypeptide-accessory polypeptide.

In another aspect of the invention, the depot module comprises a polypeptide that is specifically sensitive to serum proteases (FIG. 8). Protease cleavage of the depot module releases biologically active polypeptide. The protease sites can be engineered to be sensitive to specific proteases, such as to a serum protease, or to display different rates of protease cleavage. Thus the rate or site of release can be controlled through engineering of the protease cleavage site of the depot module. The modified polypeptide so engineered can be formulated with a polymeric matrix as described herein.

In a further aspect of the invention, the depot module can also be modified to produce high avidity binding modules. This can be accomplished by replacing some protease sensitive modules with protease resistant modules. For example, by producing accessory polypeptide-biologically active polypeptide fusion proteins with protease-sensitive depot modules between every fourth biologically active polypeptide, proteolysis of the fusion protein will release tetravalent binding modules. Tetravalent species have significantly increased target avidity relative to monomeric binding modules and are particularly desirable for targeting cell surface receptors (FIG. 53a-c).

In yet a further aspect of the invention, the depot module is designed to provide a tetravalent accessory protein-biologically active polypeptide fusion protein, for example, to increase target avidity and/or for slow release applications. The depot module is designed to contain an amino acid or amino acids for the site-specific conjugation of the small molecule biotin. Biotin is a common vitamin found in over-the-counter nutritional supplements. It serves as a "co-factor" for several enzymes including those involved in the biosynthesis of fatty acids. Biotin is also extensively used in biotechnology applications because it forms a very high affinity complex with the proteins avidin, neutravidin, and streptavidin. In this embodiment, avidin, streptavidin, or neutravidin, which each bind to four molecules of biotin, can be used to form highly stable accessory polypeptide-biologically active polypeptide fusion protein tetramers (FIG. 5).

Lysine (K) and cysteine (C) residues can be modified by chemical reaction with succidimidyl esters or maleimides, respectively, under mild conditions with high yield and specificity. When the accessory polypeptide does not contain any lysine (K) or cysteine (C) residues, these can be easily incorporated into the depot module. The depot module can comprise one, two, or more lysine or cysteine residues.

The depot module can also include the use of a "hot cysteine" to ensure site-specific modification. A "hot cysteine" is flanked by lysine residues, for example (KCKK) (SEQ ID NO: 446), where K is lysine and C is cysteine. The proximal lysine residues shift the pKa of the cysteine, increasing its nucleophilicity and making this residue more reactive. Several groups have shown that a "hot cysteine" can be preferentially modified (greater than 90%) even in the background of 23 other cysteine residues present on the same protein [Okten, Z., et al. (2004) Nat Struct Mol Biol, 11:884-7]. Thus, the depot module can yield site-specific, efficient modification of the accessory polypeptide or the accessory polypeptide-biologically active polypeptide fusion in vitro. Biotin conjugated to either of these reactive groups is commercially available.

The addition of biotin-binding proteins such as avidin, streptavidin, or neutravidin can induce the formation of a very stable accessory polypeptide-binding protein polypeptide tetramer. The accessory polypeptide-binding protein polypeptide tetramer can then be formulated with polymeric matrix (e.g., encapsulated into microspheres) as described below. An accessory polypeptide-binding protein polypeptide tetramer exhibits a very large hydrodynamic radius, ensuring slow release from the polymeric matrix, e.g., microspheres. An accessory polypeptide-binding protein polypeptide tetramer will also have an increased avidity towards its biological target. Because the accessory polypeptide-binding protein polypeptide tetramer can interact with four target molecules, for example on the plasma membrane of a cell, the off-rate of the accessory polypeptide-binding protein polypeptide will be dramatically reduced. Increased avidity may enhance the biological activity or reduce the required dose of the accessory polypeptide-binding protein polypeptide.

In a further aspect of the invention, the depot module with the same active residues can be modified with poly-ethylene glycol instead of the reactive biotin. Of particular interest are four- and eight-armed PEG molecules. These PEG molecules can be covalently attached to depot module described herein, thus generating homogeneous tetramer and octamer species. Protein therapeutics conjugated in this manner will have a significantly enhanced avidity towards their biological targets, particularly toward cell surface proteins.

Counterions for Making Protein Precipitate

The present invention also relates to the use of counterions for regulating the solubility of the protein of interest, i.e. making protein precipitate for a depot formulation. A counterion is an ion, the presence of which allows the formation of an overall neutrally charged species. For example, in the (neutral) species NaCl the sodium cation is countered by the chloride anion and vice versa. The mechanism of poorly water-soluble salt formation with a cation exchanger is depicted by the following formula: $rPEG^{n+} + nC^- \rightarrow rPEG.C_n$ (insoluble) in which $rPEG^{n+}$ represents the positively charged peptide ion, whereas $C^-$ represents a negatively charged counterion. The participating amino acid residues in this reaction include Arg, Lys and the N-terminus. The mechanism of poorly water-soluble salt formation with an anion exchanger is depicted by the following formula: $rPEG^{n-} + nC^+ \rightarrow rPEG.C_n$ (insoluble) in which $rPEG^{n-}$ represents the negatively charged peptide ion, whereas $C^+$ represents a positively charged counterion. The participating amino acid residues in this reaction include Asp, Glu and the C-terminus.

In a preferred embodiment, the counterion displays mixed hydrophobic and ionic character. Thus, once the charge of the counterion is neutralized by complex formation with the protein of interest, the hydrophobic nature of the counterion dominates the resultant complex, causing its aqueous solubility to decrease significantly. In addition, the counterions must be compatible with in vivo administration within the clinical indication intended for the protein of interest in terms of acute and chronic toxicity, carcinogenicity, reproductive effects, etc. Non-limiting examples of mixed counterions suitable for this application are provided below:

Anions:
    Behenate
    Cholesteryl sulfate
    Deoxycholate
    Dodecane sulfonate
    Epigallocatechin gallate
    Hexadecane sulfonate
    Pamoate
    Pentagalloyl Glucose
    Stearate
    Tannate Cations:
    Choline derivatives
    Peptide counterions: eg H-Lys-(Leu)$_n$-NH2; H-(Leu)$_n$-NH2

Lipids:
    Phosphatidylcholine

Polymeric materials:
    Chitosan
    Collagen

Hyaluronic Acid
Poly β-amino esters
PLA/PLGA
Poly(ethylene glycol)bis(2-aminoethyl)

In one embodiment, a protein of interest is mixed at a defined ratio with a counterion comprising both hydrophobic and charged character as described above. Upon interaction, the protein and counterion form an insoluble complex which precipitates from the solution. In a preferred embodiment, greater than or equal to 20%, 40%, 60%, or 80% of the total protein is precipitated under these conditions, which can be assessed by quantitative assay of the protein remaining in solution. Optimization of the protein:counterion ratio, inclusion of organic solvents, pH adjustment, ionic strength, and/or temperature adjustment may be employed to modulate the efficiency of the precipitation reaction. The precipitate can be separated from the liquid phase using standard methods (i.e. filtration, centrifugation), and can be stored in a dry form or as a suspension in an inert buffer. For a pharmaceutical composition, protein stability upon storage is a critical parameter for determining the viability of a given formulation. In one embodiment, the protein is stable under the defined storage conditions and formulation for greater than 1, 2, 3, 6, 12, 18, or 24 months.

The present invention also embodies the method of administering the above described protein complex into a subject in vivo. Compounds of the invention may be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. In a preferred embodiment, the protein complex is administered to a subject via parenteral injection. As used herein, the term "parenteral" refers to introduction of the complex into the body not through the intestines, but rather by injection through intravenous (i.v.), intraarterial (i.a.), intraperitoneal (i.p.), intramuscular (i.m.), intraventricular, intrabronchial, and subcutaneous (s.c.) routes. To be administered via parenteral injection (e.g. bolus injection or continuous infusion), the precipitate is resuspended in a buffer compatible with the route of administration. In the preferred embodiment, the precipitate is resuspended as a homogeneous suspension capable of passing through a 18, 22, 25, 26, 27, or 28 gauge needle with minimal occlusion. Milling or similar processing can be performed in order to improve the resuspension properties as well as reducing the size of the particles to enable efficient passage through higher gauge needles. Detergents or other excipients capable of modifying the surface tension, viscosity, or wetting properties of the solution can also be useful in improving the homogeneity of the precipitate suspension for injection.

The present invention also relates to the protein release rate in a depot formulation upon introduction of the precipitate into an in vivo environment via, for example, parenteral injection. The protein release rate can be approximated in vitro by suspension of the protein:counterion precipitate in an isotonic buffer (e.g. phosphate buffered saline) and measuring the concentration of soluble protein over time. A preferred embodiment uses physiological temperatures in order to better mimic the in vivo conditions, although a higher or lower temperature may be employed to modify the resolubilization rate depending on the experimental setup. The optimal release rate for a given protein is dependent upon its in vivo clearance rate and mechanism, as well as the required exposure for in vivo efficacy. In order to achieve significant accumulation of the protein, the resolubilization rate should be faster than the natural clearance rate. Serum concentration of the protein is expected to be proportional to the ratio of the resolubilization rate to the clearance rate. The kinetics of the protein complex between its soluble and precipitates states is depicted in the following equation:

$$\text{Protein}^{n-}\text{:nCI}^{+}(s) \underset{k_{precipitation}}{\overset{k_{solubilization}}{\rightleftharpoons}} \text{Protein}^{n-}(aq) \xrightarrow{k_{clearance}} \text{Removal}$$

Assuming that the rate of reprecipitation into the complex is negligible: [Protein$^{n-}$] is approximately equal to $k_{solubilization}/k_{clearance}$ (i.e. the ratio of the resolubilization rate to the clearance rate).

The actual serum concentration achieved in vivo is also dependent upon a number of other factors including total amount of complex injected, surface area of the precipitate particles, protein absorption rate, binding of the protein to its cognate receptors, and recycling mechanisms.

The resolubilization properties of the precipitate may be modified by various treatments of the precipitate. For example, heat treatment or ultraviolet crosslinking of the counterion can be used to modify the chemical (and resolubilization) properties of the precipitate. The precipitate may also be formed by direct removal of solvent (e.g. spray drying, lyophilization), followed by treatment with a counterion or coating material to achieve the desired depot characteristics.

Excipients may be included in the complex formation reaction to control the rate and efficiency of complex formation, as well as to modulate the rate of resolubilization of the protein:counterion complex upon transfer to an in vivo environment. Excipients are typically uncharged, inert molecules which are included in the complex formation reaction buffer and comprise a varying degree of the final precipitate mass. Excipients may also comprise a coating applied to the surface of the precipitate particle which serves to modulate the surface area of the precipitate particle to solvent and hence modulate the resolubilization rate and/or stability of the protein. Examples of excipients include, but are not limited to, the following:

Polymers
- Polyethylene glycol 500
- Polyethylene glycol 2000
- Polyethylene glycol 5000
- Polyethylene glycol 8000
- Polyethylene glycol 20000
- Polylysine
- PLA/PLGA Detergents
- Polysorbate 20 (Tween 20)
- Polysorbate 80 (Tween 80)
- Triton X-100

Sugars/Polyalcohols
- Glucose
- Glycerine
- Glycerol
- Mannitol
- Mannose
- Sorbitol
- Sucrose
- Trehalose Another embodiment of the present invention includes a formulation such that depot formation occurs in situ upon injection. For example, the protein and counterion are chosen such that a precipitate is formed close to physiological pH (i.e. pH 7.4). The protein and counterion are formulated at an optimal concentration ratio relative to one another, but at a pH sufficiently different from physiological pH (e.g. pH 4 or pH 10) such that no complex formation occurs. Upon parenteral injection, preferably subcutaneous or intramuscular injection, the inherent buffering capacity of the tissue causes the solution to adjust to pH 7.4, resulting in the precipitation of the protein:counterion complex at the site of injection and the resultant slow release thereof. Temperature change upon injection and complex formation of the injected protein with a natural counterion found in vivo are also methods by which a slow releasing protein depot may be formed in situ.

Production of Accessory-Linked Polypeptides

The present invention provides methods of producing biologically active polypeptide, comprising a) providing a polynucleotide sequence coding for a modified polypeptide comprising the biologically active polypeptide linked with an accessory polypeptide such that expression of the modified polypeptide in a host cell yields a higher quantity of soluble form of biologically active polypeptide as compared to expression of the biologically active polypeptide by itself, and b) causing the modified polypeptide to be expressed in said host cell, thereby producing the biologically active polypeptide. Expression of the modified biologically active polypeptides may yield at least about 100%, 200%, 500% or 1000% more soluble form of biologically active polypeptide as compared to expression of the biologically active polypeptide by itself. In some embodiments, the expression of the modified biologically active polypeptides may yield at least between 100%, and 1000% more soluble form of biologically active polypeptide as compared to expression of the biologically active polypeptide by itself.

Methods of the invention may involve culturing a cell transformed with a chimeric DNA molecule encoding an accessory polypeptide under conditions whereby the DNA is expressed, thereby producing the accessory-linked polypeptide; and extracting an expression product of the chimeric DNA molecule from the cell or culture medium.

Standard recombinant techniques in molecular biology can be used to make the accessory-linked polypeptides of the present invention. In one embodiment, a construct is first prepared containing the DNA sequence corresponding to the accessory polypeptide. For example, a gene or polynucleotide encoding the biologically active protein can be first cloned into a construct, which can be a plasmid or other vector. In a later step, a second gene or polynucleotide coding for the accessory polypeptide is cloned into the construct adjacent and in frame with the gene coding for the biologically active polypeptide. This second step can occur through a ligation or multimerization step.

In this manner, a chimeric DNA molecule coding for a modified polypeptide is generated within the construct. Optionally, this chimeric DNA molecule may be transferred or cloned into another construct that is a more appropriate expression vector. At this point, a host cell capable of expressing the chimeric DNA molecule is transformed with the chimeric DNA molecule. The transformation may occur with or without the utilization of a carrier, such as an expression vector. Then, the transformed host cell is cultured under conditions suitable for expression of the chimeric DNA molecule, resulting in the encoding of the accessory polypeptide. Methods of ligation or multimerization useful in the present invention are well known. See, Joseph Sambrook, et al., Molecular Cloning: A Laboratory Manual, 2nd ed., 1.53 (Cold Spring Harbor Laboratory Press 1989).

Several cloning strategies are envisioned to be suitable for performing the present invention, many of which can be used to generate a construct that comprises a gene coding for the accessory polypeptide of the present invention.

The vectors containing the DNA segments of interest can be transferred into the host cell by well-known methods, depending on the type of cellular host. For example, calcium chloride transfection is commonly utilized for prokaryotic cells, whereas calcium phosphate treatment, lipofection, or electroporation may be used for other cellular hosts. Other methods used to transform mammalian cells include the use of polybrene, protoplast fusion, liposomes, electroporation, and microinjection (see, generally, Sambrook et al., supra). Prokaryotic or eukaryotic cells are envisioned as hosts. Accessory polypeptides can be produced in a variety of expression systems including prokaryotic and eukaryotic systems. Suitable expression hosts are for instance yeast, fungi, mammalian cell culture, and insect cells.

Useful expression vectors that can be used include, for example, segments of chromosomal, non-chromosomal and synthetic DNA sequences. Suitable vectors include, but are not limited to, derivatives of SV40 and pcDNA and known bacterial plasmids such as col E1, pCR1, pBR322, pMa1-C2, pET, pGEX as described by Smith, et al., Gene 57:31-40 (1988), pMB9 and derivatives thereof, plasmids such as RP4, phage DNAs such as the numerous derivatives of phage I such as NM98 9, as well as other phage DNA such as M13 and filamentous single stranded phage DNA; yeast plasmids such as the 2 micron plasmid or derivatives of the 2m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like. The requirements are that the vectors are replicable and viable in the host cell of choice. Low- or high-copy number vectors may be used as desired.

For example in a baculovirus expression system, both non-fusion transfer vectors, such as, but not limited to pVL941 (BamHI cloning site, available from Summers, et al., Virology 84:390-402 (1978)), pVL1393 (BamHI, Sma1, Xba1, EcoRI, IVot1, Xma111, BgIII and Pst1 cloning sites; Invitrogen), pVL1392 (BgIII, Pst1, NotI, XmaIII, EcoRI, Xba11, Sma1 and BamHI cloning site; Summers, et al., Virology 84:390-402 (1978) and Invitrogen) and pBlueBacIII (BamHI, BgIII, Pst1, Nco1 and Hindi II cloning site, with blue/white recombinant screening, Invitrogen), and fusion transfer vectors such as, but not limited to, pAc7 00 (BamHI and Kpn1 cloning sites, in which the BamHI recognition site begins with the initiation codon; Summers, et al., Virology 84:390-402 (1978)), pAc701 and pAc70-2 (same as pAc700, with different reading frames), pAc360 [BamHI cloning site 36 base pairs downstream of a polyhedrin initiation codon; Invitrogen (1995)) and pBlueBacHisA, B, C (three different reading frames with BamH I, BgI II, Pst1, Nco 1 and Hind III cloning site, an Nterminal peptide for ProBond purification and blue/white recombinant screening of plaques; Invitrogen (220) can be used.

Mammalian expression vectors can comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. Mammalian expression vectors contemplated for use in the invention include vectors with inducible promoters, such as the dihydrofolate reductase promoters, any expression vector with a DHFR expression cassette or a DHFR/methotrexate co-amplification vector such as pED (Pst1, Sai1, Sba1, Sma1 and EcoRI cloning sites, with the vector expressing both the cloned gene and DHFR; Randal J. Kaufman, 1991, Randal J. Kaufman, Current Protocols in Molecular Biology, 16, 12 (1991)). Alternatively a glutamine synthetase/methionine sulfoximine co-amplification vector, such as pEE14 (HindIII, Xba11, Sma1, Sba1, EcoRI and Se11 cloning sites in which the vector expresses glutamine synthetase and the cloned gene; Celltech). A vector that directs episomal expression under the control of the Epstein Barr Virus (EBV) or nuclear antigen (EBNA) can be used such as pREP4 (BamHI r SfH, Xho1, NotI, Nhe1, Hindi II, NheI, PvuII and Kpn1 cloning sites, constitutive RSV-LTR promoter, hygromycin selectable marker; Invitrogen), pCEP4 (BamHI, SfH, Xho1, NotI, Nhe1, Hind111, Nhe1, PvuII and Kpn1 cloning sites, constitutive hCMV immediate early gene promoter, hygromycin selectable marker; Invitrogen), pMEP4 (.Kpn1, Pvu1, Nhe1, Hind111, NotI, Xho1, Sfi1, BamHI cloning sites, inducible methallothionein H a gene promoter, hygromycin selectable marker, Invitrogen), pREP8 (BamHI, Xho1, NotI, Hind111, Nhe1 and Kpn1 cloning sites, RSV-LTR promoter, histidinol selectable marker; Invitrogen), pREP9 (Kpn1, Nhe1, Hind 111, NotI, Xho 1, Sfi 1, BamH I cloning sites, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen).

Selectable mammalian expression vectors for use in the invention include, but are not limited to, pRc/CMV (Hind 111, BstXI, NotI, Sba1 and Apa1 cloning sites, G418 selection, Invitrogen), pRc/RSV (Hind III, Spe1, BstXI, NotI, Xba1 cloning sites, G418 selection, Invitrogen) and the like. Vaccinia virus mammalian expression vectors (see, for example, Randall J. Kauftnan, Current Protocols in Molecular Biology 16.12 (Frederick M. Ausubel, et al., eds. Wiley 1991) that can be used in the present invention include, but are not limited to, pSC11 (Sma1 cloning site, TK- and beta-gal selection), pMJ601 (Sal 1, Sma 1, A fII, Nar1, BspM1I, BamHI, Apa1, Nhe1, SacII, Kpn1 and Hind111 cloning sites; TK- and -gal selection), pTKgptF1S (EcoRI, Pst1, SaIII, Acc1, HindII, Sba1, BamHI and Hpa cloning sites, TK or XPRT selection) and the like.

Yeast expression systems that can also be used in the present include, but are not limited to, the non-fusion pYES2 vector (XJba1, Sph1, Sho1, NotI, GstXI, EcoRI, BstXI, BamHI, Sad, KpnI and HindIII cloning sites, Invitrogen), the fusion pYESHisA, B, C (Xba11, Sph1, Sho1, NotI, BstXI, EcoRI, BamHI, Sad, Kpn1 and Hindi II cloning sites, N-terminal peptide purified with ProBond resin and cleaved with enterokinase; Invitrogen), pRS vectors and the like.

In addition, the expression vector containing the chimeric DNA molecule may include drug selection markers. Such markers aid in cloning and in the selection or identification of vectors containing chimeric DNA molecules. For example, genes that confer resistance to neomycin, puromycin, hygromycin, dihydrofolate reductase (DHFR), guanine phosphoribosyl transferase (GPT), zeocin, and histidinol are useful selectable markers. Alternatively, enzymes such as herpes simplex virus thymidine kinase (tk) or chloramphenicol acetyltransferase (CAT) may be employed. Immunologic markers also can be employed. Any known selectable marker may be employed so long as it is capable of being expressed simultaneously with the nucleic acid encoding a gene product. Further examples of selectable markers are well known to one of skill in the art and include reporters such as enhanced green fluorescent protein (EGFP), beta-galactosidase (β-gal) or chloramphenicol acetyltransferase (CAT).

Consequently, mammalian and typically human cells, as well as bacterial, yeast, fungi, insect, nematode and plant cells can used in the present invention as host cells and may be transformed by the expression vector as defined herein.

Examples of suitable cells include, but are not limited to, VERO cells, HELA cells such as ATCC No. CCL2, CHO cell lines, COS cells, WI38 cells, BHK cells, HepG2 cells, 3T3 cells, A549 cells, PC12 cells, K562 cells, 293 cells, Sf9 cells and CvI cells.

Other suitable cells that can be used in the present invention include, but are not limited to, prokaryotic host cells strains such as *Escherichia coli*, (e.g., strain DH5-α), *Bacillus subtilis, Salmonella typhimurium*, or strains of the genera of *Pseudomonas, Streptomyces* and *Staphylococcus*. Non-limiting examples of suitable prokaryotes include those from the genera: *Actinoplanes; Archaeoglobus; Bdellovibrio; Borrelia; Chloroflexus; Enterococcus; Escherichia; Lactobacillus; Listeria; Oceanobacillus; Paracoccus; Pseudomonas; Staphylococcus; Streptococcus; Streptomyces; Thermoplasma*; and *Vibrio*. Non-limiting examples of specific strains include: *Archaeoglobus fulgidus; Bdellovibrio bacteriovorus; Borrelia burgdorferi; Chloroflexus aurantiacus; Enterococcus faecalis; Enterococcus faecium; Lactobacillus johnsonii; Lactobacillus plantarum; Lactococcus lactis; Listeria innocua; Listeria monocytogenes; Oceanobacillus iheyensis; Paracoccus zeaxanthinifaciens; Pseudomonas mevalonii; Staphylococcus aureus; Staphylococcus epidermidis; Staphylococcus haemolyticus; Streptococcus agalactiae; Streptomyces griseolosporeus; Streptococcus mutans; Streptococcus pneumoniae; Streptococcus pyogenes; Thermoplasma acidophilum; Thermoplasma volcanium; Vibrio cholerae; Vibrio parahaemolyticus*; and *Vibrio vulnificus*.

Further suitable cells that can be used in the present invention include yeast cells such as those of *Saccharomyces* such as *Saccharomyces cerevisiae*.

A key advantage of using bacterial expression to perform the present invention is the absence of glycosylation. While glycosylation of the accessory polypeptide increases its molecular weight and generally increases its serum half-life, quality control of glycosylated products is notoriously difficult to perform When many glycosylation sites are present and the expression level of the protein is high, the glycosylation machinery may not be able to keep up and glycosylation is likely to be incomplete due to incomplete processing, resulting in carbohydrate structures that are heterogeneous, which greatly complicates purification, characterization, quality control and reproducibility.

Depending on how the protein is expressed in bacteria (secreted to media, to periplasm, soluble in cyplasm or as insoluble inclusion bodies in the cytoplasm), the product or intermediate may contain a formylated N-terminus.

Additional post-translational modifications to which accessory polypeptides or the accessory-modified polypeptides of the invention may be subjected to include, but are not limited to acylation, acetylation, alkylation, demethylation, amidation, biotinylation, formylation, gamma-carboxylation, glutamylation, glycosylation, glycylation, attachment of heme moiety, hydroxylation, iodination, isoprenylation, lipoylation, prenylation, myristoylation, farnesylation, geranylgeranylation, ADP-ribosylation, flavin attachment, oxidation, pegylation, attachment of phosphatidylinositol, phosphopantetheinylation, phosphorylation, pyroglutamate formation, racemization of proline by prolyl isomerase, tRNA-mediation addition of amino acids such as arginylation, sulfation and selenoylation.

Host cells containing the polynucleotides of interest can be cultured in conventional nutrient media (e.g., Ham's nutrient mixture) modified as appropriate for activating promoters, selecting transformants or amplifying genes. The culture conditions, such as temperature, pH and the like, are those previously used with the host cell selected for expression, and will be apparent to the ordinarily skilled artisan. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, all of which are well known to those skilled in the art. Embodiments that involve cell lysis may entail use of a buffer that contains protease inhibitors that limit degradation after expression of the chimeric DNA molecule. Suitable protease inhibitors include leupeptin, pepstatin or aprotinin. The supernatant then may be precipitated in successively increasing concentrations of saturated ammonium sulfate.

The accessory polypeptides product may be purified via methods known to one skilled in the art. Procedures such as gel filtration, affinity purification, salt fractionation, ion exchange chromatography, size exclusion chromatography, hydroxylapatite adsorption chromatography, hydrophobic interaction chromatography and gel electrophoresis may be used. Some accessory polypeptides may require refolding. Methods of purification are described in Robert K. Scopes, Protein Purification: Principles and Practice (Charles R. Castor, ed., Springer-Verlag 1994) and Joseph Sambrook, Molecular Cloning: A Laboratory Manual, 2nd edition (Cold Spring Harbor Laboratory Press 1989). Multi-step purification separations are also described in Baron, et al., Crit. Rev. Biotechnol. 10:179-90 (1990) and Below, et al., J. Chromatogr. A. 679:67-83 (1994).

Production of Crosslinked Accessory Polypeptides

Crosslinked accessory polypeptides can be produced by a variety of methods. Both the non-cross-linking and the cross-linking components can be generated by chemical synthesis or using recombinant techniques. Of particular utility is the recombinant manufacture of the non-cross-linking component, which can be achieved in a variety of microbial as well as eukaryotic expression systems, for example as described above. The non-cross-linking component can be purified to remove interfering or contaminating by-products prior to cross linking. Of particular utility are chemical crosslinkers that can be activated for coupling. Examples are shown in FIG. 22. The resulting coupling products can be further purified by a variety of methods, in particular size exclusion chromatography and ion exchange chromatography.

Multiple different non-crosslinking components can be conjugated to a crosslinking component using methods that allow the control of product structure. For instance one can use cross-linking components that carry several different reactive groups that allow different conjugation chemistries. Alternatively, one can use crosslinking components that carry protecting groups on some of their reactive groups. Such partially-protected crosslinking components can be coupled to one or more non-crosslinking components. Subsequently, one can remove the protecting groups from the crosslinking components and conjugate additional non-crosslinking components to the crosslinking component. This process can be repeated by using multiple different protecting groups that allow selective removal.

In another embodiment of the present invention, a recombinant cross-linking component may be used. The cross-linking component can be amino acids sequences that can be manufactured by recombinant technology using a variety of expression systems. For example, fMet amino acids incorporated in the sequence of a noncross-linking component may be conjugated to amino groups in a recombinant cross-linking component.

One preferred embodiment provides for cross-linking components that comprise one or more glutamate and/or aspartate residues, which contain side chains that can serve as reactive groups and can be effectively conjugated to non-cross-linking components that have a free amino group as reactive group. A variety of carbodiimides can be used to activate free carboxyl groups but many more chemistries are suitable. Free amino groups in the recombinant cross-linking component may be blocked by acetylation or succinylation.

Alternatively, the cross-linking component can be a protein that has multiple high-affinity binding sites. Examples are avidin, streptavidin, IgGs or IgMs. For instance one can form Crosslinked accessory polypeptides by contacting biotinylated non-cross-linking components with streptavidin, which will lead to the formation of a tetravalent complex. The process is illustrated in FIG. 25. In a similar way one could use for instance an IgM or IgG with specificity for a peptide epitope in conjunction with non-cross-linking components that comprise said peptide epitope.

The accessory polypeptides of the present invention may be assayed in order to determine the effect of which to a biologically active polypeptide. Methods of assaying biologically active polypeptides are commonly known in the art. For example, serum half-life can be measured by combining the protein with human (or mouse, rat, monkey, as appropriate) serum or plasma, typically for a range of days (ie 0.25, 0.5, 1, 2, 4, 8, 16 days) at 37° C. The samples for these timepoints can then be run on a Western assay and the protein is detected with an antibody. The antibody can be to a tag in the protein. If the protein shows a single band on the western, where the protein's size is identical to that of the injected protein, then no degradation has occurred. The timepoint where 50% of the protein is degraded, as judged by Western Blots or equivalent techniques, is determined to be the serum degradation half-life or "serum half-life" of the protein.

The accessory polypeptides of the present invention may be used to modulate the expression or activity of a variety of cellular targets, including without limitation those named in the section "Biologically active polypeptides". In some embodiments, the expression of a target will be reduced by administration of accessory polypeptides, while in other embodiments it will be increased. The accessory polypeptide may interfere with the activity of a cellular target by interaction with functional sites on the target.

Slow Release Agents

The modified polypeptides of the invention may be incorporated, encapsulated, formulated or otherwise included into compositions which allow for controlled release of the polypeptides in desired applications. Generally, the modified polypeptides of the invention may interact with the slow release agents of the invention in various manners, including and not limited to covalent attachment, ionic interaction, or encapsulation within a polymer or a formulation.

Various types of slow release agents suitable for use in the present invention are described below.

Polymer Matrices

In general, microspheres are substantially spherical colloidal structures having a size ranging from about one or greater up to about 1000 microns. Microcapsules are generically described as structures in which a substance, such as a polymeric formulation, is covered by a coating of some type. The term "microparticle" may be used to describe structures that may not be readily placed into either of the above two categories or as a generic term for both. For structures that are less than about one micron in diameter the corresponding terms "nanosphere," "nanocapsule," and "nanoparticle" may be utilized, but these are encompassed in the terms "microsphere," microcapsule" and "microparticle," respectively. In certain embodiments, nanospheres, nanocapsules or nanoparticles have a size of about 500, 200, 100, 50 or 10 nm.

The slow release formulations of the invention may also take the form of microparticles, which may comprise microcapsules or microspheres.

In a microparticle, the modified polypeptides may be centrally located within a membrane formed by the polymer molecules, or can be dispersed throughout the microparticle. The internal structure may comprise a matrix of the modified polypeptide and a polymer excipient. Typically, the outer surface of the microsphere is permeable to water, which allows aqueous fluids to enter the microsphere, as well as solubilized modified polypeptide and polymer to exit the microsphere. In one embodiment, the polymer membrane comprises a crosslinked polymer. The modified polypeptide may be released by diffusion and/or by degradation of the polymer membrane.

Possible materials for the outer layer of microparticles include the following categories of polymers: (1) carbohydrate-based polymers, such as methylcellulose, carboxymethyl cellulose-based polymers, dextran, polydextrose, chitins, chitosan, and starch (including hetastarch), and derivatives thereof; (2) polyaliphatic alcohols such as polyethylene oxide and derivatives thereof including polyethylene glycol (PEG), PEG-acrylates, polyethyleneimine, polyvinyl acetate, and derivatives thereof; (3) poly(vinyl) polymers such as poly(vinyl) alcohol, poly(vinyl)pyrrolidone, poly(vinyl)phosphate, poly(vinyl)phosphonic acid, and derivatives thereof; (4) polyacrylic acids and derivatives thereof; (5) polyorganic acids, such as polymaleic acid, and derivatives thereof; (6) polyamino acids, such as polylysine, and poly-imino acids, such as polyimino tyrosine, and derivatives thereof; (7) co-polymers and block co-polymers, such as poloxamer 407 or Pluronic L-101T polymer, and derivatives thereof; (8) tert-polymers and derivatives thereof; (9) polyethers, such as poly(tetramethylene ether glycol), and derivatives thereof; (10) naturally occurring polymers, such as zein, chitosan and pullulan, and derivatives thereof; (11) polyimids, such as poly n-tris(hydroxymethyl)methylmethacrylate, and derivatives thereof; (12) surfactants, such as polyoxyethylene sorbitan, and derivatives thereof; (13) polyesters such poly(ethylene glycol) (n) monomethyl ether mono(succinimidyl succinate)ester, and derivatives thereof; (14) branched and cyclo-polymers, such as branched PEG and cyclodextrins, and derivatives thereof; and (15) polyaldehydes, such as poly(perfluoropropylene oxide-b-perfluoroformaldehyde), and derivatives thereof as disclosed in U.S. Pat. No. 6,268,053, the contents of which are incorporated herein by reference. Other typical polymers known to those of ordinary skill in the art include poly(lactide-co-glycolide, polylactide homopolymer; polyglycolide homopolymer; polycaprolactone; polyhydroxybutyrate-polyhydroxyvalerate copolymer; poly(lactide-co-caprolactone); polyesteramides; polyorthoesters; poly 13-hydroxybutyric acid; and polyanhydrides as disclosed in U.S. Pat. No. 6,517,859, the contents of which are incorporated herein by reference. In some embodiments, the polymer may comprise alginate polymers, (hydroxyethyl) methacrylated dextran polymers, or chitosan polymers may be used.

The modified polypeptides of the invention may be mixed with physiologically acceptable carriers, excipients, or stabilizers (Remington's Pharmaceutical Sciences, 16th edition, Oslo, A., Ed., 1980), in the form of lyophilized cake or aqueous solutions. Acceptable carriers, excipients, or stabilizers for the preparation of microparticles are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobins; hydrophilic polymers such as olyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics, or polyethylene glycol (PEG).

The microspheres of this invention are manufactured by standard techniques. For example, in one embodiment, volume exclusion is performed by mixing the active agent in solution with a polymer or mixture of polymers in solution in the presence of an energy source for a sufficient amount of time to form particles as disclosed in U.S. Pat. No. 6,268,053. The pH of the solution is adjusted to the desired pH. Next, the solution is exposed to an energy source, such as heat, radiation, or ionization, alone or in combination with sonication, vortexing, mixing or stirring, to form microparticles. The resulting microparticles are then separated from any unincorporated components present in the solution by physical separation methods well known to those skilled in the art and may then be washed.

In some embodiments, a suspension of microparticles is prepared by vigorously mixing an aqueous solution containing the modified polypeptide and an organic solution (typically dichloromethane) in which the polymer is dissolved. This water-in-oil suspension is then diluted into aqueous buffer containing an emulgent (typically poly-vinylalcohol). Finally, the microspheres are removed from this water-in-oil-in-water (W/O/W) emulsification and freeze-dried. This well known and tested W/O/W process generally yields microspheres that are 0.1-100 μm in diameter. Microspheres of these dimensions are readily prepared as suspensions for subcutaneous injection. Alternatively, microspheres can be prepared by the single-emulsion solvent extraction/evaporation (O/W), the solid/oil/oil methods (S/O/O), and all variants of these methods described in the literature.

Known manufacturing procedures are also described in U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025, the contents of which are incorporated by reference in their entirety. The preparation and formulation of microparticles is also described in the following publications: (Bittner, B., et al. (1998) Eur J Pharm Biopharm, 45:295-305; Rosa, G. D., et al. (2000) J Control Release, 69:283-95; Kissel, T., et al. (2002) Adv Drug Deliv Rev, 54:99-134; Kwon, Y. M. and Kim, S. W. (2004) Pharm Res, 21:339-43; Lane, M. E., et al. (2006) Int J Pharm, 307:16-22; Jackson, J. K., et al. (2007) Int J Pharm).

Microparticles are also well known and readily available to one of ordinary skill in the art from companies experienced in providing such technologies for extended release drug delivery. For example, Epic Therapeutics, a subsidiary of Baxter Healthcare Corp., developed PROMAXX™, a protein-matrix drug delivery system that produces bioerodible protein microspheres in a totally water-based process; OctoPlus developed OctoDEX™, crosslinked dextran microspheres that release active ingredients based on bulk degradation of matrix rather than based on surface erosion; and Brookwood Pharmaceuticals advertises the availability of its microparticle technologies for drug delivery.

A search of patents, published patent applications and related publications will also provide those skilled in the art reading this disclosure with significant possible microparticle technologies. For example, U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025, the contents of which are incorporated by reference in their entirety, describe microspheres and methods for their manufacture. One skilled in the art, considering both the disclosure of this invention and the disclosures of these other patents could make and use microparticles for the extended release of the modified polypeptides of the invention.

Further modifications are provided by the invention. Because microparticles such as PLGA beads still release significant levels of drug immediately after administration, the present invention provides ways of ameliorating this bolus effect by including accessory polypeptides and optional depot modules as part of the modified polypeptide, as described hereinabove.

If desired, release of the therapeutic protein can be further controlled if microparticles with two or more layers are used. In one embodiment, the microspheres have an inner layer as well as an outer layer. The composition or the thickness of the outer layer may be modified to introduce differences in the time it takes to expose the modified-polypeptide-containing center of the bead. In one embodiment, microspheres may have an inner layer containing the modified polypeptide at high concentration, while the outer layer may contain a lower concentration of the modified polypeptide or no modified polypeptide. Alternatively, the outer layer varies in thickness between different microspheres. The microspheres with a thin outer layer will release modified polypeptide earlier (for example, from day 1-5), while the beads with a medium thickness of outer layer release modified polypeptide at a later time (for example, from day 4-8), and the beads with a thicker outer layer release modified polypeptide even later (for example, from day 7-11). Thus, a more constant rate of release is obtained in this embodiment.

The rate of drug release from polymeric matrix formulations can be dependent on the accessory polypeptide attached to the biologically active peptide. The accessory polypeptide significantly increases the hydrodynamic radius of the modified polypeptide. Thus the accessory polypeptide module provides means to control the rate of drug release from the microparticles. Any of the accessory polypeptides described herein can be formulated with a polymeric matrix to achieve beneficial effects in controlled-release, serum half-life stability, and other desirable properties described herein.

In a further aspect of the invention, the depot modules described herein can be designed to enhance the non-covalent interactions between the accessory polypeptide-biologically active polypeptide and the polymer matrix and to slow down the rate of release of the modified polypeptide from the matrix beads. For example, alginate is a polymer consisting of mannuronic and guluronic acid and alginate microspheres can be prepared via water/oil emulsion methods [Srivastava, R., et al. (2005) J Microencapsul, 22: 397-411], similar to the preparation of PLGA microspheres. Unlike PLGA microspheres, alginate forms highly porous microspheres from which protein release is usually complete in days. This present invention provides the use of a depot module in conjunction with the volume enhancing module and biologically active polypeptide to increase the retention of the fusion protein within alginate microspheres.

Each unit of the alginate polymer matrix contains a carboxyl group that has a −1 charge at physiological pH. Thus alginate polymers have a large net negative charge under physiological conditions. The depot module is designed to have a basic isoelectric point (that is positively charged at physiological pH) and will therefore be retained much longer within alginate microspheres (FIG. 6). This depot module comprises a human polypeptide containing multiple lysine (K) and/or arginine (R) residues, for example. At physiological pH the lysine amino acids will carry a net positive charge, thus increasing its non-covalent binding to the alginate polymer. The depot module may include naturally occurring polypeptides or designed/engineered or selected polypeptides. Potential depot modules can be rapidly evaluated for their ability to interact with alginate. Additionally, polypeptides that bind only weakly to alginate can be combined to form repeating depot module units in order to strengthen the interactions with the polymer.

In a further embodiment of the invention, a divalent cation chelating polymer matrix (e.g. hydrogel; Lin, C. C. and Metters, A. T. (2007) J Biomed Mater Res A) is used in conjunction with a depot module that binds to divalent cations. For example, both the depot module and the chelating polymer matrix binds to $Cu^{2+}$, $Co^{2+}$ and $Ni^{2+}$ cations and the strong non-covalent interactions between the depot module and the divalent cations serve as an efficient mechanism to achieve sustained release of the therapeutic protein from the hydrogel (FIG. 7). FIG. 46 illustrates the sustained release of accessory-modified polypeptides. For example, the depot module can incorporate poly-histidine tagged protein. Poly-histidine sequences are routinely used as purification tags, because such sequences bind tightly to $Ni^{2+}$ cations on solid support. Alternative depot modules can be similarly designed in light of the teachings hereinabove. The depot module can be attached directly to the accessory polypeptide, instead of the biologically active polypeptide, if the poly-histidine sequence is otherwise likely to interfere with the biological activity of the therapeutic polypeptide.

Thus, any number of variations and choice of polymer matrix, accessory polypeptide, depot module and/or biologically active polypeptide can be combined to achieve the desired effect in a patient.

The present invention provides pharmaceutical compositions comprising the modified polypeptide. They can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition, the pharmaceutical compositions can also contain other pharmaceutically active compounds or a plurality of compounds of the invention.

The compositions of the invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils.

More particularly, the present pharmaceutical compositions may be administered for therapy by any suitable route including oral, rectal, nasal, topical (including transdermal, aerosol, buccal and sublingual), vaginal, parental (including subcutaneous, intramuscular, intravenous and intradermal)

and pulmonary. It will also be appreciated that the preferred route will vary with the condition and age of the recipient, and the disease being treated.

Extended release formulations useful in the present invention may be oral formulations comprising a matrix and a coating composition. Suitable matrix materials may include waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition may comprise an insoluble matrix polymer and/or a water soluble material. Water soluble materials can be polymers such as polyethylene glycol, hydroxypropyl cellulose, hydroxypropyl methyl cellulose, polyvinylpyrrolidone, polyvinyl alcohol, or monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Optionally, an enteric polymer may be incorporated into the coating composition. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups. The coating composition may be plasticised by adding suitable plasticisers such as, for example, diethyl phthalate, citrate esters, polyethylene glycol, glycerol, acetylated glycerides, acetylated citrate esters, dibutylsebacate, and castor oil. The coating composition may also include a filler, which can be an insoluble material such as silicon dioxide, titanium dioxide, talc, kaolin, alumina, starch, powdered cellulose, MCC, or polacrilin potassium. The coating composition may be applied as a solution or latex in organic solvents or aqueous solvents or mixtures thereof. Solvents such as water, lower alcohol, lower chlorinated hydrocarbons, ketones, or mixtures thereof may be used.

The modified polypeptides of the invention may be formulated using a variety of excipients. Suitable excipients include microcrystalline cellulose (e.g. Avicel PH102, Avicel PH101), polymethacrylate, poly(ethyl acrylate, methyl methacrylate, trimethylammonioethyl methacrylate chloride) (such as Eudragit RS-30D), hydroxypropyl methylcellulose (Methocel K100M, Premium CR Methocel K100M, Methocel E5, Opadry®), magnesium stearate, talc, triethyl citrate, aqueous ethylcellulose dispersion (Surelease®). The slow release agent may also comprise a carrier, which can comprise, for example, solvents, dispersion media, coatings, antibacterial and antifungal agents, isotonic and absorption delaying agents. Pharmaceutically acceptable salts can also be used in these slow release agents, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes may also be used as a carrier.

Administration via transdermal formulations can be performed using methods also known in the art, including those described generally in, e.g., U.S. Pat. Nos. 5,186,938 and 6,183,770, 4,861,800, 6,743,211, 6,945,952, 4,284,444, and WO 89/09051, incorporated herein by reference in their entireties. A transdermal patch is a particularly useful embodiment with polypeptides having absorption problems. Patches can be made to control the release of skin-permeable active ingredients over a 12 hour, 24 hour, 3 day, and 7 day period. In one example, a 2-fold daily excess of a polypeptide of the present invention is placed in a non-volatile fluid. The compositions of the invention are provided in the form of a viscous, non-volatile liquid. The penetration through skin of specific formulations may be measures by standard methods in the art (for example, Franz et al., J. Invest. Derm. 64:194-195 (1975)). Examples of suitable patches are passive transfer skin patches, iontophoretic skin patches, or patches with microneedles such as Nicoderm.

In other embodiments, the composition may be delivered via intranasal, buccal, or sublingual routes to the brain to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs. Preparation of a pharmaceutical composition for delivery in a subdermally implantable device can be performed using methods known in the art, such as those described in, e.g., U.S. Pat. Nos. 3,992,518; 5,660, 848; and 5,756,115.

Osmotic Pumps may be used as slow release agents in the form of tablets, pills, capsules or implantable devices. Osmotic pumps are well known in the art and readily available to one of ordinary skill in the art from companies experienced in providing osmotic pumps for extended release drug delivery. Examples are ALZA's DUROS™; ALZA's OROS™; Osmotica Pharmaceutical's Osmodex™ system; Shire Laboratories' EnSoTrol™ system; and Alzet™. Patents that describe osmotic pump technology are U.S. Pat. Nos. 6,890,918; 6,838,093; 6,814,979; 6,713,086; 6,534,090; 6,514,532; 6,361,796; 6,352,721; 6,294,201; 6,284,276; 6,110,498; 5,573,776; 4,200,0984; and 4,088,864, the contents of which are incorporated herein by reference. One skilled in the art, considering both the disclosure of this invention and the disclosures of these other patents could produce an osmotic pump for the extended release of the polypeptides of the present invention.

Syringe Pumps may also be used as slow release agents. Syringe pumps are known to one skilled in the art and readily available. Such devices are described in U.S. Pat. Nos. 4,976, 696; 4,933,185; 5,017,378; 6,309,370; 6,254,573; 4,435,173; 4,398,908; 6,572,585; 5,298,022; 5,176,502; 5,492,534; 5,318,540; and 4,988,337, the contents of which are incorporated herein by reference. One skilled in the art, considering both the disclosure of this invention and the disclosures of these other patents could produce a syringe pump for the extended release of the polypeptides of the present invention.

In another embodiment, the modified polypeptides of the present invention are encapsulated in liposomes, which have demonstrated utility in delivering beneficial active agents in a controlled manner over prolonged periods of time. Liposomes are closed bilayer membranes containing an entrapped aqueous volume. Liposomes may also be unilamellar vesicles possessing a single membrane bilayer or multilamellar vesicles with multiple membrane bilayers, each separated from the next by an aqueous layer. The structure of the resulting membrane bilayer is such that the hydrophobic (nonpolar) tails of the lipid are oriented toward the center of the bilayer while the hydrophilic (polar) heads orient towards the aqueous phase. In one embodiment, the liposome may be coated with a flexible water soluble polymer that avoids uptake by the organs of the mononuclear phagocyte system, primarily the liver and spleen. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973; 6,043,094, the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1[(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3[N—(N',N'-dimethylaminoethane)carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

Liposomes are also well known in the art and readily available from companies experienced in providing liposomes for extended release drug delivery. For example, ALZA's (formerly Sequus Pharmaceuticals') STEALTH™ liposomal technology for intravenous drug delivery uses a polyethylene glycol coating on liposomes to evade recognition by the immune system; Gilead Sciences (formerly Nexstar's) liposomal technology was incorporated into AmBisome™, and FDA approved treatment for fungal infections; and NOF Corp. offers a wide variety of GMP-grade phospholipids, phospholipids derivatives, and PEG-phospholipids under the tradenames COATSOME™ and SUNBRIGHT™.

Additional possible liposomal technologies are described in U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479, the contents of which are incorporated herein by reference. These describe liposomes and lipid-coated microbubbles, and methods for their manufacture. Thus, one skilled in the art, considering both the disclosure of this invention and the disclosures of these other patents could produce a liposome for the extended release of the polypeptides of the present invention.

Diseases amenable to treatment by administration of the compositions of the invention include without limitation cancer, inflammatory diseases, arthritis, osteoporosis, infections in particular hepatitis, bacterial infections, viral infections, genetic diseases, pulmonary diseases, diabetes, hormone-related disease, Alzheimer's disease, cardiac diseases, myocardial infarction, deep vain thrombosis, diseases of the circulatory system, hypertension, hypotension, allergies, pain relief, dwarfism and other growth disorders, intoxications, blot clotting diseases, diseases of the innate immune system, embolism, wound healing, healing of burns, Crohn's disease, asthma, ulcer, sepsis, glaucoma, cerebrovascular ischemia, respiratory distress syndrome, corneal ulcers, renal disease, diabetic foot ulcer, anemia, factor IX deficiency, factor VIII deficiency, factor VII deficiency, mucositis, dysphagia, thrombocyte disorder, lung embolism, infertility, hypogonadism, leucopenia, neutropenia, endometriosis, Gaucher disease, obesity, lysosome storage disease, AIDS, premenstrual syndrome, Turners syndrome, cachexia, muscular dystrophy, Huntington's disease, colitis, SARS, Kaposi sarcoma, liver tumor, breast tumor, glioma, Non-Hodgkin lymphoma, Chronic myelocytic leukemia; Hairy cell leukemia; Renal cell carcinoma; Liver tumor; Lymphoma; Melanoma, multiple sclerosis, Kaposis sarcoma, papilloma virus, emphysema, bronchitis, periodontal disease, dementia, parturition, non small cell lung cancer, pancreas tumor, prostate tumor, acromegaly, psoriasis, ovary tumor, Fabry disease, lysosome storage disease.

The ability to fine-tune the secretion halflife of any agent (protein or reporter agent or other) and the ability to modulate the tissue distribution is of particular interest for In Vivo Diagnostics applications, such as imaging by PET, ultrasound, NMR, computed tomography, or radionuclear imaging. Thus, compositions of the invention can also be used to generate imaging agents. Examples are agents for gastrointestinal imaging, myocardial perfusion imaging agents, MRI imaging agents, gadolinium chelates, ultrasound agents for cardiac wall motion abnormalities and other ultrasound applications, or reagents for contrast enhanced computer tomography.

Optimization of Production of Modified Polypeptide

Additionally, the accessory polypeptides of the invention may comprise additional sequences which allow improved folding or purification during expression. This concept is described generally in FIG. 32. For example, accessory polypeptides may be linked to affinity or solubility tags to aid in purification. Non-limiting examples include His-tag, FLAG, Streptag II, HA-tag, Softag1, Softag 3, c-myc, T7-tag, S-tag, Elastin-like peptides, Chitin-binding domain, Thioredoxin, Xylanase 10A, Glutathione S-transferase (GST), Maltose binding protein (MBP), NusA, and Cellulose binding protein.

Accessory polypeptides may also comprise protease cleavage sites or other sequences that allow the modified polypeptide to be cleaved following expression. Such site or sites may be located anywhere within the modified polypeptide. For example, a protease cleavage site may be introduced between a sequence that improves solubility and another sequence comprising an affinity tag, such that the affinity tag is removed by protease treatment. Alternatively, the cleavage site may be located between the biologically active protein and the accessory polypeptide, such that a specific protease would cleave off the entire accessory polypeptide sequence. Various enzymatic methods for cleaving proteins are known. Such methods include enterokinase (DDDK) (SEQ ID NO: 447), Factor Xa (IDGR) (SEQ ID NO: 448), thrombin (LVPR/GS) (SEQ ID NO: 449), PreScission™ (LEVLFQ/GP) (SEQ ID NO: 450), TEV protease (EQLYFQ/G) (SEQ ID NO: 451), 3C protease (ETLFQ/GP) (SEQ ID NO: 452), Sortase A (LPET/G) (SEQ ID NO: 453), Granzyme B (D/X, N/X, M/N or S/X), inteins, SUMO, DAPase (TAGZyme™),

*Aeromonas* aminopeptidase, Aminopeptidase M, and carboxypeptidases A and B. Additional methods are disclosed in Arnau et al, Prot Expr and Purif (2006) 48, 1-13.

Analysis of Protein Expression

The activity of the expressed proteins may be measured to ascertain the degree of correct folding. Such assays are well known in the art depending on the specific modified polypeptide expressed. Such assays may include cell based assays, including assays for proliferation, cell death, apoptosis and cell migration. Other possible assays may determine receptor binding of expressed polypeptides, wherein the assay may comprise soluble receptor molecules, or may determine the binding to cell-expressed receptors. Additionally, techniques such as flow cytometry or surface plasmon resonance can be used to detect binding events. Specific in vivo biological assays may be used to assess the activity of each biologically active polypeptide of the invention. For example, the properties of hGH may be determined using an ESTA bioassay, or alternatively by measuring rhGH induced dose-related body weight gain and bone growth, or receptor binding. Additional methods are disclosed in Dattani, M. T., et al. (1996) Horm Res, 46: 64-73; Alam, K. S., et al. (1998) J Biotechnol, 65: 183-90; Clark, R., et al. (1996) J Biol Chem, 271: 21969-77; Clarg R G et al, (1996) Endocrinology. 137:4308-15.

Specific assays for measuring the physical properties of expressed proteins are described below. A variety of methods for determining properties such as protein aggregation, folding state, melting properties, contamination and water content are known in the art and may be applied to the present invention. Such methods include analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Arnau et al, Prot Expr and Purif (2006) 48, 1-13. Application of these methods to the invention would be within the grasp of a person skilled in the art.

More specifically, cellular localization of expressed polypeptides of the invention can be determined by any of the methods named above. For example, a crude lysate obtained from cells expressing the polypeptide of interest may be centrifuged in order to separate soluble expressed protein in the cytosolic fraction from insoluble protein in the inclusion bodies. If desired, the soluble (cytosolic) and insoluble (inclusion body) fractions can then be analyzed by Western Blot or similar techniques to determine the ratio of expression as soluble vs. insoluble protein.

Soluble protein in the lysate may be purified further by techniques such as anion exchange or size exclusion chromatography, techniques which can be applied preparatively or analytically (FIGS. 35-39, 47, 48, 50 and 51). Confirmation of the purity of the final product may be obtained by techniques known in the art such as SDS-PAGE, HPLC (e.g. reverse phase or size exclusion) or mass spectrometry. The purification steps may be preceded or followed by protease cleavage steps to remove affinity/solubility tags and/or the accessory polypeptide, or both. Further purification steps by any of the methods outlined above may be needed to remove, for example, the used protease from digestion mixtures. Such steps would be well within the grasp of a person skilled in the art. Several such methods are also described in more detail in the Examples section.

Formulation, Pharmacokinetics, and Administration of rPEG Fusion Products

Figures 88A, 88B, 88C:
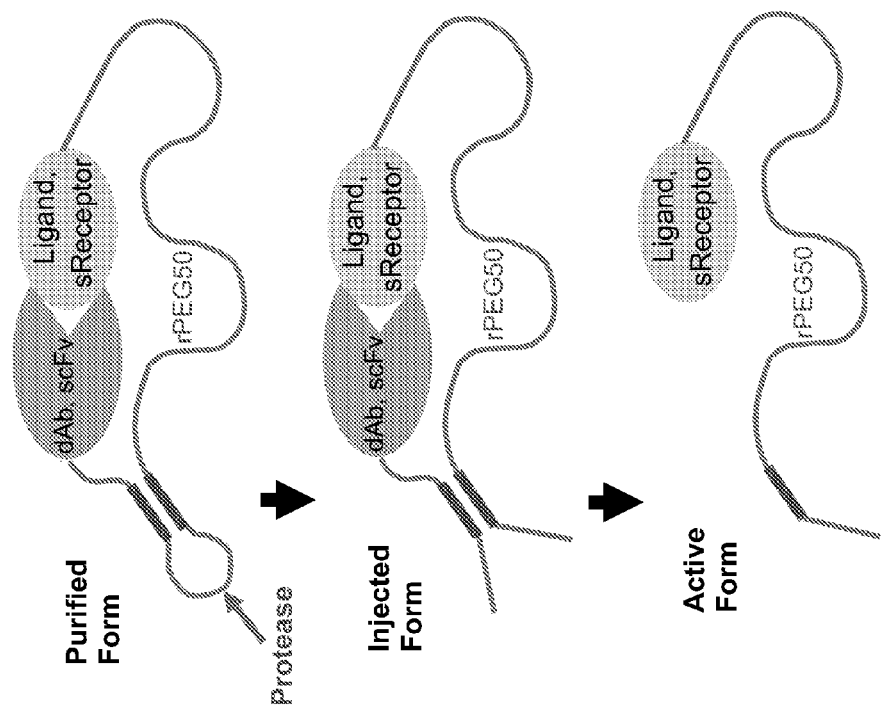
FIG. 88 shows how an association peptide, such as SKVILF(E) (SEQ ID NO: 8) or RARADADA (SEQ ID NO: 9), which bind to another copy of the same sequence in an antiparallel orientation, can be used to create a prodrug. In this case the drug is protease-cleaved in the last manufacturing step, but the cleavage does not activate the drug since the two chains are still associated by the association peptides. Only after the drug is injected into the blood and the concentration is greatly reduced, the small, non-rPEG-containing protein chain will leave the complex (at a rate that depends on affinity, especially the off-rate) and is likely to be cleared via the kidney, thereby activating the r-PEG-containing drug module.

The present invention also relates to the composition and method of engineering the rPEG fusion products for administration into a subject. An association peptide, such as SKVILF(E) (SEQ ID NO: 8) or RARADADA (SEQ ID NO: 9), which bind to another copy of the same sequence in an antiparallel orientation, can be used to create a prodrug, as shown in FIG. 88*a-c*. In one embodiment, the drug is protease-cleaved in the last step of manufacture, but the cleavage does not activate the drug since the two chains are still associated by the association peptides. Only after the drug is injected into a subject and the concentration is greatly reduced, the small, non-rPEG-containing protein chain leaves the complex at a rate that depends on the affinity, and is likely to be cleared via the kidney, thereby activating the r-PEG-containing drug module.

Figures 89A, 89B, 89C:
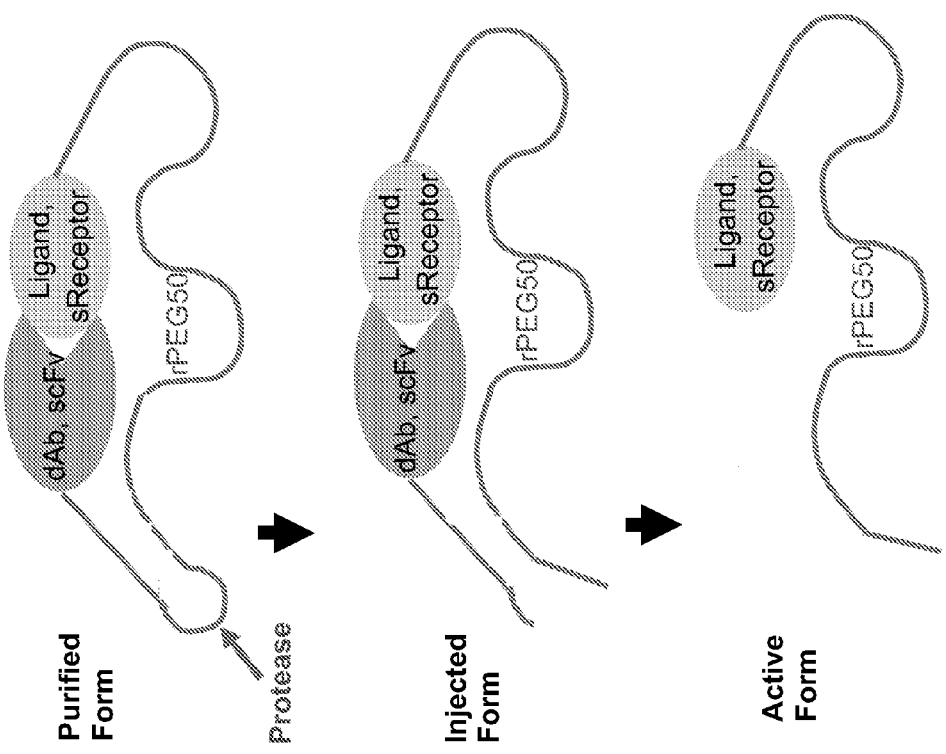
FIG. 89 shows the proteolytic cleavage which converts the manufactured single-chain protein into a complex of two protein chains. This cleavage can occur as the last manufacturing step (before injection) or it can occur after injection, by proteases in the patient's blood.

In another embodiment, the rPEG50 contains a proteolytic site and the proteolytic cleavage converts the manufactured single-chain protein into a complex of two protein chains (FIG. 89*a-c*). This cleavage can occur as the last manufacturing step before injection into a subject or it can occur after injection into a subject, by proteases present in the subject.

Figure 94A:
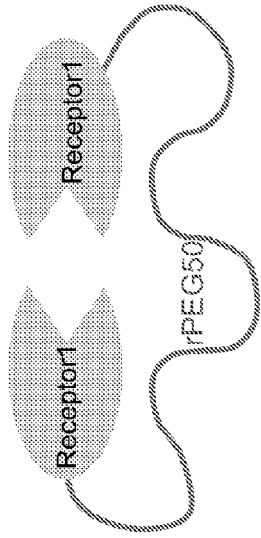
FIG. 94*a* shows an rPEG flanked by identical receptor domains (or domains having the same binding function, or domains that can bind simultaneously to the same target). If both receptors can bind the target simultaneously, then the binding of one receptor stabilizes binding of the second receptor and the effective/apparent affinity/avidity is increased, typically by 10-100-fold, but at least 3-fold. The rPEG provides serum halflife. One option is to pre-load the product with a ligand. In that case the injected product is inactive for as long as it remains bound to the ligand. This approach reduces peak dose toxicity and also reduces receptor-mediated clearance and may thus be useful in application where this is important.
Figure 94B:
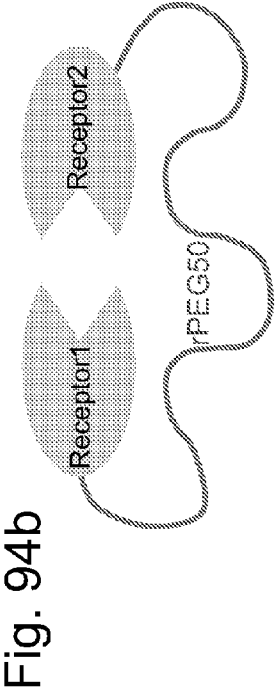
FIG. 94b shows a product with rPEG flanked by two different receptors that can bind the ligand simultaneously, which results in mutual stabilization of the complex and increased apparent affinity (avidity), with the rPEG serving as a valency bridge that increases the effective concentration of the receptors.
Figure 94C:
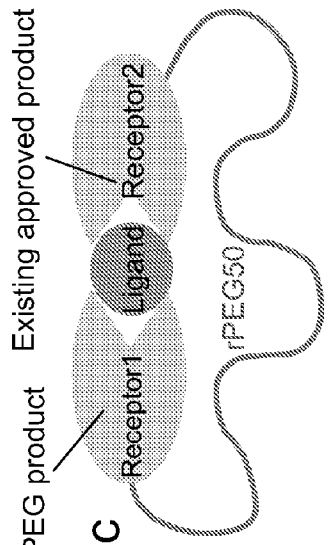
FIG. 94c One option is to pre-load the product with a ligand. In that case the injected product is inactive for as long as it remains bound to the ligand. When the ligand un-binds, it is likely to be rapidly cleared via the kidney, resulting in activation of the product, which has a long halflife because of the rPEG tail. This approach reduces peak dose toxicity and also reduces receptor-mediated clearance and may thus be useful in application where this is important.
Figure 99:
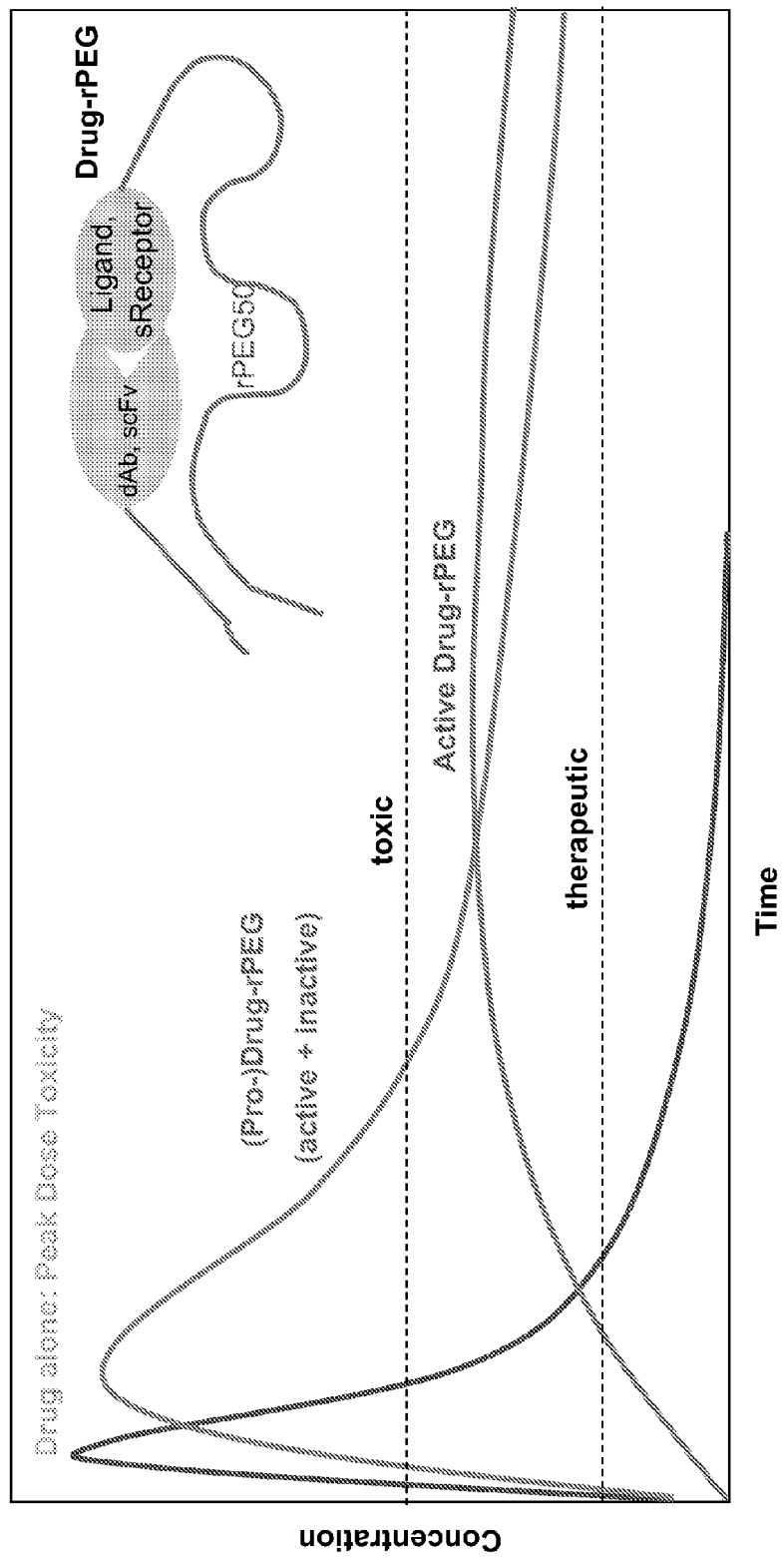
FIG. 99 shows how a Pro-drug-rPEG can increase serum halflife by avoiding receptor-mediated clearance.

Another embodiment includes an rPEG flanked by identical receptor domains or domains having the same binding function, or domains that can bind simultaneously to the same target (FIG. 94*a-c*). If both receptors can bind the target simultaneously, then the binding of one receptor stabilizes binding of the second receptor, resulting in mutal stabilization of the complex, thereby increasing the apparent affinity (avidity) typically by 10 to 100-fold, but at least 3-fold, with the rPEG serving as a valency bridge that increases the effective concentration of the receptors (FIG. 94*b*). In one embodiment, the rPEG product is pre-loaded with a ligand (FIG. 94*c*). When administered into a subject, the injected product is inactive for as long as it remains bound to the ligand. When the ligand dissociates, it is likely to be rapidly cleared via the kidney, resulting in activation of the product, which has a long halflife attributed to the rPEG tail. This approach reduces the peak dose toxicity and receptor-mediated clearance, thereby extending the serum secretion halflife, as illustrated in FIG. 99.

As shown in FIG. 94, some pro-drug formats do not need a cleavage or other activation site. A single protein chain can contain two or more drug modules separated by rPEG. These modules can be of a single type or of two or more different types. This rPEG containing product is complexed with a second, complementary protein to form a receptor-ligand-receptor interaction. In this format the ligand may be dimeric or multimeric, but may also be monomeric, especially if the two drug modules are different. Both modules bind to a third protein. X and Y can be the same or different, and X and Y can be a drug module or bind to a drug module. In each case in FIGS. 94*a-c*, X and Y (and rPEG) comprise one protein chain, and the molecule they bind to is a separate molecule, typically protein or small molecule. It is possible to have more than two binding proteins combined in a single protein chain.

Figure 100:
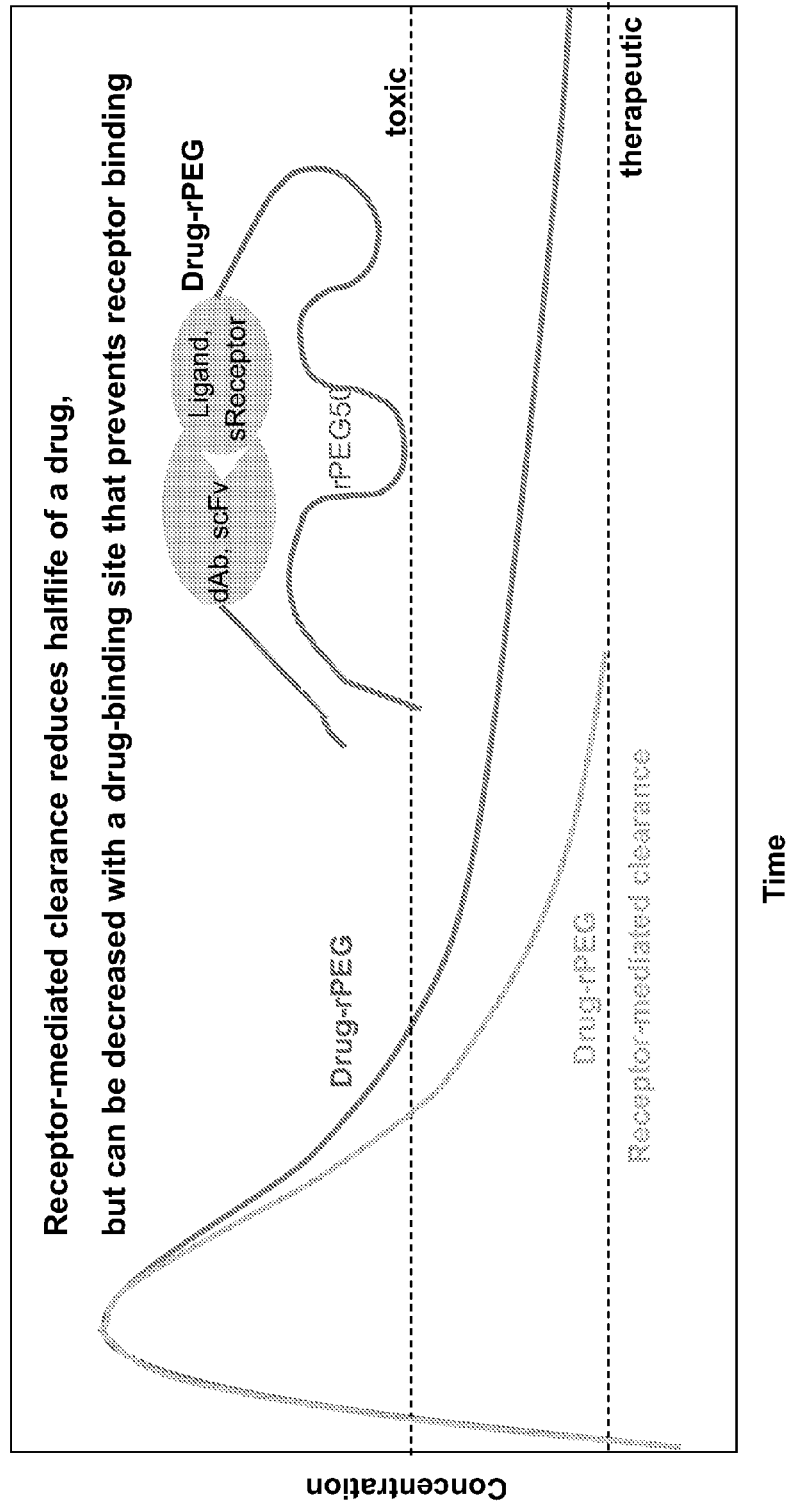
FIG. 100 shows how drug concentration changes over time after IV injection. The goal in typical therapies is maintain the drug at a concentration that is higher than the therapeutic does, but lower than the toxic dose. A typical bolus injection (IV, IM, SC, IP or similar) of a drug with a short halflife results in a peak concentration that is much higher than the toxic dose, followed by an elimination phase that causes the drug concentration to rapidly drop below the therapeutic dose. This PK profile tends to cause toxicity and long periods of ineffective treatment, while the drug is present at therapeutic concentrations for only short time (blue line). The addition of rPEG to a drug decreases the peak concentration and thereby decreases toxicity, and increases the period of time that the drug is present at a therapeutic, non-toxic dose. The creation of a Pro-drug by addition of rPEG plus a drug-binding protein can prevent the 'burst release' or toxic peak dose (red line), because the drug is only gradually activated over several hours and the length of time between the toxic dose and the therapeutic dose is increased compared to other formats.

It is generally desirable in therapies that the drug be maintained at a concentration that is higher than the therapeutic does, but lower than the toxic dose. A typical bolus injection (IV, IM, SC, IP or similar) of a drug with a short halflife results in a peak concentration that is much higher than the toxic dose, followed by an elimination phase that causes the drug concentration to rapidly drop below the therapeutic dose. FIG. 100 illustrates the drug concentration changes over time after an i.v. injection of a drug alone as compared to the drug linked to an rPEG. The drug alone is present at therapeutic concentrations for only a short time (blue line). The addition of rPEG to a drug decreases the peak concentration and thereby decreases toxicity, and increases the period of time that the drug is present at a therapeutic, non-toxic dose. The creation of a pro-drug by addition of rPEG plus a drug-binding protein can prevent the "burst release" or toxic peak dose (red line), as the drug is only gradually activated over hours and the length of time between the toxic dose and the therapeutic dose is increased compared to the other formats.

Figure 106:
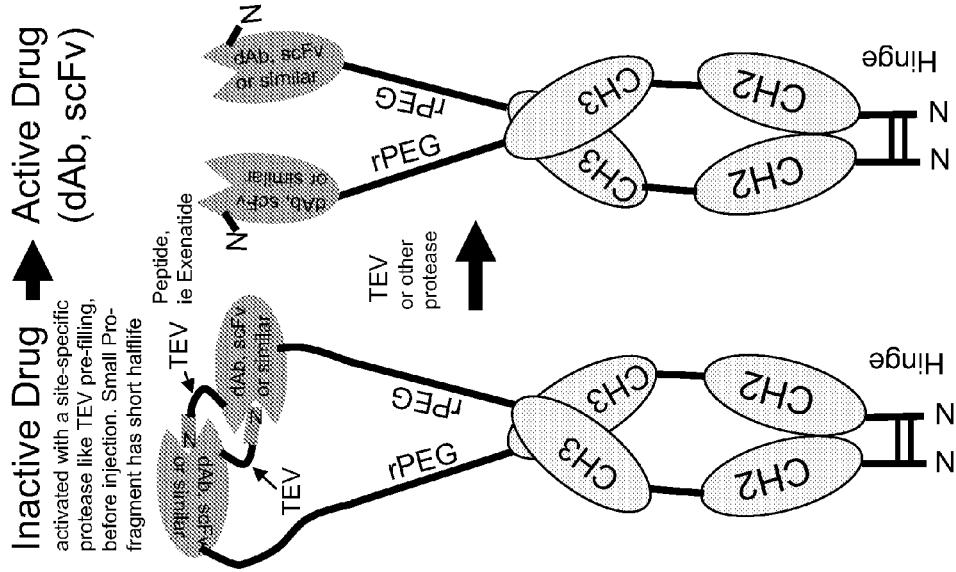
FIG. 106 shows the conversion of an inactive drug to an active drug by a sitespecific protease. In this example the blue domain (dAb, scFv, other) is the therapeutic entity.
Figure 105:
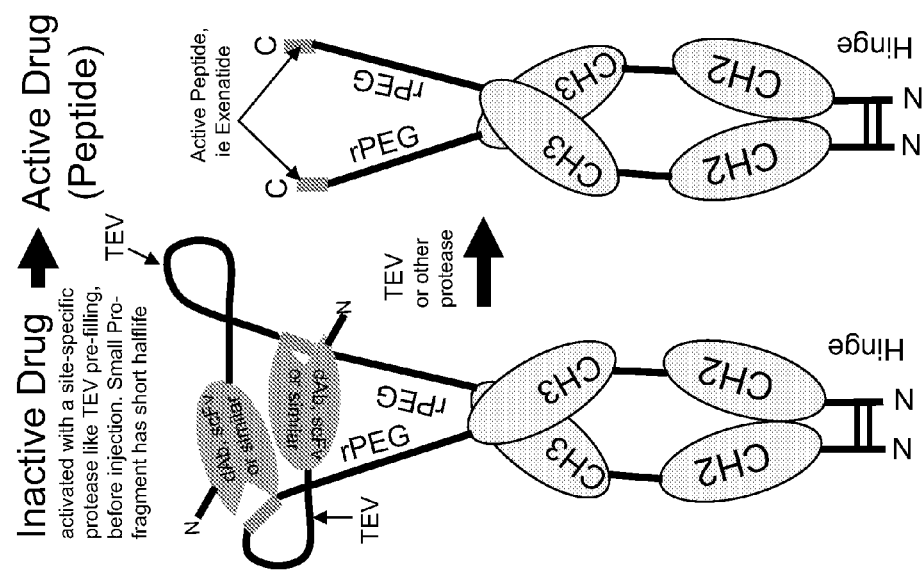
FIG. 105 shows the conversion of an inactive protein to an active protein by a sitespecific protease, either in serum or before injection. In this example the red sequence is the active therapeutic.

In another embodiment, the rPEG fusion products are either cleaved before administration into a subject or administered as an inactive pro-drug (i.e. cleaved after administration into a subject and activated in vivo). The process is illustrated in FIG. 96 a-h. The inactivation of the drug is mediated by a binding protein that is linked to the drug by rPEG such that all three modules are manufactured as a single protein chain. If the drug is a receptor, then the binding protein may be a ligand of that receptor; if the drug is an antibody fragment, then the binding site may be an antigen. In these examples, the drug is activated by protease cleavage of a site between the two binding domains, herein termed X and Y. If protein Y is the active product, then Y retains the rPEG and the protease cleavage site needs to be close to X. If protein Y is the active product, then X retains the rPEG and the cleavage site is close to Y. There can be one or multiple cleavage sites, as shown by the blue crossbars (FIG. 96a-g). The drug module includes, but is not limited to, a receptor, a ligand, one or more Ig domains, an antibody fragment, a peptide, a microprotein, or an epitope for an antibody. The protein that binds to the drug module includes, but is not limited to, a binding protein, a receptor, a ligand, one or more Ig domains, an antibody fragment, a peptide, a microprotein, or an epitope for an antibody. FIGS. 105 and 106 illustrate the conversion of an inactive protein (i.e. pro-drug) to an active protein (i.e. either an active peptide or a dAb or scFv) by a site-specific protease, either present in the serum of a subject or given before administration into a subject.

Another embodiment describes an inactive pro-drug created by adding a binding peptide to a drug module (FIG. 97). The peptide neutralizes the target binding capacity of the drug and the peptide is gradually cleared from the system of the subject, which is administered with the pro-drug, at a higher rate than the rPEG-containing drug. Such a peptide can be natural or obtained by phage panning of random peptide libraries against the drug module. The peptide is preferably made synthetically, but it can be a recombinant peptide.

A single-chain protein drug may also contain multiple bio-active peptides, which can be at the same end of rPEG or at an opposite end of rPEG (FIG. 98). These peptides can have the same activity or different activities. Having multiple peptides in a single chain increases their effective potency through binding avidity without complicating manufacturing.

EXAMPLES

Example 1

Design of Human Growth Hormone (hGH) Fused to Accessory Polypeptides

This example describes the preparation of an rPEG-hGH fusion protein with increased active, cytoplasmic yield and having improved serum half-life. Human growth hormone products typically require daily or twice-daily injections because the halflife of hGH in the serum is only about 30 minutes. Halflife extension through PEGylation is not feasible as hGH contains multiple lysines that are required for therapeutic activity and these cannot be used for conjugation. hGH is typically manufactured by expression in the cytoplasm of E. coli, where it can aggregate and form inclusion bodies containing inactive protein. Typically, these inclusion bodies are solubilized and the protein is refolded to obtain active protein. In this example, rPEG-hGH is expressed in the cytoplasm in soluble and active form, avoiding the step of refolding from inclusion bodies.

The amino acid sequence of hGH used in this experiment is:

(SEQ ID NO: 454)
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF.

hGH contains 191 amino acids, with a pI of 5.27 and a molecular weight of 22.130 kD. hGH contains 13 Glutamate residues, 11 Aspartate residues (24 total negative residues), 8 Lysine residues and 11 Arginine residues (19 total positive residues), for a net charge of −5 and a net charge density of −0.026 (calculated as −5/191 amino acids). This net charge density correlates with the experimental pI value of 5.27.

Various hGH-rPEG fusion proteins are designed as follows.

Design 1. Construction of rPEG-Modified hGH with Net Charge Density of −0.1.

This design describes a polypeptide modified with a short-length accessory polypeptide and a net charge density of −0.1.

The goal of this design is to produce a protein with a net charge density of −0.1 while adding only a few amino acids. The number of charges needed to create an hGH protein with a −0.1 charge density is 14.1 (19.1−5=14.1) without accounting for the increase in total length resulting from the added charged amino acids. The addition of 16 negatively charged amino acids brings the net charge density of the modified hGH polypeptide to −0.1 (calculated as (16+5)/(191+16) amino acids).

Design 2. Construction of rPEG-Modified hGH with Net Charge Density of −0.2.

This design describes a polypeptide modified with a short-length accessory polypeptide and net charge density of −0.2.

This design incorporates an accessory protein with 41 negative charges, for a total of 46 combined negatively charged amino acid residues in the entire polypeptide. The total length of the modified polypeptide is 232 amino acids (calculated as 191+41 amino acids). Consequently, a charge density of −0.2 requires a total of 46 negatively charged amino acid residues (calculated as 0.2×232 amino acids), which means the accessory protein contains 41 negatively charged residues (calculated as 46-5).

Design 3. Construction of rPEG-Modified hGH with Net Charge Density of +0.1.

This design describes a polypeptide modified with a short-length accessory polypeptide and +0.1 net charge density.

An accessory protein with positively charged amino acids can be designed to reach a net charge density of +0.1. This fusion protein includes a net positive charge of +22, which can be achieved by addition of an accessory protein containing 27 positive charges (calculated as 27−5=22 amino acids), resulting in a combined polypeptide length of 287 amino acids (calculated as 191+27 amino acids).

Design 4. Construction of rPEG_J288-GFP, rPEG_J288-hGH and rPEG_J288-GLP1 Modified Polypeptides.

This design describes a polypeptide modified with a long hydrophilic accessory polypeptide of 288 amino acids comprising 16.6% glutamate residues.

rPEG_J288 has the sequence (GGSGGE)$_{48}$ (SEQ ID NO: 455) and contains 48 E residues (FIG. 17). When rPEG_J288 was added to hGH, the total length of the modified polypeptide became 479 amino acids (calculated as 191+288) and the net charge became 53 (calculated as 48+5), thus yielding a net charge density of (calculated as 53/479=0.11). In this design, the accessory polypeptide itself has a net charge density of 16% due to the presence of many Glycine and Serine residues, whereas in Design 1 the accessory polypeptide is entirely composed of charged residues. As the experimental results demonstrated, this design yields highly soluble and active polypeptide. It appears that a net charge density of −0.11 can be sufficient to keep the protein in solution if the charges are spread out by the addition of Serines and/or Glycines. This example describes the construction of a fusion gene encoding an accessory polypeptide of 144 amino acids and the sequence (GGSGGE)$_{48}$ (SEQ ID NO: 455). A stuffer vector pCW0051 is constructed as shown in FIG. 16. The sequence of the expression cassette in pCW0051 is shown in FIG. 18. An insert is obtained essentially as described below for rPEG_L288 but by annealing a synthetic oligonucleotide encoding the rPEG sequence rPEG_J288 (FIG. 11) with a pair of oligonucleotides encoding an adaptor to the KpnI site. The following oligonucleotides are used as forward and reverse primers:

```
pr_LCW0057for:
                                        (SEQ ID NO: 456)
AGGTAGTGGWGGWGARGGWGGWTCYGGWGGAGAAGG, pr_LCW0057rev:
                                        (SEQ ID NO: 457)
ACCTCCTTCTCCWCCRGAWCCWCCYTCWCCWCCACT,
```

The following oligonucleotides are used as stopper primers:

```
pr_3KpnIstopperFor:
                                        (SEQ ID NO: 458)
AGGTTCGTCTTTCACTCGAGGGTAC, pr_3KpIstopperRev:
                                        (SEQ ID NO: 459)
CCTCGAGTGAAGACGA.
```

By varying the ratio of forward/reverse primers to stopper primers, the size of the resulting PCR products can be controlled. The insert was used to generate a plasmid encoding the rPEG_J288-modified GFP and cells expressing this plasmid in a fashion similar to rPEG_L288-modified GFP (FIG. 16). A similar insert was used to generate a plasmid encoding the rPEG_J288-modified hGH and rPEG_J288-modified GLP1 and cells expressing this plasmid in a fashion similar to rPEG_L288-modified GFP (FIG. 12).

The purity of rPEG_J288-modified GFP was confirmed by SDS-PAGE (FIG. 36), analytical size exclusion chromatography (see FIG. 37), mass spectrometry (FIG. 39). The apparent molecular weight of rPEG_J288-modified GFP was also measured as previously described (FIG. 41). FIG. 49 illustrates the increase in apparent molecular weight observed upon linking a biologically active polypeptide (GLP1) to rPEG_J288 accessory polypeptide. Little immunogenicity in in vivo experiments could be observed with this polypeptide (FIG. 44).

Design 5. Construction of rPEG_L288-GFP, rPEG_L288-hGH and rPEG_L288-GLP1 Modified Polypeptides.

This design describes a polypeptide modified with a long hydrophilic accessory polypeptide of 288 amino acids comprising 25% glutamate residues. rPEG_L288 has the sequence (SSESSSSESSSE)$_{24}$ (SEQ ID NO: 40) and contains 72 E residues. When rPEG_L288 is added to hGH, the total length of the fusion becomes 479 amino acids (calculated as 191+288 amino acids) and the net charge becomes 77 (calculated as 72+5), yielding a net charge density of 0.16 (calculated as 77/479 amino acids). As the experimental results described below demonstrated, this design with a net charge density of −0.16 showed excellent solubility and the protein was active. Some gel formation was observed at low temperatures but this did not appear to be a problem.

This section describes the construction of a codon optimized gene encoding a accessory polypeptide, rPEG_L288 with 288 amino acids and the sequence (SSSESSESSSSE)$_{24}$ (SEQ ID NO: 460). A stuffer vector pCWO150 which is based on a pET vector and includes a T7 promoter is constructed as shown in FIG. 9. The vector encodes a Flag sequence followed by a stuffer sequence that is flanked by BsaL BbsI, and KpnI sites. The stuffer sequence was followed by a His6 tag (SEQ ID NO: 1) and the gene of green fluorescent protein (GFP). GFP was chosen as the biologically active protein and may be used in imaging applications or as a selection marker. The stuffer sequence contains stop codons and thus E. coli cells carrying the stuffer plasmid pCWO150 form non-fluorescent colonies. The stuffer vector pCWO150 was digested with BsaI and KpnI. A codon library encoding accessory polypeptides of 36 amino acid length was constructed. The accessory polypeptide was designated rPEG_L36 and had the amino acid sequence (SSSESSESSSSE)$_3$ (SEQ ID NO: 461). The insert was obtained by annealing synthetic oligonucleotide pairs encoding the amino acid sequence SSESSESSSSES (SEQ ID NO: 462) as well as a pair of oligonucleotides that encode an adaptor to the KpnI site. The following oligonucleotides were used as forward and reverse primers:

```
pr_LCW0148for:
                                        (SEQ ID NO: 463)
TTCTAGTGARTCYAGYGARTCYAGYTCYAGYGAATC, pr_LCW0148rev:
                                        (SEQ ID NO: 464)
AGAAGATTCRCTRGARCTRGAYTCRCTRGAYTCACT,
```

The following oligonucleotides are used as stopper primers:

```
pr_3KpnIstopperForTTCT:
                                        (SEQ ID NO: 465)
TTCTTCGTCTTCACTCGAGGGTAC, pr_3KpnIstopperRev:
                                        (SEQ ID NO: 459)
CCTCGAGTGAAGACGA.
```

By varying the ratio of forward/reverse primers to stopper primers, the size of the resulting PCR products can be controlled. The annealed oligonucleotide pairs were ligated, which resulted in a mixture of products with varying length that represents the varying number of (SSSESSESSSSE) (SEQ ID NO: 362) repeats. The product corresponding to the length of rPEG_L36 was isolated from the mixture by agarose gel electrophoresis and ligated into the BsaI/KpnI digested stuffer vector pCWO150. Cells transformed with vector showed green fluorescence after induction which shows that the sequence of rPEG_L36 had been ligated in frame with the GFP gene. The resulting library was designated LCW0148. Isolates (e.g., 312 isolates) from library LCW0148 were screened for high level of fluorescence. Isolates (e.g., 70 isolates) with strong fluorescence were analyzed by PCR to verify the length of the rPEG_L segment and 34 clones were identified that had the expected length of rPEG_L36. This process resulted in a collection of 34 isolates of rPEG_L36 showing high expression and differing in their codon usage. A plasmid mixture was digested with BsaI/NcoI and a fragment comprising the rPEG_L36 sequence and a part of GFP was isolated. The same plasmid mixture was also digested with BbsI/NcoI and the vector fragment comprising rPEG_L36, most of the plasmid vector, and the remainder of the GFP gene was isolated. Both fragments were mixed, ligated, and transformed into BL21Gold(DE3) and isolates were screened for fluorescence. This process of dimerization was repeated two more rounds. During each round, the length of the rPEG_L gene was doubled and ultimately a collection of genes that encode rPEG_L288 were obtained. The rPEG_L288 module contains segments of rPEG_L36 that differ in their nucleotide sequence despite having identical amino acid sequence. Thus, internal homology in the gene is minimized and as a result the risk of spontaneous recombination is reduced. E. coli BL21Gold(DE3) harboring plasmids encoding rPEG_L288 were cultured for at least 20 doublings and no spontaneous recombination was observed.

E. coli BL21Gold(DE3) cells harboring plasmids encoding rPEG_L288 were grown overnight in Terrific Broth (TB) and diluted 200-fold into fresh TB the following day. When the culture reached an A600 nm=0.6, expression of rPEG_L288-GFP was induced with the addition of IPTG to 0.2 mM final concentration. The cells were harvested following 18 hr at 26 C and can be stored at −80 C until further processing. The cells were resuspended in 90 ml of 50 mM Tris-HCl, 200 mM sodium chloride, 0.1% Tween-20, 10% glycerol, pH 8.0 per liter of bacterial culture. Protease inhibitors, lysozyme (final 20 ug/ml), and benzonase nuclease were added to the bacterial suspension prior to lysis. The cells were lysed by sonication on ice for four minutes followed by heat treatment at 80° C. for 20 min. The lysate was subsequently cooled on ice and centrifuged for 20 min at 15000 rpm in a Sorvall SS-34 rotor. The soluble recombinant protein was purified by immobilized metal ion affinity chromatography (IMAC) of the supernatant. The protein was further purified by ion exchange chromatography (IEC) and gel filtration chromatography. Optionally, the protein can be further purified by a column with immobilized anti-FLAG antibody using standard techniques. Purity and homogeneity of the protein was assessed using standard biochemical methods including SDS-PAGE, native-PAGE, analytical gel filtration chromatography, light scattering, and mass spectrometry. A purity of at least 90% was obtained. Additionally, the modified polypeptides rPEG_L288-hGH and rPEG_L288-GLP1 were obtained in a similar manner.

The purity of rPEG_L288-modified GFP was confirmed by SDS-PAGE (FIG. 36), analytical reverse phase HPLC (FIG. 38). The apparent molecular weight of rPEG_L288-modified GFP was also measured as previously described (FIG. 41). FIG. 49 illustrates the increase in apparent molecular weight observed upon linking a biologically active polypeptide (GLP1) to rPEG_L288 accessory polypeptide. The in vivo stability in rat and human serum was determined as shown in FIG. 42. rPEG is stable in rat and human serum, and rPEG288 has a halflife of about 10 to 20 hours in rats (FIG. 43). Little immunogenicity in in vivo experiments could be observed with this polypeptide (FIG. 44).

Design 6. Construction of rPEG_K288-GFP, rPEG_K288-hGH and rPEG_K288-GLP1 Accessory Polypeptides.

This design describes a polypeptide modified with a long hydrophilic accessory polypeptide of 288 amino acids comprising 33% glutamate residues. rPEG_K288 has the sequence (GEGGGEGGE)$_{32}$ (SEQ ID NO: 466) and contains 96 E residues. When rPEG_K288 was added to hGH, the total length of the fusion became 479 amino acids (calculated as 191+288) and the net charge became 101 (calculated as 96+5), yielding a net charge density of 0.21 (calculated as 101/479). As predicted and confirmed by the experimental results described below, this design with a net charge density of −0.21 showed the highest degree of solubility and the protein was active. No gel formation was observed at the temperature or salt concentrations tested.

This section describes the construction of a fusion gene encoding an accessory polypeptide of the sequence (GEGGGEGGE)$_{32}$ (SEQ ID NO: 466). An insert is obtained essentially as described for rPEG_L288 but by annealing a synthetic oligonucleotide encoding the rPEG sequence rPEG_K288 with a pair of oligonucleotides encoding an adaptor to the KpnI site. The following oligonucleotides were used as forward and reverse primers:

```
pr_LCW0147for:
                                        (SEQ ID NO: 467)
AGGTGAAGGWGARGGWGGWGGWGAAGG pr_LCW0147rev:
                                        (SEQ ID NO: 468)
ACCTCCTTCWCCWCCWCCYTCWCCTTC
```

The following oligonucleotides are used as stopper primers:

```
pr_3KpnIstopperFor:
                                        (SEQ ID NO: 458)
AGGTTCGTCTTCACTCGAGGGTAC pr_3KpnIstopperRev:
                                        (SEQ ID NO: 459)
CCTCGAGTGAAGACGA.
```

By varying the ratio of forward/reverse primers to stopper primers, the size of the resulting PCR products can be controlled. The insert is used to generate a plasmid encoding the rPEG_K288-modified GFP and cells expressing this plasmid in a fashion similar to rPEG_L288-modified GFP. Additionally, the modified polypeptides rPEG_K288-hGH and rPEG_K288-GLP1 were obtained in a similar manner.

The purity of rPEG_K288-modified GFP was confirmed by SDS-PAGE (FIG. 36) and analytical size exclusion chromatography (see FIG. 37). The apparent molecular weight of rPEG_K288-modified GFP was also measured as previously described (FIG. 41). FIG. 49 illustrates the increase in apparent molecular weight observed upon linking a biologically active polypeptide (GLP1) to rPEG_K288 accessory polypeptide. The in vivo stability in rat and human serum was determined as shown in FIG. 42, and in vivo pharmacokinetic properties are indicated in FIG. 43. rPEG is stable in rat and human serum, and rPEG288 has a halflife of about 10 to 20 hours in rats (FIG. 43). Little immunogenicity in in vivo experiments could be observed with this polypeptide (FIG. 44).

Protein Expression

Designs 4, 5 and 6 were constructed and protein was expressed and characterized as follows. Briefly, the hGH gene was fused to the rPEG sequences of the plasmid harboring the T7 promoter and the coding sequences of 288 amino acids of rPEG-J, -K or -L described above (designs 4, 5 or 6 respectively), replacing the GFP gene. In this example the rPEG was followed by the gene for hGH although other formats can be envisioned, such as having the rPEG at C terminal end of the modified polypeptide. The plasmid was transformed into BL21(DE3)-star E. coli strain (Novagen) and plated on an LB-agar plate with the appropriate antibiotics and grown overnight at 37° C. A single colony was inoculated into 5 ml of TB125 medium and grown overnight at 37° C. The next day the inoculum was transformed into a 2 L vessel with 500 ml of TB125, and grown until an OD=0.6 was reached, followed by continued grown at 26° C. for 16 hr with 100 mM IPTG.

Cells were collected by centrifugation and the cell pellet was resuspended in 50 ml Buffer containing 50 mM Tris pH=8.0, 100 mM NaCl, Protease inhibitors, 10% (v/v) glycerol, 0.1% Triton X-100 and DNAse. Cells were disrupted using an ultrasonic sonicator cell disruptor, and cell debris was removed by centrifugation at 15000 RPM at 4° C. Cellular supernatant was applied on an anion-exchanger (Q-sepharose, Pharmacia), washed with buffer A (25 mM Tris pH=8.0) and eluted from the column using a linear gradient of the same buffer with 1M NaCl. Protein eluted at about 500 mM NaCl. The eluted fusion protein was pooled, dialyzed and loaded on the anion-exchanger (Q-sepharose, Pharmacia), washed with buffer A (25 mM Tris pH=8.0) and eluted from the column using a shallow linear gradient of the same buffer with 1M NaCl. The eluted fusion protein was pooled, dialyzed against buffer A, concentrated, and purified by size-exclusion chromatography (SEC) as the final purification. Protein purity was estimated to be above 98%, which was unexpected considering only ion exchange and SEC had been used to purify the protein in an rPEG-specific manner from whole cells. The quantity of eluted fusion protein was determined by SDS-PAGE analysis and by measurement of total protein concentration. A high quantity of eluted fusion protein reflects higher solubility of the fusion protein relative to hGH alone.

Testing of Accessory Polypeptide-Modified hGH in an hGH Receptor Binding Assay

To determine whether the purified hGH-rPEG_K288 is in its active, native conformation we tested its ability to bind to the human growth hormone receptor. Briefly, 500 ng of recombinant hGH receptor (purchased from R&D Systems) dissolved in phosphate buffer saline (PBS) was absorbed to the wells of a microplate overnight at 4° C. Unbound receptor was subsequently removed by washing with PBS containing 0.5% Tween-20 (PBST). Further non-specific binding was blocked by the addition of 1% bovine serum albumin in PBS (binding buffer). Following additional washes with PBST, 200 nM of hGH-rPEG_K288 or recombinant hGH (purchased from R&D Systems) diluted in binding buffer was added to the hGH receptor coated wells. Bound hGH-rPEG_K288 and hGH were detected with a polyclonal rabbit anti-hGH antibody and a horseradish peroxidase (HRP) conjugated anti-rabbit secondary antibody. The HRP substrate, 2,2'-azino-bis(3-ethylbenzthiazoline-6-sulphonic acid) was added and absorption at 405 nm was measured after 30 minutes. As shown in FIG. 34, hGH-rPEG_K288 bound to the hGH receptor as well as recombinant hGH. This result demonstrates that hGH, when expressed as an rPEG fusion protein in the cytoplasm, is soluble, correctly folded and in its active conformation. This result contrasts with native human growth hormone (hGH), which typically forms inclusion bodies composed of inactive protein in the cytoplasm of E. coli and must be unfolded and refolded to become active. This shows that hGH can be expressed in a soluble, active form in the cytoplasm of E. coli when fused to a rPEG polypeptide. The data show that a net charge density of 0.1 charges/AA (as with hGH-rPEG_J288) is sufficient to make the fusion protein soluble, a net charge density of 0.16, as obtained with hGH-rPEG_L288, yields a more soluble protein and a net charge density of 0.21, as obtained with hGH-rPEG_K288, similarly improve solubility.

Designs 1, 2 and 3 are similarly prepared but include 16 negatively charged amino acids (glutamate in all three cases), 41 negatively charged amino acids or 27 positively charged amino acids, respectively, instead of the rPEG-J, -K and -L sequences, and can have improved solubility properties.

In designing accessory polypeptide sequences, the overall desired properties of the therapeutic protein may b6 considered, including, for example, serum stability, expression level and immunogenicity, which as described hereinabove, can also be influenced by the choice of amino acids incorporated into the accessory polypeptides.

Example 2

Expression of Human Growth Hormone (hGH)—Cleavable rPEG-Modified Polypeptide

This example, as illustrated in FIG. 13, describes the preparation of an rPEG_K288-linked human growth hormone polypeptide having a protease cleavage sequence in between the therapeutic protein and the accessory polypeptide. The accessory polypeptide moiety improves solubility during recombinant expression to the extent that the active protein can be easily isolated in large quantities, whereas the protease cleavage site allows the optional removal of the rPEG by protease digestion. The final protein product is a pure and active hGH.

A plasmid harboring hGH, N-terminally fused to 288 amino acids of rPEG-K288 and, having the repetitive sequence (GEGGGEGGE)$_{32}$ (SEQ ID NO: 466) and a TEV protease cleavage site (ENLYFQ/X) (SEQ ID NO: 469), following the T7 promoter (i.e. T7 promoter-hGH-TEV-rPEG_K288), is transformed into BL21(DE3)-star E. coli strain and is grown as described above. Cells are collected by centrifugation and the cell pellet is resuspended in 50 ml Buffer containing 50 mM Tris pH=8.0, 100 mM NaCl, Protease inhibitors, 10% (v/v) glycerol, 0.1% Triton X-100 and DNAse. Cells are disrupted using an ultrasonic sonicator cell disruptor, and cell debris is removed by centrifugation at 15000 RPM at 4° C. Cellular supernatant is applied on an anion-exchanger (Q-sepharose, Pharmacia), washed with buffer A (25 mM Tris pH=8.0) and eluted from the column using a linear gradient of the same buffer with 1M NaCl. Protein elutes at about 500rnM NaCl. The eluted fusion protein is pooled, dialyzed and TEV digested. The digestion mixture is reloaded on the anion-exchange (Q-sepharose, Pharmacia), washed with buffer A (25 mM Tris pH=8.0) and eluted from the column using a shallow linear gradient of the same buffer with 1M NaCl. The eluted hGH protein is pooled, dialyzed against buffer A, concentrated, and purified by size-exclusion chromatography (SEC) as the final purification. Protein purity is estimated to be above 98%.

Example 3

Expression of Human Growth Hormone (hGH) Fused to CBD and rPEG_K288

This example describes the preparation of a CBD-TEV-rPEG_K288-hGH fusion protein. After digestion with TEV protease, and purification, the final protein product is –rPEG_K288-hGH.

A pET-series vector was constructed with T7 promoter, which expresses a protein containing cellulose binding domain (CBD) at the N-terminus, followed by a Tomato Etch Virus (TEV) protease cleavage site, followed by the hGH coding sequence, and by the rPEG_K288 coding sequence: CBD-TEV-rPEG_K288-hGH. The rPEG_K288 has the repetitive sequence (GEGGGEGGE)$_{32}$ (SEQ ID NO: 466). The CBD sequence used is shown in Swissprot file Q06851 and the purification of CBD fusion proteins is described in Ofir, K. et al. (2005) Proteomics 5:1806. The sequence of the TEV cleavage site is ENLYFQ/X (SEQ ID NO: 524); G was used in the X position. This construct was transformed into BL21(DE3)-star *E. coli* strain and grown essentially as described above, except that the CBD sequence was introduced N-terminal to the rPEG sequence. Cells were collected and disrupted essentially as described above. The cellular supernatant was applied on beaded cellulose resin (Perloza 100), washed with buffer A (25 mM Tris pH=8.0) and eluted from the column with 20 mM NaOH. pH was adjusted by reutilizing the sample with 1M Tris buffer pH=8.0. Protein purity was estimated to be above 90%.

After applying a TEV digest as described in Example 2, the digested sample was applied on beaded cellulose resin (Perloza 100), where the CBD was retained on the column, and the rPEG_K288-hGH was found in the column flow-through. The pooled flow-through was loaded on the anion-exchange (Q-sepharose, Pharmacia), washed with buffer A (25 mM Tris pH=8.0) and eluted from the column using a shallow linear gradient of same buffer with 1M NaCl. The eluted fusion protein was pooled, dialyzed against buffer A, concentrated, and purified by size-exclusion chromatography (SEC) as the final purification. Protein purity was estimated to be above 98% (FIGS. 50 and 51). The final protein is rPEG_K288-hGH.

Example 4

Expression of CBD-Human Growth Hormone (hGH) Fused to rPEG_K288

This example describes the preparation of CBD-rPEG_K288-TEV-hGH, fusion protein. After TEV protease digest and purification, the final protein product is pure hGH.

A plasmid harboring hGH, N-terminally fused to the TEV protease recognition site and to CBD following the T7 promoter, and also C-terminally fused to rPEG-K288 having the repetitive sequence (GEGGGEGGE)$_{32}$ (SEQ ID NO: 466), resulting in a vector containing CBD-rPEG_K288-TEV-hGH, is transformed into the BL21(DE3)-star *E. coli* strain (Novagen) and grown essentially as described in Example 3. Cells are collected and disrupted essentially as described in Example 3 and the cellular supernatant is applied on beaded cellulose resin (Perloza 100; Iontosorb Inc.), washed with buffer A (25 mM Tris pH=8.0). After applying the TEV digest performed essentially as described in Example 3, hGH is found in the column flow-through, while CBD-rPEG_K288 remains on the column. The pooled flow-through is loaded on the anion-exchange (Q-sepharose, Pharmacia), washed with buffer A (25 mM Tris pH=8.0) and eluted from the column using a shallow linear gradient of same buffer with 1M NaCl. The eluted hGH protein is pooled, dialyzed against buffer A, concentrated, and purified by size-exclusion chromatography (SEC) as the final purification. Protein purity is estimated to be above 98%. The final protein product is a pure and active hGH.

Example 5

Expression of rPEG_K288-VHH, a Domain Antibody that Binds Lysozyme

This example describes the preparation of rPEG_K288 fused to a VHH domain antibody (dAb).

A plasmid harboring hGH, N-terminally fused to 288 amino acids of rPEG-K, having the repetitive sequence (GEGGGEGGE)$_{32}$ (SEQ ID NO: 466) following the T7 promoter, is prepared essentially as described in Example 1 but replacing the hGH coding sequence with a domain antibody coding sequence. The domain antibody coding sequence is provided in Dumoulin, M. et al., Protein Science 11:500-505 (2002). Amino acid residues 1-113 of clone dAb-Lys3 are incorporated into the rPEG construct. This sequence is a domain antibody that binds to hen egg lysozyme with a Kd of 11 nM. This domain antibody sequence yields only inclusion bodies composed of inactive protein when expressed in the cytoplasm of *E. coli* in the absence of additional solubility enhancing sequences; alternatively it can be expressed in active form in the periplasm if guided by a leader sequence. The VHH dAb sequence is inserted upstream of the rPEG_K288 sequence and the resulting plasmid is transformed into BL21(DE3)-star *E. coli* strain (Novagen). Cells are grown, collected and disrupted essentially as described above. The cellular supernatant is applied on an anion-exchange (Q-sepharose, Pharmacia), washed with buffer A (25 mM Tris pH=8.0) and protein is eluted from the column using a linear gradient of the same buffer with 1M NaCl. Protein elutes at about 500 mM NaCl. The eluted fusion protein is pooled, dialyzed and loaded on the anion-exchange (Q-sepharose, Pharmacia), washed with buffer A (25 mM Tris pH=8.0) and eluted from the column using a shallow linear gradient of same buffer with 1M NaCl. The eluted fusion protein is pooled, dialyzed against buffer A, concentrated, and purified by size-exclusion chromatography (SEC) as the final purification. Protein purity is estimated to be above 98%.

The resulting VHH-rPEG_K288 protein is assayed by ELISA for the ability to bind to its target, hen egg lysozyme (Sigma). The protein was shown to bind specifically to lysozyme but not to three control proteins, demonstrating that the addition of rPEG_K288 to the VHH caused it to express in soluble and active form in the cytoplasm of *E. coli*.

Example 6

Expression of IFNa2a-rPEG

This example describes the preparation of an IFNa2a-rPEG fusion protein.

Interferon alpha 2a has 165 amino acids, a pI of 5.99, and a molecular weight of 19241.62 corresponding to the sequence:

(SEQ ID NO: 470)
CDLPQTHSLGSRRTLMLLAQMRKISLFSCLKDRHDFGFPQEEFGNQFQKA

-continued

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE

The polypeptide has 14 glutamate residues and 8 aspartate residues, adding up to a total of 22 negative residues. Similarly, the 11 lysine and 8 arginine residues add a total of 19 positive charges to the protein, resulting in a net charge of −3. Thus the charge density is −0.018 (calculated as −3/165 amino acids). This net charge density correlates well with the experimental pI value of 5.99. The desired charge density for improved solubility was chosen as 0.1 negative charges/amino acid. To achieve this charge density, an additional 13.5 negative charges are needed calculated as (16.5-3)

The addition of 15 negatively charged amino acids to interferon alpha brings the net charge density of the fusion protein to −0.1 (calculated as (15+3)/(165+15)), which is desirable for increased solubility. A higher charge density of −0.2 charges/amino acid may be obtained by including about 26 additional negatively charged amino acid residues in the protein, for a total of 41 negatively charged amino acid residues. Since the combined length is 206 amino acids (calculated as 165+41), a charge density of −0.2 requires 41 total negatively charged amino acid residues (calculated as 0.2×205 amino acids), which means the accessory protein may include 38 negatively charged residues (calculated as 41-3).

By similar reasoning, to reach a net charge density of +0.1, the accessory polypeptide may include 15+6=21 positively charged amino acids.

rPEG_J288 has the sequence GGSGGE (SEQ ID NO: 62) and contains 48 E residues and can therefore be used to increase the charge density of IFNa2a. When rPEG_J288 is added to IFNa2a, the total length of the fusion protein is 453 amino acids (calculated as 165+288 amino acids) and the net charge is 51 (48+3), yielding a net charge density of 0.11 (calculated as 51/453), which allows expression of IFNa2a in soluble, active form in the cell cytoplasm. The constructs, expression and purification methods are prepared and carried out essentially as described in Example 1. The fusion protein proved to be soluble and active, although some tendency towards aggregation could still be observed under some conditions. This can be overcome by increasing the net charge density to keep the protein in solution. rPEGs of the same size but with more charges, such as rPEG_L (288AA, 25% E) and rPEG_K (288AA, 33% E), may be able to make the IFNa2a-rPEG fusion protein completely soluble and actively folded. For IFNa2a-rPEG_K288 the number of negatively charged amino acid residues in the accessory polypeptide is 96, such that the total net charge of the fusion protein is 99 (calculated as 96+3), which means that the net charge density is 0.218 (calculated as 99/(288+165)).

Example 7

Expression of G-CSF-rPEGJ-288

This example describes the preparation of a G-CSF-rPEG fusion protein.

G-CSF has a length of 174 amino acids, a pI of 5.65 and a molecular weight of 18672.29 corresponding to the sequence:

(SEQ ID NO: 471)

TPLGPASSLPQSFLLKCLEQVRKIQGDGAALQEKLCATYKLCHPEELVLL

GHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGG

VLVASHLQSFLEVSYRVLRHLAQP.

The polypeptide has 9 glutamate residues and 4 aspartate residues, adding up to a total of 13 negative residues. Similarly, the 4 lysine and 5 arginine residues add a total of 9 positive charges to the protein, resulting in a net charge of 4. Thus the charge density is −0.023 (calculated as −4/174 amino acids). This net charge density correlates well with the experimental pI value of 5.65.

The desired charge density for improved solubility was chosen as 0.1 negative charges/amino acid. To achieve this charge density, an additional 13.4 negatively charged amino acid residues are needed (calculated as 17.4-4)

For GCSF, the addition of 14 negatively charged amino acids brings the net charge density of the fusion protein to about −0.1 (calculated as (14+4)/(174+14)), which is typically desirable for solubility. The preferred charge density of −0.2 would require about 26 additional negatively charged amino acid residues, for a total of 41 negatively charged amino acid residues, since combined length is 217 amino acids (calculated as 174+43). An alternatively chosen charge density of −0.2 requires 43 total negatively charged amino acid residues (calculated as 0.2×217 amino acids), which means the accessory protein should contain 39 negatively charged residues (calculated as 43-4).

In another alternative design, an accessory protein with positively charged amino acids to reach a net charge density of +0.1 is desired, which requires a net positive charge of +21. This could be achieved by addition of an accessory protein containing 25 positive charges (calculated as 25−4=21), resulting in a combined fusion protein length of 209 amino acids.

Experimental Results:

rPEG_J1288 has the sequence GGSGGE (SEQ ID NO: 62) and contains 48 E residues. When rPEG_J288 is added to GCSF, the total length of the fusion becomes 174+288=462 amino acids and the net charge becomes 48+3=51, yielding a net charge density of 0.11 (calculated as 51/462). This charge is expected to be sufficient to switch GCSF from >80% aggregation to >80% soluble protein. A higher charge density of 0.15 or 0.2 can also be used.

Using standard molecular biological techniques any of the examples provided hereinabove may be modified to use a different rPEG module fused to the therapeutic protein. The present inventors have shown that a net charge density of 0.1 provides improved solubility of proteins in the cytoplasm (e.g., with GFP, hGH and IFNa2a), whereas a net charge density of around 0.2 provides highly soluble proteins with no tendency towards aggregation.

Example 8

Solubility of Different rPEG Sequences Fused to GFP when Recombinantly-Expressed in the Cytoplasm of *E. coli.*

The following protein sequences were prepared and tested in this experiment:

rPEG_J288-GFP— represents the protein sequence composed of the repetitive sequence $(GSGGEG)_{48}$ (SEQ ID NO: 472) fused to GFP protein sequence.

rPEG_K288-GFP— represents the protein sequence composed of the repetitive sequence (GEGEGGGEG)$_{32}$ (SEQ ID NO: 473) fused to GFP sequence.

rPEG_L288-GFP— represents the protein sequence composed of the repetitive sequence (SSESSESSSSES)$_{24}$ (SEQ ID NO: 474) fused to GFP sequence.

rPEG_O336-GFP— represents the protein sequence composed of the repetitive sequence (SSSSSESSSSSES)$_{24}$ (SEQ ID NO: 475) fused to GFP sequence.

rPEG_P320-GFP— represents protein sequence composed of the repetitive sequence (SSSESSSSES)$_{32}$ (SEQ ID NO: 476) fused to GFP sequence.

rPEG J288, K288, L288, O336 and P320, each fused to the N-terminus of GFP, were introduced in to the *E. coli* strain BL21-Star, grown on LB-Kan agar plates, and incubated for 16 hours at 37° C. The next day a single colony of each construct was inoculated into 2 mL of TB125 growth medium and grown for 5 hr. 100 ul of the each bacterial broth were transferred into 10 ml flasks with TB125 medium+Kan, and grown until the OD$_{600}$ has reached ~0.6. The growth flasks were transferred to 26 C, and induced with 100 uM IPTG for 16 hours with shaking. Bacterial cells were centrifuged and resuspended in 10 ml of PBS, and later disrupted by sonication. 100 μl aliquots of each sample were centrifuged and their supernatant collected. Finally, 100 μl of cellular lysate and soluble fractions were read and compared for GFP florescence.

The results are shown in FIG. 33. GFP modified with rPEG accessory polypeptides J, K and L had most of the GFP signal in the soluble form, while a substantial fraction of GFP fluorescence was retained in the insoluble form in rPEG 0 and rPEG P fusion sequences. Furthermore, GFP fused to Ser-rich rPEG sequences expressed better then Gly-rich sequences, while the Gly-rich rPEG sequences retained the majority of the GFP fluorescence in the soluble form.

Example 9

Determination of Properties of Accessory-Linked Polypeptides

Determination of Serum Stability of an Accessory-Linked Polypeptide.

The fusion protein Flag-rPEG_J288-H6-GFP, purified as shown in FIG. 19, containing an N-terminal Flag tag and the accessory sequence rPEG_J288 fused to the N-terminus of green fluorescent protein is incubated in 50% mouse serum at 37 C for 3 days. Samples are withdrawn at various time points and analyzed by SDS PAGE followed by detection using Western analysis. An antibody against the N-terminal flag tag is used for Western detection. FIG. 20 indicates that the accessory protein is stable in serum for at least three days.

Determination of Plasma Half-Life of an Accessory-Linked Polypeptide.

The plasma half-life of accessory-linked polypeptides can be measured after i.v. or i.p. injection of the accessory polypeptide into catheterized rats essentially as described by [Pepinsky, R. B., et al. (2001) J Pharmacol Exp Ther, 297: 1059-66]. Blood samples can be withdrawn at various time points (5 min, 15 min, 30 min, 1 h, 3 h, 5 h, 1 d, 2 d, 3 d) and the plasma concentration of the accessory polypeptide can be measured using ELISA. Pharmacokinetic parameters can be calculated using WinNonlin version 2.0 (Scientific Consulting Inc., Apex, N.C.). To analyze the effect of the rPEG-linked polypeptide one can compare the plasma half-life of a protein containing the rPEG polypeptide with the plasma half-life of the same protein lacking the rPEG polypeptide.

The in vivo halflife or LCW0057 and LCW0066 was studied in rats. Both proteins were injected intravenously into rats. Serum samples were analyzed for the presence of GFP between 5 min and 3 days after injection. For rats injected with LCW0057 no GFP was detectable 24 h after protein injection. This suggests a halflife of the protein of 1-3 h. In contrast, LCW0066 was detectable even 48 h after injection and one rat showed detectable GFP even 3 days after injection. This shows that LCW0066 has a serum halflife in rats of about 10 hours which is much longer than expected for a protein with a calculated molecular weight of 52 kDa.

Solubility Testing of Accessory-Linked Polypeptides.

Solubility of accessory-linked polypeptides can be determined by concentrating purified samples of accessory-linked polypeptides in physiological buffers like phosphate buffered saline to various concentrations in the range of 0.01 mg/ml to 10 mg/ml. Samples can be incubated for up to several weeks. Samples where the concentration exceeds the solubility of the accessory-linked polypeptide show precipitation as indicated by turbidity, which can be measured in an absorbance reader. One can remove precipitated material by centrifugation or filtration and measure the concentration of remaining protein in the supernatant using a protein assay like the Bradford assay of by measuring the absorbance at 280 nm. Solubility studies can be accelerated by freezing the samples at −20 C and subsequent thawing. This process frequently leads to the precipitation of poorly soluble proteins.

Size Exclusion Chromatography of GFP Modified with an Accessory Polypeptide.

rPEG with the sequence (GGSGGE)$_{48}$ (SEQ ID NO: 455) was fused to green fluorescent protein (GFP) yielding clone LCW0066. The fusion protein also carried an N-terminal Flag tag and a His6 tag (SEQ ID NO: 1) between rPEG and GFP. The fusion protein was expressed in *E. coli* using a standard T7 expression vector. Cells were cultured in LB medium and expression was induced with IPTG. After expression, the cells were lyzed by heating the pellet to 70° C. for 15 min. Most *E. coli* proteins denatured during this heat step and could be removed by centrifugation. The fusion protein was purified from the supernatant by IMAC chromatography followed by purification by immobilized anti-Flag (Sigma). The fusion proteins were analyzed by size exclusion chromatography (SEC) using 10/30 Superdex-200 (GE, Amersham). The column was calibrated with globular proteins (diamonds). The fusion protein comprising rPEG_J288 and GFP eluted significantly earlier from the column then predicted based on its calculated molecular weight. Based on the calibration with globular proteins SEC measured an apparent molecular weight of the fusion protein of 243 kDa, which is almost 5 times larger than the calculated molecular weight of 52 kDa. A related fusion protein (LCW0057) contained rPEG36 and had an apparent molecular weight of 55 kDa versus a calculated molecular weight of 32 kDa. Comparison of the LCW0066 and LCW0057 shows a difference in apparent molecular weight of 189 kDa which is caused by the addition of an rPEG chain with a calculated molecular weight of 20 kDa. Thus, one can calculate that the addion of an rPEG tail with a calculated molecular weight of 20 kDa lead to an increase in molecular weight of 189 kDa.

Example 10

Controlled-Release Formulations of Modified Polypeptides

Microencapsulation of rPEG-GFP Fusion Protein

Resomer-PEG copolymers are commercially available (e.g. Boehringer-Ingelheim). Microspheres containing rPEG (L288)-GFP or GFP alone are prepared by the double emulsion solvent extraction/evaporation (W/O/W, water-in-oil-in-water) method. Protein (1% weight/volume) and Resomer-PEG copolymers (9% weight/volume) are dissolved in dichloromethane. Thus the theoretical microsphere loading efficiency is 10% weight by weight protein. The protein polymer mixture is then vortexed vigorously for five minutes: The mixture was diluted 50-fold into an aqueous solution containing 1% polyvinylalcohol and stirred vigorously for several hours at room temperature. The hardened microspheres are washed several times with ultrapure water, dried, and stored at 4° C. in a dessicator.

Various modifications to this protocol can be made including varying the protein:copolymer ratio, using protein samples in aqueous solution instead of lyophilized protein samples, and freeze-drying the hardened microspheres. Different polymer matrices can also be utilized, for example by replacing Resomer-PEG copolymers with diblock (PLGA-PEG) or triblock (PLGA-PEG-PLGA) copolymers. Similarly, microspheres can be stored under various conditions, for example, at –20 C or –80 C. Multiple coatings of particles can also be utilized to have a gradient of drug concentrations, so that the inner layers, which have a smaller surface area, yield the same drug release per unit time due to a higher concentration of the drug.

Measurement of Encapsulation Efficiency

To assess the encapsulation efficiency of rPEG(L288)-GFP into the microspheres, 200 mg of microspheres are dissolved in dichloromethane. The rPEG(L288)-GFP is then extracted in 3 volumes of phosphate buffered saline (PBS). The amount of rPEG(L288)-GFP extracted from the microspheres is measured by a sandwich ELISA assay using purified recombinant rPEG(L288)-GFP as a standard. Briefly, the released rPEG (L288)-GFP is captured in microtiter plate wells that have been coated with α-FLAG antibody. The captured protein is detected with a polyclonal α-GFP antibody and a secondary antibody conjugated to horseradish peroxidase (HRP). The amount of protein in the wells was quantitated by comparison to a standard curve generated using purified rPEG(L288)-GFP.

Measuring In Vitro Release of rPEG-GFP from Microspheres

In vitro release of the rPEG-GFP fusion and GFP is measured by the following procedure. First, microspheres (200 mg) are suspended in 1 ml of PBS. The suspension of microspheres is incubated at 37° C. with gentle agitation. Aliquots (10-100 µL) are then removed every 24 hr for at least two weeks. The quantity of released rPEG-GFP and GFP is quantitated by sandwich ELISA as described above. Possible modifications to this procedure include measuring the release of rPEG-GFP from beads suspended in serum or serum/PBS mixtures.

Determination of Serum Concentration of rPEG-GFP Following Subcutaneous Injection of Encapsulated Protein The serum concentration of rPEG-GFP and GFP can be tested by following a single subcutaneous injection of rPEG-GFP microspheres or GFP microspheres, respectively, in a model laboratory organism. Encapsulated rPEG-GFP or encapsulated GFP is injected into mice, rats, rabbits, or other model organisms (1 mL/kg of body weight) to evaluate in vivo release rates. Serum samples are collected daily for one month. Serum concentrations or rPEG-GFP are measured using the sandwich ELISA assay described above. rPEG-GFP fusion polypeptides are present at a high concentration much longer than GFP due to a slower release from the microspheres and a longer subsequent half life.

Example 11

Polymer Encapsulated Interferon-Alpha (IFN-Alpha) Linked to an Accessory Polypeptide This example describes a depot formulation of rPEG-IFN-alpha which can extend the dosing interval of this polypeptide. The rPEG-fused IFN-alpha is constructed essentially as described for the hGH-rPEG fusion construct in Example 3, except GLP-1 encoding sequences are replaced by IFN-alpha coding sequence. All other methodologies and techniques, including encapsulation methodologies, are essentially as described in Example 10.

Using standard molecular biological techniques, any of the examples provided herein may be modified to use a different accessory polypeptide fused to the biologically active polypeptide. The accessory polypeptide may include any of the sequences previously described and may be up to hundreds of amino acids in length. Similarly, the examples can be modified to apply to any of the therapeutic proteins described herein, such as, and without limitation, rPEG-insulin, rPEG-IFN-beta, rPEG-erythropoietin and rPEG-tumor necrosis factor-alpha. The recombinant proteins described in these examples may be expressed in and purified from E. coli according to standard biochemistry techniques. As is apparent to the artisan, rPEG-erythropoietin and rPEG-tumor necrosis factor-alpha, for example, require post-translational glycosylation and must therefore be produced in human tissue culture cells. In such cases, the accessory polypeptide may be expressed in human cells and may be codon-optimized for better expression in human cells. Codon-optimization may be performed using standard molecular biology methods.

Example 12

Construction of Non-Repetitive Accessory Polypeptides

This example describes the construction of a library of accessory polypeptide segments from synthetic oligonucleotides. FIG. 78 lists the amino acid sequences of that were encoded by synthetic oligonucleotides. For each amino acid sequence we used two complementary oligonucleotides. The sequences were designed as codon libraries, i.e. multiple different codons were allowed but all sequences encoded just one amino acid sequence. The complementary oligonucleotides were annealed by heating followed by cooling. The oligonucleotides were designed to generate 4 base-pair overlaps during annealing as illustrated in FIG. 79. Two additional annealed oligonucleotides were also added that acted as terminators during the multimerization by ligation reaction. FIG. 79 shows the ligation of annealed oligonucleotides that yielded gene fragments encoding accessory polypeptide segments of varying length. The resulting ligation mixture was separated by electrophoresis as shown in FIG. 79 and the ligation product encoding URP36 was isolated. This ligation product was ligated into an expression vector and the library of URP36 segments was expressed as fusion protein to GFP.

Accessory polypeptide sequences prepared in this manner are shown in FIG. 80. Additional sequences are disclosed below:

LCW0219.040

(SEQ ID NO: 477)
GEGSGEGSEGEGSEGSGEGEGSEGSGEGEGGSEGSEGEGGSEGSEGEGGS

EGSEGEGSGEGSEGEGGSEGSEGEGSGEGSEGEGSEGGSEGEGGSEGSEG

EGSGEGSEGEGGEGGSEGEGSEGSGEGEGSGEGSEGEGSEGSGEGEGSGE

GSEGEGSEGSGEGEGSEGEGGSEGSEGEGSEGSGEGEGGEGSGEGE

GSGEGSEGEGGGEGSEGEGSGEGGEGEGSEGGSEGEGGSEGGEGEGSEGS

GEGEGSEGGSEGEGSEGGSEGEGSEGSGEGEGSEGSGE

LCW0219.068

(SEQ ID NO: 478)
GEGSGEGSEGEGSEGSGEGEGSEGGSEGEGSEGSGEGEGSEGSGEGEGGE

GSGEGEGSGEGSEGEGGGESEGEGGSEGSEGEGGSEGSEGEGGEGSGEG

EGSEGSGEGEGSGEGSEGEGSEGSGEGEGSEGSGEGEGGSEGSEGEGSGE

GSEGEGSEGSGEGEGSEGSGEGEGGSEGSEGEGGSEGSEGEGGSEGSEGE

GSGEGSEGEGGSEGSEGEGSGEGSEGEGGSEGSEGEGGSEGSEGEGSGEG

SEGEGGEGGSEGEGSEGSGEGEGSGEGSEGEGSEGSGE

LCW0220.038

(SEQ ID NO: 479)
SEGESEESSESGGGESSSGGGSEESSEEGSGGGSEGEGEESSGSEGGGGSG

EGSEGGSEEGSEESSEGESEESSESGGESSSGGGSEESSEEGSGGGSGES

GSGSSGSESEGGSEGESEESSGGGGSEGSEGESEESSESGGESSSGGGSE

ESSEEGSGGGSEEESGEGSGEGSEGSSGEGSEESSGGSEGGGSGGSGGEG

SGESGSGSSGSESEGGSEGESEESSGGGGSEGSSEESGGSSEEGSEGSSG

GESEESSEGESGGGSGGGSEGS

LCW0220.055

(SEQ ID NO: 480)
SEGESEESSESGGGESSSGGGSEESSEEGSGGGSEGESEESSESGGESSSG

GGSEESSEEGSGGGSGESGSGSSGSESEGGSEGESEESSGGGGSEGSESE

GEEGSEEGSGEGSGEGGGESSEEGSESSGESGSGSSGSESEGGSEGESE

ESSGGGGSEGSGESGSGSSGSESEGGSEGESEESSGGGGSEGSGESGSGS

SGSESEGGSEGESEESSGGGGSEGSSEESGGSSEEGSEGSSGGESEESSE

GESGGGSGGGSEGS

LCW0220.064

(SEQ ID NO: 481)
SEGESEESSESGGGESSSGGGSEESSEEGSGGGSEGEGEESSGSEGGGGSG

EGSEGGSEEGSEESSEGESEESSESGGESSSGGGSEESSEEGSGGGSGES

GSGSSGSESEGGSEGESEESSGGGGSEGSGESGSGSSGSESEGGSEGESE

ESSGGGGSEGSESEGEESSEEGSGEGSGEGGGESSEEGESESSEGESEES

SESGGESSSGGGSEESSEEGSGGGSGESGSGSSGSESEGGSEGESEESSE

GESGGGSGGGSEGS

LCW0220.093

(SEQ ID NO: 482)
SEGESEESSESGGGESSSGGGSEESSEEGSGGGSGESGSGSSGSESEGGSE

GESEESSGGGGSEGSEGESEESSGGESSSGGGSEESSEEGSGGGSEEG

SGESSGGSESEGSGGESEGGSGEGGGESGESGSGSSGSESEGGSEGESE

ESSGGGGSEGSSEESGGSSEEGSEGSSGGESEESSEGESGGGSGGGSEGS

SGESGSGSSGSESEGGSEGESEESSGGGGSEGSSGEGEESSEGEGGESSE

EGSGGSSEEGSGEG

Example 13

Construction of rPEG_Y576

Figure 79A:
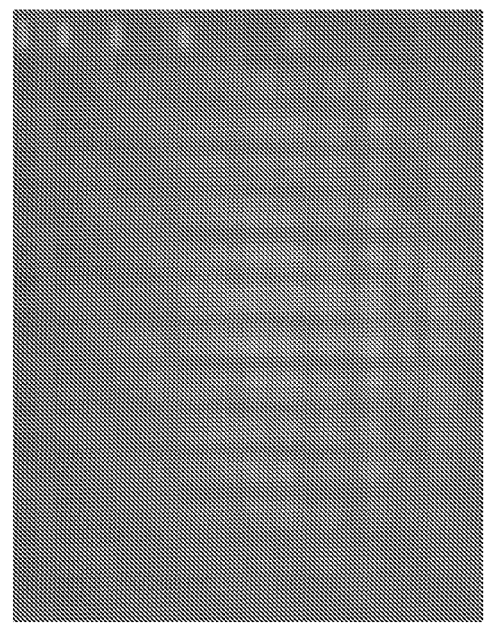
FIG. 79*a* shows the ligation reaction. Repeating segments are encoded by partially overlapping oligonucleotides that are phosphorylated. A second pair of annealed oligonucleotides is added to terminate chain elongation. One of these capping oligonucleotides is not phosphorylated, which prevents ligation at one end.
Figure 79B:
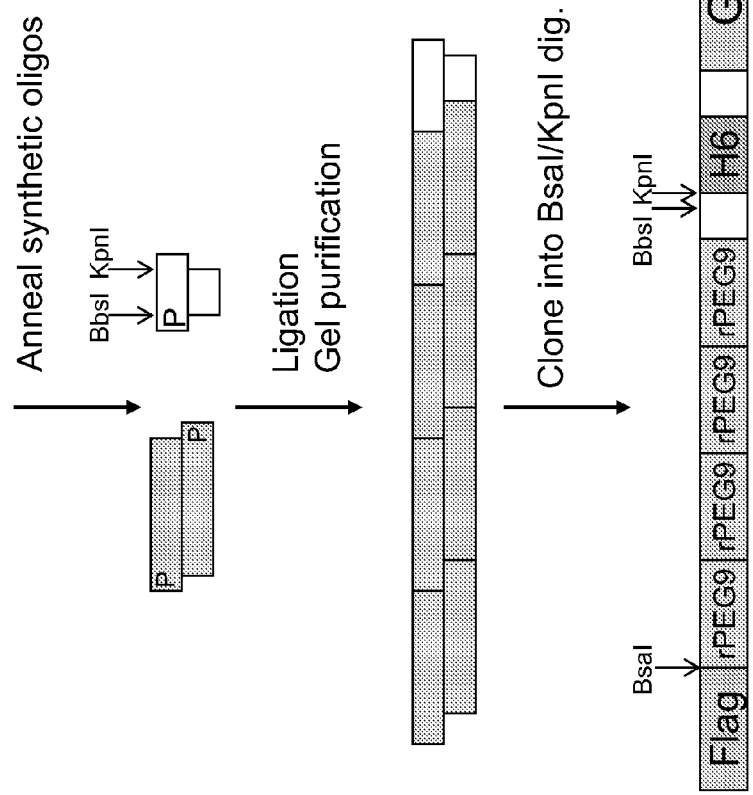
FIG. 79*b* shows an agarose gel of a ligation reaction.

This example describes the construction of a library of URP segments from synthetic oligonucleotides. FIG. 78 lists the amino acid sequences encoded by the synthetic oligonucleotides. For each amino acid sequence we used two complementary oligonucleotides. The sequences were designed as codon libraries, i.e. multiple different codons were allowed but all sequences encoded only one amino acid sequence. The complementary oligonucleotides were annealed by heating followed by cooling. The oligonucleotides were designed to generate 4 base-pair overlaps during annealing as illustrated in FIG. 79a. We also added two additional annealed oligonucleotides that acted as terminators during the multimerization by ligation reaction. FIG. 79b illustrates the ligation of annealed oligonucleotides that yielded gene fragments encoding URP segments of varying lengths. The resulting ligation mixture was separated by electrophoresis as shown in FIG. 79b and the ligation product encoding URP36 was isolated. This ligation product was ligated into an expression vector and the library of URP36 segments was expressed as fusion protein to GFP (FIG. 81). Library members with good expression were identified based on their strong fluorescence intensity.

The library members of URP36 were dimerized and the resulting library of URP72 was screened for high level expression. This process of dimerization and screening was repeated one more time to generate URP144. FIG. 80 shows a collection of sequences. The sequences conform to the design of the libraries but most library members differ in their actual sequences. This collection of URP_Y144 was dimerized two more times to generate collections of URP_Y288 and URP_Y576. The amino acid sequence of one isolate of URP_Y576 is shown in FIG. 80. The resulting isolates were evaluated for expression, aggregation, and immunogenicity to identify URP that is most suitable for fusion to a drug protein.

Example 14

Construction of scFv-rPEG50 Fusions

Construction of Anti-Her2 and Anti-EGFR

This example describes the construction of scFv-rPEG50 fusions. Two scFvs were made, one that binds Her2 and one that binds epidermal growth factor receptor (EGFR). Each scFv was genetically fused to the N-terminus of rPEG50, respectively. The scFv constructs were cloned into an expression vector with T7 promoter and encoding rPEG50-FLAG-tag-hexahistidine (SEQ ID NO: 1), resulting in constructs expressing scFv-rPEG50-FLAG-His6 (SEQ ID NO: 1). The stuffer fragment was removed by restriction digest using NdeI and BsaI endonucleases. The synthetic scFv fragments were amplified by polymerase chain reaction (PCR), which introduced NdeI and BbsI restriction sites that are compatible with the stuffer construct. Restriction digested scFv fragments and stuffer construct were ligated using T4 DNA ligase and electrotransformed into *E. coli* BL21 (DE3) Gold. The resulting DNA construct is shown in FIG. 64*a*, where the light chain (vL) and heavy chain (vH) variable fragments are separated by rPEGY30, a 30 amino acid sequence (SGEGSEG-EGGGEGSEGEGSGEGGEGEGS) (SEQ ID NO: 483). The Y30-amino acid-encoding sequence was flanked by AgeI and KpnI restriction sites for convenient removal or replacement of the linker sequence between vL and vH. The constructs were confirmed by DNA sequencing. The protein sequences for the aHer230-rPEG (M.W.=80,044 Da) and aEGFR30-rPEG (M.W.=80,102 Da) constructs are shown in FIG. 64*b* and *d*, respectively.

The anti-Her230-rPEG and aEGFR30-rPEG fusions in *E. coli* BL21 (DE3) Gold were expressed by inducing with 0.2 mM isopropyl β-D-1 thiogalactopyranoside (IPTG) at 20° C. Cells were harvested by centrifugation and lysed in Bug-Buster plus Benzonase in phosphate buffered saline. Lysates were clarified by centrifugation and supernatants (soluble fractions) loaded onto 4-12% SDS PAGE gels. The scFv-rPEG fusions are overexpressed and visible in *E. coli* lysates at approximately 80 kDa (FIG. 64*c*).

Example 15

Characterization of the scFv-rPEG50 Fusion aHer230-rPEG

Purification

A single-chain fragment variable (scFv) antibody fragment targeting the Her2 receptor and fused to rPEG, to yield aHer230-rPEG, which was expressed and purified from the cytosol of *E. coli*. The aHer230-rPEG plasmid was transformed into BL21(DE3)-Gold and expression of the recombinant antibody fragment was induced with 0.2 mM isopropyl β-D-1 thiogalactopyranoside (IPTG) at 20° C. Cells were harvested by centrifugation and resuspended in 30 mM sodium phosphate, 0.3 M sodium chloride, 10% glycerol, and 20 mM imidazole, pH 7.5. Lysis was accomplished by sonication and the soluble protein was purified by standard chromatographic methods including, immobilized metal affinity chromatography (IMAC), hydrophobic interaction chromatography (HIC), and ion exchange chromatography (IEC).

Binding

Figure 62:
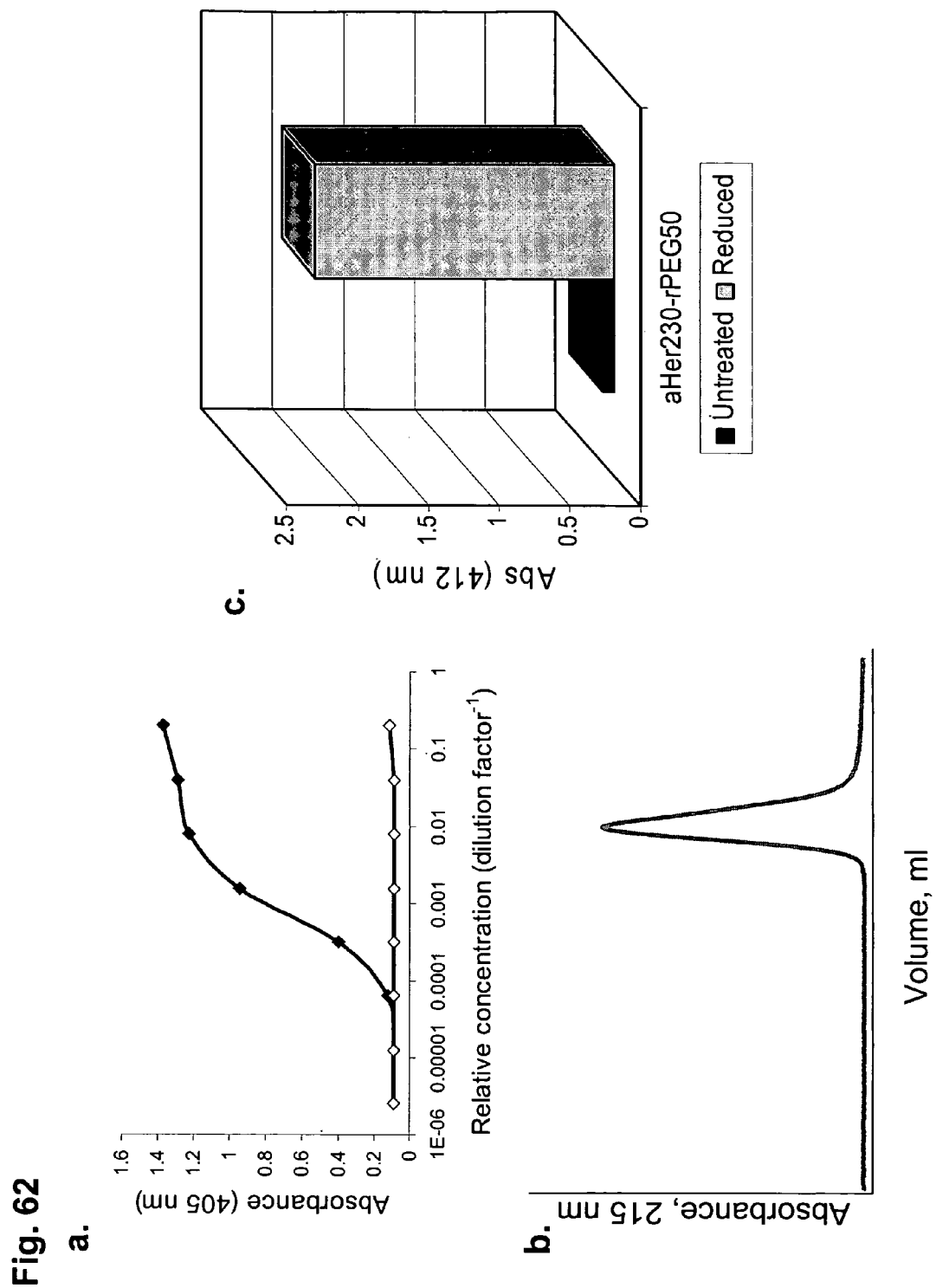
FIG. 62: Purification, characterization and binding activity of an anti Her-2 scFv fused to rPEG50. 62a: binding activity. Filled diamonds: binding to coated Her-2; open diamonds: binding to coated IgG. 62b: Size exclusion chromatography; 62c: Detection of free SH groups.

To evaluate target (Her2) binding, aHer230-rPEG was expressed in BL21(DE3)-Gold as described above. Cells were lysed by resuspension in phosphate buffer saline (PBS) containing BugBuster reagent and 5 U/ml of benzonase (Novagen). The suspension was incubated for 20 minutes at room temperature prior to centrifugation at 10000 rpm for 10 minutes. The soluble fraction was then serially diluted five-fold into PBS containing 1% bovine serum albumin (BSA) and 0.05% Tween-20. Serially diluted aHer230-rPEG was added to the wells of a 96-well plate which had been coated with a Her2-Fc fusion protein (R&D Systems) and blocked with 1% BSA. The binding reaction was incubated at room temperature for 2 hours with gentle agitation. The wells were thoroughly washed with PBS containing 0.05% Tween-20 and the bound aHer230-rPEG was detected with an HRP-conjugated anti-FLAG antibody (Sigma). FIG. 62*a* shows that aHer230-rPEG binds to Her2-Fc fusion protein and does not non-specifically bind to human IgG. The binding data are presented as a function of the sample dilution. The half maximal binding (EC50) is estimated to be achieved at approximately 10 nM aHer230-rPEG.

Purified aHer230-rPEG was analyzed by size-exclusion HPLC (SE-HPLC) to determine its oligomerization state. SE-HPLC analysis of aHer230-rPEG was performed on a TSK-gel G4000SWXL column. aHer230-rPEG forms only monomers, as shown in FIG. 62*b*. The addition of the rPEG accessory polypeptide to an anti-Her2 scFv effectively eliminates the formation of dimers that have been commonly observed for non-rPEG fused scFv.

SS-Bond Oxidation

The expression of disulfide containing proteins in the cytoplasm of *E. coli* is often unsuccessful due to the highly reducing nature of the cytoplasm, which inhibits disulfide formation. However, disulfide bonds may form following cell lysis when the proteins are exposed to more oxidizing conditions. As demonstrated above, aHer230-rPEG expressed in *E. coli* binds to its target, Her2, suggesting that the protein is properly folded. To test whether the two disulfide bonds, one each in the vH and vL domains, of aHer230-rPEG were properly formed in the purified protein, the number of free sulfhydryls in the denatured, purified protein was compared to a fully reduced form of the scFv. Purified aHer230-rPEG was denatured in 6 M urea or in 6 M urea supplemented with 10 mM Tris[2-carboxyethyl]phosphine (TCEP) for 1 hour at room temperature. The samples were then desalted on Sephadex G-25 resin to remove the urea and the TCEP. Immediately, Ellman's reagent (5,5'-dithio-bis-[2-nitrobenzoic acid]) was added to a final concentration of 20 mM and the reaction proceeded for 15 minutes. Finally, the absorbance of each solution was measured at 412 nm. Denatured aHer230-rPEG exhibits very little absorbance, which suggests that the purified sample is completely oxidized (FIG. 62*c*). The denatured and reduced reaction (FIG. 62*c*) shows the signal expected if all of the cysteines in aHer230-rPEG were in the reduced state. Thus, all of the disulfides within the anti-Her2 scFv were properly formed.

Example 16

Construction of the Diabody aHer203-rPEG

A diabody can be formed by linking the vH and vL domains with a linker less than 10 amino acids. The short linker does not allow scFv formation and as a result the vH and vL domains bind to a complementary, second vH-vL chain, forming a 4-domain, 2 chain 50 kD complex. The diabody was constructed from a single-chain fragment variable (scFv) antibody fragment that binds Her2, which was genetically fused to the N-terminus of rPEG50. Constructs were generated by replacing the Y30 scFv linker sequence from Example 1 with three amino acids (SGE) to allow a diabody format (FIG. 65*a*). The SGE sequence was introduced by polymerase chain reaction (PCR), also introducing NdeI and BbsI restriction sites that are compatible with the rPEG stuffer construct. Diabody-encoding fragments were then cloned as in Example 1. The construct was confirmed by DNA sequencing. The protein sequence for the aHer203-rPEG diabody (M.W.=156,598 Da as diabody or 78,299 Da monomer sequence, including rPEG) is shown in FIG. 65*b*.

The aHer203-rPEG in BL21 (DE3) Gold was expressed by inducing with 0.2 mM isopropyl β-D-1 thiogalactopyranoside (IPTG) at 20° C. Cells were harvested by centrifugation and lysed in BugBuster/Benzonase in phosphate buffered saline. Lysates were clarified by centrifugation and supernatants (soluble fractions) loaded onto 4-12% SDS PAGE gels. The aHer203-rPEG diabody was detected in *E. coli* lysates at approximately 90 kDa (FIG. 65*c*).

Example 17

Characterization of the Diabody-rPEG50 Fusion aHer203-rPEG

Purification

A diabody can be formed by linking the vH and vL domains with a linker comprising fewer than 10 amino acids. The short linker does not allow scFv formation and as a result the vH and vL domains bind to a complementary vH-vL chain. The diabody is a useful format to generate a bivalent, and possibly bispecific, therapeutic lacking effector Fc function.

A diabody that binds to Her2 was designed as described above. To evaluate target (Her2) binding, recombinant aHer203-rPEG diabody was expressed and purified as described for aHer230-rPEG. aHer203-rEPG50 was transformed into BL21 (DE3)-Gold and expression of the recombinant antibody fragment was induced with 0.2 mM isopropyl β-D-1 thiogalactopyranoside (IPTG) at 20° C. Cells were harvested by centrifugation and resuspended in 30 mM sodium phosphate, 0.3 M sodium chloride, 10% glycerol, an 20 mM imidazole, pH 7.5. Lysis was accomplished by sonication and the soluble protein was purified by standard chromatographic methods including, immobilized metal affinity chromatography (IMAC), hydrophobic interaction chromatography (HIC), and ion exchange chromatography (IEC).

Binding

Figure 63:
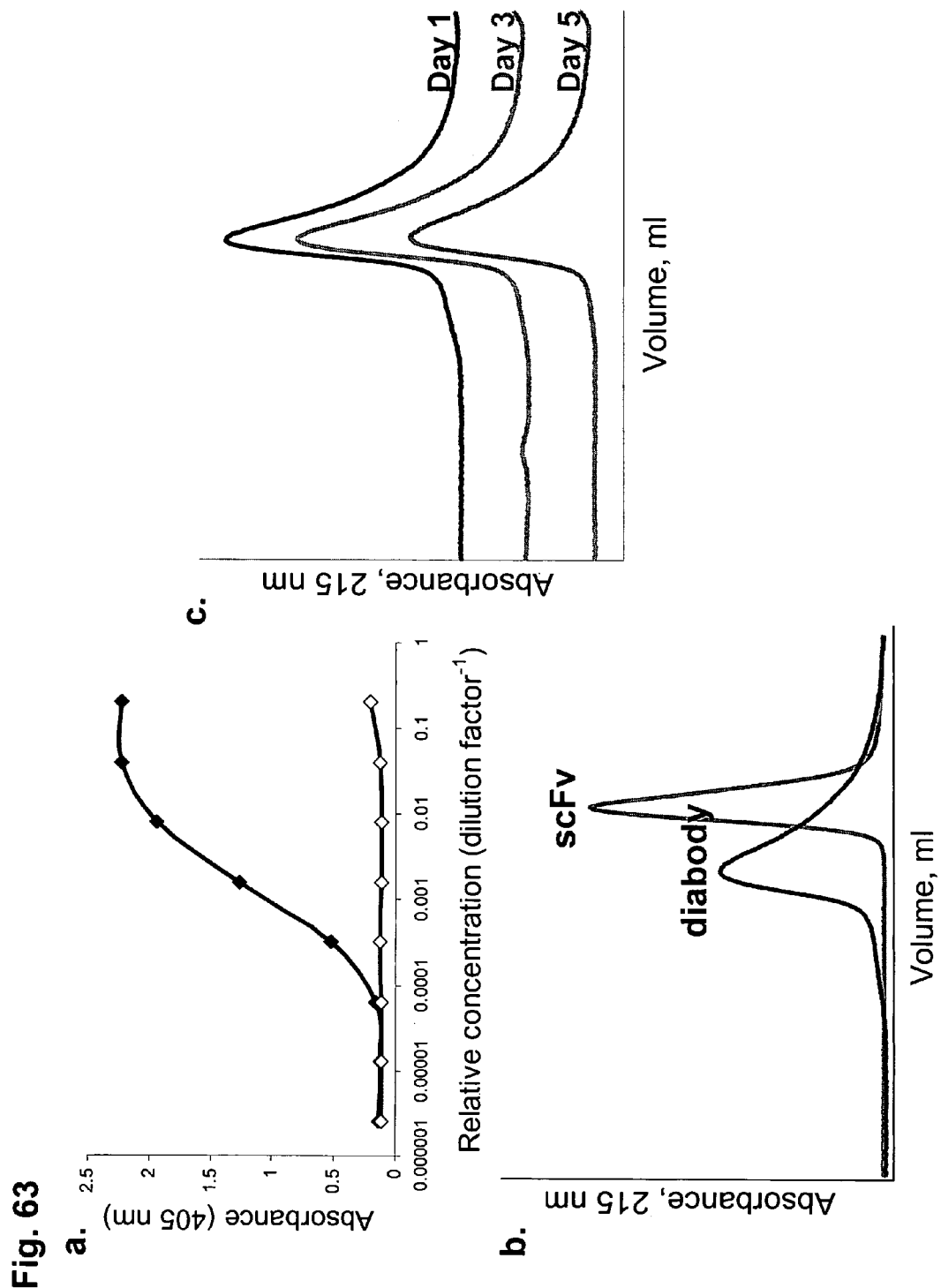
FIG. 63: Purification, characterization and binding activity of an anti Her-2 diabody, aHer203-rPEG50. 63a: binding activity. Filled diamonds: binding to coated Her-2; open diamonds: binding to coated IgG. 63b: Size exclusion chromatography of diabody aHer203-rPEG50 and scFv aHer230-rPEG50; 63c: SEC of aHer203-rPEG50 over time shows no increase in higher multimers.

Binding of the aHer203-rPEG diabody to its target was performed as described for aHer230-rPEG. Cells were lysed by resuspension in phosphate buffer saline (PBS) containing BugBuster reagent and 5 U/ml of benzonase (Novagen). The suspension was incubated for 20 minutes at room temperature prior to centrifugation at 10000 rpm for 10 minutes. The soluble fraction was then serially diluted five-fold into PBS containing 1% bovine serum albumin (BSA) and 0.05% Tween-20, hereafter referred to as ELISA binding buffer. Serially diluted aHer203-rPEG diabody was added to the wells of a 96-well plate which had been coated with a Her2-Fc fusion protein (R&D Systems) and blocked with 1% BSA. The binding reaction was incubated at room temperature for 2 hours with gentle agitation. The wells were thoroughly washed with PBS containing 0.05% Tween-20 and the bound aHer203-rPEG diabody was detected with an HRP-conjugated anti-FLAG antibody (M2, Sigma). FIG. 63a shows that the aHer203-rPEG diabody binds to the Her2-Fc fusion proteins and does not non-specifically bind to human IgG. The binding data are presented as a function of the sample dilution. The half maximal binding (EC50) is estimated to be achieved at approximately 10 nM aHer203-rPEG diabody. Thus, a functional aHer203 diabody with an rPEG accessory polypeptide can be expressed in the cytosol of E. coli.

SE-HPLC

Diabodies have been explored as potential bivalent therapeutics, however, their propensity to reassort into higher order oligomers—trimers, tetramers, etc.—has limited their utility. Reassortment is particularly problematic for manufacturing, because after purifying a monomeric scFv, upon storage in liquid form it will slowly but predictably reassort to yield dimers, and higher multimers. This leads not only to large losses in the amount of protein of the correct format that can finally be obtained, but it also leads to heterogeneity in the product upon storage and heterogeneity in pharmacokinetics and in efficacy. The equilibrium between monomers and multimers of scFv can be affected by the length of the linker between vH and vL domains. In general constructs with linkers of more than 12 to 14 amino acids occur predominantly in monomeric form while scFv with linkers shorter than 12-amino acids occur mostly in multimeric form [Desplancq, D., et al. (1994) Protein Eng, 7: 1027] [Whitlow, M., et al. (1994) Protein Eng, 7: 1017] [Hudson, P. J., et al. (1999) J Immunol Methods, 231: 177]. Increasing the length of the linker between vH and vL to 30 amino acids shifts the equilibrium into the direction of monomers [Desplancq, D., et al. (1994) Protein Eng, 7: 1027]. Linker lengths between 3 and 7 amino acids favor the formation of diabodies [Dolezal, O., et al. (2000) Protein Eng, 13: 565] [Kortt, A. A., et al. (1997) Protein Eng, 10: 423]. Linkers of 5-10 amino acids give rise to mostly dimer. Antigen presence and ionic strength can affect monomer-dimer transition [Arndt, K. M., et al. (1998) Biochemistry, 37: 12918]. Linkers shorter than 3 amino acids favor the formation of triabodies and tetrabodies [Le Gall, F., et al. (1999) FEBS Lett, 453: 164] [Dolezal, O., et al. (2000) Protein Eng, 13: 565] [Kortt, A. A., et al. (1997) Protein Eng, 10: 423].

The oligomerization state of the aHer203-rPEG diabody by SE-HPLC has been evaluated and demonstrated that it does not reassort. FIG. 63b, shows the size-exclusion chromatograms of aHer230-rPEG single chain and the aHer203-rPEG diabody. It demonstrates that the diabody is largely dimeric and, significantly, it contains less than 3% trimer or tetramer forms. The oligomerization state of the aHer203-rPEG diabody has also been monitored during storage at 4° C. and reassortment was not observed (FIG. 63c). The rPEG accessory polypeptide helps prevent the reassortment of the diabody, thus enabling the purification and formulation of a homogenous product.

Example 18

Codon Optimization of an Fc Domain for Bacterial Expression

Figure 66A:
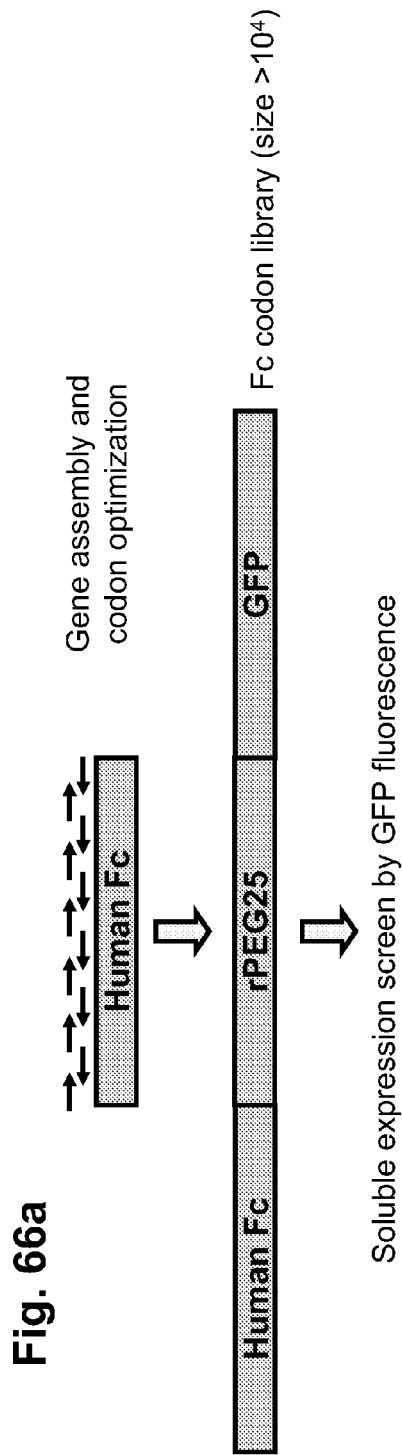
FIG. 66: Codon optimization of an Fc domain for bacterial expression: 66a: Illustration of the process and oligonucleotide design. The sequence encoding the human Fc was assembled from semi-random oligonucleotides and cloned in front of rPEG25 and GFP that served as reported. 66b: SDS/PAGE of clones that were selected from the library. The arrow indicates the band of the desired fusion protein. 66c: Amino acid (SEQ ID NO: 509) and nucleotide sequence (SEQ ID NO: 508) of and optimized human Fc gene.
Figure 66B:
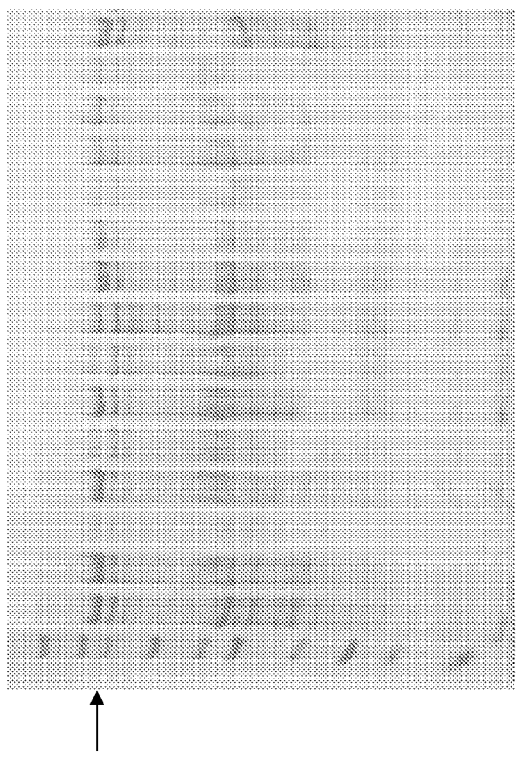

The Human IgG1 constant fragment (Fc) was synthesized and fused to rPEG25-Green Fluorescent Protein (GFP) to yield Fc-rPEG25-GFP, as shown in FIG. 66a. The DNA encoding the Fc sequence was constructed in vitro using E. coli optimized codons. The Fc codon library was assembled using 60-mer oligonucleotides with 20 nucleotide overlap (annealing) regions. Multiple codons were introduced in the non-overlapping regions of the synthetic oligonucleotides. The resulting codon library had a theoretical size of approximately 10,000 such that all nucleotide sequences encode the desired Fc sequence. A total of 18 oligonucleotides were assembled in the presence of dNTPs and DNA polymerase to a final size of 684 bp. The Fc codon library was amplified by PCR using primers that create NdeI and BbsI compatible ends. The DNA fragment was restriction digested and ligated into an rPEG25-GFP vector at NdeI and BsaI restriction digestion sites. The ligated DNA was transformed into BL21 (DE3) Gold. A total of 1000 clones were isolated, grown in 96-well format, and replicated to plates containing 0.2 mM IPTG to induce expression. Constructs that were well-expressed showed high levels of fluorescence under ultraviolet light. A total of 17 clones were characterized as highly fluorescent. These clones were expressed in 1 ml cultures using 0.2 mM IPTG, cells were harvested by centrifugation, and lysed with Bugbuster plus Benzonase in phosphate buffered saline. Soluble fractions were loaded onto 4-12% SDS PAGE gels (FIG. 66b). Recombinant Fc-rPEG fusions have an observed molecular weight on SDS-PAGE of approximately 80-90 kDa (predicted MW is about 80 but the rPEG causes proteins to run high). The DNA sequence of a codon optimized Fc is shown in FIG. 66*c*.

Example 19

Expression and Characterization of Fc-rPEG Fusion Proteins

The Fc fragment of IgG1 was fused to rPEG as detailed in Example 5 (and variants are illustrated in FIG. 31), and expressed in the cytoplasm of *E. coli*. Cells expressing the fusion protein were resuspended in buffer, in this case 20 mM sodium phosphate pH 7.0, and the cells were lysed by sonication. The insoluble material was removed by centrifugation and Fc-rPEG-GFP was purified from the soluble fraction. Intact, folded Fc fragment binds to Protein A and therefore can be conveniently purified by affinity chromatography using immobilized recombinant Protein A. Soluble lysate containing the Fc fusion was applied to a Protein A column (GE Healthcare) and microbial proteins were removed by extensive washing with phosphate buffer. The Fc-rPEG-GFP fusion protein was eluted from the Protein A column using either glycine buffer or sodium citrate buffer pH 3.0. The pH of the elution fractions was immediately adjusted with and equal amount of Tris buffer pH 8.5. The purified protein was analyzed by SDS-PAGE under reducing and oxidizing conditions. A single band of approximately 80 kDa was detected under reducing conditions, while bands at 160 kDa (hinge oxidized) and 80 kDa (hinge reduced) were detected under oxidizing conditions. The addition of either $CuSO_4$, dehydroascorbic acid, or other oxidizing reagents was used to catalyze the complete oxidation of the hinge cysteines.

Example 20

Construction and Bacterial Expression of a Fab-rPEG Fusion Protein

Figure 67:
FIG. 67: Cartoon illustrating expression constructs for Fab-rPEG fusion proteins

This example describes the construction and bacterial expression of a Fab-rPEG fusion protein. The fragment, antigen binding (Fab) of an IgG can be fused to rPEG as a means of improving soluble Fab expression as well as half-life extension. The expression construct was designed a bicistronic RNA message that is under the control of an inducible arabinose promoter (FIG. 67). The bicistronic message is terminated at a hairpin terminator, such as the T7 terminator sequence. Each cistron or gene has a ribosomal binding site (RBS) to initiate translation and a stop codon (TAA, TGA, or TAG) to stop translation. The light chain (vL/cL) or heavy chain (vH/cH) sequence can be genetically fused to rPEG and followed by an affinity tag such as HA (hemagglutinin), H (hexahistidine) (SEQ ID NO: 1), and/or FLAG tag. DNA constructs can encode the heavy chain first or light chain last (HL) or light chain first and heavy chain last (LH) as shown in FIG. 67. Protein expression from this type of construct yields two approximately 50 kDa chains that form a full Fab fragment of approximately 100 kDa in size, which includes a total of 50 kDa of rPEG sequence.

Example 21

PK Analysis of GFP-rPEG50

The amino acid sequence of GFP-rPEG50 is shown in FIG. 69. The protein was expressed in BL21(DE3) using a T7 promoter similar to example 1. The protein was purified by ion exchange chromatography followed by hydrophobic interaction chromatography. The pharmacokinetics of GFP-rPEG50 was studied in cynomolgous macaques monkeys following s.c. and i.v. injection. Three cynomolgous macaques monkeys were divided into 2 groups, 2 animals dosed i.v and one dosed s.c. at 0.15 mg/kg with GFP-rPEG50. Serial blood samples were taken from each monkey, the plasma was separated, and the test article plasma concentration was measured by ELISA Assays. The half-life for the i.v. dosed animals was 17.4 hours and 13.8 Hrs for the s.c. dosed animals. The bioavailability for the test article was approximately 54.6% as shown in FIG. 70.

Example 22

PK Analysis of Ex4-rPEG50

Ex4-rPEG50 is a fusion protein between exendin-4 and rPEG50. It was produced as a fusion protein with a cellulose binding domain (CBD), which was designed to be removed by cleavage with TEV protease as illustrated in FIG. 71*b*. The amino acid sequence of the fusion protein is shown in FIG. 71. The expression plasmid and purification protein were similar as in Example 1 with the addition of a step for TEV proteolysis. The cleaved CBD was removed by incubation with beaded cellulose. The pharmacokinec of Ex4-rPEG50 was studied in cynomologos monkeys. Four cynomolgous macaques monkeys were divided into 2 groups, 2 animals per group and dosed s.c. and i.v., at 0.15 mg/kg with Ex4-rPEG50. Serial blood samples were taken from each monkey and the test article plasma concentration was measured by ELISA assay. The half-life was 9.5 hours and 9.1 hours for the s.c. and i.v. dosing, respectively as shown in FIG. 70.

Example 23

PK Analysis of GFP-rPEG50 in Rodents

This example compares the s.c. and i.v. pharmacokinetics of GFP-rPEG25 and GFP-rPEG50. 15 rats were divided into 5 groups, 3 rats per group and dosed both s.c. and i.v. at 1.67 mg/kg with either GFP-rPEGY25 and GFP-rPEG_Y288. GFP-rPEG25 had approximately an 8-9 $t_{0.5}$ when injected s.c versus 11-15 hr $t_{0.5}$ for GFP-rPEG50. GFP-rPEG25 was approximately 25% s.c bioavailability versus 11% s.c bioavailability for GFP-rPEG50. In mice, $^{125}$I-GFP-rPEG50 was dosed into in nude mice. The half-life was 13.4 hours.

Example 24

PK Analysis of Human Growth Hormone Fused to rPEG50 rPEG50 was fused to either the C- or N-terminus of human growth hormone (hGH). Proteins were purified as described in example 8. The pharmacokinetics was studied in cynomologos monkeys. Two cynomolgous macaques monkeys were divided into 2 groups, 1 animal per group. Each monkey was i.v. dosed at 0.15 mg/kg with the one growth hormone construct, either hGH-rPEG50 or rPEG50-hGH. The two growth hormone constructs had half-life of 7 and 10.5 hrs, respectively.

Example 25

Mouse Immunogenicity and Toxicology Study of Ex4-rPEG50

This example describes the immunogenicity and potential toxicity associated with ten s.c. 50 µg doses of Ex4-rPEG50

(1/week) into a mouse. 20 mice (Swiss Webster) total, each 30-40 g with 10 mice/group, 5 males and 5 females/group, using 2 groups dosed weekly with either Ex4-rPEG50 or ELSPAR that served as control as illustrated in FIG. 72a. Before each dose a blood sample was taken and the IgG was measured by ELISA Assay as shown in FIGS. 72b and 72c. ELSPAR resulted in a significant immune response that increased over time. In contrast Ex4-rPEG50 gave a very weak response that showed a maximum after 6 antigen injections and decreased in the sample obtained after 10 antigen injections. All mice gained weight during the study and showed no behavioral signs of toxicity and necropsy revealed no unusual finding with regard to organ morphology. After completion of the in life portion blood samples, blood smears, and plasma and tissue samples were shipped to RADIL (Columbia, Mo.) for toxicology analysis. Histology analysis showed that no distinct cytoplasmic vacuolation was present in the distal or proximal tubules, which is a major concern for chemical conjugates with PEG. Evaluation of liver histology showed mild inflammation in all four analyzed samples. This is a common finding in the livers of apparently healthy animals. Analysis of the spleen showed that all four mice have moderate to marked megakaryocytosis and moderate hematopoiesis. Clinical chemistry revealed ALT and ALP levels that were moderately high for one of the animal indicating hepatocellular damage/necrosis. It is not severe or chronic based on the observation. Hematology revealed that all four mice had at least one slightly elevated blood cell count, hemoglobin, hematocrit percentage or blood total protein concentration. Overall, multiple injections of rPEG fusion protein resulted in very minor immunogenicity and toxicity.

Example 26

Size Exclusion Chromatography of GFP-rPEG Fusion Proteins

Figure 73:
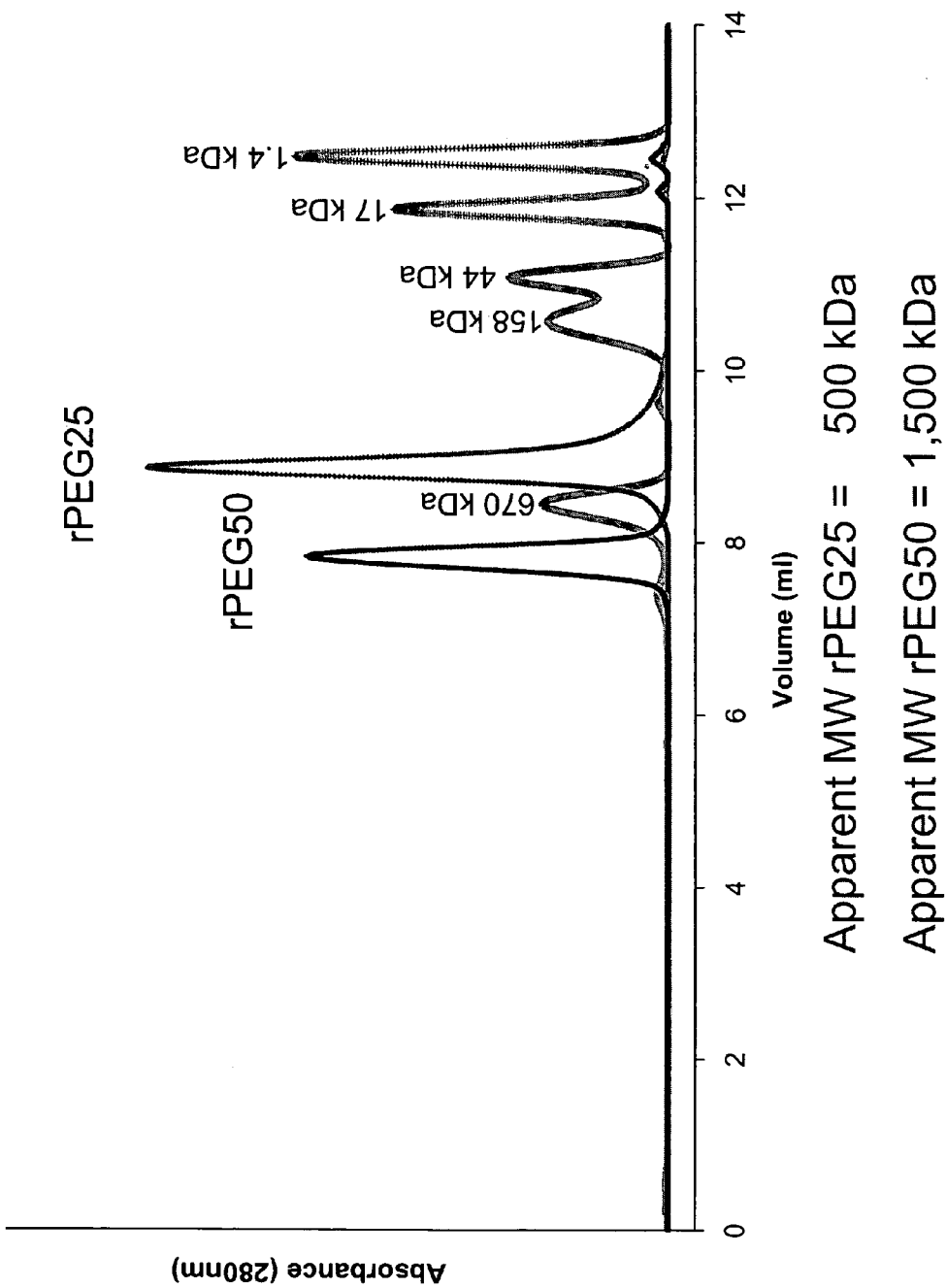
FIG. 73: Size exclusion chromatography of GFP-rPEG25 and GFP-rPEG50. Grey line indicates molecular weigh standard using globular proteins.

GFP fused to rPEG_Y25 and rPEG_Y50 was expressed as discussed in Example 8. The proteins were analyzed by analytical SEC using a TSK G4000 SWXL (Tosoh, Grove City, Ohio) as shown in FIG. 73. The column was calibrated using a commercial standard of globular proteins and molecular weights of the controls are shown in FIG. 73. GFP-rPEG25 eluted at an apparent molecular weight of 500 kDa whereas GFP-rPEG50 eluted at an apparent molecular weight of 1500 kDa.

Example 27

Formulation and In Vivo Administration of GFP-rPEGY Fusion Proteins

A solution of GFP-rPEGY at 10 mg/mL in PBS is mixed with an equal volume of 5 mg/mL Chitosan in PBS and incubated at room temperature for 30 minutes. Precipitate is collected by centrifugation at 5,000×g for 10 minutes, and washed quickly one time with 0.1 volume sterile PBS. The precipitate is then lyophilized to remove excess fluid and ground to a fine powder. 15 mg of powder is then resuspended in 1 mL sterile PBS and homogenized by pipetting up and down. The homogenate is stored rotating at 37° C. for 2 weeks, with 10 uL samples removed at regular intervals. Samples are prepared immediately by centrifugation to remove insoluble material, and resolubilized protein is quantitated in the supernatant by GFP fluorescence, optical density, and rPEGY ELISA. Supernatant concentration is plotted as a function of time and fit to a single exponential process to determine the resolubilization rate. To determine in vivo release rates, Sprague-Dawly rats are injected subcutaneously with a freshly prepared suspension of 20 mg powder in 1 mL PBS at a dosage of 1 mL/kg (5 mg/kg effective dose). Intravenous and subcutaneous injections of uncomplexed GFP-rPEGY are injected at 5 mg/kg into independent cohorts of animals in parallel. Blood samples are taken at regular intervals, and serum concentration of protein is determined by GFP and rPEGY ELISAs. Pharmacokinetic parameters including clearance rate, $C_{max}$, $C_{ss}$, $V_D$, AUC and serum half-life are determined by standard methods (ie WinNonLin analysis). Bioavailability and effective dose for subcutaneous and depot formulations are determined by comparison to intravenous dosing.

Thus, while preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a soluble form of a modified polypeptide comprising a biologically active polypeptide linked to an accessory polypeptide, wherein said accessory polypeptide comprises at least 40 contiguous amino acids and further wherein
   (a) the accessory polypeptide consists of three types of amino acids selected from a group consisting of glycine (G), aspartate (D), alanine (A), serine (S), threonine (T), glutamate (E) and proline (P) residues contained in the accessory polypeptide; and
   (b) at least 50% of the amino acids are devoid of secondary structure as determined by Chou-Fasman algorithm,
and wherein said modified polypeptide has an increased solubility in a host cell in which the modified polypeptide is expressed as compared to biologically active polypeptide lacking said accessory polypeptide.

2. The composition of claim 1, wherein the accessory polypeptide has a serum half-life greater than about 4 hours in a subject.

3. The composition of claim 1, wherein the types of amino acids of the accessory polypeptide are selected from the group consisting of glutamic acid (E), glycine (G) and serine (S).

4. The composition of claim 1, wherein less than 50% of all residues of the accessory polypeptide are glycine (G) residues.

5. The composition of claim 1, wherein the biologically active polypeptide is selected from the group consisting of human growth hormone (hGH), glucagon-like peptide-1

(GLP-1), granulocyte-colony stimulating factor (G-CSF), interferon-alpha, interferon-beta, interferon-gamma, insulin, erythropoietin, tumor necrosis factor-alpha (TNF-alpha), interleukin-1 receptor antagonist (IL-1RA), exenatide, uricase and pramlintide.

6. The composition of claim 1, wherein the accessory polypeptide provides a net negative charge of the modified polypeptide about −0.1 or lower.

7. The composition of claim 1, wherein said modified polypeptide yields an apparent molecular weight factor of greater than 3, and further wherein said apparent molecular weight factor is determined as a ratio of an apparent molecular weight of the modified polypeptide as measured by size exclusion chromatography relative to a predicted molecular weight of the modified polypeptide.

8. The composition of claim 1, wherein the apparent molecular weight factor of said modified polypeptide is greater than 5.

9. The composition of claim 1, wherein the apparent molecular weight factor of said modified polypeptide is greater than 7.

10. The composition of claim 1, wherein the apparent molecular weight factor of said modified polypeptide is greater than 9.

11. The composition of claim 1, wherein said accessory polypeptide comprises more than about 100 amino acids.

12. The composition of claim 1, wherein the accessory polypeptide comprises proline but does not contain one or more amino acids selected from the group consisting of cysteine, methionine, asparagine, and glutamine.

* * * * *